(12) United States Patent
Garrett et al.

(10) Patent No.: US 11,578,367 B2
(45) Date of Patent: Feb. 14, 2023

(54) DIAGNOSIS OF SEPSIS

(71) Applicant: Becton, Dickinson and Company, Franklin Lakes, NJ (US)

(72) Inventors: James A. Garrett, Baltimore, MD (US); Sha-Sha Wang, Cockeysville, MD (US); Keith Thornton, Owing Mills, MD (US); Richard L. Moore, Glenville, PA (US); William Keating, Reisterstown, MD (US); William A. Nussbaumer, Lutherville, MD (US); Craig C. Whiteford, York, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 16/596,481

(22) Filed: Oct. 8, 2019

(65) Prior Publication Data

US 2021/0087632 A1  Mar. 25, 2021

Related U.S. Application Data

(63) Continuation of application No. 14/850,933, filed on Sep. 10, 2015, now Pat. No. 10,443,099, which is a continuation of application No. 13/965,038, filed on Aug. 12, 2013, now abandoned, which is a continuation of application No. 12/776,245, filed on May 7, 2010, now abandoned, which is a continuation of application No. 11/404,744, filed on Apr. 14, 2006, now Pat. No. 7,767,395.

(60) Provisional application No. 60/674,046, filed on Apr. 22, 2005, provisional application No. 60/671,620, filed on Apr. 15, 2005.

(51) Int. Cl.
*C12Q 1/68* (2018.01)
*C12P 19/34* (2006.01)
*C12Q 1/6883* (2018.01)
*G01N 33/68* (2006.01)
*G01N 33/569* (2006.01)
*C12Q 1/6888* (2018.01)

(52) U.S. Cl.
CPC ......... *C12Q 1/6883* (2013.01); *C12Q 1/6888* (2013.01); *G01N 33/56911* (2013.01); *G01N 33/6893* (2013.01); *C12Q 2600/112* (2013.01); *C12Q 2600/158* (2013.01); *C12Q 2600/16* (2013.01); *G01N 2333/5412* (2013.01); *G01N 2333/5421* (2013.01); *G01N 2800/26* (2013.01); *G01N 2800/50* (2013.01)

(58) Field of Classification Search
CPC ... G01N 2333/5412; G01N 2333/5421; C12Q 2600/158; C12Q 2600/118
See application file for complete search history.

(56) References Cited

U.S. PATENT DOCUMENTS

| | | |
|---|---|---|
| 4,198,389 A | 4/1980 | Wadsworth |
| 4,329,152 A | 5/1982 | Lauwerys et al. |
| 4,721,730 A | 1/1988 | Furuyoshi et al. |
| 4,770,774 A | 9/1988 | Ida et al. |
| 4,872,983 A | 10/1989 | Dimantoglou et al. |
| 4,952,323 A | 8/1990 | Nakabayashi et al. |
| 5,051,185 A | 9/1991 | Watanabe et al. |
| 5,051,371 A | 9/1991 | Nissen et al. |
| 5,093,271 A | 3/1992 | Yamamoto |
| 5,175,113 A | 12/1992 | Nissen et al. |
| 5,272,258 A | 12/1993 | Siegel et al. |
| 5,358,852 A | 10/1994 | Wu |
| 5,426,181 A | 6/1995 | Lee et al. |
| 5,484,705 A | 1/1996 | White et al. |
| 5,500,345 A | 3/1996 | Soe et al. |
| 5,639,617 A | 6/1997 | Bohuon |
| 5,646,005 A | 7/1997 | Kudsk |
| 5,780,237 A | 7/1998 | Bursten et al. |
| 5,804,367 A | 9/1998 | White et al. |
| 5,804,370 A | 9/1998 | Romaschin et al. |
| 5,830,679 A | 11/1998 | Bianchi et al. |

(Continued)

FOREIGN PATENT DOCUMENTS

| | | |
|---|---|---|
| EP | 1369693 A1 | 12/2003 |
| EP | 1619505 A2 | 1/2006 |

(Continued)

OTHER PUBLICATIONS

Armstrong, L. et al. "Differential expression of Toll-like receptor (TLR)-2 and TLR-4 on monocytes in human sepsis" Clin Exp Immunol 2004; 136:312-319 (Year: 2004).*

(Continued)

*Primary Examiner* — Stephen T Kapushoc
(74) *Attorney, Agent, or Firm* — Knobbe, Martens, Olson & Bear, LLP

(57) ABSTRACT

Methods for predicting the development of sepsis in a subject at risk for developing sepsis are provided. In one method, features in a biomarker profile of the subject are evaluated. The subject is likely to develop sepsis if these features satisfy a particular value set. Methods for predicting the development of a stage of sepsis in a subject at risk for developing a stage of sepsis are provided. In one method, a plurality of features in a biomarker profile of the subject is evaluated. The subject is likely to have the stage of sepsis if these feature values satisfy a particular value set. Methods of diagnosing sepsis in a subject are provided. In one such method, a plurality of features in a biomarker profile of the subject is evaluated. The subject is likely to develop sepsis when the plurality of features satisfies a particular value set.

8 Claims, 85 Drawing Sheets

(56) References Cited

U.S. PATENT DOCUMENTS

| | | | |
|---|---|---|---|
| 5,882,872 A | 3/1999 | Kudsk | |
| 5,904,663 A | 5/1999 | Braverman et al. | |
| 5,928,624 A | 7/1999 | Wright et al. | |
| 5,981,180 A | 11/1999 | Chandler et al. | |
| 6,077,665 A | 6/2000 | Weirich et al. | |
| 6,159,683 A | 12/2000 | Romaschin et al. | |
| 6,190,872 B1 | 2/2001 | Slotman | |
| 6,200,766 B1 | 3/2001 | Davis | |
| 6,248,553 B1 | 6/2001 | Small et al. | |
| 6,251,598 B1 | 6/2001 | di Giovine et al. | |
| 6,268,222 B1 | 7/2001 | Chandler et al. | |
| 6,303,321 B1 | 10/2001 | Tracey et al. | |
| 6,316,199 B1 | 11/2001 | Vockley et al. | |
| 6,376,202 B1 | 4/2002 | Davis | |
| 6,406,862 B1 | 6/2002 | Krakauer | |
| 6,416,487 B1 | 7/2002 | Braverman et al. | |
| 6,420,526 B1 | 7/2002 | Ruben et al. | |
| 6,423,505 B1 | 7/2002 | Davis | |
| 6,534,648 B1 | 3/2003 | Pardy et al. | |
| 6,548,646 B1 | 4/2003 | Ebrahim et al. | |
| 6,579,719 B1 | 6/2003 | Hutchens et al. | |
| 6,592,822 B1 | 7/2003 | Chandler | |
| 6,599,331 B2 | 7/2003 | Chandler et al. | |
| 6,675,104 B2 | 1/2004 | Paulse et al. | |
| 6,682,741 B1 | 1/2004 | Ribaudo et al. | |
| 6,692,916 B2 | 2/2004 | Bevilacqua et al. | |
| 6,756,483 B1 | 6/2004 | Bergmann et al. | |
| 6,838,250 B2 | 1/2005 | Scalice et al. | |
| 6,872,541 B2 | 3/2005 | Mills | |
| 6,930,085 B2 | 8/2005 | Fogelman et al. | |
| 6,951,727 B2 | 10/2005 | Davis | |
| 6,960,439 B2 | 11/2005 | Bevilacqua et al. | |
| 6,964,850 B2 | 11/2005 | Bevilacqua et al. | |
| 7,015,022 B2 | 3/2006 | Laskin et al. | |
| 7,465,555 B2 | 12/2008 | Anderson et al. | |
| 7,632,685 B2 | 12/2009 | Ivey et al. | |
| 7,645,573 B2 | 1/2010 | Ivey et al. | |
| 7,645,613 B2 | 1/2010 | Ivey et al. | |
| 7,767,395 B2 | 8/2010 | Garrett et al. | |
| 7,807,696 B2 | 10/2010 | Al-Abed et al. | |
| 8,183,050 B2 | 5/2012 | Shi et al. | |
| 8,669,113 B2 | 3/2014 | Shi et al. | |
| 9,091,698 B2 | 7/2015 | Shi et al. | |
| 9,708,661 B2 | 7/2017 | Shi et al. | |
| 9,885,084 B2 | 2/2018 | Shi et al. | |
| 10,221,453 B2 | 3/2019 | Shi et al. | |
| 10,443,099 B2 | 10/2019 | Garrett et al. | |
| 2001/0051344 A1 | 12/2001 | Shalon et al. | |
| 2002/0019704 A1 | 2/2002 | Tusher et al. | |
| 2002/0119554 A1 | 8/2002 | Vockley et al. | |
| 2002/0150534 A1 | 10/2002 | Yu et al. | |
| 2003/0004402 A1 | 1/2003 | Hitt et al. | |
| 2003/0027176 A1 | 2/2003 | Dailey | |
| 2003/0044790 A1 | 3/2003 | Das et al. | |
| 2003/0049851 A1 | 3/2003 | Toh et al. | |
| 2003/0057106 A1 | 3/2003 | Shen et al. | |
| 2003/0059937 A1 | 3/2003 | Ruben et al. | |
| 2003/0087285 A1 | 5/2003 | Chow et al. | |
| 2003/0091565 A1 | 5/2003 | Beltzer et al. | |
| 2003/0100122 A1 | 5/2003 | Heinecke et al. | |
| 2003/0165919 A1 | 9/2003 | Schmitz et al. | |
| 2003/0194752 A1 | 10/2003 | Anderson et al. | |
| 2003/0207278 A1 | 11/2003 | Khan et al. | |
| 2003/0219771 A1 | 11/2003 | Bevilacqua et al. | |
| 2003/0223996 A1 | 12/2003 | Ruben et al. | |
| 2003/0228625 A1 | 12/2003 | Toh et al. | |
| 2003/0228648 A1 | 12/2003 | Laskin et al. | |
| 2003/0229455 A1 | 12/2003 | Bevilacqua et al. | |
| 2003/0235816 A1 | 12/2003 | Slawin et al. | |
| 2004/0009503 A1 | 1/2004 | Fu et al. | |
| 2004/0038201 A1 | 2/2004 | Nau et al. | |
| 2004/0072237 A1 | 4/2004 | Schweitzer | |
| 2004/0096917 A1 | 5/2004 | Ivey et al. | |
| 2004/0097460 A1 | 5/2004 | Ivey et al. | |
| 2004/0106142 A1 | 6/2004 | Ivey et al. | |
| 2004/0121343 A1 | 6/2004 | Buechler et al. | |
| 2004/0121350 A1 | 6/2004 | Anderberg et al. | |
| 2004/0126767 A1 | 7/2004 | Anderberg et al. | |
| 2004/0133352 A1 | 7/2004 | Bevilacqua et al. | |
| 2004/0157242 A1 | 8/2004 | Ivey et al. | |
| 2004/0175754 A1 | 9/2004 | Bar-Or et al. | |
| 2004/0180396 A1 | 9/2004 | Bergmann et al. | |
| 2004/0219568 A1 | 11/2004 | Bevilacqua et al. | |
| 2004/0225447 A1 | 11/2004 | Bevilacqua et al. | |
| 2004/0225449 A1 | 11/2004 | Bevilacqua et al. | |
| 2004/0253637 A1 | 12/2004 | Buechler et al. | |
| 2004/0259090 A1 | 12/2004 | Zipel et al. | |
| 2005/0009074 A1 | 1/2005 | Thompson | |
| 2005/0037344 A1 | 2/2005 | Stuhmuller et al. | |
| 2005/0059104 A1 | 3/2005 | Bergmann | |
| 2005/0060101 A1 | 3/2005 | Bevilacqua et al. | |
| 2005/0064506 A1 | 3/2005 | Bergmann | |
| 2005/0069958 A1 | 3/2005 | Mills et al. | |
| 2005/0074811 A1 | 4/2005 | Bergmann | |
| 2005/0079490 A1 | 4/2005 | Stuber et al. | |
| 2005/0106645 A1 | 5/2005 | Bergmann | |
| 2005/0130242 A1 | 6/2005 | Bergmann et al. | |
| 2005/0148029 A1 | 7/2005 | Buechler et al. | |
| 2005/0164238 A1 | 7/2005 | Valkirs et al. | |
| 2005/0181386 A1 | 8/2005 | Diamond et al. | |
| 2005/0196817 A1 | 9/2005 | Kingsmore et al. | |
| 2005/0239150 A1 | 10/2005 | Bergmann | |
| 2005/0249724 A1 | 11/2005 | Lihme et al. | |
| 2005/0250148 A1 | 11/2005 | Bevilacqua et al. | |
| 2006/0024744 A1 | 2/2006 | Mills et al. | |
| 2006/0062789 A1 | 3/2006 | Ruben et al. | |
| 2006/0127912 A1 | 6/2006 | Pachot | |
| 2006/0211752 A1 | 9/2006 | Kohn et al. | |
| 2006/0241040 A1 | 10/2006 | Visintin et al. | |
| 2006/0246495 A1 | 11/2006 | Garrett et al. | |
| 2007/0021465 A1 | 1/2007 | Al-Abed et al. | |
| 2007/0111316 A1 | 5/2007 | Shi et al. | |
| 2007/0184512 A1 | 8/2007 | Ivey et al. | |
| 2008/0050829 A1 | 2/2008 | Ivey et al. | |
| 2011/0105350 A1 | 5/2011 | Garrett et al. | |
| 2011/0118569 A1 | 5/2011 | Shi et al. | |
| 2014/0141435 A1 | 5/2014 | Garrett et al. | |
| 2014/0302533 A1 | 10/2014 | Shi et al. | |
| 2016/0040233 A1 | 2/2016 | Shi et al. | |
| 2016/0168638 A1 | 6/2016 | Garrett et al. | |
| 2018/0002752 A1 | 1/2018 | Shi et al. | |

FOREIGN PATENT DOCUMENTS

| | | |
|---|---|---|
| EP | 1940231 B1 | 5/2011 |
| JP | H0933525 A | 2/1997 |
| JP | 2002-017938 | 1/2002 |
| JP | 2003524762 | 8/2003 |
| RU | 2072103 | 8/1997 |
| SU | 1504597 | 9/1993 |
| WO | WO 1992/021364 | 12/1992 |
| WO | WO 1994/028418 | 12/1994 |
| WO | WO 1995/020163 | 7/1995 |
| WO | WO 1996/041291 | 12/1996 |
| WO | WO 1998/001738 | 1/1998 |
| WO | WO 1999/020756 | 4/1999 |
| WO | WO 2000/042222 | 7/2000 |
| WO | WO 2000/046603 | 8/2000 |
| WO | WO 2000/052472 | 9/2000 |
| WO | WO 2001/004630 | 1/2001 |
| WO | WO 2001/063280 | 8/2001 |
| WO | WO 2001/096864 | 12/2001 |
| WO | WO 2002/042733 | 5/2002 |
| WO | WO 2002/058721 | 8/2002 |
| WO | WO 2002/088744 | 11/2002 |
| WO | WO 2002/088747 | 11/2002 |
| WO | WO 2003/048776 | 6/2003 |
| WO | WO 2003/048777 | 6/2003 |
| WO | WO 2003/048778 | 6/2003 |
| WO | WO 2003/048782 | 6/2003 |
| WO | WO 2003/073099 | 9/2003 |
| WO | WO 2003/084388 | 10/2003 |
| WO | WO 2004/005539 | 1/2004 |
| WO | WO 2004/043223 | 5/2004 |

(56) References Cited

FOREIGN PATENT DOCUMENTS

| | | |
|---|---|---|
| WO | WO 2004/043236 | 5/2004 |
| WO | WO 2004/044554 | 5/2004 |
| WO | WO 2004/044555 | 5/2004 |
| WO | WO 2004/044556 | 5/2004 |
| WO | WO 2004/053148 | 6/2004 |
| WO | WO 2004/053155 | 6/2004 |
| WO | WO 2004/053457 | 6/2004 |
| WO | WO 2004/057034 | 7/2004 |
| WO | WO 2004/059293 | 7/2004 |
| WO | WO 2004/008138 | 8/2004 |
| WO | WO 2004/086043 | 10/2004 |
| WO | WO 2004/087949 | 10/2004 |
| WO | WO 2004/088324 | 10/2004 |
| WO | WO 2004/108957 | 12/2004 |
| WO | WO 2005/033327 | 4/2005 |
| WO | WO 2005/048823 | 6/2005 |
| WO | WO 2005/064307 | 7/2005 |
| WO | WO 2005/065015 | 7/2005 |
| WO | WO 2005/078456 | 8/2005 |
| WO | WO 2006/061644 | 6/2006 |
| WO | WO 2006/071583 | 7/2006 |
| WO | WO 2006/077471 | 7/2006 |
| WO | WO 2006/085984 | 8/2006 |
| WO | WO 2006/102408 | 9/2006 |
| WO | WO 2006/113529 | 10/2006 |
| WO | WO 2007/038758 | 9/2007 |
| WO | WO 2009/123737 | 10/2009 |

OTHER PUBLICATIONS

Adam et al., "Serum protein fingerprinting coupled with a pattern-matching algorithm distinguishes prostate cancer from benigh prostate hyperplasia and healthy men", Canc Res. (2002) 62(13):3609-3614.
Affymetrix, "Gene Chip Human Genome UI33 Set," (Data Sheet) retrieved May 21, 2003 from Affymetrix Official Site website: http://www.affymetrix.com; 4 pages.
Akaike, H., "A new look at the statistical model identification," IEEE Transactions on Automatic Control (1974) 19(6): 716-723.
Ambroise et al., "Selection bias in gene extraction on the basis of microarray geneexpression data," Proc. Nat'l Acad. Sci. USA 99(10): 6562-66 (2002).
Angus et al., "Epidemiology of severe sepsis in the United States: analysis of incidence, outcome, and associated costs of care," Crit Care Med. 29(7): 1303-1310 (2001).
Anonymous, "The Nomenclature of Lipids (Recommendations 1976)" IUPAC-IUB Commission on Biochemical Nomenclature; Biochem J. (1978) 171(1): 21-35.
Anthony et al., "Rapid diagnosis of bacteremia by universal amplification of 23S ribosomal DNA followed by hybridization to an oligonucleotide array," J. Clin. Microbiol. 38(2): 781-788 (2000).
Aoyama N., "Characteristics and problems of instructive reaction system H2O2—POD Series", Rinsho Kensa/Journal of Medical Technology (1997) 41: 1014-1019.
Asadullah et al., "Immunodepression Following Neurosurgical Procedures," Crit Care Med 23(12):1976-1983 (1995).
Balci et al., "Usefulness of procalcitonin for diagnosis of sepsis in the intensive care unit", Crit Care (2003); 7:85-90 and Erratum.
Barth et al., "Peaks of Endogenous G-CSF Serum Concentrations are followed by an Increase in Respiratory Burst Activity of Granulocytes in Patients with Septic Shock," Cytokine, 17:275-284 (2002).
BD Cytometric Bead Array (CBA), 2004, "Human Inflammation Kit Instruction manual", BD Biosciences. Kit Instruction Manual, BD Biiosciences.
Beloborodova et al., 2000, "Small molecules originating from microbes (SMOM) and their role in microbes-host relationship," Microb. Ecol. Health and Disease; 12:12-21.
Beutler et al., "From phenomenon to phenotype and from phenotype to gene: Forward genetics and the problem of sepsis," J Infect Dis. 187(Suppl. 2):S321-326 (2003).

Bone et al., "Definitions for Sepsis and Organ Failure," Critical Care Medicine 20(6): 724-726 (1992).
Bozza et al., "Beyond sepsis pathophysiology with cytokines: what is their value as biomarkers for disease severity?" Mem Inst Oswaldo Cruz, (2005) 100(1):271-221.
Bright el al., "Rapid typing of bacteria using matrix-assisted laser desorption ionization time-of-flight mass spectrometry and pattern recognition software," J Microb Methods 48:127-138 (2002).
Brunkhorst et al., "Procalcitonin for early diagnosis and differentiation of SIRS, sepsis, severe sepsis, and septic shock", Intens Care Med. (2000) 26(Suppl 2):S148-152.
Brunkhorst et al., "Diagnostic approach to sepsis—State of the art," Zentralblatt für Chirurgie; 127(3):165-173 (2002).
Bulger et al., "Lipid mediators in the pathophysiology of critical illness", Crit Care Med. (2000) 28(4 Suppl):N27-N36.
Butler, J. E., "The amplified ELISA: Principles of and applications for the comparative quantitation of class and subclass antibodies and the distribution of antibodies and antigens in biochemical separates", Meth Enzymol. (1981) 73: 482-523.
Calandra, T., "Pathogenesis of Septic Shock: Implications for Prevention and Treatment", Chemother. (2001) 13(1):173-180.
Cariou et al., "The era of genomics: impact on sepsis clinical trial design," Crit. Care Med. 30(Suppl.):S341-S348 (2002).
Carraway et al., "Differential Expression of Arginase and iNOS in the Lung in Sepsis," Exp. Lung Res., 24(3):253-268 (1998).
Chan E. "Integrating transcriptomics and proteomics." Genomics & Proteomics, (2006) available online from www.genpromag.com, pp. 1-5.
Cheadle, "The Human Leukocyte Antigens and Their Relationship to Infection," Am J Surgery 165 (2A Suppl):75S-81S (1993).
Chen et al., „Study of tetra-substituted amino aluminum phthalocyanine as a new red-region substrate for the fluorometric determination of peroxidase and hydrogen peroxide,Analytica Chimica Acta (2001) 434(1): 51-58.
Cheung et al., "Natural variation in human gene expression assessed in lymphoblastoid cells." Nat Genet. (2003) 33(3):422-425.
Chinnaiyan et al., "Molecular signatures of sepsis: Multiorgan gene expression profiles of systemic inflammation," Am J Pathol. 159(4):1199-1209 (2001).
Christie, W.W., "Phosphatidylcholine and Related Lipids: Structure, Occurrence, Biochemistry and Analysis," Scottish Crop Research Institute (and Mylnefield Lipid Analysis), Invergowrie, Dundee (DD2 5DA), Scotland (Feb. 6, 2008).
Cobb et al., 2002, "Sepsis gene expression profiling: murine splenic compared with hepatic responses determined by using complementarv DNA microarravs," Crit. Care Med. 30(12):2711-2721.
Creighton et al., "Expression of matrix metalloproteinase 9 (MMP-9/gelatinase B) in adenocarcinomas strongly correlated with expression of immune response genes," In Silico Biol. 3(3):301-311 (2003).
Dalluge, "Mass spectrometry for direct determination of proteins in cells: applications in biotechnology and microbiology," Fresenius J Anal Chem. 366:701-11 (2000).
Das, Undurti., "Role of lipids in sepsis", Crit Care Shock, Indonesian Soc of Crit Care Med. (2004) 7(2):87-92.
Das, Undurti., "Can Sepsis and Other Critical Illnesses be Predicted and Prognosticated?", Advances in Sepsis, 5(2):52-59 (2006).
De Bont et al., "Plasma IL-8 and IL-6 Levels can be used to Define a Group of Low Risk of Septicaemia Among Cancer Patients with Fever and Neurtopenia," Brit J Haematol. 107:375-380 (1999).
Desborough et al., "The Stress Response to Trauma and Surgery," Br. J. Anaesth, 85:109-17 (2000).
Ditschkowski et al., "HLA-DR Expression and Soluble HLA-DR Levels in Septic Patients after Trauma," Ann Surg. 229(2):246-254 (1999).
Døllner et al., 2001, "Early diagnostic markers for neonatal sepsis: Comparing C-reactive protein, interleukin-6,soluble tumour necrosis factor receptors and soluble adhesion molecules," J Clin Epidemiol; 54(12): 1251-1257.
Drobnik et al., 2003, "Plasma ceramide and lysophosphatidylcholine inversely correlate with mortality in sepsis patients," J Lipid Res; 44(4):754-761.

(56) References Cited

OTHER PUBLICATIONS

Dudoit et al., "Comparison of discrimination methods for the classification of tumors using gene expression data", JASA (2002) 97: 77-87.

Ernst et al., "Three Genes for the Human High Affinity Fc Receptor for IgG (FcγRI) Encode Four Distinct Transcription Products," J Biol. Chem., 267(22):15692-15700 (1992).

Feezor et al., 2003, "Molecular Characterization of the Acute Inflammatory Response to Infections with GramNegative versus Gram-Positive Bacteria," Infect Immun; 71(10):5803-13.

Ferreira et al., "Serial Evaluation of the SOFA score to predict outcome in critically ill patients", Jama (2002) 286: 1754-1758.

Fischer et al., "CD64 Surface Expression on Neutrophils is Transiently Upregulated in Patients with Septic Shock," Int Care Med., 27(12):1848-1852 (2001).

Fung et al., 2002, "ProteinChip® Clinical Proteomics: Computational Challenges and Solutions," Biotechniques; 32 Suppl:S34-S41.

Gagnon et at., "Endoplasmic reticulum-mediated phagocytosis is a mechanism of entry into macrophages," Cell 110:119-131 (2002).

Gaut et al., 2001, "Neutrophils employ the myeloperoxidase system to generate antimicrobial brominating and chlorinating oxidants during sepsis," Proc Natl Acad Sci USA; 98(21):11961-11966.

GenBank Locus AY442689, "Mus musculus osmosensing scaffold for MEKK3 mRNA, complete cds." (2003) from www.ncbi.nlm.nih.gov; 2 pages.

GenBank Locus NM_001966, *Homo sapiens* enoyl-Coenzyme A, hydratase/3-hydroxyacyl Coenzyme A dehydrogenase (EHHADH), mRNA. from www.ncbi.nlm.nih.gov, 4 pages.

GenBank Locus NM_004139, *Homo sapiens* lipopolysaccharide binding protein (LBP), mRNA. from www.ncbi.nlm.nih.gov, 5 pages.

Genbank GI:13543892, "*Homo sapiens* Matrix Metallopeptidase 9 (gelatinase B, 92kDa Gelatinase, 92kDa Type IV Collagenase), mRNA (cDNA Clone MGC:I2688 IMAGE:4054882)," Complete CDS—3 pages.

Genbank NM_000566 [GI:24431940], Oct. 31, 2002, *Homo sapiens* c fragment of IgG, high affinity Ia, receptor (CD64) (FCGRIA), mRNA, pp. 1-4, downloaded from http://www.ncbi.nlm.nih.gov/entrez/viewer.fcgi?db~nuccore&id~24431940.

Genbank NM_001172 [GI: 1094711 O], Oct. 23, 2000, *Homo sapiens* arginase, type II (ARG2), nuclear gene encoding mitochondrial protein, mRNA, 3 pages, downloaded from http://www.ncbi.nlm.nih.gov/entrez/viewer.fcgi?val~ 10947110.

Giannoudis et al., "Stimulation of Inflammatory Markers after Blunt Trauma," Brit J Surg. 85:986-990 (1998).

Groeneveld et al., "Circulating inflammatory mediators in patients with fever: predicting bloodstream infection," Clin Diag Lab Immunol. 8(6): 1189-1195 (2001).

Hagberg, "From magnetic resonance spectroscopy to classification of tumors: a review of pattern recognition methods," NMR Biomed. 11:148-156 (1998).

Harbarth et al., 2001, "Diagnostic value of procalcitonin, interleukin-6, and interleukin-8 in critically ill patients admitted with suspected sepsis," Am J Respir Crit Care Med; 164(3):396-402.

Hastie et al., The Elements of Statistical Learning (Springer-Verlag 2001); TOC, 16 pages.

Healy, "New and emerging therapies for sepsis," Annuls Pharmacother. 36:648-654 (2002).

Hecker et al., "Inhibition of Arginase by NG-hydroxy-L-arginine in Alveolar Macrophages: Implications for the Utilization of L-Arginine for Nitric Oxide Synthesis," FEBS Letters, 359:251-254 (1995).

Hey et al., "Nitric Oxide Synthase Activity is Inducible in Rat, but not Rabbit Alveolar Macrophages, with a Concomitant Reduction in ArginaseActivity," Naunyn Schmiedebergs Arch Pharmacol., 351(6):651-659 (1995).

Hirayama et al., "Concentrations of Tluombopoietin in Bone Marrow in Normal Subjects and in Patients With Idiopathic Thrombocytopenic Purpura, Aplastic Anemia, and Essential Thrombocythemia Correlate With Its mRNA Expression of Bone Marrow Stromal Cells." Blood, 92:46-52, (1998).

Holmes et al., "Genetic Polymorphisms in Sepsis and Septic Shock: Role in Prognosis and Potential for Therapy", Chest, (2003) 124: 1103-1115.

Hoshikawa et al., "Hypoxia induces different genes in the lungs of rats compared with mice." Physiol Genomics. (2003) 12(3):209-19.

IUPAC-IUB Commission on Biochemical Nomenclature, "The Nomenclature of Lipids", Eur J Biochem. (1977) 79: 11-21.

IUPAC-IUB Commission on Biochemical Nomenclature; "The Nomenclature of Lipids", Mol Cell Biochem. (Oct. 7, 1977) 17(3): 157-171.

Jackson et al., "Lysophospholipid acyltransferases in monocyte inflammatory responses and sepsis", Immunobiol. (2004) 209(1-2):31-38.

Jacoby et al., "Platelet Activation and Function after Trauma," J. Trauma 51(4):639-47 (2001).

Joles et al. "Endothelial function in proteinuric renal disease", Kidney International (1999) 56(Suppl. 71):S57-S61.

Joyce et al., "Gene Expression Profile of antithrombotic protein C defines new mechanisms modulating inflammation and apoptosis." J Biol Chem. 276(14): 11199-11203 (2001).

Karzai et al., "Sepsis: definitions and diagnosis," Int'l J Crit Practice 95(Suppl.): 44-48 (1998).

Kiba et al., "Flow-through Micro Sensor Using Immobilized Peroxidase with Chemiluminometric FIA System for Determinning Hydrogen Peroxide", Analytical Science (2003) 19(6): 823-827.

Kinasewitz et al., Universal changes in biomarkers of coagulation and inflammation occur in patients with severe sepsis, regardless of causative micro-organism, Crit Care, (2004), 8(2):R82-R90.

Kishimoto et al., "An Enzymatic Assay for Lysophosphatidylcholine concentration in human serum and plasma", Clin Biochem. (2002) 35(5):411-416.

Knaus et al., "APACHE II: a severity of disease classification system," Crit Care Med. (1985) 13(10):818-829.

Knaus et al., "The Apache III Prognostic System—Risk Prediction of Hospital Morality for Critically Ill Hospitalized Adults," Chest 100 (6):1619-1636 (1991).

Küster et al., 1998, "Interleukin-I receptor antagonist and interleukin-6 for early diagnosis of neonatal sepsis 2 days before clinical manifestation," Lancet 352(9136):1271-1277.

Lakhani et al., "Toll-like receptor signaling in sepsis", Curr. Opin. Pediatr. (2003) 15(3):278-282.

Lam et al., "Time course of early and late changes in plasma DNA in trauma patients," Clin. Chem. 49(8): 1286-1291 (2003).

Layseca-Espinosa et al., "Expression of CD64 as a Potential Marker of Neonatal Sepsis," Pediatr Allergy Immunol., 13(5):319-327 (2002).

Le Gall et al., "A simplified acute physiology score for ICU patients", Crit Care Med. (1984) 12(11): 975-977.

Le Gall et al., "A new Simplified Acute Physiology Score (SAPS II) based on a European/North American Multicenter Study", JAMA (1993) 270(24): 2957-2963.

Le Gall et al., "The Logistic Organ Dysfunction system. A new way to assess organ dysfunction in the intensive care unit. ICU Scrogin Group"; JAMA (1996) 276(10): 802-810.

Levy et al., "2001 SCCN/ESICM/ACCP/ATS/SIS International Sepsis Defnitions Conference," Intensive Care Med. 29(4):530-538 (2003).

Liebman et al., (Eds.) "Pyrolysis and GC in Polymer Analysis", Chemical Data Systems; Marcel Dekker, Inc. (1985) TOC; 4 pages.

Lissauer et al., "Decreased Tysophosphatidylcholine levels are associated with sepsis compared to uninfected inflammation prior to onset of sepsis", J Surg Res. [No. 128.] (2007) 137(2):206.

Llewelyn et al., "Diagnosis of infection in sepsis," Intens Care Med. 27(Suppl 1):S10-S32 (2001).

Manjuck et al., "Decreased Response to Recall Antigens is Associated with Depressed Costimulatory Receptor Expression in Septic Critically Ill Patients," J Lab Clin Med. 135(2):153-160 (2000).

Marshall et al., "Multiple organ dysfunction score: a reliable descriptor of a complex clinical outcome", Crit. Care Med (1995) 23(10): 1638-1652.

(56) References Cited

OTHER PUBLICATIONS

Marshall et al., "Measures, markers, and mediators: Toward a staging system for clinical sepsis. A report from the Fifth Toronto Sepsis Roundtable, Toronto, Ontario, Canada, Oct. 25-26, 2000," Crit Care Med. 31(5):1560-1567 (2003).
Mehta, "Lysophosphatidylcholine: An Enigmatic Lysolipid", Am. J. Physiol. Lung Cell. Mol. Physiol., (2005) 289:L174-L175.
Members of the American College of Chest Physicians/Society of Critical Care Medicine Consensus Conference Committee, "American College of Chest Physicians/Society of Critical Care Medicine Consensus Conference: definitions for sepsis and organ failure and guidelines for the use of innovative therapies in sepsis," Crit Care Med. 20(6): 864-874 (1992).
Millili et al., "Predicting Surgical Outcome Using Bayesian Analysis," J Surg Res. 77:45-49 (1998).
Misaki H., "Biochemistry. Principle of supersensitive measuring method by enzyme cycling method", Kensa to gijutsu/Modern Medical Laboratory (1999) 27(8): 973-980.
Mitaka C., "Clinical laboratory differentiation of infectious versus non-infectious systemic inflammatory response syndrome", CI Chim Acta. (2005) 351(1-2):17-29.
Morgenthaler et al., "Detection of procalcitonin (PCT) in healthy controls and patients with local infection by a sensitive ILMA", Clin Lab. (2002) 48(5-6): 263-270.
Müller et al., "Calcitonin Precursors are Reliable Markers of Sepsis in a Medical Intensive Care Unit," Crit Care Med. 4:977-983 (2000).
Muret et al., "Ex vivo T-lymphocyte derived cytokine production in SIRS patients is influenced by experimental procedures", Shock 13(3):169-174 (2000).
Nadel, "Helping to understand studies examining genetic susceptibility to sepsis," Clin Exp Immunol. 127: 191-192 (2002).
Natanson et al., "The sirens' songs of confirmatory sepsis trials: selection bias and sampling error," Crit. Care Med. 26(12):1927-1931 (1998).
Nupponen et al., "Neutrophil CD11b Expression and Circulating Interleukin-8 as Diagnostic Markers for Early-Onset Neonatal Sepsis," Pediatrics 108(1):1-6 (2001).
Oberholzer et al., "Sepsis syndromes: understanding the role of innate and acquired immunity," Shock 16(2): 83-96 (2001).
Oczenski, "HLA-DR as a Marker for Increased Risk for Systemic Inflammation and Septic Complications after Cardiac Surgery," Int Care Med. 29:1253-1257 (2003).
Paleologos et al. "Spectrofluorometric Determination of Vanadium Based on the Formation of a Ternary Complex between Vanadium, Peroxides, and 2-alpha-pyridylthioquinaldinamide. Application to the determination of Hydrogen Peroxide and Peroxy Acids", Anal Chem. (2002) 74(1): 100-106.
Pappas et al., "Determination of hydrogen peroxide by using a flow injection system with immobilized peroxidase and long pathlenght capillary spectrophotometry", Analytica Chimica Acta (2002) 455(2): 305-313.
Paterson et al., Sepsis and the systemic inflammatory response syndrome, J R Coll. Surg Edinb. 45:178-182 (2000).
Pathan et al., 2003, "The complexity of the inflammatory response to the meningococcal sepsis revealed by gene expression profiling using cDNA microarrays," Crit. Care Med; 31(12 Suppl.): A47 (Abstract).
Perry et al., "Is Low Monocyte HLA-DR Expression Helpful to Predict Outcome in Severe Sepsis?" Int Care Med. 29:1245-1252 (2003).
Petricoin et al., "Use of proteomic patterns in serum to identify ovarian cancer," Lancet 359: 572-577 (2002).
Presto Elgstoen et al., 2001, "Potential of capillary electrophoresis, tandem mass spectrometry and coupled capillary electrophoresis-tandem mass spectrometry as diagnostic tools," J. Chromatogr. A; 914: 265-275.
Pugin, et al., "Human Neutrophils Secrete Gelatinase B In Vitro and In Vivo in Response to Endotoxin and Proinflammatory Mediators", Am J Resp Cell Molec Biol. (1999) 20(3):458-464.
Punyadeera et al., "A biomarker panel to discriminate between systemic inflammatory response syndrome and sepsis and sepsis severity", J Emerg Trauma Shock. (2010) 3(1):26-35.
Rangel-Frausto et al., "The natural history of the systemic inflammatory response syndrome (SIRS)," J Am Med Ass'n. 273:117-123 (1995).
Rangel-Frausto et al., "The Dynamics of Disease Progression in Sepsis: Markov Modeling Describing the Natural History and the Likely Impast of Effective Antisepsis Agents," Clinical Infectious Diseases 27:185-190 (1998).
Read et al., "Toll receptors and sepsis", Curr. Opin. Crit. Care (2001) 7(5):371-375.
Reinhart et al., "Markers of endothelial damage in organ dysfunction and sepsis," Crit Care Med. 30(5): S302-S312 (2002).
Rixen et al., "'Sepsis/SIRS', Physiologic Classification, Severity Stratification, Relation to Cytokine Elaboration and Outcome Prediction in Posttrauma Illness," J. Trauma 41 (4):581-598 (1996).
Ross et al., "Classification of pediatric acute lymphblastic leukemia by gene expression profiling", Blood (2003) 102(8):2951-2959.
Roumen et al., "Scoring systems and blood lactate concentrations in relation to the development of Adult Respiratory Distress Syndrome and Multiple Organ Failure in severely traumatized patients," J. Trauma 35(3):349-355 (1993).
Sage, L., "Research Profile Digging for disease markers of sepsis", J. Proteome Res. (2006) 5(11):2885.
Sambrook et al., Molecular Cloning (3rd Ed., Cold Spring Harbor Laboratory Press 2001); TOC, 20 pages.
Sauaia et al., "Early Predictors of Postinjury Multiple Organ Failure," Arch. Surgery 129(1):39-45 (1994).
Selberg et al., "Discrimination of Sepsis and Systematic Inflammatory Response Syndrome by Determination of Circulating Plasma Concentrations of Procalcitonin, Protein Complement 3a, and Interieukin-6," Crit Care Med. 28(8):2793-2798 (2000).
Shoemaker et al., "Recent developments in DNA microarrays," Curr Opin Microbial. 5:334-337 (2002).
Slotman et al., "Multivariate Regression Modeling for the Prediction of Inflammation, Systemic Pressure, and End-organ Function in Severe Sepsis," Shock 8(3):225-231 (1997).
Slotman, "Prospectively Validated Prediction of Physiologic Variables and Organ Failure in Septic Patents: The Systemic Mediator Associated Response Test (SMART)," Crit Care Med. 30 (5):1035-1045 (2002).
Slotman, "Prospectively validated predictions of shock and organ failure in individual septic surgical patients: the Systemic Mediator Associated Response Test," Crit Care 2000 4(5):319-326 (2000).
Smith et al., 2004, "Impact of immunomodulatory oligodeoxynucleotides on cytokine production in the lipopolvsaccharide-stimulated human whole blood model," Surgery 136(2):464-472.
Spittler et al., "Relationship Between Interleukin-6 plasma Concentration in Patients with Sepsis, Monocyte Phenotype, Monocyte Phagocytic Properties, and Cytokine Production," Clin. Infect Dis., 31(6):1338-1342 (2000).
Stordeur et al., "Cytokine mRNA quantification by real-time PCR," J Immunol Methods 259:55-64 (2002).
Suzuki et al., 2000, "Comprehensive gene expression profile ofLPS-stimulated human monocytes by SAGE," Blood; 96(7):2584-2591.
Schwarz G., "Estimating the dimension of a model," Annals of Statistics (1978) 6(2): 461-464.
Takala et al., "Systemic inflammatory response syndrome without systemic inflammation in acutely ill patients admitted to hospital in a medical emergency," Clin Sci. 96:287-295 (1999).
Takala et al., "Markers of inflammation in sepsis," Annuls Med. 34(7-08):614-23 (2002).
Tan et al., "The gene expression fingerprint of human heart failure," Proc. Nat'l Acad Sci USA 99:11387-92 (2002).
Tang et al., "Accuracy of procalcitonin for sepsis diagnosis in critically ill patients: Systematic review and meta-analysis", Lancet Infect Dis. (2007) 7(3):210-217.
Taniguchi et al., "Change in the Ratio of Interleukin-6 to Interleukin-10 Predicts a Poor Outcome in Patients with Systemic Inflammatory Response Syndrome," Crit Care Med. 27(7):1262-1264 (1999).

(56) References Cited

OTHER PUBLICATIONS

Tárnok et al., "Cytometric bead array to measure six cytokines in twenty-five microliters of serum," Clin. Chem. 49(6):1000-1002 (2003).
Thisted R.A., "What is a P-value?" May 1998, available from http://www.stat.uchicago.edu; pp. 1-6.
Titus, "Latest assay opens another sepsis frontier," College of American Pathologists, CAP Today, at http://www.cap.org/apps/docs/cap_today/feature_stories/sepsis.html (posted May 2003); 5 pages.
Uettwiller-Geiger, "Clinical Applications of Procalcitonin (PCT)", J Clin Ligand Assay (2007) 30:20-28.
Van Den Berk et al., "Low HLA-DR Expression on Monocytes as a Prognostic Marker for Bacterial Sepsis after Liver Transplantation," Transplantation 63(12):1846-1848 (1997).
Van Leeuwen et al., "Lipoprotein metabolism in patients with severe sepsis," Crit. Care Med. 31(5):1359-1366 (2003).
Venables et al., "Modern Applied Statistics with S-Plus," (4th Ed., Springer 2002); TOC, 7 pages.
Ventetuolo et al., "Biomarkers: diagnosis and risk assessment in sepsis", Clin Chest Med. (2008) 29(4):591-603.
Vincent et al., "The Sepsis Text," (Carlet et al. Eds., Kluwer Academic Publishers 2002); TOC, 4 pages.
Vockley et al., "Cloning and Characterization of Human Type II Arginase Gene," Genomics, 38(2):118-123 (1996).
Voller A., 1978, "The Enzyme Linked Immunosorbent Assay (ELISA)(theory, technique and applications)", Ric Clin Lab. (1978) 8(4): 289-298.
Voller et al., "Enzyme immunoassays with special reference to ELISA Techniques", J Clin Pathol. (1978) 31: 507-520.
Von Landenberg et al., "New approaches in the diagnosis of sepsis," Isr Med Assoc J. 3: 439-442 (2001).
Wagner et al., "Daily Prognostic Estimates for Critically Ill Adults in Intensive Care Units: Results from a Prospective, Multicenter, Inception Cohort Analysis,"• Crit Care Med. 22(9): 1359-1372 (1994).
Wagner et al., "Interpretation of static time-of-flight secondary ion mass spectra of adsorbed protein films by multivariate pattern recognition," Anal Chem. 74: 1824-35 (2002).
Wakefield et al., "Changes in Major Histocompatibility Complex Class II Expression In Monocytes and T cells of Patients Developing Infection after Surgery,"• Brit J Surgery 80(2):205-209 (1993).
Wakefield et al., "Polymorphonuclear Leukocyte Activation. An Early Marker of the Postsurgical Sepsis Response," Arch Surg. 128:390-395 (1993).
Wakefield et al., "Surgery and the Release of a Neutrophil FcGamma Receptor," Am J Surg. 170:277-284 (1995).
Wang et al., "Co-Induction of Arginase and Nitric Oxide Synthase in Murine Macrophages Activated by Lipopolysaccharide," Biochem Biophys Res Comm. 210(3):1009-1016 (1995).
Wang et al., 1998, "Tissue coexpression of LBP and CD14 mRNA in a mouse model of sepsis," J. Surg. Res. 76(1):67-73.
Wang et al., "Lipid Unites Disparate Syndromes of Sepsis", Nature Med. (2004) 10(2):124-125.
Weglöhner et al., "Isolation and characterization of serum procalcitonin from patients with sepsis," Peptides 22:2099-2103 (2001).
Wei et al., "Desorption-ionization mass spectrometry on porous silicon," Nature 399:243-246 (1999).
Weigand et al., 1999, "Gene Expression Pattern in Human Monocytes as a Surrogate Marker for Systemic Inflammatory Response Syndrome (SIRS)," Mol Med; 5(3):192-202.
Weinstein et al., "The clinical significance of positive blood cultures in the 1990s: a prospective comprehensive evaluation of the microbiology, epidemiology, and outcome of bacteremia and fungemia in adults," Clin Infect Diseases. 24:584-602 (1997).
Weirich et al., "Neutrophil CD11b Expression as a Diagnostic Marker for Early-Onset Neonatal Infection," J Pediat. 132 (SS.3, 1):445-451 (1998).
Weiss et al., "Filgrastim (RHG-CSF) Related Modulation of the Inflammatory Response in Patients at Risk of Sepsis or with Sepsis," Cytokine, 8(3):260-265 (1996).
Wert et al., 2000, "Increased metalloproteinase activity, oxidant production, and emphysema in surfactant protein D gene-inactivated mice," Proc. Natl. Acad. Sci. USA 97(11):5972-5977.
Yan et al., "Therapeutic Effects of Lysophosphatidylcholine in Experimental Sepsis", Nat Med. (2004) 10(2): 161-167.
Yang et al., "Tissue prostanoids as biomarkers for chemoprevention of colorectal neoplasia: correlation between prostanoid synthesis and clinical response in familial adenormatous polyposis", Prostagl & other Lipid Mediat. (2000) 60:83-96.
Yao et al., "Changes in Toll-like Receptor 2 and 4 Gene Expression in Vital Organs in Septic Rats and Their Regulation Mechanisms", Chin. Crit. Care Med. (2003) 15(11):646-650.
Yassen et al., "Matrix metalloproteinase-9 concentrations in critically ill patients", Anaesthesia, (2001) 56(8):729-732.
Zhang et al., "Optimal Conditions and sample storage for the determination of $H_2O_2$ in marine waters by the scopoletin-horseradish peroxidase fluorometric method", Talanta (1999) 48(5):1031-1038.
Zhang et al., 2001, "Recursive partitioning for tumor classification with gene expression microarray data," Proc Natl Acad Sci U S A; 98(12):6730-6735.
Zhao et al., "Human endothelial cell response to gram-negative lipopolysaccharide assessed with cDNA microarrays," Am J Physiol Cell Physiol. 281(5):C1587-1595 (2001).
Zhu et al., 1997, "Effects of prolactin and metoclopramide on macrophage cytokine gene expression in late sepsis," Cytokine 9(6):437-446.
Zou, et al., "Application of cDNA microarrays to generate a molecular taxonomy capable of distinguishing between colon cancer and normal colon," Oncogene 21:4855-4862 (2002).
Zweigner et al., "High concentrations of lipopolysaccharide-binding protein in serum of patients with severe sepsis or septic shock inhibit the lipopolysaccharide response in human monocytes", Blood, (2001) 98(13):3800-3808.
International Search Report and Written Opinion dated May 24, 2007 for Application No. PCT/US2006/014241.
European Supplemental Search Report dated Apr. 7, 2010 for EP Application No. 06740954.
B.R.A.H.M.S. GmbH; PTAB Petition for Post-Grant Review dated Apr. 27, 2016 of U.S. Pat. No. 9,091,698, issued Jul. 28, 2015—PGR2016-00018; 84 pages.
B.R.A.H.M.S. GmbH; Exhibit 1002—Declaration of Prof. Dr. med. Philipp Schuetz, MPH signed Feb. 23, 2016; 106 pages.
Becton, Dickinson & Co.; PTAB Preliminary Response dated Aug. 3, 2016—PGR2016-00018; 91 pages.
PTAB Decision Institution of Post Grant Review dated Nov. 2, 2016—PGR2016-00018; 33 pages.
Muller Kobold et al., "Leukocyte activation in sepsis; correlations with disease state and mortality," Intensive Care Med. (2000) 26(7):883.
PTAB Joint Motion to Terminate/Request to File Settlement Agreement dated Mar. 8, 2017—PGR2016-00018, 5 pages.
PTAB Order Termination of the Proceeding dated Mar. 17, 2017—PGR2016-00018; 4 pages.

\* cited by examiner

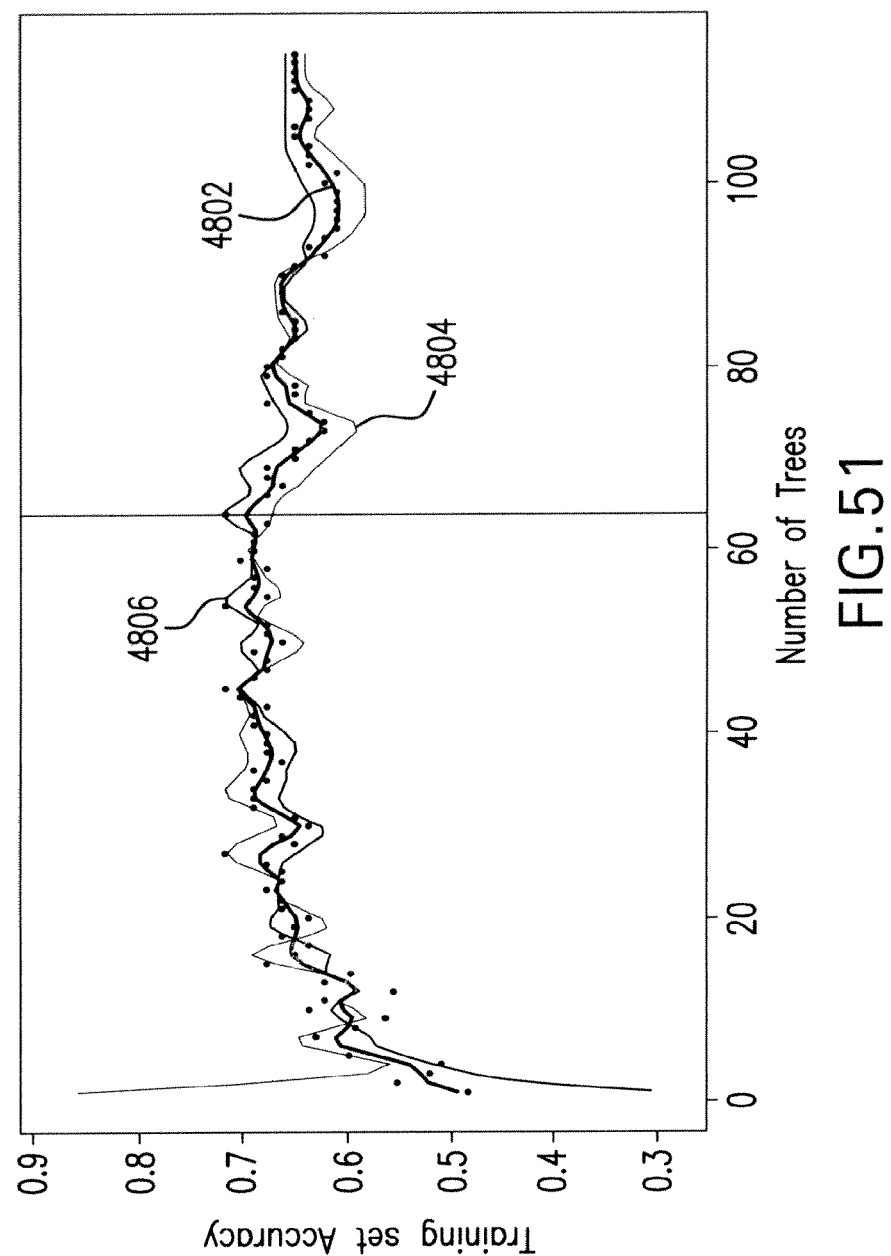

DIAGNOSIS OF SEPSIS

CROSS-REFERENCE TO RELATED APPLICATIONS

This application is a continuation of U.S. patent application Ser. No. 14/850,933, filed Sep. 10, 2015, now patented as U.S. Pat. No. 10,443,099, which is a continuation of U.S. patent application Ser. No. 13/965,038, filed Aug. 12, 2013, now abandoned, which is a continuation of U.S. patent application Ser. No. 12/776,245, filed May 7, 2010, now abandoned, which is a continuation of U.S. patent application Ser. No. 11/404,744, filed Apr. 14, 2006, now patented as U.S. Pat. No. 7,767,395, which claims the benefit of U.S. Provisional Patent Application No. 60/671,620, filed Apr. 15, 2005, and U.S. Provisional Patent Application No. 60/674,046, filed Apr. 22, 2005, each of which is hereby incorporated by reference in its entirety into this application.

1. FIELD OF THE INVENTION

The present invention relates to methods and compositions for diagnosing or predicting sepsis and/or its stages of progression in a subject. The present invention also relates to methods and compositions for diagnosing systemic inflammatory response syndrome in a subject.

2. BACKGROUND OF THE INVENTION

Early detection of a disease condition typically allows for a more effective therapeutic treatment with a correspondingly more favorable clinical outcome. In many cases, however, early detection of disease symptoms is problematic due to the complexity of the disease; hence, a disease may become relatively advanced before diagnosis is possible. Systemic inflammatory conditions represent one such class of diseases. These conditions, particularly sepsis, typically, but not always, result from an interaction between a pathogenic microorganism and the host's defense system that triggers an excessive and dysregulated inflammatory response in the host. The complexity of the host's response during the systemic inflammatory response has complicated efforts towards understanding disease pathogenesis (reviewed in Healy, 2002, Annul. Pharmacother. 36:648-54). An incomplete understanding of the disease pathogenesis, in turn, contributes to the difficulty in finding useful diagnostic biomarkers. Early and reliable diagnosis is imperative, however, because of the remarkably rapid progression of sepsis into a life-threatening condition.

The development of sepsis in a subject follows a well-described course, progressing from systemic inflammatory response syndrome ("SIRS")-negative, to SIRS-positive, and then to sepsis, which may then progress to severe sepsis, septic shock, multiple organ dysfunction ("MOD"), and ultimately death. Sepsis may also arise in an infected subject when the subject subsequently develops SIRS. "Sepsis" is commonly defined as the systemic host response to infection with SIRS plus a documented infection. "Severe sepsis" is associated with MOD, hypotension, disseminated intravascular coagulation ("DIC") or hypoperfusion abnormalities, including lactic acidosis, oliguria, and changes in mental status. "Septic shock" is commonly defined as sepsis-induced hypotension that is resistant to fluid resuscitation with the additional presence of hypoperfusion abnormalities.

Documenting the presence of the pathogenic microorganisms that are clinically significant to sepsis has proven difficult. Causative microorganisms typically are detected by culturing a subject's blood, sputum, urine, wound secretion, in-dwelling line catheter surfaces, etc. Causative microorganisms, however, may reside only in certain body microenvironments such that the particular material that is cultured may not contain the contaminating microorganisms. Detection may be complicated further by low numbers of microorganisms at the site of infection. Low numbers of pathogens in blood present a particular problem for diagnosing sepsis by culturing blood. In one study, for example, positive culture results were obtained in only 17% of subjects presenting clinical manifestations of sepsis (Rangel-Frausto et al., 1995, JAMA 273:117-123). Diagnosis can be further complicated by contamination of samples by non-pathogenic microorganisms. For example, only 12.4% of detected microorganisms were clinically significant in a study of 707 subjects with septicemia (Weinstein et al., 1997, Clinical Infectious Diseases 24:584-602).

The difficulty in early diagnosis of sepsis is reflected by the high morbidity and mortality associated with the disease. Sepsis currently is the tenth leading cause of death in the United States and is especially prevalent among hospitalized patients in non-coronary intensive care units (ICUs), where it is the most common cause of death. The overall rate of mortality is as high as 35%, with an estimated 750,000 cases per year occurring in the United States alone. The annual cost to treat sepsis in the United States alone is on the order of billions of dollars.

A need, therefore, exists for a method of diagnosing sepsis, using techniques that have satisfactory specificity and sensitivity performance, sufficiently early to allow effective intervention and prevention.

3. SUMMARY OF THE INVENTION

The present invention relates to methods and compositions for diagnosing sepsis, including the onset of sepsis, in a test subject. The present invention also relates to methods and compositions for predicting sepsis in a test subject.

The present invention further relates to methods and compositions for diagnosing or predicting stages of sepsis progression in a test subject. The present invention still further relates to methods and compositions for diagnosing systemic inflammatory response syndrome (SIRS) in a test subject.

In one aspect, the present invention provides a method of predicting the development of sepsis in a test subject at risk for developing sepsis. This method comprises evaluating whether a plurality of features in a biomarker profile of the test subject satisfies a value set, wherein satisfying the value set means that the test subject will develop sepsis with a likelihood that is determined by the accuracy of the decision rule to which the plurality of features are applied in order to determine whether they satisfy the value set. In some embodiments, the accuracy of the decision rule is at least 60%. Therefore, correspondingly, the likelihood that the test subject will develop sepsis when the plurality of features satisfies the value set is at least 60%.

Yet another aspect of the invention comprises a method of diagnosing sepsis in a test subject. These methods comprise evaluating whether a plurality of features in a biomarker profile of the test subject satisfies a value set, wherein satisfying the value set predicts that the test subject has sepsis with a likelihood that is determined by the accuracy of the decision rule to which the plurality of features are applied in order to determine whether they satisfy the value set. In some embodiments, the accuracy of the decision rule is at least 60%. Therefore, correspondingly, the likelihood that the test subject has sepsis when the plurality of features satisfies the value set is at least 60%.

In a particular embodiment, the biomarker profile comprises at least two features, each feature representing a feature of a corresponding biomarker listed in column four or five of Table 30. In one embodiment, the biomarker profile comprises at least two different biomarkers listed in column four or five of Table 30. In such an embodiment, the biomarker profile can comprise a respective corresponding feature for the at least two biomarkers. Generally, the at least two biomarkers are derived from at least two different genes. In the case where a biomarker in the at least two different biomarkers is listed in column four of Table 30, the biomarker can be, for example, a transcript made by the listed gene, a complement thereof, or a discriminating fragment or complement thereof, or a cDNA thereof, or a discriminating fragment of the cDNA, or a discriminating amplified nucleic acid molecule corresponding to all or a portion of the transcript or its complement, or a protein encoded by the gene, or a discriminating fragment of the protein, or an indication of any of the above. Further still, the biomarker can be, for example, a protein listed in column five of Table 30, or a discriminating fragment of the protein, or an indication of any of the above. Here, a discriminating molecule or fragment is a molecule or fragment that, when detected, indicates presence or abundance of the above-identified transcript, cDNA, amplified nucleic acid, or protein. In accordance with this embodiment, the biomarker profiles of the present invention can be obtained using any standard assay known to those skilled in the art, or in an assay described herein, to detect a biomarker. Such assays are capable, for example, of detecting the products of expression (e.g., nucleic acids and/or proteins) of a particular gene or allele of a gene of interest (e.g., a gene disclosed in Table 30). In one embodiment, such an assay utilizes a nucleic acid microarray. In some embodiments, the biomarker profile comprises at least two different biomarkers from column four or five of Table 32. In some embodiments, the biomarker profile comprises at least 2, 3, 4, 5, 6, 7, 8, 9, 10, 11, 12, 13, 14, 15, 16, 17, 18, 19, 20, 21, 22, 23, 24, 25, 30, 35, 40, 45, or 50 different biomarkers from Table 30.

In a particular embodiment, the biomarker profile comprises at least two different biomarkers that each contain one of the probesets listed in column 2 of Table 30, biomarkers that contain the complement of one of the probesets of Table 30, or biomarkers that contain an amino acid sequence encoded by a gene that either contains one of the probesets of Table 30 or the complement of one of the probesets of Table 30. Such biomarkers can be, for example, mRNA transcripts, cDNA or some other nucleic acid, for example amplified nucleic acid, or proteins. The biomarker profile further comprises a respective corresponding feature for the at least two biomarkers. Generally, the at least two biomarkers are derived from at least two different genes. In the case where a biomarker is based upon a gene that includes the sequence of a probeset listed in Table 30, the biomarker can be, for example, a transcript made by the gene, a complement thereof, or a discriminating fragment or complement thereof, or a cDNA thereof, or a discriminating fragment of the cDNA, or a discriminating amplified nucleic acid molecule corresponding to all or a portion of the transcript or its complement, or a protein encoded by the gene, or a discriminating fragment of the protein, or an indication of any of the above. Further still, the biomarker can be, for example, a protein encoded by a gene that includes a probeset sequence described in Table 30, or a discriminating fragment of the protein, or an indication of any of the above.

Here, a discriminating molecule or fragment is a molecule or fragment that, when detected, indicates presence or abundance of the above-identified transcript, cDNA, amplified nucleic acid, or protein. In some embodiments, the biomarker profile comprises at least 2, 3, 4, 5, 6, 7, 8, 9, or 10 different biomarkers from any one of Table 31, 32, 33, 34, or 36.

In a particular embodiment, the biomarker profile comprises at least two different biomarkers listed in column three of Table 31. The biomarker profile further comprises a respective corresponding feature for the at least two biomarkers. Generally, the at least two biomarkers are derived from at least two different genes. The biomarker can be, for example, a transcript made by gene listed in Table 31, a complement thereof, or a discriminating fragment or complement thereof, or a cDNA thereof, or a discriminating fragment of the cDNA, or a discriminating amplified nucleic acid molecule corresponding to all or a portion of the transcript or its complement, or a protein encoded by the gene, or a discriminating fragment of the protein, or an indication of any of the above. Further still, the biomarker can be, for example, a protein encoded by a gened listed in column three of Table 31, or a discriminating fragment of the protein, or an indication of any of the above. Here, a discriminating molecule or fragment is a molecule or fragment that, when detected, indicates presence or abundance of the above-identified transcript, cDNA, amplified nucleic acid, or protein. In accordance with this embodiment, the biomarker profiles of the present invention can be obtained using any standard assay known to those skilled in the art, or in an assay described herein, to detect a biomarker. Such assays are capable, for example, of detecting the products of expression (e.g., nucleic acids and/or proteins) of a particular gene or allele of a gene of interest (e.g., a gene disclosed in Table 31). In one embodiment, such an assay utilizes a nucleic acid microarray.

In a particular embodiment, the biomarker profile comprises at least two different biomarkers that each contain one of the probesets listed in column 2 of Table 31, biomarkers that contain the complement of one of the probesets of Table 31, or biomarkers that contain an amino acid sequence encoded by a gene that either contains one of the probesets of Table 31 or the complement of one of the probesets of Table 31. Such biomarkers can be, for example, mRNA transcripts, cDNA or some other nucleic acid, for example amplified nucleic acid, or proteins. The biomarker profile further comprises a respective corresponding feature for the at least two biomarkers. Generally, the at least two biomarkers are derived from at least two different genes. In the case where a biomarker is based upon a gene that includes the sequence of a probeset listed in Table 31, the biomarker can be, for example, a transcript made by the gene, a complement thereof, or a discriminating fragment or complement thereof, or a cDNA thereof, or a discriminating fragment of the cDNA, or a discriminating amplified nucleic acid molecule corresponding to all or a portion of the transcript or its complement, or a protein encoded by the gene, or a discriminating fragment of the protein, or an indication of any of the above. Further still, the biomarker can be, for example, a protein encoded by a gene that includes a probeset sequence described in Table 31, or a discriminating fragment of the protein, or an indication of any of the above. Here, a discriminating molecule or fragment is a molecule or fragment that, when detected, indicates presence or abundance of the above-identified transcript, cDNA, amplified nucleic acid, or protein. In some embodiments, the biomarker profile comprises at least 2, 3, 4, 5, 6, 7, 8, 9, 10, 11, 12, 13, 14, 15, 16, 17, 18, 19, 20, 21, 22, 23, 24, 25, 30, 35, 40, 45, or 50 different biomarkers from Table 31.

In a particular embodiment, the biomarker profile comprises at least three features, each feature representing a feature of a corresponding biomarker listed in column 3 or four of Table I. In one embodiment, the biomarker profile comprises at least three different biomarkers listed in column three or four of Table I. In such an embodiment, the biomarker profile can comprise a respective corresponding feature for the at least three biomarkers. Generally, the at least three biomarkers are derived from at least three different genes listed in Table I. In the case where a biomarker in the at least three different biomarkers is listed in column three of Table I, the biomarker can be, for example, a transcript made by the listed gene, a complement thereof, a splice variant thereof, a complement of a splice variant thereof, or a discriminating fragment or complement of any of the foregoing, a cDNA of any of the forgoing, a discriminating fragment of the cDNA, or a discriminating amplified nucleic acid molecule corresponding to all or a portion of the transcript or its complement, or a protein encoded by the gene, or a discriminating fragment of the protein, or an indication of any of the above. Further still, the biomarker can be, for example, a protein listed in column four of Table I, or a discriminating fragment of the protein, or an indication of any of the above. Here, a discriminating molecule or fragment is a molecule or fragment that, when detected, indicates presence or abundance of the above-identified transcript, cDNA, amplified nucleic acid, splice-variant thereof or protein. In accordance with this embodiment, the biomarker profiles of the present invention can be obtained using any standard assay known to those skilled in the art, or in an assay described herein, to detect a biomarker. Such assays are capable, for example, of detecting the products of expression (e.g., nucleic acids and/or proteins) of a particular gene or allele of a gene of interest (e.g., a gene disclosed in Table I). In one embodiment, such an assay utilizes a nucleic acid microarray. In some embodiments, the biomarker profile comprises at least 2, 3, 4, 5, 6, 7, 8, 9, 10, 11, 12, 13, 14, 15, 16, 17, 18, 19, 20, 21, 22, 23, 24, 25, 30, 35, 40, 45, or 50 different biomarkers from Table I.

In a particular embodiment, the biomarker profile comprises at least three features, each feature representing a feature of a corresponding biomarker listed in column 3 or four of Table J. In one embodiment, the biomarker profile comprises at least three different biomarkers listed in column three or four of Table J. In such an embodiment, the biomarker profile can comprise a respective corresponding feature for the at least three biomarkers. Generally, the at least three biomarkers are derived from at least three different genes. In the case where a biomarker in the at least three different biomarkers is listed in column three of Table J, the biomarker can be, for example, a transcript made by the listed gene, a complement thereof, a splice variant thereof, a complement of a splice variant thereof, or a discriminating fragment or complement of any of the foregoing, a cDNA of any of the forgoing, a discriminating fragment of the cDNA, or a discriminating amplified nucleic acid molecule corresponding to all or a portion of the transcript or its complement, or a protein encoded by the gene, or a discriminating fragment of the protein, or an indication of any of the above. Further still, the biomarker can be, for example, a protein listed in column four of Table J, or a discriminating fragment of the protein, or an indication of any of the above. Here, a discriminating molecule or fragment is a molecule or fragment that, when detected, indicates presence or abundance of the above-identified transcript, cDNA, amplified nucleic acid, splice-variant thereof or protein. In accordance with this embodiment, the biomarker profiles of the present invention can be obtained using any standard assay known to those skilled in the art, or in an assay described herein, to detect a biomarker. Such assays are capable, for example, of detecting the products of expression (e.g., nucleic acids and/or proteins) of a particular gene or allele of a gene of interest (e.g., a gene disclosed in Table J). In one embodiment, such an assay utilizes a nucleic acid microarray. In some embodiments, the biomarker profile comprises at least 2, 3, 4, 5, 6, 7, 8, 9, 10, 11, 12, 13, 14, 15, 16, 17, 18, 19, 20, 21, 22, 23, 24, 25, 30, 35, 40 different biomarkers from Table J.

In a particular embodiment, the biomarker profile comprises at least three features, each feature representing a feature of a corresponding biomarker listed in column 3 or four of Table K. In one embodiment, the biomarker profile comprises at least three different biomarkers listed in column three or four of Table K. In such an embodiment, the biomarker profile can comprise a respective corresponding feature for the at least three biomarkers. Generally, the at least two or three biomarkers are derived from at least two or three different genes, respectively. In the case where a biomarker in the at least two or three different biomarkers is listed in column three of Table K, the biomarker can be, for example, a transcript made by the listed gene, a complement thereof, a splice variant thereof, a complement of a splice variant thereof, or a discriminating fragment or complement of any of the foregoing, a cDNA of any of the forgoing, a discriminating fragment of the cDNA, or a discriminating amplified nucleic acid molecule corresponding to all or a portion of the transcript or its complement, or a protein encoded by the gene, or a discriminating fragment of the protein, or an indication of any of the above. Further still, the biomarker can be, for example, a protein listed in column four of Table K, or a discriminating fragment of the protein, or an indication of any of the above. Here, a discriminating molecule or fragment is a molecule or fragment that, when detected, indicates presence or abundance of the above-identified transcript, cDNA, amplified nucleic acid, splice-variant thereof or protein. In accordance with this embodiment, the biomarker profiles of the present invention can be obtained using any standard assay known to those skilled in the art, or in an assay described herein, to detect a biomarker. Such assays are capable, for example, of detecting the products of expression (e.g., nucleic acids and/or proteins) of a particular gene or allele of a gene of interest (e.g., a gene disclosed in Table K). In one embodiment, such an assay utilizes a nucleic acid microarray. In some embodiments, the biomarker profile comprises at least 2, 3, 4, 5, 6, 7, 8, 9, 10 different biomarkers from Table K.

Although the methods of the present invention are particularly useful for detecting or predicting the onset of sepsis in SIRS subjects, one of skill in the art will understand that the present methods may be used for any subject: including, but not limited to, subjects suspected of having SIRS or of being at any stage of sepsis. For example, a biological sample can be taken from a subject, and a profile of biomarkers in the sample can be evaluated in light of biomarker profiles obtained from several different types of training populations. Representative training populations variously include, for example, populations that include subjects who are SIRS-negative, populations that include subjects who are SIRS-positive, and/or populations that include subjects at a particular stage of sepsis. Evaluation of the biomarker profile in light of each of these different training populations can be used to determine whether the test subject is SIRS-negative, SIRS-positive, is likely to become septic, or has a particular stage of sepsis. Based on the diagnosis resulting from the methods of the present invention, an appropriate treatment regimen can then be initiated.

In particular embodiments, the invention also provides kits that are useful in diagnosing or predicting the development of sepsis or SIRS in a subject (see Section 5.3, infra). The kits of the present invention comprise at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 96, 100, 105, 110, 115, 120, 125, 130, 135, 140, 145, 150, 155, 160, 165, 170, 175, 180, 185, 190, 195 or 200 or more biomarkers and/or reagents used to detect the presence or abundance of such biomarkers. In some embodiments, each of these biomarkers is from Table 30. In some embodiments, each of these biomarkers is from Table 31. In some embodiments, each of these biomarkers is from Table 32. In some embodiments, each of these biomarkers is from Table 33. In some embodiments, each of these biomarkers is from Table 36. In some embodiments, each of these biomarkers is from FIG. 39, FIG. 43, FIG. 52, FIG. 53, or FIG. 56. In another embodiment, the kits of the present invention comprise at least two, but as many as several hundred or more biomarkers and/or reagents used to detect the presence or abundance of such biomarkers.

In a specific embodiment, the kits of the present invention comprise at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 96, 100, 105, 110, 115, 120, 125, 130, 135, 140, 145, 150, 155, 160, 165, 170, 175, 180, 185, 190, 195 or 200 or more reagents that specifically bind the biomarkers of the present invention. For example, such kits can comprise nucleic acid molecules and/or antibody molecules that specifically bind to biomarkers of the present invention.

Specific exemplary biomarkers that are useful in the present invention are set forth in Section 5.6, Section 5.11, as well as Tables 30, 31, 32, 34 and 36 of Section 6. The biomarkers of the kit can be used to generate biomarker profiles according to the present invention. Examples of types of biomarkers and/or reagents within such kits include, but are not limited to, proteins and fragments thereof, peptides, polypeptides, antibodies, proteoglycans, glycoproteins, lipoproteins, carbohydrates, lipids, nucleic acids (mRNA, DNA, cDNA), organic and inorganic chemicals, and natural and synthetic polymers or a discriminating molecule or fragment thereof.

In particular embodiments, the invention also provides still other kits that are useful in diagnosing or predicting the development of sepsis or SIRS in a subject (see Section 5.3, infra). The kits of the present invention comprise at least 2, 3, 4, 5, 6, 7, 8, 9, 10, 11, 12, 13, 14, 15, 16, 17, 18, 19, 20, 25, 30, 35, 40, 45, 50 or more biomarkers. In some embodiments, each of these biomarkers is from Table I. In some embodiments, each of these biomarkers is from Table J. In some embodiments, each of these biomarkers is from Table K. In some embodiments, each of these biomarkers is found in Table I or Table 30. In some embodiments, each of these biomarkers is found in Table I or Table 31. In some embodiments, each of these biomarkers is from FIG. 39, FIG. 43, FIG. 52, FIG. 53, or FIG. 56. In another embodiment, the kits of the present invention comprise at least two, but as many as 50 or more biomarkers. In a specific embodiment, the kits of the present invention comprise at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 96, 100, 105, 110, 115, 120, 125, 130, 135, 140, 145, 150, 155, 160, 165, 170, 175, 180, 185, 190, 195 or 200 or more reagents that specifically bind the biomarkers of the present invention. Specific biomarkers that are useful in the present invention are set forth in Section 5.6, Section 5.11, as well as Tables I, J, K, L, M, N, and O. The biomarkers of the kits can be used to generate biomarker profiles according to the present invention. Examples of classes of compounds of the kits include, but are not limited to, proteins and fragments thereof, peptides, polypeptides, proteoglycans, glycoproteins, lipoproteins, carbohydrates, lipids, nucleic acids (mRNA, DNA, cDNA), organic and inorganic chemicals, and natural and synthetic polymers or a discriminating molecule or fragment thereof.

Still another aspect of the present invention comprises computers and computer readable media for evaluating whether a test subject is likely to develop sepsis or SIRS. For instance, one embodiment of the present invention provides a computer program product for use in conjunction with a computer system. The computer program product comprises a computer readable storage medium and a computer program mechanism embedded therein. The computer program mechanism comprises instructions for evaluating whether a plurality of features in a biomarker profile of a test subject at risk for developing sepsis satisfies a first value set. Satisfaction of the first value set predicts that the test subject is likely to develop sepsis. The features are measurable aspects of a plurality of biomarkers comprising at least three biomarkers listed in Table I. In some embodiments, the computer program product further comprises instructions for evaluating whether the plurality of features in the biomarker profile of the test subject satisfies a second value set. Satisfaction of the second value set predicts that the test subject is not likely to develop sepsis. In some embodiments, the biomarker profile has between 3 and 50 biomarkers listed in Table I, between 3 and 40 biomarkers listed in Table I, at least four biomarkers listed in Table I, or at least six biomarkers listed in Table I.

Another computer embodiment of the present invention comprises a central processing unit and a memory coupled to the central processing unit. The memory stores instructions for evaluating whether a plurality of features in a biomarker profile of a test subject at risk for developing sepsis satisfies a first value set. Satisfaction of the first value set predicts that the test subject is likely to develop sepsis. The features are measurable aspects of a plurality of biomarkers. This plurality of biomarkers comprises at least three biomarkers from Table I. In some embodiments, the memory further stores instructions for evaluating whether the plurality of features in the biomarker profile of the test subject satisfies a second value set, wherein satisfying the second value set predicts that the test subject is not likely to develop sepsis. In some embodiments, the biomarker profile consists of between 3 and 50 biomarkers listed in Table I, between 3 and 40 biomarkers listed in Table I, at least four biomarkers listed in Table I, or at least eight biomarkers listed in Table I.

Another computer embodiment in accordance with the present invention comprises a computer system for determining whether a subject is likely to develop sepsis. The computer system comprises a central processing unit and a memory, coupled to the central processing unit. The memory stores instructions for obtaining a biomarker profile of a test subject. The biomarker profile comprises a plurality of features. The plurality of biomarkers comprises at least three biomarkers listed in Table I. The memory further comprises instructions for transmitting the biomarker profile to a remote computer. The remote computer includes instructions for evaluating whether the plurality of features in the biomarker profile of the test subject satisfies a first value set. Satisfaction of the first value set predicts that the test subject is likely to develop sepsis. The memory further comprises instructions for receiving a determination, from the remote computer, as to whether the plurality of features in the biomarker profile of the test subject satisfies the first value set. The memory also comprises instructions for reporting whether the plurality of features in the biomarker profile of the test subject satisfies the first value set. In some embodiments, the remote computer further comprises instructions for evaluating whether the plurality of features in the biomarker profile of the test subject satisfies a second value set. Satisfaction of the second value set predicts that the test subject is not likely to develop sepsis. In such embodiments, the memory further comprises instructions for receiving a determination, from the remote computer, as to whether the plurality of features in the biomarker profile of the test subject satisfies the second set as well as instructions for reporting whether the plurality of features in the biomarker profile of the test subject satisfies the second value set. In some embodiments, the plurality of biomarkers comprises at least four biomarkers listed in Table I. In some embodiments, the plurality of biomarkers comprises at least six biomarkers listed in Table I.

Still another embodiment of the present invention comprises a digital signal embodied on a carrier wave comprising a respective value for each of a plurality of features in a biomarker profile. The features are measurable aspects of a plurality of biomarkers. The plurality of biomarkers comprises at least three biomarkers listed in Table I. In some embodiments, the plurality of biomarkers comprises at least four biomarkers listed in Table I. In some embodiments, the plurality of biomarkers comprises at least eight biomarkers listed in Table I.

Still another aspect of the present invention provides a digital signal embodied on a carrier wave comprising a determination as to whether a plurality of features in a biomarker profile of a test subject satisfies a value set. The features are measurable aspects of a plurality of biomarkers. This plurality of biomarkers comprises at least three biomarkers listed in Table I. Satisfying the value set predicts that the test subject is likely to develop sepsis. In some embodiments, the plurality of biomarkers comprises at least four biomarkers listed in Table I. In some embodiments, the plurality of biomarkers comprises at least eight biomarkers listed in Table I.

Still another embodiment provides a digital signal embodied on a carrier wave comprising a determination as to whether a plurality of features in a biomarker profile of a test subject satisfies a value set. The features are measurable aspects of a plurality of biomarkers. The plurality of biomarkers comprises at least three biomarkers listed in Table I. Satisfaction of the value set predicts that the test subject is not likely to develop sepsis. In some embodiments, the plurality of biomarkers comprises at least four biomarkers listed in Table I. In some embodiments, the plurality of biomarkers comprises at least eight biomarkers listed in Table I.

Still another embodiment of the present invention provides a graphical user interface for determining whether a subject is likely to develop sepsis. The graphical user interface comprises a display field for a displaying a result encoded in a digital signal embodied on a carrier wave received from a remote computer. The features are measurable aspects of a plurality of biomarkers. The plurality of biomarkers comprises at least three biomarkers listed in Table I. The result has a first value when a plurality of features in a biomarker profile of a test subject satisfies a first value set. The result has a second value when a plurality of features in a biomarker profile of a test subject satisfies a second value set. In some embodiments, the plurality of biomarkers comprises at least four biomarkers listed in Table I. In some embodiments, the plurality of biomarkers comprises at least eight biomarkers listed in Table I.

Yet another aspect of the present invention provides a computer system for determining whether a subject is likely to develop sepsis. The computer system comprises a central processing unit and a memory, coupled to the central processing unit. The memory stores instructions for obtaining a biomarker profile of a test subject. The biomarker profile comprises a plurality of features. The features are measurable aspects of a plurality of biomarkers. The plurality of biomarkers comprise at least three biomarkers listed in Table I. The memory further stores instructions for evaluating whether the plurality of features in the biomarker profile of the test subject satisfies a first value set. Satisfying the first value set predicts that the test subject is likely to develop sepsis. The memory also stores instructions for reporting whether the plurality of features in the biomarker profile of the test subject satisfies the first value set. In some embodiments, the plurality of biomarkers comprises at least four biomarkers listed in Table I. In some embodiments, the plurality of biomarkers comprises at least eight biomarkers listed in Table I.

4. BRIEF DESCRIPTION OF THE FIGURES

Figure 18:
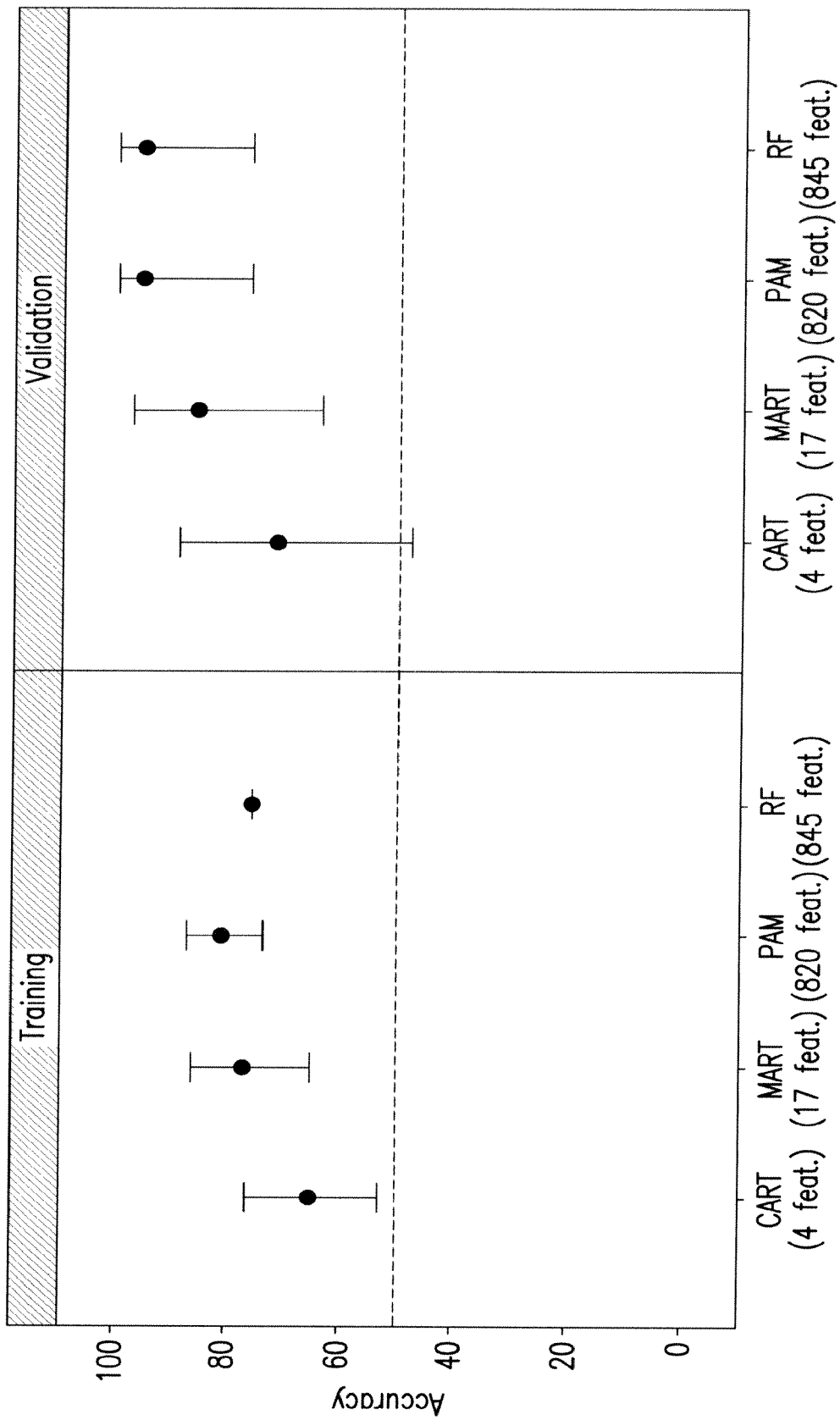

FIG. 18 provides a summary of the CART, MART, PAM, and random forests (RF) classification algorithm (decision rule) performance and associated 95% confidence intervals using $T_{-12}$ static data obtained from a training population.

Figure 19:
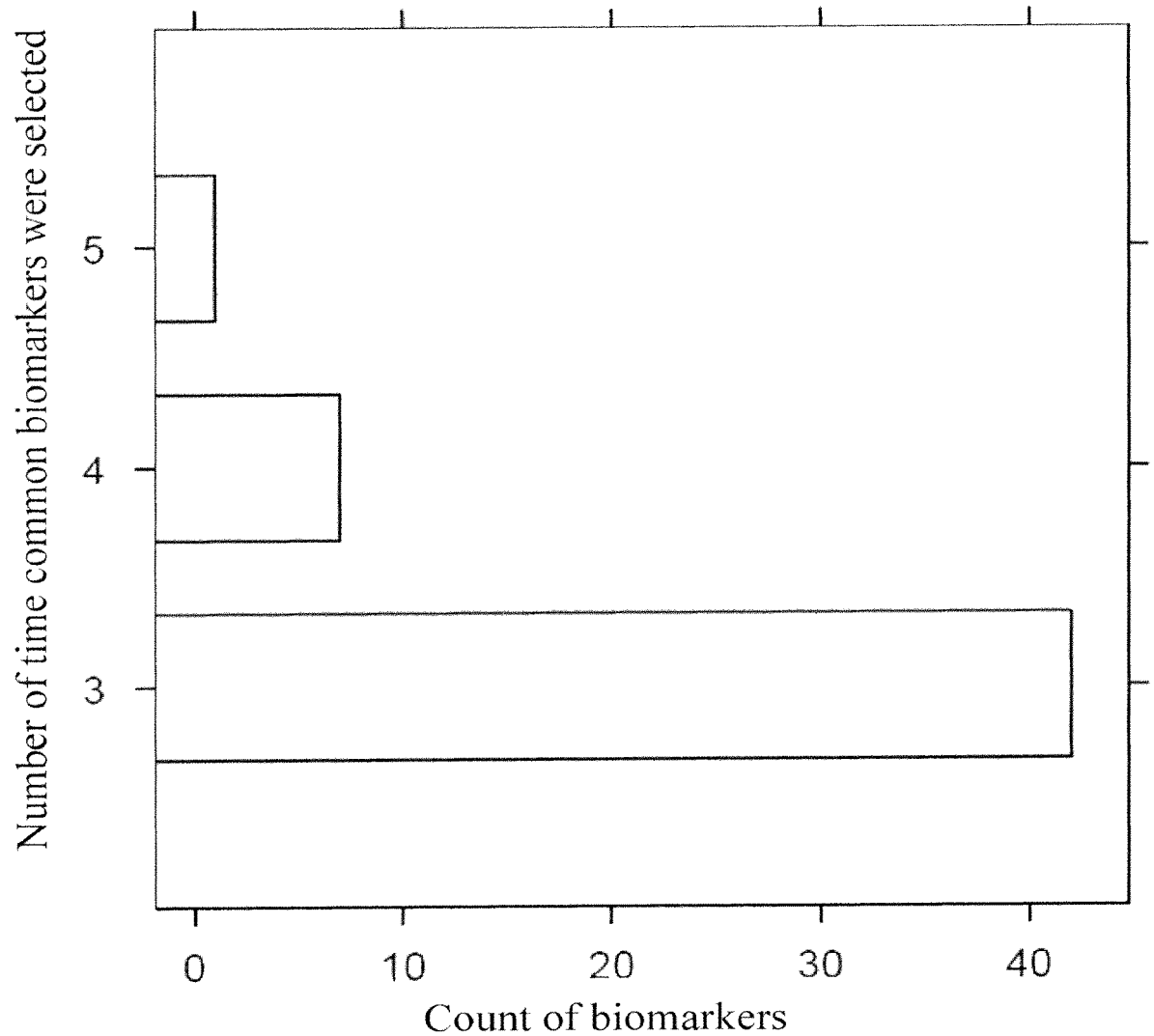

FIG. 19 illustrates the number of times that common biomarkers were found to be important across the decision rules developed using (i) CART, (ii) MART, (iii) PAM, (iv) random forests, and (v) the Wilcoxon (adjusted) test using $T_{-12}$ static data obtained from a training population. The biomarkers are referenced by their corresponding Affymetrix U133 plus 2.0 probeset names given in Table 30.

Figure 20:
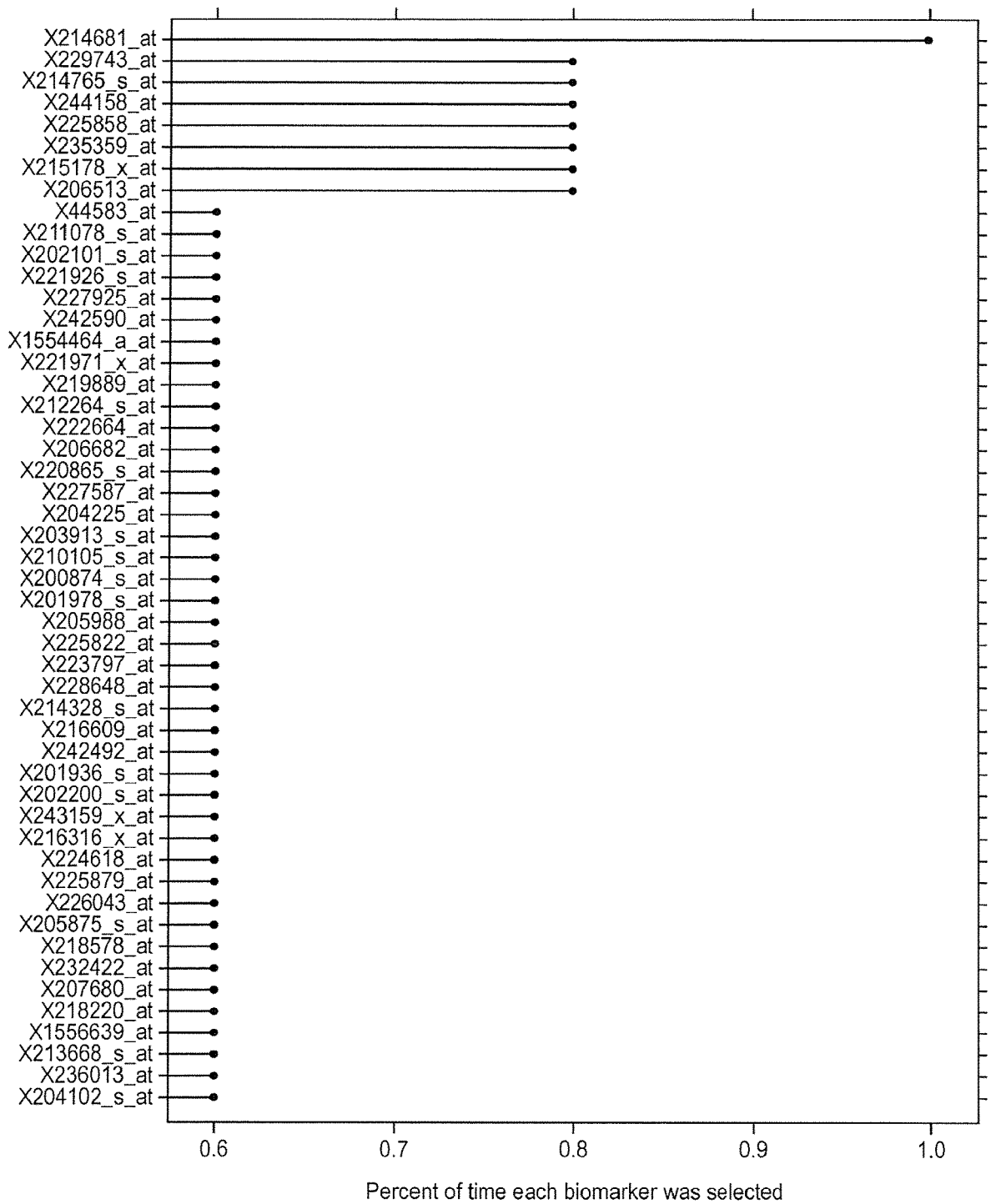

FIG. 20 illustrates an overall ranking of biomarkers using $T_{-12}$ static data obtained from a training population.

Figure 21:
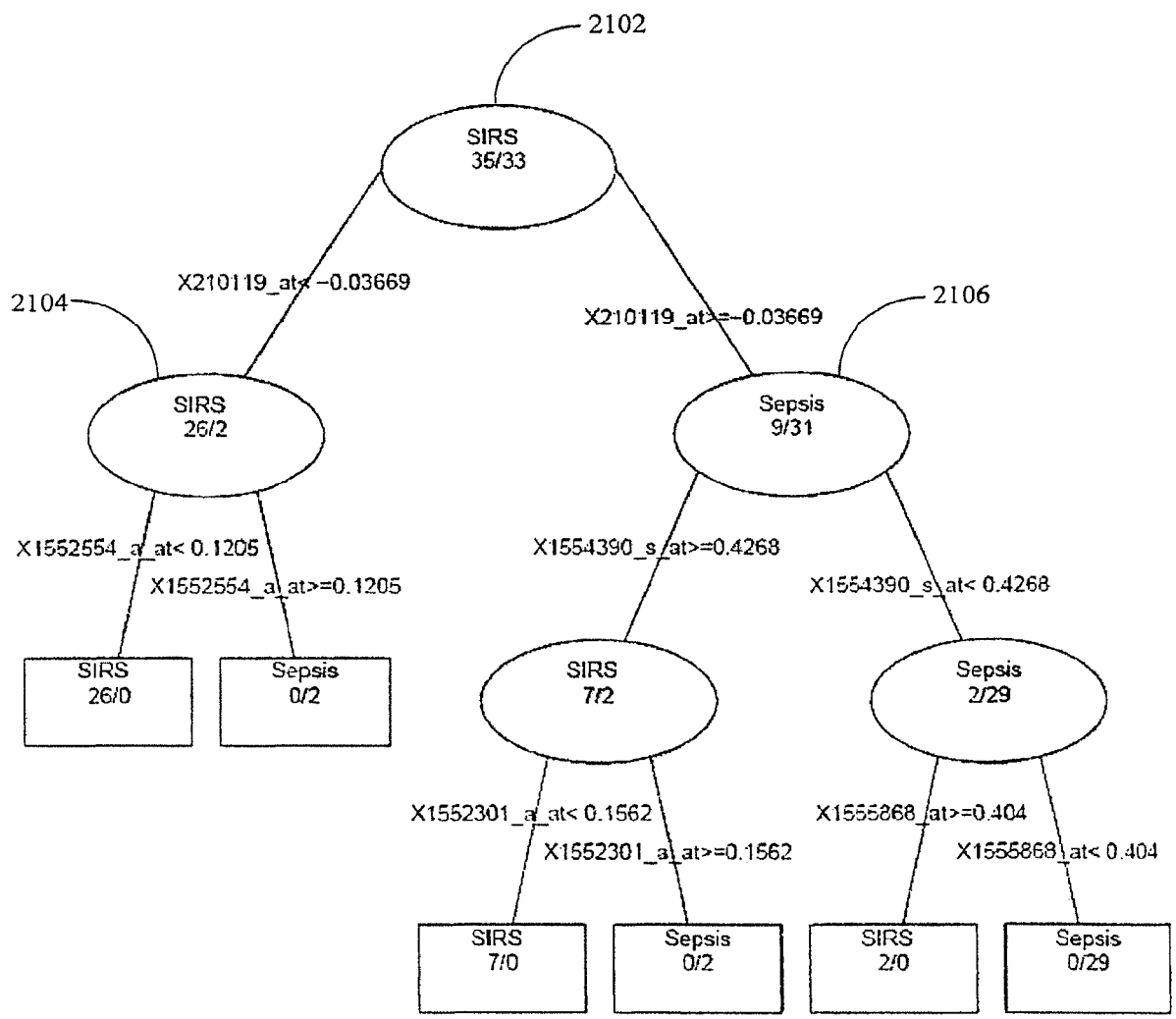

FIG. 21 illustrates a classification and regression tree for discriminating between a SIRS phenotypic state characterized by the onset of sepsis and a SIRS phenotypic state characterized by the absence of sepsis using $T_{-12}$ baseline data obtained from a training population in accordance with an embodiment of the present invention.

Figure 22:
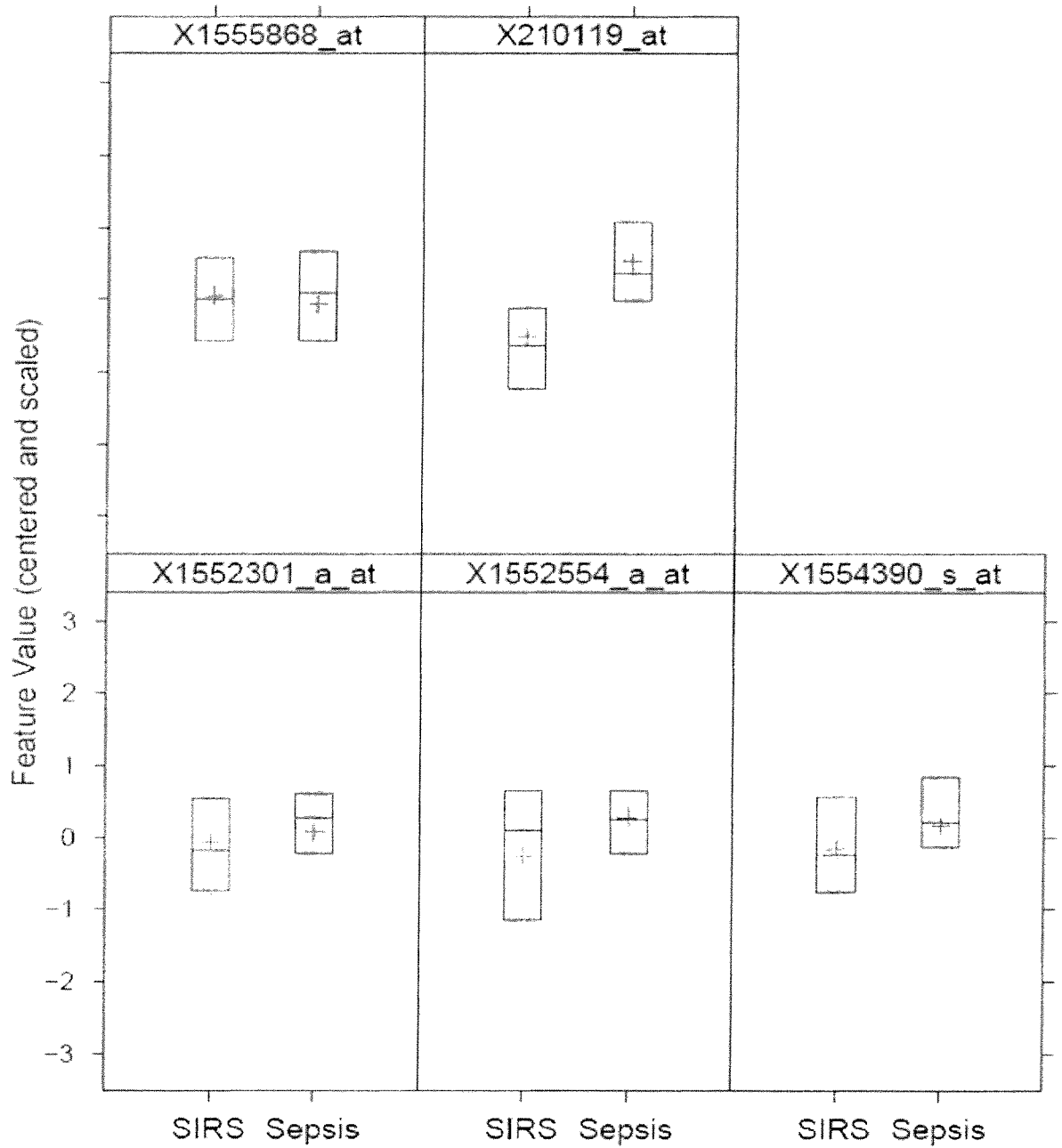

FIG. 22 shows the distribution of the feature values of five biomarkers used in the decision tree of FIG. 21 using $T_{-12}$ baseline data obtained from a training population in accordance with an embodiment of the present invention. The biomarkers are referenced by their corresponding Affymetrix U133 plus 2.0 probeset names given in Table 30.

Figure 23:
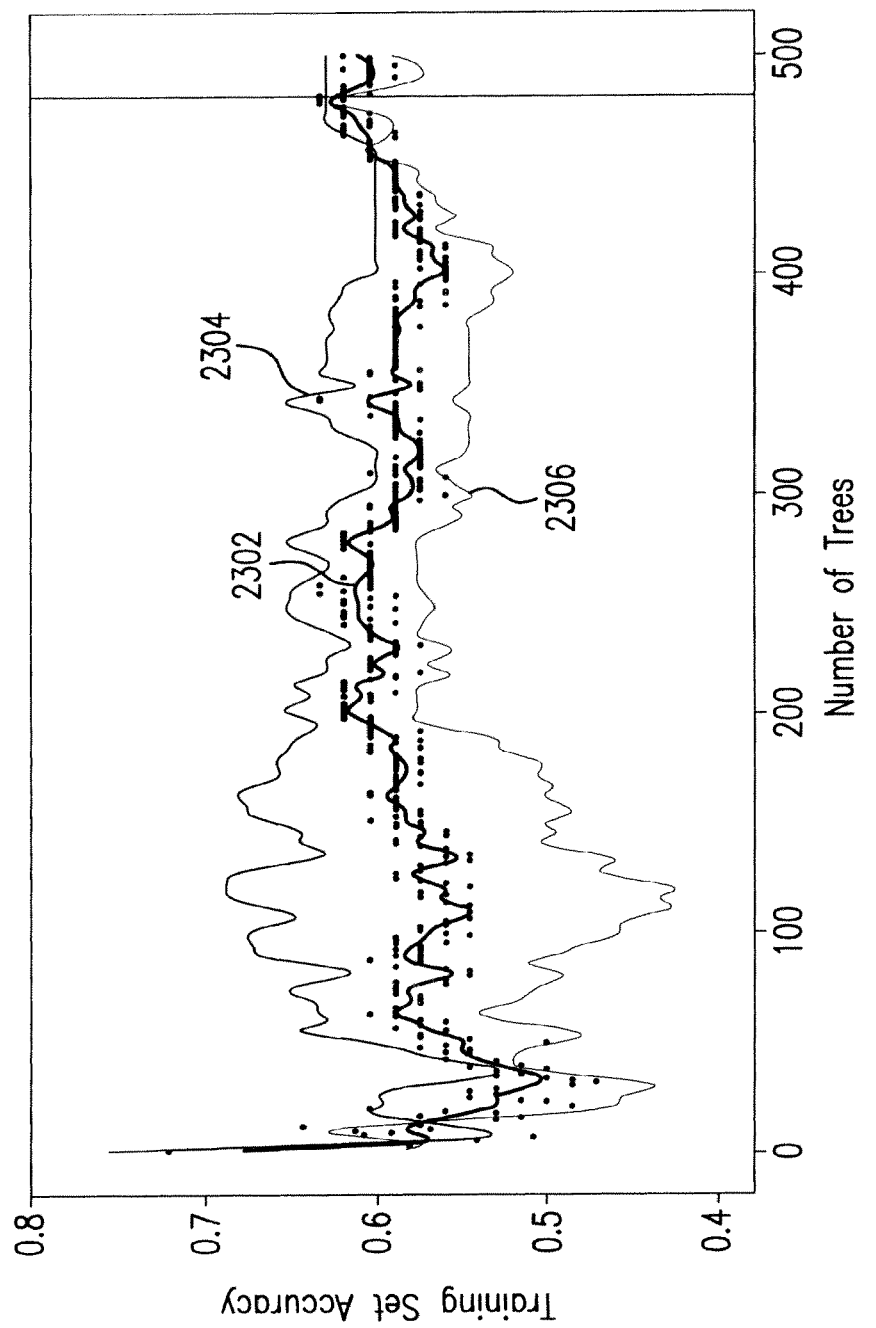

FIG. 23 illustrates the overall accuracy, sensitivity, and specificity of 500 trees used to train a decision tree using the Random Forests method using $T_{-12}$ baseline data obtained from a training population in accordance with an embodiment of the present invention.

Figure 24:
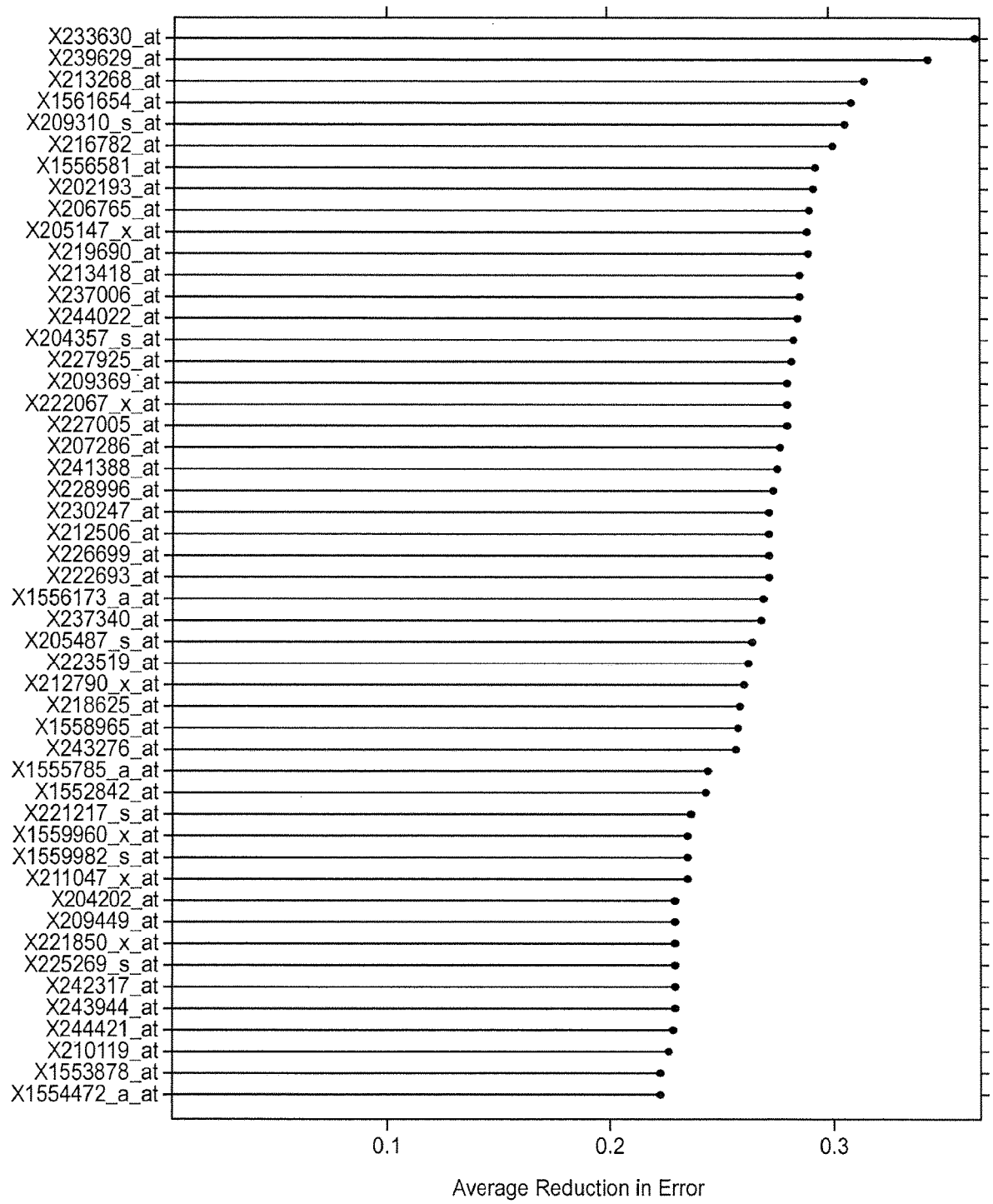

FIG. 24 illustrates the biomarker importance in the decision rule trained using the trees of FIG. 23. The biomarkers are referenced by their corresponding Affymetrix U133 plus 2.0 probeset names given in Table 30.

Figure 25:
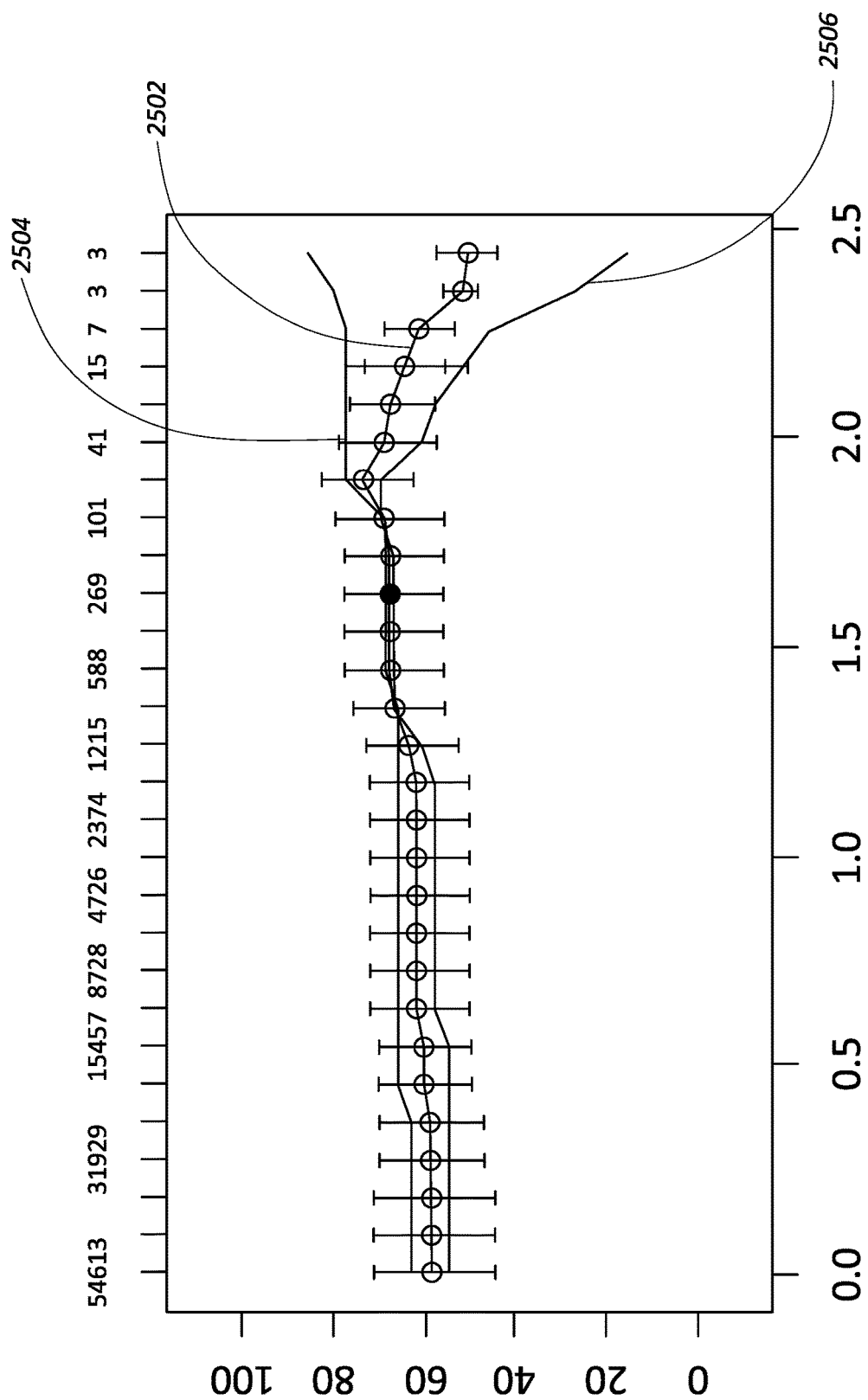

FIG. 25 illustrates the overall accuracy, with 95% confidence interval bars, specificity, and sensitivity of a decision rule developed with predictive analysis of microarrays (PAM) using select biomarkers of the present invention and $T_{-12}$ baseline data obtained from a training population.

Figure 26:
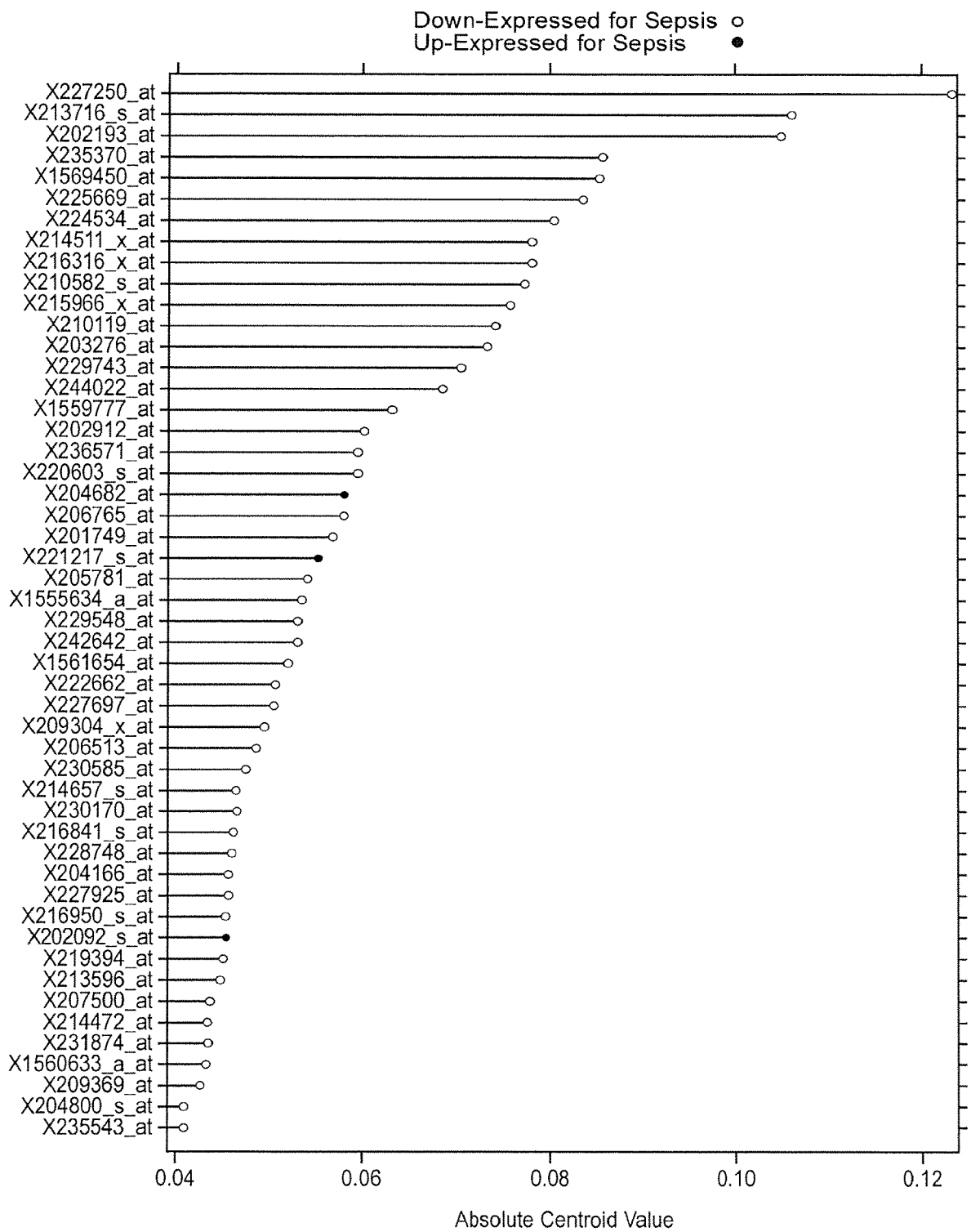

FIG. 26 is a list of biomarkers, rank-ordered by their respective degrees of discriminatory power, identified by PAM using $T_{-12}$ baseline data obtained from a training population. The biomarkers are referenced by their corresponding Affymetrix U133 plus 2.0 probeset names given in Table 30.

Figure 27:
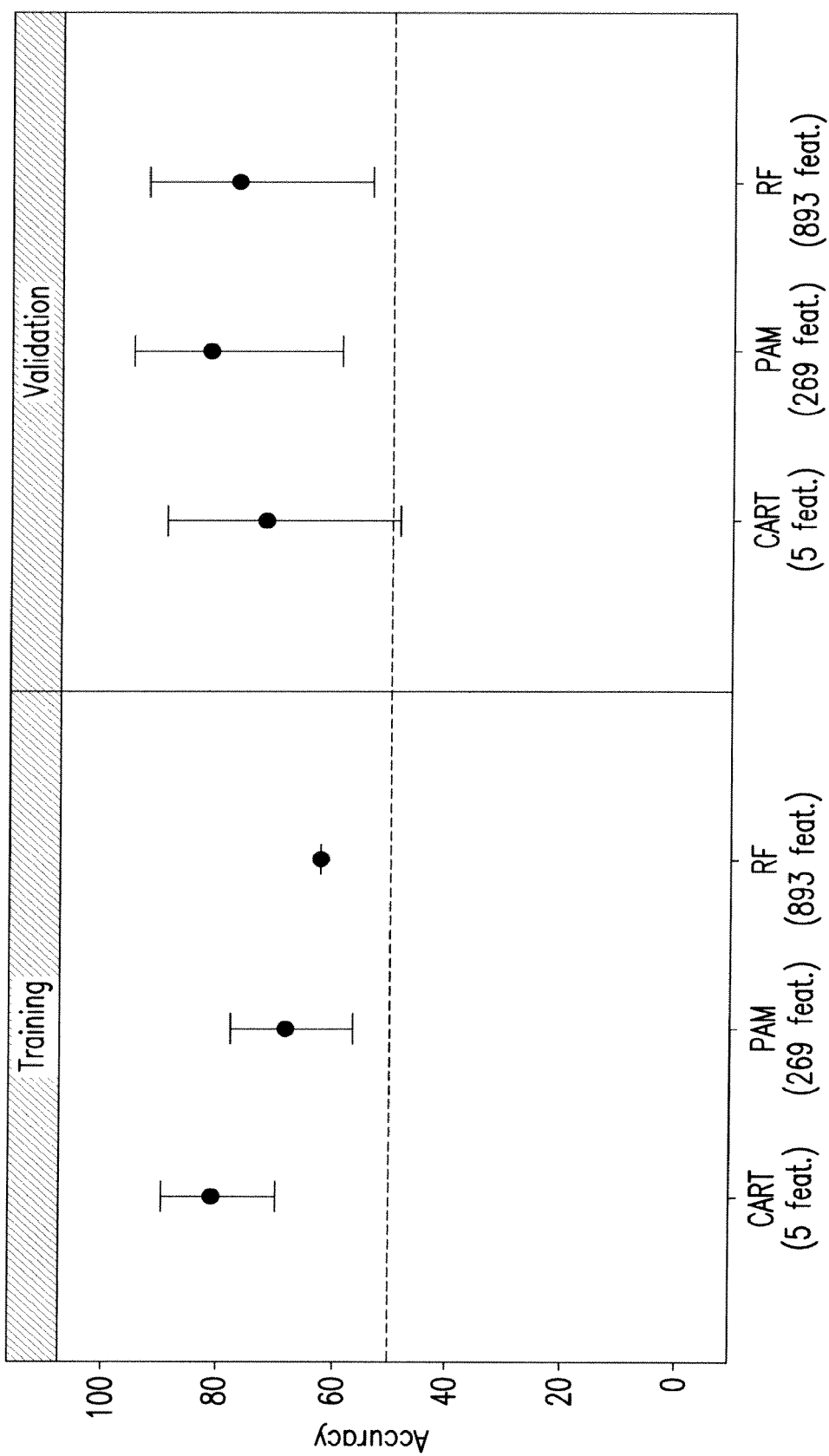

FIG. 27 illustrates CART, PAM, and random forests classification algorithm (decision rule) performance data, and associated 95% confidence intervals, using $T_{-12}$ baseline data obtained from a training population in accordance with an embodiment of the present invention.

Figure 28:
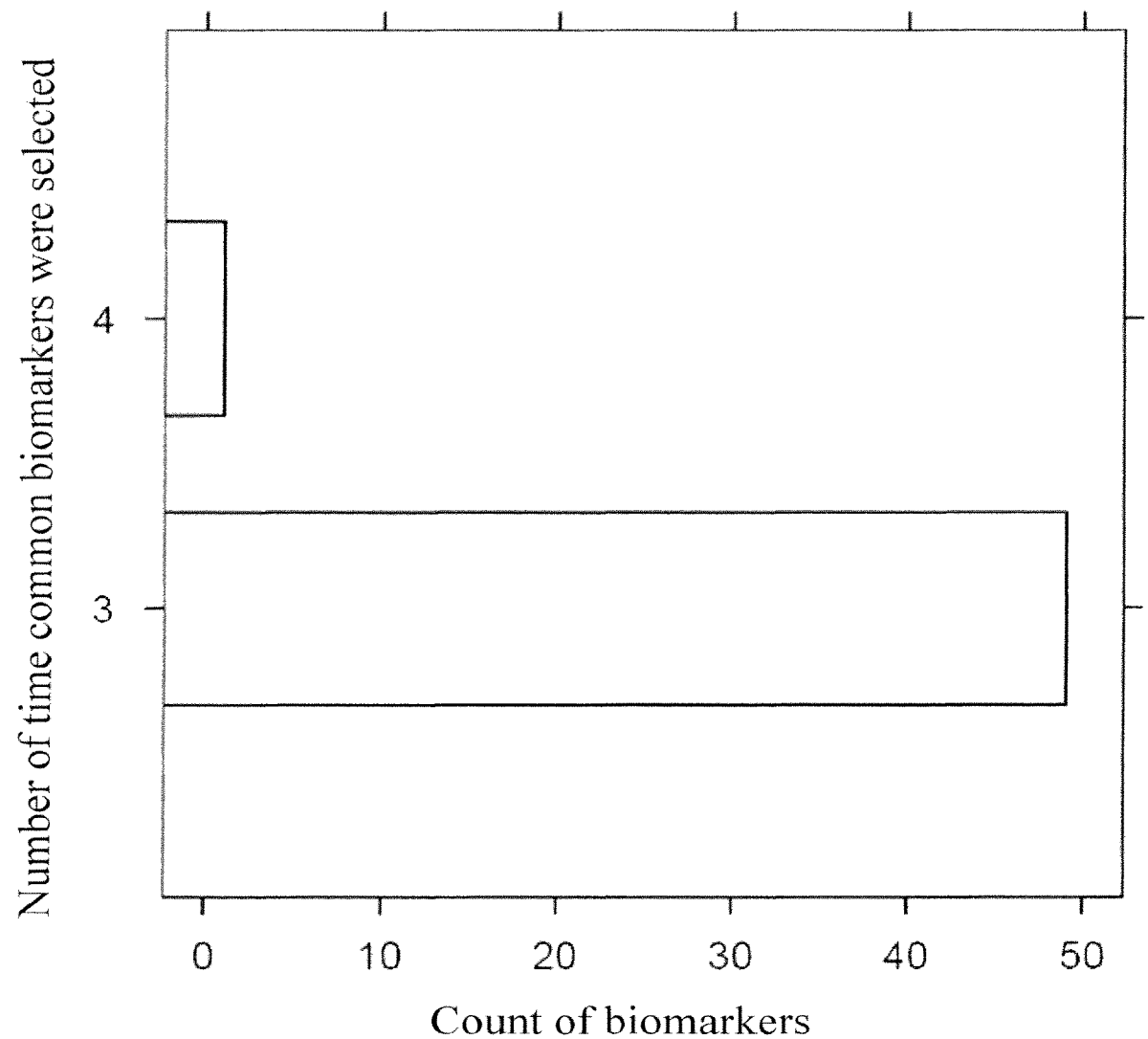

FIG. 28 illustrates the number of times that common biomarkers were found to be important across the decision rules developed using (i) CART, (ii) PAM, (iii) random forests, and (iv) the Wilcoxon (adjusted) test using $T_{-12}$ baseline data obtained from a training population.

Figure 29:
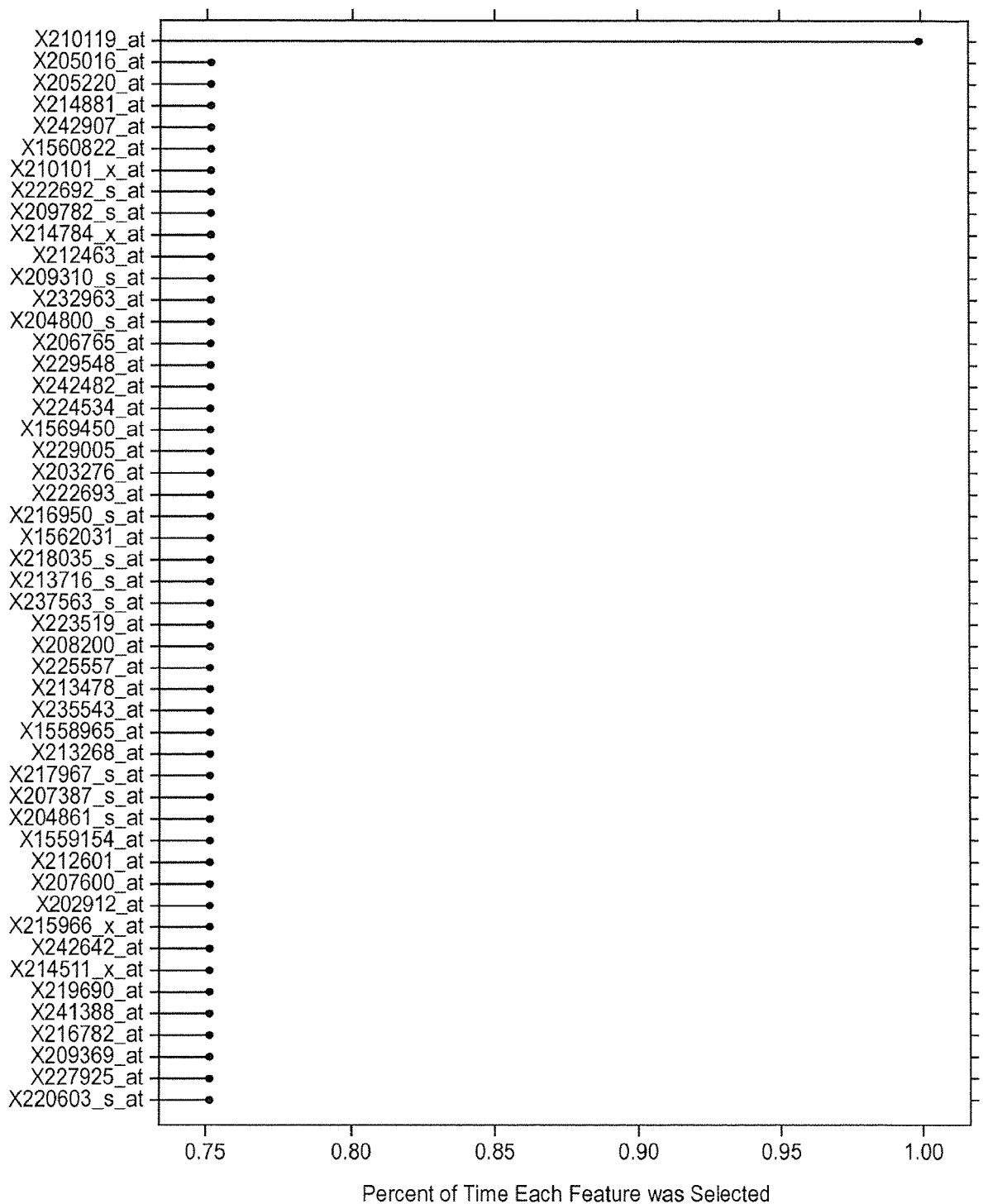

FIG. 29 illustrates an overall ranking of biomarkers for data obtained using $T_{-12}$ baseline data obtained from a training population. The biomarkers are referenced by their corresponding Affymetrix U133 plus 2.0 probeset names given in Table 30.

Figure 30:
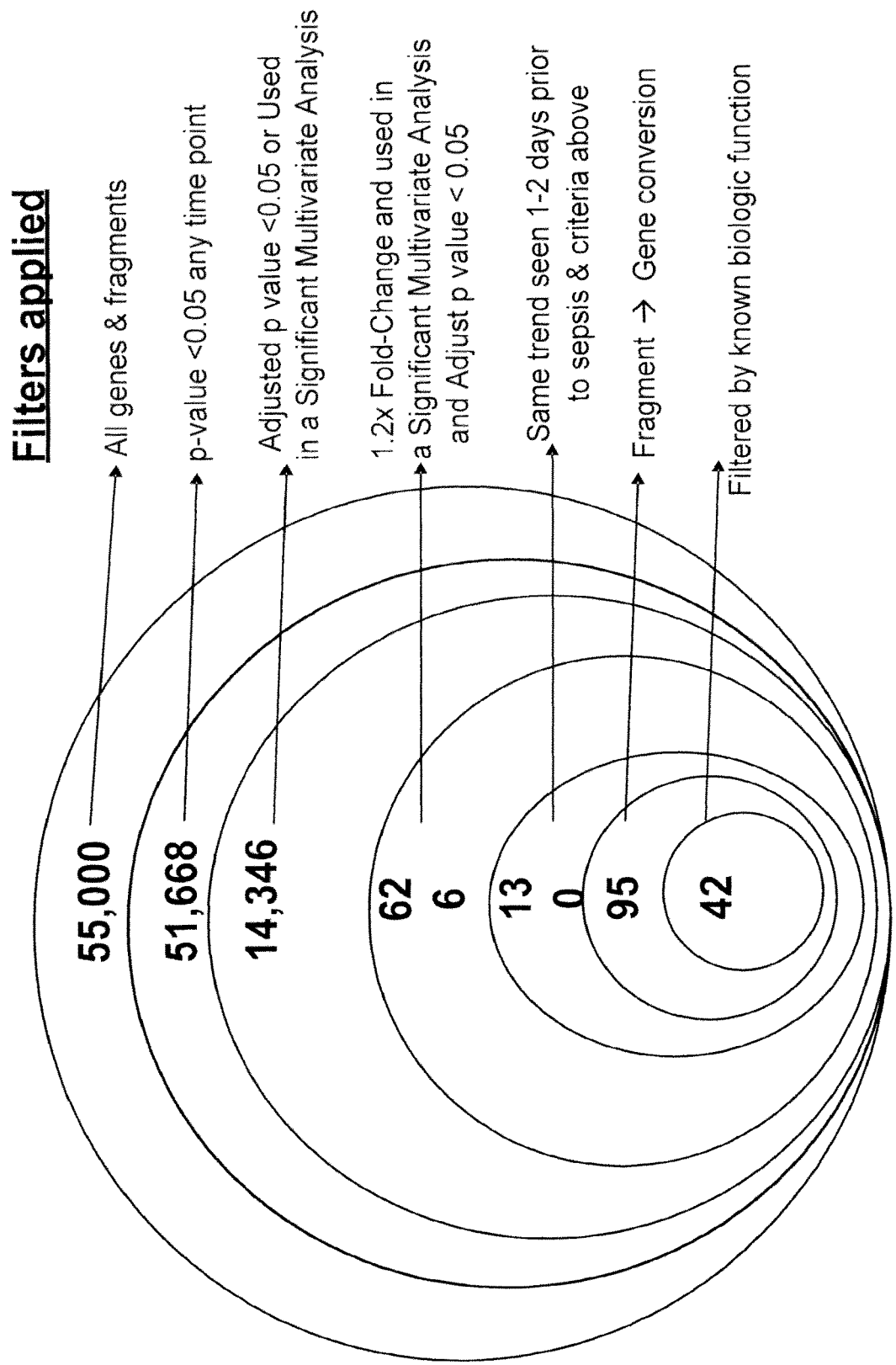

FIG. 30 illustrates the filters applied to identify biomarkers that discriminate between subjects that will get sepsis during a defined time period and subjects that will not get sepsis during the defined time period using data obtained from a training population, in accordance with an embodiment of the present invention. Other combinations of biomarkers are disclosed herein including, for example, in Section 5.3 and in Section 6.

Figure 31:
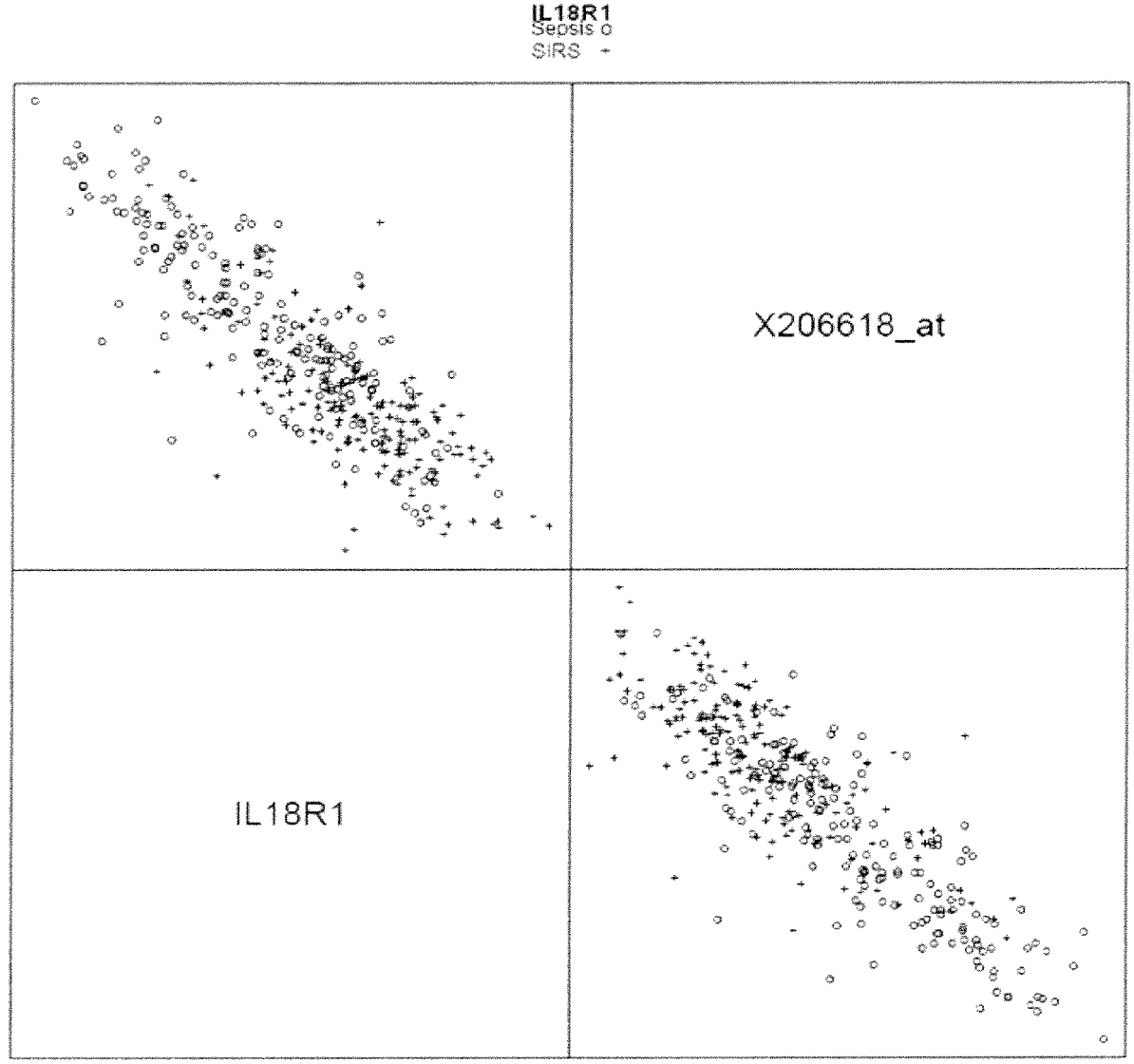

FIG. 31 shows the correlation between IL18R1 expression, as determined by RT-PCR, and the intensity of the X206618_at probeset, as determined using Affymetrix U133 plus 2.0 microarray measurements, across a training population.

Figure 32:
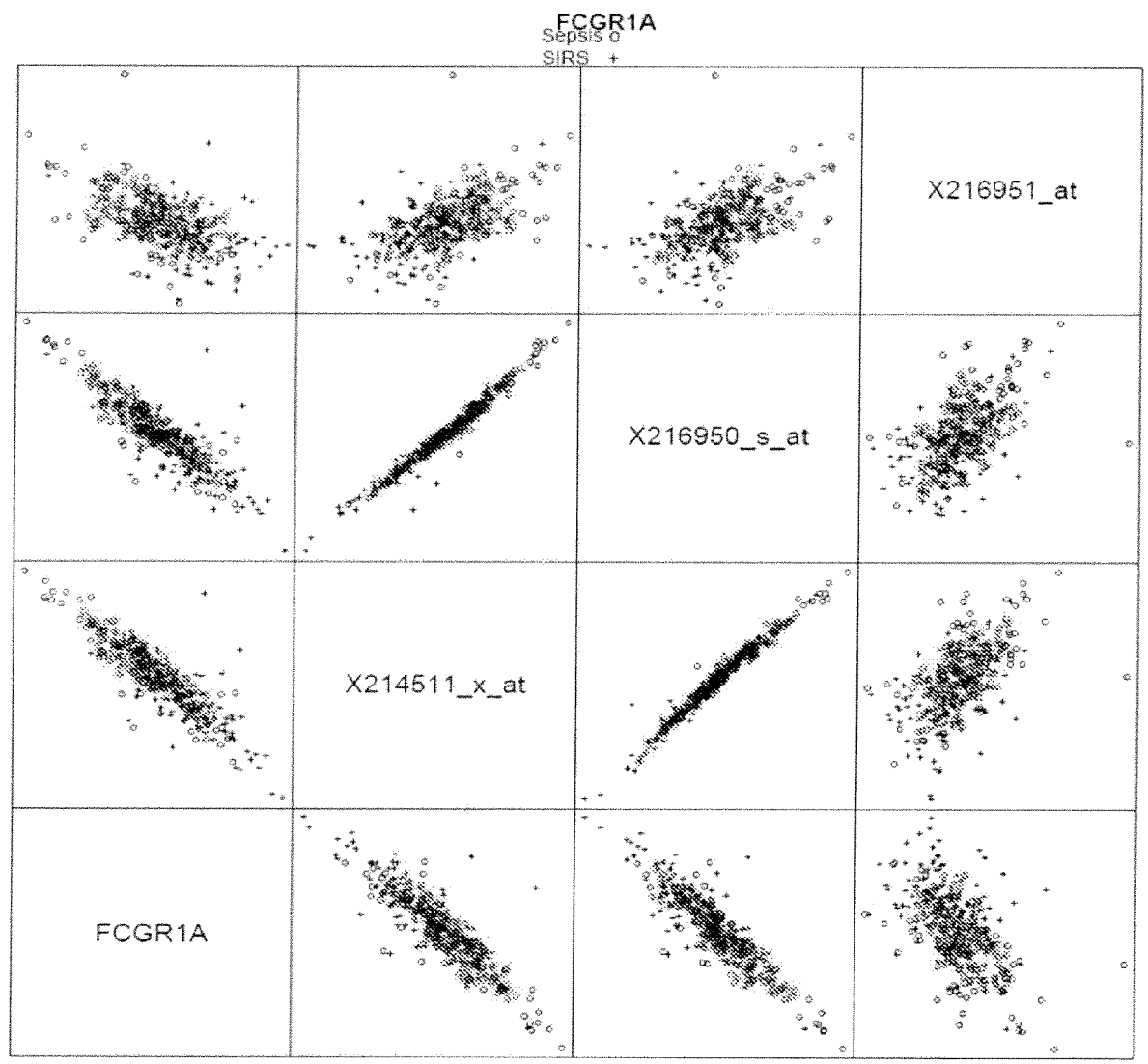

FIG. 32 shows the correlation between FCGR1A expression, as determined by RT-PCR, and the intensity of the X214511_x_at, X216950_s_at and X216951_at probesets, as determined using Affymetrix U133 plus 2.0 microarray measurements, across a training population.

Figure 33:
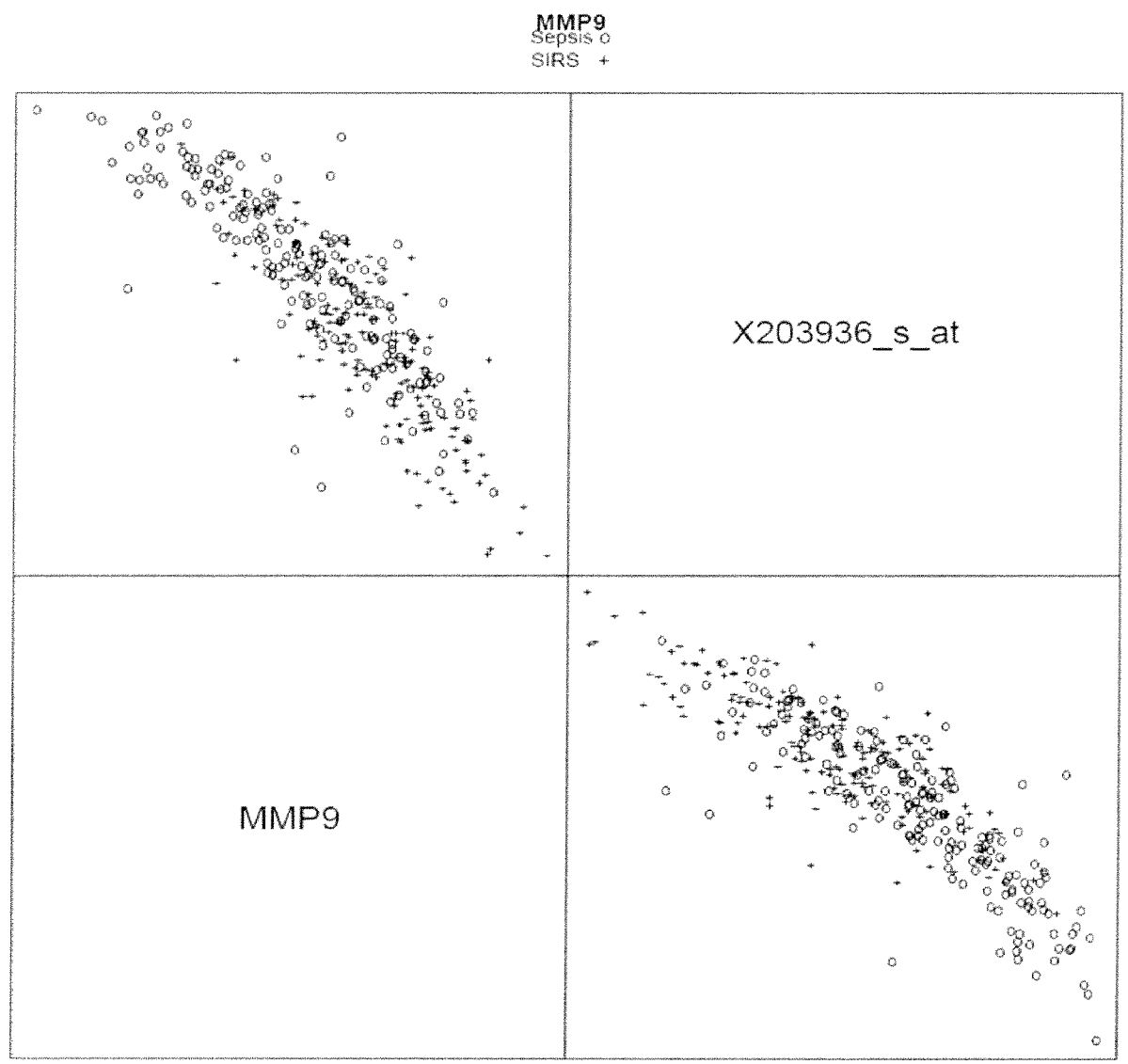

FIG. 33 shows the correlation between MMP9 expression, as determined by RT-PCR, and the intensity of the X203936_s_at probeset, as determined using Affymetrix U133 plus 2.0 microarray measurements, across a training population.

Figure 34:
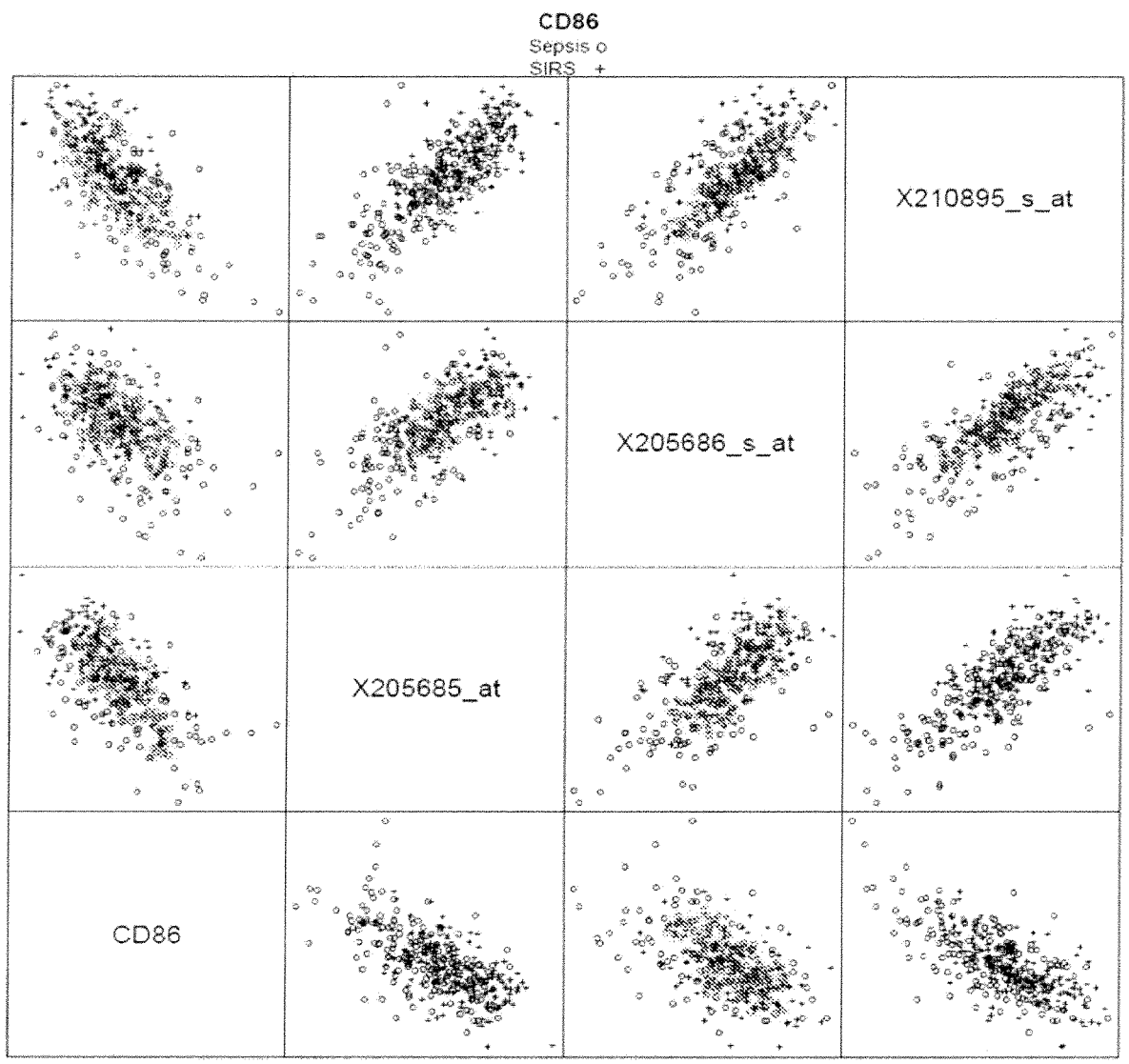

FIG. 34 shows the correlation between CD86 expression, as determined by RT-PCR, and the intensity of the X205685_at, X205686_s_at, and X210895_s_at probesets, as determined using Affymetrix U133 plus 2.0 microarray measurements, across a training population.

Figure 35:
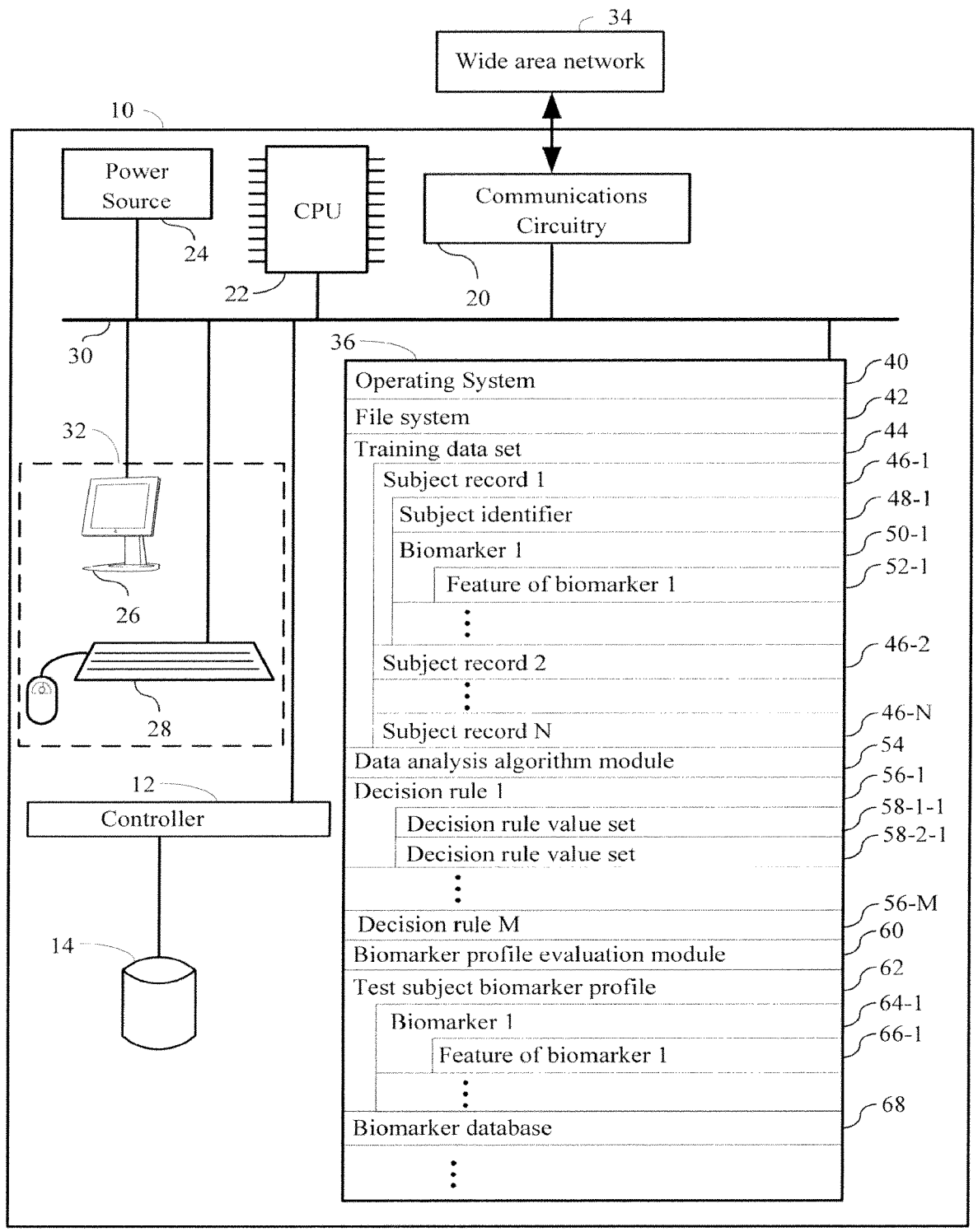

FIG. 35 shows a computer system in accordance with the present invention.

Figure 36:
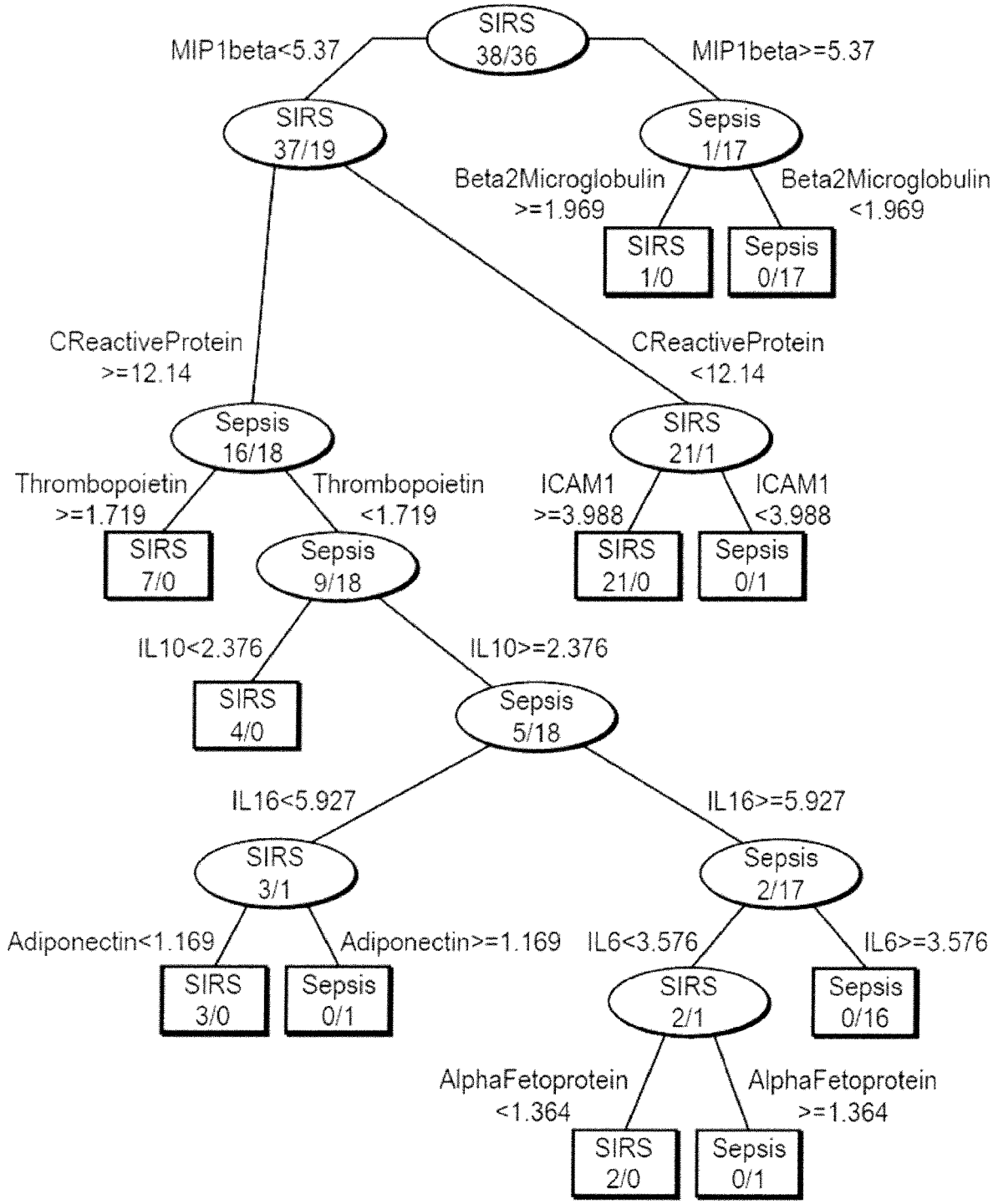

FIG. 36 illustrates a classification and regression tree for discriminating between a SIRS phenotypic state characterized by the onset of sepsis and a SIRS phenotypic state characterized by the absence of sepsis using $T_{-12}$ static data obtained from an RT-PCR discovery training population in accordance with an embodiment of the present invention.

Figure 37:
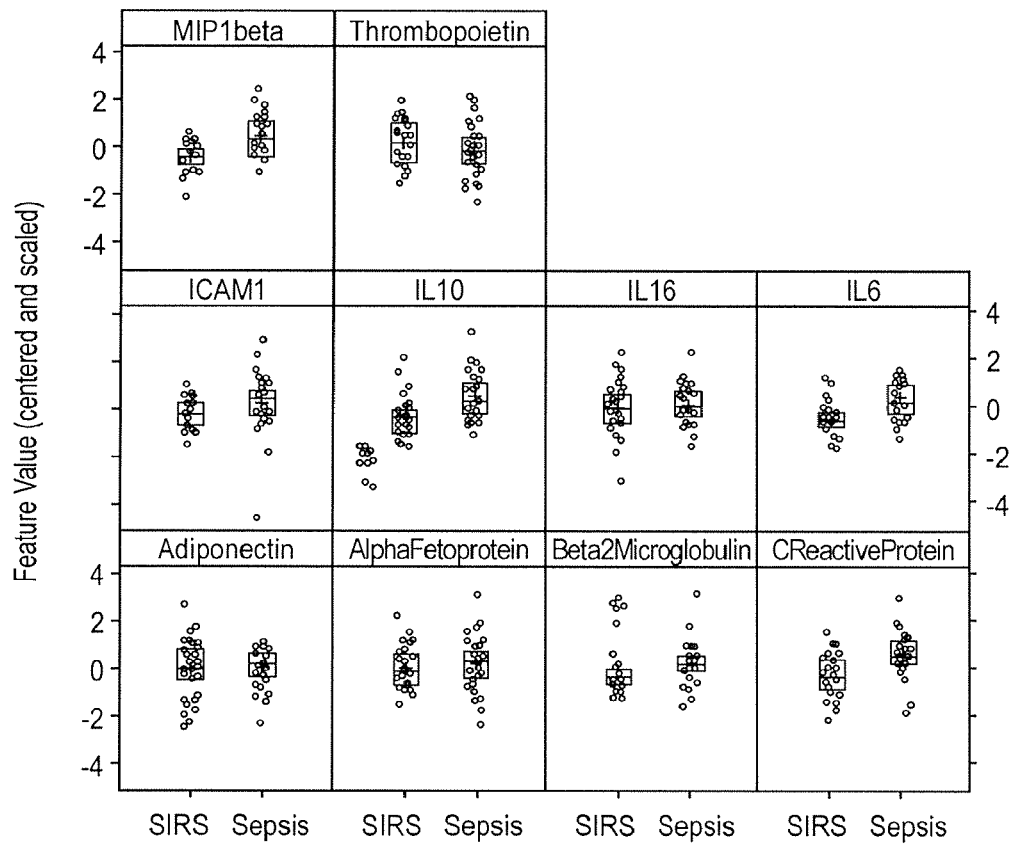

FIG. 37 shows the distribution of feature values for seven biomarkers used in the decision tree of FIG. 36 across $T_{-12}$ static data obtained from an RT-PCR discovery training population in accordance with an embodiment of the present invention.

Figure 38:
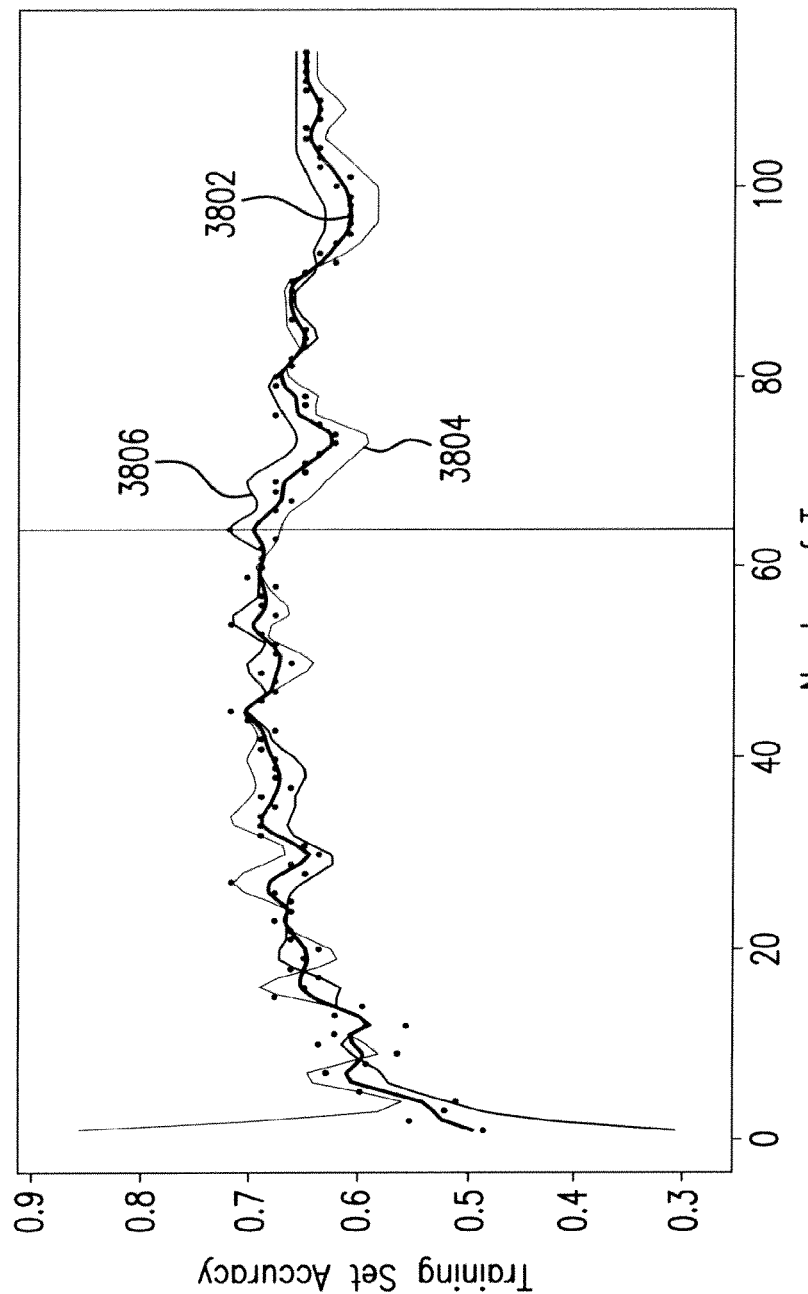

FIG. 38 illustrates the overall accuracy, sensitivity, and specificity of 462 trees used to train a decision tree using the Random Forests method based upon $T_{-12}$ static data obtained from an RT-PCR discovery training population in accordance with an embodiment of the present invention.

Figure 39:
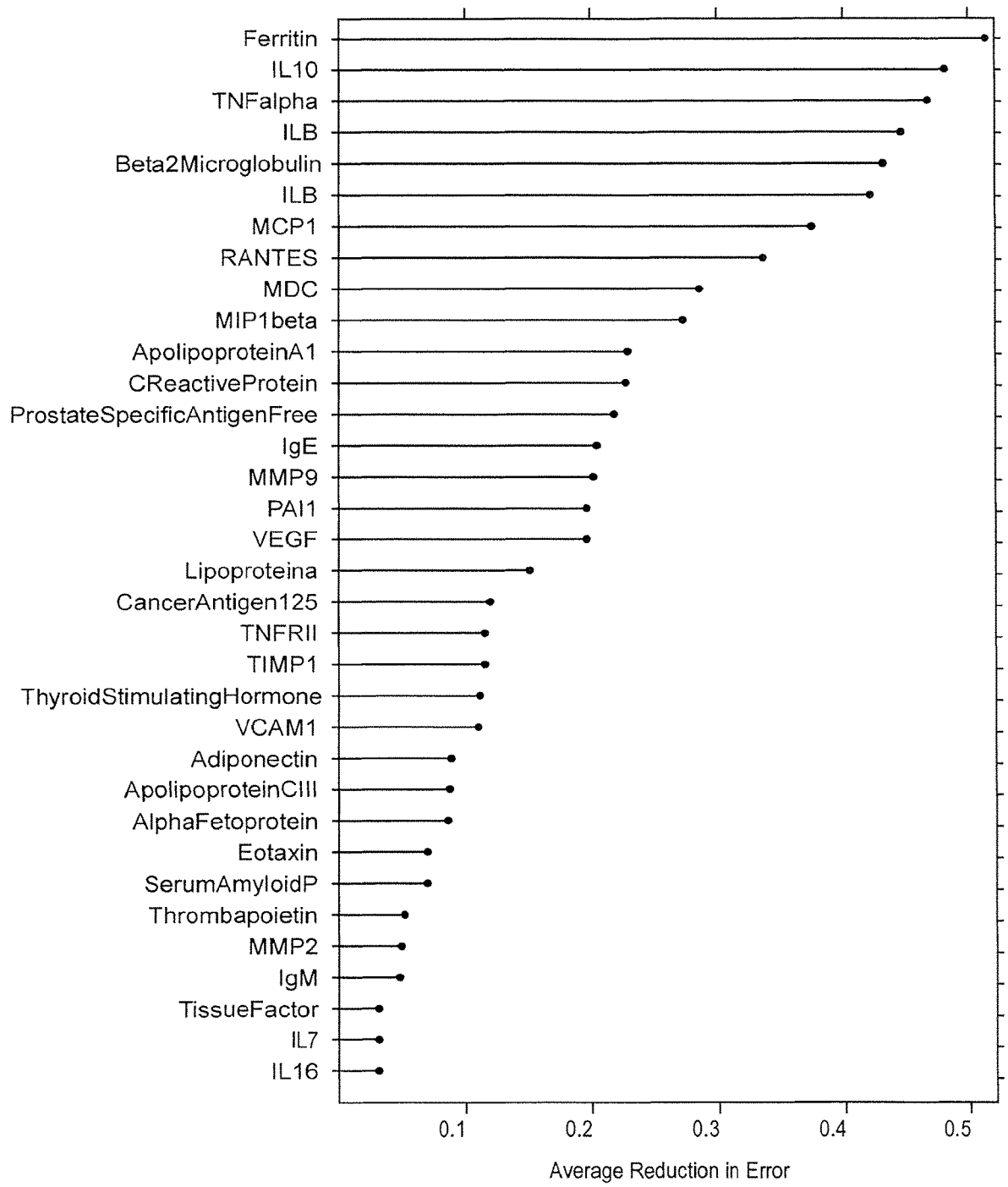

FIG. 39 illustrates the biomarker importance in the decision rule trained using the trees of FIG. 38.

Figure 40:
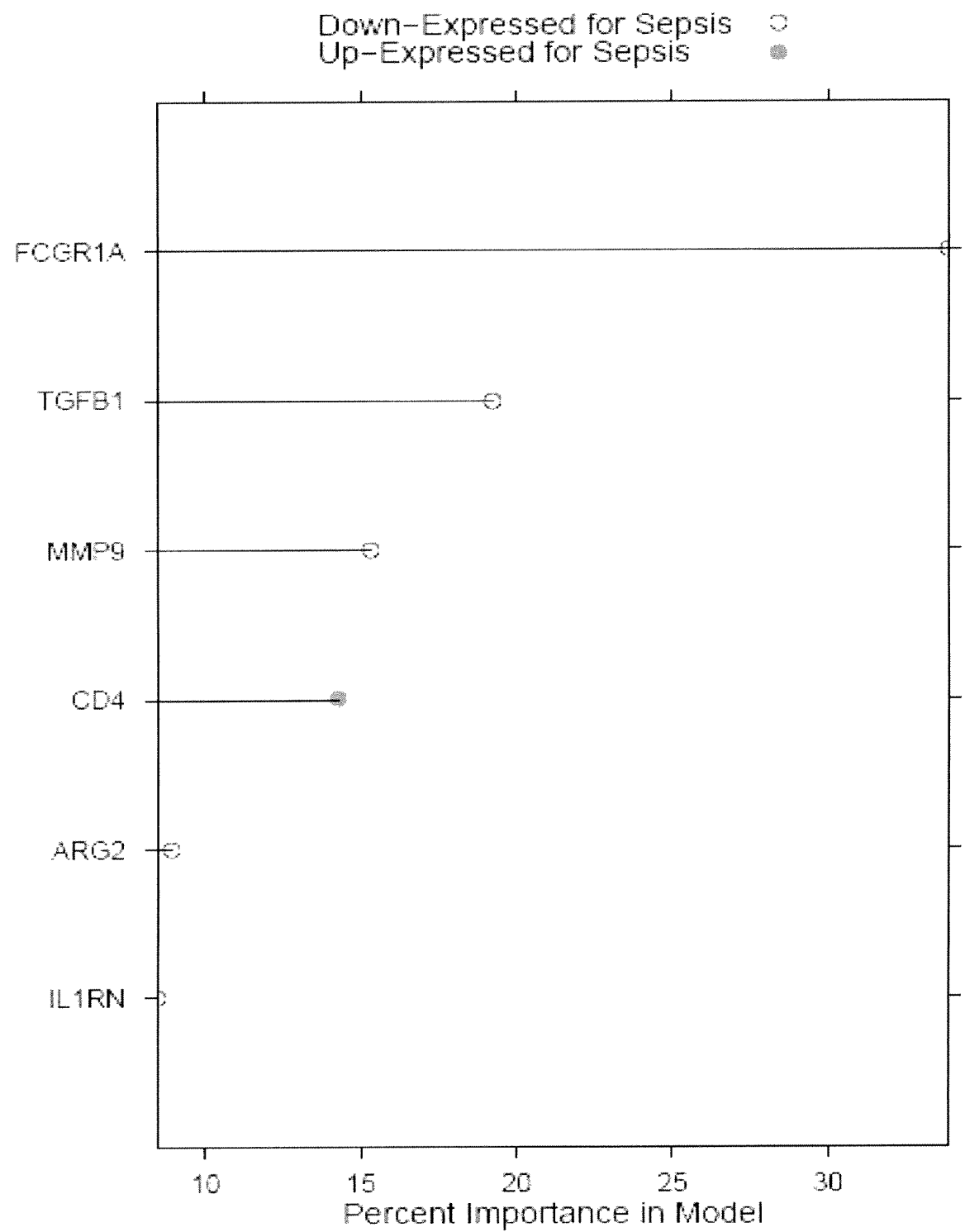

FIG. 40 illustrates a calculation of biomarker importance, summing to 100%, determined by a multiple additive regression tree (MART) approach using $T_{-12}$ static data obtained from an RT-PCR discovery training population.

Figure 41:
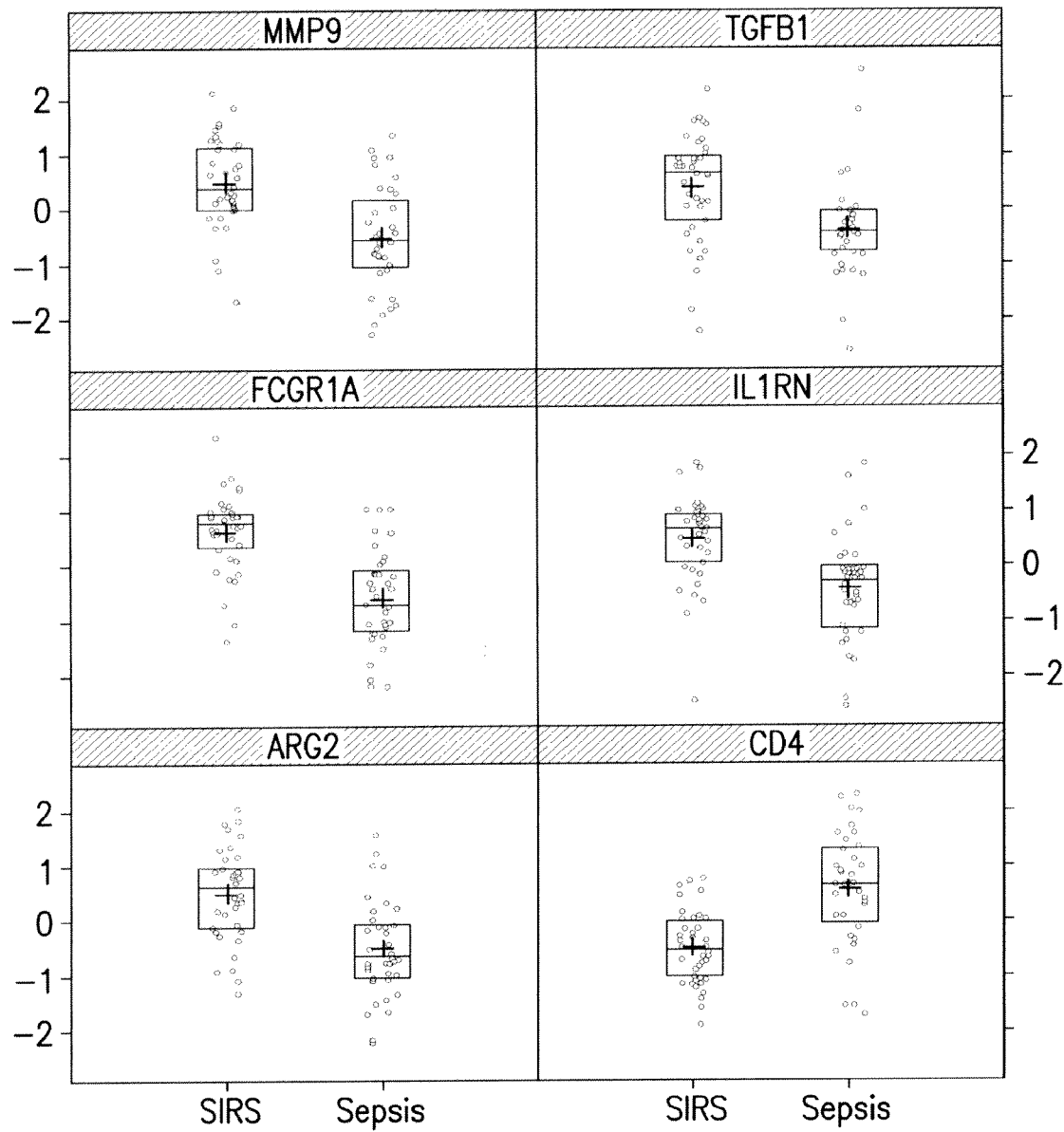

FIG. 41 illustrates the distribution of feature values of the biomarkers selected by the MART approach illustrated in FIG. 40 between the Sepsis and SIRS groups using $T_{-12}$ static data obtained from an RT-PCR discovery training population.

Figure 42:
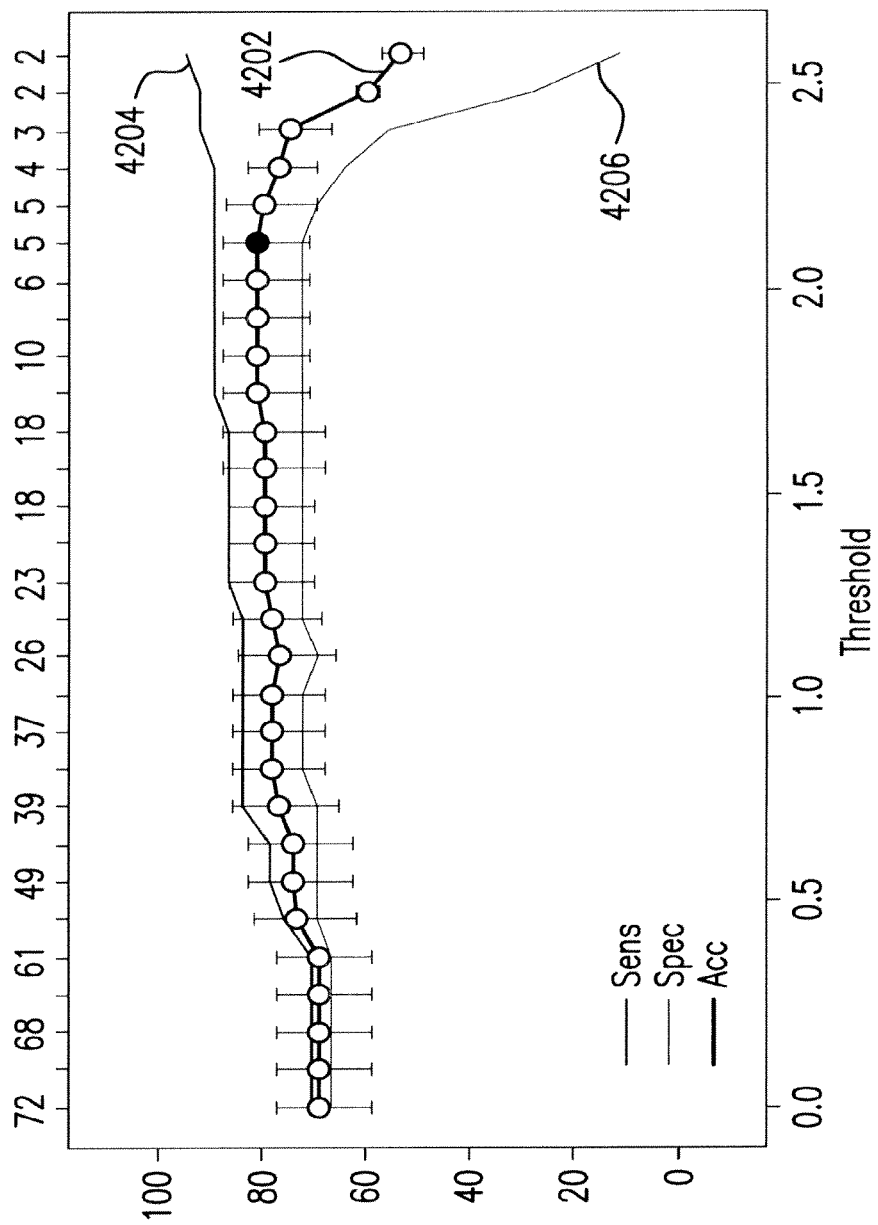

FIG. 42 illustrates the overall accuracy, with 95% confidence interval bars, specificity, and sensitivity of a decision rule developed with predictive analysis of microarrays (PAM) using the biomarkers of the present invention using $T_{-12}$ static data obtained from an RT-PCR discovery training population.

Figure 43:
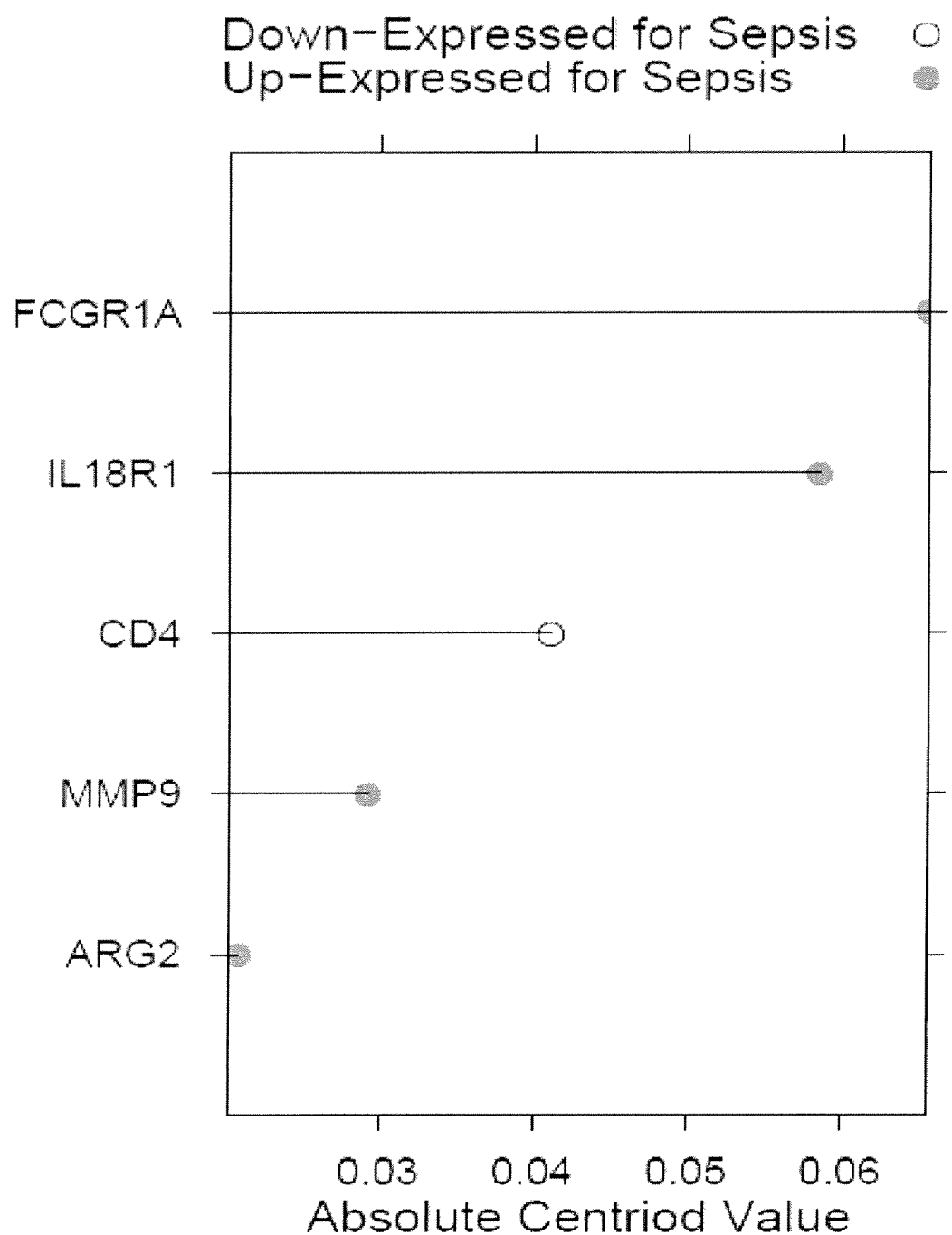

FIG. 43 is a list of biomarkers, rank-ordered by their respective degrees of discriminatory power, identified by PAM using $T_{-12}$ static data obtained from an RT-PCR discovery training population.

Figure 44:
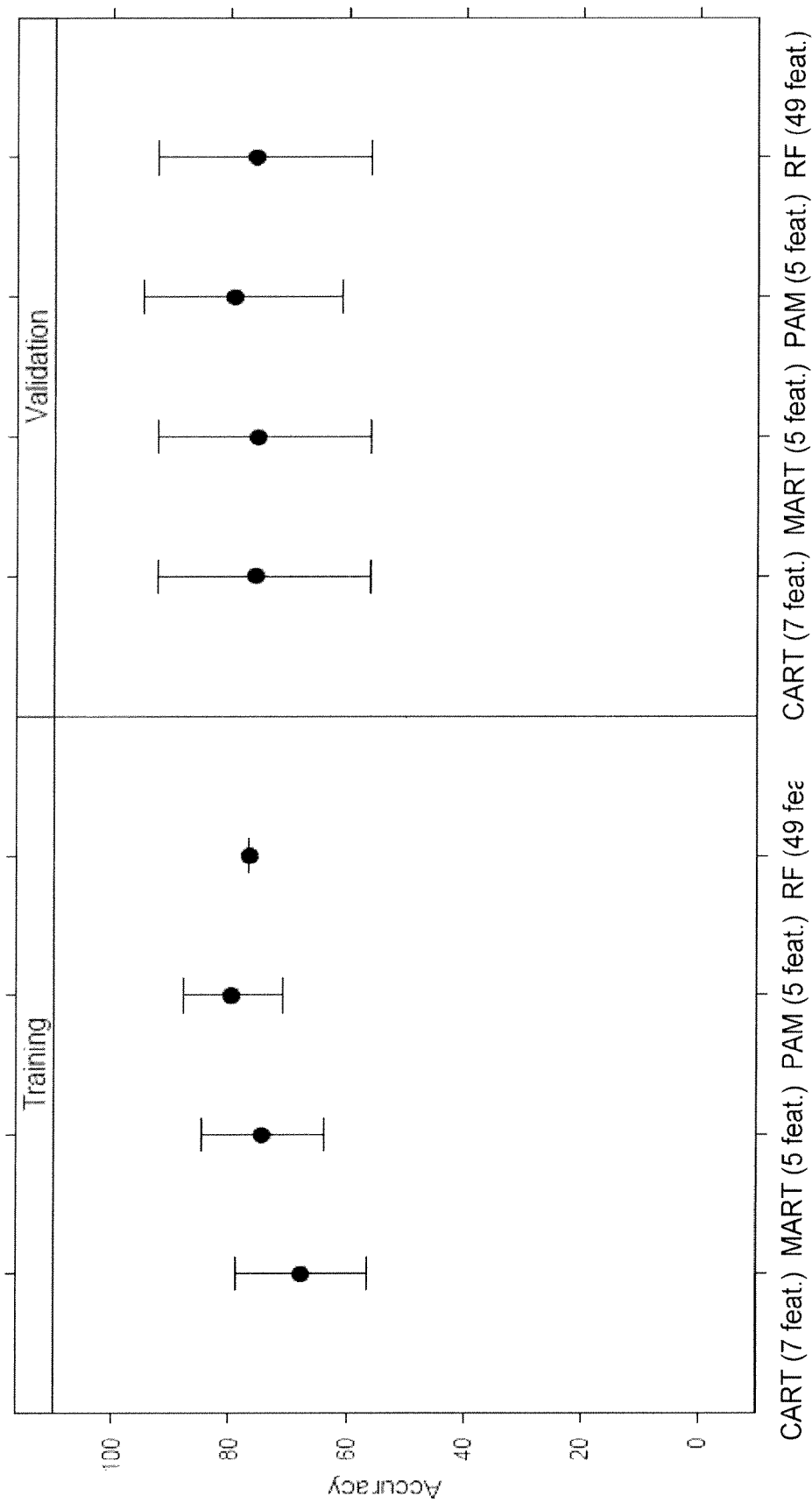

FIG. 44 provides a summary of the CART, MART, PAM, and random forests (RF) classification algorithm (decision rule) performance and associated 95% confidence intervals using $T_{-12}$ static data obtained from an RT-PCR discovery training population.

Figure 45:
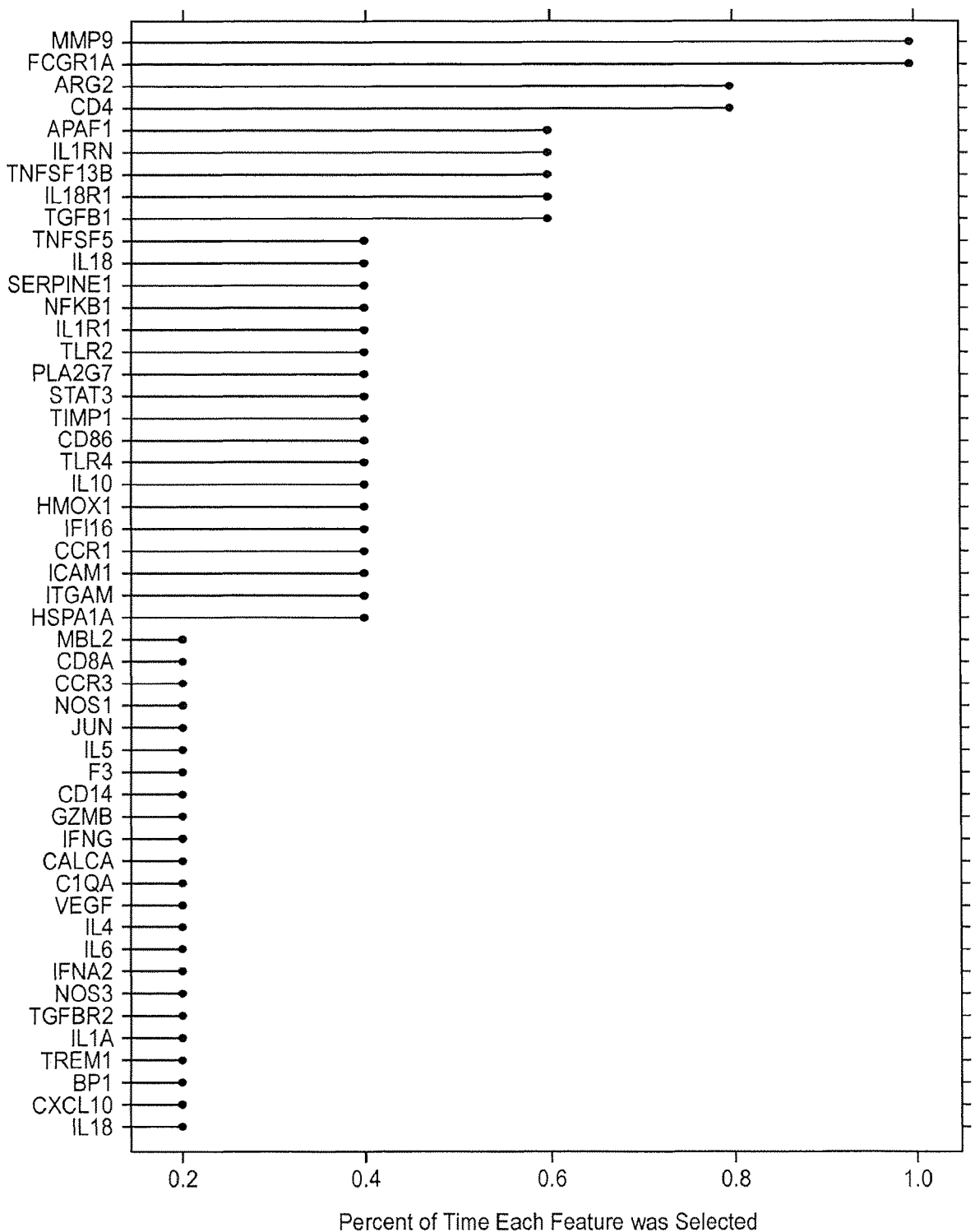

FIG. 45 identified fifty selected biomarkers selected based on the decision rule performance summarized in FIG. 44.

Figure 46:
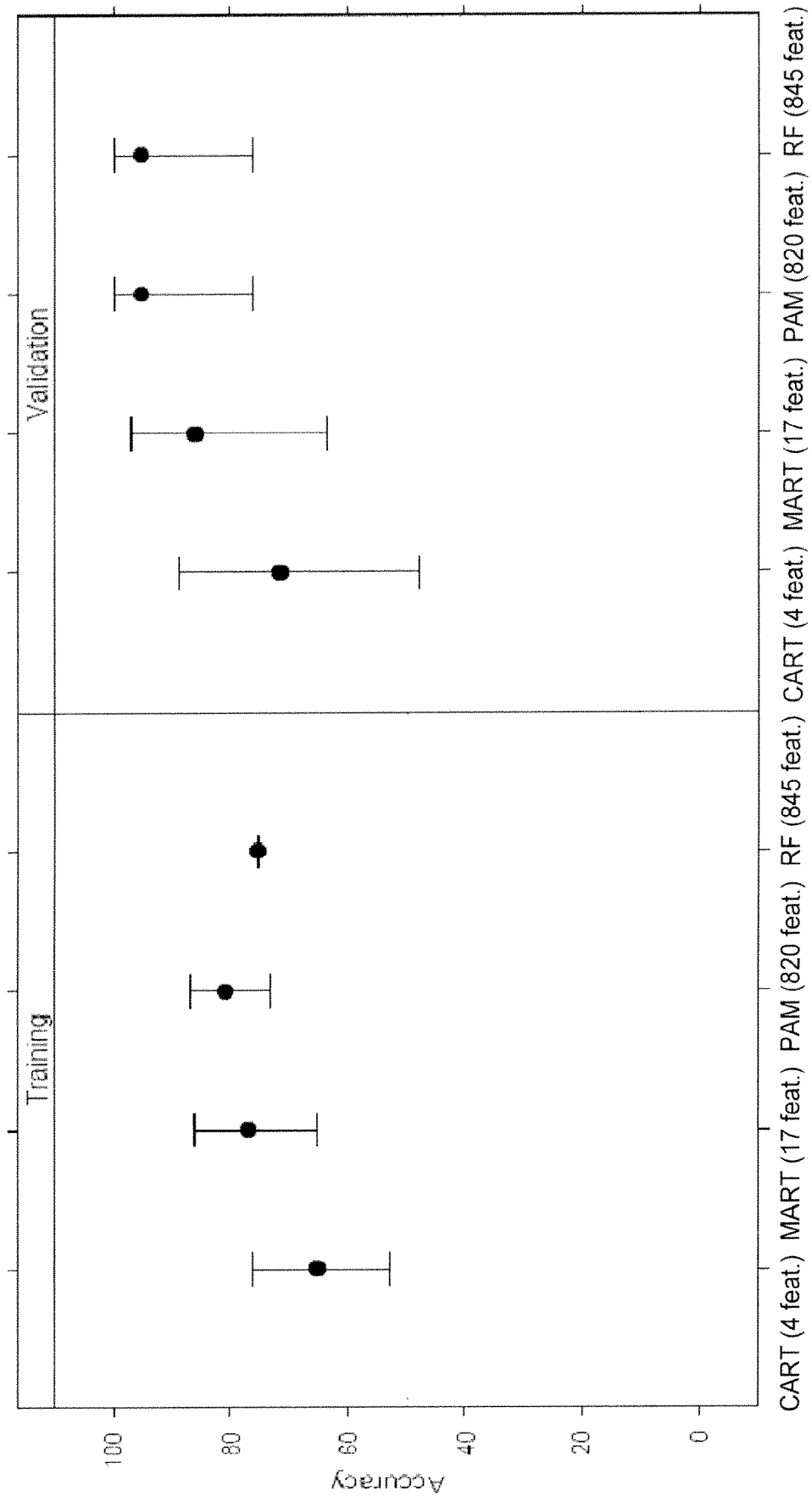

FIG. 46 provides a summary of the CART, MART, PAM, and random forests (RF) classification algorithm (decision rule) performance and associated 95% confidence intervals using $T_{-12}$ static data obtained from an Affymetrix gene chip discovery training population.

Figure 47:
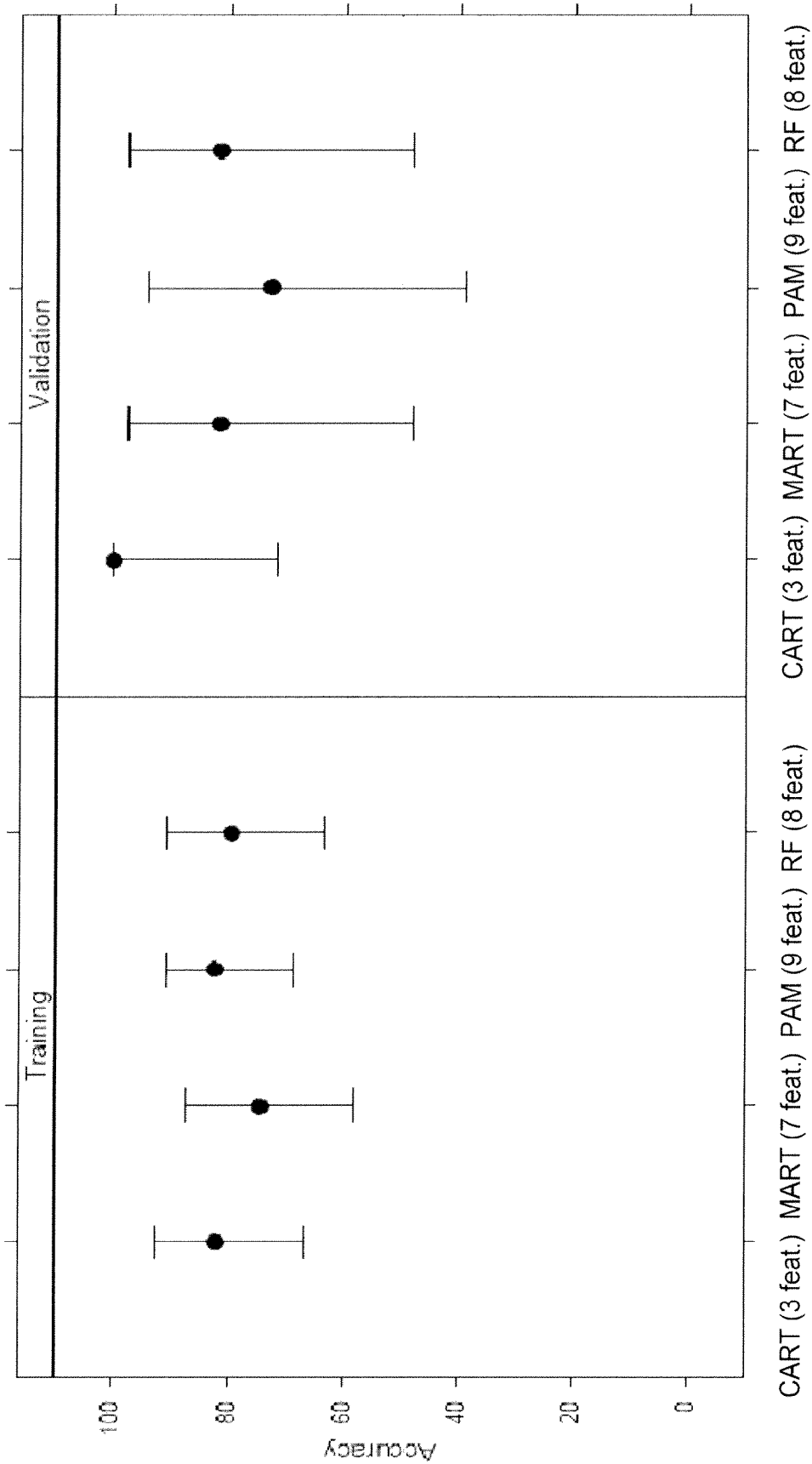

FIG. 47 provides a summary of the CART, MART, PAM, and random forests (RF) classification algorithm (decision rule) performance and associated 95% confidence intervals using $T_{-12}$ static data obtained from an RT-PCR confirmatory training population.

Figure 48:
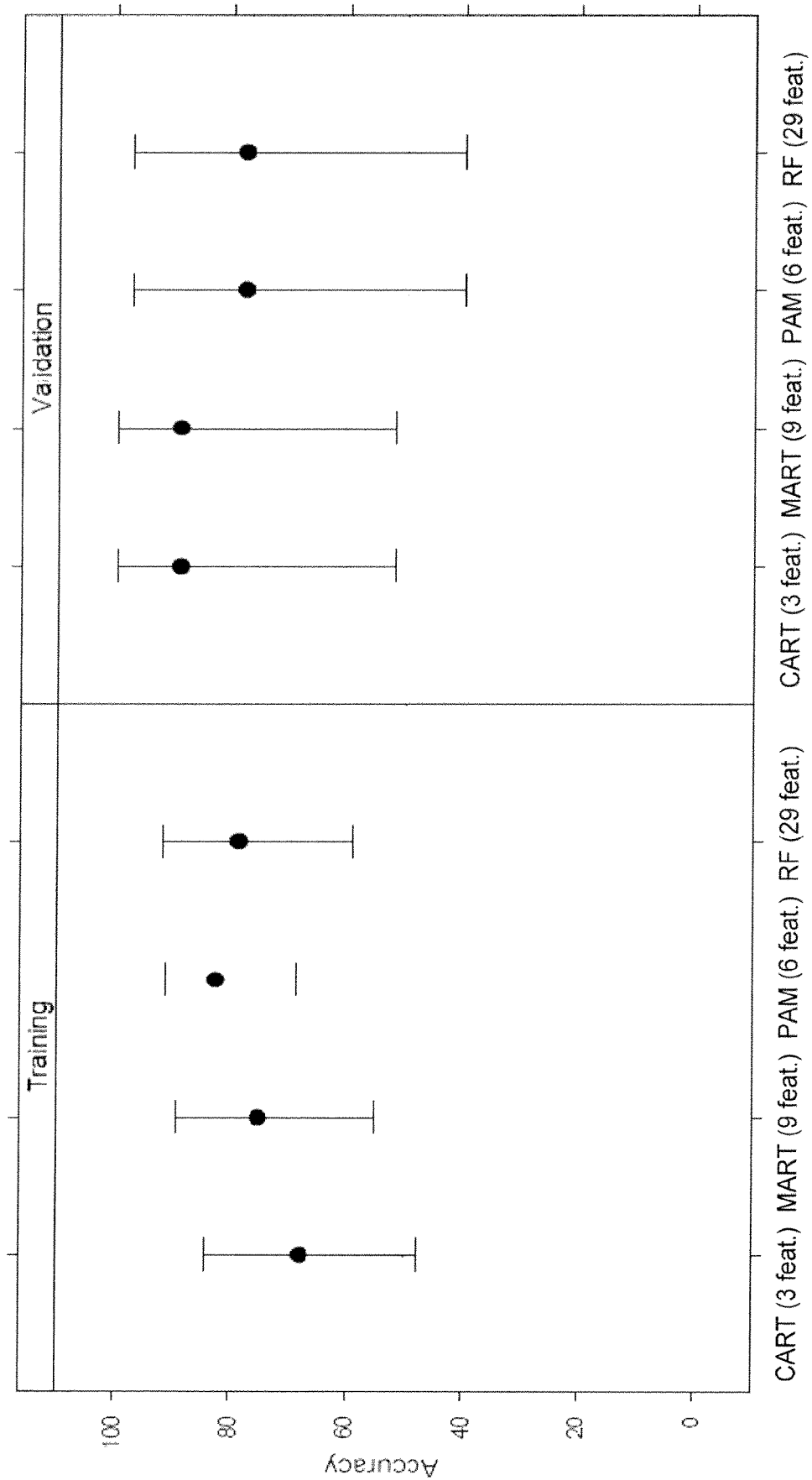

FIG. 48 provides a summary of the CART, MART, PAM, and random forests (RF) classification algorithm (decision rule) performance and associated 95% confidence intervals using $T_{-12}$ static data obtained from a combined pool of a Affymetrix gene chip confirmatory training population and an RT-PCR confirmatory training population.

Figure 49:
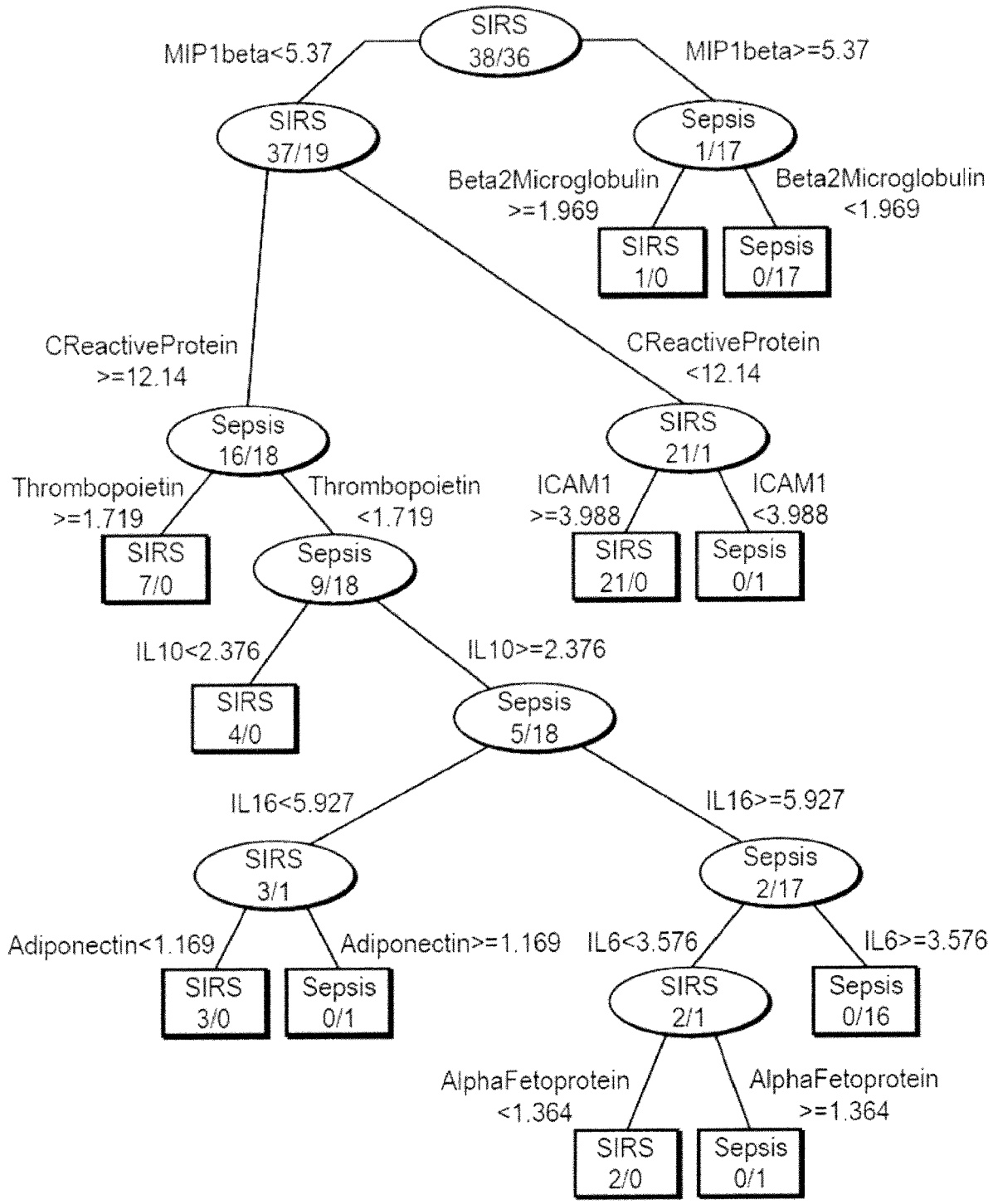

FIG. 49 illustrates a classification and regression tree for discriminating between a SIRS phenotypic state characterized by the onset of sepsis and a SIRS phenotypic state characterized by the absence of sepsis using $T_{-12}$ static data obtained from a bead-based protein discovery training population in accordance with an embodiment of the present invention.

Figure 50A:
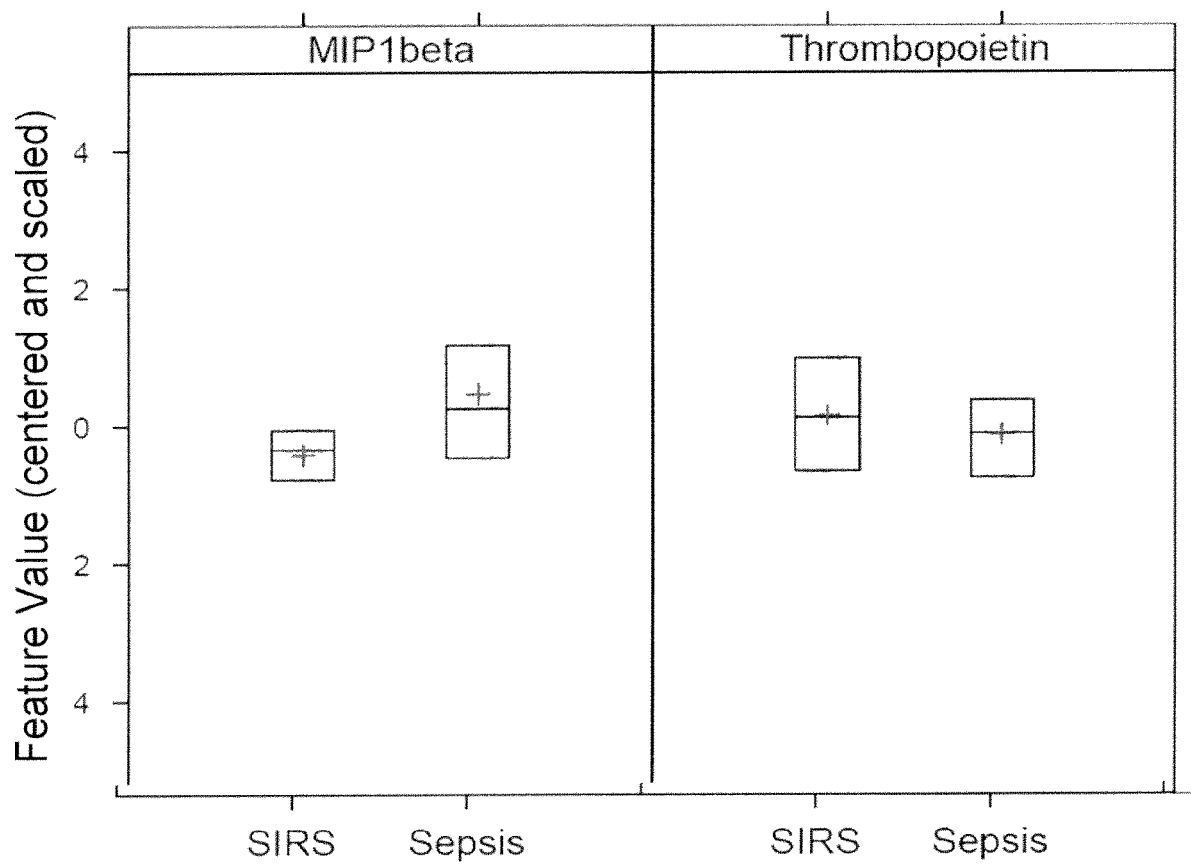
Figure 50B:
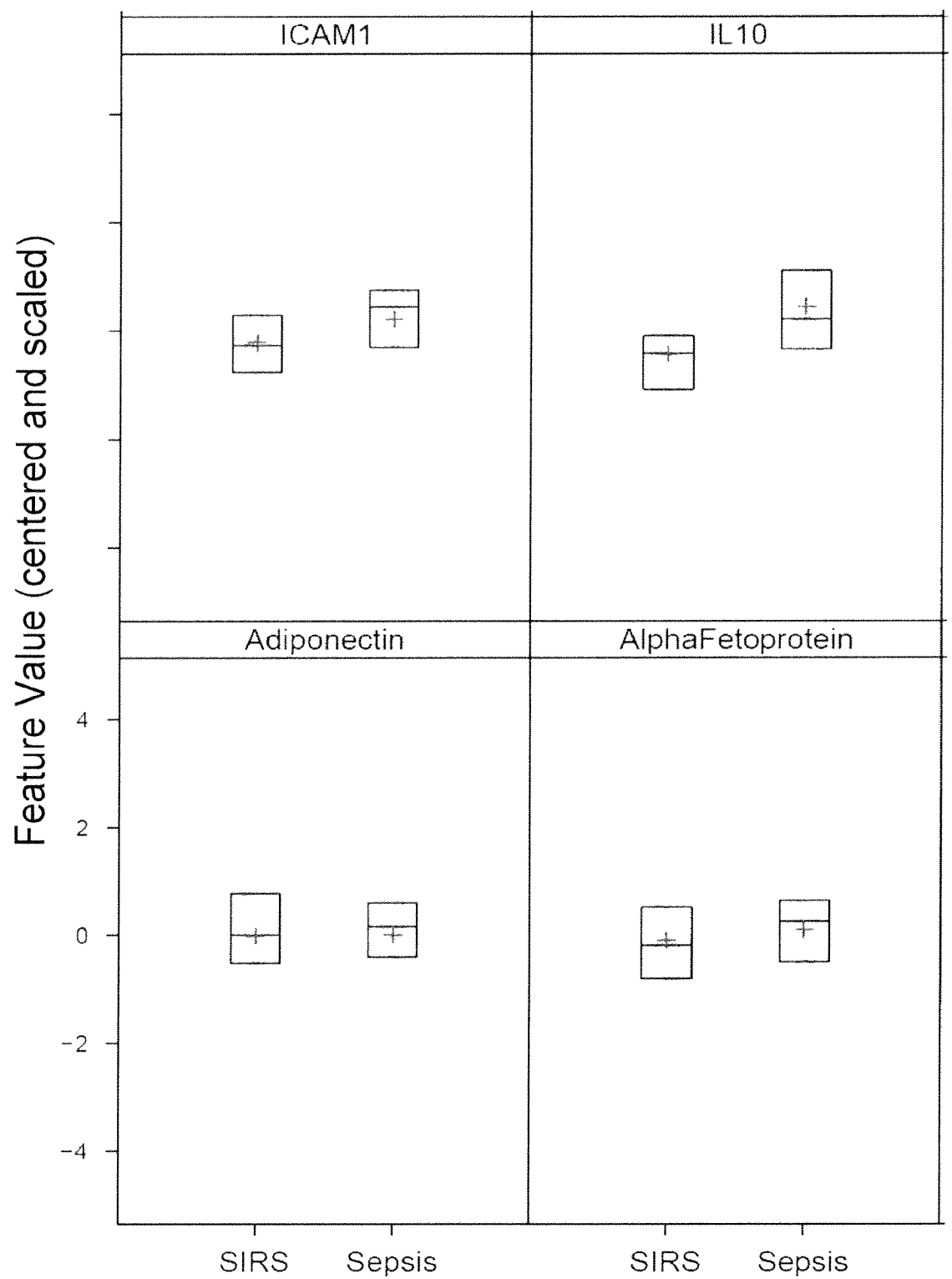
Figure 50C:
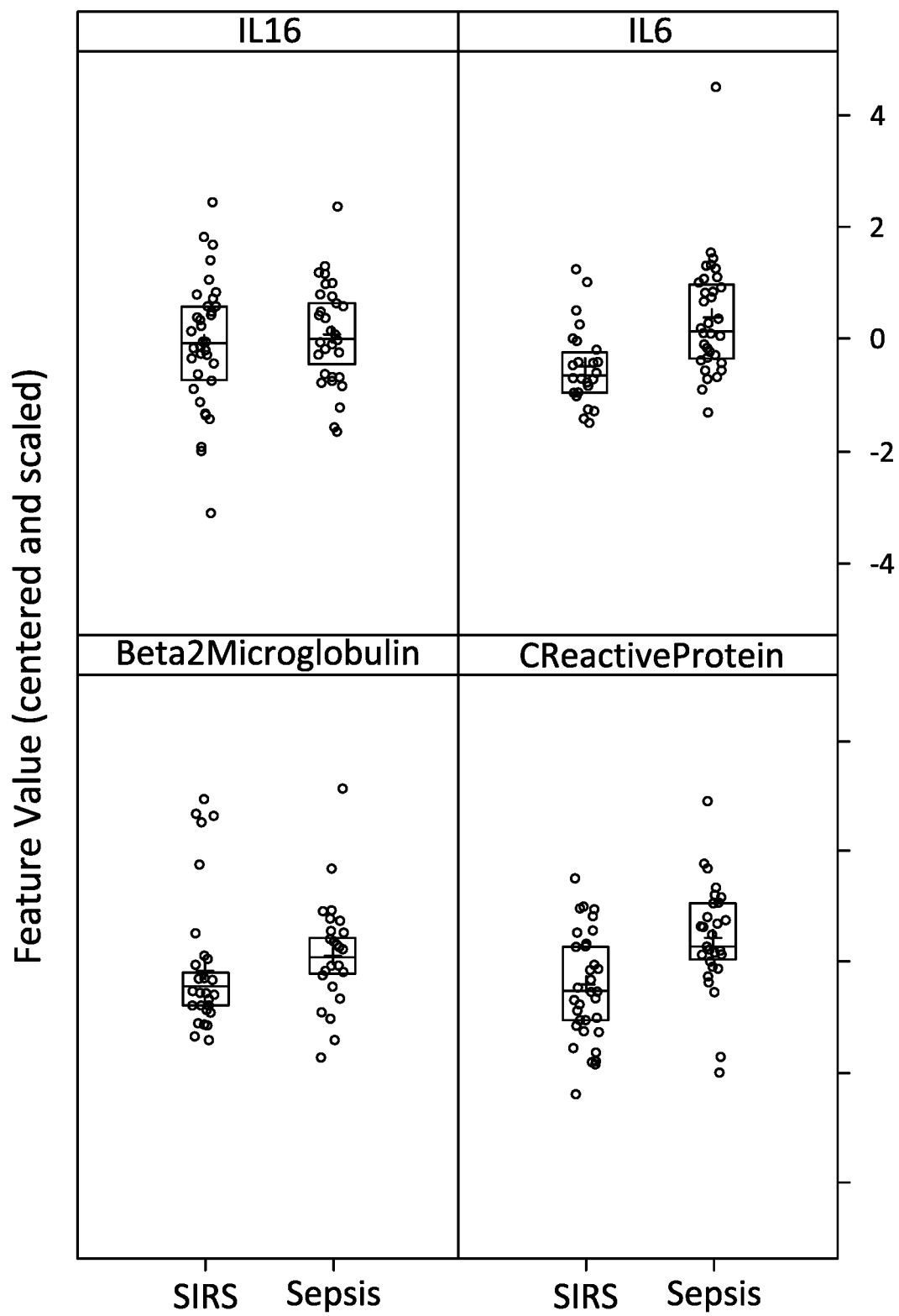

FIGS. 50A, 50B and 50C shows the distribution of feature values for ten biomarkers: (A) MIP1beta, thrombopoietin; (B) ICAM1, IL-10, adiponectin, alpha fetoprotein; and (C) IL-16, IL-6, beta-2 microglobulin, and C reactive protein; used in the decision tree of FIG. 49 across $T_{-12}$ static data obtained from a bead-based protein discovery training population in accordance with an embodiment of the present invention.

FIG. 51 illustrates the overall accuracy, sensitivity, and specificity of 64 trees used to train a decision tree using the Random Forests method based upon $T_{-12}$ static data obtained from a bead-based protein discovery training population in accordance with an embodiment of the present invention.

Figure 52:
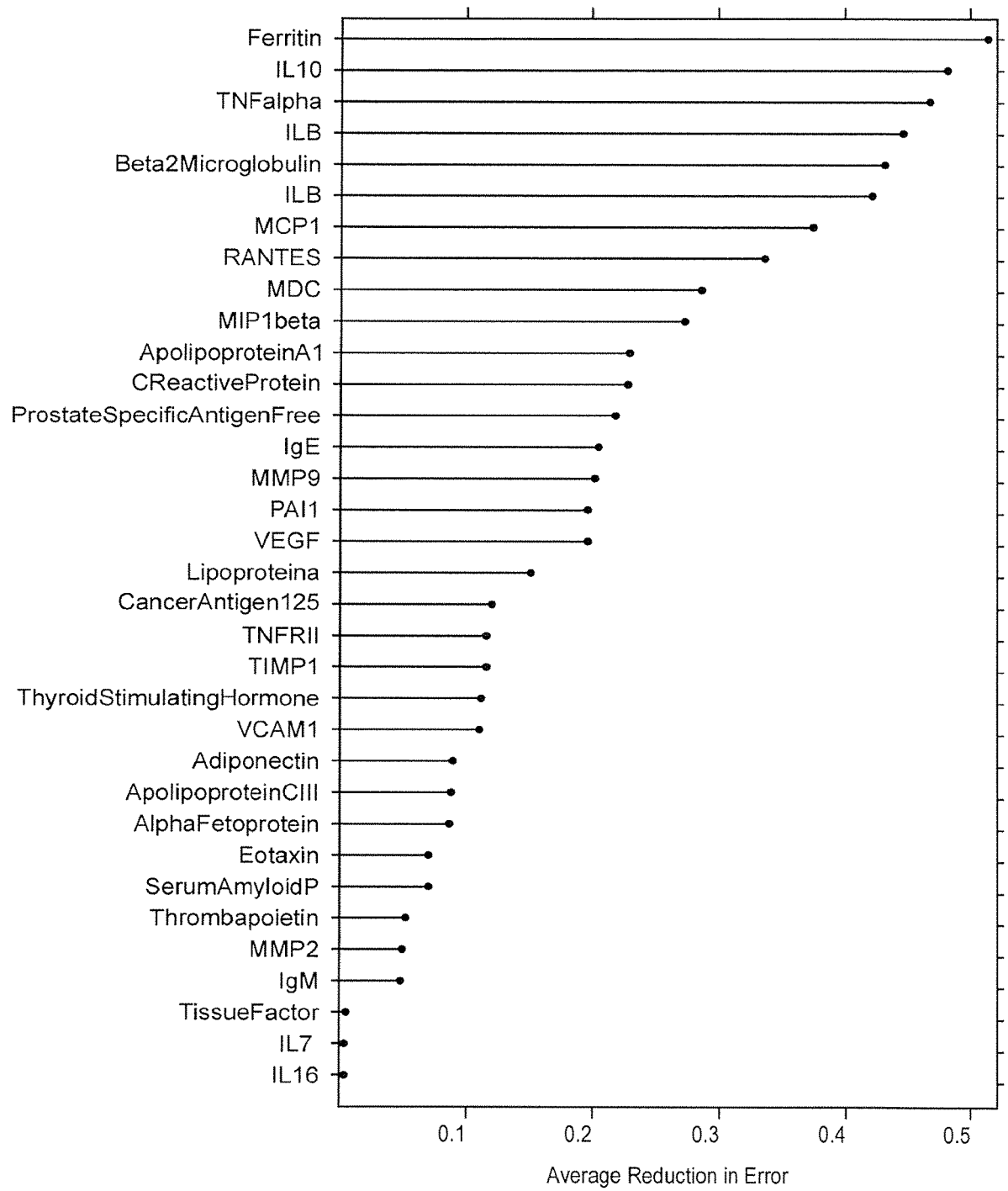

FIG. 52 illustrates the biomarker importance in the decision rule trained using the trees of FIG. 51.

Figure 53:
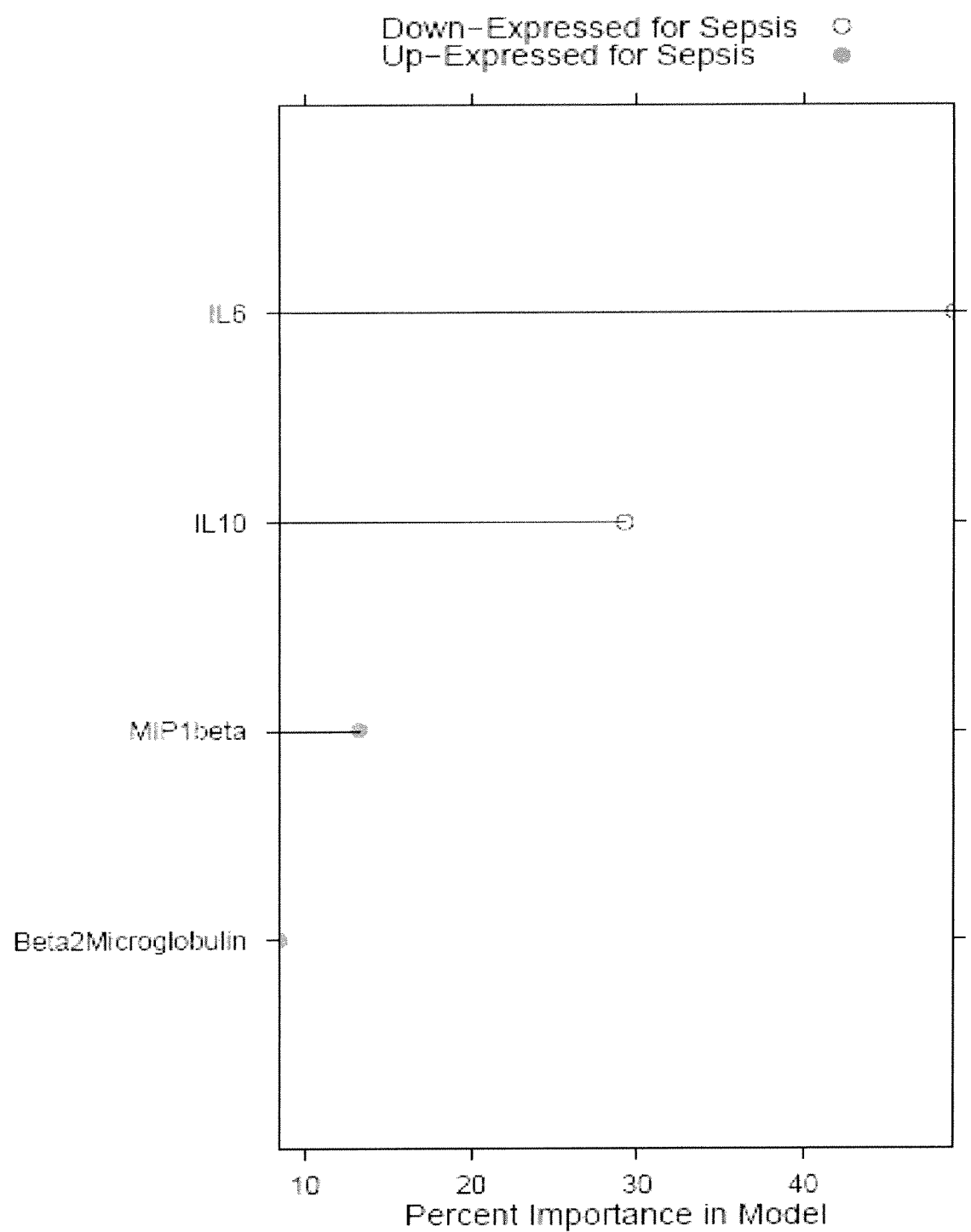

FIG. 53 illustrates a calculation of biomarker importance, summing to 100%, determined by a multiple additive regression tree (MART) approach using $T_{-12}$ static data obtained from a bead-based protein discovery training population in accordance with an embodiment of the present invention.

Figure 54:
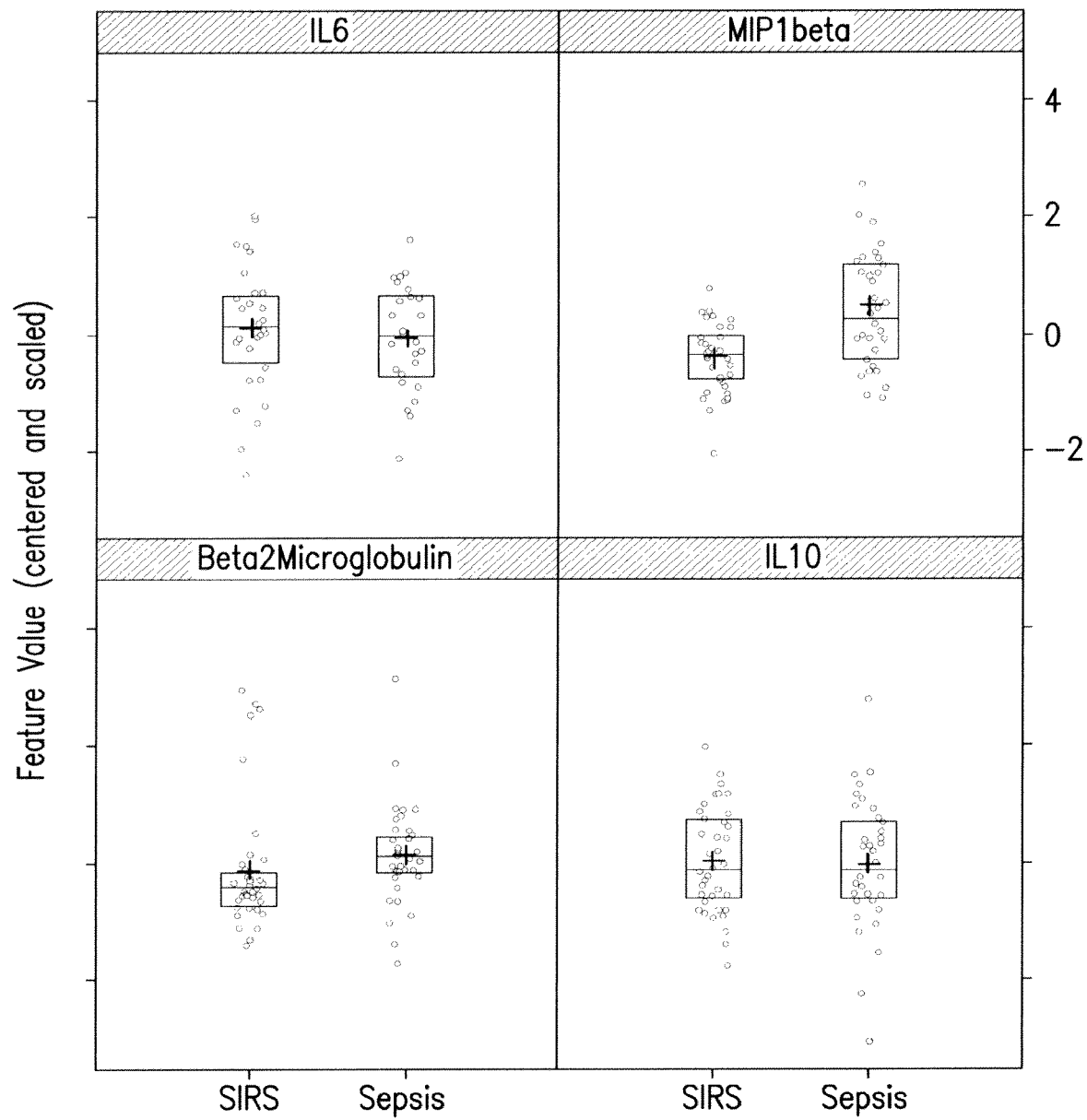

FIG. 54 illustrates the distribution of feature values of the biomarkers selected by the MART approach illustrated in FIG. 53 between the Sepsis and SIRS groups using $T_{-12}$ static data obtained from a bead-based protein discovery training population in accordance with an embodiment of the present invention.

Figure 55:
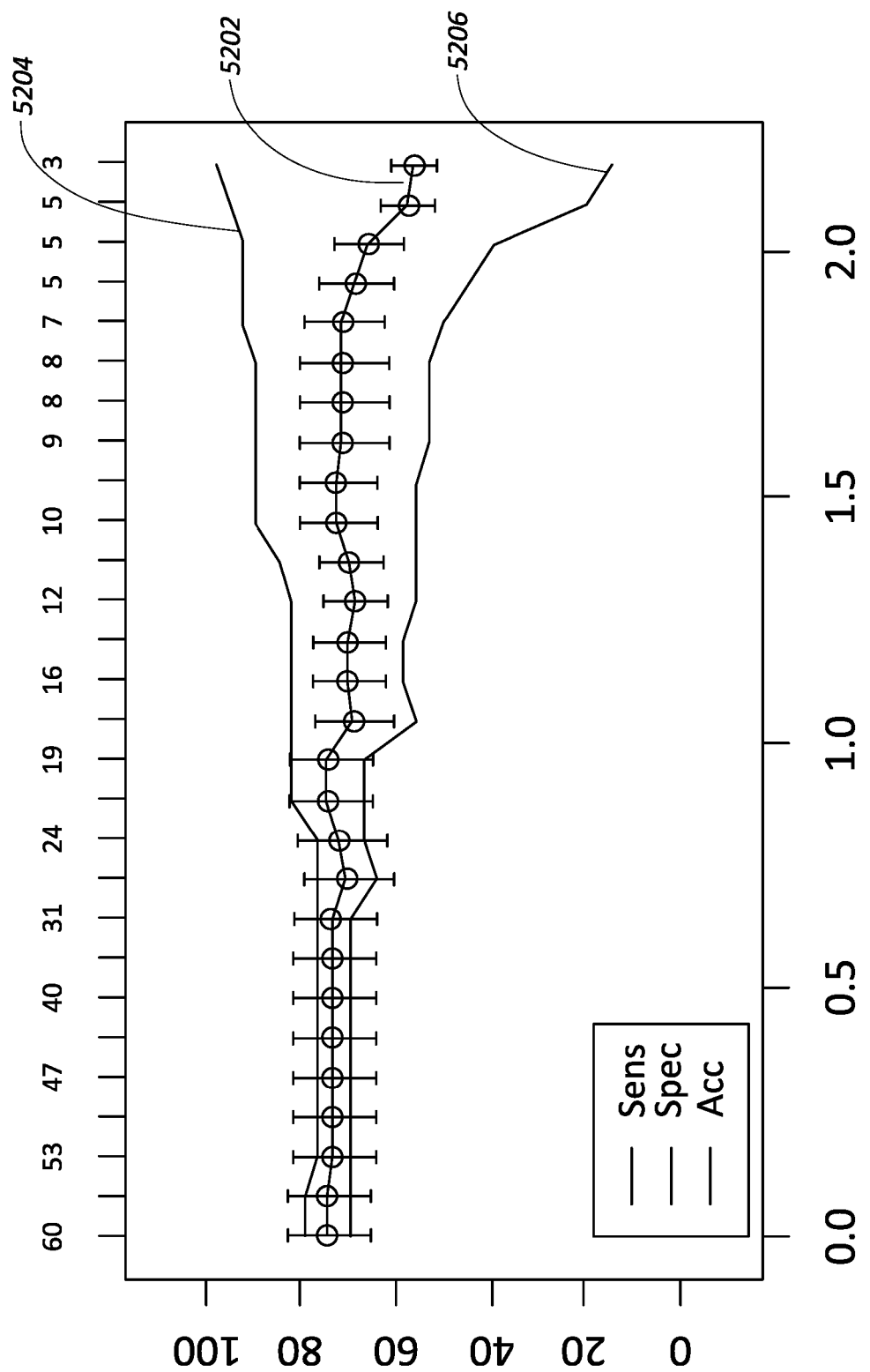

FIG. 55 illustrates the overall accuracy, with 95% confidence interval bars, specificity, and sensitivity of a decision rule developed with predictive analysis of microarrays (PAM) using the biomarkers of the present invention using $T_{-12}$ static data obtained from a bead-based protein discovery training population in accordance with an embodiment of the present invention.

Figure 56:
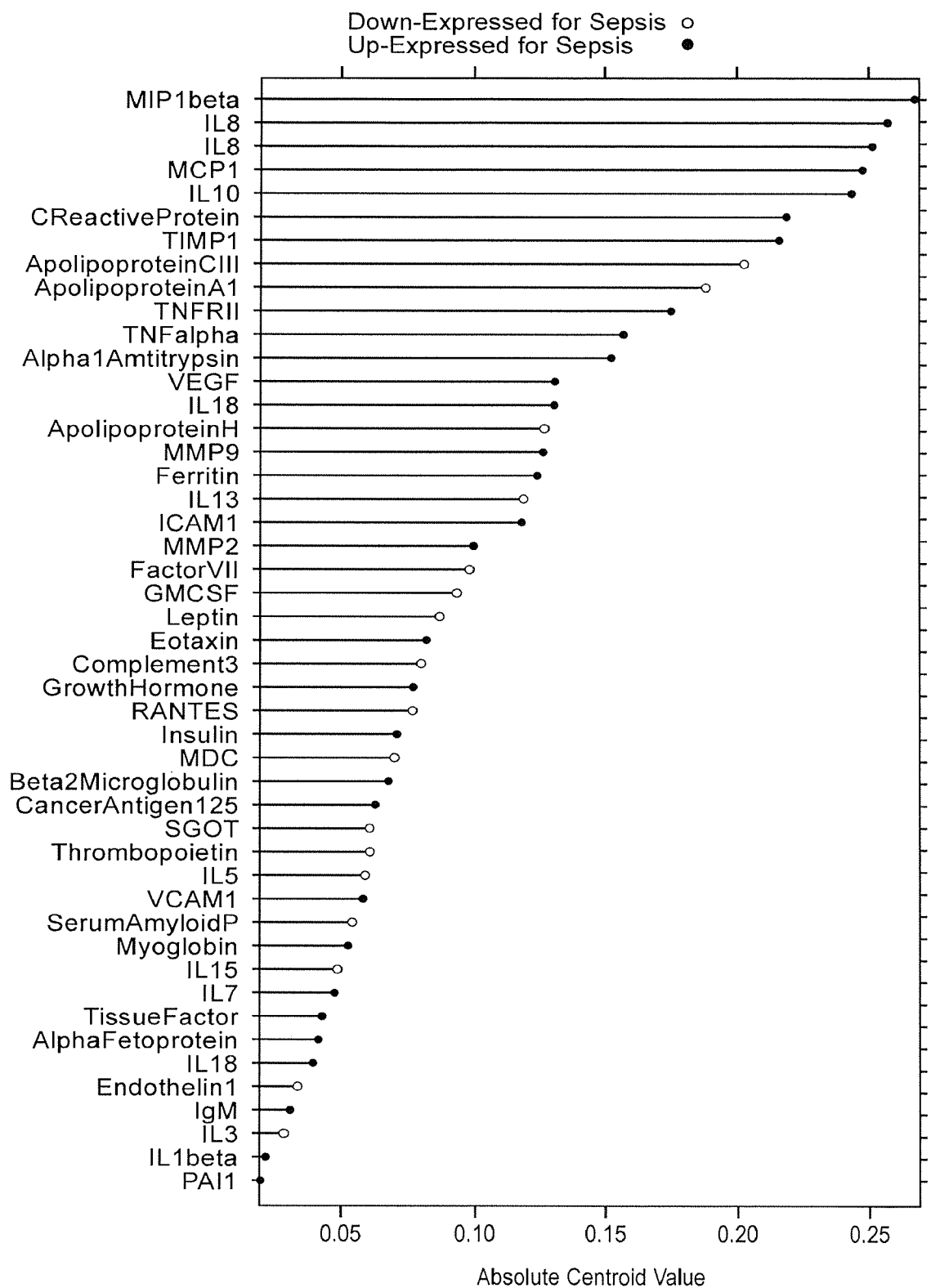

FIG. 56 is a list of biomarkers, rank-ordered by their respective degrees of discriminatory power, identified by PAM using $T_{-12}$ static data obtained from a bead-based protein discovery training population in accordance with an embodiment of the present invention.

Figure 57:
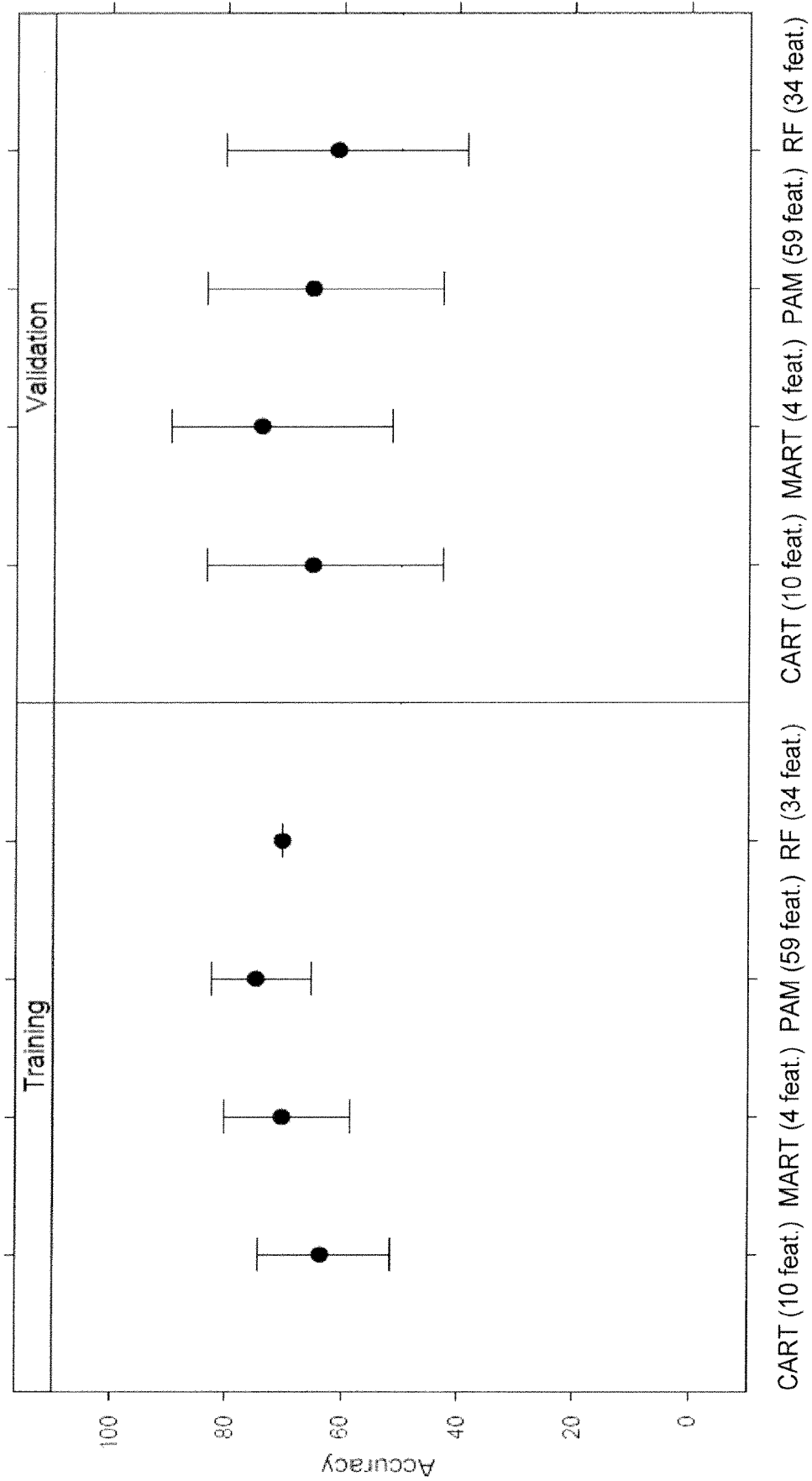

FIG. 57 provides a summary of the CART, MART, PAM, and random forests (RF) classification algorithm (decision rule) performance and associated 95% confidence intervals using $T_{-12}$ static data obtained from a bead-based protein discovery training population in accordance with an embodiment of the present invention.

Figure 58:
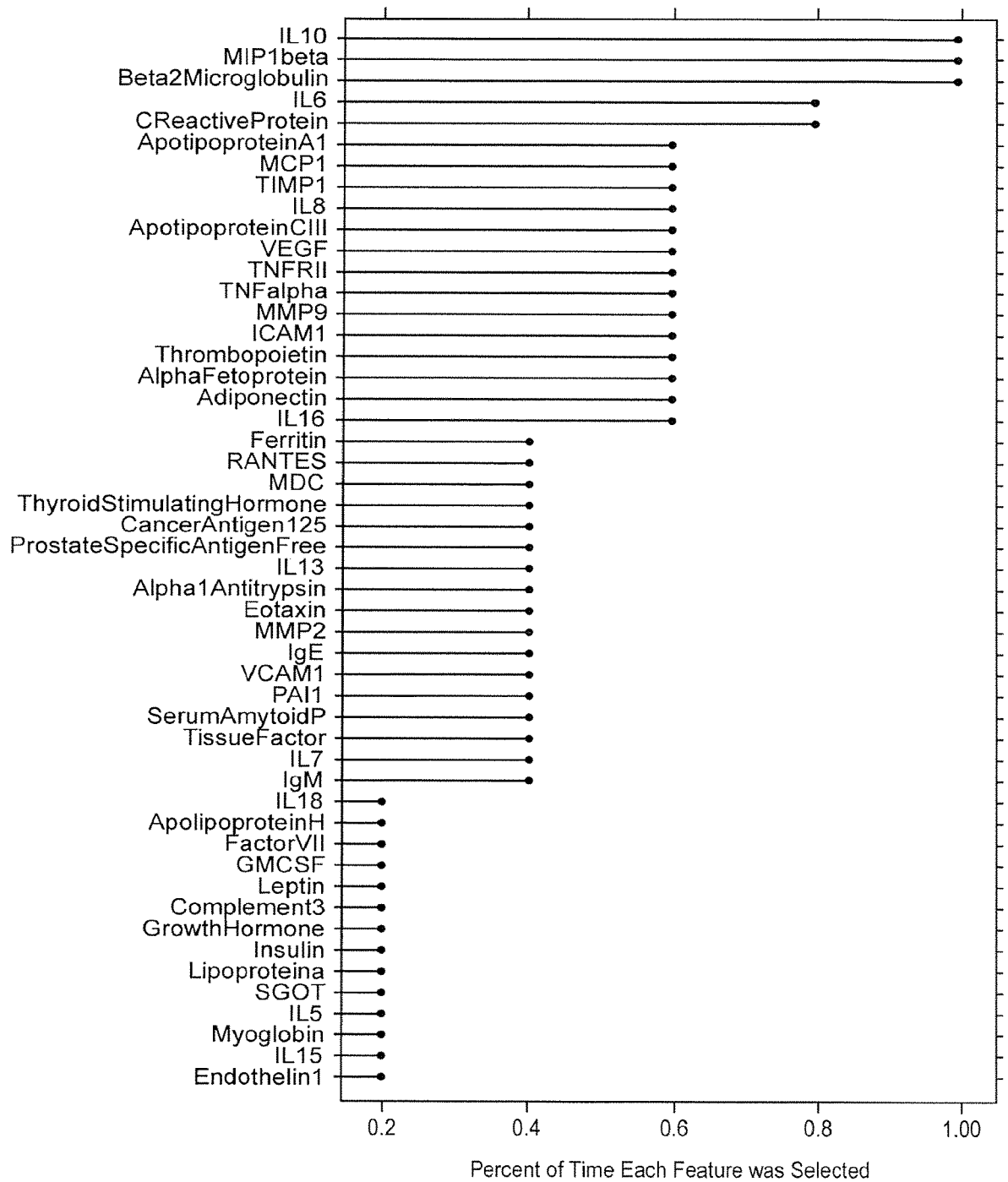

FIG. 58 illustrates the number of times that common biomarkers were found to be important across the decision rules developed using (i) CART, (ii) MART, (iii) PAM, (iv) random forests, and (v) the Wilcoxon (adjusted) test using $T_{-12}$ static data obtained from a bead-based protein discovery training population in accordance with an embodiment of the present invention.

Figure 59:
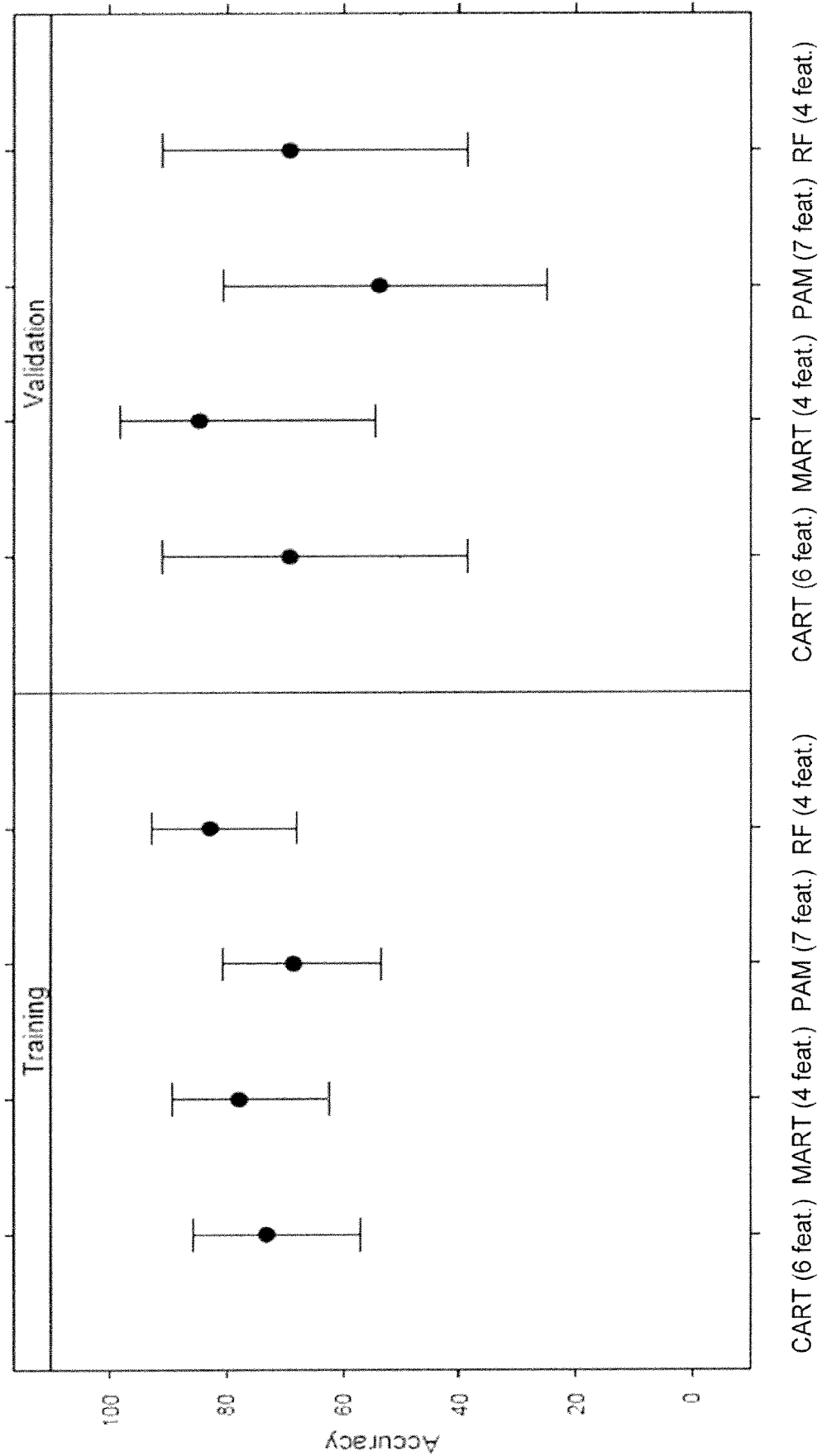

FIG. 59 provides a summary of the CART, MART, PAM, and random forests (RF) classification algorithm (decision rule) performance and associated 95% confidence intervals using $T_{-12}$ static data obtained from a bead-based protein confirmation training population in accordance with an embodiment of the present invention.

Figure 60A:
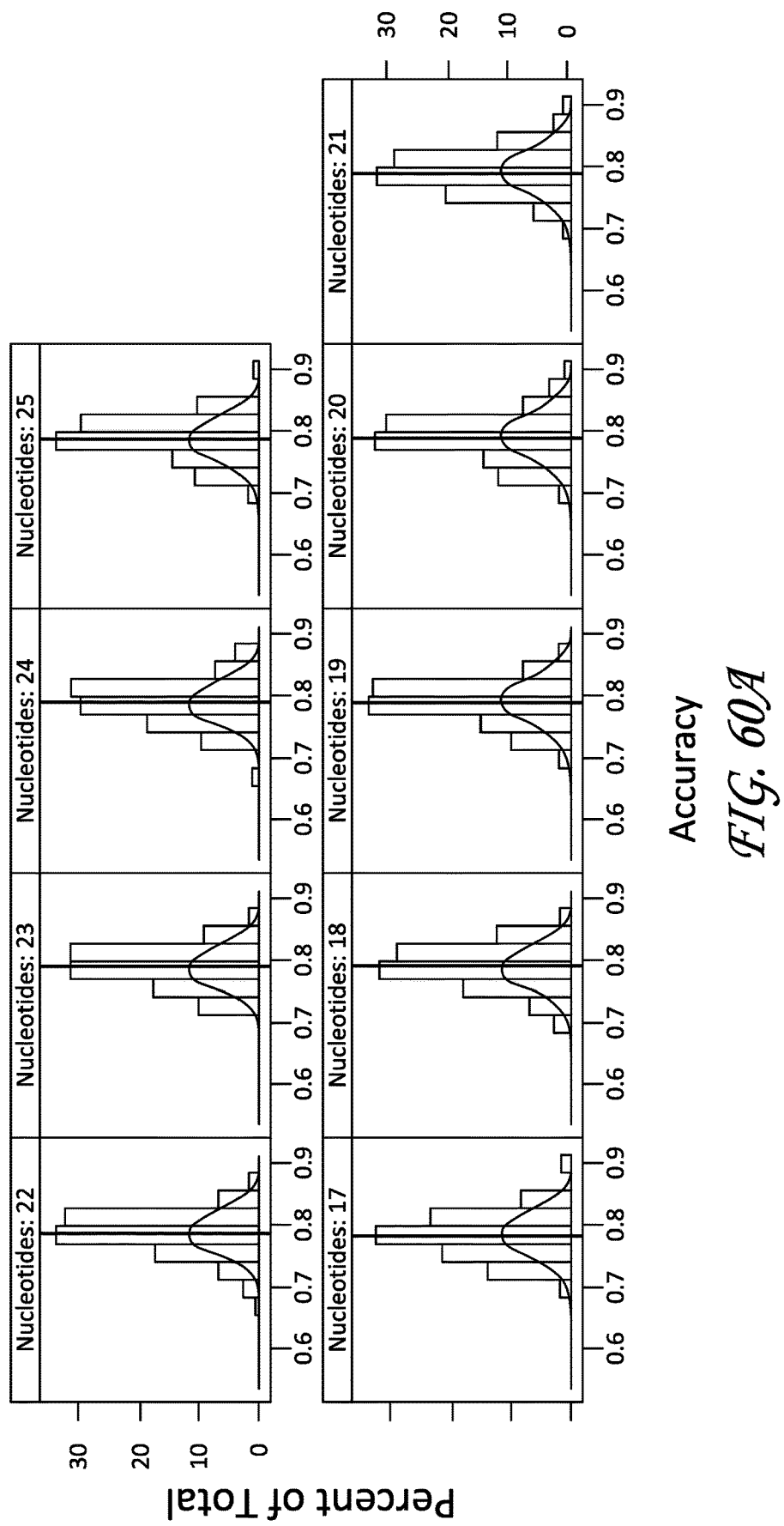
Figure 60B:
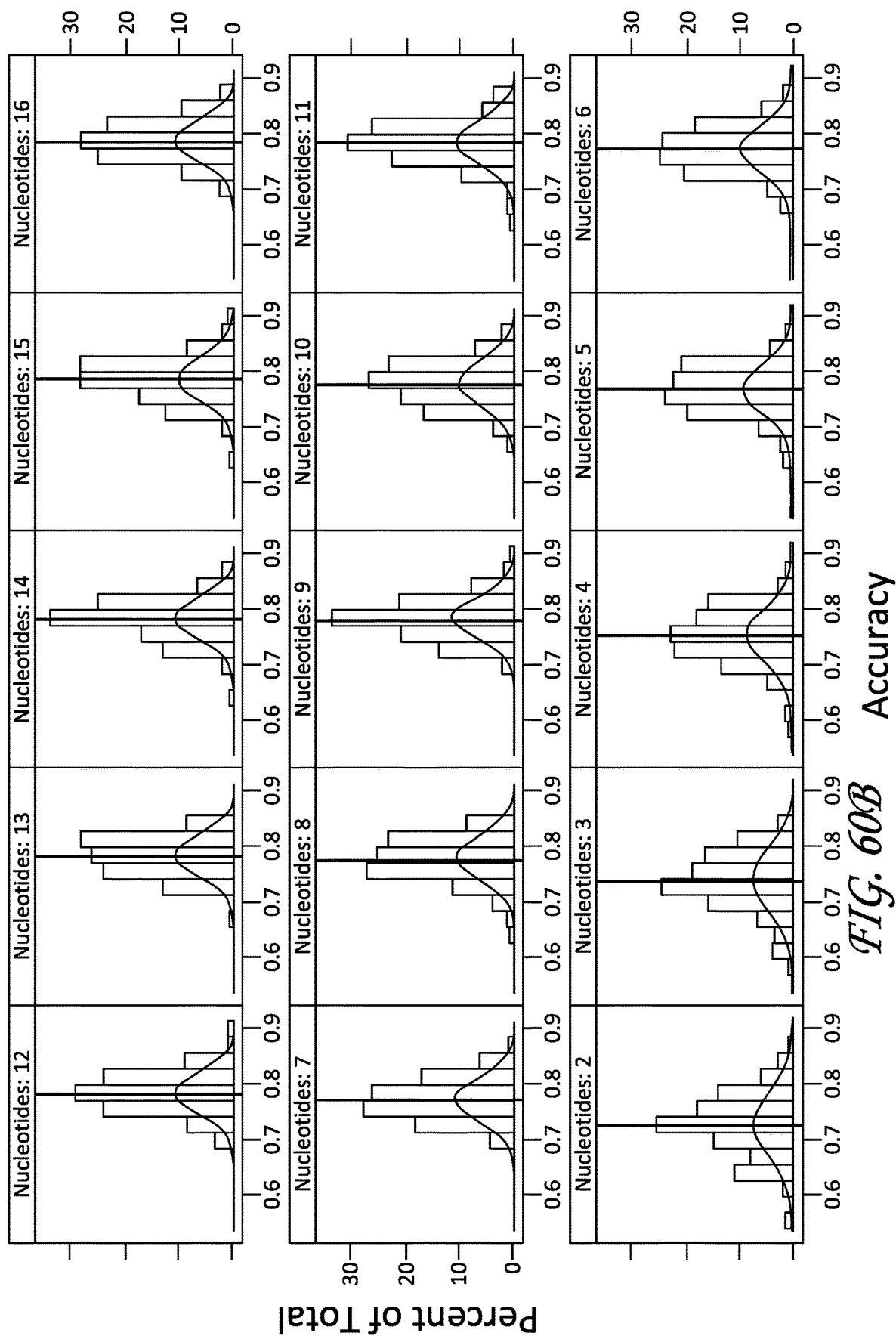

FIGS. 60A and 60B plot the sepsis predicting accuracy of each of 24 families of subcombinations from Table J, using $T_{-12}$ nucleic acid data, in a bar graph fashion, in accordance with an embodiment of the present invention: (A) 17-25 nucleotides; (B) 2-16 nucleotides.

Figure 61A:
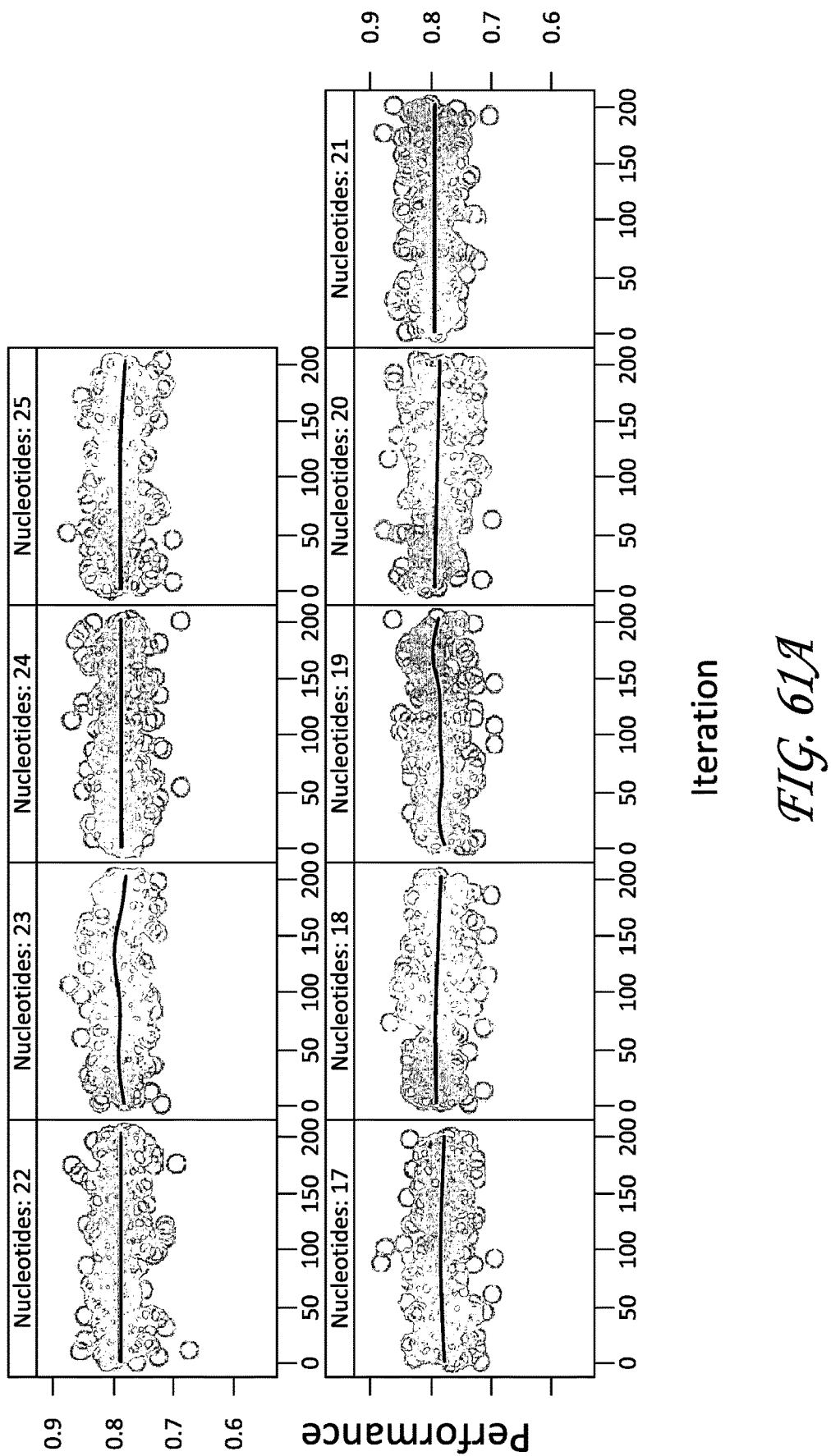
Figure 61B:
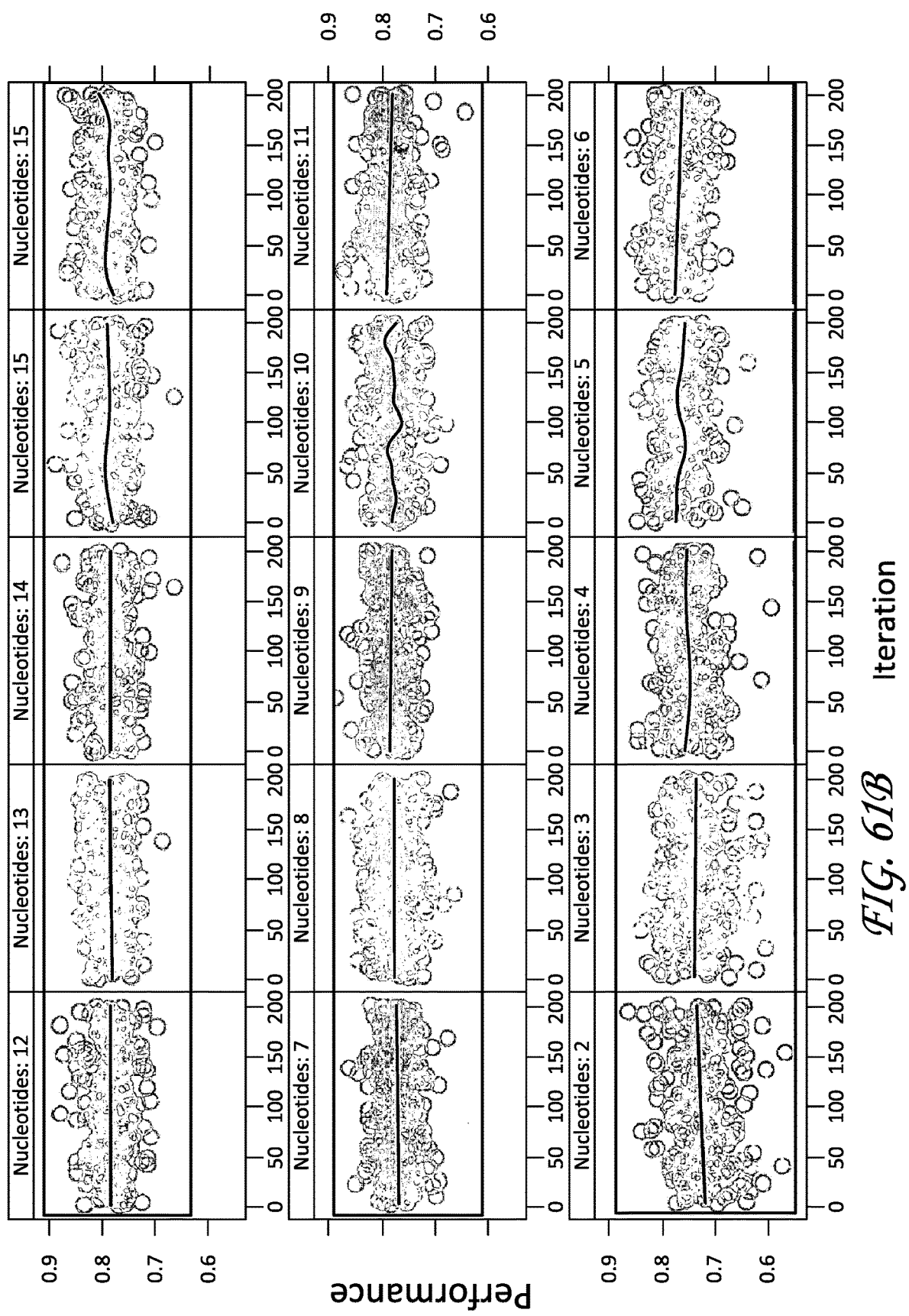

FIGS. 61A and 61B plot the sepsis predicting performance (accuracy) of each individual subcombination in each of 24 families of subcombinations, for a total of 4800 subcombinations from Table J, using $T_{-12}$ nucleic acid data, in accordance with an embodiment of the present invention: (A) 17-25 nucleotides; (B) 2-16 nucleotides.

Figure 62A:
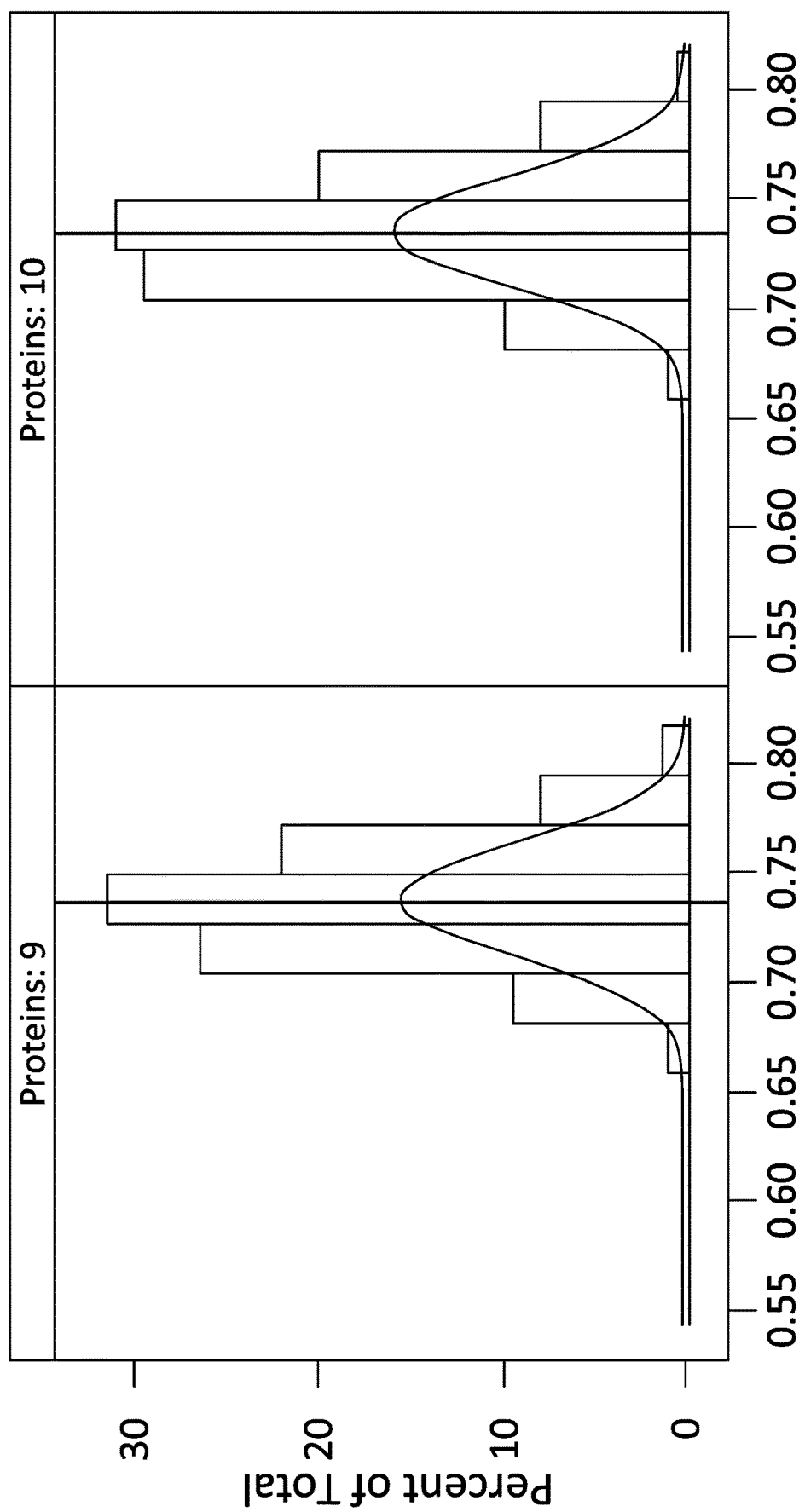
Figure 62B:
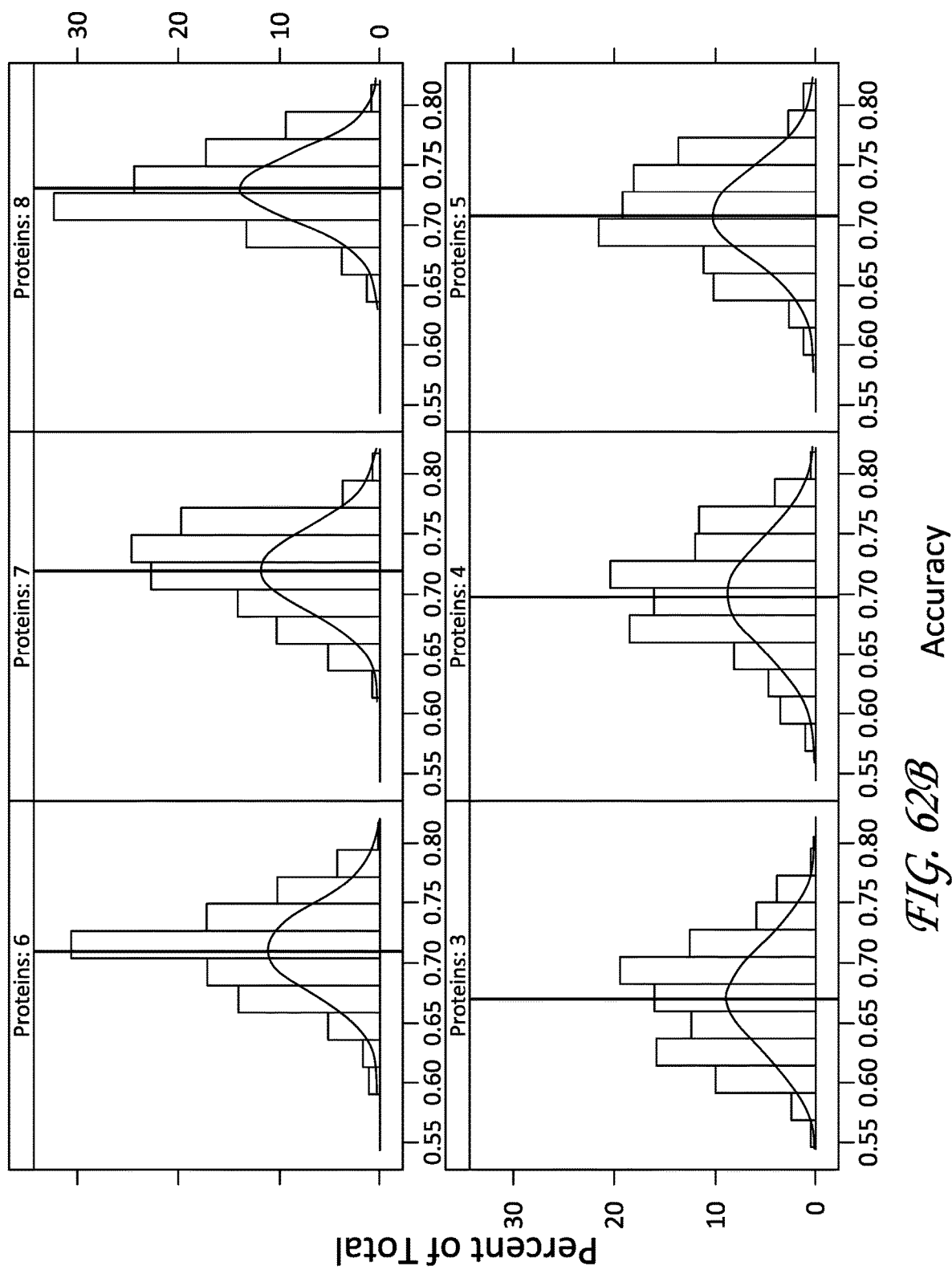

FIGS. 62A and 62B plot the sepsis predicting accuracy of each of 8 families of subcombinations from Table K, using $T_{-12}$ protein data, in a bar graph fashion, in accordance with an embodiment of the present invention: (A) 9-10 proteins; (B) 3-8 proteins.

Figure 63A:
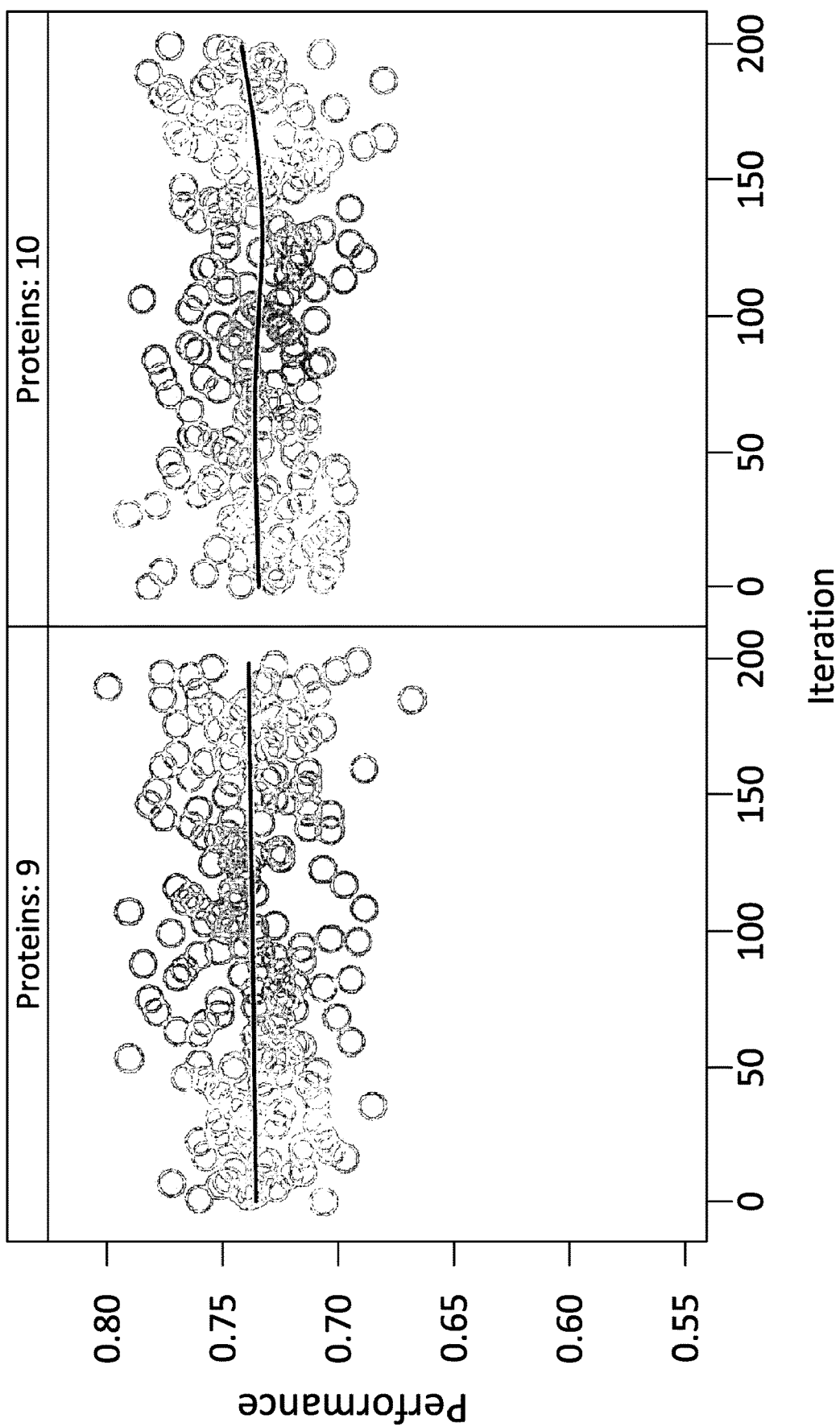
Figure 63B:
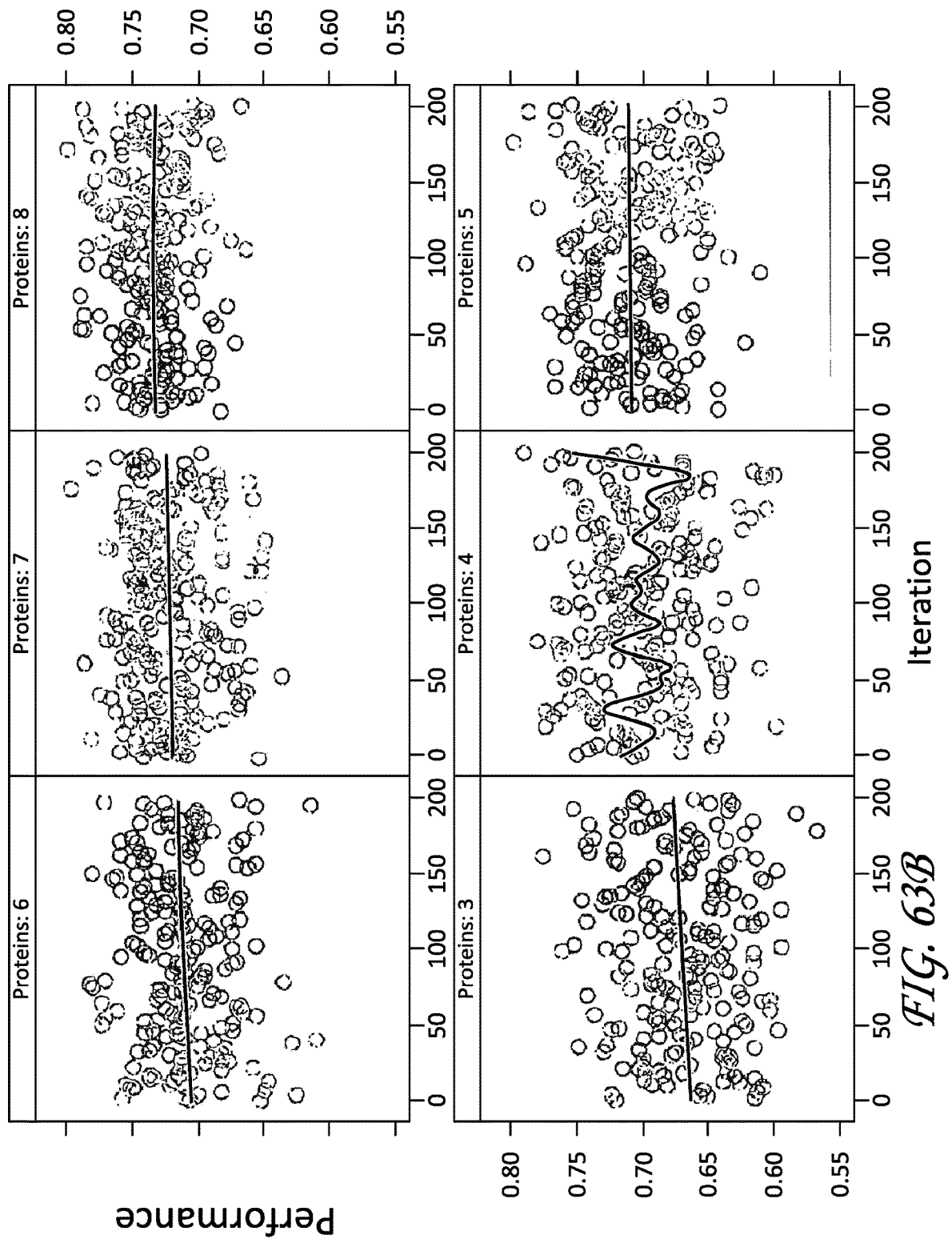

FIGS. 63A and 63B plot the sepsis predicting performance (accuracy) of each individual subcombination in each of 8 families of subcombinations, for a total of 1600 subcombinations from Table K, using $T_{-12}$ protein data, in accordance with an embodiment of the present invention: (A) 9-10 proteins; (B) 3-8 proteins.

Figure 64A:
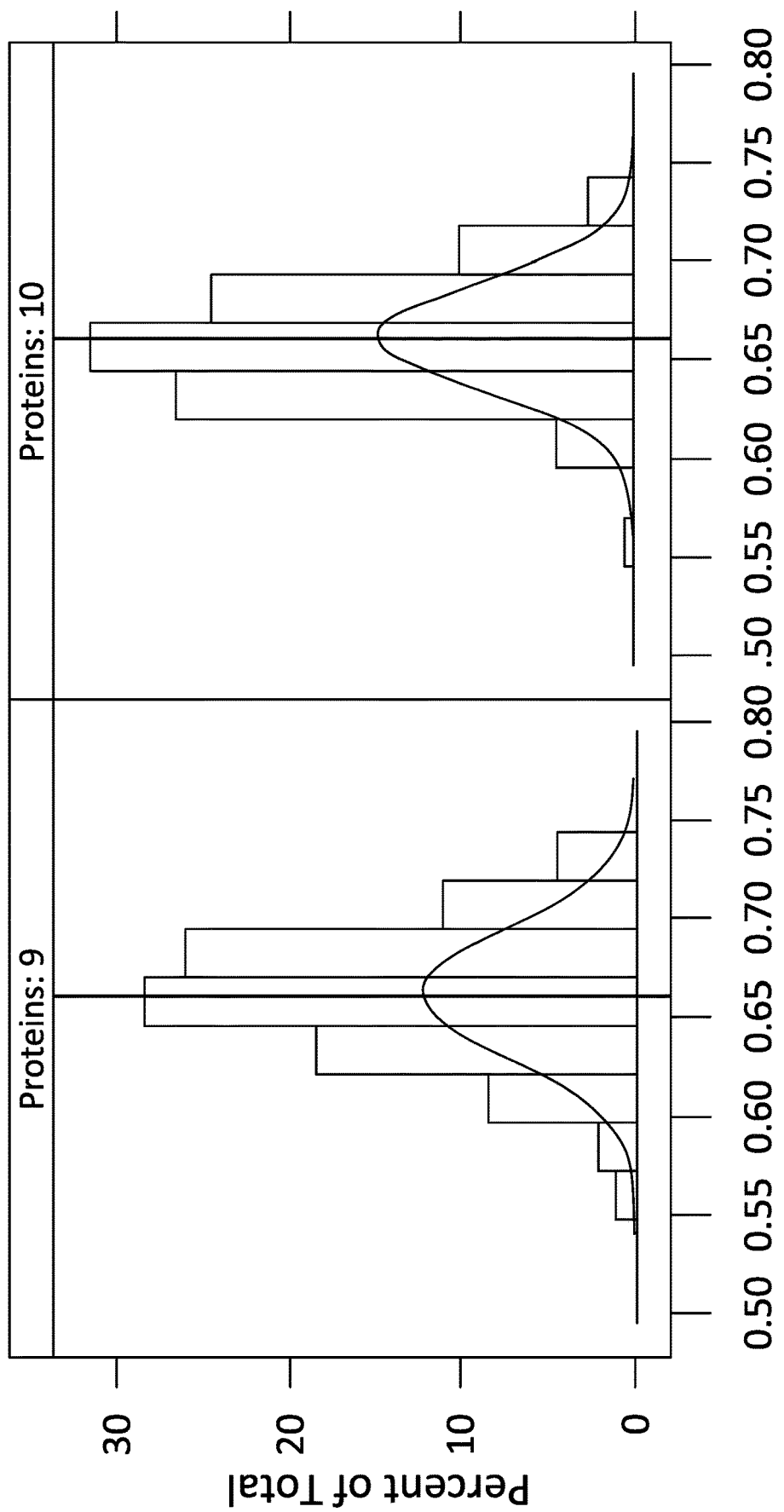
Figure 64B:
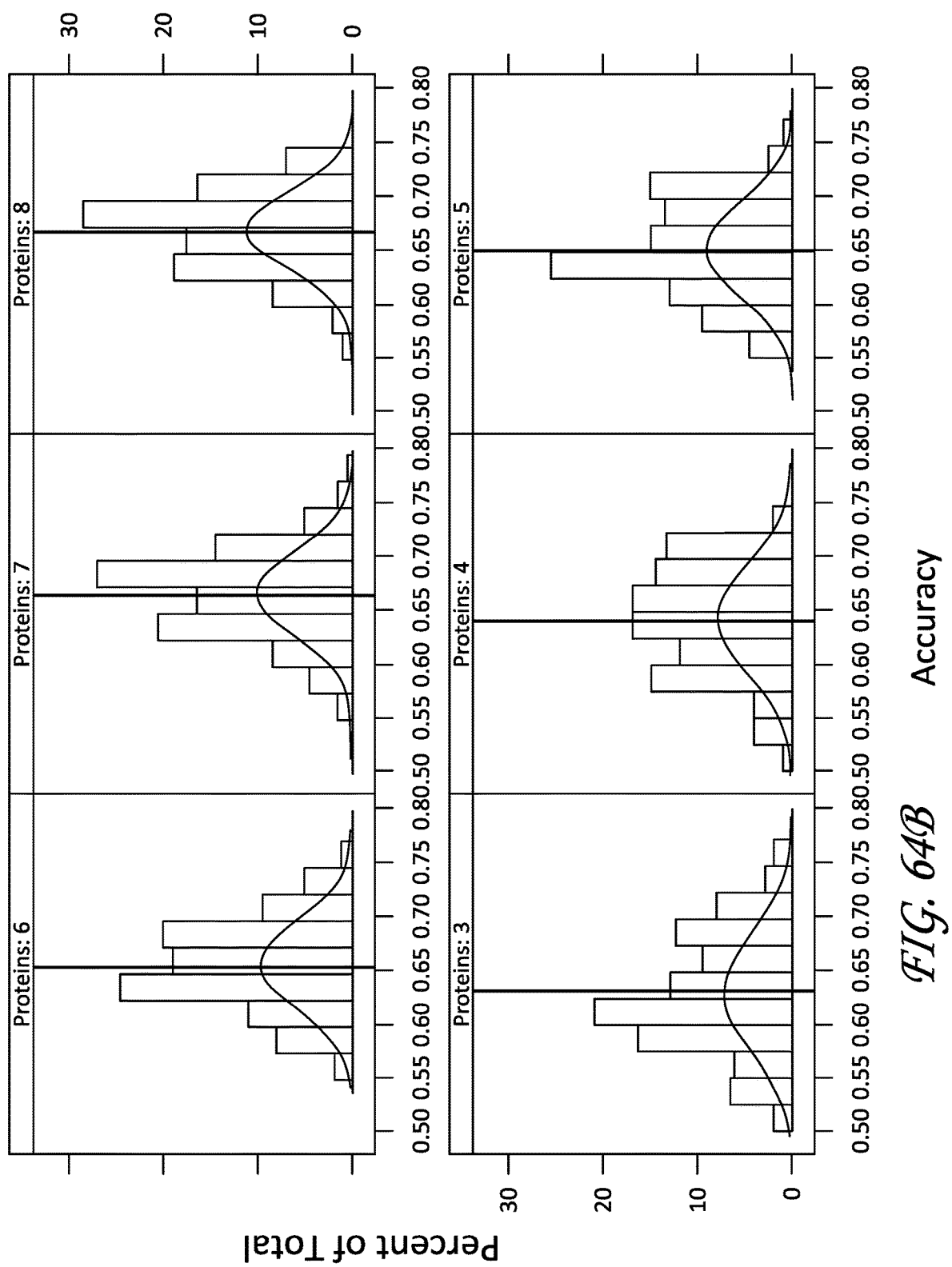

FIGS. 64A and 64B plot the sepsis predicting accuracy of each of 8 families of subcombinations from Table K, using $T_{-36}$ protein data, in a bar graph fashion, in accordance with an embodiment of the present invention: (A) 9-10 proteins; (B) 3-8 proteins.

Figure 65A:
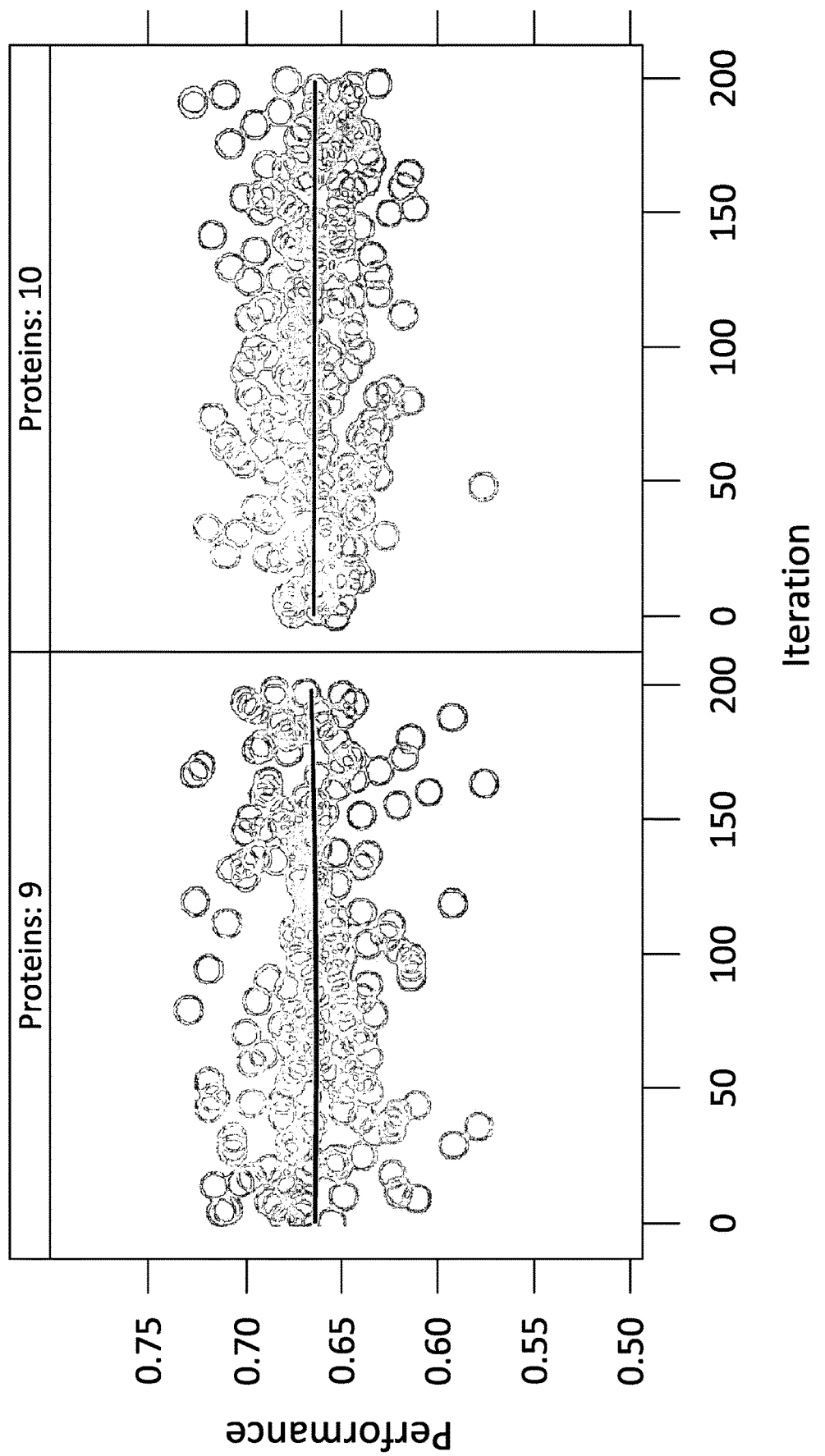
Figure 65B:
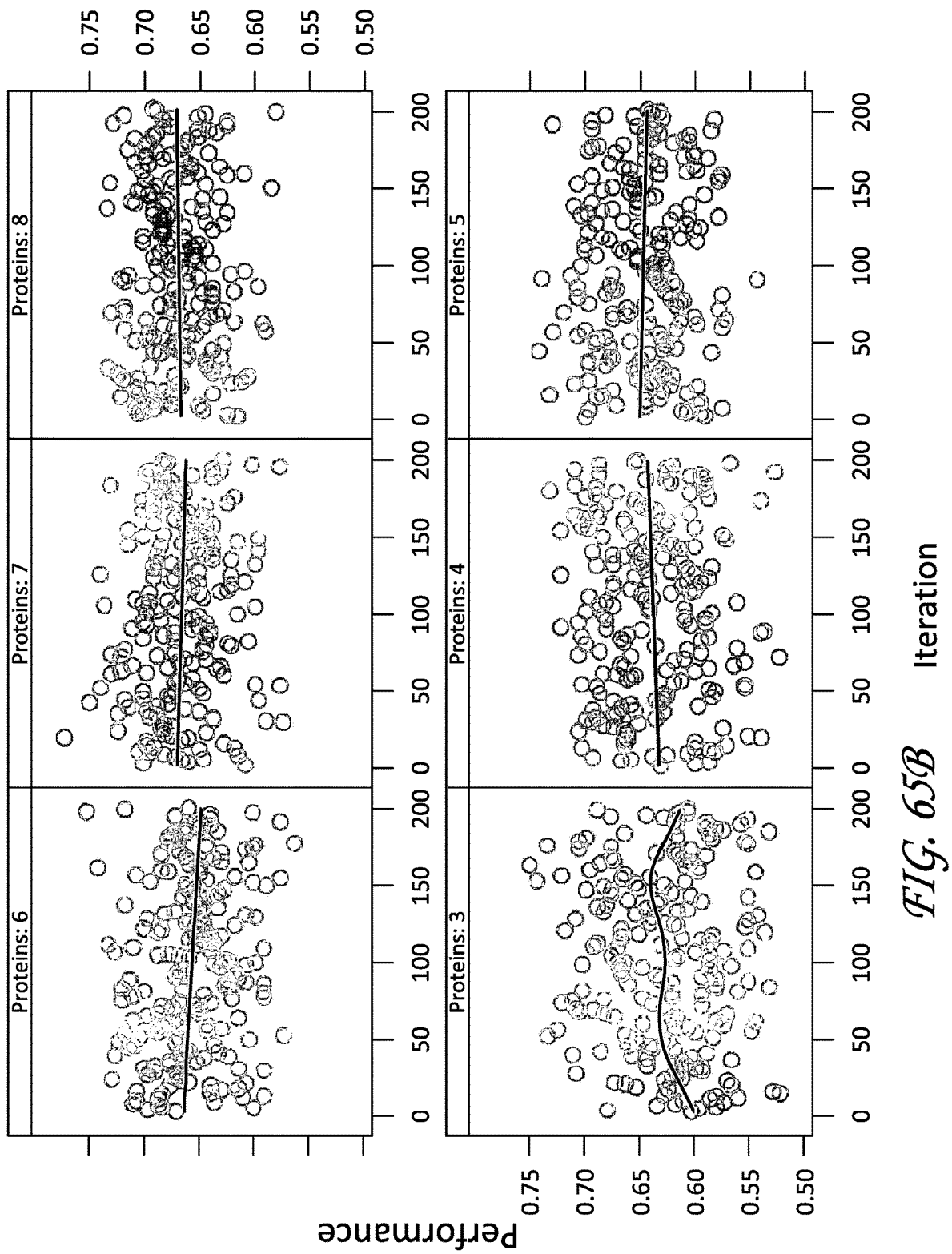

FIGS. 65A and 65B plot the sepsis predicting performance (accuracy) of each individual subcombination in each of 8 families of subcombinations, for a total of 1600 subcombinations from Table K, using $T_{-36}$ protein data, in accordance with an embodiment of the present invention: (A) 9-10 proteins; (B) 3-8 proteins.

Figure 66A:
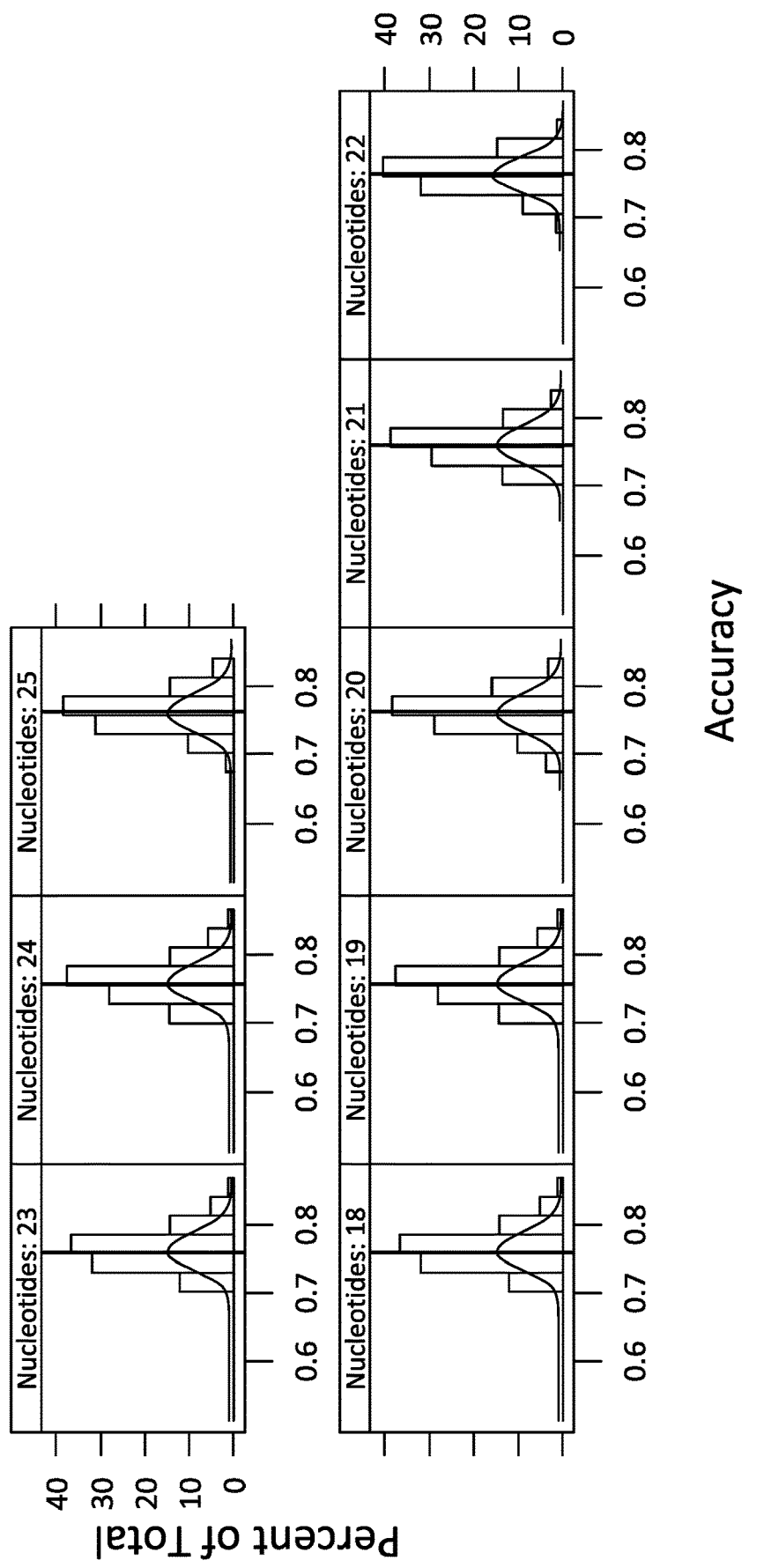
Figure 66B:
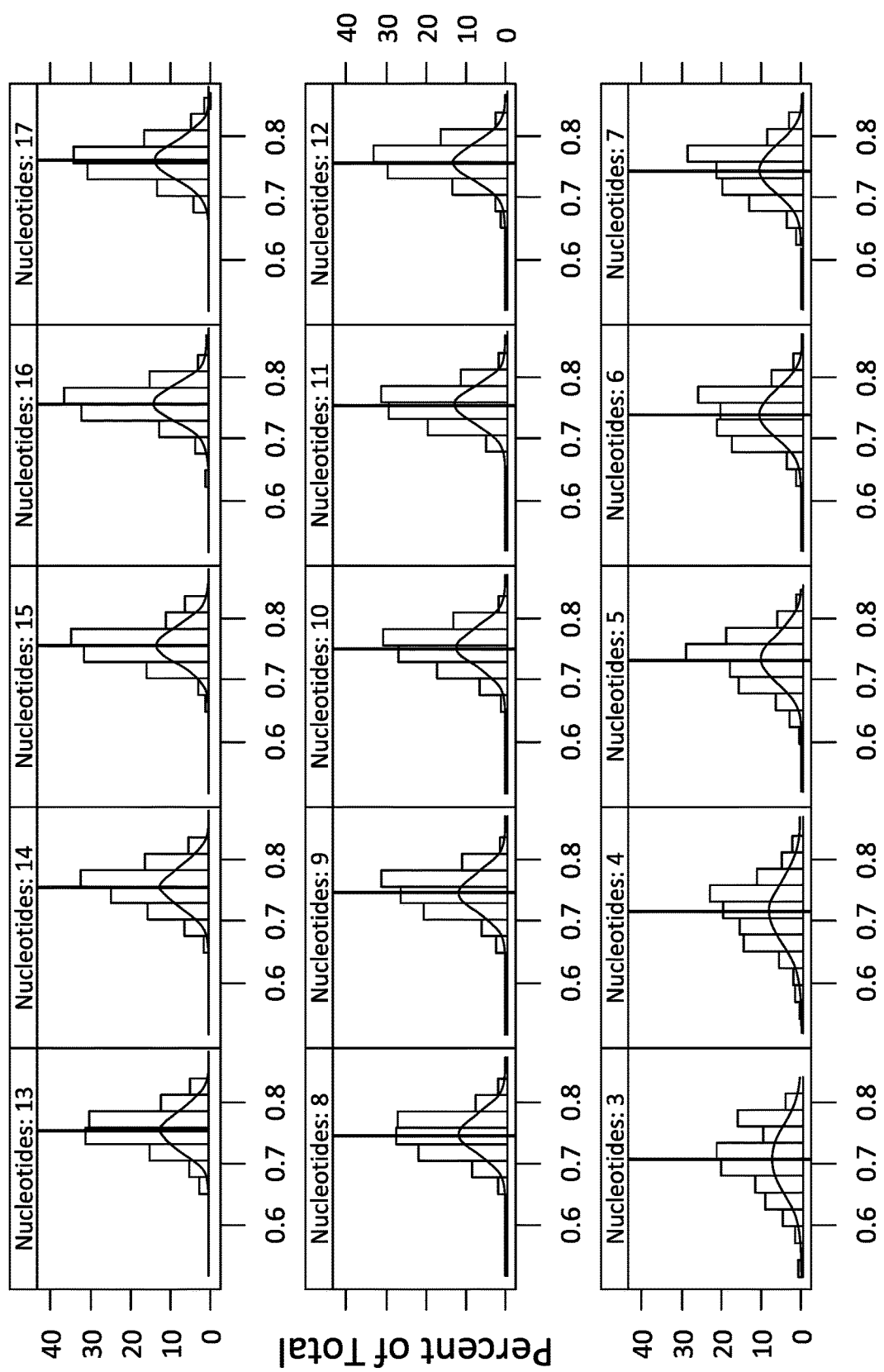

FIGS. 66A and 66B plot the sepsis predicting accuracy of each of 23 families of subcombinations from Table J, using $T_{-36}$ nucleic acid data, in a bar graph fashion, in accordance with an embodiment of the present invention: (A) 18-25 nucleotides; (B) 3-17 nucleotides.

Figure 67A:
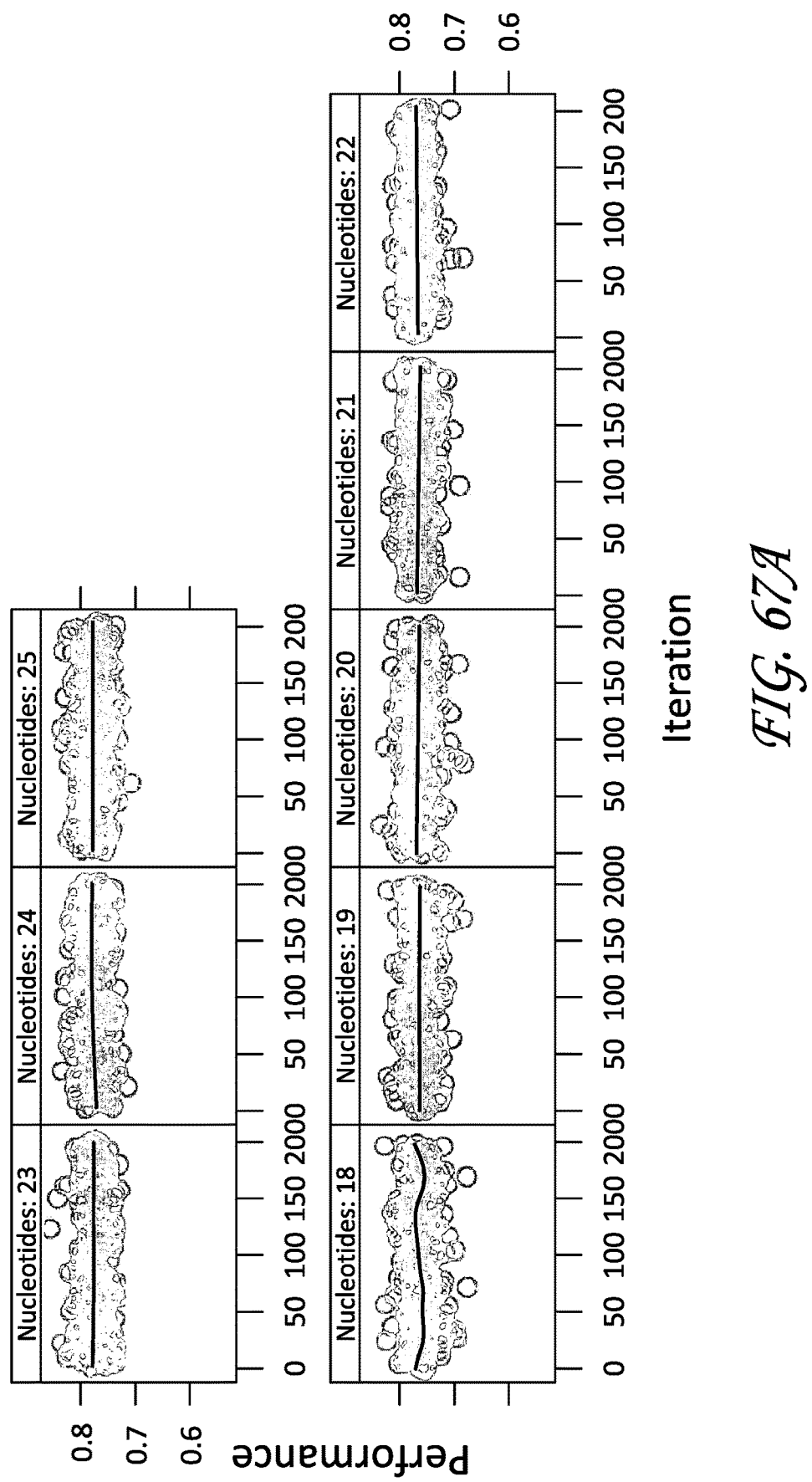
Figure 67B:
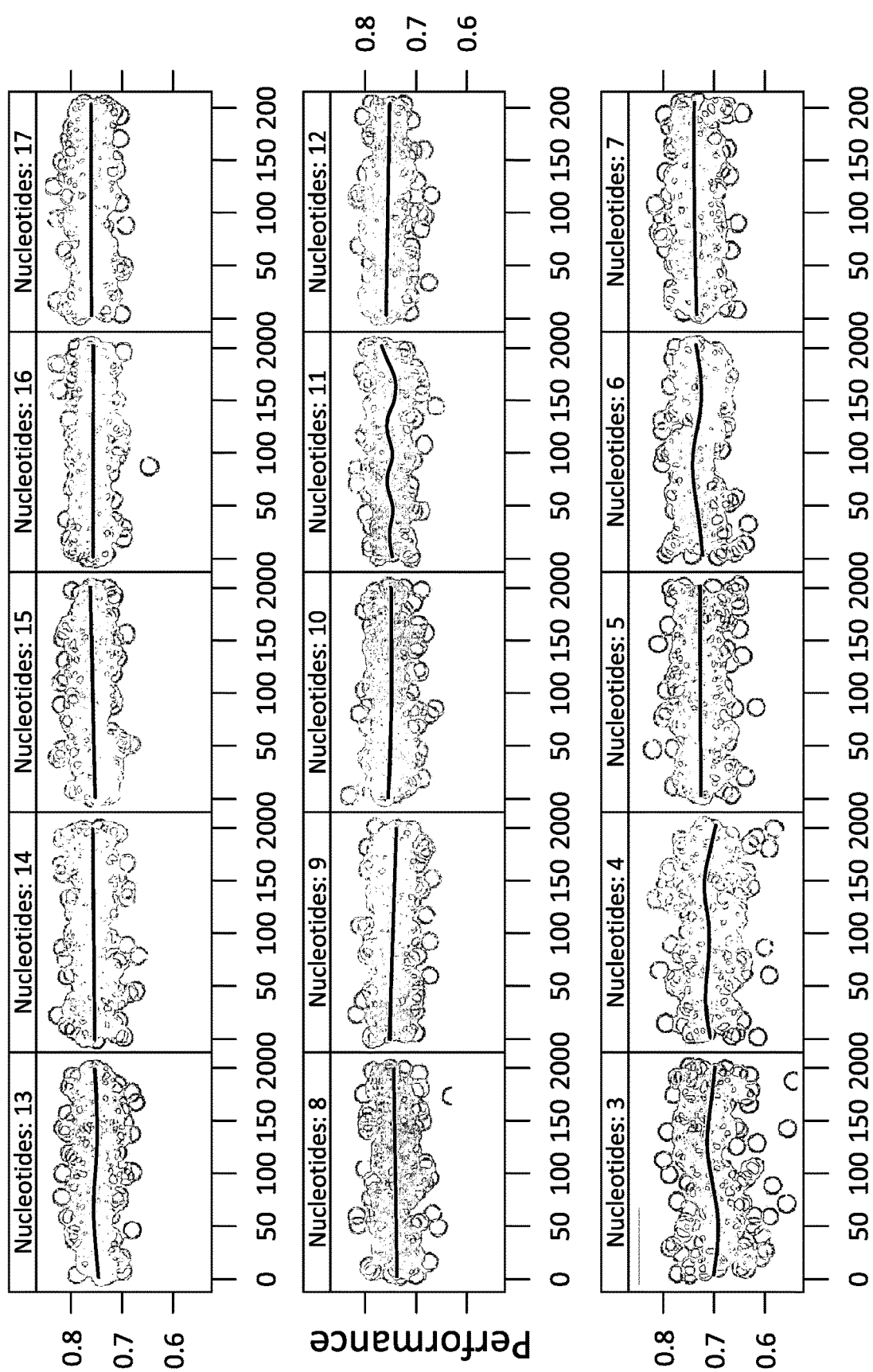

FIGS. 67A and 67B plot the sepsis predicting performance (accuracy) of each individual subcombination in each of 23 families of subcombinations, for a total of 4600 subcombinations from Table J, using $T_{-36}$ nucleic acid data, in accordance with an embodiment of the present invention: (A) 18-25 nucleotides; (B) 3-17 nucleotides.

Figure 68A:
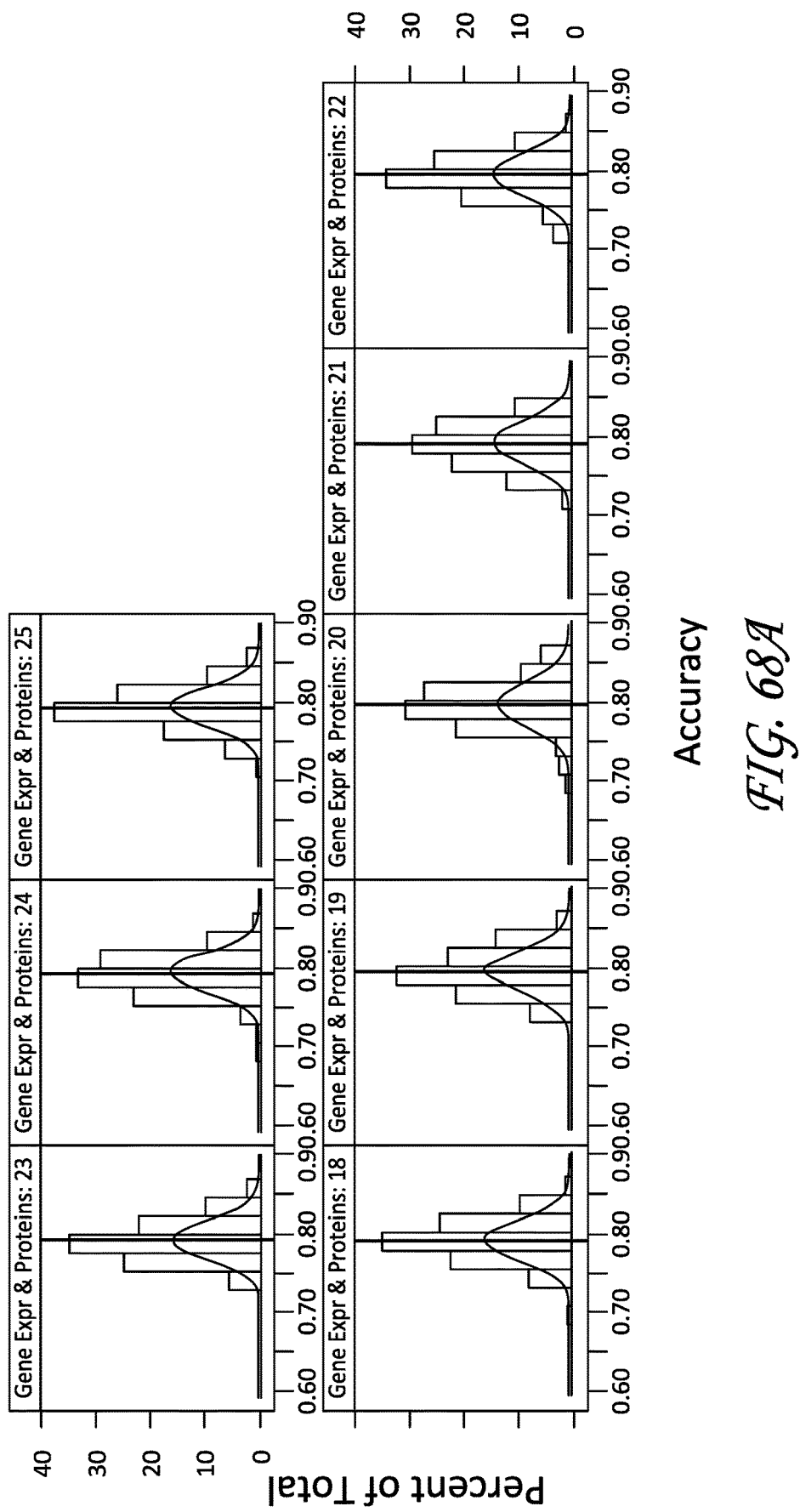
Figure 68B:
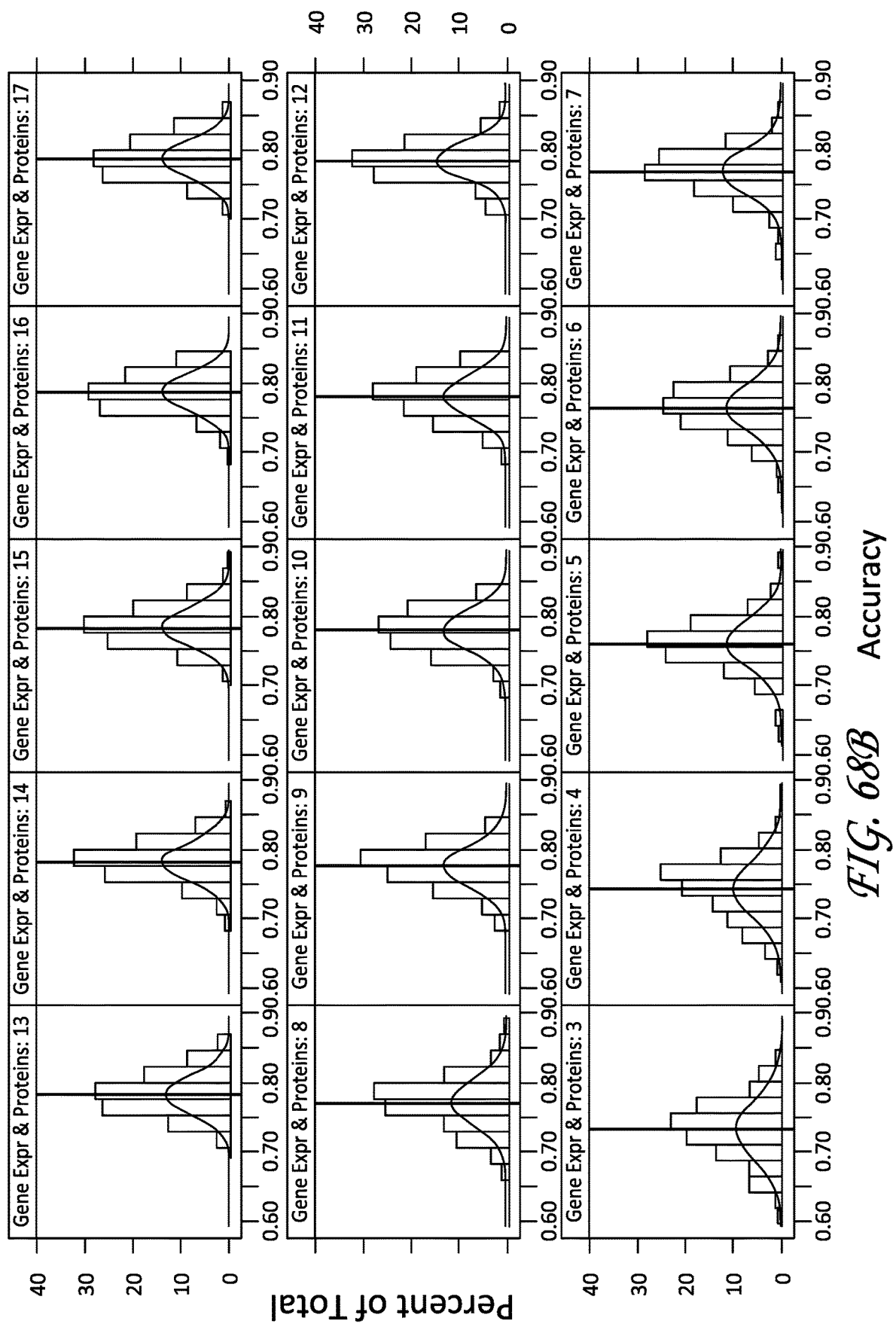

FIGS. 68A and 68B plot the sepsis predicting accuracy of each of 23 families of subcombinations from Table I, using $T_{-12}$ combined protein and nucleic acid data, in a bar graph fashion, in accordance with an embodiment of the present invention: (A) 18-25 gene expression and proteins; (B) 3-17 gene expression and proteins.

Figure 69A:
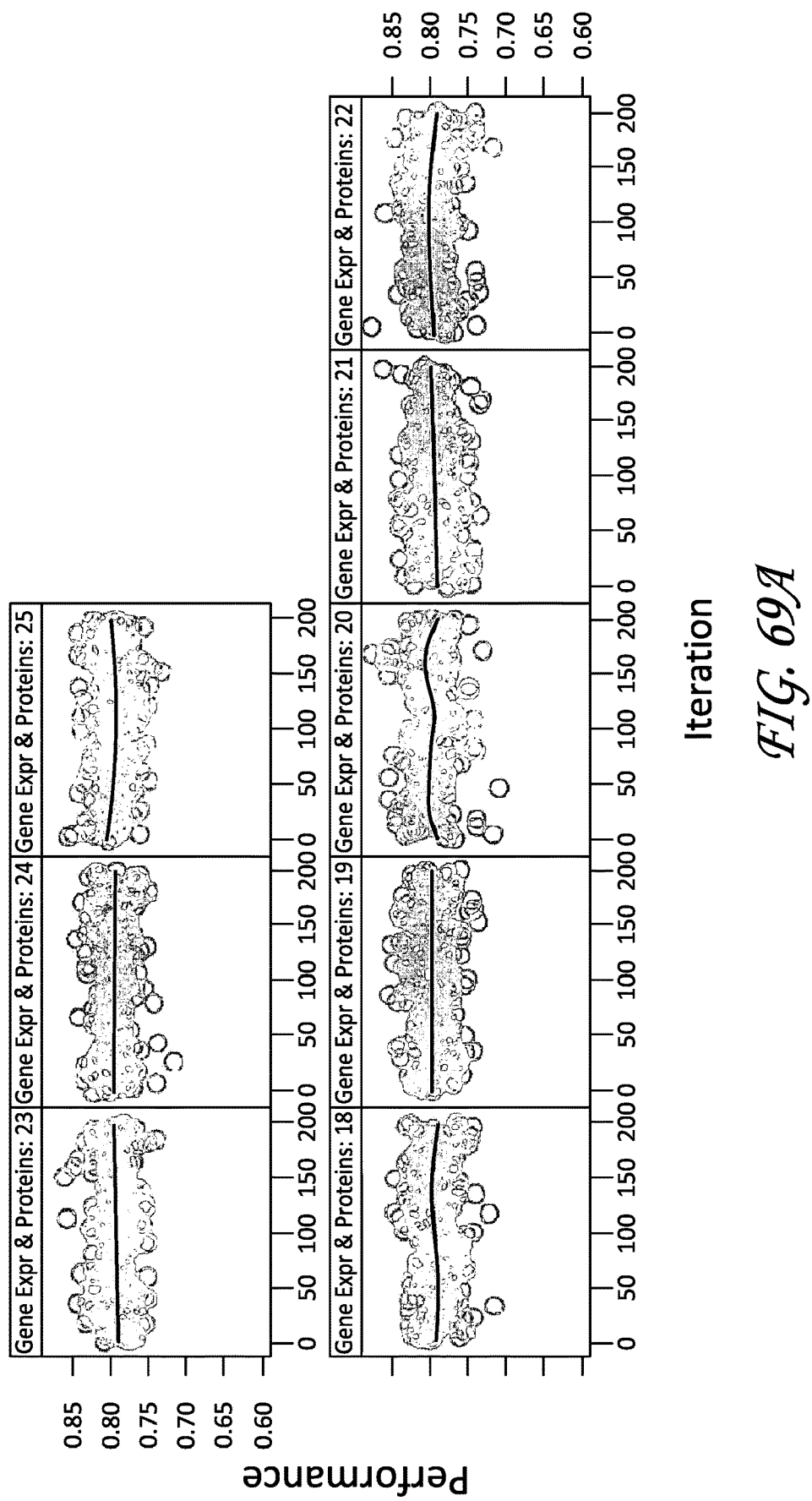
Figure 69B:
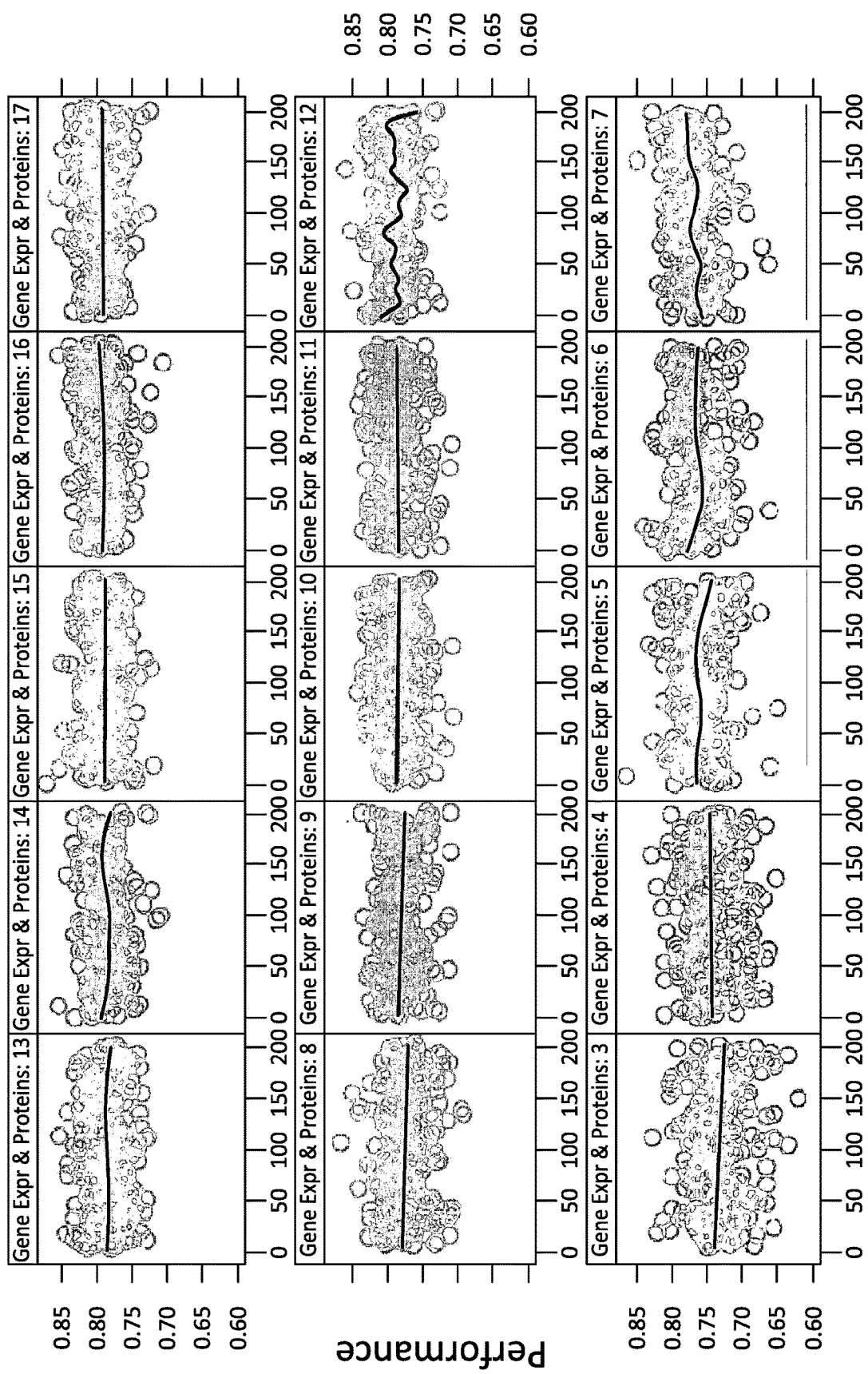

FIGS. 69A and 69B plot the sepsis predicting performance (accuracy) of each individual subcombination in each of 23 families of subcombinations, for a total of 4600 subcombinations from Table I, using $T_{-12}$ combined protein and nucleic acid data, in accordance with an embodiment of the present invention: (A) 18-25 gene expression and proteins; (B) 3-17 gene expression and proteins.

Figure 70A:
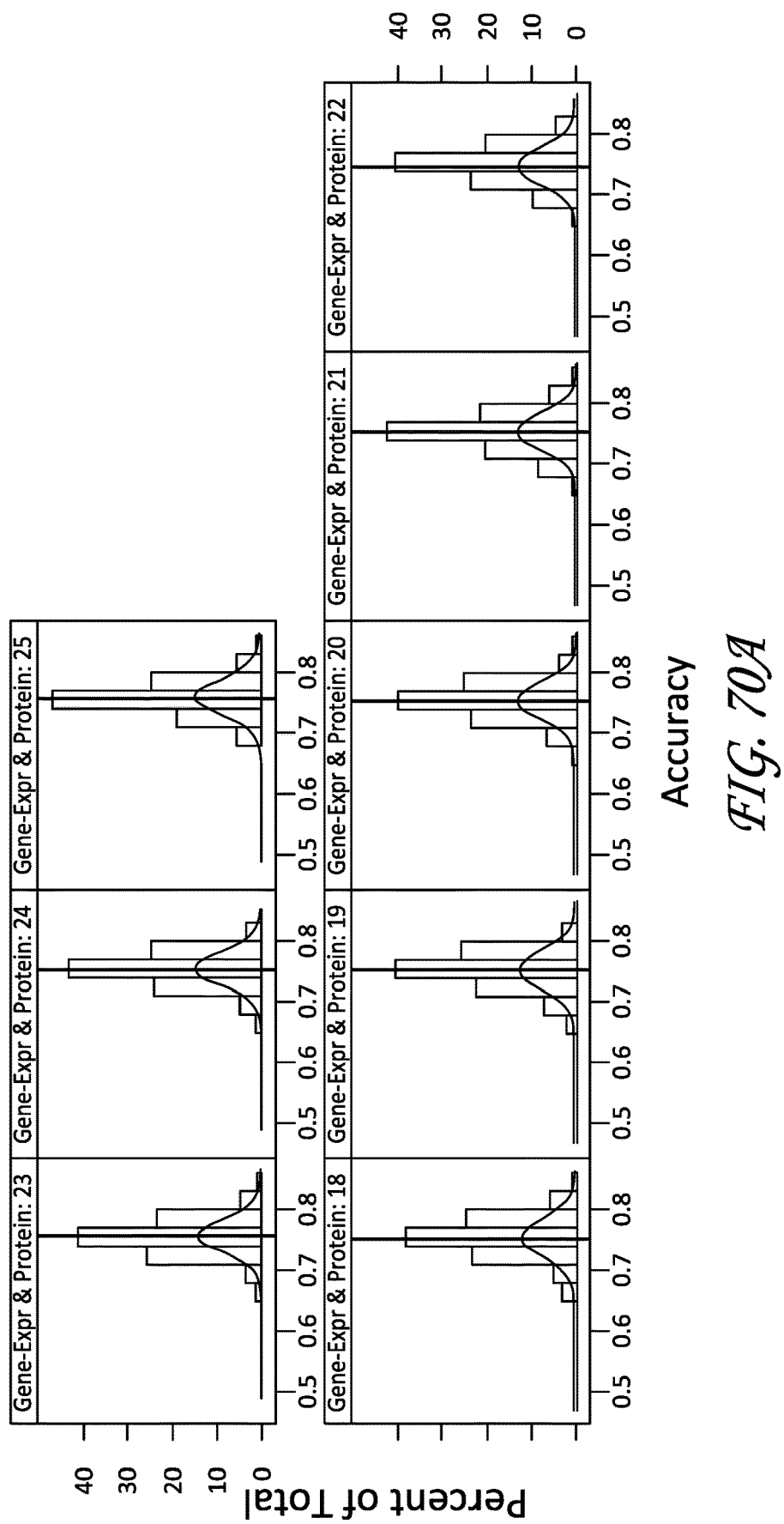
Figure 70B:
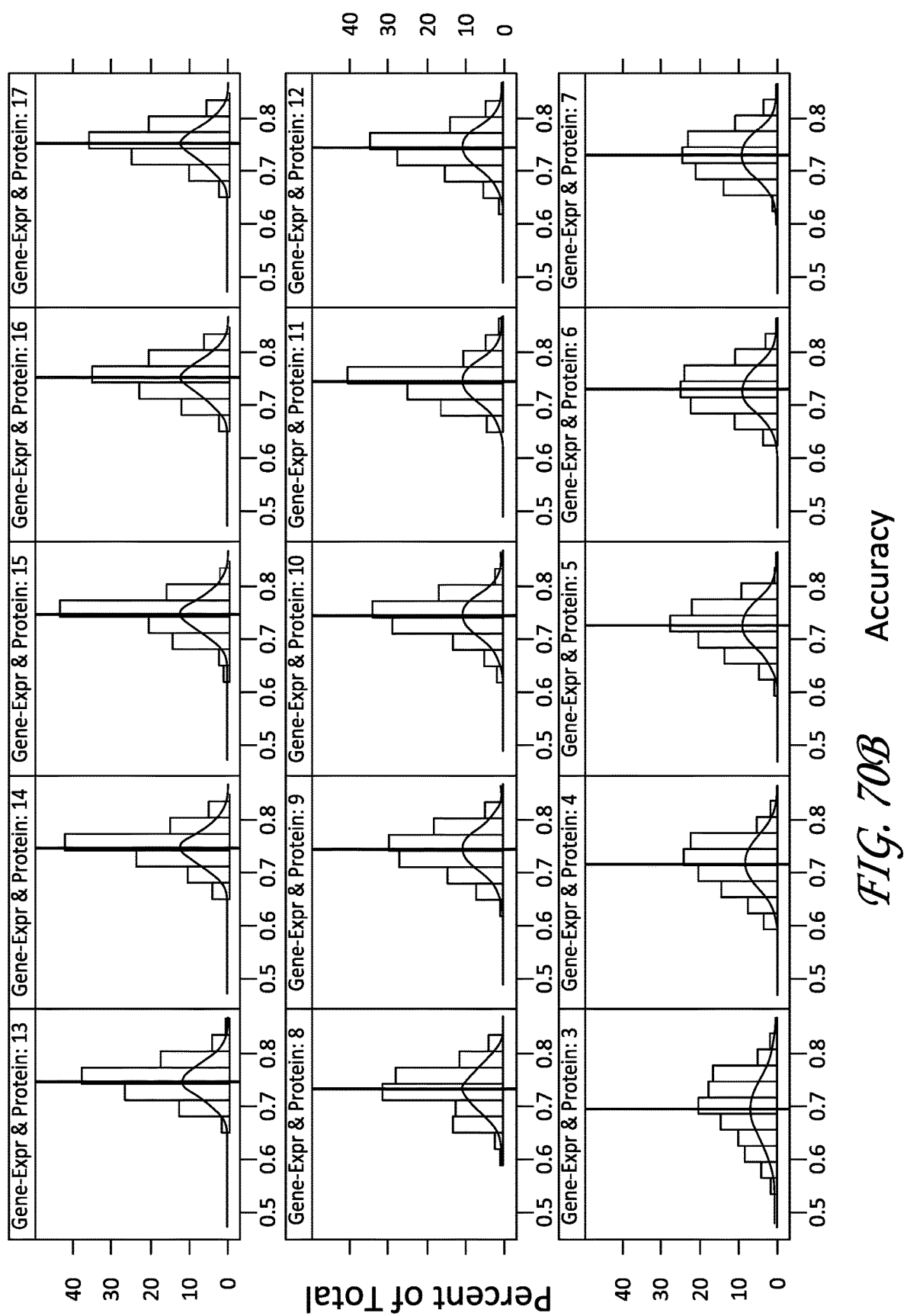

FIGS. 70A and 70B plot the sepsis predicting accuracy of each of 23 families of subcombinations from Table I, using $T_{-36}$ combined protein and nucleic acid data, in a bar graph fashion, in accordance with an embodiment of the present invention: (A) 18-25 gene expression and proteins; (B) 3-17 gene expression and proteins.

Figure 71A:
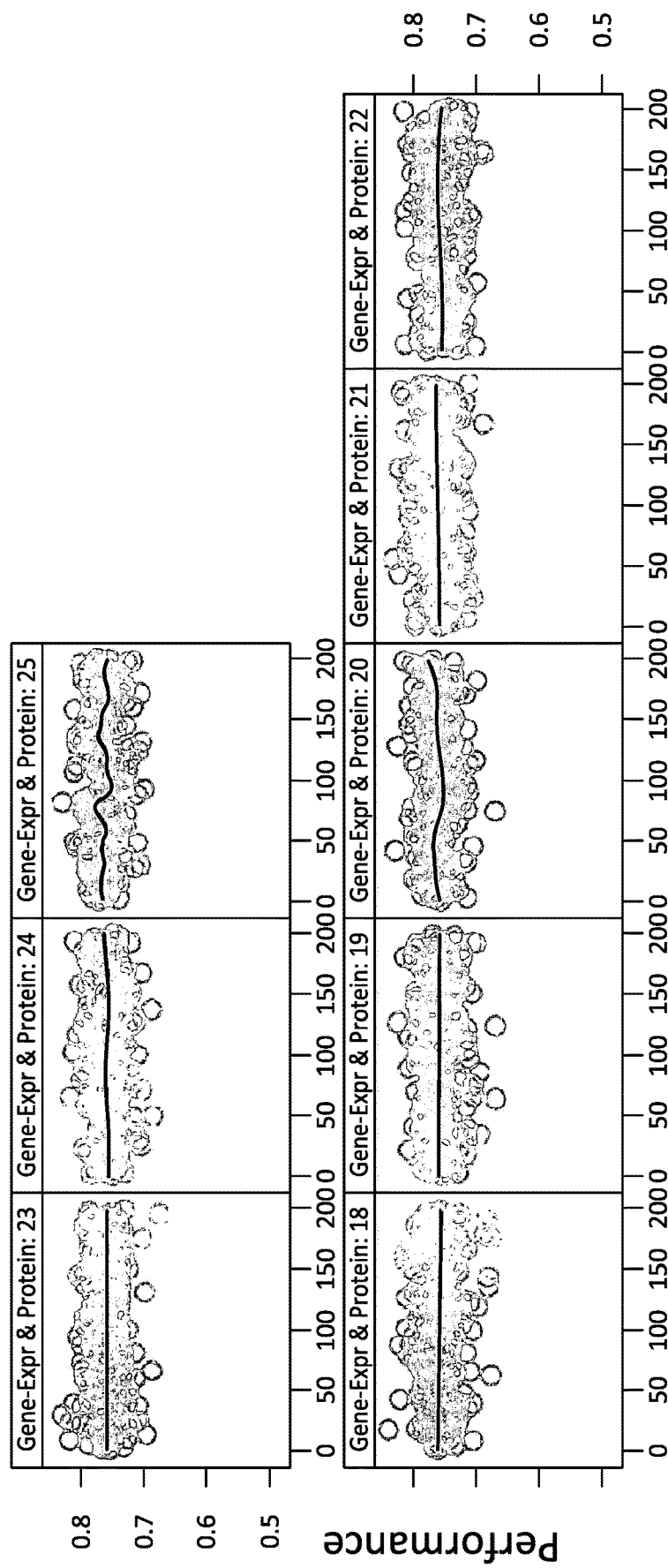
Figure 71B:
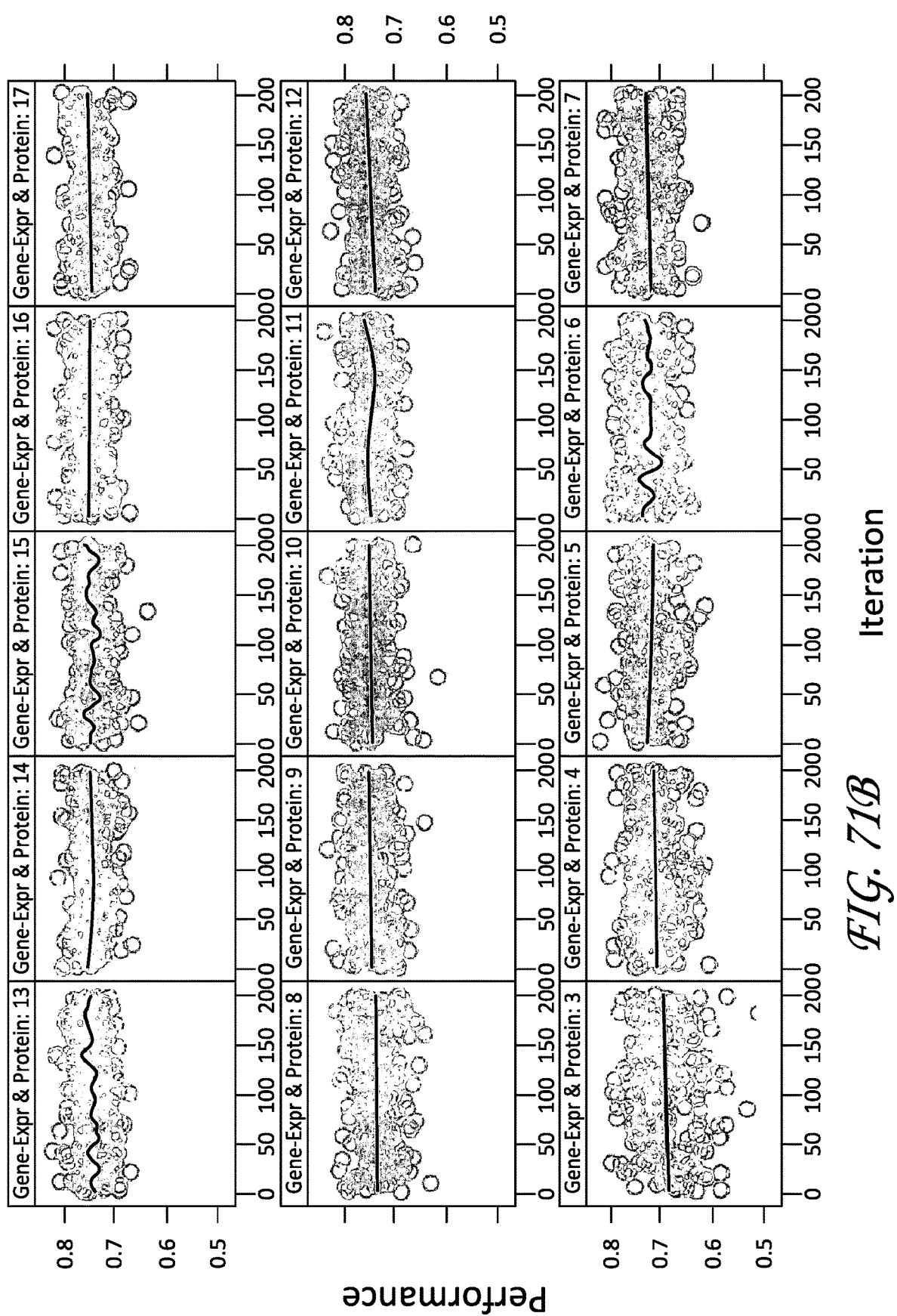

FIGS. 71A and 71B plot the sepsis predicting performance (accuracy) of each individual subcombination in each of 23 families of subcombinations, for a total of 4600 subcombinations from Table I, using $T_{-36}$ combined protein and nucleic acid data, in accordance with an embodiment of the present invention: (A) 18-25 gene expression and proteins; (B) 3-17 gene expression and proteins.

5. DETAILED DESCRIPTION OF THE PREFERRED EMBODIMENTS

The present invention allows for the rapid and accurate diagnosis or prediction of sepsis by evaluating biomarker features in biomarker profiles. These biomarker profiles can be constructed from one or more biological samples of subjects at a single time point ("snapshot"), or multiple such time points, during the course of time the subject is at risk for developing sepsis. Advantageously, sepsis can be diagnosed or predicted prior to the onset of conventional clinical sepsis symptoms, thereby allowing for more effective therapeutic intervention.

5.1 Definitions

"Systemic inflammatory response syndrome," or "SIRS," refers to a clinical response to a variety of severe clinical insults, as manifested by two or more of the following conditions within a 24-hour period:

body temperature greater than 38° C. (100.4° F.) or less than 36° C. (96.8° F.);

heart rate (HR) greater than 90 beats/minute;

respiratory rate (RR) greater than 20 breaths/minute, or $P_{CO2}$ less than 32 mmHg, or requiring mechanical ventilation; and white blood cell count (WBC) either greater than $12.0 \times 10^9$/L or less than $4.0 \times 10^9$/L.

These symptoms of SIRS represent a consensus definition of SIRS that can be modified or supplanted by other definitions in the future. The present definition is used to clarify current clinical practice and does not represent a critical aspect of the invention (see, e.g., American College of Chest Physicians/Society of Critical Care Medicine Consensus Conference: Definitions for Sepsis and Organ Failure and Guidelines for the Use of Innovative Therapies in Sepsis, 1992, *Crit. Care. Med.* 20, 864-874, the entire contents of which are herein incorporated by reference).

A subject with SIRS has a clinical presentation that is classified as SIRS, as defined above, but is not clinically deemed to be septic. Methods for determining which subjects are at risk of developing sepsis are well known to those in the art. Such subjects include, for example, those in an ICU and those who have otherwise suffered from a physiological trauma, such as a burn, surgery or other insult. A hallmark of SIRS is the creation of a proinflammatory state that can be marked by tachycardia, tachypnea or hyperpnea, hypotension, hypoperfusion, oliguria, leukocytosis or leukopenia, pyrexia or hypothermia and the need for volume infusion. SIRS characteristically does not include a documented source of infection (e.g., bacteremia).

"Sepsis" refers to a systemic host response to infection with SIRS plus a documented infection (e.g., a subsequent laboratory confirmation of a clinically significant infection such as a positive culture for an organism). Thus, sepsis refers to the systemic inflammatory response to a documented infection (see, e.g., American College of Chest Physicians Society of Critical Care Medicine, Chest, 1997, 101:1644-1655, the entire contents of which are herein incorporated by reference). As used herein, "sepsis" includes all stages of sepsis including, but not limited to, the onset of sepsis, severe sepsis, septic shock and multiple organ dysfunction ("MOD") associated with the end stages of sepsis.

The "onset of sepsis" refers to an early stage of sepsis, e.g., prior to a stage when conventional clinical manifestations are sufficient to support a clinical suspicion of sepsis. Because the methods of the present invention are used to detect sepsis prior to a time that sepsis would be suspected using conventional techniques, the subject's disease status at early sepsis can only be confirmed retrospectively, when the manifestation of sepsis is more clinically obvious. The exact mechanism by which a subject becomes septic is not a critical aspect of the invention. The methods of the present invention can detect the onset of sepsis independent of the origin of the infectious process.

"Severe sepsis" refers to sepsis associated with organ dysfunction, hypoperfusion abnormalities, or sepsis-induced hypotension. Hypoperfusion abnormalities include, but are not limited to, lactic acidosis, oliguria, or an acute alteration in mental status.

"Septic shock" refers to sepsis-induced hypotension that is not responsive to adequate intravenous fluid challenge and with manifestations of peripheral hypoperfusion.

A "converter" or "converter subject" refers to a SIRS-positive subject who progresses to clinical suspicion of sepsis during the period the subject is monitored, typically during an ICU stay.

A "non-converter" or "non-converter subject" refers to a SIRS-positive subject who does not progress to clinical suspicion of sepsis during the period the subject is monitored, typically during an ICU stay.

A "biomarker" is virtually any detectable compound, such as a protein, a peptide, a proteoglycan, a glycoprotein, a lipoprotein, a carbohydrate, a lipid, a nucleic acid (e.g., DNA, such as cDNA or amplified DNA, or RNA, such as mRNA), an organic or inorganic chemical, a natural or synthetic polymer, a small molecule (e.g., a metabolite), or a discriminating molecule or discriminating fragment of any of the foregoing, that is present in or derived from a biological sample. "Derived from" as used in this context refers to a compound that, when detected, is indicative of a particular molecule being present in the biological sample. For example, detection of a particular cDNA can be indicative of the presence of a particular RNA transcript in the biological sample. As another example, detection of or binding to a particular antibody can be indicative of the presence of a particular antigen (e.g., protein) in the biological sample. Here, a discriminating molecule or fragment is a molecule or fragment that, when detected, indicates presence or abundance of an above-identified compound.

A biomarker can, for example, be isolated from the biological sample, directly measured in the biological sample, or detected in or determined to be in the biological sample. A biomarker can, for example, be functional, partially functional, or non-functional. In one embodiment of the present invention, a biomarker is isolated and used, for example, to raise a specifically-binding antibody that can facilitate biomarker detection in a variety of diagnostic assays. Any immunoassay may use any antibodies, antibody fragment or derivative thereof capable of binding the biomarker molecules (e.g., Fab, F(ab')$_2$, Fv, or scFv fragments). Such immunoassays are well-known in the art. In addition, if the biomarker is a protein or fragment thereof, it can be sequenced and its encoding gene can be cloned using well-established techniques.

As used herein, the term "a species of a biomarker" refers to any discriminating portion or discriminating fragment of a biomarker described herein, such as a splice variant of a particular gene described herein (e.g., a gene listed in Table 30, or Table I, or Table J, or Table K, infra). Here, a discriminating portion or discriminating fragment is a portion or fragment of a molecule that, when detected, indicates presence or abundance of the above-identified transcript, cDNA, amplified nucleic acid, or protein.

As used herein, the terms "protein", "peptide", and "polypeptide" are, unless otherwise indicated, interchangeable.

A "biomarker profile" comprises a plurality of one or more types of biomarkers (e.g., an mRNA molecule, a cDNA molecule, a protein and/or a carbohydrate, etc.), or an indication thereof, together with a feature, such as a measurable aspect (e.g., abundance) of the biomarkers. A biomarker profile comprises at least two such biomarkers or indications thereof, where the biomarkers can be in the same or different classes, such as, for example, a nucleic acid and a carbohydrate. A biomarker profile may also comprise at least 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 or more biomarkers or indications thereof. In one embodiment, a biomarker profile comprises hundreds, or even thousands, of biomarkers or indications thereof. A biomarker profile can further comprise one or more controls or internal standards. In one embodiment, the biomarker profile comprises at least one biomarker, or indication thereof, that serves as an internal standard. In another embodiment, a biomarker profile comprises an indication of one or more types of biomarkers. The term "indication" as used herein in this context merely refers to a situation where the biomarker profile contains symbols, data, abbreviations or other similar indicia for a biomarker, rather than the biomarker molecular entity itself. For instance, consider an exemplary biomarker profile of the present invention that comprises the Affymetrix (Santa Clara, Calif.) U133 plus 2.0 205013_s_at and 209369_at probesets. Another exemplary biomarker profile of the present invention comprises the name of genes used to derive the Affymetrix (Santa Clara, Calif.) U133 plus 2.0 205013_s_at and 209369_at probesets. In still another exemplary biomarker profile of the present invention, the biomarker profile comprises a physical quantity of a transcript of a gene from which the 205013_s_at probeset was derived, and a physical quantity of a transcript of a gene from which the 209369_at probeset was derived. In another embodiment, the biomarker profile comprises a nominal indication of the quantity of a transcript of a gene from which the 205013_s_at probeset was derived and a nominal indication of the quantity of transcript of a gene from which the 209369_at probeset was derived. Still another exemplary biomarker profile of the present invention comprises a microarray to which a physical quantity of a gene transcript from which the 205013_s_at probeset was derived is bound at a first probe spot on the microarray and an abundance of a gene transcript from which the 209369_at probeset was derived is bound to a second probe spot on the microarray. In this last exemplary biomarker profile, at least twenty percent, forty percent, or more than forty percent of the probes spots are based on sequences in the probesets given in Table 30. In another exemplary biomarker profile, at least twenty percent, forty percent, or more than forty percent of the probes spots are based on sequences in the probesets given in Table 31.

Each biomarker in a biomarker profile includes a corresponding "feature." A "feature", as used herein, refers to a measurable aspect of a biomarker. A feature can include, for example, the presence or absence of biomarkers in the biological sample from the subject as illustrated in exemplary biomarker profile 1:

Exemplary Biomarker Profile 1.

| Biomarker | Feature<br>Presence in sample |
| --- | --- |
| transcript of gene A | Present |
| transcript of gene B | Absent |

In exemplary biomarker profile 1, the feature value for the transcript of gene A is "presence" and the feature value for the transcript of gene B is "absence."

A feature can include, for example, the abundance of a biomarker in the biological sample from a subject as illustrated in exemplary biomarker profile 2:

Exemplary Biomarker Profile 2.

| Biomarker | Feature<br>Abundance in sample<br>in relative units |
| --- | --- |
| transcript of gene A | 300 |
| transcript of gene B | 400 |

In exemplary biomarker profile 2, the feature value for the transcript of gene A is 300 units and the feature value for the transcript of gene B is 400 units.

A feature can also be a ratio of two or more measurable aspects of a biomarker as illustrated in exemplary biomarker profile 3:

Exemplary Biomarker Profile 3.

| Biomarker | Feature<br>Ratio of abundance of transcript of<br>gene A/transcript of gene B |
| --- | --- |
| transcript of gene A<br>transcript of gene B | 300/400 |

In exemplary biomarker profile 3, the feature value for the transcript of gene A and the feature value for the transcript of gene B is 0.75 (300/400).

A feature may also be the difference between a measurable aspect of the corresponding biomarker that is taken from two samples, where the two samples are collected from a subject at two different time points. For example, consider the case where the biomarker is a transcript of a gene A and the "measurable aspect" is abundance of the transcript, in samples obtained from a test subject as determined by, e.g., RT-PCR or microarray analysis. In this example, the abundance of the transcript of gene A is measured in a first sample as well as a second sample. The first sample is taken from the test subject a number of hours before the second sample. To compute the feature for gene A, the abundance of the transcript of gene A in one sample is subtracted from the abundance of the transcript of gene A in the second sample. A feature can also be an indication as to whether an abundance of a biomarker is increasing in biological samples obtained from a subject over time and/or an indication as to whether an abundance of a biomarker is decreasing in biological samples obtained from a subject over time.

In some embodiments, there is a one-to-one correspondence between features and biomarkers in a biomarker profile as illustrated in exemplary biomarker profile 1, above. In some embodiments, the relationship between features and biomarkers in a biomarker profile of the present invention is more complex, as illustrated in Exemplary biomarker profile 3, above.

Those of skill in the art will appreciate that other methods of computation of a feature can be devised and all such methods are within the scope of the present invention. For example, a feature can represent the average of an abundance of a biomarker across biological samples collected from a subject at two or more time points. Furthermore, a feature can be the difference or ratio of the abundance of two or more biomarkers from a biological sample obtained from a subject in a single time point. A biomarker profile may also comprise at least three, four, five, 10, 20, 30 or more features. In one embodiment, a biomarker profile comprises hundreds, or even thousands, of features.

In some embodiments, features of biomarkers are measured using microarrays. The construction of microarrays and the techniques used to process microarrays in order to obtain abundance data is well known, and is described, for example, by Draghici, 2003, *Data Analysis Tools for DNA Microarrays*, Chapman & Hall/CRC, and international publication number WO 03/061564, each of which is hereby incorporated by reference in its entirety. A microarray comprises a plurality of probes. In some instances, each probe recognizes, e.g., binds to, a different biomarker. In some instances, two or more different probes on a microarray recognize, e.g., bind to, the same biomarker. Thus, typically, the relationship between probe spots on the microarray and a subject biomarker is a two to one correspondence, a three to one correspondence, or some other form of correspondence. However, it can be the case that there is a unique one-to-one correspondence between probes on a microarray and biomarkers.

A "phenotypic change" is a detectable change in a parameter associated with a given state of the subject. For instance, a phenotypic change can include an increase or decrease of a biomarker in a bodily fluid, where the change is associated with SIRS, sepsis, the onset of sepsis or with a particular stage in the progression of sepsis. A phenotypic change can further include a change in a detectable aspect of a given state of the subject that is not a change in a measurable aspect of a biomarker. For example, a change in phenotype can include a detectable change in body temperature, respiration rate, pulse, blood pressure, or other physiological parameter. Such changes can be determined via clinical observation and measurement using conventional techniques that are well-known to the skilled artisan.

As used herein, the term "complementary," in the context of a nucleic acid sequence (e.g., a nucleotide sequence encoding a gene described herein), refers to the chemical affinity between specific nitrogenous bases as a result of their hydrogen bonding properties. For example, guanine (G) forms a hydrogen bond with only cytosine (C), while adenine forms a hydrogen bond only with thymine (T) in the case of DNA, and uracil (U) in the case of RNA. These reactions are described as base pairing, and the paired bases (G with C, or A with T/U) are said to be complementary. Thus, two nucleic acid sequences may be complementary if their nitrogenous bases are able to form hydrogen bonds. Such sequences are referred to as "complements" of each other. Such complement sequences can be naturally occurring, or, they can be chemically synthesized by any method known to those skilled in the art, as for example, in the case of antisense nucleic acid molecules which are complementary to the sense strand of a DNA molecule or an RNA molecule (e.g., an mRNA transcript). See, e.g., Lewin, 2002, Genes VII. Oxford University Press Inc., New York, N.Y., which is hereby incorporated by reference.

As used herein, "conventional techniques" in the context of diagnosing or predicting sepsis or SIRS are those techniques that classify a subject based on phenotypic changes without obtaining a biomarker profile according to the present invention.

A "decision rule" is a method used to evaluate biomarker profiles. Such decision rules can take on one or more forms that are known in the art, as exemplified in Hastie et al., 2001, *The Elements of Statistical Learning*, Springer-Verlag, New York, which is hereby incorporated by reference in its entirety. A decision rule may be used to act on a data set of features to, inter alia, predict the onset of sepsis, to determine the progression of sepsis, or to diagnose sepsis. Exemplary decision rules that can be used in some embodiments of the present invention are described in further detail in Section 5.5, below.

"Predicting the development of sepsis" is the determination as to whether a subject will develop sepsis. Any such prediction is limited by the accuracy of the means used to make this determination. The present invention provides a method, e.g., by utilizing a decision rule(s), for making this determination with an accuracy that is 60% or greater. As used herein, the terms "predicting the development of sepsis" and "predicting sepsis" are interchangeable. In some embodiments, the act of predicting the development of sepsis (predicting sepsis) is accomplished by evaluating one or more biomarker profiles from a subject using a decision rule that is indicative of the development of sepsis and, as a result of this evaluation, receiving a result from the decision rule that indicates that the subject will become septic. Such an evaluation of one or more biomarker profiles from a test subject using a decision rule uses some or all the features in the one or more biomarker profiles to obtain such a result.

The terms "obtain" and "obtaining," as used herein, mean "to come into possession of," or "coming into possession of," respectively. This can be done, for example, by retrieving data from a data store in a computer system. This can also be done, for example, by direct measurement.

As used herein, the term "specifically," and analogous terms, in the context of an antibody, refers to peptides, polypeptides, and antibodies or fragments thereof that specifically bind to an antigen or a fragment and do not specifically bind to other antigens or other fragments. A peptide or polypeptide that specifically binds to an antigen may bind to other peptides or polypeptides with lower affinity, as determined by standard experimental techniques, for example, by any immunoassay well-known to those skilled in the art. Such immunoassays include, but are not limited to, radioimmunoassays (RIAs) and enzyme-linked immunosorbent assays (ELISAs). Antibodies or fragments that specifically bind to an antigen may be cross-reactive with related antigens. Preferably, antibodies or fragments thereof that specifically bind to an antigen do not cross-react with other antigens. See, e.g., Paul, ed., 2003, Fundamental Immunology, 5th ed., Raven Press, New York at pages 69-105, which is incorporated by reference herein, for a discussion regarding antigen-antibody interactions, specificity and cross-reactivity, and methods for determining all of the above.

As used herein, a "subject" is an animal, preferably a mammal, more preferably a non-human primate, and most preferably a human. The terms "subject" "individual" and "patient" are used interchangeably herein.

As used herein, a "test subject," typically, is any subject that is not in a training population used to construct a decision rule. A test subject can optionally be suspected of either having sepsis at risk of developing sepsis.

As used herein, a "tissue type," is a type of tissue. A tissue is an association of cells of a multicellular organism, with a common embryoloical origin or pathway and similar structure and function. Often, cells of a tissue are contiguous at cell membranes but occasionally the tissue may be fluid (e.g., blood). Cells of a tissue may be all of one type (a simple tissue, e.g., squamous epithelium, plant parentchyma) or of more than one type (a mixed tissue, e.g., connective tissue).

As used herein, a "training population" is a set of samples from a population of subjects used to construct a decision rule, using a data analysis algorithm, for evaluation of the biomarker profiles of subjects at risk for developing sepsis. In a preferred embodiment, a training population includes samples from subjects that are converters and subjects that are non-converters.

As used herein, a "data analysis algorithm" is an algorithm used to construct a decision rule using biomarker profiles of subjects in a training population. Representative data analysis algorithms are described in Section 5.5. A "decision rule" is the final product of a data analysis algorithm, and is characterized by one or more value sets, where each of these value sets is indicative of an aspect of SIRS, the onset of sepsis, sepsis, or a prediction that a subject will acquire sepsis. In one specific example, a value set represents a prediction that a subject will develop sepsis. In another example, a value set represents a prediction that a subject will not develop sepsis.

As used herein, a "validation population" is a set of samples from a population of subjects used to determine the accuracy of a decision rule. In a preferred embodiment, a validation population includes samples from subjects that are converters and subjects that are nonconverters. In a preferred embodiment, a validation population does not include subjects that are part of the training population used to train the decision rule for which an accuracy measurement is sought.

As used herein, a "value set" is a combination of values, or ranges of values for features in a biomarker profile. The nature of this value set and the values therein is dependent upon the type of features present in the biomarker profile and the data analysis algorithm used to construct the decision rule that dictates the value set. To illustrate, reconsider exemplary biomarker profile 2:

Exemplary Biomarker Profile 2.

| Biomarker | Feature Abundance in sample in relative units |
|---|---|
| transcript of gene A | 300 |
| transcript of gene B | 400 |

Figure 1:
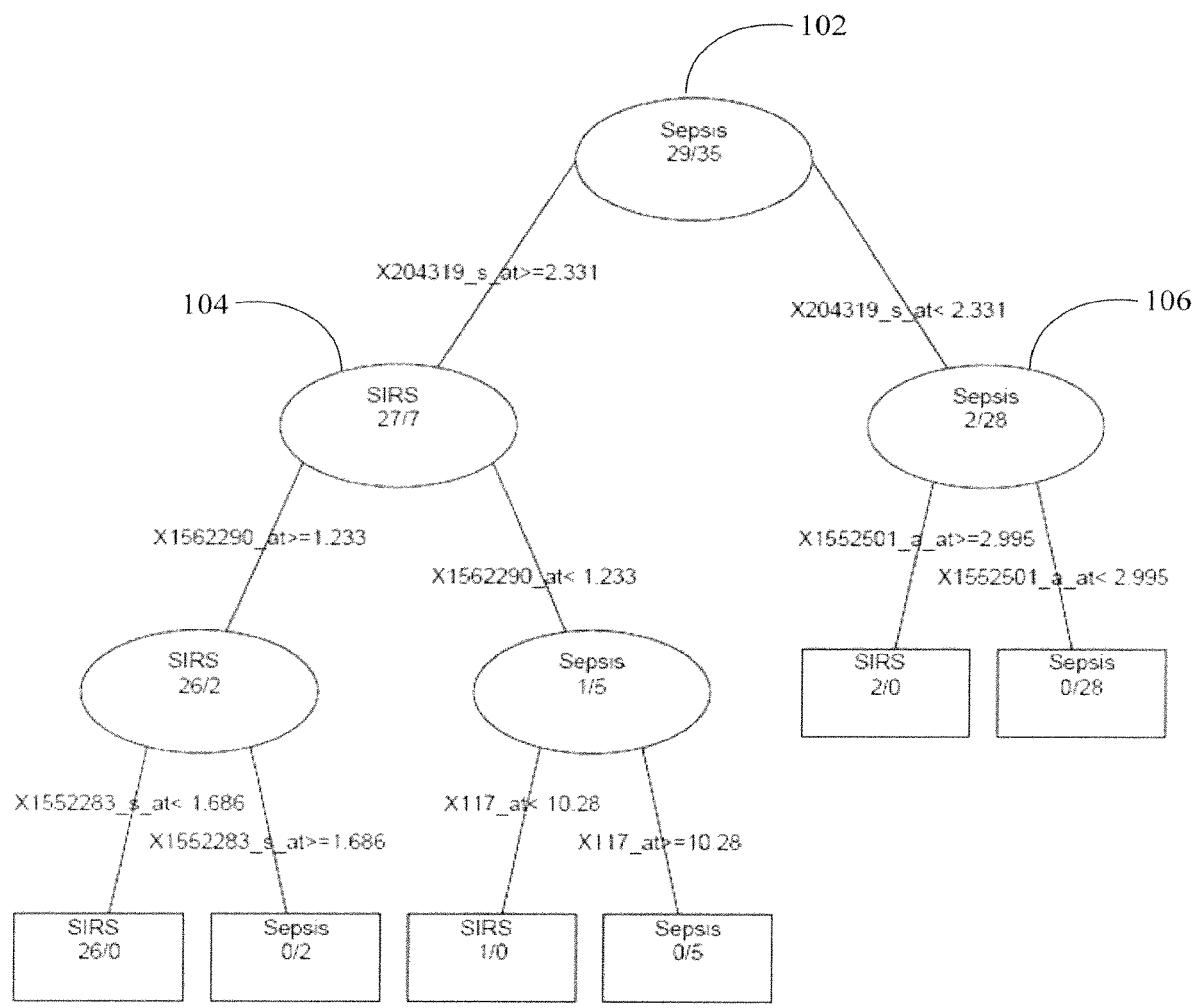
FIG. 1 illustrates a classification and regression tree for discriminating between a SIRS phenotypic state characterized by the onset of sepsis and a SIRS phenotypic state characterized by the absence of sepsis using $T_{-36}$ static data obtained from a training population in accordance with an embodiment of the present invention.

In this example, the biomarker profile of each member of a training population is obtained. Each such biomarker profile includes a measured feature, here abundance, for the transcript of gene A, and a measured feature, here abundance, for the transcript of gene B. These feature values, here abundance values, are used by a data analysis algorithm to construct a decision rule. In this example, the data analysis algorithm is a decision tree, described in Section 5.5.1 and the final product of this data analysis algorithm, the decision rule, is a decision tree. An exemplary decision tree is illustrated in FIG. 1. The decision rule defines value sets. One such value set is predictive of the onset of sepsis. A subject whose biomarker feature values satisfy this value set is likely to become septic. An exemplary value set of this class is exemplary value set 1:

Exemplary Value Set 1.

| Biomarker | Value set component (Abundance in sample in relative units) |
|---|---|
| transcript of gene A | <400 |
| transcript of gene B | <600 |

Another such value set is predictive of a septic-free state. A subject whose biomarker feature values satisfy this value set is not likely to become septic. An exemplary value set of this class is exemplary value set 2:

Exemplary Value Set 2.

| Biomarker | Value set component (Abundance in sample in relative units) |
|---|---|
| transcript of gene A | >400 |
| transcript of gene B | >600 |

In the case where the data analysis algorithm is a neural network analysis and the final product of this neural network analysis is an appropriately weighted neural network, one value set is those ranges of biomarker profile feature values that will cause the weighted neural network to indicate that onset of sepsis is likely. Another value set is those ranges of biomarker profile feature values that will cause the weighted neural network to indicate that onset of sepsis is not likely.

As used herein, the term "probe spot" in the context of a microarray refers to a single stranded DNA molecule (e.g., a single stranded cDNA molecule or synthetic DNA oligomer), referred to herein as a "probe," that is used to determine the abundance of a particular nucleic acid in a sample. For example, a probe spot can be used to determine the level of mRNA in a biological sample (e.g., a collection of cells) from a test subject. In a specific embodiment, a typical microarray comprises multiple probe spots that are placed onto a glass slide (or other substrate) in known locations on a grid. The nucleic acid for each probe spot is a single stranded contiguous portion of the sequence of a gene or gene of interest (e.g., a 10-mer, 11-mer, 12-mer, 13-mer, 14-mer, 15-mer, 16-mer, 17-mer, 18-mer, 19-mer, 20-mer, 21-mer, 22-mer, 23-mer, 24-mer, 25-mer or larger) and is a probe for the mRNA encoded by the particular gene or gene of interest. Each probe spot is characterized by a single nucleic acid sequence, and is hybridized under conditions that cause it to hybridize only to its complementary DNA strand or mRNA molecule. As such, there can be many probe spots on a substrate, and each can represent a unique gene or sequence of interest. In addition, two or more probe spots can represent the same gene sequence. In some embodiments, a labeled nucleic acid sample is hybridized to a probe spot, and the amount of labeled nucleic acid specifically hybridized to a probe spot can be quantified to determine the levels of that specific nucleic acid (e.g., mRNA transcript of a particular gene) in a particular biological sample. Probes, probe spots, and microarrays, generally, are described in Draghici, 2003, *Data Analysis Tools for DNA Microarrays*, Chapman & Hall/CRC, Chapter, 2, which is hereby incorporated by reference in its entirety.

As used herein, the term "annotation data" refers to any type of data that describes a property of a biomarker. Annotation data includes, but is not limited to, biological pathway membership, enzymatic class (e.g., phosphodiesterase, kinase, metalloproteinase, etc.), protein domain information, enzymatic substrate information, enzymatic reaction information, protein interaction data, disease association, cellular localization, tissue type localization, and cell type localization.

As used herein, the term "$T_{-12}$" refers to the last time blood was obtained from a subject before the subject is clinically diagnosed with sepsis. Since, in the present invention, blood is collected from subjects each 24 hour period, $T_{-12}$ references the average time period prior to the onset of sepsis for a pool of patients, with some patients turning septic prior to the 12 hour mark and some patients turning septic after the 12 hour mark. However, across a pool of subjects, the average time period for this last blood sample is the 12 hour mark, hence the name "$T_{-12}$."

5.2 Methods for Screening Subjects

The present invention allows for accurate, rapid prediction and/or diagnosis of sepsis through detection of two or more features of a biomarker profile of a test individual suspected of or at risk for developing sepsis in each of one or more biological samples from a test subject. In one embodiment, only a single biological sample taken at a single point in time from the test subject is needed to construct a biomarker profile that is used to make this prediction or diagnosis of sepsis. In another embodiment, multiple biological samples taken at different points in time from the test subject are used to construct a biomarker profile that is used to make this prediction or diagnosis of sepsis.

In specific embodiments of the invention, subjects at risk for developing sepsis or SIRS are screened using the methods of the present invention. In accordance with these embodiments, the methods of the present invention can be employed to screen, for example, subjects admitted to an ICU and/or those who have experienced some sort of trauma (such as, e.g., surgery, vehicular accident, gunshot wound, etc.).

In specific embodiments, a biological sample such as, for example, blood, is taken upon admission. In some embodiments, a biological sample is blood, plasma, serum, saliva, sputum, urine, cerebral spinal fluid, cells, a cellular extract, a tissue specimen, a tissue biopsy, or a stool specimen. In some embodiments a biological sample is whole blood and this whole blood is used to obtain measurements for a biomarker profile. In some embodiments a biological sample is some component of whole blood. For example, in some embodiments some portion of the mixture of proteins, nucleic acid, and/or other molecules (e.g., metabolites) within a cellular fraction or within a liquid (e.g., plasma or serum fraction) of the blood is resolved as a biomarker profile. This can be accomplished by measuring features of the biomarkers in the biomarker profile. In some embodiments, the biological sample is whole blood but the biomarker profile is resolved from biomarkers in a specific cell type that is isolated from the whole blood. In some embodiments, the biological sample is whole blood but the biomarker profile is resolved from biomarkers expressed or otherwise found in monocytes that are isolated from the whole blood. In some embodiments, the biological sample is whole blood but the biomarker profile is resolved from biomarkers expressed or otherwise found in red blood cells that are isolated from the whole blood. In some embodiments, the biological sample is whole blood but the biomarker profile is resolved from biomarkers expressed or otherwise found in platelets that are isolated from the whole blood. In some embodiments, the biological sample is whole blood but the biomarker profile is resolved from biomarkers expressed or otherwise found in neutriphils that are isolated from the whole blood. In some embodiments, the biological sample is whole blood but the biomarker profile is resolved from biomarkers expressed or otherwise found in eosinophils that are isolated from the whole blood. In some embodiments, the biological sample is whole blood but the biomarker profile is resolved from biomarkers expressed or otherwise found in basophils that are isolated from the whole blood. In some embodiments, the biological sample is whole blood but the biomarker profile is resolved from biomarkers expressed or otherwise found in lymphocytes that are isolated from the whole blood. In some embodiments, the biological sample is whole blood but the biomarker profile is resolved from biomarkers expressed or otherwise found in monocytes that are isolated from the whole blood. In some embodiments, the biological sample is whole blood but the biomarker profile is resolved from one, two, three, four, five, six, or seven cell types from the group of cells types consisting of red blood cells, platelets, neutrophils, eosinophils, basophils, lymphocytes, and monocytes.

A biomarker profile comprises a plurality of one or more types of biomarkers (e.g., an mRNA molecule, a cDNA molecule, a protein and/or a carbohydrate, etc.), or an indication thereof, together with features, such as a measurable aspect (e.g., abundance) of the biomarkers. A biomarker profile can comprise at least two such biomarkers or indications thereof, where the biomarkers can be in the same or different classes, such as, for example, a nucleic acid and a carbohydrate. In some embodiments, a biomarker profile comprises at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 96, 100, 105, 110, 115, 120, 125, 130, 135, 140, 145, 150, 155, 160, 165, 170, 175, 180, 185, 190, 195 or 200 or more biomarkers or indications thereof. In one embodiment, a biomarker profile comprises hundreds, or even thousands, of biomarkers or indications thereof. In some embodiments, a biomarker profile comprises at least 2, 3, 4, 5, 6, 7, 8, 9, 10, 11, 12, 13, 14, 15, 16, 17, 18, 19, 20, 25, 30, 35, 40, 45, 50, or more biomarkers or indications thereof. In one example, in some embodiments, a biomarker profile comprises at least 2, 3, 4, 5, 6, 7, 8, 9, 10, 11, 12, 13, 14, 15, 16, 17, 18, 19, 20, 25, 30, 35, 40, 45, 50, or more biomarkers selected from Table I of Section 5.11, or indications thereof. In another example, in some embodiments, a biomarker profile comprises at least 2, 3, 4, 5, 6, 7, 8, 9, 10, 11, 12, 13, 14, 15, 16, 17, 18, 19, 20, 25, 30, 35, 40 or more biomarkers selected from Table J of Section 5.11, or indications thereof. In another example, in some embodiments, a biomarker profile comprises any 2, 3, 4, 5, 6, 7, 8, 9, or all ten biomarkers in Table K of Section 5.11, or indications thereof.

In typical embodiments, each biomarker in the biomarker profile is represented by a feature. In other words, there is a correspondence between biomarkers and features. In some embodiments, the correspondence between biomarkers and features is 1:1, meaning that for each biomarker there is a feature. In some embodiments, there is more than one feature for each biomarker. In some embodiments the number of features corresponding to one biomarker in the biomarker profile is different than then number of features corresponding to another biomarker in the biomarker profile. As such, in some embodiments, a biomarker profile can include at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 96, 100, 105, 110, 115, 120, 125, 130, 135, 140, 145, 150, 155, 160, 165, 170, 175, 180, 185, 190, 195 or 200 or more features, provided that there are at least 2, 3, 4, 5, 6, or 7 or more biomarkers in the biomarker profile. In some embodiments, a biomarker profile can include at least 2, 3, 4, 5, 6, 7, 8, 9, 10, 11, 12, 13, 14, 15, 16, 17, 18, 19, 20, 25, 30, 35, 40, 45, 50, or more features. Regardless of embodiment, these features can be determined through the use of any reproducible measurement technique or combination of measurement techniques. Such techniques include those that are well known in the art including any technique described herein or, for example, any technique disclosed in Section 5.4, infra. Typically, such techniques are used to measure feature values using a biological sample taken from a subject at a single point in time or multiple samples taken at multiple points in time. In one embodiment, an exemplary technique to obtain a biomarker profile from a sample taken from a subject is a cDNA microarray (see, e.g., Section 5.4.1.2 and Section 6, infra). In another embodiment, an exemplary technique to obtain a biomarker profile from a sample taken from a subject is a protein-based assay or other form of protein-based technique such as described in the BD Cytometric Bead Array (CBA) Human Inflammation Kit Instruction Manual (BD Biosciences) or the bead assay described in U.S. Pat. No. 5,981,180, each of which is incorporated herein by reference in their entirety, and in particular for their teachings of various methods of assay protein concentrations in biological samples. In still another embodiment, the biomarker profile is mixed, meaning that it comprises some biomarkers that are nucleic acids, or indications thereof, and some biomarkers that are proteins, or indications thereof. In such embodiments, both protein based and nucleic acid based techniques are used to obtain a biomarker profile from one or more samples taken from a subject. In other words, the feature values for the features associated with the biomarkers in the biomarker profile that are nucleic acids are obtained by nucleic acid based measurement techniques (e.g., a nucleic acid microarray) and the feature values for the features associated with the biomarkers in the biomarker profile that are proteins are obtained by protein based measurement techniques. In some embodiments biomarker profiles can be obtained using a kit, such as a kit described in Section 5.3 below.

In specific embodiments, a subject is screened using the methods and compositions of the invention as frequently as necessary (e.g., during their stay in the ICU) to diagnose or predict sepsis or SIRS in a subject. In a preferred embodiment, the subject is screened soon after they arrive in the ICU. In some embodiments, the subject is screened daily after they arrive in the ICU. In some embodiments, the subject is screened every 1 to 4 hours, 1 to 8 hours, 8 to 12 hours, 12 to 16 hours, or 16 to 24 hours after they arrive in the ICU.

5.3 Kits

The invention also provides kits that are useful in diagnosing or predicting the development of sepsis or diagnosing SIRS in a subject. In some embodiments, the kits of the present invention comprise at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 96, 100, 105, 110, 115, 120, 125, 130, 135, 140, 145, 150, 155, 160, 165, 170, 175, 180, 185, 190, 195 or 200 or more biomarkers and/or reagents to detect the presence or abundance of such biomarkers. In other embodiments, the kits of the present invention comprise at least 2, but as many as several hundred or more biomarkers. In some embodiments, the kits of the present invention comprise at least 2, 3, 4, 5, 6, 7, 8, 9, 10, 11, 12, 13, 14, 15, 16, 17, 18, 19, 20, 25, 30, 35, 40, 45, 50 or more biomarkers selected from Table I of Section 5.11. In some embodiments, the kits of the present invention comprise at least 2, 3, 4, 5, 6, 7, 8, 9, 10, 11, 12, 13, 14, 15, 16, 17, 18, 19, 20, 25, 30, 35, 40 or more biomarkers selected from Table J of Section 5.11. In some embodiments, the kits of the present invention comprise at least 2, 3, 4, 5, 6, 7, 8, 9, or all 10 of the biomarkers in Table K of Section 5.11. In accordance with the definition of biomarkers given in Section 5.1, in some instances, a biomarker is in fact a discriminating molecule of, for example, a gene, mRNA, or protein rather than the gene, mRNA, or protein itself. Thus, a biomarker could be a molecule that indicates the presence or abundance of a particular gene or protein, or fragment thereof, identified in any one of Tables I, J, or K of Section 5.11 rather than the actual gene or protein itself. Such discriminating molecules are sometimes referred to in the art as "reagents." In some embodiments, the kits of the present invention comprise at least 2, but as many as several hundred or more biomarkers.

The biomarkers of the kits of the present invention can be used to generate biomarker profiles according to the present invention. Examples of classes of compounds of the kit include, but are not limited to, proteins and fragments thereof, peptides, proteoglycans, glycoproteins, lipoproteins, carbohydrates, lipids, nucleic acids (e.g., DNA, such as cDNA or amplified DNA, or RNA, such as mRNA), organic or inorganic chemicals, natural or synthetic polymers, small molecules (e.g., metabolites), or discriminating molecules or discriminating fragments of any of the foregoing. In a specific embodiment, a biomarker is of a particular size, (e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 1000, 2000, 3000, 5000, 10 k, 20 k, 100 k Daltons or greater). The biomarker(s) may be part of an array, or the biomarker(s) may be packaged separately and/or individually. The kit may also comprise at least one internal standard to be used in generating the biomarker profiles of the present invention. Likewise, the internal standard or standards can be any of the classes of compounds described above.

In one embodiment, the invention provides kits comprising probes and/or primers that may or may not be immobilized at an addressable position on a substrate, such as found, for example, in a microarray. In a particular embodiment, the invention provides such a microarray.

In a specific embodiment, the invention provides a kit for predicting the development of sepsis in a test subject that comprises a plurality of antibodies that specifically bind the protein-based biomarkers listed in any one of Tables 30, 31, 32, 33, 34, 36, I, J, or K. In such embodiments, the antibodies themselves are biomarkers within the scope of the present invention. In accordance with this embodiment, the kit may comprise a set of antibodies or functional fragments or derivatives thereof (e.g., Fab, F(ab')$_2$, Fv, or scFv fragments) that specifically bind at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 or more of the protein-based biomarkers set forth in any one of Tables 30, 31, 32, 33, 34, 36, I, J, or K. In accordance with this embodiment, the kit may include antibodies, fragments or derivatives thereof (e.g., Fab, F(ab')$_2$, Fv, or scFv fragments) that are specific for the biomarkers of the present invention. In one embodiment, the antibodies may be detectably labeled.

In a specific embodiment, the invention provides a kit for predicting the development of sepsis in a test subject comprises a plurality of antibodies that specifically bind a plurality of the protein-based biomarkers listed in Table I of Section 5.11. In accordance with this embodiment, the kit may comprise a set of antibodies or functional fragments or derivatives thereof (e.g., Fab, F(ab')$_2$, Fv, or scFv fragments) that specifically bind at least 2, 3, 4, 5, 6, 7, 8, 9, 10, 11, 12, 13, 14, 15, 16, 17, 18, 19, 20, 25, 30, 35, 40, 45, 50 or more of the biomarkers set forth in Table I. In accordance with this embodiment, the kit may include antibodies, fragments or derivatives thereof (e.g., Fab, F(ab')$_2$, Fv, or scFv fragments) that are specific for the biomarkers of the present invention. In one embodiment, the antibodies may be detectably labeled.

In other embodiments of the invention, a kit may comprise a specific biomarker binding component, such as an aptamer. If the biomarkers comprise a nucleic acid, the kit may provide an oligonucleotide probe that is capable of forming a duplex with the biomarker or with a complementary strand of a biomarker. The oligonucleotide probe may be detectably labeled. In such embodiments, the probes are themselves biomarkers that fall within the scope of the present invention.

The kits of the present invention may also include additional compositions, such as buffers, that can be used in constructing the biomarker profile. Prevention of the action of microorganisms can be ensured by the inclusion of various antibacterial and antifungal agents, for example, paraben, chlorobutanol, phenol sorbic acid, and the like. It may also be desirable to include isotonic agents such as sugars, sodium chloride, and the like.

Some kits of the present invention comprise a microarray. In one embodiment this microarray comprises a plurality of probe spots, wherein at least twenty percent of the probe spots in the plurality of probe spots correspond to biomarkers in any one of Tables 30, 31, 32, 33, 34, 36, I, J, or K. In some embodiments, at least twenty-five percent, at least thirty percent, at least thirty-five percent, at least forty percent, or at least sixty percent, or at least eighty percent of the probe spots in the plurality of probe spots correspond to biomarkers in any one of Tables 30, 31, 32, 33, 34, 36, I, J, or K. Such probe spots are biomarkers within the scope of the present invention. In some embodiments, the microarray consists of between about three and about one hundred probe spots on a substrate. In some embodiments, the microarray consists of between about three and about one hundred probe spots on a substrate. As used in this context, the term "about" means within five percent of the stated value, within ten percent of the stated value, or within twenty-five percent of the stated value. In some embodiments, such microarrays contain one or more probe spots for inter-microarray calibration or for calibration with other microarrays such as reference microarrays using techniques that are known to those of skill in the art. In some embodiments such microarrays are nucleic acid microarrays. In some embodiments, such microarrays are protein microarrays.

Some kits of the invention may further comprise a computer program product for use in conjunction with a computer system, wherein the computer program product comprises a computer readable storage medium and a computer program mechanism embedded therein. In such kits, the computer program mechanism comprises instructions for evaluating whether a plurality of features in a biomarker profile of a test subject at risk for developing sepsis satisfies a first value set. Satisfying the first value set predicts that the test subject is likely to develop sepsis. In one embodiment, the plurality of features corresponds to biomarkers listed in any one of Tables 30, 31, 32, 33, 34, 36, I, J, or K. In some kits, the computer program product further comprises instructions for evaluating whether the plurality of features in the biomarker profile of the test subject satisfies a second value set. Satisfying the second value set predicts that the test subject is not likely to develop sepsis.

Some kits of the present invention comprise a computer having a central processing unit and a memory coupled to the central processing unit. The memory stores instructions for evaluating whether a plurality of features in a biomarker profile of a test subject at risk for developing sepsis satisfies a first value set. Satisfying the first value set predicts that the test subject is likely to develop sepsis. In one embodiment, the plurality of features corresponds to biomarkers listed in any one of Tables 30, 31, 32, 33, 34, 36, I, J, or K.

FIG. 35 details an exemplary system that supports the functionality described above. The system is preferably a computer system 10 having:
- a central processing unit 22;
- a main non-volatile storage unit 14, for example, a hard disk drive, for storing software and data, the storage unit 14 controlled by storage controller 12;
- a system memory 36, preferably high speed random-access memory (RAM), for storing system control programs, data, and application programs, comprising programs and data loaded from non-volatile storage unit 14; system memory 36 may also include read-only memory (ROM);
- a user interface 32, comprising one or more input devices (e.g., keyboard 28) and a display 26 or other output device;
- a network interface card 20 for connecting to any wired or wireless communication network 34 (e.g., a wide area network such as the Internet);
- an internal bus 30 for interconnecting the aforementioned elements of the system; and
- a power source 24 to power the aforementioned elements.

Operation of computer 10 is controlled primarily by operating system 40, which is executed by central processing unit 22. Operating system 40 can be stored in system memory 36. In addition to operating system 40, in a typical implementation, system memory 36 includes:
- file system 42 for controlling access to the various files and data structures used by the present invention;
- a training data set 44 for use in construction one or more decision rules in accordance with the present invention;
- a data analysis algorithm module 54 for processing training data and constructing decision rules;
- one or more decision rules 56;
- a biomarker profile evaluation module 60 for determining whether a plurality of features in a biomarker profile of a test subject satisfies a first value set or a second value set;
- a test subject biomarker profile 62 comprising biomarkers 64 and, for each such biomarkers, features 66; and
- a database 68 of select biomarkers of the present invention (e.g., Table 30 and/or Table I and/or Table J and/or Table K, and/or Table L and/or Table M and/or Table N and/or Table O etc.) and/or one or features for each of these select biomarkers.

Training data set 46 comprises data for a plurality of subjects 46. For each subject 46 there is a subject identifier 48 and a plurality of biomarkers 50. For each biomarker 50, there is at least one feature 52. Although not shown in FIG. 35, for each feature 52, there is a feature value. For each decision rule 56 constructed using data analysis algorithms, there is at least one decision rule value set 58.

As illustrated in FIG. 35, computer 10 comprises software program modules and data structures. The data structures stored in computer 10 include training data set 44, decision rules 56, test subject biomarker profile 62, and biomarker database 68. Each of these data structures can comprise any form of data storage system including, but not limited to, a flat ASCII or binary file, an Excel spreadsheet, a relational database (SQL), or an on-line analytical processing (OLAP) database (MDX and/or variants thereof). In some specific embodiments, such data structures are each in the form of one or more databases that include hierarchical structure (e.g., a star schema). In some embodiments, such data structures are each in the form of databases that do not have explicit hierarchy (e.g., dimension tables that are not hierarchically arranged).

In some embodiments, each of the data structures stored or accessible to system 10 are single data structures. In other embodiments, such data structures in fact comprise a plurality of data structures (e.g., databases, files, archives) that may or may not all be hosted by the same computer 10. For example, in some embodiments, training data set 44 comprises a plurality of Excel spreadsheets that are stored either on computer 10 and/or on computers that are addressable by computer 10 across wide area network 34. In another example, training data set 44 comprises a database that is either stored on computer 10 or is distributed across one or more computers that are addressable by computer 10 across wide area network 34.

It will be appreciated that many of the modules and data structures illustrated in FIG. 35 can be located on one or more remote computers. For example, some embodiments of the present application are web service-type implementations. In such embodiments, biomarker profile evaluation module 60 and/or other modules can reside on a client computer that is in communication with computer 10 via network 34. In some embodiments, for example, biomarker profile evaluation module 60 can be an interactive web page.

In some embodiments, training data set 44, decision rules 56, and/or biomarker database 68 illustrated in FIG. 35 are on a single computer (computer 10) and in other embodiments one or more of such data structures and modules are hosted by one or more remote computers (not shown). Any arrangement of the data structures and software modules illustrated in FIG. 35 on one or more computers is within the scope of the present invention so long as these data structures and software modules are addressable with respect to each other across network 34 or by other electronic means. Thus, the present invention fully encompasses a broad array of computer systems.

Still another kit of the present invention comprises computers and computer readable media for evaluating whether a test subject is likely to develop sepsis or SIRS. For instance, one embodiment of the present invention provides a computer program product for use in conjunction with a computer system. The computer program product comprises a computer readable storage medium and a computer program mechanism embedded therein. The computer program mechanism comprises instructions for evaluating whether a plurality of features in a biomarker profile of a test subject at risk for developing sepsis satisfies a first value set. Satisfaction of the first value set predicts that the test subject is likely to develop sepsis. The plurality of features are measurable aspects of a plurality of biomarkers, the plurality of biomarkers comprising at least three biomarkers listed in Table I. In certain embodiments, the plurality of biomarkers comprises at least six biomarkers listed in Table I, wherein the plurality of biomarkers comprises both IL-6 and IL-8. In some embodiments, the computer program product further comprises instructions for evaluating whether the plurality of features in the biomarker profile of the test subject satisfies a second value set. Satisfaction of the second value set predicts that the test subject is not likely to develop sepsis. In some embodiments, the biomarker profile has between 3 and 50 biomarkers listed in Table I, between 3 and 40 biomarkers listed in Table I, at least four biomarkers listed in Table I, or at least eight biomarkers listed in Table I.

Another kit of the present invention comprises a central processing unit and a memory coupled to the central processing unit. The memory stores instructions for evaluating whether a plurality of features in a biomarker profile of a test subject at risk for developing sepsis satisfies a first value set. Satisfaction of the first value set predicts that the test subject is likely to develop sepsis. The plurality of features are measurable aspects of a plurality of biomarkers. This plurality of biomarkers comprises at least three biomarkers from Table I. In some embodiments, the plurality of biomarkers comprises at least six biomarkers listed in Table I when the plurality of biomarkers comprises both IL-6 and IL-8. In some embodiments, the memory further stores instructions for evaluating whether the plurality of features in the biomarker profile of the test subject satisfies a second value set, wherein satisfying the second value set predicts that the test subject is not likely to develop sepsis. In some embodiments, the biomarker profile consists of between 3 and 50 biomarkers listed in Table I, between 3 and 40 biomarkers listed in Table I, at least four biomarkers listed in Table I., or at least eight biomarkers listed in Table I.

Another kit in accordance with the present invention comprises a computer system for determining whether a subject is likely to develop sepsis. The computer system comprises a central processing unit and a memory, coupled to the central processing unit. The memory stores instructions for obtaining a biomarker profile of a test subject. The biomarker profile comprises a plurality of features. Each feature in the plurality of features is a measurable aspect of a corresponding biomarker in a plurality of biomarkers. The plurality of biomarkers comprises at least three biomarkers listed in Table I. The memory further comprises instructions for transmitting the biomarker profile to a remote computer. The remote computer includes instructions for evaluating whether the plurality of features in the biomarker profile of the test subject satisfies a first value set. Satisfaction of the first value set predicts that the test subject is likely to develop sepsis. The memory further comprises instructions for receiving a determination, from the remote computer, as to whether the plurality of features in the biomarker profile of the test subject satisfies the first value set. The memory also comprises instructions for reporting whether the plurality of features in the biomarker profile of the test subject satisfies the first value set. In some embodiments, the plurality of biomarkers comprises at least six biomarkers listed in Table I when the plurality of biomarkers comprises both IL-6 and IL-8. In some embodiments, the remote computer further comprises instructions for evaluating whether the plurality of features in the biomarker profile of the test subject satisfies a second value set. Satisfaction of the second value set predicts that the test subject is not likely to develop sepsis. In such embodiments, the memory further comprises instructions for receiving a determination, from the remote computer, as to whether the plurality of features in the biomarker profile of the test subject satisfies the second set as well as instructions for reporting whether the plurality of features in the biomarker profile of the test subject satisfies the second value set. In some embodiments, the plurality of biomarkers comprises at least four biomarkers listed in Table I. In some embodiments, the plurality of biomarkers comprises at least six biomarkers listed in Table I.

Still another aspect of the present invention comprises a digital signal embodied on a carrier wave comprising a respective value for each of a plurality of features in a biomarker profile. The plurality of features are measurable aspects of a plurality of biomarkers. The plurality of biomarkers comprises at least three biomarkers listed in Table I. In some embodiments, the plurality of biomarkers comprises at least six biomarkers listed in Table I when the plurality of biomarkers comprises both IL-6 and IL-8. In some embodiments, the plurality of biomarkers comprises at least four biomarkers listed in Table I. In some embodiments, the plurality of biomarkers comprises at least eight biomarkers listed in Table I.

Still another aspect of the present invention provides a digital signal embodied on a carrier wave comprising a determination as to whether a plurality of features in a biomarker profile of a test subject satisfies a value set. The plurality of features are measurable aspects of a plurality of biomarkers. This plurality of biomarkers comprises at least three biomarkers listed in Table I. Satisfying the value set predicts that the test subject is likely to develop sepsis. In some embodiments, the plurality of biomarkers comprises at least six biomarkers listed in Table I when the plurality of biomarkers comprises both IL-6 and IL-8. In some embodiments, the plurality of biomarkers comprises at least four biomarkers listed in Table I. In some embodiments, the plurality of biomarkers comprises at least eight biomarkers listed in Table I.

Still another embodiment provides a digital signal embodied on a carrier wave comprising a determination as to whether a plurality of features in a biomarker profile of a test subject satisfies a value set. The plurality of features are measurable aspects of a plurality of biomarkers. The plurality of biomarkers comprise at least three biomarkers listed in Table I. Satisfaction of the value set predicts that the test subject is not likely to develop sepsis. In some embodiments, the plurality of biomarkers comprises at least six biomarkers listed in Table I when the plurality of biomarkers comprises both IL-6 and IL-8. In some embodiments, the plurality of biomarkers comprises at least four biomarkers listed in Table I. In some embodiments, the plurality of biomarkers comprises at least eight biomarkers listed in Table I.

Still another embodiment of the present invention provides a graphical user interface for determining whether a subject is likely to develop sepsis. The graphical user interface comprises a display field for a displaying a result encoded in a digital signal embodied on a carrier wave received from a remote computer. The plurality of features are measurable aspects of a plurality of biomarkers. The plurality of biomarkers comprise at least three biomarkers listed in Table I. The result has a first value when a plurality of features in a biomarker profile of a test subject satisfies a first value set. The result has a second value when a plurality of features in a biomarker profile of a test subject satisfies a second value set. In some embodiments, the plurality of biomarkers comprises at least six biomarkers listed in Table I when the plurality of biomarkers comprises IL-6 and IL-8. In some embodiments, the plurality of biomarkers comprises at least four biomarkers listed in Table I. In some embodiments, the plurality of biomarkers comprises at least eight biomarkers listed in Table I.

Yet another kit of the present invention provides a computer system for determining whether a subject is likely to develop sepsis. The computer system comprises a central processing unit and a memory, coupled to the central processing unit. The memory stores instructions for obtaining a biomarker profile of a test subject. The biomarker profile comprises a plurality of features. The plurality of features are measurable aspects of a plurality of biomarkers. The plurality of biomarkers comprise at least three biomarkers listed in Table I. The memory further stores instructions for evaluating whether the plurality of features in the biomarker profile of the test subject satisfies a first value set. Satisfying the first value set predicts that the test subject is likely to develop sepsis. The memory also stores instructions for reporting whether the plurality of features in the biomarker profile of the test subject satisfies the first value set. In some embodiments, the plurality of biomarkers comprises at least six biomarkers listed in Table I when the plurality of biomarkers comprises both IL-6 and IL-8. In some embodiments, the plurality of biomarkers comprises at least four biomarkers listed in Table I. In some embodiments, the plurality of biomarkers comprises at least eight biomarkers listed in Table I.

5.4 Generation of Biomarker Profiles

According to one embodiment, the methods of the present invention comprise generating a biomarker profile from a biological sample taken from a subject. The biological sample may be, for example, whole blood, plasma, serum, red blood cells, platelets, neutrophils, eosinophils, basophils, lymphocytes, monocytes, saliva, sputum, urine, cerebral spinal fluid, cells, a cellular extract, a tissue sample, a tissue biopsy, a stool sample or any sample that may be obtained from a subject using techniques well known to those of skill in the art. In a specific embodiment, a biomarker profile is determined using samples collected from a subject at one or more separate time points. In another specific embodiment, a biomarker profile is generated using samples obtained from a subject at separate time points. In one example, these samples are obtained from the subject either once or, alternatively, on a daily basis, or more frequently, e.g., every 4, 6, 8 or 12 hours. In a specific embodiment, a biomarker profile is determined using samples collected from a single tissue type. In another specific embodiment, a biomarker profile is determined using samples collected from at least two different tissue types.

5.4.1 Methods of Detecting Nucleic Acid Biomarkers

In specific embodiments of the invention, biomarkers in a biomarker profile are nucleic acids. Such biomarkers and corresponding features of the biomarker profile may be generated, for example, by detecting the expression product (e.g., a polynucleotide or polypeptide) of one or more genes described herein (e.g., a gene listed in Table 30, Table I, Table J, or Table K.). In a specific embodiment, the biomarkers and corresponding features in a biomarker profile are obtained by detecting and/or analyzing one or more nucleic acids expressed from a gene disclosed herein (e.g., a gene listed in Table 30, Table I, Table J, or Table K) using any method well known to those skilled in the art including, but by no means limited to, hybridization, microarray analysis, RT-PCR, nuclease protection assays and Northern blot analysis.

In certain embodiments, nucleic acids detected and/or analyzed by the methods and compositions of the invention include RNA molecules such as, for example, expressed RNA molecules which include messenger RNA (mRNA) molecules, mRNA spliced variants as well as regulatory RNA, cRNA molecules (e.g., RNA molecules prepared from cDNA molecules that are transcribed in vitro) and discriminating fragments thereof. Nucleic acids detected and/or analyzed by the methods and compositions of the present invention can also include, for example, DNA molecules such as genomic DNA molecules, cDNA molecules, and discriminating fragments thereof (e.g., oligonucleotides, ESTs, STSs, etc.).

The nucleic acid molecules detected and/or analyzed by the methods and compositions of the invention may be naturally occurring nucleic acid molecules such as genomic or extragenomic DNA molecules isolated from a sample, or RNA molecules, such as mRNA molecules, present in, isolated from or derived from a biological sample. The sample of nucleic acids detected and/or analyzed by the methods and compositions of the invention comprise, e.g., molecules of DNA, RNA, or copolymers of DNA and RNA. Generally, these nucleic acids correspond to particular genes or alleles of genes, or to particular gene transcripts (e.g., to particular mRNA sequences expressed in specific cell types or to particular cDNA sequences derived from such mRNA sequences). The nucleic acids detected and/or analyzed by the methods and compositions of the invention may correspond to different exons of the same gene, e.g., so that different splice variants of that gene may be detected and/or analyzed.

In specific embodiments, the nucleic acids are prepared in vitro from nucleic acids present in, or isolated or partially isolated from biological a sample. For example, in one embodiment, RNA is extracted from a sample (e.g., total cellular RNA, poly(A)$^+$ messenger RNA, fraction thereof) and messenger RNA is purified from the total extracted RNA. Methods for preparing total and poly(A)$^+$ RNA are well known in the art, and are described generally, e.g., in Sambrook et al., 2001, Molecular Cloning: A Laboratory Manual. 3$^{rd}$ ed. Cold Spring Harbor Laboratory Press (Cold Spring Harbor, N.Y.), which is incorporated by reference herein in its entirety. In one embodiment, RNA is extracted from a sample using guanidinium thiocyanate lysis followed by CsCl centrifugation and an oligo dT purification (Chirgwin et al., 1979, *Biochemistry* 18:5294-5299). In another embodiment, RNA is extracted from a sample using guanidinium thiocyanate lysis followed by purification on RNeasy columns (Qiagen, Valencia, Calif.). cDNA is then synthesized from the purified mRNA using, e.g., oligo-dT or random primers. In specific embodiments, the target nucleic acids are cRNA prepared from purified messenger RNA extracted from a sample. As used herein, cRNA is defined here as RNA complementary to the source RNA. The extracted RNAs are amplified using a process in which doubled-stranded cDNAs are synthesized from the RNAs using a primer linked to an RNA polymerase promoter in a direction capable of directing transcription of anti-sense RNA. Anti-sense RNAs or cRNAs are then transcribed from the second strand of the double-stranded cDNAs using an RNA polymerase (see, e.g., U.S. Pat. Nos. 5,891,636, 5,716, 785; 5,545,522 and 6,132,997, which are hereby incorporated by reference). Both oligo-dT primers (U.S. Pat. Nos. 5,545,522 and 6,132,997, hereby incorporated by reference herein) or random primers that contain an RNA polymerase promoter or complement thereof can be used. In some embodiments the target nucleic acids are short and/or fragmented nucleic acid molecules which are representative of the original nucleic acid population of the sample.

In one embodiment, nucleic acids of the invention can be detectably labeled. For example, cDNA can be labeled directly, e.g., with nucleotide analogs, or indirectly, e.g., by making a second, labeled cDNA strand using the first strand as a template. Alternatively, the double-stranded cDNA can be transcribed into cRNA and labeled.

In some embodiments the detectable label is a fluorescent label, e.g., by incorporation of nucleotide analogs. Other labels suitable for use in the present invention include, but are not limited to, biotin, iminobiotin, antigens, cofactors, dinitrophenol, lipoic acid, olefinic compounds, detectable polypeptides, electron rich molecules, enzymes capable of generating a detectable signal by action upon a substrate, and radioactive isotopes. Suitable radioactive isotopes include $^{32}P$, $^{35}S$, $^{14}C$, $^{15}N$ and $^{125}I$. Fluorescent molecules suitable for the present invention include, but are not limited to, fluorescein and its derivatives, rhodamine and its derivatives, Texas red, 5' carboxy-fluorescein ("FMA"), 6-carboxy-4',5'-dichloro-2',7'-dimethoxyfluorescein, succinimidyl ester ("JOE"), 6-carboxytetramethylrhodamine ("TAMRA"), 6 carboxy-X-rhodamine ("ROX"), HEX, TET, IRD40, and IRD41. Fluorescent molecules that are suitable for the invention further include, but are not limited to: cyamine dyes, including by not limited to Cy3, Cy3.5 and Cy5; BODIPY dyes including but not limited to BODIPY-FL, BODIPY-TR, BODIPY-TMR, BODIPY-630/650, BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron-rich indicator molecules suitable for the present invention include, but are not limited to, ferritin, hemocyanin, and colloidal gold. Alternatively, in some embodiments the target nucleic acids may be labeled by specifically complexing a first group to the nucleic acid. A second group, covalently linked to an indicator molecules and which has an affinity for the first group, can be used to indirectly detect the target nucleic acid. In such an embodiment, compounds suitable for use as a first group include, but are not limited to, biotin and iminobiotin. Compounds suitable for use as a second group include, but are not limited to, avidin and streptavidin.

5.4.1.1 Nucleic Acid Arrays

In certain embodiments of the invention, nucleic acid arrays are employed to generate features of biomarkers in a biomarker profile by detecting the expression of any one or more of the genes described herein (e.g., a gene listed in Table 30, Table I, Table J or Table K). In one embodiment of the invention, a microarray, such as a cDNA microarray, is used to determine feature values of biomarkers in a biomarker profile. The diagnostic use of cDNA arrays is well known in the art. (See, e.g., Zou et. al., 2002, Oncogene 21:4855-4862; as well as Draghici, 2003, Data Analysis Tools for DNA Microarrays, Chapman & Hall/CRC, each of which is hereby incorporated by reference herein in its entirety). Exemplary methods for cDNA microarray analysis are described below, and in the examples in Section 6, infra.

In certain embodiments, the feature values for biomarkers in a biomarker profile are obtained by hybridizing to the array detectably labeled nucleic acids representing or corresponding to the nucleic acid sequences in mRNA transcripts present in a biological sample (e.g., fluorescently labeled cDNA synthesized from the sample) to a microarray comprising one or more probe spots.

Nucleic acid arrays, for example, microarrays, can be made in a number of ways, of which several are described herein below. Preferably, the arrays are reproducible, allowing multiple copies of a given array to be produced and results from said microarrays compared with each other. Preferably, the arrays are made from materials that are stable under binding (e.g., nucleic acid hybridization) conditions. Those skilled in the art will know of suitable supports, substrates or carriers for hybridizing test probes to probe spots on an array, or will be able to ascertain the same by use of routine experimentation.

Arrays, for example, microarrays, used can include one or more test probes. In some embodiments each such test probe comprises a nucleic acid sequence that is complementary to a subsequence of RNA or DNA to be detected. Each probe typically has a different nucleic acid sequence, and the position of each probe on the solid surface of the array is usually known or can be determined. Arrays useful in accordance with the invention can include, for example, oligonucleotide microarrays, cDNA based arrays, SNP arrays, spliced variant arrays and any other array able to provide a qualitative, quantitative or semi-quantitative measurement of expression of a gene described herein (e.g., a gene listed in Table 30, Table I, Table J or Table K). Some types of microarrays are addressable arrays. More specifically, some microarrays are positionally addressable arrays. In some embodiments, each probe of the array is located at a known, predetermined position on the solid support so that the identity (e.g., the sequence) of each probe can be determined from its position on the array (e.g., on the support or surface). In some embodiments, the arrays are ordered arrays. Microarrays are generally described in Draghici, 2003, Data Analysis Tools for DNA Microarrays, Chapman & Hall/CRC, which is hereby incorporated herein by reference in its entirety.

In some embodiments of the present invention, an expressed transcript (e.g., a transcript of a gene described herein) is represented in the nucleic acid arrays. In such embodiments, a set of binding sites can include probes with different nucleic acids that are complementary to different sequence segments of the expressed transcript. Exemplary nucleic acids that fall within this class can be of length of 15 to 200 bases, 20 to 100 bases, 25 to 50 bases, 40 to 60 bases or some other range of bases. Each probe sequence can also comprise one or more linker sequences in addition to the sequence that is complementary to its target sequence. As used herein, a linker sequence is a sequence between the sequence that is complementary to its target sequence and the surface of support. For example, the nucleic acid arrays of the invention can comprise one probe specific to each target gene or exon. However, if desired, the nucleic acid arrays can contain at least 2, 5, 10, 100, or 1000 or more probes specific to some expressed transcript (e.g., a transcript of a gene described herein, e.g., in Table 30, Table I, Table J, or Table K). For example, the array may contain probes tiled across the sequence of the longest mRNA isoform of a gene.

It will be appreciated that when cDNA complementary to the RNA of a cell, for example, a cell in a biological sample, is made and hybridized to a microarray under suitable hybridization conditions, the level of hybridization to the site in the array corresponding to a gene described herein (e.g., a gene listed in Table 30, Table I, Table J, or Table K) will reflect the prevalence in the cell of mRNA or mRNAs transcribed from that gene. Alternatively, in instances where multiple isoforms or alternate splice variants produced by particular genes are to be distinguished, detectably labeled (e.g., with a fluorophore) cDNA complementary to the total cellular mRNA can be hybridized to a microarray, and the site on the array corresponding to an exon of the gene that is not transcribed or is removed during RNA splicing in the cell will have little or no signal (e.g., fluorescent signal), and a site corresponding to an exon of a gene for which the encoded mRNA expressing the exon is prevalent will have a relatively strong signal. The relative abundance of different mRNAs produced from the same gene by alternative splicing is then determined by the signal strength pattern across the whole set of exons monitored for the gene.

In one embodiment, hybridization levels at different hybridization times are measured separately on different, identical microarrays. For each such measurement, at hybridization time when hybridization level is measured, the microarray is washed briefly, preferably in room temperature in an aqueous solution of high to moderate salt concentration (e.g., 0.5 to 3 M salt concentration) under conditions which retain all bound or hybridized nucleic acids while removing all unbound nucleic acids. The detectable label on the remaining, hybridized nucleic acid molecules on each probe is then measured by a method which is appropriate to the particular labeling method used. The resulting hybridization levels are then combined to form a hybridization curve. In another embodiment, hybridization levels are measured in real time using a single microarray. In this embodiment, the microarray is allowed to hybridize to the sample without interruption and the microarray is interrogated at each hybridization time in a non-invasive manner. In still another embodiment, one can use one array, hybridize for a short time, wash and measure the hybridization level, put back to the same sample, hybridize for another period of time, wash and measure again to get the hybridization time curve.

In some embodiments, nucleic acid hybridization and wash conditions are chosen so that the nucleic acid biomarkers to be analyzed specifically bind or specifically hybridize to the complementary nucleic acid sequences of the array, typically to a specific array site, where its complementary DNA is located.

Arrays containing double-stranded probe DNA situated thereon can be subjected to denaturing conditions to render the DNA single-stranded prior to contacting with the target nucleic acid molecules. Arrays containing single-stranded probe DNA (e.g., synthetic oligodeoxyribonucleic acids) may need to be denatured prior to contacting with the target nucleic acid molecules, e.g., to remove hairpins or dimers which form due to self complementary sequences.

Optimal hybridization conditions will depend on the length (e.g., oligomer versus polynucleotide greater than 200 bases) and type (e.g., RNA, or DNA) of probe and target nucleic acids. General parameters for specific (i.e., stringent) hybridization conditions for nucleic acids are described in Sambrook et al., (supra), and in Ausubel et al., 1988, *Current Protocols in Molecular Biology*, Greene Publishing and Wiley-Interscience, New York. When the cDNA microarrays of Shena et al. are used, typical hybridization conditions are hybridization in 5×SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Shena et al., 1996, *Proc. Natl. Acad. Sci. U.S.A.* 93:10614). Useful hybridization conditions are also provided in, e.g., Tijessen, 1993, *Hybridization With Nucleic Acid Probes*, Elsevier Science Publishers B.V.; Kricka, 1992, Nonisotopic DNA Probe Techniques, Academic Press, San Diego, Calif.; and Zou et. al., 2002, *Oncogene* 21:4855-4862; and Draghici, *Data Analysis Tools for DNA Microanalysis*, 2003, CRC Press LLC, Boca Raton, Fla., pp. 342-343, which are hereby incorporated by reference herein in their entirety.

In a specific embodiment, a microarray can be used to sort out RT-PCR products that have been generated by the methods described, for example, below in Section 5.4.1.2.

5.4.1.2 RT-PCR

In certain embodiments, to determine the feature values of biomarkers in a biomarker profile of the invention, the level of expression of one or more of the genes described herein (e.g., a gene listed in Table 30, Table I, Table J, or Table K) is measured by amplifying RNA from a sample using reverse transcription (RT) in combination with the polymerase chain reaction (PCR). In accordance with this embodiment, the reverse transcription may be quantitative or semi-quantitative. The RT-PCR methods taught herein may be used in conjunction with the microarray methods described above, for example, in Section 5.4.1.1. For example, a bulk PCR reaction may be performed, the PCR products may be resolved and used as probe spots on a microarray. See also Section 6.10, infra.

Total RNA, or mRNA from a sample is used as a template and a primer specific to the transcribed portion of the gene(s) is used to initiate reverse transcription. Methods of reverse transcribing RNA into cDNA are well known and described in Sambrook et al., 2001, supra. Primer design can be accomplished based on known nucleotide sequences that have been published or available from any publicly available sequence database such as GenBank. For example, primers may be designed for any of the genes described herein (see, e.g., in Table 30, Table I, Table J, or Table K). Further, primer design may be accomplished by utilizing commercially available software (e.g., Primer Designer 1.0, Scientific Software etc.). The product of the reverse transcription is subsequently used as a template for PCR.

PCR provides a method for rapidly amplifying a particular nucleic acid sequence by using multiple cycles of DNA replication catalyzed by a thermostable, DNA-dependent DNA polymerase to amplify the target sequence of interest. PCR requires the presence of a nucleic acid to be amplified, two single-stranded oligonucleotide primers flanking the sequence to be amplified, a DNA polymerase, deoxyribonucleoside triphosphates, a buffer and salts. The method of PCR is well known in the art. PCR, is performed, for example, as described in Mullis and Faloona, 1987, Methods Enzymol. 155:335, which is hereby incorporated herein by reference in its entirety.

PCR can be performed using template DNA or cDNA (at least 1 fg; more usefully, 1-1000 ng) and at least 25 pmol of oligonucleotide primers. A typical reaction mixture includes:

2 µl of DNA, 25 pmol of oligonucleotide primer, 2.5 µl of 10 M PCR buffer 1 (Perkin-Elmer, Foster City, Calif.), 0.4 µl of 1.25 M dNTP, 0.15 µl (or 2.5 units) of Taq DNA polymerase (Perkin Elmer, Foster City, Calif.) and deionized water to a total volume of 25 µl. Mineral oil is overlaid and the PCR is performed using a programmable thermal cycler.

The length and temperature of each step of a PCR cycle, as well as the number of cycles, are adjusted according to the stringency requirements in effect. Annealing temperature and timing are determined both by the efficiency with which a primer is expected to anneal to a template and the degree of mismatch that is to be tolerated. The ability to optimize the stringency of primer annealing conditions is well within the knowledge of one of moderate skill in the art. An annealing temperature of between 30° C. and 72° C. is used. Initial denaturation of the template molecules normally occurs at between 92° C. and 99° C. for 4 minutes, followed by 20-40 cycles consisting of denaturation (94-99° C. for 15 seconds to 1 minute), annealing (temperature determined as discussed above; 1-2 minutes), and extension (72° C. for 1 minute). The final extension step is generally carried out for 4 minutes at 72° C., and may be followed by an indefinite (0-24 hour) step at 4° C.

Quantitative RT-PCR ("QRT-PCR"), which is quantitative in nature, can also be performed to provide a quantitative measure of gene expression levels. In QRT-PCR reverse transcription and PCR can be performed in two steps, or reverse transcription combined with PCR can be performed concurrently. One of these techniques, for which there are commercially available kits such as Taqman (Perkin Elmer, Foster City, Calif.) or as provided by Applied Biosystems (Foster City, Calif.) is performed with a transcript-specific antisense probe. This probe is specific for the PCR product (e.g. a nucleic acid fragment derived from a gene) and is prepared with a quencher and fluorescent reporter probe complexed to the 5' end of the oligonucleotide. Different fluorescent markers are attached to different reporters, allowing for measurement of two products in one reaction. When Taq DNA polymerase is activated, it cleaves off the fluorescent reporters of the probe bound to the template by virtue of its 5'-to-3' exonuclease activity. In the absence of the quenchers, the reporters now fluoresce. The color change in the reporters is proportional to the amount of each specific product and is measured by a fluorometer; therefore, the amount of each color is measured and the PCR product is quantified. The PCR reactions are performed in 96-well plates so that samples derived from many individuals are processed and measured simultaneously. The Taqman system has the additional advantage of not requiring gel electrophoresis and allows for quantification when used with a standard curve.

A second technique useful for detecting PCR products quantitatively is to use an intercolating dye such as the commercially available QuantiTect SYBR Green PCR (Qiagen, Valencia Calif.). RT-PCR is performed using SYBR green as a fluorescent label which is incorporated into the PCR product during the PCR stage and produces a flourescense proportional to the amount of PCR product.

Both Taqman and QuantiTect SYBR systems can be used subsequent to reverse transcription of RNA. Reverse transcription can either be performed in the same reaction mixture as the PCR step (one-step protocol) or reverse transcription can be performed first prior to amplification utilizing PCR (two-step protocol).

Additionally, other systems to quantitatively measure mRNA expression products are known including Molecular Beacons® which uses a probe having a fluorescent molecule and a quencher molecule, the probe capable of forming a hairpin structure such that when in the hairpin form, the fluorescence molecule is quenched, and when hybridized the fluorescence increases giving a quantitative measurement of gene expression.

Additional techniques to quantitatively measure RNA expression include, but are not limited to, polymerase chain reaction, ligase chain reaction, Qbeta replicase (see, e.g., International Application No. PCT/US87/00880, which is hereby incorporated by reference), isothermal amplification method (see, e.g., Walker et al., 1992, PNAS 89:382-396, which is hereby incorporated herein by reference), strand displacement amplification (SDA), repair chain reaction, Asymmetric Quantitative PCR (see, e.g., U.S. Publication No. US 2003/30134307A1, herein incorporated by reference) and the multiplex microsphere bead assay described in Fuja et al., 2004, Journal of Biotechnology 108:193-205, herein incorporated by reference.

The level of expression of one or more of the genes described herein (e.g., the genes listed in Table 30, Table I, Table J, or Table K) can, for example, be measured by amplifying RNA from a sample using amplification (NASBA). See, e.g., Kwoh et al., 1989, PNAS USA 86:1173; International Publication No. WO 88/10315; and U.S. Pat. No. 6,329,179, each of which is hereby incorporated by reference. In NASBA, the nucleic acids may be prepared for amplification using conventional methods, e.g., phenol/chloroform extraction, heat denaturation, treatment with lysis buffer and minispin columns for isolation of DNA and RNA or guanidinium chloride extraction of RNA. These amplification techniques involve annealing a primer that has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once with a polymerase such as T7 or SP6. The resulting products, whether truncated or complete, indicate target specific sequences.

Several techniques may be used to separate amplification products. For example, amplification products may be separated by agarose, agarose-acrylamide or polyacrylamide gel electrophoresis using conventional methods. See Sambrook et al., 2001. Several techniques for detecting PCR products quantitatively without electrophoresis may also be used according to the invention (see, e.g., *PCR Protocols, A Guide to Methods and Applications*, Innis et al., 1990, Academic Press, Inc. N.Y., which is hereby incorporated by reference). For example, chromatographic techniques may be employed to effect separation. There are many kinds of chromatography which may be used in the present invention: adsorption, partition, ion-exchange and molecular sieve, HPLC, and many specialized techniques for using them including column, paper, thin-layer and gas chromatography (Freifelder, Physical Biochemistry Applications to Biochemistry and Molecular Biology, 2nd ed., Wm. Freeman and Co., New York, N.Y., 1982, which is hereby incorporated by reference).

Another example of a separation methodology is to covalently label the oligonucleotide primers used in a PCR reaction with various types of small molecule ligands. In one such separation, a different ligand is present on each oligonucleotide. A molecule, perhaps an antibody or avidin if the ligand is biotin, that specifically binds to one of the ligands is used to coat the surface of a plate such as a 96 well ELISA plate. Upon application of the PCR reactions to the surface of such a prepared plate, the PCR products are bound with specificity to the surface. After washing the plate to remove unbound reagents, a solution containing a second molecule that binds to the first ligand is added. This second molecule is linked to some kind of reporter system. The second molecule only binds to the plate if a PCR product has been produced whereby both oligonucleotide primers are incorporated into the final PCR products. The amount of the PCR product is then detected and quantified in a commercial plate reader much as ELISA reactions are detected and quantified. An ELISA-like system such as the one described here has been developed by Raggio Italgene (under the C-Track tradename.

Amplification products should be visualized in order to confirm amplification of the nucleic acid sequences of interest, i.e., nucleic acid sequences of one or more of the genes described herein (e.g., a gene listed in Table 30, Table I, Table J, or Table K). One typical visualization method involves staining of a gel with ethidium bromide and visualization under UV light. Alternatively, if the amplification products are integrally labeled with radio- or fluorometrically-labeled nucleotides, the amplification products may then be exposed to x-ray film or visualized under the appropriate stimulating spectra, following separation.

In one embodiment, visualization is achieved indirectly. Following separation of amplification products, a labeled, nucleic acid probe is brought into contact with the amplified nucleic acid sequence of interest, i.e., nucleic acid sequences of one or more of the genes described herein (e.g., a gene listed in Table 30, Table I, Table J, or Table K). The probe preferably is conjugated to a chromophore but may be radiolabeled. In another embodiment, the probe is conjugated to a binding partner, such as an antibody or biotin, where the other member of the binding pair carries a detectable moiety.

In another embodiment, detection is by Southern blotting and hybridization with a labeled probe. The techniques involved in Southern blotting are well known to those of skill in the art and may be found in many standard books on molecular protocols. See Sambrook et al., 2001. Briefly, amplification products are separated by gel electrophoresis. The gel is then contacted with a membrane, such as nitrocellulose, permitting transfer of the nucleic acid and noncovalent binding. Subsequently, the membrane is incubated with a chromophore-conjugated probe that is capable of hybridizing with a target amplification product. Detection is by exposure of the membrane to x-ray film or ion-emitting detection devices. One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

5.4.1.3 Nuclease Protection Assays

In particular embodiments, feature values for biomarkers in a biomarker profile can be obtained by performing nuclease protection assays (including both ribonuclease protection assays and S1 nuclease assays) to detect and quantify specific mRNAs (e.g., mRNAs of a gene described in Table 30, Table I, Table J, or Table K). Such assays are described in, for example, Sambrook et al., 2001, supra. In nuclease protection assays, an antisense probe (labeled with, e.g., radiolabeled or nonisotopic) hybridizes in solution to an RNA sample. Following hybridization, single-stranded, unhybridized probe and RNA are degraded by nucleases. An acrylamide gel is used to separate the remaining protected fragments. Typically, solution hybridization is more efficient than membrane-based hybridization, and it can accommodate up to 100 µg of sample RNA, compared with the 20-30 µg maximum of blot hybridizations.

The ribonuclease protection assay, which is the most common type of nuclease protection assay, requires the use of RNA probes. Oligonucleotides and other single-stranded DNA probes can only be used in assays containing S1 nuclease. The single-stranded, anti-sense probe must typically be completely homologous to target RNA to prevent cleavage of the probe:target hybrid by nuclease.

5.4.1.4 Northern Blot Assays

Any hybridization technique known to those of skill in the art can be used to generate feature values for biomarkers in a biomarker profile. In other particular embodiments, feature values for biomarkers in a biomarker profile can be obtained by Northern blot analysis (to detect and quantify specific RNA molecules (e.g., RNAs of a gene described in Table 30, Table I, Table J, or Table K). A standard Northern blot assay can be used to ascertain an RNA transcript size, identify alternatively spliced RNA transcripts, and the relative amounts of one or more genes described herein (in particular, mRNA) in a sample, in accordance with conventional Northern hybridization techniques known to those persons of ordinary skill in the art. In Northern blots, RNA samples are first separated by size via electrophoresis in an agarose gel under denaturing conditions. The RNA is then transferred to a membrane, crosslinked and hybridized with a labeled probe. Nonisotopic or high specific activity radiolabeled probes can be used including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes. The labeled probe, e.g., a radiolabelled cDNA, either containing the full-length, single stranded DNA or a fragment of that DNA sequence may be at least 20, at least 30, at least 50, or at least 100 consecutive nucleotides in length. The probe can be labeled by any of the many different methods known to those skilled in this art. The labels most commonly employed for these studies are radioactive elements, enzymes, chemicals that fluoresce when exposed to ultraviolet light, and others. A number of fluorescent materials are known and can be utilized as labels. These include, but are not limited to, fluorescein, rhodamine, auramine, Texas Red, AMCA blue and Lucifer Yellow. The radioactive label can be detected by any of the currently available counting procedures. Non-limiting examples of isotopes include $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$. Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Any enzymes known to one of skill in the art can be utilized. Examples of such enzymes include, but are not limited to, peroxidase, beta-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

5.4.2 Methods of Detecting Proteins

In specific embodiments of the invention, feature values of biomarkers in a biomarker profile can be obtained by detecting proteins, for example, by detecting the expression product (e.g., a nucleic acid or protein) of one or more genes described herein (e.g., a gene listed in Table 30, Table I, Table J, or Table K), or post-translationally modified, or otherwise modified, or processed forms of such proteins. In a specific embodiment, a biomarker profile is generated by detecting and/or analyzing one or more proteins and/or discriminating fragments thereof expressed from a gene disclosed herein (e.g., a gene listed in Table 30, Table I, Table J, or Table K) using any method known to those skilled in the art for detecting proteins including, but not limited to protein microarray analysis, immunohistochemistry and mass spectrometry.

Standard techniques may be utilized for determining the amount of the protein or proteins of interest (e.g., proteins expressed from genes listed in Table 30, Table I, Table J, or Table K) present in a sample. For example, standard techniques can be employed using, e.g., immunoassays such as, for example Western blot, immunoprecipitation followed by sodium dodecyl sulfate polyacrylamide gel electrophoresis, (SDS-PAGE), immunocytochemistry, and the like to determine the amount of protein or proteins of interest present in a sample. One exemplary agent for detecting a protein of interest is an antibody capable of specifically binding to a protein of interest, preferably an antibody detectably labeled, either directly or indirectly.

For such detection methods, if desired a protein from the sample to be analyzed can easily be isolated using techniques which are well known to those of skill in the art. Protein isolation methods can, for example, be such as those described in Harlow and Lane, 1988, *Antibodies: A Laboratory Manual*, Cold Spring Harbor Laboratory Press (Cold Spring Harbor, N.Y.), which is incorporated by reference herein in its entirety.

In certain embodiments, methods of detection of the protein or proteins of interest involve their detection via interaction with a protein-specific antibody. For example, antibodies directed to a protein of interest (e.g., a protein expressed from a gene described herein, e.g., a protein listed in Table 30, Table I, Table J, or Table K). Antibodies can be generated utilizing standard techniques well known to those of skill in the art. In specific embodiments, antibodies can be polyclonal, or more preferably, monoclonal. An intact antibody, or an antibody fragment (e.g., scFv, Fab or F(ab')$_2$) can, for example, be used.

For example, antibodies, or fragments of antibodies, specific for a protein of interest can be used to quantitatively or qualitatively detect the presence of a protein. This can be accomplished, for example, by immunofluorescence techniques. Antibodies (or fragments thereof) can, additionally, be employed histologically, as in immunofluorescence or immunoelectron microscopy, for in situ detection of a protein of interest. In situ detection can be accomplished by removing a biological sample (e.g., a biopsy specimen) from a patient, and applying thereto a labeled antibody that is directed to a protein of interest (e.g., a protein expressed from a gene in Table 30, Table I, Table J, or Table K). The antibody (or fragment) is preferably applied by overlaying the antibody (or fragment) onto a biological sample. Through the use of such a procedure, it is possible to determine not only the presence of the protein of interest, but also its distribution, in a particular sample. A wide variety of well-known histological methods (such as staining procedures) can be utilized to achieve such in situ detection.

Immunoassays for a protein of interest typically comprise incubating a biological sample of a detectably labeled antibody capable of identifying a protein of interest, and detecting the bound antibody by any of a number of techniques well-known in the art. As discussed in more detail, below, the term "labeled" can refer to direct labeling of the antibody via, e.g., coupling (i.e., physically linking) a detectable substance to the antibody, and can also refer to indirect labeling of the antibody by reactivity with another reagent that is directly labeled. Examples of indirect labeling include detection of a primary antibody using a fluorescently labeled secondary antibody.

The biological sample can be brought in contact with and immobilized onto a solid phase support or carrier such as nitrocellulose, or other solid support which is capable of immobilizing cells, cell particles or soluble proteins. The support can then be washed with suitable buffers followed by treatment with the detectably labeled fingerprint gene-specific antibody. The solid phase support can then be washed with the buffer a second time to remove unbound antibody. The amount of bound label on solid support can then be detected by conventional methods.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides and magnetite. The nature of the carrier can be either soluble to some extent or insoluble for the purposes of the present invention. The support material can have virtually any possible structural configuration so long as the coupled molecule is capable of binding to an antigen or antibody. Thus, the support configuration can be spherical, as in a bead, or cylindrical, as in the inside surface of a test tube, or the external surface of a rod. Alternatively, the surface can be flat such as a sheet, test strip, etc. Preferred supports include polystyrene beads. Those skilled in the art will know many other suitable carriers for binding antibody or antigen, or will be able to ascertain the same by use of routine experimentation.

One of the ways in which an antibody specific for a protein of interest can be detectably labeled is by linking the same to an enzyme and use in an enzyme immunoassay (EIA) (Voller, 1978, "The Enzyme Linked Immunosorbent Assay (ELISA)", Diagnostic Horizons 2:1-7, Microbiological Associates Quarterly Publication, Walkersville, Md.; Voller et al., 1978, J. Clin. Pathol. 31:507-520; Butler, J. E., 1981, Meth. Enzymol. 73:482-523; Maggio (ed.), 1980, *Enzyme Immunoassay*, CRC Press, Boca Raton, Fla.; Ishikawa et al., (eds.), 1981, *Enzyme Immunoassay*, Kgaku Shoin, Tokyo, each of which is hereby incorporated by reference in its entirety). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, betagalactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection can also be accomplished by visual comparison of the extent of enzymatic reaction of a substrate in comparison with similarly prepared standards.

Detection can also be accomplished using any of a variety of other immunoassays. For example, by radioactively labeling the antibodies or antibody fragments, it is possible to detect a protein of interest through the use of a radioimmunoassay (RIA) (see, for example, Weintraub, 1986, *Principles of Radioimmunoassays*, Seventh Training Course on Radioligand Assay Techniques, The Endocrine Society, which is hereby incorporated by reference herein). The radioactive isotope (e.g., $^{125}$I, $^{131}$I, $^{35}$S or $^{3}$H) can be detected by such means as the use of a gamma counter or a scintillation counter or by autoradiography.

It is also possible to label the antibody with a fluorescent compound. When the fluorescently labeled antibody is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound can be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

In another embodiment, specific binding molecules other than antibodies, such as aptamers, may be used to bind the biomarkers. In yet another embodiment, the biomarker profile may comprise a measurable aspect of an infectious agent (e.g., lipopolysaccharides or viral proteins) or a component thereof.

In some embodiments, a protein chip assay (e.g., The ProteinChip® Biomarker System, Ciphergen, Fremont, Calif.) is used to measure feature values for the biomarkers in the biomarker profile. See also, for example, Lin, 2004, Modern Pathology, 1-9; Li, 2004, Journal of Urology 171, 1782-1787; Wadsworth, 2004, Clinical Cancer Research, 10, 1625-1632; Prieto, 2003, Journal of Liquid Chromatography & Related Technologies 26, 2315-2328; Coombes, 2003, Clinical Chemistry 49, 1615-1623; Mian, 2003, Proteomics 3, 1725-1737; Lehre et al., 2003, BJU International 92, 223-225; and Diamond, 2003, Journal of the American Society for Mass Spectrometry 14, 760-765, each of which is hereby incorporated by reference in its entirety.

In some embodiments, a bead assay is used to measure feature values for the biomarkers in the biomarker profile. One such bead assay is the Becton Dickinson Cytometric Bead Array (CBA). CBA employs a series of particles with discrete fluorescence intensities to simultaneously detect multiple soluble analytes. CBA is combined with flow cytometry to create a multiplexed assay. The Becton Dickinson CBA system, as embodied for example in the Becton Dickinson Human Inflammation Kit, uses the sensitivity of amplified fluorescence detection by flow cytometry to measure soluble analytes in a particle-based immunoassay. Each bead in a CBA provides a capture surface for a specific protein and is analogous to an individually coated well in an ELISA plate. The BD CBA capture bead mixture is in suspension to allow for the detection of multiple analytes in a small volume sample.

In some embodiments the multiplex analysis method described in U.S. Pat. No. 5,981,180 ("the '180 patent"), herein incorporated by reference in its entirety, and in particular for its teachings of the general methodology, bead technology, system hardware and antibody detection, is used to measure feature values for the biomarkers in a biomarker profile. For this analysis, a matrix of microparticles is synthesized, where the matrix consists of different sets of microparticles. Each set of microparticles can have thousands of molecules of a distinct antibody capture reagent immobilized on the microparticle surface and can be color-coded by incorporation of varying amounts of two fluorescent dyes. The ratio of the two fluorescent dyes provides a distinct emission spectrum for each set of microparticles, allowing the identification of a microparticle a set following the pooling of the various sets of microparticles. U.S. Pat. Nos. 6,268,222 and 6,599,331 also are incorporated herein by reference in their entirety, and in particular for their teachings of various methods of labeling microparticles for multiplex analysis.

5.4.3 Use of Other Methods of Detection

In some embodiments, a separation method may be used determine feature values for biomarkers in a biomarker profile, such that only a subset of biomarkers within the sample is analyzed. For example, the biomarkers that are analyzed in a sample may be mRNA species from a cellular extract which has been fractionated to obtain only the nucleic acid biomarkers within the sample, or the biomarkers may be from a fraction of the total complement of proteins within the sample, which have been fractionated by chromatographic techniques.

Feature values for biomarkers in a biomarker profile can also, for example, be generated by the use of one or more of the following methods described below. For example, methods may include nuclear magnetic resonance (NMR) spectroscopy, a mass spectrometry method, such as electrospray ionization mass spectrometry (ESI-MS), ESI-MS/MS, ESI-MS/(MS)$^n$ (n is an integer greater than zero), matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)$^n$, atmospheric pressure photoionization mass spectrometry (APPI-MS), APPI-MS/MS, and APPI-(MS)$^n$. Other mass spectrometry methods may include, inter alia, quadrupole, Fourier transform mass spectrometry (FTMS) and ion trap. Other suitable methods may include chemical extraction partitioning, column chromatography, ion exchange chromatography, hydrophobic (reverse phase) liquid chromatography, isoelectric focusing, one-dimensional polyacrylamide gel electrophoresis (PAGE), two-dimensional polyacrylamide gel electrophoresis (2D-PAGE) or other chromatography, such as thin-layer, gas or liquid chromatography, or any combination thereof. In one embodiment, the biological sample may be fractionated prior to application of the separation method.

In one embodiment, laser desorption/ionization time-of-flight mass spectrometry is used to create determine feature values in a biomarker profile where the biomarkers are proteins or protein fragments that have been ionized and vaporized off an immobilizing support by incident laser radiation and the feature values are the presence or absence of peaks representing these fragments in the mass spectra profile. A variety of laser desorption/ionization techniques are known in the art (see, e.g., Guttman et al., 2001, *Anal. Chem.* 73:1252-62 and Wei et al., 1999, *Nature* 399:243-246, each of which is hereby incorporated by herein be reference in its entirety).

Laser desorption/ionization time-of-flight mass spectrometry allows the generation of large amounts of information in a relatively short period of time. A biological sample is applied to one of several varieties of a support that binds all of the biomarkers, or a subset thereof, in the sample. Cell lysates or samples are directly applied to these surfaces in volumes as small as 0.5 μL, with or without prior purification or fractionation. The lysates or sample can be concentrated or diluted prior to application onto the support surface. Laser desorption/ionization is then used to generate mass spectra of the sample, or samples, in as little as three hours.

5.5 Data Analysis Algorithms

Biomarkers whose corresponding feature values are capable of discriminating between converters and nonconverters are identified in the present invention. The identity of these biomarkers and their corresponding features (e.g., expression levels) can be used to develop a decision rule, or plurality of decision rules, that discriminate between converters and nonconverters. Section 6 below illustrates how data analysis algorithms can be used to construct a number of such decision rules. Each of the data analysis algorithms described in Section 6 use features (e.g., expression values) of a subset of the biomarkers identified in the present invention across a training population that includes converters and nonconverters. Typically, a SIRS subject is considered a nonconverter when the subject does not develop sepsis in a defined time period (e.g., observation period). This defined time period can be, for example, twelve hours, twenty four hours, forty-eight hours, a day, a week, a month, or longer. Specific data analysis algorithms for building a decision rule, or plurality of decision rules, that discriminate between subjects that develop sepsis and subjects that do not develop sepsis during a defined period will be described in the subsections below. Once a decision rule has been built using these exemplary data analysis algorithms or other techniques known in the art, the decision rule can be used to classify a test subject into one of the two or more phenotypic classes (e.g., a converter or a nonconverter). This is accomplished by applying the decision rule to a biomarker profile obtained from the test subject. Such decision rules, therefore, have enormous value as diagnostic indicators.

The present invention provides, in one aspect, for the evaluation of a biomarker profile from a test subject to biomarker profiles obtained from a training population. In some embodiments, each biomarker profile obtained from subjects in the training population, as well as the test subject, comprises a feature for each of a plurality of different biomarkers. In some embodiments, this comparison is accomplished by (i) developing a decision rule using the biomarker profiles from the training population and (ii) applying the decision rule to the biomarker profile from the test subject. As such, the decision rules applied in some embodiments of the present invention are used to determine whether a test subject having SIRS will or will not likely acquire sepsis.

In some embodiments of the present invention, when the results of the application of a decision rule indicate that the subject will likely acquire sepsis, the subject is diagnosed as a "sepsis" subject. If the results of an application of a decision rule indicate that the subject will not acquire sepsis, the subject is diagnosed as a "SIRS" subject. Thus, in some embodiments, the result in the above-described binary decision situation has four possible outcomes:

(i) truly septic, where the decision rule indicates that the subject will acquire sepsis and the subject does in fact acquire sepsis during the definite time period (true positive, TP);

(ii) falsely septic, where the decision rule indicates that the subject will acquire sepsis and the subject, in fact, does not acquire sepsis during the definite time period (false positive, FP);

(iii) truly SIRS, where the decision rule indicates that the subject will not acquire sepsis and the subject, in fact, does not acquire sepsis during the definite time period (true negative, TN); or (iv) falsely SIRS, where the decision rule indicates that the subject will not acquire sepsis and the subject, in fact, does acquire sepsis during the definite time period (false negative, FN).

It will be appreciated that other definitions for TP, FP, TN, FN can be made. For example, TP could have been defined as instances where the decision rule indicates that the subject will not acquire sepsis and the subject, in fact, does not acquire sepsis during the definite time period. While all such alternative definitions are within the scope of the present invention, for ease of understanding the present invention, the definitions for TP, FP, TN, and FN given by definitions (i) through (iv) above will be used herein, unless otherwise stated.

As will be appreciated by those of skill in the art, a number of quantitative criteria can be used to communicate the performance of the comparisons made between a test biomarker profile and reference biomarker profiles (e.g., the application of a decision rule to the biomarker profile from a test subject). These include positive predicted value (PPV), negative predicted value (NPV), specificity, sensitivity, accuracy, and certainty. In addition, other constructs such a receiver operator curves (ROC) can be used to evaluate decision rule performance. As used herein:

$$PPV = \frac{TP}{TP + FP}$$

$$NPV = \frac{TN}{TN + FN}$$

$$\text{specificity} = \frac{TN}{TN + FP}$$

$$\text{sensitivity} = \frac{TP}{TP+FN}$$

$$\text{accuracy} = \text{certainty} = \frac{TP+TN}{N}$$

Here, N is the number of samples compared (e.g., the number of test samples for which a determination of sepsis or SIRS is sought). For example, consider the case in which there are ten subjects for which SIRS/sepsis classification is sought. Biomarker profiles are constructed for each of the ten test subjects. Then, each of the biomarker profiles is evaluated by applying a decision rule, where the decision rule was developed based upon biomarker profiles obtained from a training population. In this example, N, from the above equations, is equal to 10. Typically, N is a number of samples, where each sample was collected from a different member of a population. This population can, in fact, be of two different types. In one type, the population comprises subjects whose samples and phenotypic data (e.g., feature values of biomarkers and an indication of whether or not the subject acquired sepsis) was used to construct or refine a decision rule. Such a population is referred to herein as a training population. In the other type, the population comprises subjects that were not used to construct the decision rule. Such a population is referred to herein as a validation population. Unless otherwise stated, the population represented by N is either exclusively a training population or exclusively a validation population, as opposed to a mixture of the two population types. It will be appreciated that scores such as accuracy will be higher (closer to unity) when they are based on a training population as opposed to a validation population. Nevertheless, unless otherwise explicitly stated herein, all criteria used to assess the performance of a decision rule (or other forms of evaluation of a biomarker profile from a test subject) including certainty (accuracy) refer to criteria that were measured by applying the decision rule corresponding to the criteria to either a training population or a validation population. Furthermore, the definitions for PPV, NPV, specificity, sensitivity, and accuracy defined above can also be found in Draghici, *Data Analysis Tools for DNA Microanalysis,* 2003, CRC Press LLC, Boca Raton, Fla., pp. 342-343, which is hereby incorporated herein by reference.

In some embodiments the training population comprises nonconverters and converters. In some embodiments, biomarker profiles are constructed from this population using biological samples collected from the training population at some time period prior to the onset of sepsis by the converters of the population. As such, for the converters of the training population, a biological sample can be collected two week before, one week before, four days before, three days before, one day before, or any other time period before the converters became septic. In practice, such collections are obtained by collecting a biological sample at regular time intervals after admittance into the hospital with a SIRS diagnosis. For example, in one approach, subjects who have been diagnosed with SIRS in a hospital are used as a training population. Once admitted to the hospital with SIRS, the biological samples are collected from the subjects at selected times (e.g., hourly, every eight hours, every twelve hours, daily, etc.). A portion of the subjects acquire sepsis and a portion of the subjects do not acquire sepsis. For the subjects that acquire sepsis, the biological sample taken from the subjects just prior to the onset of sepsis are termed the $T_{-12}$ biological samples. All other biological samples from the subjects are retroactively indexed relative to these biological samples. For instance, when a biological sample has been taken from a subject on a daily basis, the biological sample taken the day before the $T_{-12}$ sample is referred to as the $T_{-36}$ biological sample. Time points for biological samples for a nonconverter in the training population are identified by "time-matching" the nonconverter subject with a converter subject. To illustrate, consider the case in which a subject in the training population became clinically-defined as septic on his sixth day of enrollment. For the sake of illustration, for this subject, $T_{-36}$ is day four of the study, and the $T_{-36}$ biological sample is the biological sample that was obtained on day four of the study. Likewise, $T_{-36}$ for the matched nonconverter subject is deemed to be day four of the study on this paired nonconverter subject.

In some embodiments, N is more than one, more than five, more than ten, more than twenty, between ten and 100, more than 100, or less than 1000 subjects. A decision rule (or other forms of comparison) can have at least about 99% certainty, or even more, in some embodiments, against a training population or a validation population. In other embodiments, the certainty is at least about 97%, at least about 95%, at least about 90%, at least about 85%, at least about 80%, at least about 75%, at least about 70%, at least about 65%, or at least about 60% against a training population or a validation population (and therefore against a single subject that is not part of a training population such as a clinical patient). The useful degree of certainty may vary, depending on the particular method of the present invention. As used herein, "certainty" means "accuracy." In one embodiment, the sensitivity and/or specificity is at is at least about 97%, at least about 95%, at least about 90%, at least about 85%, at least about 80%, at least about 75%, or at least about 70% against a training population or a validation population. In some embodiments, such decision rules are used to predict the development of sepsis with the stated accuracy. In some embodiments, such decision rules are used to diagnoses sepsis with the stated accuracy. In some embodiments, such decision rules are used to determine a stage of sepsis with the stated accuracy.

The number of features that may be used by a decision rule to classify a test subject with adequate certainty is two or more. In some embodiments, it is three or more, four or more, ten or more, or between 10 and 200. Depending on the degree of certainty sought, however, the number of features used in a decision rule can be more or less, but in all cases is at least two. In one embodiment, the number of features that may be used by a decision rule to classify a test subject is optimized to allow a classification of a test subject with high certainty.

In some of the examples in Section 6 below, microarray data abundance data was collected for a plurality of biomarkers in each subject. That is, for each biomarker in a biomarker profile, a feature, microarray abundance data for the biomarker, was measured. Decision rules are developed from such biomarker profiles from a training population using data analysis algorithms in order to predict sample phenotypes based on observed gene expression patterns. While new and microarray specific classification tools are constantly being developed, the existing body of pattern recognition and prediction algorithms provide effective data analysis algorithms for constructing decision rules. See, for example, National Research Council; Panel on Discriminant Analysis Classification and Clustering, *Discriminant Analysis and Clustering,* Washington, D.C.: National Academy Press, which is hereby incorporated by reference. Furthermore, the techniques described in Dudoit et al., 2002, "Comparison of discrimination methods for the classification of tumors using gene expression data." JASA 97; 77-87, hereby incorporated by reference herein in its entirety, can be used to develop such decision rules.

Relevant data analysis algorithms for developing a decision rule include, but are not limited to, discriminant analysis including linear, logistic, and more flexible discrimination techniques (see, e.g., Gnanadesikan, 1977, *Methods for Statistical Data Analysis of Multivariate Observations*, New York: Wiley 1977, which is hereby incorporated by reference herein in its entirety); tree-based algorithms such as classification and regression trees (CART) and variants (see, e.g., Breiman, 1984, *Classification and Regression Trees*, Belmont, Calif.: Wadsworth International Group, which is hereby incorporated by reference herein in its entirety, as well as Section 5.1.3, below); generalized additive models (see, e.g., Tibshirani, 1990, *Generalized Additive Models*, London: Chapman and Hall, which is hereby incorporated by reference herein in its entirety); and neural networks (see, e.g., Neal, 1996, *Bayesian Learning for Neural Networks*, New York: Springer-Verlag; and Insua, 1998, Feedforward neural networks for nonparametric regression In: *Practical Nonparametric and Semiparametric Bayesian Statistics*, pp. 181-194, New York: Springer, which is hereby incorporated by reference herein in its entirety, as well as Section 5.5.6, below).

In one embodiment, comparison of a test subject's biomarker profile to a biomarker profiles obtained from a training population is performed, and comprises applying a decision rule. The decision rule is constructed using a data analysis algorithm, such as a computer pattern recognition algorithm. Other suitable data analysis algorithms for constructing decision rules include, but are not limited to, logistic regression (see Section 5.5.10, below) or a nonparametric algorithm that detects differences in the distribution of feature values (e.g., a Wilcoxon Signed Rank Test (unadjusted and adjusted)). The decision rule can be based upon two, three, four, five, 10, 20 or more features, corresponding to measured observables from one, two, three, four, five, 10, 20 or more biomarkers. In one embodiment, the decision rule is based on hundreds of features or more. Decision rules may also be built using a classification tree algorithm. For example, each biomarker profile from a training population can comprise at least three features, where the features are predictors in a classification tree algorithm (see Section 5.5.1, below). The decision rule predicts membership within a population (or class) with an accuracy of at least about at least about 70%, of at least about 75%, of at least about 80%, of at least about 85%, of at least about 90%, of at least about 95%, of at least about 97%, of at least about 98%, of at least about 99%, or about 100%.

Suitable data analysis algorithms are known in the art, some of which are reviewed in Hastie et al., supra. In a specific embodiment, a data analysis algorithm of the invention comprises Classification and Regression Tree (CART; Section 5.5.1, below), Multiple Additive Regression Tree (MART; Section 5.5.4, below), Prediction Analysis for Microarrays (PAM; Section 5.5.2, below) or Random Forest analysis (Section 5.5.1, below). Such algorithms classify complex spectra from biological materials, such as a blood sample, to distinguish subjects as normal or as possessing biomarker expression levels characteristic of a particular disease state. In other embodiments, a data analysis algorithm of the invention comprises ANOVA and nonparametric equivalents, linear discriminant analysis (Section 5.5.10, below), logistic regression analysis (Section 5.5.10, below), nearest neighbor classifier analysis (Section 5.5.9, below), neural networks (Section 5.5.6, below), principal component analysis (Section 5.5.8, below), quadratic discriminant analysis (Section 5.5.11, below), regression classifiers (Section 5.5.5, below) and support vector machines (Section 5.5.12, below). While such algorithms may be used to construct a decision rule and/or increase the speed and efficiency of the application of the decision rule and to avoid investigator bias, one of ordinary skill in the art will realize that computer-based algorithms are not required to carry out the methods of the present invention.

Decision rules can be used to evaluate biomarker profiles, regardless of the method that was used to generate the biomarker profile. For example, suitable decision rules that can be used to evaluate biomarker profiles generated using gas chromatography, as discussed in Harper, "Pyrolysis and GC in Polymer Analysis," Dekker, New York (1985). Further, Wagner et al., 2002, *Anal. Chem.* 74:1824-1835 disclose a decision rule that improves the ability to classify subjects based on spectra obtained by static time-of-flight secondary ion mass spectrometry (TOF-SIMS). Additionally, Bright et al., 2002, *J. Microbiol. Methods* 48:127-38, hereby incorporated by reference herein in its entirety, disclose a method of distinguishing between bacterial strains with high certainty (79-89% correct classification rates) by analysis of MALDI-TOF-MS spectra. Dalluge, 2000, *Fresenius J. Anal. Chem.* 366:701-711, hereby incorporated by reference herein in its entirety, discusses the use of MALDI-TOF-MS and liquid chromatography-electrospray ionization mass spectrometry (LC/ESI-MS) to classify profiles of biomarkers in complex biological samples.

5.5.1 Decision Trees

One type of decision rule that can be constructed using the feature values of the biomarkers identified in the present invention is a decision tree. Here, the "data analysis algorithm" is any technique that can build the decision tree, whereas the final "decision tree" is the decision rule. A decision tree is constructed using a training population and specific data analysis algorithms. Decision trees are described generally by Duda, 2001, *Pattern Classification*, John Wiley & Sons, Inc., New York. pp. 395-396, which is hereby incorporated by reference. Tree-based methods partition the feature space into a set of rectangles, and then fit a model (like a constant) in each one.

The training population data includes the features (e.g., expression values, or some other observable) for the biomarkers of the present invention across a training set population. One specific algorithm that can be used to construct a decision tree is a classification and regression tree (CART). Other specific decision tree algorithms include, but are not limited to, ID3, C4.5, MART, and Random Forests. CART, ID3, and C4.5 are described in Duda, 2001, *Pattern Classification*, John Wiley & Sons, Inc., New York. pp. 396-408 and pp. 411-412, which is hereby incorporated by reference. CART, MART, and C4.5 are described in Hastie et al., 2001, *The Elements of Statistical Learning*, Springer-Verlag, New York, Chapter 9, which is hereby incorporated by reference in its entirety. Random Forests are described in Breiman, 1999, "Random Forests-Random Features," Technical Report 567, Statistics Department, U.C. Berkeley, September 1999, which is hereby incorporated by reference in its entirety.

In some embodiments of the present invention, decision trees are used to classify subjects using features for combinations of biomarkers of the present invention. Decision tree algorithms belong to the class of supervised learning algorithms. The aim of a decision tree is to induce a classifier (a tree) from real-world example data. This tree can be used to classify unseen examples that have not been used to derive the decision tree. As such, a decision tree is derived from training data. Exemplary training data contains data for a plurality of subjects (the training population). For each respective subject there is a plurality of features the class of the respective subject (e.g., sepsis/SIRS). In one embodiment of the present invention, the training data is expression data for a combination of biomarkers across the training population.

The following algorithm describes an exemplary decision tree derivation:

---
Tree(Examples,Class,Features)

Create a root node
If all Examples have the same Class value, give the root this label
Else if Features is empty label the root according to the
most common value
Else begin
   Calculate the information gain for each Feature
   Select the Feature A with highest information gain
   and make this the root Feature
   For each possible value, v, of this Feature
     Add a new branch below the root, corresponding to A = v
     Let Examples(v) be those examples with A = v
     If Examples(v) is empty, make the new branch a leaf
     node labeled with the most common value among Examples
     Else let the new branch be the tree created by
     Tree(Examples(v),Class,Features - {A})
end
---

A more detailed description of the calculation of information gain is shown in the following. If the possible classes $v_i$ of the examples have probabilities $P(v_i)$ then the information content I of the actual answer is given by:

$$I(P(y_1), ..., P(v_n)) = \sum_{i=1}^{n} -P(v_i)\log_2 P(v_i)$$

The I-value shows how much information we need in order to be able to describe the outcome of a classification for the specific dataset used. Supposing that the dataset contains p positive (e.g. will develop sepsis) and n negative (e.g. will not develop sepsis) examples (e.g. subjects), the information contained in a correct answer is:

$$I\left(\frac{p}{p+n}, \frac{p}{p+n}\right) = -\frac{p}{p+n}\log_2\frac{p}{p+n} - \frac{n}{p+n}\log_2\frac{n}{p+n}$$

where $\log_2$ is the logarithm using base two. By testing single features the amount of information needed to make a correct classification can be reduced. The remainder for a specific feature A (e.g. representing a specific biomarker) shows how much the information that is needed can be reduced.

$$Remainder(A) = \sum_{i=1}^{v} \frac{p_i + n_i}{p+n} I\left(\frac{p_i}{p_i + n_i}, \frac{n_i}{p_i + n_i}\right)$$

"v" is the number of unique attribute values for feature A in a certain dataset, "i" is a certain attribute value, "$p_i$" is the number of examples for feature A where the classification is positive (e.g. will develop sepsis), "$n_i$" is the number of examples for feature A where the classification is negative (e.g. will not develop sepsis).

The information gain of a specific feature A is calculated as the difference between the information content for the classes and the remainder of feature A:

$$Gain(A) = I\left(\frac{p}{p+n}, \frac{n}{p+n}\right) - Remainder(A)$$

The information gain is used to evaluate how important the different features are for the classification (how well they split up the examples), and the feature with the highest information.

In general there are a number of different decision tree algorithms, many of which are described in Duda, *Pattern Classification*, Second Edition, 2001, John Wiley & Sons, Inc. Decision tree algorithms often require consideration of feature processing, impurity measure, stopping criterion, and pruning. Specific decision tree algorithms include, but are not limited to classification and regression trees (CART), multivariate decision trees, ID3, and C4.5.

In one approach, when a decision tree is used, the gene expression data for a select combination of genes described in the present invention across a training population is standardized to have mean zero and unit variance. The members of the training population are randomly divided into a training set and a test set. For example, in one embodiment, two thirds of the members of the training population are placed in the training set and one third of the members of the training population are placed in the test set. The expression values for a select combination of biomarkers described in the present invention is used to construct the decision tree. Then, the ability for the decision tree to correctly classify members in the test set is determined. In some embodiments, this computation is performed several times for a given combination of biomarkers. In each computational iteration, the members of the training population are randomly assigned to the training set and the test set. Then, the quality of the combination of biomarkers is taken as the average of each such iteration of the decision tree computation.

In addition to univariate decision trees in which each split is based on a feature value for a corresponding biomarker, among the set of biomarkers of the present invention, or the relative feature values of two such biomarkers, multivariate decision trees can be implemented as a decision rule. In such multivariate decision trees, some or all of the decisions actually comprise a linear combination of feature values for a plurality of biomarkers of the present invention. Such a linear combination can be trained using known techniques such as gradient descent on a classification or by the use of a sum-squared-error criterion. To illustrate such a decision tree, consider the expression:

$$0.04x_1 + 0.16x_2 < 500$$

Here, $x_1$ and $x_2$ refer to two different features for two different biomarkers from among the biomarkers of the present invention. To poll the decision rule, the values of features $x_1$ and $x_2$ are obtained from the measurements obtained from the unclassified subject. These values are then inserted into the equation. If a value of less than 500 is computed, then a first branch in the decision tree is taken. Otherwise, a second branch in the decision tree is taken. Multivariate decision trees are described in Duda, 2001, *Pattern Classification*, John Wiley & Sons, Inc., New York, pp. 408-409, which is hereby incorporated by reference.

Another approach that can be used in the present invention is multivariate adaptive regression splines (MARS). MARS is an adaptive procedure for regression, and is well suited for the high-dimensional problems addressed by the present invention. MARS can be viewed as a generalization of stepwise linear regression or a modification of the CART method to improve the performance of CART in the regression setting. MARS is described in Hastie et al., 2001, *The Elements of Statistical Learning*, Springer-Verlag, New York, pp. 283-295, which is hereby incorporated by reference in its entirety.

5.5.2 Predictive Analysis of Microarrays (PAM)

One approach to developing a decision rule using feature values of biomarkers of the present invention is the nearest centroid classifier. Such a technique computes, for each class (sepsis and SIRS), a centroid given by the average feature levels of the biomarkers in the class, and then assigns new samples to the class whose centroid is nearest. This approach is similar to k-means clustering except clusters are replaced by known classes. This algorithm can be sensitive to noise when a large number of biomarkers are used. One enhancement to the technique uses shrinkage: for each biomarker, differences between class centroids are set to zero if they are deemed likely to be due to chance. This approach is implemented in the Prediction Analysis of Microarray, or PAM. See, for example, Tibshirani et al., 2002, *Proceedings of the National Academy of Science USA* 99; 6567-6572, which is hereby incorporated by reference in its entirety. Shrinkage is controlled by a threshold below which differences are considered noise. Biomarkers that show no difference above the noise level are removed. A threshold can be chosen by cross-validation. As the threshold is decreased, more biomarkers are included and estimated classification errors decrease, until they reach a bottom and start climbing again as a result of noise biomarkers—a phenomenon known as overfitting.

5.5.3 Bagging, Boosting, and the Random Subspace Method

Bagging, boosting, the random subspace method, and additive trees are data analysis algorithms known as combining techniques that can be used to improve weak decision rules. These techniques are designed for, and usually applied to, decision trees, such as the decision trees described in Section 5.5.1, above. In addition, such techniques can also be useful in decision rules developed using other types of data analysis algorithms such as linear discriminant analysis.

In bagging, one samples the training set, generating random independent bootstrap replicates, constructs the decision rule on each of these, and aggregates them by a simple majority vote in the final decision rule. See, for example, Breiman, 1996, Machine Learning 24, 123-140; and Efron & Tibshirani, *An Introduction to Boostrap*, Chapman & Hall, New York, 1993, which is hereby incorporated by reference in its entirety.

In boosting, decision rules are constructed on weighted versions of the training set, which are dependent on previous classification results. Initially, all features under consideration have equal weights, and the first decision rule is constructed on this data set. Then, weights are changed according to the performance of the decision rule. Erroneously classified features get larger weights, and the next decision rule is boosted on the reweighted training set. In this way, a sequence of training sets and decision rules is obtained, which is then combined by simple majority voting or by weighted majority voting in the final decision rule. See, for example, Freund & Schapire, "Experiments with a new boosting algorithm," Proceedings 13th International Conference on Machine Learning, 1996, 148-156, which is hereby incorporated by reference in its entirety.

To illustrate boosting, consider the case where there are two phenotypes exhibited by the population under study, phenotype 1 (e.g., acquiring sepsis during a defined time periond), and phenotype 2 (e.g., SIRS only, meaning that the subject does acquire sepsis within a defined time period). Given a vector of predictor biomarkers (e.g., a vector of features that represent such biomarkers) from the training set data, a decision rule G(X) produces a prediction taking one of the type values in the two value set:{phenotype 1, phenotype 2}. The error rate on the training sample is $$\overline{err} = \frac{1}{N}\sum_{i=1}^{N} I(y_i \neq G(x_i))$$

where N is the number of subjects in the training set (the sum total of the subjects that have either phenotype 1 or phenotype 2). For example, if there are 49 organisms that acquire sepsis and 72 organisms that remain in the SIRS state, N is 121. A weak decision rule is one whose error rate is only slightly better than random guessing. In the boosting algorithm, the weak decision rule is repeatedly applied to modified versions of the data, thereby producing a sequence of weak decision rules $G_m(x)$, m, =1, 2, ..., M. The predictions from all of the decision rules in this sequence are then combined through a weighted majority vote to produce the final decision rule:

$$G(x) = \text{sign}\left(\sum_{m=1}^{M} \alpha_m G_m(x)\right)$$

Here $\alpha_1, \alpha_2, \ldots, \alpha_M$ are computed by the boosting algorithm and their purpose is to weigh the contribution of each respective decision rule Gm(x). Their effect is to give higher influence to the more accurate decision rules in the sequence.

The data modifications at each boosting step consist of applying weights $w_1, w_2, \ldots, w_n$ to each of the training observations $(x_i, y_i)$, i=1, 2, ..., N. Initially all the weights are set to $w_i=1/N$, so that the first step simply trains the decision rule on the data in the usual manner. For each successive iteration m=2, 3, ..., M the observation weights are individually modified and the decision rule is reapplied to the weighted observations. At step m, those observations that were misclassified by the decision rule $G_m-1(x)$ induced at the previous step have their weights increased, whereas the weights are decreased for those that were classified correctly. Thus as iterations proceed, observations that are difficult to correctly classify receive ever-increasing influence. Each successive decision rule is thereby forced to concentrate on those training observations that are missed by previous ones in the sequence.

The exemplary boosting algorithm is summarized as follows:

1. Initialize the observation weights $w_i = 1/N$, $i = 1, 2, \ldots, N$.
2. For m = 1 to M:
   (a) Fit a decision rule $G_m(x)$ to the training set using weights $w_i$.
   (b) Compute
   $$\text{err}_m = \frac{\sum_{i=1}^{N} w_i I(y_i \neq G_m(x_i))}{\sum_{i=1}^{N} w_i}$$
   (c) Compute $\alpha_m = \log((1 - \text{err}_m)/\text{err}_m)$.
   (d) Set $w_i \leftarrow w_i \cdot \exp[\alpha_m \cdot I(y_i \neq G_m(x_i))]$, $i = 1, 2, \ldots, N$.
3. Output $G(x) = \text{sign}\left[\sum_{m=1}^{M} \alpha_m G_m(x)\right]$ In one embodiment in accordance with this algorithm, each object is, in fact, a factor. Furthermore, in the algorithm, the current decision rule $G_m(x)$ is induced on the weighted observations at line 2a. The resulting weighted error rate is computed at line 2b. Line 2c calculates the weight $\alpha_m$ given to $G_m(x)$ in producing the final classifier $G(x)$ (line 3). The individual weights of each of the observations are updated for the next iteration at line 2d. Observations misclassified by $G_m(x)$ have their weights scaled by a factor $\exp(\alpha_m)$, increasing their relative influence for inducing the next classifier $G_m+1(x)$ in the sequence. In some embodiments, modifications of the Freund and Schapire, 1997, Journal of Computer and System Sciences 55, pp. 119-139, boosting methods are used. See, for example, Hasti et al., *The Elements of Statistical Learning*, 2001, Springer, New York, Chapter 10, which is hereby incorporated by reference in its entirety. For example, in some embodiments, feature preselection is performed using a technique such as the nonparametric scoring methods of Park et al., 2002, Pac. Symp. Biocomput. 6, 52-63, which is hereby incorporated by reference in its entirety. Feature preselection is a form of dimensionality reduction in which the genes that discriminate between classifications the best are selected for use in the classifier. Then, the LogitBoost procedure introduced by Friedman et al., 2000, Ann Stat 28, 337-407 is used rather than the boosting procedure of Freund and Schapire. In some embodiments, the boosting and other classification methods of Ben-Dor et al., 2000, Journal of Computational Biology 7, 559-583, hereby incorporated by reference in its entirety, are used in the present invention. In some embodiments, the boosting and other classification methods of Freund and Schapire, 1997, Journal of Computer and System Sciences 55, 119-139, hereby incorporated by reference in its entirety, are used.

In the random subspace method, decision rules are constructed in random subspaces of the data feature space. These decision rules are usually combined by simple majority voting in the final decision rule. See, for example, Ho, "The Random subspace method for constructing decision forests," IEEE Trans Pattern Analysis and Machine Intelligence, 1998; 20(8): 832-844, which is hereby incorporated by reference in its entirety.

5.5.4 Multiple Additive Regression Trees

Multiple additive regression trees (MART) represents another way to construct a decision rule that can be used in the present invention. A generic algorithm for MART is:

1. Initialize $f0(x) = \arg\min_\gamma \sum_{i=1}^{N} L(y_i, \gamma)$.
2. For m = 1 to M:
   (a) For $I = 1, 2, \ldots, N$ compute
   $$r_{im} = -\left[\frac{\partial L(y_i, f(x_i))}{\partial f(x_i)}\right]_{f=f_{m-1}}$$
   (b) Fit a regression tree to the targets rim giving terminal regions Rjm, $j = 1, 2, \ldots, Jm$.
   (c) For $j = 1, 2, \ldots, Jm$ compute
   $$\gamma_{jm} = \arg\min_\gamma \sum_{x_i \in R_{jm}} L(y_i, f_{m-1}(x_i) + \gamma).$$
   (d) Update $fm(x) = fm - 1(x) + \sum_{j=1}^{Jm} \gamma_{jm} I(x \in R_{jm})$
3. Ouput $\hat{f}(x) = f_M(x)$.

Specific algorithms are obtained by inserting different loss criteria $L(y, f(x))$. The first line of the algorithm initializes to the optimal constant model, which is just a single terminal node tree. The components of the negative gradient computed in line 2(a) are referred to as generalized pseudo residuals, r. Gradients for commonly used loss functions are summarized in Table 10.2, of Hastie et al., 2001, *The Elements of Statistical Learning*, Springer-Verlag, New York, p. 321, which is hereby incorporated by reference. The algorithm for classification is similar and is described in Hastie et al., Chapter 10, which is hereby incorporated by reference in its entirety. Tuning parameters associated with the MART procedure are the number of iterations M and the sizes of each of the constituent trees $J_m$, $m=1, 2, \ldots, M$.

5.5.5 Decision Rules Derived by Regression

In some embodiments, a decision rule used to classify subjects is built using regression. In such embodiments, the decision rule can be characterized as a regression classifier, preferably a logistic regression classifier. Such a regression classifier includes a coefficient for each of the biomarkers (e.g., a feature for each such biomarker) used to construct the classifier. In such embodiments, the coefficients for the regression classifier are computed using, for example, a maximum likelihood approach. In such a computation, the features for the biomarkers (e.g., RT-PCR, microarray data) is used. In particular embodiments, molecular marker data from only two trait subgroups is used (e.g., trait subgroup a: will acquire sepsis in a defined time period and trait subgroup b: will not acquire sepsis in a defined time period) and the dependent variable is absence or presence of a particular trait in the subjects for which biomarker data is available.

In another specific embodiment, the training population comprises a plurality of trait subgroups (e.g., three or more trait subgroups, four or more specific trait subgroups, etc.). These multiple trait subgroups can correspond to discrete stages in the phenotypic progression from healthy, to SIRS, to sepsis, to more advanced stages of sepsis in a training population. In this specific embodiment, a generalization of the logistic regression model that handles multicategory responses can be used to develop a decision that discriminates between the various trait subgroups found in the training population. For example, measured data for selected molecular markers can be applied to any of the multi-category logit models described in Agresti, *An Introduction to Categorical Data Analysis*, 1996, John Wiley & Sons, Inc., New York, Chapter 8, hereby incorporated by reference in its entirety, in order to develop a classifier capable of discriminating between any of a plurality of trait subgroups represented in a training population.

5.5.6 Neural Networks

In some embodiments, the feature data measured for select biomarkers of the present invention (e.g., RT-PCR data, mass spectrometry data, microarray data) can be used to train a neural network. A neural network is a two-stage regression or classification decision rule. A neural network has a layered structure that includes a layer of input units (and the bias) connected by a layer of weights to a layer of output units. For regression, the layer of output units typically includes just one output unit. However, neural networks can handle multiple quantitative responses in a seamless fashion.

In multilayer neural networks, there are input units (input layer), hidden units (hidden layer), and output units (output layer). There is, furthermore, a single bias unit that is connected to each unit other than the input units. Neural networks are described in Duda et al., 2001, *Pattern Classification*, Second Edition, John Wiley & Sons, Inc., New York; and Hastie et al., 2001, *The Elements of Statistical Learning*, Springer-Verlag, New York, each of which is hereby incorporated by reference in its entirety. Neural networks are also described in Draghici, 2003, *Data Analysis Tools for DNA Microarrays*, Chapman & Hall/CRC; and Mount, 2001, *Bioinformatics: sequence and genome analysis*, Cold Spring Harbor Laboratory Press, Cold Spring Harbor, N.Y., each of which is hereby incorporated by reference in its entirety. What is disclosed below is some exemplary forms of neural networks.

The basic approach to the use of neural networks is to start with an untrained network, present a training pattern to the input layer, and to pass signals through the net and determine the output at the output layer. These outputs are then compared to the target values; any difference corresponds to an error. This error or criterion function is some scalar function of the weights and is minimized when the network outputs match the desired outputs. Thus, the weights are adjusted to reduce this measure of error. For regression, this error can be sum-of-squared errors. For classification, this error can be either squared error or cross-entropy (deviation). See, e.g., Hastie et al., 2001, *The Elements of Statistical Learning*, Springer-Verlag, New York, which is hereby incorporated by reference in its entirety.

Three commonly used training protocols are stochastic, batch, and on-line. In stochastic training, patterns are chosen randomly from the training set and the network weights are updated for each pattern presentation. Multilayer nonlinear networks trained by gradient descent methods such as stochastic back-propagation perform a maximum-likelihood estimation of the weight values in the classifier defined by the network topology. In batch training, all patterns are presented to the network before learning takes place. Typically, in batch training, several passes are made through the training data. In online training, each pattern is presented once and only once to the net.

In some embodiments, consideration is given to starting values for weights. If the weights are near zero, then the operative part of the sigmoid commonly used in the hidden layer of a neural network (see, e.g., Hastie et al., 2001, *The Elements of Statistical Learning*, Springer-Verlag, New York, hereby incorporated by reference) is roughly linear, and hence the neural network collapses into an approximately linear classifier. In some embodiments, starting values for weights are chosen to be random values near zero. Hence the classifier starts out nearly linear, and becomes nonlinear as the weights increase. Individual units localize to directions and introduce nonlinearities where needed. Use of exact zero weights leads to zero derivatives and perfect symmetry, and the algorithm never moves. Alternatively, starting with large weights often leads to poor solutions.

Since the scaling of inputs determines the effective scaling of weights in the bottom layer, it can have a large effect on the quality of the final solution. Thus, in some embodiments, at the outset all expression values are standardized to have mean zero and a standard deviation of one. This ensures all inputs are treated equally in the regularization process, and allows one to choose a meaningful range for the random starting weights. With standardization inputs, it is typical to take random uniform weights over the range [−0.7, +0.7].

A recurrent problem in the use of three-layer networks is the optimal number of hidden units to use in the network. The number of inputs and outputs of a three-layer network are determined by the problem to be solved. In the present invention, the number of inputs for a given neural network will equal the number of biomarkers selected from the training population. The number of output for the neural network will typically be just one. However, in some embodiments more than one output is used so that more than just two states can be defined by the network. For example, a multi-output neural network can be used to discriminate between, healthy phenotypes, various stages of SIRS, and/or various stages of sepsis. If too many hidden units are used in a neural network, the network will have too many degrees of freedom and is trained too long, there is a danger that the network will overfit the data. If there are too few hidden units, the training set cannot be learned. Generally speaking, however, it is better to have too many hidden units than too few. With too few hidden units, the classifier might not have enough flexibility to capture the nonlinearities in the date; with too many hidden units, the extra weight can be shrunk towards zero if appropriate regularization or pruning, as described below, is used. In typical embodiments, the number of hidden units is somewhere in the range of 5 to 100, with the number increasing with the number of inputs and number of training cases.

One general approach to determining the number of hidden units to use is to apply a regularization approach. In the regularization approach, a new criterion function is constructed that depends not only on the classical training error, but also on classifier complexity. Specifically, the new criterion function penalizes highly complex classifiers; searching for the minimum in this criterion is to balance error on the training set with error on the training set plus a regularization term, which expresses constraints or desirable properties of solutions:

$$J = J_{pat} + \lambda J_{reg}.$$

The parameter $\lambda$ is adjusted to impose the regularization more or less strongly. In other words, larger values for $\lambda$ will tend to shrink weights towards zero: typically cross-validation with a validation set is used to estimate $\lambda$. This validation set can be obtained by setting aside a random subset of the training population. Other forms of penalty have been proposed, for example the weight elimination penalty (see, e.g., Hastie et al., 2001, *The Elements of Statistical Learning*, Springer-Verlag, New York, hereby incorporated by reference).

Another approach to determine the number of hidden units to use is to eliminate—prune—weights that are least needed. In one approach, the weights with the smallest magnitude are eliminated (set to zero). Such magnitude-based pruning can work, but is nonoptimal; sometimes weights with small magnitudes are important for learning and training data. In some embodiments, rather than using a magnitude-based pruning approach, Wald statistics are computed. The fundamental idea in Wald Statistics is that they can be used to estimate the importance of a hidden unit (weight) in a classifier. Then, hidden units having the least importance are eliminated (by setting their input and output weights to zero). Two algorithms in this regard are the Optimal Brain Damage (OBD) and the Optimal Brain Surgeon (OBS) algorithms that use second-order approximation to predict how the training error depends upon a weight, and eliminate the weight that leads to the smallest increase in training error.

Optimal Brain Damage and Optimal Brain Surgeon share the same basic approach of training a network to local minimum error at weight w, and then pruning a weight that leads to the smallest increase in the training error. The predicted functional increase in the error for a change in full weight vector δw is:

$$\delta J = \left(\frac{\partial J}{\partial w}\right)^t \cdot \delta w + \frac{1}{2} \delta w^t \cdot \frac{\partial^2 J}{\partial w^2} \cdot \delta w + O(\|\delta w\|^3)$$

where $$\frac{\partial^2 J}{\partial w^2}$$

is the Hessian matrix. The first term vanishes at a local minimum in error; third and higher order terms are ignored. The general solution for minimizing this function given the constraint of deleting one weight is:

$$\delta w = -\frac{w_q}{[H^{-1}]_{qq}} H^{-1} \cdot u_q \text{ and } L_q = \frac{1}{2} \frac{w_q^2}{[H^{-1}]_{qq}}$$

Here, $u_q$ is the unit vector along the qth direction in weight space and $L_q$ is approximation to the saliency of the weight q—the increase in training error if weight q is pruned and the other weights updated δw. These equations require the inverse of H. One method to calculate this inverse matrix is to start with a small value, $H_0^{-1} = \alpha^{-1} I$, where α is a small parameter—effectively a weight constant. Next the matrix is updated with each pattern according to $$H_{m+1}^{-1} = H_m^{-1} - \frac{H_m^{-1} X_{m+1} X_{m+1}^T H_m^{-1}}{\frac{n}{a_m} + X_{m+1}^T H_m^{-1} X_{m+1}} \quad \text{Eqn. 1}$$

where the subscripts correspond to the pattern being presented and $a_m$ decreases with m. After the full training set has been presented, the inverse Hessian matrix is given by $H^{-1} = H_n^{-1}$. In algorithmic form, the Optimal Brain Surgeon method is:

begin initialize $n_H$, w, θ
train a reasonably large network to minimum error
do compute $H^{-1}$ by Eqn. 1

-continued $q^* \leftarrow \arg\min_q w_q^2 / (2[H^{-1}]_{qq})$ (saliency $L_q$)

$w \leftarrow w - \frac{w_{q^*}}{[H^{-1}]_{q^*q^*}} H^{-1} e_{q^*}$ (saliency $L_q$)

until J(w) > θ
return w
end

The Optimal Brain Damage method is computationally simpler because the calculation of the inverse Hessian matrix in line 3 is particularly simple for a diagonal matrix. The above algorithm terminates when the error is greater than a criterion initialized to be θ. Another approach is to change line 6 to terminate when the change in J(w) due to elimination of a weight is greater than some criterion value. In some embodiments, the back-propagation neural network See, for example Abdi, 1994, "A neural network primer," J. Biol System. 2, 247-283, hereby incorporated by reference in its entirety.

5.5.7 Clustering

In some embodiments, features for select biomarkers of the present invention are used to cluster a training set. For example, consider the case in which ten features (corresponding to ten biomarkers) described in the present invention is used. Each member m of the training population will have feature values (e.g. expression values) for each of the ten biomarkers. Such values from a member m in the training population define the vector:

$X_{1m} X_{2m} X_{3m} X_{4m} X_{5m} X_{6m} X_{7m} X_{8m} X_{9m} X_{10m}$ where $X_{im}$ is the expression level of the $i^{th}$ biomarker in organism m. If there are m organisms in the training set, selection of i biomarkers will define m vectors. Note that the methods of the present invention do not require that each the expression value of every single biomarker used in the vectors be represented in every single vector m. In other words, data from a subject in which one of the $i^{th}$ biomarkers is not found can still be used for clustering. In such instances, the missing expression value is assigned either a "zero" or some other normalized value. In some embodiments, prior to clustering, the feature values are normalized to have a mean value of zero and unit variance.

Those members of the training population that exhibit similar expression patterns across the training group will tend to cluster together. A particular combination of genes of the present invention is considered to be a good classifier in this aspect of the invention when the vectors cluster into the trait groups found in the training population. For instance, if the training population includes class a: subjects that do not develop sepsis, and class b: subjects that develop sepsis, an ideal clustering classifier will cluster the population into two groups, with one cluster group uniquely representing class a and the other cluster group uniquely representing class b.

Clustering is described on pages 211-256 of Duda and Hart, *Pattern Classification and Scene Analysis*, 1973, John Wiley & Sons, Inc., New York, (hereinafter "Duda 1973") which is hereby incorporated by reference in its entirety. As described in Section 6.7 of Duda 1973, the clustering problem is described as one of finding natural groupings in a dataset. To identify natural groupings, two issues are addressed. First, a way to measure similarity (or dissimilarity) between two samples is determined. This metric (similarity measure) is used to ensure that the samples in one cluster are more like one another than they are to samples in other clusters. Second, a mechanism for partitioning the data into clusters using the similarity measure is determined.

Similarity measures are discussed in Section 6.7 of Duda 1973, where it is stated that one way to begin a clustering investigation is to define a distance function and to compute the matrix of distances between all pairs of samples in a dataset. If distance is a good measure of similarity, then the distance between samples in the same cluster will be significantly less than the distance between samples in different clusters. However, as stated on page 215 of Duda 1973, clustering does not require the use of a distance metric. For example, a nonmetric similarity function s(x, x') can be used to compare two vectors x and x'. Conventionally, s(x, x') is a symmetric function whose value is large when x and x' are somehow "similar". An example of a nonmetric similarity function s(x, x') is provided on page 216 of Duda 1973.

Once a method for measuring "similarity" or "dissimilarity" between points in a dataset has been selected, clustering requires a criterion function that measures the clustering quality of any partition of the data. Partitions of the data set that extremize the criterion function are used to cluster the data. See page 217 of Duda 1973. Criterion functions are discussed in Section 6.8 of Duda 1973.

More recently, Duda et al., *Pattern Classification*, $2^{nd}$ edition, John Wiley & Sons, Inc. New York, has been published. Pages 537-563 describe clustering in detail. More information on clustering techniques can be found in Kaufman and Rousseeuw, 1990, *Finding Groups in Data: An Introduction to Cluster Analysis*, Wiley, New York, N.Y.; Everitt, 1993, *Cluster analysis* (3d ed.), Wiley, New York, N.Y.; and Backer, 1995, *Computer-Assisted Reasoning in Cluster Analysis*, Prentice Hall, Upper Saddle River, N.J. Particular exemplary clustering techniques that can be used in the present invention include, but are not limited to, hierarchical clustering (agglomerative clustering using nearest-neighbor algorithm, farthest-neighbor algorithm, the average linkage algorithm, the centroid algorithm, or the sum-of-squares algorithm), k-means clustering, fuzzy k-means clustering algorithm, and Jarvis-Patrick clustering.

5.5.8 Principle Component Analysis

Principal component analysis (PCA) has been proposed to analyze gene expression data. More generally, PCA can be used to analyze feature value data of biomarkers of the present invention in order to construct a decision rule that discriminates converters from nonconverters. Principal component analysis is a classical technique to reduce the dimensionality of a data set by transforming the data to a new set of variable (principal components) that summarize the features of the data. See, for example, Jolliffe, 1986, *Principal Component Analysis*, Springer, New York, which is hereby incorporated by reference. Principal component analysis is also described in Draghici, 2003, *Data Analysis Tools for DNA Microarrays*, Chapman & Hall/CRC, which is hereby incorporated by reference. What follows is non-limiting examples of principal components analysis.

Principal components (PCs) are uncorrelated and are ordered such that the $k^{th}$ PC has the kth largest variance among PCs. The $k^{th}$ PC can be interpreted as the direction that maximizes the variation of the projections of the data points such that it is orthogonal to the first k−1 PCs. The first few PCs capture most of the variation in the data set. In contrast, the last few PCs are often assumed to capture only the residual 'noise' in the data.

PCA can also be used to create a classifier in accordance with the present invention. In such an approach, vectors for the select biomarkers of the present invention can be constructed in the same manner described for clustering above. In fact, the set of vectors, where each vector represents the feature values (e.g., abundance values) for the select genes from a particular member of the training population, can be viewed as a matrix. In some embodiments, this matrix is represented in a Free-Wilson method of qualitative binary description of monomers (Kubinyi, 1990, *3D QSAR in drug design theory methods and applications*, Pergamon Press, Oxford, pp 589-638), and distributed in a maximally compressed space using PCA so that the first principal component (PC) captures the largest amount of variance information possible, the second principal component (PC) captures the second largest amount of all variance information, and so forth until all variance information in the matrix has been considered.

Then, each of the vectors (where each vector represents a member of the training population) is plotted. Many different types of plots are possible. In some embodiments, a one-dimensional plot is made. In this one-dimensional plot, the value for the first principal component from each of the members of the training population is plotted. In this form of plot, the expectation is that members of a first subgroup (e.g. those subjects that do not develop sepsis in a determined time period) will cluster in one range of first principal component values and members of a second subgroup (e.g., those subjects that develop sepsis in a determined time period) will cluster in a second range of first principal component values.

In one ideal example, the training population comprises two subgroups: "sepsis" and "SIRS." The first principal component is computed using the molecular marker expression values for the select biomarkers of the present invention across the entire training population data set. Then, each member of the training set is plotted as a function of the value for the first principal component. In this ideal example, those members of the training population in which the first principal component is positive are the "responders" and those members of the training population in which the first principal component is negative are "subjects with sepsis."

In some embodiments, the members of the training population are plotted against more than one principal component. For example, in some embodiments, the members of the training population are plotted on a two-dimensional plot in which the first dimension is the first principal component and the second dimension is the second principal component. In such a two-dimensional plot, the expectation is that members of each subgroup represented in the training population will cluster into discrete groups. For example, a first cluster of members in the two-dimensional plot will represent subjects that develop sepsis in a given time period and a second cluster of members in the two-dimensional plot will represent subjects that do not develop sepsis in a given time period.

5.5.9 Nearest Neighbor Analysis

Nearest neighbor classifiers are memory-based and require no classifier to be fit. Given a query point $x_0$, the k training points $x_{(r)}$, r, . . . , k closest in distance to $x_0$ are identified and then the point $x_0$ is classified using the k nearest neighbors. Ties can be broken at random. In some embodiments, Euclidean distance in feature space is used to determine distance as:

$$d_{(i)}=\|x_{(i)}-x_o\|.$$

Typically, when the nearest neighbor algorithm is used, the expression data used to compute the linear discriminant is standardized to have mean zero and variance 1. In the present invention, the members of the training population are randomly divided into a training set and a test set. For example, in one embodiment, two thirds of the members of the training population are placed in the training set and one third of the members of the training population are placed in the test set. A select combination of biomarkers of the present invention represents the feature space into which members of the test set are plotted. Next, the ability of the training set to correctly characterize the members of the test set is computed. In some embodiments, nearest neighbor computation is performed several times for a given combination of biomarkers of the present invention. In each iteration of the computation, the members of the training population are randomly assigned to the training set and the test set. Then, the quality of the combination of biomarkers is taken as the average of each such iteration of the nearest neighbor computation.

The nearest neighbor rule can be refined to deal with issues of unequal class priors, differential misclassification costs, and feature selection. Many of these refinements involve some form of weighted voting for the neighbors. For more information on nearest neighbor analysis, see Duda, *Pattern Classification*, Second Edition, 2001, John Wiley & Sons, Inc; and Hastie, 2001, *The Elements of Statistical Learning*, Springer, New York, each of which is hereby incorporated by reference in its entirety.

5.5.10 Linear Discriminant Analysis

Linear discriminant analysis (LDA) attempts to classify a subject into one of two categories based on certain object properties. In other words, LDA tests whether object attributes measured in an experiment predict categorization of the objects. LDA typically requires continuous independent variables and a dichotomous categorical dependent variable. In the present invention, the feature values for the select combinations of biomarkers of the present invention across a subset of the training population serve as the requisite continuous independent variables. The trait subgroup classification of each of the members of the training population serves as the dichotomous categorical dependent variable.

LDA seeks the linear combination of variables that maximizes the ratio of between-group variance and within-group variance by using the grouping information. Implicitly, the linear weights used by LDA depend on how the feature values of a molecular marker across the training set separates in the two groups (e.g., a group a that develops sepsis during a defined time period and a group b that does not develop sepsis during a defined time period) and how these feature values correlate with the feature values of other biomarkers. In some embodiments, LDA is applied to the data matrix of the N members in the training sample by K biomarkers in a combination of biomarkers described in the present invention. Then, the linear discriminant of each member of the training population is plotted. Ideally, those members of the training population representing a first subgroup (e.g. those subjects that develop sepsis in a defined time period) will cluster into one range of linear discriminant values (e.g., negative) and those member of the training population representing a second subgroup (e.g. those subjects that will not develop sepsis in a defined time period) will cluster into a second range of linear discriminant values (e.g., positive). The LDA is considered more successful when the separation between the clusters of discriminant values is larger. For more information on linear discriminant analysis, see Duda, *Pattern Classification*, Second Edition, 2001, John Wiley & Sons, Inc; and Hastie, 2001, *The Elements of Statistical Learning*, Springer, New York; and Venables & Ripley, 1997, *Modern Applied Statistics with s-plus*, Springer, New York, each of which is hereby incorporated by reference in its entirety.

5.5.11 Quadratic Discriminant Analysis

Quadratic discriminant analysis (QDA) takes the same input parameters and returns the same results as LDA. QDA uses quadratic equations, rather than linear equations, to produce results. LDA and QDA are interchangeable, and which to use is a matter of preference and/or availability of software to support the analysis. Logistic regression takes the same input parameters and returns the same results as LDA and QDA.

5.5.12 Support Vector Machines

In some embodiments of the present invention, support vector machines (SVMs) are used to classify subjects using feature values of the genes described in the present invention. SVMs are a relatively new type of learning algorithm. See, for example, Cristianini and Shawe-Taylor, 2000, *An Introduction to Support Vector Machines*, Cambridge University Press, Cambridge; Boser et al., 1992, "A training algorithm for optimal margin classifiers," in *Proceedings of the 5th Annual ACM Workshop on Computational Learning Theory*, ACM Press, Pittsburgh, Pa., pp. 142-152; Vapnik, 1998, *Statistical Learning Theory*, Wiley, New York; Mount, 2001, *Bioinformatics: sequence and genome analysis*, Cold Spring Harbor Laboratory Press, Cold Spring Harbor, N.Y., Duda, *Pattern Classification*, Second Edition, 2001, John Wiley & Sons, Inc.; and Hastie, 2001, *The Elements of Statistical Learning*, Springer, New York; and Furey et al., 2000, Bioinformatics 16, 906-914, each of which is hereby incorporated by reference in its entirety. When used for classification, SVMs separate a given set of binary labeled data training data with a hyper-plane that is maximally distance from them. For cases in which no linear separation is possible, SVMs can work in combination with the technique of 'kernels', which automatically realizes a non-linear mapping to a feature space. The hyper-plane found by the SVM in feature space corresponds to a non-linear decision boundary in the input space.

In one approach, when a SVM is used, the feature data is standardized to have mean zero and unit variance and the members of a training population are randomly divided into a training set and a test set. For example, in one embodiment, two thirds of the members of the training population are placed in the training set and one third of the members of the training population are placed in the test set. The expression values for a combination of genes described in the present invention is used to train the SVM. Then the ability for the trained SVM to correctly classify members in the test set is determined. In some embodiments, this computation is performed several times for a given combination of molecular markers. In each iteration of the computation, the members of the training population are randomly assigned to the training set and the test set. Then, the quality of the combination of biomarkers is taken as the average of each such iteration of the SVM computation.

5.5.13 Evolutionary Methods

Inspired by the process of biological evolution, evolutionary methods of decision rule design employ a stochastic search for an decision rule. In broad overview, such methods create several decision rules—a population—from a combination of biomarkers described in the present invention. Each decision rule varies somewhat from the other. Next, the decision rules are scored on feature data across the training population. In keeping with the analogy with biological evolution, the resulting (scalar) score is sometimes called the fitness. The decision rules are ranked according to their score and the best decision rules are retained (some portion of the total population of decision rules). Again, in keeping with biological terminology, this is called survival of the fittest. The decision rules are stochastically altered in the next generation—the children or offspring. Some offspring decision rules will have higher scores than their parent in the previous generation, some will have lower scores. The overall process is then repeated for the subsequent generation: the decision rules are scored and the best ones are retained, randomly altered to give yet another generation, and so on. In part, because of the ranking, each generation has, on average, a slightly higher score than the previous one. The process is halted when the single best decision rule in a generation has a score that exceeds a desired criterion value. More information on evolutionary methods is found in, for example, Duda, *Pattern Classification*, Second Edition, 2001, John Wiley & Sons, Inc.

5.5.14 Other Data Analysis Algorithms

The data analysis algorithms described above are merely examples of the types of methods that can be used to construct a decision rule for discriminating converters from nonconverters. Moreover, combinations of the techniques described above can be used. Some combinations, such as the use of the combination of decision trees and boosting, have been described. However, many other combinations are possible. In addition, in other techniques in the art such as Projection Pursuit and Weighted Voting can be used to construct decision rules.

5.6 Biomarkers

In specific embodiments, the present invention provides biomarkers that are useful in diagnosing or predicting sepsis and/or its stages of progression in a subject. While the methods of the present invention may use an unbiased approach to identifying predictive biomarkers, it will be clear to the artisan that specific groups of biomarkers associated with physiological responses or with various signaling pathways may be the subject of particular attention. This is particularly the case where biomarkers from a biological sample are contacted with an array that can be used to measure the amount of various biomarkers through direct and specific interaction with the biomarkers (e.g., an antibody array or a nucleic acid array). In this case, the choice of the components of the array may be based on a suggestion that a particular pathway is relevant to the determination of the status of sepsis or SIRS in a subject. The indication that a particular biomarker has a feature that is predictive or diagnostic of sepsis or SIRS may give rise to an expectation that other biomarkers that are physiologically regulated in a concerted fashion likewise may provide a predictive or diagnostic feature. The artisan will appreciate, however, that such an expectation may not be realized because of the complexity of biological systems. For example, if the amount of a specific mRNA biomarker were a predictive feature, a concerted change in mRNA expression of another biomarker might not be measurable, if the expression of the other biomarker was regulated at a post-translational level. Further, the mRNA expression level of a biomarker may be affected by multiple converging pathways that may or may not be involved in a physiological response to sepsis.

Biomarkers can be obtained from any biological sample, which can be, by way of example and not of limitation, whole blood, plasma, saliva, serum, red blood cells, platelets, neutrophils, eosinophils, basophils, lymphocytes, monocytes, urine, cerebral spinal fluid, sputum, stool, cells and cellular extracts, or other biological fluid sample, tissue sample or tissue biopsy from a host or subject. The precise biological sample that is taken from the subject may vary, but the sampling preferably is minimally invasive and is easily performed by conventional techniques.

Measurement of a phenotypic change may be carried out by any conventional technique. Measurement of body temperature, respiration rate, pulse, blood pressure, or other physiological parameters can be achieved via clinical observation and measurement. Measurements of biomarker molecules may include, for example, measurements that indicate the presence, concentration, expression level, or any other value associated with a biomarker molecule. The form of detection of biomarker molecules typically depends on the method used to form a profile of these biomarkers from a biological sample. See Section 5.4, above, and Tables 30, I, J, K, L, and M below.

In a particular embodiment, the biomarker profile comprises at least two different biomarkers listed in column four or five of Table 30. The biomarker profile further comprises a respective corresponding feature for the at least two biomarkers. Such biomarkers can be, for example, mRNA transcripts, cDNA or some other nucleic acid, for example amplified nucleic acid, or proteins. Generally, the at least two biomarkers are derived from at least two different genes. In the case where a biomarker in the at least two different biomarkers is listed in column four of Table 30, the biomarker can be, for example, a transcript made by the listed gene, a complement thereof, or a discriminating fragment or complement thereof, or a cDNA thereof, or a discriminating fragment of the cDNA, or a discriminating amplified nucleic acid molecule corresponding to all or a portion of the transcript or its complement, or a protein encoded by the gene, or a discriminating fragment of the protein, or an indication of any of the above. Further still, the biomarker can be, for example, a protein listed in column five of Table 30, or a discriminating fragment of the protein, or an indication of any of the above. Here, a discriminating molecule or fragment is a molecule or fragment that, when detected, indicates presence or abundance of the above-identified transcript, cDNA, amplified nucleic acid, or protein. In accordance with this embodiment, the biomarker profiles of the present invention can be obtained using any standard assay known to those skilled in the art, or in an assay described herein, to detect a biomarker. Such assays are capable, for example, of detecting the products of expression (e.g., nucleic acids and/or proteins) of a particular gene or allele of a gene of interest (e.g., a gene disclosed in Table 30). In one embodiment, such an assay utilizes a nucleic acid microarray.

In a particular embodiment, the biomarker profile comprises at least two different biomarkers that each contain one of the probesets listed in column 2 of Table 30, biomarkers that contain the complement of one of the probesets of Table 30, or biomarkers that contain an amino acid sequence encoded by a gene that either contains one of the probesets of Table 30 or the complement of one of the probesets of Table 30. Such biomarkers can be, for example, mRNA transcripts, cDNA or some other nucleic acid, for example amplified nucleic acid, or proteins. The biomarker profile further comprises a respective corresponding feature for the at least two biomarkers. Generally, the at least two biomarkers are derived from at least two different genes. In the case where a biomarker is based upon a gene that includes the sequence of a probeset listed in Table 30, the biomarker can be, for example, a transcript made by the gene, a complement thereof, or a discriminating fragment or complement thereof, or a cDNA thereof, or a discriminating fragment of the cDNA, or a discriminating amplified nucleic acid molecule corresponding to all or a portion of the transcript or its complement, or a protein encoded by the gene, or a discriminating fragment of the protein, or an indication of any of the above. Further still, the biomarker can be, for example, a protein encoded by a gene that includes a probeset sequence described in Table 30, or a discriminating fragment of the protein, or an indication of any of the above. Here, a discriminating molecule or fragment is a molecule or fragment that, when detected, indicates presence or abundance of the above-identified transcript, cDNA, amplified nucleic acid, or protein.

In some embodiments the biomarker profile has between 2 and 626 biomarkers listed in Table 30. In some embodiments, the biomarker profile has between 3 and 50 biomarkers listed in Table 30. In some embodiments, the biomarker profile has between 4 and 25 biomarkers listed in Table 30. In some embodiments, the biomarker profile has at least 3 biomarkers listed in Table 30. In some embodiments, the biomarker profile has at least 4 biomarkers listed in Table 30. In some embodiments, the biomarker profile has at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 96, or 100 biomarkers listed in Table 30. In some embodiments, each such biomarker is a nucleic acid. In some embodiments, each such biomarker is a protein.

In some embodiments, some of the biomarkers in the biomarker profile are nucleic acids and some of the biomarkers in the biomarker profile are proteins. In some embodiments the biomarker profile has between 2 and 130 biomarkers listed in Table 31. In some embodiments, the biomarker profile has between 3 and 50 biomarkers listed in Table 31. In some embodiments, the biomarker profile has between 4 and 25 biomarkers listed in Table 31. In some embodiments, the biomarker profile has at least 3 biomarkers listed in Table 31. In some embodiments, the biomarker profile has at least 4 biomarkers listed in Table 30. In some embodiments, the biomarker profile has at least 6, 10, 15, 20, 25, 30, 35, 40, 45, 50, 55, 60, 65, 70, 75, 80, 85, 90, 95, 96, or 100 biomarkers listed in Table 31.

In some embodiments the biomarker profile has between 2 and 10 biomarkers listed in Table 33. In some embodiments, the biomarker profile has between 3 and 10 biomarkers listed in Table 32. In some embodiments, the biomarker profile has between 4 and 10 biomarkers listed in Table 32. In some embodiments, the biomarker profile has at least 3 biomarkers listed in Table 32. In some embodiments, the biomarker profile has at least 4 biomarkers listed in Table 32. In some embodiments, the biomarker profile has at least 6, 7, 8, 9, or 10 biomarkers listed in Table 32. In some embodiments, each such biomarker is a nucleic acid. In some embodiments, each such biomarker is a protein. In some embodiments, some of the biomarkers in the biomarker profile are nucleic acids and some of the biomarkers in the biomarker profile are proteins.

In some embodiments the biomarker profile has between 2 and 10 biomarkers listed in Table 33. In some embodiments, the biomarker profile has between 3 and 10 biomarkers listed in Table 33. In some embodiments, the biomarker profile has between 4 and 10 biomarkers listed in Table 33. In some embodiments, the biomarker profile has at least 3 biomarkers listed in Table 33. In some embodiments, the biomarker profile has at least 4 biomarkers listed in Table 33. In some embodiments, the biomarker profile has at least 6, 7, 8, 9, or 10 biomarkers listed in Table 33. In some embodiments, each such biomarker is a nucleic acid. In some embodiments, each such biomarker is a protein. In some embodiments, some of the biomarkers in the biomarker profile are nucleic acids and some of the biomarkers in the biomarker profile are proteins.

In some embodiments the biomarker profile has between 2 and 130 biomarkers listed in Table 34. In some embodiments, the biomarker profile has between 3 and 40 biomarkers listed in Table 34. In some embodiments, the biomarker profile has between 4 and 25 biomarkers listed in Table 34. In some embodiments, the biomarker profile has at least 3, 4, 5, 6, 7, 8, 9, 10, 11, 12, 13, 14, 15, 16, 17, 18, 19, 20, 25, 30, 35, or 40 biomarkers listed in Table 34. In some embodiments, each such biomarker is a nucleic acid. In some embodiments, each such biomarker is a protein. In some embodiments, some of the biomarkers in the biomarker profile are nucleic acids and some of the biomarkers in the biomarker profile are proteins.

In some embodiments the biomarker profile has between 2 and 7 biomarkers listed in Table 36. In some embodiments, the biomarker profile has between 3 and 6 biomarkers listed in Table 36. In some embodiments, the biomarker profile has between 4 and 7 biomarkers listed in Table 36. In some embodiments, the biomarker profile has at least 3 biomarkers listed in Table 36. In some embodiments, the biomarker profile has at least 4 biomarkers listed in Table 36. In some embodiments, the biomarker profile has at least 6, 7, 8, 9, or 10 biomarkers listed in Table 36. In some embodiments, each such biomarker is a nucleic acid. In some embodiments, each such biomarker is a protein. In some embodiments, some of the biomarkers in the biomarker profile are nucleic acids and some of the biomarkers in the biomarker profile are proteins.

In some embodiments the biomarker profile has between 2 and 53 biomarkers listed in Table I. In some embodiments, the biomarker profile has between 3 and 50 biomarkers listed in Table I. In some embodiments, the biomarker profile has between 4 and 25 biomarkers listed in Table I. In some embodiments, the biomarker profile has at least 3 biomarkers listed in Table I. In some embodiments, the biomarker profile has at least 4 biomarkers listed in Table I. In some embodiments, the biomarker profile has at least 5, 6, 7, 8, 9, 10, 11, 12, 13, 14, 15, 15, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53 biomarkers listed in Table I. In some embodiments, each of the biomarkers in the biomarker profile is a nucleic acid in Table I. In some embodiments, each of the biomarkers in the biomarker profile is a protein in Table I. In some embodiments, some of the biomarkers in a biomarker profile are proteins in Table I and some of the biomarkers in the same biomarker profile are nucleic acids in Table I.

In some embodiments the biomarker profile has between 2 and 44 biomarkers listed in Table J. In some embodiments, the biomarker profile has between 3 and 44 biomarkers listed in Table J. In some embodiments, the biomarker profile has between 4 and 25 biomarkers listed in Table J. In some embodiments, the biomarker profile has at least 3 biomarkers listed in Table J. In some embodiments, the biomarker profile has at least 4 biomarkers listed in Table J. In some embodiments, the biomarker profile has at least 5, 6, 7, 8, 9, 10, 11, 12, 13, 14, 15, 15, 17, 18, 19, 20, 21, 22, 23, 24, 25, 26, 27, 28, 29, 30, 31, 32, 33, 34, 35, 36, 37, 38, 39, 40, 41, 42, or 43 biomarkers listed in Table J. In some embodiments, each of the biomarkers in the biomarker profile is a nucleic acid in Table J. In some embodiments, each of the biomarkers in the biomarker profile is a protein in Table J. In some embodiments, some of the biomarkers in a biomarker profile are proteins in Table J and some of the biomarkers in the same biomarker profile are nucleic acids in Table J.

In some embodiments the biomarker profile has between 2 and 10 biomarkers listed in Table K. In some embodiments, the biomarker profile has between 3 and 10 biomarkers listed in Table K. In some embodiments, the biomarker profile has between 4 and 10 biomarkers listed in Table K. In some embodiments, the biomarker profile has at least 3 biomarkers listed in Table K. In some embodiments, the biomarker profile has at least 4 biomarkers listed in Table K. In some embodiments, the biomarker profile has at least 5, 6, 7, 8, or 9 biomarkers listed in Table K. In some embodiments, each of the biomarkers in the biomarker profile is a nucleic acid in Table K. In some embodiments, each of the biomarkers in the biomarker profile is a protein in Table K. In some embodiments, some of the biomarkers in a biomarker profile are proteins in Table K and some of the biomarkers in the same biomarker profile are nucleic acids in Table K.

5.6.1 Isolation of Useful Biomarkers

The biomarkers of the present invention may, for example, be used to raise antibodies that bind the biomarker if it is a protein (using methods described in Section 5.4.2, supra, or any method well known to those of skill in the art), or they may be used to develop a specific oligonucleotide probe, if it is a nucleic acid, for example, using a method described in Section 5.4.1, supra, or any method well known to those of skill in the art. The skilled artisan will readily appreciate that useful features can be further characterized to determine the molecular structure of the biomarker. Methods for characterizing biomarkers in this fashion are well-known in the art and include X-ray crystallography, high-resolution mass spectrometry, infrared spectrometry, ultraviolet spectrometry and nuclear magnetic resonance. Methods for determining the nucleotide sequence of nucleic acid biomarkers, the amino acid sequence of polypeptide biomarkers, and the composition and sequence of carbohydrate biomarkers also are well-known in the art.

5.7 Application of the Present Invention to SIRS Subjects

In one embodiment, the presently described methods are used to screen SIRS subjects who are at risk for developing sepsis. A biological sample is taken from a SIRS-positive subject and used to construct a biomarker profile. The biomarker profile is then evaluated to determine whether the feature values of the biomarker profile satisfy a first value set associated with a particular decision rule. This evaluation classifies the subject as a converter or a nonconverter. A treatment regimen may then be initiated to forestall or prevent the progression of sepsis when the subject is classified as a converter.

5.8 Application of the Present Invention to Stages of Sepsis

In one embodiment, the presently described methods are used to screen subjects who are particularly at risk for developing a certain stage of sepsis. A biological sample is taken from a subject and used to construct a biomarker profile. The biomarker profile is then evaluated to determine whether the feature values of the biomarker profile satisfy a first value set associated with a particular decision rule. This evaluation classifies the subject as having or not having a particular stage of sepsis. A treatment regimen may then be initiated to treat the specific stage of sepsis. In some embodiments, the stage of sepsis is for example, onset of sepsis, severe sepsis, septic shock, or multiple organ dysfunction.

5.9 Exemplary Embodiments

In some embodiments of the present invention, a biomarker profile is obtained using a biological sample from a test subject, particularly a subject at risk of developing sepsis, having sepsis, or suspected of having sepsis. The biomarker profile in such embodiments is evaluated. This evaluation can be made, for example, by applying a decision rule to the test subject. The decision rule can, for example, be or have been constructed based upon the biomarker profiles obtained from subjects in the training population. The training population, in one embodiment, includes (a) subjects that had SIRS and were then diagnosed as septic during an observation time period as well as (b) subjects that had SIRS and were not diagnosed as septic during an observation time period. If the biomarker profile from the test subject contains appropriately characteristic features, then the test subject is diagnosed as having a more likely chance of becoming septic, as being afflicted with sepsis or as being at the particular stage in the progression of sepsis. Various populations of subjects including those who are suffering from SIRS (e.g., SIRS-positive subjects) or those who are suffering from an infection but who are not suffering from SIRS (e.g., SIRS-negative subjects) can serve as training populations. Accordingly, the present invention allows the clinician to distinguish, inter alia, between those subjects who do not have SIRS, those who have SIRS but are not likely to develop sepsis within a given time frame, those who have SIRS and who are at risk of eventually becoming septic, and those who are suffering from a particular stage in the progression of sepsis. For more details on suitable training populations and suitable data collected from such populations, see Section 5.5, above.

5.10 Use of Annotation Data to Identify Discriminating Biomarkers

In some embodiments, data analysis algorithms identify a large set of biomarkers whose features discriminate between converters and nonconverters. For example, in some embodiments, application of a data analysis algorithm to a training population results in the selection of more than 500 biomarkers, more than 1000 biomarkers, or more than 10,000 biomarkers. In some embodiments, further reduction in the number of biomarkers that are deemed to be discriminating is desired. Accordingly, in some embodiments, filtering rules that are complementary to data analysis algorithms (e.g., the data analysis algorithms of Section 5.5) are used to further reduce the list of discriminating biomarkers identified by the data analysis algorithms. Specifically, the list of biomarkers identified by application of one or more data analysis algorithms to the biomarker profile data measured in a training population is further refined by application of annotation data based filtering rules to the list. In such embodiments, those biomarkers in the set of biomarkers identified by the one or more data analysis algorithms that satisfy the one or more applied annotation data based filtering rules remain in the set of discriminating biomarkers. In some instances, those biomarkers in the set of biomarkers identified by the one or more data analysis algorithms that do not satisfy the one or more applied annotation data based filtering rules are removed from the set. In other instances, those biomarkers in the set of biomarkers identified by the one or more data analysis algorithms that do not satisfy the one or more applied annotation data based filtering rules stay in the set and those that satisfy the one or more applied annotation data based filtering rules are removed from the set. In this way, annotation data can be used to reduce the number of biomarkers in the set of discriminating biomarkers identified by the data analysis algorithms.

Annotation data based filtering rules are rules based upon annotation data. Annotation data refers to any type of data that describes a property of a biomarker. An example of annotation data is the identification of biological pathways to which a given biomarker belongs. Another example of annotation data is enzymatic class (e.g., phosphodiesterases, kinases, metalloproteinases, etc.). Still other examples of annotation data include, but are not limited to, protein domain information, enzymatic substrate information, enzymatic reaction information, and protein interaction data. Yet another example of annotation data is disease association, in other words, which disease process a given biomarker has been linked to or otherwise affects. Another form of annotation data is any type of data that associates biomarker expression, other forms of biomarker abundance, and/or biomarker activity, with cellular localization, tissue type localization, and/or cell type localization.

As the name implies, annotation data is used to construct an annotation data based filtering rule. An example of an annotation data based filtering rule is:
Annotation Rule 1:
  remove all transcription factors from the training set.
Application of this filtering rule to a set of biomarkers will remove all transcription factors from the set.
  Another type of annotation data based filtering rule is:
Annotation Rule 2:
  keep all biomarkers that are enriched for annotation X in a biomarker list.
Application of this filtering rule will only keep those biomarkers in a given list that are enriched (overrepresented) for annotation X in the list. To more fully appreciate this filtering rule, consider an exemplary biomarker set that has been identified by application of a data analysis algorithm (Section 5.5) to biomarker profiles measured using training population data measured in accordance with a technique disclosed in Section 5.4. This exemplary biomarker set has 500 biomarkers. Assume, for in this illustrative example, that the full set of biomarkers in a human consists of 25,000 biomarkers. Here, the 25,000 biomarkers is a population and the 500 biomarker set is the sample. As used here, the term "population" consists of all possible observable biomarkers. The term "sample" is the data that is actually considered. Now, for this example, let X=kinases. Suppose there are 800 known human kinases and further suppose that the set of 500 biomarkers was randomly selected with respect to kinases. Under these circumstances, the list of 500 biomarkers identified by the data analysis algorithms should select about (500/25,000)*800=16 kinases. Since there are, in fact, 50 kinases in the sample, a conclusion can be reached that kinases are indeed enriched in the sample relative to the population.

More formally, in this example, a determination can be made as to whether kinases are enriched in the set of biomarkers identified by the data analysis algorithm (the sample) relative to the population by analysis of the two-way contingency table that describes the observed sample and population:

| Group | Kinase | | Total |
| --- | --- | --- | --- |
| | Yes | No | |
| Population | 800 | 24,200 | 25,000 |
| Sample | 50 | 450 | 500 |

Following Agresti, 1996, *An Introduction to Categorical Data Analysis*, John Wiley & Sons, New York, which is hereby incorporated by reference in its entirety, this two-way contingency table can be analyzed by treating each row as an independent bionomial variable. In such instances, the true difference in proportions, termed $\pi_1-\pi_2$, compares the probabilities in the two rows. This difference falls between $-1$ and $+1$. It equals zero when $\pi_1=\pi_2$; that is, when the selection of kinases in the sample from the population is independent of the kinase annotation. Of the $N_1=25,000$ biomarkers in the population, 800 are kinases, a proportion of $p_1=800/25,000=0.032$. Of the $N_2=500$ biomarkers in the sample identified using a data analysis algorithm, 50 are kinases, a proportion $p_2$ of $50/500=0.10$. The sample difference of proportions is $0.032-0.10=-0.068$. In accordance with Agresti, when the counts in the two rows are independent binomial samples, the estimated standard error of $p_1-p_2$ is:

$$\hat{\sigma}(p_1 - p_2) = \sqrt{\frac{p_1(1-p_1)}{N_1} + \frac{p_2(1-p_2)}{N_2}}$$

where $N_1$ and $N_2$ are the samples sizes for the population and the sample selected by data analysis algorithm, respectively. The standard error decreases, and hence the estimate of $\pi_1-\pi_2$ improves, as the sample sizes increase. A large-sample $(100(1-\alpha))$ % confidence interval for $\pi_1-\pi_2$ is $$(p_1+p_2) \pm z_{\alpha/2} = z_{0.025} = 1.96$$

Thus, for this example, the estimated error is $$\sqrt{\frac{0.032(1-0.032)}{25,000} + \frac{0.10(1-0.10)}{500}} = 0.013$$

and a 95% confidence interval for the true difference $\pi_1-\pi_2$ is $-0.068 \pm 1.96(0.013)$, or $-0.068 \pm 0.025$. Since the 95% confidence interval contains only negative values, the conclusion can be reached that kinases are enriched in the sample (the biomarker set produced by the data analysis algorithm) relative to the population of 25,000 biomarkers.

The two-way contingency table in the example above can be analysed using methods known in the art other than the one disclosed above. For example, the chi-square test for independence and/or Fisher's exact test can be used to test the null hypothesis that the row and column classification variables of the two-way contingency table are independent.

The term "X" in annotation rule 2 can be any form of annotation data. In one embodiment, "X" is any biological pathway. As such the annotation data based filtering rule has the following form.

Annotation Rule 3:
Select all biomarkers that are in any biological pathway that is enriched in the biomarker list.

To determine whether a particular biological pathway is enriched, the number of biomarkers in a particular biological pathway in the sample is compared with the number of biomarkers that are in the particular biological pathway in the population using, for example, the two-way contingency table analysis described above, or other techniques known in the art. If the biological pathway is enriched in the sample, then all biomarkers in the sample that are also in the biological pathway are retained for further analysis, in accordance with the annotation data based filtering rule.

An example of enrichment, in which it was shown that the proportion of kinases in the sample was greater than the proportion of kinases in the population across its entire 95% confidence interval has been given. In one embodiment, biomarkers having a given annotation are considered enriched in the sample relative to the population when the proportion of biomarkers having the annotation in the sample is greater than the proportion of biomarkers having the annotation in the population across its entire 95% degree confidence interval as determined by two-way contingency table analysis. In another embodiment, biomarkers having a given annotation are considered enriched in the sample relative to the population if a p value as determined by the Fisher exact test, Chi-square test, or relative algorithms is 0.05 or less, 0.005 or less or 0.0005 or less.

Another form of annotation data based filtering rule has the following form:

Annotation Rule 4:
Select all biomarkers that are in biological pathway X.

In an embodiment, a set of biomarkers is determined using a data analysis algorithm. Exemplary data analysis algorithms are disclosed in Section 5.5. In addition, Section 6 describes certain tests that can also serve as data analysis algorithms. These tests include, but are not limited to a Wilcoxon test and the like with a statistically significant p value (e.g., 0.05 or less, 0.04, or less, etc.), and/or a requirement that a biomarker exhibit a mean differential abundance between biological samples obtained from converters and biological samples obtained from nonconverters in a training population. Upon application of the data analysis algorithm, a set of biomarkers that discriminates between converters and nonconverters is determined. Next, an annotation rule, for example annotation rule 4, is applied to the set of discriminating biomarkers in order to further reduce the set of biomarkers. Those of skill in the art will appreciate that the order in which these rules are applied is generally not important. For example, annotation rule 4 can be applied first and then certain data analysis algorithms can be applied, or vice versa. In some embodiments, biomarkers ultimately deemed as discriminating between converters and nonconverters satisfy each of the following criteria: (i) a p value of 0.05 or less (p<0.05) as determined from a Wilcoxon adjusted test using static (single time point) data; (ii) a mean-fold change of 1.2 or greater between converters and nonconverters across the training set using static (single time point data), and (iii) present in a specific biological pathway. See also, Section 6.7, infra, for a detailed example. In this example, there is no requirement that members of the pathway are enriched in the set of biomarkers identified by the data analysis algorithms. Furthermore, it is noted that criteria (i) and (ii) are forms of data analysis algorithms and criterion (iii) is a annotation data based filtering rule.

In another embodiment, once a list of discriminating biomarkers is identified, the biomarkers can then be used to determine the identity of the particular biological pathways from which the discriminating biomarkers are implicated. In certain embodiments, annotation data-based filtering rules are applied to the list of discriminating biomarkers identified by the methods of the present invention (e.g., the methods described in Sections 5.4, 5.5 and 6). Such annotation data-based filtering rules identify the particular biological pathway or pathways that are enriched in the discriminating list of biomarkers identified by the data analysis algorithms. In an exemplary embodiment of the invention, DAVID 2.0 software, available at apps1.niaid.nih.gov/david/, is used to identify and apply such annotation data-based filtering rules to the set of biomarkers identified by the data analysis algorithms in order to identify pathways that are enriched in the set. In some embodiments, those biomarkers that are in an enriched biological pathway are selected for use as discriminating biomarkers in the kits of the present invention.

In some embodiments of the present invention, biomarkers that are in biological pathways that are enriched in the biomarker set determined by application of a data analysis algorithm to a training population that includes converters and nonconverters can be used as filtering step to reduce the number of biomarkers in the set. In one such approach, biological samples from subjects in a training population are obtained using, e.g., any of one or more of the methods described in Section 5.4, supra, and in Section 6, infra. In accordance with this embodiment, a nucleic acid array, such as a cDNA microarray, may be employed to generate features of biomarkers in a biomarker profile by detecting the expression of any one or more of the genes known to be or suspected to be involved in the selected biological pathways. Data derived from the cDNA microarray analysis may then be analyzed using any one or more of the analysis algorithms described in Section 5.5, supra, to identify biomarkers whose features discriminate between converters and nonconverters. Biomarkers whose corresponding feature values are capable of discriminating, for example, between converters (i.e., SIRS patients who subsequently develop sepsis) and non-converters (i.e., SIRS patients who do not subsequently develop sepsis) can thus be identified and classified as discriminating biomarkers. Biomarkers that are in enriched biological pathways can be selected from this set by applying Annotation rule 3, from above. Representative biological pathways that could be found include, for example, genes involved in the Th1/Th2 cell differentiation pathway). In one embodiments, biomarkers ultimately deemed as discriminating between converters and nonconverters satisfy each of the following criteria: (i) a p value of 0.05 or less (p<0.05) as determined from a Wilcoxon adjusted test; (ii) a mean-fold change of 1.2 or greater between converters and nonconverters across the training set, and (iii) present in a biological pathway that is enriched in the set of biomarkers derived by application of criteria (i) and (ii).

In some embodiments of the present invention, annotation data based filtering rules are used to identify biological pathways that are enriched in a given biomarker set. This biomarker set can be, for example, a set of biomarkers that is identified by application of a data analysis algorithm to training data comprising converters and nonconverters. Then, biomarkers in these enriched biological pathways are analyzed using any of the data analysis algorithms disclosed herein in order to identify biomarkers that discriminate between converters and nonconverters. In some instances, some of the biomarkers analyzed in the enriched biological pathways were not among the biomarkers in the original given biomarker set. In some instances, some of the biomarkers in the enriched biological pathways are among the biomarkers in the original given biomarker set. In some embodiments, a secondary assay is used to collect feature data for biomarkers that are in enriched pathways and it is this data that is used to determine whether the biomarkers in the enriched biological pathways discriminate between converters and nonconverters.

In some embodiments, biomarkers in biological pathways of interest are identified. In one example, genes involved in the Th1/Th2 cell differentiation pathway are identified. Then, these biomarkers are evaluated using the data analysis algorithms disclosed herein to determine whether they discriminate between converters and nonconverters.

5.11 Representative Embodiment in Accordance with the Present Invention

Sections 6.11 through 6.13 identify a number of biomarkers that are of interest in one embodiment in accordance with the present invention. Specifically, one embodiment of the present invention comprises the 10 biomarkers identified in Table 48 of Section 6.11.1, the 34 biomarkers listed in Table 59 of Section 6.11.2, and the 10 biomarkers listed in Table 93 of Section 6.13.1, below. Table 48 and Table 93 each identify MMP9 as a discriminating biomarker. Thus, the total number of biomarkers in Table I is one less than the sum of the biomarkers identified in Tables 48, Table 59, and Table 93, (34+10+10−1) or 53. These biomarkers are reproduced in Table I, below. Section 5.11.1 provides details on each of the individual biomarkers. Section 5.11.2, below, provides more details on select combinations of the biomarkers listed in Tables I, J, and K. Each of the biomarkers listed in Table I were selected based on the experimental results summarized in Sections 6.11 through 6.13. In some experiments, the identified biomarkers were proteins or fragments thereof. Such protein biomarkers, which discriminate between sepsis and SIRS, are listed in Table I with a "P" designation in column 5. In some experiments, the identified biomarkers were nucleic acids or fragment thereof. Such nucleic acid biomarkers, which discriminate between sepsis and SIRS, are listed in Table I with an "N" designation in column 5. As indicated above, one biomarker MMP9, was identified both as a protein and as a nucleic acid biomarker. Table J below lists the biomarkers in accordance with one embodiment of the present invention in which the biomarkers were discovered using nucleic acid based assays described in Section 6, such as RT-PCR. Table K below lists the biomarkers in accordance with one embodiment of the present invention in which the biomarkers were discovered using protein based assays, described in Section 6, such as bead assays. One embodiment of the invention comprises at least 3, 4, 5, 6, 7, 8, 9, or 10 biomarkers from any one of Tables 48, 59, or 93.

Unless indicated in specific embodiments below, the biomarkers of Tables I, J and K are not limited by their physical form in the experiments summarized in Sections 6.11 through 6.13. For example, although the discriminatory nature of a biomarker may have been discovered by the abundance of the biomarker, in nucleic acid form, in a nucleic acid assay such as RT-PCR and accordingly listed in Table I on this basis with an "N" designation in column 5 of Table I, the physical manifestation of the biomarker in the methods, kits, and biomarker profiles of the present invention is not limited to nucleic acids. Rather, any physical manifestation of the biomarker as defined for the term "biomarker" in Section 5.1 is encompassed in the present invention. Column 6 of Table I indicates, based on the data summarized in Section 6 below, whether the biomarker is up-regulated or down-regulated in the subjects that will convert to sepsis (the converters) relative to the subjects that will not convert (the SIRS subjects). Thus, if a biomarker has the designation UP, in column 6, that means that the biomarker, in the form indicated in column 5, was, on average, more abundant in subjects that will convert to sepsis (sepsis subjects) relative to subjects that will not convert to sepsis (SIRS subjects). Furthermore, if a biomarker has the designation DOWN, in column 6, that means that the biomarker, in the form indicated in column 5, was, on average, less abundant in subjects that will convert to sepsis (sepsis subjects), relative to subjects that will not convert to sepsis (SIRS subjects).

TABLE I

Biomarkers in accordance with an embodiment of the present invention.

| Gene Symbol 1 | Gene Name 2 | Gene Accession Number 3 | Protein Accession Number 4 | Source 5 | Regulation in SEPSIS 6 |
|---|---|---|---|---|---|
| AFP | ALPHA-FETOPROTEIN | NM_001134 | CAA79592 | P | UP |
| ANKRD22 | ANKYRIN REPEAT DOMAIN 22 | NM_144590 | NP_653191 | N | UP |
| ANXA3 | ANNEXIN A3 | NM_005139 | NP_005130 | N | UP |
| APOC3 | APOLIPOPROTEIN CIII | NM_000040 | CAA25648 | P | DOWN |
| ARG2 | ARGINASE TYPE II | NM_001172 | CAG38787 | N | UP |
| B2M | BETA-2 MICROGLOBULIN | NM_004048 | AAA51811 | P | UP |
| BCL2A1 | BCL2-RELATED PROTEIN A1 | NM_004049 | NP_004040 | N | UP |
| CCL5 | CHEMOKINE (C-C MOTIF) LIGAND 5 | NM_002985 | NP_002976 | N | DOWN |

TABLE I-continued

Biomarkers in accordance with an embodiment of the present invention.

| Gene Symbol 1 | Gene Name 2 | Gene Accession Number 3 | Protein Accession Number 4 | Source 5 | Regulation in SEPSIS 6 |
|---|---|---|---|---|---|
| CD86 | CD86 ANTIGEN (CD28 ANTIGEN LIGAND 2, B7-2 ANTIGEN) | NM_006889 NM_175862 | NP_008820 NP_787058 | N | DOWN |
| CEACAM1 | CARCINOEMBRYONIC ANTIGEN-RELATED CELL ADHESION MOLECULE 1 | NM_001712 | NP_001703 | N | UP |
| CRP | C REACTIVE PROTEIN | NM_000567 | CAA39671 | P | UP |
| CRTAP | CARTILAGE-ASSOCIATED PROTEIN | NM_006371 | NP_006362 | N | DOWN |
| CSF1R | COLONY STIMULATING FACTOR 1 RECEPTOR, FORMERLY MCDONOUGH FELINE SARCOMA VIRAL (V-FMS) ONCOGENE HOMOLOG | NM_005211 | NP_005202 | N | DOWN |
| FAD104 | FIBRONECTIN TYPE III DOMAIN CONTAINING 3B (FNDC3B) | NM_022763 | NP_073600 | N | UP |
| FCGR1A | FC FRAGMENT OF IGG, HIGH AFFINITY IA | NM_000566 | NP_000557 | N | UP |
| GADD45A | GROWTH ARREST AND DNA-DAMAGE-INDUCIBLE, ALPHA | NM_001924 | NP_001915 | N | UP |
| GADD45B | GROWTH ARREST- AND DNA DAMAGE-INDUCIBLE GENE GADD45 | NM_015675 | NP_056490 | N | UP |
| HLA-DRA | MAJOR HISTOCOMPATIBILITY COMPLEX, CLASS II, DR ALPHA | NM_002123 | NP_002114 | N | DOWN |
| IFNGR1 | INTERFERON GAMMA RECEPTOR 1 | NM_000416 | NP_000407 | N | UP |
| IL1RN | INTERLEUKIN = 1 RECEPTOR ANTAGONIST GENE | NM_000577, NM_173841, NM_173842, NM_173843 | AAN87150 | N | UP |
| IL-6 | INTERLEUKIN 6 | NM_000600 | NP_000591 | P | UP |
| IL-8 | INTERLEUKIN 8 | M28130 | AAA59158 | P | UP |
| IL-10 | INTERLEUKIN 10 | NM_000572 | CAH73907 | P | UP |
| IL10RA | INTERLEUKIN 10 RECEPTOR, ALPHA | NM_001558 | NP_001549 | N | DOWN |
| IL18R1 | INTERLEUKIN 18 RECEPTOR 1 | NM_003855 | NP_003846 | N | UP |
| INSL3 | INSULIN-LIKE 3 (LEYDIG CELL) | NM_005543 | NP_005534 | N | UP |
| IRAK2 | INTERLEUKIN-1 RECEPTOR-ASSOCIATED KINASE 2 | NM_001570 | NP_001561 | N | UP |
| IRAK4 | INTERLEUKIN-1 RECEPTOR-ASSOCIATED KINASE 4 | NM_016123 | NP_057207 | N | UP |
| ITGAM | INTEGRIN, ALPHA M (COMPLEMENT COMPONENT RECEPTOR 3, ALPHA; ALSO KNOWN AS CD11B (P170), MACROPHAGE ANTIGEN ALPHA POLYPEPTIDE) | NM_000632 | NP_000623 | N | UP |
| JAK2 | JANUS KINASE 2 (A PROTEIN TYROSINE KINASE) | NM_004972 | NP_004963 | N | UP |

TABLE I-continued

Biomarkers in accordance with an embodiment of the present invention.

| Gene Symbol 1 | Gene Name 2 | Gene Accession Number 3 | Protein Accession Number 4 | Source 5 | Regulation in SEPSIS 6 |
|---|---|---|---|---|---|
| LDLR | LOW DENSITY LIPOPROTEIN RECEPTOR | NM_000527 | NP_000518 | N | UP |
| LY96 | LYMPHOCYTE ANTIGEN 96 | NM_015364 | NP_056179 | N | UP |
| MAP2K6 | MITOGEN-ACTIVATED PROTEIN KINASE KINASE 6 | NM_002758 NM_031988 | NP_002749 NP_114365 | N | UP |
| MAPK14 | MAPK14 MITOGEN-ACTIVATED PROTEIN KINASE 14 | NM_001315 NM_139012 NM_139013 NM_139014 | NP_001306 NP_620581 NP_620582 NP_620583 | N | UP |
| MCP1 | MONOCYTE CHEMOATTRACTANT PROTEIN 1 | AF493698, AF493697 | AAQ75526 | P | UP |
| MKNK1 | MAP KINASE INTERACTING SERINE/THREONINE KINASE 1 | NM_003684 NM_198973 | NP_003675 NP_945324 | N | UP |
| MMP9 | MATRIX METALLOPROTEINASE 9 (GELATINASE B, 92KDA GELATINASE, 92KDA TYPE IV COLLAGENASE) | NM_004994 | NP_004985 | N/P | UP (both protein and nucleic acid) |
| NCR1 | NATURAL CYTOTOXICITY TRIGGERING RECEPTOR 1 | NM_004829 | NP_004820 | N | UP |
| OSM | ONCOSTATIN M | NM_020530 | NP_065391 | N | UP |
| PFKFB3 | 6-PHOSPHOFRUCTO-2-KINASE/FRUCTOSE-2,6-BISPHOSPHATASE 3 | NM_004566 | NP_004557 | N | UP |
| PRV1 | NEUTROPHIL-SPECIFIC ANTIGEN 1 (POLYCYTHEMIA RUBRA VERA 1) | NM_020406 | NP_065139 | N | UP |
| PSTPIP2 | PROLINE/SERINE/ THREONINE PHOSPHATASE-INTERACTING PROTEIN 1 (PROLINE-SERINE-THREONINE PHOSPHATASE INTERACTING PROTEIN 2) | NM_024430 | NP_077748 | N | UP |
| SOCS3 | SUPPRESSOR OF CYTOKINE SIGNALING 3 | NM_003955 | NP_003946 | N | UP |
| SOD2 | SUPEROXIDE DISMUTASE 2, MITOCHONDRIAL | NM_000636 | NP_000627 | N | UP |
| TDRD9 | TUDOR DOMAIN CONTAINING 9 | NM_153046 | NP_694591 | N | UP |
| TGFBI | TRANSFORMING GROWTH FACTOR, BETA-1 (TRANSFORMING GROWTH FACTOR, BETA-INDUCED, 68KDA) | NM_000358 | NP_000349 | N | DOWN |
| TIFA | TRAF-INTERACTING PROTEIN WITH A FORKHEAD-ASSOCIATED DOMAIN | NM_052864 | NP_443096 | N | UP |
| TIMP1 | TISSUE INHIBITOR OF METALLOPROTEINASE 1 | NM_003254 | AAA75558 | P | UP |
| TLR4 | TOLL-LIKE RECEPTOR 4 | AH009665 | AAF05316 | N | UP |

TABLE I-continued

Biomarkers in accordance with an embodiment of the present invention.

| Gene Symbol 1 | Gene Name 2 | Gene Accession Number 3 | Protein Accession Number 4 | Source 5 | Regulation in SEPSIS 6 |
|---|---|---|---|---|---|
| TNFRSF6 | TUMOR NECROSIS FACTOR RECEPTOR SUPERFAMILY, MEMBER 6 | NM_152877 | NP_000034 | N | UP |
| TNFSF10 | TUMOR NECROSIS FACTOR (LIGAND) SUPERFAMILY, MEMBER 10 | NM_003810 | NP_003801 | N | UP |
| TNFSF13B | TUMOR NECROSIS FACTOR (LIGAND) SUPERFAMILY, MEMBER 13B | NM_006573 | NP_006564 | N | UP |
| VNN1 | VANIN 1 | NM_004666 | NP_004657 | N | UP |

Each of the sequences, genes, proteins, and probesets identified in Table I is hereby incorporated by reference.

TABLE J

Biomarkers identified based on the ability of the nucleic acid form of the biomarker to discriminate between SIRS and sepsis

| Gene Symbol 1 | Gene Name 2 | Gene Accession Number 3 | Protein Accession Number 4 |
|---|---|---|---|
| FCGR1A | FC FRAGMENT OF IGG, HIGH AFFINITY IA | NM_000566 | NP_000557 |
| MMP9 | MATRIX METALLOPROTEINASE 9 | NM_004994 | NP_004985 |
| IL18R1 | INTERLEUKIN 18 RECEPTOR 1 | NM_003855 | NP_003846 |
| ARG2 | ARGINASE TYPE II | NM_001172 | CAG38787 |
| IL1RN | INTERLEUKIN-1 RECEPTOR ANTAGONIST GENE | NM_000577, NM_173841, NM_173842, NM_173843 | AAN87150 |
| TNFSF13B | TUMOR NECROSIS FACTOR SUPERFAMILY, MEMBER 13B | NM_006573 | NP_006564 |
| ITGAM | INTEGRIN, ALPHA M | NM_000632 | NP_000623 |
| TGFB1 | TRANSFORMING GROWTH FACTOR, BETA-1 | NM_000358 | NP_000349 |
| CD86 | CD86 ANTIGEN | NM_006889 NM_175682 | NP_008820 NP_787058 |
| TLR4 | TOLL-LIKE RECEPTOR 4 | AH009665 | AAF05316 |
| | BCL2-RELATED PROTEIN A1 | NM_004049 | NP_004040 |
| CCL5 | CHEMOKINE (C-C MOTIF) LIGAND 5 | NM_002985 | NP_002976 |
| CSF1R | COLONY STIMULATING FACTOR 1 RECEPTOR, FORMERLY MCDONOUGH FELINE SARCOMA VIRAL (V-FMS) ONCOGENE HOMOLOG | NM_005211 | NP_005202 |
| GADD45A | GROWTH ARREST AND DNA-DAMAGE-INDUCIBLE, ALPHA | NM_001924 | NP_001915 |
| GADD45B | GROWTH ARREST- AND DNA DAMAGE- INDUCIBLE GENE GADD45 | NM_015675 | NP_056490 |
| IFNGR1 | INTERFERON GAMMA RECEPTOR 1 | NM_000416 | NP_000407 |
| IL10RA | INTERLEUKIN 10 RECEPTOR, ALPHA | NM_001558 | NP_001549 |
| IRAK2 | INTERLEUKIN-1 RECEPTOR- ASSOCIATED KINASE 2 | NM_001570 | NP_001561 |
| IRAK4 | INTERLEUKIN-1 RECEPTOR- ASSOCIATED KINASE 4 | NM_016123 | NP_057207 |
| JAK2 | JANUS KINASE 2 (A PROTEIN TYROSINE KINASE) | NM_004972 | NP_004963 |
| LY96 | LYMPHOCYTE ANTIGEN 96 | NM_015364 | NP_056179 |
| MAP2K6 | MITOGEN- ACTIVATED PROTEIN KINASE 6 | NM_002758 NM_031988 | NP_002749 NP_114365 |
| MAPK14 | MAPK14 MITOGEN- ACTIVATED PROTEIN KINASE 14 | NM_001315 NM_139012 NM_139013 NM_139014 | NP_001306 NP_620581 NP_620582 NP_620583 |
| MKNK1 | MAP KINASE INTERACTING SERINE/THREONINE KINASE 1 | NM_003684 NM_198973 | NP_003675 NP_945324 |
| OSM | ONCOSTATIN M | NM_020530 | NP_065391 |
| SOCS3 | SUPPRESSOR OF CYTOKINE SIGNALING 3 | NM_003955 | NP_003946 |
| TDRD9 | TUDOR DOMAIN CONTAINING 9 | NM_153046 | NP_694591 |
| TNFRSF6 | TUMOR NECROSIS FACTOR RECEPTOR SUPERFAMILY, MEMBER 6 | NM_152877 | NP_000034 |
| TNFSF10 | TUMOR NECROSIS FACTOR (LIGAND) SUPERFAMILY, MEMBER 10 | NM_003810 | NP_003801 |

TABLE J-continued

Biomarkers identified based on the ability of the nucleic acid form of the biomarker to discriminate between SIRS and sepsis

| Gene Symbol | Gene Name | Gene Accession Number | Protein Accession Number |
|---|---|---|---|
| ANKRD22 | ANKYRIN REPEAT DOMAIN 22 | NM_144590 | NP_653191 |
| ANXA3 | ANNEXIN A3 | NM_005139 | NP_005130 |
| CEACAM1 | CARCINOEMBRYONIC ANTIGEN-RELATED CELL ADHESION MOLECULE 1 | NM_001712 | NP_001703 |
| LDLR | LOW DENSITY LIPOPROTEIN RECEPTOR | NM_000527 | NP_000518 |
| PFKFB3 | 6-PHOSPHOFRUCTO-2-KINASE/FRUCTOSE-2,6-BISPHOSPHATASE 3 | NM_004566 | NP_004557 |
| PRV1 | NEUTROPHIL-SPECIFIC ANTIGEN 1 (POLYCYTHEMIA RUBRA VERA 1) | NM_020406 | NP_065139 |
| PSTPIP2 | PROLINE/SERINE/THREONINE PHOSPHATASE-INTERACTING PROTEIN 1 (PROLINE-SERINE-THREONINE PHOSPHATASE INTERACTING PROTEIN 2) | NM_024430 | NP_077748 |
| TIFA | TRAF-INTERACTING PROTEIN WITH A FORKHEAD-ASSOCIATED DOMAIN | NM_052864 | NP_443096 |
| VNN1 | VANIN 1 | NM_004666 | NP004657 |
| NCR1 | NATURAL CYTOTOXICITY TRIGGERING RECEPTOR 1 | NM_004829 | NP_004820 |
| FAD104 | FIBRONECTIN TYPE III DOMAIN CONTAINING 3B (FNDC3B) | NM_022763 | NP_073600 |
| INSL3 | INSULIN-LIKE 3 (LEYDIG CELL) | NM_005543 | NP_005534 |
| CRTAP | CARTILAGE-ASSOCIATED PROTEIN | NM_006371 | NP_006362 |
| HLA-DRA | MAJOR HISTOCOMPATIBILITY COMPLEX, CLASS II, DR ALPHA | NM_002123 | NP_002114 |
| SOD2 | SUPEROXIDE DISMUTASE 2, MITOCHONDRIAL | NM_000636 | NP_000627 |

TABLE K

Biomarkers identified based on the ability of the protein form of the biomarker to discriminate between SIRS and sepsis

| Gene Symbol | Gene Name | Gene Accession Number | Protein Accession Number |
|---|---|---|---|
| IL-6 | INTERLEUKIN 6 | NM_000600 | NP_000591 |
| IL-8 | INTERLEUKIN 8 | M28130 | AAA59158 |
| CRP | C Reactive protein | CAA39671 | NM_000567 |
| IL-10 | INTERLEUKIN 10 | NM_000572 | CAH73907 |
| APOC3 | APOLIPOPROTEIN CIII | NM_000040 | CAA25648 |
| MMP9 | MATRIX METALLOPROTEINASE 9 (GELATINASE B, 92KDA GELATINASE, 92KDA TYPE IV COLLAGENASE) | NM_004994 | NP_004985 |
| TIMP1 | TISSUE INHIBITOR OF METALLOPROTEINASE 1 | NM_003254 | AAA75558 |
| MCP1 | MONOCYTE CHEMOATTRACTANT PROTEIN 1 | AF493698, AF493697 | AAQ75526 |
| AFP | ALPHA-FETOPROTEIN | NM_001134 | CAA79592 |
| B2M | BETA-2 MICROGLOBULIN | NM_004048 | AAA51811 |

5.11.1 Biomarker Descriptions

The references for the biomarkers in this section merely provide exemplary sequences for the biomarkers set forth in the present application.

The nucleotide sequence of AFP (identified by accession no. NM_001134) is disclosed in, e.g., Beattie et al., 1982, "Structure and evolution of human alpha-fetoprotein deduced from partial sequence of cloned cDNA" Gene 20 (3): 415-422, Harper, M. E. et al., 1983, "Linkage of the evolutionarily-related serum albumin and alpha-fetoprotein genes within q11-22 of human chromosome 4," Am. J. Hum. Genet. 35 (4):565-572, Morinaga, T. et al., 1983, "Primary structures of human alpha-fetoprotein and its mRNA," Proc. Natl. Acad. Sci. U.S.A. 80 (15):4604-4608, and the amino acid sequence of AFP (identified by accession no. CAA79592) is disclosed in, e.g., McVey, 1993, Direct Submission, Clinical Research Centre, Haemostasis Research Group, Watford Road, Harrow, UK, HA1 3UJ, McVey et al., 1993, "A G→A substitution in an HNF I binding site in the human alpha-fetoprotein gene is associated with hereditary persistence of alpha-fetoprotein (HPAFP)," Hum. Mol. Genet. 2 (4): 379-384, each of which is incorporated by reference herein in its entirety.

The nucleotide sequence of ANKRD22 (identified by accession no. NM_144590) is disclosed in, e.g., Strausberg, 2002, "Homo sapiens ankyrin repeat domain 22, mRNA (cDNA clone MGC:22805 IMAGE:3682099)," unpublished, and the amino acid sequence of ANKRD22 (identified by accession no. NP_653191) is disclosed in, e.g., Strausberg, 2002, "Homo sapiens ankyrin repeat domain 22, mRNA (cDNA clone MGC:22805 IMAGE:3682099)," unpublished, each of which is incorporated by reference herein in its entirety.

The nucleotide sequence of ANXA3 (identified by accession no. NM_005139) is disclosed in, e.g., Pepinsky, R. B. et al., 1988," Five distinct calcium and phospholipid binding proteins share homology with lipocortin I," J. Biol. Chem. 263 (22): 10799-10811, Tait, J. F. et al., 1988, "Placental anticoagulant proteins: isolation and comparative characterization four members of the lipocortin family," Biochemistry 27 (17):6268-6276, Ross, T. S. et al., 1990, "Identity of inositol 1,2-cyclic phosphate 2-phosphohydrolase with lipocortin III," Science 248 (4955):605-607, and the amino acid sequence of ANXA3 (identified by accession no. NP_005130) is disclosed in, e.g., Pepinsky, R. B et al., 1988," Five distinct calcium and phospholipid binding proteins share homology with lipocortin I," J. Biol. Chem. 263 (22): 10799-10811, Tait, J. F. et al., 1988, "Placental anticoagulant proteins: isolation and comparative characterization four members of the lipocortin family," Biochemistry 27 (17):6268-6276, Ross, T. S. et al., 1990, "Identity of inositol 1,2-cyclic phosphate 2-phosphohydrolase with lipocortin III," Science 248 (4955):605-607, each of which is incorporated by reference herein in its entirety.

The nucleotide sequence of Apolipoprotein CIII (APOC3) (identified by accession no. NM_000040) is disclosed in, e.g., Ruiz-Narvaez. et al., 2005 "APOC3/A5 haplotypes, lipid levels, and risk of myocardial infarction in the Central Valley of Costa Rica," J. Lipid Res. 46 (12), 2605-2613; Garenc et al., 2005, "Effect of the APOC3 Sst I SNP on fasting triglyceride levels in men heterozygous for the LPL P207L deficiency," Eur. J. Hum. Genet. 13, 1159-1165; Baum. et al., 2005, "Effect of hepatic lipase-514C→T polymorphism and its interactions with apolipoprotein C3-482C→T and apolipoprotein E exon 4 polymorphisms on the risk of nephropathy in chinese type 2 diabetic patients," Diabetes Care 28, 1704-1709, and the amino acid sequence of APOC3 (identified by accession no. CAA25648) is disclosed in, e.g., Protter et al., 1984, "Isolation and sequence analysis of the human apolipoprotein CIII gene and the intergenic region between the apo AI and apo CIII," DNA 3, 449-456, each of which is incorporated by reference herein in its entirety.

The nucleotide sequence of ARG2 (identified by accession no. NM_001172) is disclosed in, e.g., Gotoh et al., 1996 "Molecular cloning of cDNA for nonhepatic mitochondrial arginase(arginase II) and comparison of its induction with nitric oxide synthase in a murine macrophage-like cell line," FEBS Lett. 395 (2-3):119-122, Vockley et al., 1996, "Cloning and characterization of the human type II arginase gene," Genomics 38 (2):118-123, Gotoh et al., 1997, "Chromosomal localization of the human arginase II gene and tissue distribution of its mRNA," Biochem. Biophys. Res. Commun. 233 (2):487-491, and the amino acid sequence of ARG2 (identified by accession no. CAG38787) is disclosed in, e.g., Halleck et al., 2004, Direct Submission, RZPD Deutsches Ressourcenzentrum fuer Genomforschung GmbH, Im Neuenheimer Feld 580, D-69120 Heidelberg, Germany, Halleck et al., unpublished, "Cloning of human full open reading frames in Gateway™ system entry vector (pDONR201)," each of which is incorporated by reference herein in its entirety.

The nucleotide sequence of B2M (identified by accession no. NM_004048) is disclosed in, e.g., Krangel, M. S. et al., 1979, "Assembly and maturation of HLA-A and HLA-B antigens in vivo," Cell 18 (4):979-991, Suggs, S. V. et al., 1981, "Use of synthetic oligonucleotides as hybridization probes: isolation of cloned cDNA sequences for human beta 2-microglobulin," Proc. Natl. Acad. Sci. U.S.A. 78 (11): 6613-6617, Rosa, F. et al., 1983, "The beta2-microglobulin mRNA in human Daudi cells has a mutated initiation codon but is still inducible by interferon," EMBO J. 2 (2):239-243, and the amino acid sequence of B2M (identified by accession no. AAA51811) is disclosed in, e.g., Gussow, D. et al., 1987, "The human beta 2-microglobulin gene. Primary structure and definition of the transcriptional unit," J. Immunol. 139 (9): 3132-3138, each of which is incorporated by reference herein in its entirety.

The nucleotide sequence of BCL2A1 (identified by accession no. NM_004049) is disclosed in, e.g., Lin, E. Y. et al., 1993, "Characterization of A1, a novel hemopoietic-specific early-response gene with sequence similarity to bcl-2," J. Immunol. 151 (4):1979-1988, Savitsky, K. et al., "The complete sequence of the coding region of the ATM gene reveals similarity to cell cycle regulators in different species," Hum. Mol. Genet. 4 (11):2025-2032, Choi, S. S. et al., 1995, "A novel Bcl-2 related gene, Bfl-1, is overexpressed in stomach cancer and preferentially expressed in bone marrow," Oncogene 11 (9):1693-1698, and the amino acid sequence of BCL2A1 (identified by accession no. NP_004040) is disclosed in, e.g., Lin, E. Y. et al., 1993, "Characterization of A1, a novel hemopoietic-specific early-response gene with sequence similarity to bcl-2," J. Immunol. 151 (4):1979-1988, Savitsky, K. et al., "The complete sequence of the coding region of the ATM gene reveals similarity to cell cycle regulators in different species," Hum. Mol. Genet. 4 (11):2025-2032, Choi, S. S. et al., 1995, "A novel Bcl-2 related gene, Bfl-1, is overexpressed in stomach cancer and preferentially expressed in bone marrow," Oncogene 11 (9):1693-1698, each of which is incorporated by reference herein in its entirety.

The nucleotide sequence of CCL5 (identified by accession no. NM_002985) is disclosed in, e.g., Schall, T. J. et al., 1988, "A human T cell-specific molecule is a member of a new gene family," J. Immunol. 141 (3):1018-1025, Donlon, T. A. et al., 1990, "Localization of a human T-cell-specific gene, RANTES (D17S136E), to chromosome 17q11.2-q12," Genomics 6 (3):548-553, Kameyoshi, Y. et al., 1992, "Cytokine RANTES released by thrombin-stimulated platelets is a potent attractant for human eosinophils," J. Exp. Med. 176 (2):587-592, and the amino acid sequence of CCL5 (identified by accession no. NP_002976) is disclosed in, e.g., Schall, T. J. et al., 1988, "A human T cell-specific molecule is a member of a new gene family," J. Immunol. 141 (3):1018-1025, Donlon, T. A. et al., 1990, "Localization of a human T-cell-specific gene, RANTES (D17S136E), to chromosome 17q11.2-q12," Genomics 6 (3):548-553, Kameyoshi, Y. et al., 1992, "Cytokine RANTES released by thrombin-stimulated platelets is a potent attractant for human eosinophils," J. Exp. Med. 176 (2):587-592, each of which is incorporated by reference herein in its entirety.

The nucleotide sequence of CD86 (identified by accession nos. NM_006889, NM_175862) is disclosed in, e.g., Azuma, M. et al., 1993, "B70 antigen is a second ligand for CTLA-4 and CD28," Nature 366 (6450):76-79, Freeman, G. J. et al., 1993, "Cloning of B7-2: a CTLA-4 counter-receptor that costimulates human T cell proliferation," Science 262 (5135):909-911, Chen, C. et al., 1994, "Molecular cloning and expression of early T cell costimulatory molecule-1 and its characterization as B7-2 molecule," J. Immunol. 152 (10):4929-4936, and the amino acid sequence of CD86 (identified by accession nos. NP_008820, NP_787058) is disclosed in, e.g., Azuma, M. et al., 1993, "B70 antigen is a second ligand for CTLA-4 and CD28," Nature 366 (6450): 76-79, Azuma, M. et al., 1993, "B70 antigen is a second ligand for CTLA-4 and CD28," Nature 366 (6450):76-79, Freeman, G. J. et al., 1993, "Cloning of B7-2: a CTLA-4 counter-receptor that costimulates human T cell proliferation," Science 262 (5135):909-911, Chen, C. et al., 1994, "Molecular cloning and expression of early T cell costimulatory molecule-1 and its characterization as B7-2 molecule," J. Immunol. 152 (10):4929-4936, each of which is incorporated by reference herein in its entirety.

The nucleotide sequence of CEACAM1 (identified by accession no. NM_001712) is disclosed in, e.g., Svenberg, T. et al., 1979, "Immunofluorescence studies on the occurrence and localization of the CEA-related biliary glycoprotein I (BGP I) in normal human gastrointestinal tissues," Clin. Exp. Immunol. 36 (3):436-441, Hinoda, Y. et al., 1988, "Molecular cloning of a cDNA coding biliary glycoprotein I: primary structure of a glycoprotein immunologically crossreactive with carcinoembryonic antigen," Proc. Natl. Acad. Sci. U.S.A. 85 (18):6959-6963, Barnett, T. R. et al., 1989, "Carcinoembryonic antigens: alternative splicing accounts for the multiple mRNAs that code for novel members of the carcinoembryonic antigen family," J. Cell Biol. 108 (2):267-276, and the amino acid sequence of CEACAM1 (identified by accession no. NP_001703) is disclosed in, e.g., Svenberg, T. et al., 1979, "Immunofluorescence studies on the occurrence and localization of the CEA-related biliary glycoprotein I (BGP I) in normal human gastrointestinal tissues," Clin. Exp. Immunol. 36 (3):436-441, Hinoda, Y. et al., 1988, "Molecular cloning of a cDNA coding biliary glycoprotein I: primary structure of a glycoprotein immunologically crossreactive with carcinoembryonic antigen," Proc. Natl. Acad. Sci. U.S.A. 85 (18):6959-6963, Barnett, T. R. et al., 1989, "Carcinoembryonic antigens: alternative splicing accounts for the multiple mRNAs that code for novel members of the carcinoembryonic antigen family," J. Cell Biol. 108 (2):267-276, each of which is incorporated by reference herein in its entirety.

The nucleotide sequence of C Reactive Protein (CRP) (identified by accession no. NM_000567) is disclosed in, e.g., Song et al., 2006, "C-reactive protein contributes to the hypercoagulable state in coronary artery disease," J. Thromb. Haemost. 4 (1), 98-106; Wakugawa et al., 2006, "C-reactive protein and risk of first-ever ischemic and hemorrhagic stroke in a general Japanese population: the Hisayama Study," Stroke 37, 27-32; Tong et al., 2005, "Association of testosterone, insulin-like growth factor-I, and C-reactive protein with metabolic syndrome in Chinese middle-aged men with a family history of type 2 diabetes," J. Clin. Endocrinol. Metab. 90, 6418-6423, and the amino acid sequence of CRP (identified by accession no. CAA39671 is described in a direct submissiong by Tenchini et al., 1990, Tenchini M. L., Dipartimento di Biologia e Genetica per le Scienze mediche, via Viotti 3, 20133 Milano, Italy, each of which is incorporated by reference herein in its entirety.

The nucleotide sequence of CRTAP (identified by accession no. NM_006371) is disclosed in, e.g., Castagnola, P. et al., 1997, "Cartilage associated protein (CASP) is a novel developmentally regulated chick embryo protein," J. Cell. Sci. 110 (PT 12):1351-1359; Tonachini, L. et al., 1999, "cDNA cloning, characterization and chromosome mapping of the gene encoding human cartilage associated protein (CRTAP)," Cytogenet. Cell Genet. 87:(3-4); Morello, R. et al., 1999, "cDNA cloning, characterization and chromosome mapping of Crtap encoding the mouse cartilage associated protein," Matrix Biol. 18 (3):319-324, and the amino acid sequence of CRTAP (identified by accession no. NP_006362) is disclosed in, e.g., Castagnola, P. et al., 1997, "Cartilage associated protein (CASP) is a novel developmentally regulated chick embryo protein," J. Cell. Sci. 110 (PT 12):1351-1359, Tonachini, L. et al., 1999, "cDNA cloning, characterization and chromosome mapping of the gene encoding human cartilage associated protein (CRTAP)," Cytogenet. Cell Genet. 87:(3-4), Morello, R. et al., 1999, "cDNA cloning, characterization and chromosome mapping of Crtap encoding the mouse cartilage associated protein," Matrix Biol. 18 (3):319-324, each of which is incorporated by reference herein in its entirety.

The nucleotide sequence of CSF1R (identified by accession no. NM_005211) is disclosed in, e.g., Verbeek, J. S. et al., 1985, "Human c-fms proto-oncogene: comparative analysis with an abnormal allele," Mol. Cell. Biol. 5 (2): 422-426; Xu, D.Q. et al., 1985, "Restriction fragment length polymorphism of the human c-fms gene," Proc. Natl. Acad. Sci. U.S.A. 82 (9):2862-2865; Sherr, C. J. et al., 1985, "The c-fms proto-oncogene product is related to the receptor for the mononuclear phagocyte growth factor, CSF-1," Cell 41 (3):665-676, and the amino acid sequence of CSF1R (identified by accession no. NP_005202) is disclosed in, e.g., Verbeek, J. S. et al., 1985, "Human c-fms proto-oncogene: comparative analysis with an abnormal allele," Mol. Cell. Biol. 5 (2):422-426, Xu, D. Q. et al., 1985, "Restriction fragment length polymorphism of the human c-fms gene," Proc. Natl. Acad. Sci. U.S.A. 82 (9):2862-2865, Sherr, C. J. et al., 1985, "The c-fms proto-oncogene product is related to the receptor for the mononuclear phagocyte growth factor, CSF-1," Cell 41 (3):665-676, each of which is incorporated by reference herein in its entirety.

The nucleotide sequence of FAD104 (identified by accession no. NM_022763) is disclosed in, e.g., Clark, H. F. et al., 2003, "The secreted protein discovery initiative (SPDI), a large-scale effort to identify novel human secreted and transmembrane proteins:a bioinformatics assessment," Genome Res. 13 (10):2265-2270, Tominaga, K. et al., 2004, "The novel gene fad104, containing a fibronectin type III domain, has a significant role in adipogenesis," FEBS Lett. 577 (1-2):49-54, and the amino acid sequence of FAD104 (identified by accession no. NP_073600) is disclosed in, e.g., Clark, H. F. et al., 2003, "The secreted protein discovery initiative (SPDI), a large-scale effort to identify novel human secreted and transmembrane proteins:a bioinformatics assessment," Genome Res. 13 (10):2265-2270, Tominaga, K. et al., 2004, "The novel gene fad104, containing a fibronectin type III domain, has a significant role in adipogenesis," FEBS Lett. 577 (1-2):49-54, each of which is incorporated by reference herein in its entirety.

The nucleotide sequence of FCGR1A (identified by accession no. NM_000566) is disclosed in, e.g., Eizuru, Y. et al., 1988, "Induction of Fc (IgG) receptor(s) by simian cytomegaloviruses in human embryonic lung fibroblasts," Intervirology 29 (6):339-345, Allen, J. M. et al., 1988, "Nucleotide sequence of three cDNAs for the human high affinity Fc receptor (FcRI)," Nucleic Acids Res. 16 (24):11824, van de Winkel, J. G. et al., 1991, "Gene organization of the human high affinity receptor for IgG, Fc gamma RI (CD64). Characterization and evidence for a second gene," J. Biol. Chem. 266 (20):13449-1345, and the amino acid sequence of FCGR1A (identified by accession no. NP_000557) is disclosed in, e.g., Eizuru, Y. et al., 1988, "Induction of Fc (IgG) receptor(s) by simian cytomegaloviruses in human embryonic lung fibroblasts," Intervirology 29 (6):339-345, Allen, J. M. et al., 1988, "Nucleotide sequence of three cDNAs for the human high affinity Fc receptor (FcRI)," Nucleic Acids Res. 16 (24):11824, van de Winkel, J. G. et al., 1991, "Gene organization of the human high affinity receptor for IgG, Fc gamma RI (CD64). Characterization and evidence for a second gene," J. Biol. Chem. 266 (20):13449-1345, each of which is incorporated by reference herein in its entirety.

The nucleotide sequence of GADD45A (identified by accession no. NM_001924) is disclosed in, e.g., Papathanasiou, M. A. et al., 1991, "Induction by ionizing radiation of the gadd45 gene in cultured human cells: lack of mediation by protein kinase C," Mol. Cell. Biol. 11 (2):1009-1016, Hollander, M. C. et al., 1993, "Analysis of the mammalian gadd45 gene and its response to DNA damage," J. Biol. Chem. 268 (32):24385-24393, Smith, M. L. et al., 1994, "Interaction of the p53-regulated protein Gadd45 with proliferating cell nuclear antigen," Science 266 (5189):1376-1380, and the amino acid sequence of GADD45A (identified by accession no. NP_001915) is disclosed in, e.g., Papathanasiou, M. A. et al., 1991, "Induction by ionizing radiation of the gadd45 gene in cultured human cells: lack of mediation by protein kinase C," Mol. Cell. Biol. 11 (2):1009-1016, Hollander, M. C. et al., 1993, "Analysis of the mammalian gadd45 gene and its response to DNA damage," J. Biol. Chem. 268 (32):24385-24393, Smith, M. L. et al., 1994, "Interaction of the p53-regulated protein Gadd45 with proliferating cell nuclear antigen," Science 266 (5189):1376-1380, each of which is incorporated by reference herein in its entirety.

The nucleotide sequence of GADD45B (identified by accession no. NM_015675) is disclosed in, e.g., Abdollahi, A. et al., 1991, "Sequence and expression of a cDNA encoding MyD118: a novel myeloid differentiation primary response gene induced by multiple cytokines," Oncogene 6 (1): 165-167, Vairapandi, M. et al., 1996, "The differentiation primary response gene MyD118, related to GADD45, encodes for a nuclear protein which interacts with PCNA and p21WAF1/CIP1," Oncogene 12 (12):2579-2594, Koonin, E. V., 1997, "Cell cycle and apoptosis: possible roles of Gadd45 and MyD118 proteins inferred from their homology to ribosomal proteins," J. Mol. Med. 75 (4):236-238, and the amino acid sequence of GADD45B (identified by accession no. NP_056490) is disclosed in, e.g., Abdollahi, A. et al., 1991, "Sequence and expression of a cDNA encoding MyD118: a novel myeloid differentiation primary response gene induced by multiple cytokines," Oncogene 6 (1):165-167, Vairapandi, M. et al., 1996, "The differentiation primary response gene MyD118, related to GADD45, encodes for a nuclear protein which interacts with PCNA and p21WAF1/CIP1," Oncogene 12 (12):2579-2594, Koonin, E. V., 1997, "Cell cycle and apoptosis: possible roles of Gadd45 and MyD118 proteins inferred from their homology to ribosomal proteins," J. Mol. Med. 75 (4):236-238, each of which is incorporated by reference herein in its entirety.

The nucleotide sequence of HLA-DRA (identified by accession no. NM_002123) is disclosed in, e.g., Larhammar, D. et al., 1981, Evolutionary relationship between HLA-DR antigen beta-chains, HLA-A, B, C antigen subunits and immunoglobulin chains," Scand. J. Immunol. 14 (6):617-622, Wiman, K. et al., 1982, "Isolation and identification of a cDNA clone corresponding to an HLA-DR antigen beta chain," Proc. Natl. Acad. Sci. U.S.A. 79 (6):1703-1707, Larhammar, D. et al., 1982, "Complete amino acid sequence of an HLA-DR antigen-like beta chain as predicted from the nucleotide sequence: similarities with immunoglobulins and HLA-A, -B, and -C antigens," Proc. Natl. Acad. Sci. U.S.A. 79 (12):3687-3691, and the amino acid sequence of HLA-DRA (identified by accession no. NP_002114) is disclosed in, e.g., Larhammar, D. et al., 1981, Evolutionary relationship between HLA-DR antigen beta-chains, HLA-A, B, C antigen subunits and immunoglobulin chains," Scand. J. Immunol. 14 (6):617-622, Wiman, K. et al., 1982, "Isolation and identification of a cDNA clone corresponding to an HLA-DR antigen beta chain," Proc. Natl. Acad. Sci. U.S.A. 79 (6):1703-1707, Larhammar, D. et al., 1982, "Complete amino acid sequence of an HLA-DR antigen-like beta chain as predicted from the nucleotide sequence: similarities with immunoglobulins and HLA-A, -B, and -C antigens," Proc. Natl. Acad. Sci. U.S.A. 79 (12):3687-3691, each of which is incorporated by reference herein in its entirety.

The nucleotide sequence of IFNGR1 (identified by accession no. NM_000416) is disclosed in, e.g., Novick, D. et al., 1987, "The human interferon-gamma receptor. Purification, characterization, and preparation of antibodies, each of which is incorporated by reference herein in its entirety," J. Biol. Chem. 262 (18): 8483-8487, Aguet, M. et al., 1988, "Molecular cloning and expression of the human interferon-gamma receptor," Cell 55 (2): 273-280, Le Coniat, M. et al., 1989, "Human interferon gamma receptor 1 (IFNGR1) gene maps to chromosome region 6q23-6q24," Hum. Genet. 84 (1):92-94, and the amino acid sequence of IFNGR1 (identified by accession no. NP_000407) is disclosed in, e.g., Novick, D. et al., 1987, "The human interferon-gamma receptor. Purification, characterization, and preparation of antibodies," J. Biol. Chem. 262 (18):8483-8487, Aguet, M. et al., 1988, "Molecular cloning and expression of the human interferon-gamma receptor," Cell 55 (2): 273-280, Le Coniat, M. et al., 1989, "Human interferon gamma receptor 1 (IFNGR1) gene maps to chromosome region 6q23-6q24," Hum. Genet. 84 (1):92-94, each of which is incorporated by reference herein in its entirety.

The nucleotide sequence of IL1RN (identified by accession nos. NM_000577, NM_173841, NM_173842, NM_173843) is disclosed in, e.g., Eisenberg, S. P. et al., 1990, "Primary structure and functional expression from complementary DNA of a human interleukin-1 receptor antagonist," Nature 343 (6256):341-346, Carter, D. B. et al., 1990, "Purification, cloning, expression and biological characterization of an interleukin-1 receptor antagonist protein," Nature 344 (6267):633-638, Seckinger, P. et al., 1990, "Natural and recombinant human IL-1 receptor antagonists block the effects of IL-1 on bone resorption and prostaglandin production," J. Immunol. 145 (12):4181-4184, and the amino acid sequence of IL1RN (identified by accession no. AAN87150) is disclosed in, e.g., Rieder, M. J. et al., 2002, Direct Submission, Genome Sciences, University of Washington, 1705 NE Pacific, Seattle, Wash. 98195, USA, each of which is incorporated by reference herein in its entirety.

The nucleotide sequence of IL-6 (identified by accession no. NM_000600) is disclosed in, e.g., Haegeman, G. et al., 1986, "Structural analysis of the sequence coding for an inducible 26-kDa protein in human fibroblasts," Eur. J. Biochem. 159 (3):625-632, Zilberstein, A. et al., 1986, "Structure and expression of cDNA and genes for human interferon-beta-2, a distinct species inducible by growth-stimulatory cytokines," EMBO J. 5 (10):2529-2537, Hirano, T. et al., 1986, "Complementary DNA for a novel human interleukin (BSF-2) that induces B lymphocytes to produce immunoglobulin," Nature 324 (6092):73-76, and the amino acid sequence of IL-6 (identified by accession no. NP_000591) is disclosed in, e.g., Haegeman, G. et al., 1986, "Structural analysis of the sequence coding for an inducible 26-kDa protein in human fibroblasts," Eur. J. Biochem. 159 (3):625-632, Zilberstein, A. et al., 1986, "Structure and expression of cDNA and genes for human interferon-beta-2, a distinct species inducible by growth-stimulatory cytokines," EMBO J. 5 (10):2529-2537, Hirano, T. et al., 1986, "Complementary DNA for a novel human interleukin (BSF-2) that induces B lymphocytes to produce immunoglobulin," Nature 324 (6092):73-76, each of which is incorporated by reference herein in its entirety.

The nucleotide sequence of IL-8 (identified by accession no. M28130) and the amino acid sequence of IL-8 (identified by accession no. AAA59158) are each disclosed in, e.g., Mukaida et al., 1989, "Genomic structure of the human monocyte-derived neutrophil chemotactic factor IL-8," J. Immunol. 143, 1366-1371 which is incorporated by reference herein in its entirety.

The nucleotide sequence of IL-10 (identified by accession no. NM_000572) is disclosed in, e.g., Ghosh, S. et al., 1975, "Anaerobic acidogenesis of wastewater sludge," Breast Cancer Res. Treat. 47 (1):30-45, Hsu, D. H. et al., 1990, "Expression of interleukin-10 activity by Epstein-Barr virus protein BCRF1," Science 250 (4982):830-832, Vieira, P. et al., 1991, "Isolation and expression of human cytokine synthesis inhibitory factor cDNA clones: homology to Epstein-Barr virus open reading frame BCRF1," Proc. Natl. Acad. Sci. U.S.A. 88 (4):1172-1176, and the amino acid sequence of IL-10 (identified by accession no. CAH73907) is disclosed in, e.g., Tracey, A., 2005, Direct Submission, Wellcome Trust Sanger Institute, Hinxton, Cambridgeshire, CB10 1SA, each of which is incorporated by reference herein in its entirety.

The nucleotide sequence of IL10RA (identified by accession no. NM_001558) is disclosed in, e.g., Tan, J. C. et al., 1993, "Characterization of interleukin-10 receptors on human and mouse cells," J. Biol. Chem. 268 (28):21053-21059, Ho, A. S. et al., 1993, "A receptor for interleukin 10 is related to interferon receptors," Proc. Natl. Acad. Sci. U.S.A. 90 (23):11267-11271, Liu, Y. et al., 1994, "Expression cloning and characterization of a human IL-10 receptor," J. Immunol. 152 (4):1821-1829, and the amino acid sequence of IL10RA (identified by accession no. NP_001549) is disclosed in, e.g., Tan, J. C. et al., 1993, "Characterization of interleukin-10 receptors on human and mouse cells," J. Biol. Chem. 268 (28):21053-21059, Ho, A. S. et al., 1993, "A receptor for interleukin 10 is related to interferon receptors," Proc. Natl. Acad. Sci. U.S.A. 90 (23):11267-11271, Liu, Y. et al., 1994, "Expression cloning and characterization of a human IL-10 receptor," J. Immunol. 152 (4):1821-1829, each of which is incorporated by reference herein in its entirety.

The nucleotide sequence of IL18R1 (identified by accession no. NM_003855) is disclosed in, e.g., Parnet, P. et al., 1996, "IL-1Rrp is a novel receptor-like molecule similar to the type I interleukin-1 receptor and its homologues T1/ST2 and IL-1R AcP," J. Biol. Chem. 271 (8):3967-3970, Lovenberg, T. W. et al., 1996, "Cloning of a cDNA encoding a novel interleukin-1 receptor related protein (IL 1R-rp2)," J. Neuroimmunol. 70 (2):113-122, Torigoe, K. et al., 1997, "Purification and characterization of the human interleukin-18 receptor," J. Biol. Chem. 272 (41):25737-25742, and the amino acid sequence of IL18R1 (identified by accession no. NP_003846) is disclosed in, e.g., Parnet, P. et al., 1996, "IL-1Rrp is a novel receptor-like molecule similar to the type I interleukin-1 receptor and its homologues T1/ST2 and IL-1R AcP," J. Biol. Chem. 271 (8):3967-3970, Lovenberg, T. W. et al., 1996, "Cloning of a cDNA encoding a novel interleukin-1 receptor related protein (IL 1R-rp2)," J. Neuroimmunol. 70 (2):113-122, Torigoe, K. et al., 1997, "Purification and characterization of the human interleukin-18 receptor," J. Biol. Chem. 272 (41):25737-25742, each of which is incorporated by reference herein in its entirety.

The nucleotide sequence of INSL3 (identified by accession no. NM_005543) is disclosed in, e.g., Adham, I. M. et al., 1993, "Cloning of a cDNA for a novel insulin-like peptide of the testicular Leydig cells," J. Biol. Chem. 268 (35):26668-26672, Burkhardt, E. et al., 1994, "Structural organization of the porcine and human genes coding for a Leydig cell-specific insulin-like peptide (LEY I-L) and chromosomal localization of the human gene (INSL3)," Genomics 20 (1):13-19, Burkhardt, E. et al., 1994, "A human cDNA coding for the Leydig insulin-like peptide (Ley I-L)," Hum. Genet. 94 (1):91-94, and the amino acid sequence of INSL3 (identified by accession no. NP_005534) is disclosed in, e.g., Adham, I. M. et al., 1993, "Cloning of a cDNA for a novel insulin-like peptide of the testicular Leydig cells," J. Biol. Chem. 268 (35):26668-26672, Burkhardt, E. et al., 1994, "Structural organization of the porcine and human genes coding for a Leydig cell-specific insulin-like peptide (LEY I-L) and chromosomal localization of the human gene (INSL3)," Genomics 20 (1):13-19, Burkhardt, E. et al., 1994, "A human cDNA coding for the Leydig insulin-like peptide (Ley I-L)," Hum. Genet. 94 (1):91-94, each of which is incorporated by reference herein in its entirety.

The nucleotide sequence of IRAK2 (identified by accession no. NM_001570) is disclosed in, e.g., Muzio, M. et al., 1997, "IRAK (Pelle) family member IRAK-2 and MyD88 as proximal mediators of IL-1 signaling," Science 278 (5343): 1612-1615, Auron, P. E., 1998, "The interleukin 1 receptor: ligand interactions and signal transduction," Cytokine Growth Factor Rev. 9 (3-4):221-237, Maschera, B. et al., 1999, "Overexpression of an enzymically inactive interleukin-1-receptor-associated kinase activates nuclear factor-kappaB," Biochem. J. 339 (PT 2):227-231, and the amino acid sequence of IRAK2 (identified by accession no. NP_001561) is disclosed in, e.g., Muzio, M. et al., 1997, "IRAK (Pelle) family member IRAK-2 and MyD88 as proximal mediators of IL-1 signaling," Science 278 (5343): 1612-1615, Auron, P. E., 1998, "The interleukin 1 receptor: ligand interactions and signal transduction," Cytokine Growth Factor Rev. 9 (3-4):221-237, Maschera, B. et al., 1999, "Overexpression of an enzymically inactive interleukin-1-receptor-associated kinase activates nuclear factor-kappaB," Biochem. J. 339 (PT 2):227-231, each of which is incorporated by reference herein in its entirety.

The nucleotide sequence of IRAK4 (identified by accession no. NM_016123) is disclosed in, e.g., Siu, G. et al., 1986, "Analysis of a human V beta gene subfamily," J. Exp. Med. 164 (5):1600-1614, Scanlan, M. J. et al., 1999, "Antigens recognized by autologous antibody in patients with renal-cell carcinoma," Int. J. Cancer 83 (4):456-464, Li, S. et al., 2002, "IRAK-4: a novel member of the IRAK family with the properties of an IRAK-kinase," Proc. Natl. Acad. Sci. U.S.A. 99 (8):5567-5572, and the amino acid sequence of IRAK4 (identified by accession no. NP_057207) is disclosed in, e.g., Siu, G. et al., 1986, "Analysis of a human V beta gene subfamily," J. Exp. Med. 164 (5):1600-1614, Scanlan, M. J. et al., 1999, "Antigens recognized by autologous antibody in patients with renal-cell carcinoma," Int. J. Cancer 83 (4):456-464, Li, S. et al., 2002, "IRAK-4: a novel member of the IRAK family with the properties of an IRAK-kinase," Proc. Natl. Acad. Sci. U.S.A. 99 (8):5567-5572, each of which is incorporated by reference herein in its entirety.

The nucleotide sequence of ITGAM (identified by accession no. NM_000632) is disclosed in, e.g., Micklem, K. J. et al., 1985, "Isolation of complement-fragment-iC3b-binding proteins by affinity chromatography. The identification of p150.95 as an iC3b-binding protein," Biochem. J. 231 (1):233-236, Pierce, M. W. et al., 1986, "N-terminal sequence of human leukocyte glycoprotein Mo1:conservation across species and homology to platelet IIb/IIIa," Biochim. Biophys. Acta 874 (3):368-371, Arnaout, M. A. et al., 1988, "Molecular cloning of the alpha subunit of human and guinea pig leukocyte adhesion glycoprotein Mo1: chromosomal localization and homology to the alpha subunits of integrins," Proc. Natl. Acad. Sci. U.S.A. 85 (8):2776-2780, and the amino acid sequence of ITGAM (identified by accession no. NP_000623) is disclosed in, e.g., Micklem, K. J. et al., 1985, "Isolation of complement-fragment-iC3b-binding proteins by affinity chromatography. The identification of p150.95 as an iC3b-binding protein," Biochem. J. 231 (1):233-236, Pierce, M. W. et al., 1986, "N-terminal sequence of human leukocyte glycoprotein Mo1: conservation across species and homology to platelet IIb/IIIa," Biochim. Biophys. Acta 874 (3):368-371, Arnaout, M. A. et al., 1988, "Molecular cloning of the alpha subunit of human and guinea pig leukocyte adhesion glycoprotein Mo1: chromosomal localization and homology to the alpha subunits of integrins," Proc. Natl. Acad. Sci. U.S.A. 85 (8):2776-2780, each of which is incorporated by reference herein in its entirety.

The nucleotide sequence of JAK2 (identified by accession no. NM_004972) is disclosed in, e.g., Wilks, A. F. et al., 1991, "Two novel protein-tyrosine kinases, each with a second phosphotransferase-related catalytic domain, define a new class of protein kinase," Mol. Cell. Biol. 11 (4):2057-2065, Pritchard, M. A. et al., 1992, "Two members of the JAK family of protein tyrosine kinases map to chromosomes 1p31.3 and 9p24," Mamm. Genome 3 (1):36-38, Witthuhn, B. A. et al., 1993, "JAK2 associates with the erythropoietin receptor and is tyrosine phosphorylated and activated following stimulation with erythropoietin," Cell 74 (2):227-236, and the amino acid sequence of JAK2 (identified by accession no. NP_004963) is disclosed in, e.g., Wilks, A. F. et al., 1991, "Two novel protein-tyrosine kinases, each with a second phosphotransferase-related catalytic domain, define a new class of protein kinase," Mol. Cell. Biol. 11 (4):2057-2065, Pritchard, M. A. et al., 1992, "Two members of the JAK family of protein tyrosine kinases map to chromosomes 1p31.3 and 9p24," Mamm. Genome 3 (1):36-38, Witthuhn, B. A. et al., 1993, "JAK2 associates with the erythropoietin receptor and is tyrosine phosphorylated and activated following stimulation with erythropoietin," Cell 74 (2):227-236, each of which is incorporated by reference herein in its entirety.

The nucleotide sequence of LDLR (identified by accession no. NM_000527) is disclosed in, e.g., Brown, M. S. et al., 1979, "Receptor-mediated endocytosis: insights from the lipoprotein receptor system," Proc. Natl. Acad. Sci. U.S.A. 76 (7):3330-3337, Goldstein, J. L. et al., 1982, "Receptor-mediated endocytosis and the cellular uptake of low density lipoprotein," Ciba Found. Symp. 92, 77-95, Tolleshaug H. et al., 1983, "The LDL receptor locus in familial hypercholesterolemia: multiple mutations disrupt transport and processing of a membrane receptor," Cell 32 (3):941-951, and the amino acid sequence of LDLR (identified by accession no. NP_000518) is disclosed in, e.g., Brown, M. S. et al., 1979, "Receptor-mediated endocytosis: insights from the lipoprotein receptor system," Proc. Natl. Acad. Sci. U.S.A. 76 (7):3330-3337, Goldstein, J. L. et al., 1982, "Receptor-mediated endocytosis and the cellular uptake of low density lipoprotein," Ciba Found. Symp. 92, 77-95, Tolleshaug, H. et al., 1983, "The LDL receptor locus in familial hypercholesterolemia: multiple mutations disrupt transport and processing of a membrane receptor," Cell 32 (3):941-951, each of which is incorporated by reference herein in its entirety.

The nucleotide sequence of LY96 (identified by accession no. NM_015364) is disclosed in, e.g., Shimazu, R. et al., 1999, "MD-2, a molecule that confers lipopolysaccharide responsiveness on Toll-like receptor 4," J. Exp. Med. 189 (11):1777-1782, Kato, K. et al., 2000, "ESOP-1, a secreted protein expressed in the hematopoietic, nervous, and reproductive systems of embryonic and adult mice," Blood 96 (1):362-364, Dziarski, R. et al., 2001, "MD-2 enables Toll-like receptor 2 (TLR2)-mediated responses to lipopolysaccharide and enhances TLR2-mediated responses to Gram-positive and Gram-negative bacteria and their cell wall components," J. Immunol. 166 (3):1938-1944, and the amino acid sequence of LY96 (identified by accession no. NP_056179) is disclosed in, e.g., Shimazu, R. et al., 1999, "MD-2, a molecule that confers lipopolysaccharide responsiveness on Toll-like receptor 4," J. Exp. Med. 189 (11): 1777-1782, Kato, K. et al., 2000, "ESOP-1, a secreted protein expressed in the hematopoietic, nervous, and reproductive systems of embryonic and adult mice," Blood 96 (1):362-364, Dziarski, R. et al., 2001, "MD-2 enables Toll-like receptor 2 (TLR2)-mediated responses to lipopolysaccharide and enhances TLR2-mediated responses to Gram-positive and Gram-negative bacteria and their cell wall components," J. Immunol. 166 (3):1938-1944, each of which is incorporated by reference herein in its entirety.

The nucleotide sequence of MAP2K6 (identified by accession nos. NM_002758, NM_031988) is disclosed in, e.g., Han, J. et al., 1996, "Characterization of the structure and function of a novel MAP kinase kinase (MKK6), J. Biol. Chem. 271 (6):2886-2891, Raingeaud, J. et al., 1996, "MKK3- and MKK6-regulated gene expression is mediated by the p38 mitogen-activated protein kinase signal transduction pathway," Mol. Cell. Biol. 16 (3), 1247-1255, Stein, B. et al., 1996, "Cloning and characterization of MEK6, a novel member of the mitogen-activated protein kinase kinase cascade," J. Biol. Chem. 271 (19): 11427-11433, and the amino acid sequence of MAP2K6 (identified by accession nos. NP_002749, NP_114365) is disclosed in, e.g., Han, J. et al., 1996, "Characterization of the structure and function of a novel MAP kinase kinase (MKK6), J. Biol. Chem. 271 (6):2886-2891, Raingeaud, J. et al., 1996, "MKK3- and MKK6-regulated gene expression is mediated by the p38 mitogen-activated protein kinase signal transduction pathway," Mol. Cell. Biol. 16 (3), 1247-1255, Stein, B. et al., 1996, "Cloning and characterization of MEK6, a novel member of the mitogen-activated protein kinase kinase cascade," J. Biol. Chem. 271 (19): 11427-11433, each of which is incorporated by reference herein in its entirety.

The nucleotide sequence of MAPK14 (identified by accession nos. NM_001315, NM_139012, NM_139013, NM_139014) is disclosed in, e.g., Zhukov-Verezhnikov, N. N. et al., 1976, "Study of the heterogenetic antigens in vaccinal preparations of *V. cholerae*," Biochem. Biophys. Res. Commun. 82 (8):961-962, Schultz, S. J. et al., 1993, Identification of 21 novel human protein kinases, including 3 members of a family related to the cell cycle regulator nimA of *Aspergillus nidulans*," Cell Growth Differ. 4 (10): 821-830, Lee, J. C. et al., 1994, "A protein kinase involved in the regulation of inflammatory cytokine biosynthesis," Nature 372 (6508):739-746, and the amino acid sequence of MAPK14 (identified by accession nos. NP_001306, NP_620581, NP_620582, NP_620583) is disclosed in, e.g., Zhukov-Verezhnikov, N. N. et al., 1976, "Study of the heterogenetic antigens in vaccinal preparations of *V. cholerae*," Biochem. Biophys. Res. Commun. 82 (8):961-962, Schultz, S. J. et al., 1993, Identification of 21 novel human protein kinases, including 3 members of a family related to the cell cycle regulator nimA of *Aspergillus nidulans*," Cell Growth Differ. 4 (10):821-830, Lee, J. C. et al., 1994, "A protein kinase involved in the regulation of inflammatory cytokine biosynthesis," Nature 372 (6508):739-746, each of which is incorporated by reference herein in its entirety.

The nucleotide sequence of Monocyte Chemoattractant Protein 1 (MCP1) (identified by accession nos. AF493698 and AF493697) is disclosed in, e.g., Shanmugasundaram et al., 2002, Virology II, National Institute of Immunology, Aruna Asag Ali Marg, J.N.U. Campus, New Delhi 110 067, India, and the amino acid sequence of MCP1 (identified by accession no. AAQ75526) is disclosed in, e.g., Nyquist et al., 2003, direct submission, Medicine, Inova Fairfax, 3300

Gallows Road, Falls Church, Va. 22402-3300, each of which is incorporated by reference herein in its entirety.

The nucleotide sequence of MKNK1 (identified by accession nos. NM_003684, NM_198973) is disclosed in, e.g., Fukunaga et al., 1997, "MNK1, a new MAP kinase-activated protein kinase, isolated by a novel expression screening method for identifying protein kinase substrates, EMBO J. 16: 1921-1933; Pyronnet et al., 1999, "Human eukaryotic translation initiation factor 4G (eIF4G) recruits mnk1 to phosphorylate eIF4E," EMBO J. 18: 270-279; Cuesta et al., 2000, "Chaperone hsp27 inhibits translation during heat shock by binding eIF4G and facilitating dissociation of cap-initiation complexes," Genes Dev. 14: 1460-1470, and the amino acid sequence of MKNK1 (identified by accession nos. NP_003675, NP_945324) is disclosed in, e.g., Fukunaga et al., 1997, "MNK1, a new MAP kinase-activated protein kinase, isolated by a novel expression screening method for identifying protein kinase substrates," EMBO J. 16:1921-1933, Pyronnet et al., 1999, "Human eukaryotic translation initiation factor 4G (eIF4G) recruits mnk1 to phosphorylate eIF4E," EMBO J. 18: 270-279, Cuesta et al., 2000, "Chaperone hsp27 inhibits translation during heat shock by binding eIF4G and facilitating dissociation of cap-initiation complexes," Genes Dev. 14: 1460-1470, each of which is incorporated by reference herein in its entirety.

The nucleotide sequence of MMP9 (identified by accession no. NM_004994) is disclosed in, e.g., Wilhelm et al., 1989, "SV40-transformed human lung fibroblasts secrete a 92-kDa type IV collagenase which is identical to that secreted by normal human macrophages," J. Biol. Chem. 264: 17213-17221, Huhtala et al., 1990, "Completion of the primary structure of the human type IV collagenase preproenzyme and assignment of the gene (CLG4) to the q21 region of chromosome 16," Genomics 6: 554-559, Collier et al., 1991, "On the structure and chromosome location of the 72- and 92-kDa human type IV collagenase genes," Genomics 9: 429-434, and the amino acid sequence of MMP9 (identified by accession no. NP_004985) is disclosed in, e.g., Wilhelm et al., 1989, "SV40-transformed human lung fibroblasts secrete a 92-kDa type IV collagenase which is identical to that secreted by normal human macrophages," J. Biol. Chem. 264: 17213-17221, Huhtala et al., 1990, "Completion of the primary structure of the human type IV collagenase preproenzyme and assignment of the gene (CLG4) to the q21 region of chromosome 16," Genomics 6: 554-559, Collier et al., 1991, "On the structure and chromosome location of the 72- and 92-kDa human type IV collagenase genes," Genomics 9: 429-434, each of which is incorporated by reference herein in its entirety.

The nucleotide sequence of NCR1 (identified by accession no. NM_004829) is disclosed in, e.g., Sivori et al., 1997, "p46, a novel natural killer cell-specific surface molecule that mediates cell activation," J. Exp. Med. 186:1129-1136, Vitale, M. et al., NKp44, 1998, "NKp44, a novel triggering surface molecule specifically expressed by activated natural killer cells, is involved in non-major histocompatibility complex-restricted tumor cell lysis," J. Exp. Med. 187: 2065-2072, Pessino et al., 1998, "Molecular cloning of NKp46: a novel member of the immunoglobulin superfamily involved in triggering of natural cytotoxicity," J. Exp. Med. 188: 953-960, and the amino acid sequence of NCR1 (identified by accession no. NP_004820) is disclosed in, e.g., Sivori et al., 1997, "p46, a novel natural killer cell-specific surface molecule that mediates cell activation," J. Exp. Med. 186:1129-1136, Vitale et al., NKp44, 1998, "NKp44, a novel triggering surface molecule specifically expressed by activated natural killer cells, is involved in non-major histocompatibility complex-restricted tumor cell lysis," J. Exp. Med. 187: 2065-2072, Pessino et al., 1998, "Molecular cloning of NKp46: a novel member of the immunoglobulin superfamily involved in triggering of natural cytotoxicity," J. Exp. Med. 188: 953-96, each of which is incorporated by reference herein in its entirety.

The nucleotide sequence of OSM (identified by accession no. NM_020530) is disclosed in, e.g., Zarling et al., 1986, "Oncostatin M: a growth regulator produced by differentiated histiocytic lymphoma cells," Proc. Natl. Acad. Sci. U.S.A. 83 (24):9739-9743, Malik et al., 1989, "Molecular cloning, sequence analysis, and functional expression of a novel growth regulator, oncostatin M," Mol. Cell. Biol. 9 (7):2847-2853, Linsley, P. S. et al., 1990, "Cleavage of a hydrophilic C-terminal domain increases growth-inhibitory activity of oncostatin M," Mol. Cell. Biol. 10 (5):1882-1890, and the amino acid sequence of OSM (identified by accession no. NP_065391) is disclosed in, e.g., Zarling, J. M. et al., 1986, "Oncostatin M: a growth regulator produced by differentiated histiocytic lymphoma cells," Proc. Natl. Acad. Sci. U.S.A. 83 (24):9739-9743, Malik, N. et al., 1989, "Molecular cloning, sequence analysis, and functional expression of a novel growth regulator, oncostatin M," Mol. Cell. Biol. 9 (7):2847-2853, Linsley, P. S. et al., 1990, "Cleavage of a hydrophilic C-terminal domain increases growth-inhibitory activity of oncostatin M," Mol. Cell. Biol. 10 (5):1882-1890, each of which is incorporated by reference herein in its entirety.

The nucleotide sequence of PFKFB3 (identified by accession no. NM_004566) is disclosed in, e.g., Sakai, A. et al., 1996, "Cloning of cDNA encoding for a novel isozyme of fructose 6-phosphate, 2-kinase/fructose 2,6-bisphosphatase from human placenta," J. Biochem. 119 (3):506-511, Hamilton, J. A. et al., 1997, "Identification of PRG1, a novel progestin-responsive gene with sequence homology to 6-phosphofructo-2-kinase/fructose-2,6-bisphosphatase," Mol. Endocrinol. 11 (4):490-502, Nicholl, J. et al., "The third human isoform of 6-phosphofructo-2-kinase/fructose-2,6-bisphosphatase (PFKFB3) map position 10p14-p15, Chromosome Res. 5 (2):150, and the amino acid sequence of PFKFB3 (identified by accession no. NP_004557) is disclosed in, e.g., Sakai, A. et al., 1996, "Cloning of cDNA encoding for a novel isozyme of fructose 6-phosphate, 2-kinase/fructose 2,6-bisphosphatase from human placenta," J. Biochem. 119 (3):506-511, Hamilton, J. A. et al., 1997, "Identification of PRG1, a novel progestin-responsive gene with sequence homology to 6-phosphofructo-2-kinase/fructose-2,6-bisphosphatase," Mol. Endocrinol. 11 (4):490-502, Nicholl, J. et al., "The third human isoform of 6-phosphofructo-2-kinase/fructose-2,6-bisphosphatase (PFKFB3) map position 10p14-p15, Chromosome Res. 5 (2):150, each of which is incorporated by reference herein in its entirety.

The nucleotide sequence of PRV1 (identified by accession no. NM_020406) is disclosed in, e.g., Lalezari, P. et al., 1971, "NB1, a new neutrophil-specific antigen involved in the pathogenesis of neonatal neutropenia," J. Clin. Invest. 50 (5):1108-1115, Goldschmeding, R. et al., 1992, "Further characterization of the NB 1 antigen as a variably expressed 56-62 kD GPI-linked glycoprotein of plasma membranes and specific granules of neutrophils," Br. J. Haematol. 81 (3):336-345, Stroncek, D. F. et al., "Neutrophil-specific antigen NB1 inhibits neutrophil-endothelial cell interactions," J. Lab. Clin. Med. 123 (2):247-255, and the amino acid sequence of PRV1 (identified by accession no. NP_065139) is disclosed in, e.g., Lalezari, P. et al., 1971, "NB1, a new neutrophil-specific antigen involved in the pathogenesis of neonatal neutropenia," J. Clin. Invest. 50

(5):1108-1115, Goldschmeding, R. et al., 1992, "Further characterization of the NB 1 antigen as a variably expressed 56-62 kD GPI-linked glycoprotein of plasma membranes and specific granules of neutrophils," Br. J. Haematol. 81 (3):336-345, Stroncek, D. F. et al., "Neutrophil-specific antigen NB1 inhibits neutrophil-endothelial cell interactions," J. Lab. Clin. Med. 123 (2):247-255, each of which is incorporated by reference herein in its entirety.

The nucleotide sequence of PSTPIP2 (identified by accession no. NM_024430) is disclosed in, e.g., Hillier, L. D. et al., 1996, "Generation and analysis of 280,000 human expressed sequence tags," Genome Res. 6 (9):807-828, Wu, Y. et al., 1998, "PSTPIP 2, a second tyrosine phosphorylated, cytoskeletal-associated protein that binds a PEST-type protein-tyrosine phosphatase," J. Biol. Chem. 273 (46): 30487-30496, Yeung, Y. G. et al., 1998, "A novel macrophage actin-associated protein (MAYP) is tyrosine-phosphorylated following colony stimulating factor-1 stimulation," J. Biol. Chem. 273 (46): 30638-30642, and the amino acid sequence of PSTPIP2 (identified by accession no. NP_077748) is disclosed in, e.g., Hillier, L. D. et al., 1996, "Generation and analysis of 280,000 human expressed sequence tags," Genome Res. 6 (9):807-828, Wu, Y. et al., 1998, "PSTPIP 2, a second tyrosine phosphorylated, cytoskeletal-associated protein that binds a PEST-type protein-tyrosine phosphatase," J. Biol. Chem. 273 (46):30487-30496, Yeung, Y. G. et al., 1998, "A novel macrophage actin-associated protein (MAYP) is tyrosine-phosphorylated following colony stimulating factor-1 stimulation," J. Biol. Chem. 273 (46): 30638-30642, each of which is incorporated by reference herein in its entirety.

The nucleotide sequence of SOCS3 (identified by accession no. NM_003955) is disclosed in, e.g., Minamoto, S. et al., 1997, "Cloning and functional analysis of new members of STAT induced STAT inhibitor (SSI) family: SSI-2 and SSI-3," Biochem. Biophys. Res. Commun. 237 (1):79-83, Masuhara, M. et al., 1997, "Cloning and characterization of novel CIS family genes," Biochem. Biophys. Res. Commun. 239 (2):439-446, Zhang, J. G. et al., 1999, "The conserved SOCS box motif in suppressors of cytokine signaling binds to elongins B and C and may couple bound proteins to proteasomal degradation," Proc. Natl. Acad. Sci. U.S.A. 96 (5):2071-2076, and the amino acid sequence of SOCS3 (identified by accession no. NP_003946) is disclosed in, e.g., Minamoto, S. et al., 1997, "Cloning and functional analysis of new members of STAT induced STAT inhibitor (SSI) family: SSI-2 and SSI-3," Biochem. Biophys. Res. Commun. 237 (1):79-83, Masuhara, M. et al., 1997, "Cloning and characterization of novel CIS family genes," Biochem. Biophys. Res. Commun. 239 (2):439-446, Zhang, J. G. et al., 1999, "The conserved SOCS box motif in suppressors of cytokine signaling binds to elongins B and C and may couple bound proteins to proteasomal degradation," Proc. Natl. Acad. Sci. U.S.A. 96 (5):2071-2076, each of which is incorporated by reference herein in its entirety.

The nucleotide sequence of SOD2 (identified by accession no. NM_000636) is disclosed in, e.g., Smith, M. et al., 1978, "Regional localization of HLA, MES, and SODM on chromosome 6," Cytogenet. Cell Genet. 22 (1-6):428-433, Beck, Y. et al., 1987, "Human Mn superoxide dismutase cDNA sequence," Nucleic Acids Res. 15 (21):9076, Ho, Y. S. et al., 1988, "Isolation and characterization of complementary DNAs encoding human manganese-containing superoxide dismutase," FEBS Lett. 229 (2):256-260, and the amino acid sequence of SOD2 (identified by accession no. NP_000627) is disclosed in, e.g., Smith, M. et al., 1978, "Regional localization of HLA, MES, and SODM on chromosome 6," Cytogenet. Cell Genet. 22 (1-6):428-433, Beck, Y. et al., 1987, "Human Mn superoxide dismutase cDNA sequence," Nucleic Acids Res. 15 (21):9076, Ho, Y. S. et al., 1988, "Isolation and characterization of complementary DNAs encoding human manganese-containing superoxide dismutase," FEBS Lett. 229 (2):256-260, each of which is incorporated by reference herein in its entirety.

The nucleotide sequence of TDRD9 (identified by accession no. NM_153046) is disclosed in, e.g., Isogai et al., 2003, "Homo sapiens cDNA FLJ43990 fis, clone TESTI4019566, weakly similar to Dosage compensation regulator," unpublished, and the amino acid sequence of TDRD9 (identified by accession no. NP_694591) is disclosed in, e.g., Isogai et al., 2003, "Homo sapiens cDNA FLJ43990 fis, clone TESTI4019566, weakly similar to Dosage compensation regulator," unpublished, each of which is incorporated by reference herein in its entirety.

The nucleotide sequence of TGFBI (identified by accession no. NM_000358) is disclosed in, e.g., Skonier et al., 1992, "cDNA cloning and sequence analysis of beta ig-h3, a novel gene induced in a human adenocarcinoma cell line after treatment with transforming growth factor-beta," DNA Cell Biol. 11 (7):511-522, Stone et al., 1994, "Three autosomal dominant corneal dystrophies map to chromosome 5q," Nat. Genet. 6 (1):47-51, Skonier et al., 1994, "beta ig-h3: a transforming growth factor-beta-responsive gene encoding a secreted protein that inhibits cell attachment in vitro and suppresses the growth of CHO cells in nude mice," DNA Cell Biol. 13 (6):571-584, and the amino acid sequence of TGFBI (identified by accession no. NP_000349) is disclosed in, e.g., Skonier et al., 1992, "cDNA cloning and sequence analysis of beta ig-h3, a novel gene induced in a human adenocarcinoma cell line after treatment with transforming growth factor-beta," DNA Cell Biol. 11 (7):511-522; Stone et al., 1994, "Three autosomal dominant corneal dystrophies map to chromosome 5q," Nat. Genet. 6 (1):47-51; Skonier et al., 1994, "beta ig-h3: a transforming growth factor-beta-responsive gene encoding a secreted protein that inhibits cell attachment in vitro and suppresses the growth of CHO cells in nude mice," DNA Cell Biol. 13: 571-584, each of which is incorporated by reference herein in its entirety.

The nucleotide sequence of TIFA (identified by accession no. NM_052864) is disclosed in, e.g., Kanamori, M. et al., 2002, "T2BP, a novel TRAF2 binding protein, can activate NF-kappaB and AP-1 without TNF stimulation," Biochem. Biophys. Res. Commun. 290 (3):1108-1113, Takatsuna, H. et al., 2003, "Identification of TIFA as an adapter protein that links tumor necrosis factor receptor-associated factor 6 (TRAF6) to interleukin-1 (IL-1) receptor-associated kinase-1 (IRAK-1) in IL-1 receptor signaling," J. Biol. Chem. 278 (14):12144-12150, Matsuda et al., 2003, "Large-scale identification and characterization of human genes that activate NF-kappaB and MAPK signaling pathways," Oncogene 22 (21):3307-3318, and the amino acid sequence of TIFA (identified by accession no. NP_443096) is disclosed in, e.g., Kanamori et al., 2002, "T2BP, a novel TRAF2 binding protein, can activate NF-kappaB and AP-1 without TNF stimulation," Biochem. Biophys. Res. Commun. 290: 1108-1113, Takatsuna et al., 2003, "Identification of TIFA as an adapter protein that links tumor necrosis factor receptor-associated factor 6 (TRAF6) to interleukin-1 (IL-1) receptor-associated kinase-1 (IRAK-1) in IL-1 receptor signaling," J. Biol. Chem. 278 (14):12144-12150, Matsuda et al., 2003, "Large-scale identification and characterization of human genes that activate NF-kappaB and MAPK signaling pathways," Oncogene 22 (21):3307-3318, each of which is incorporated by reference herein in its entirety.

The nucleotide sequence of Tissue Inhibitor of Metalloproteinase 1 (TIMP1) (identified by accession no. NM_003254) is disclosed in, e.g., Domeij et al., 2005, "ell expression of MMP-1 and TIMP-1 in co-cultures of human gingival fibroblasts and monocytes: the involvement of ICAM-1," Biochem. Biophys. Res. Commun. 338, 1825-1833; Zureik et al., "Serum tissue inhibitors of metalloproteinases 1 (TIMP-1) and carotid atherosclerosis and aortic arterial stiffness", J. Hypertens. 23, 2263-2268; Crombez, 2005, "High level production of secreted proteins: example of the human tissue inhibitor of metalloproteinases 1", Biochem. Biophys. Res. Commun. 337, 908-915 and the amino acid sequence of TIMP1 (identified by accession no. AAA75558) is disclosed in, e.g., Hardcastle et al., 1997, "Genomic organization of the human TIMP-1 gene. Investigation of a causative role in the pathogenesis of X-linked retinitis pigmentosa," Invest. Ophthalmol. Vis. Sci. 38, 1893-1896, which is incorporated by reference herein in its entirety.

The nucleotide sequence of TLR4 (identified by accession no. AH009665) is disclosed in, e.g., Arbour, N.C. et al., 1999, Direct Submission, Medicine, University of Iowa, 2182 Med Labs, Iowa City, Iowa 52242, USA, Arbour, N.C. et al., A Genetic Basis for a Blunted Response to Endotoxin in Humans, Arbour, N.C. et al., unpublished, "A Genetic Basis for a Blunted Response to Endotoxin in Humans", and the amino acid sequence of TLR4 (identified by accession no. AAF05316) is disclosed in, e.g., Beutler, 1999, Direct Submission, Department of Internal Medicine, University of Texas Southwestern Medical Center and the Howard Hughes Medical Institute, 5323 Harry Hines Boulevard, Dallas, Tex. 75235-9050, USA, Smirnova, I. et al., 2000, "Phylogenetic variation and polymorphism at the toll-like receptor 4 locus (TLR4)," Genome Biol. 1, res. 002.1-002.10, each of which is incorporated by reference herein in its entirety.

The nucleotide sequence of TNFRSF6 (identified by accession no. NM_152877) is disclosed in, e.g., Oehm, A. et al., 1992, "Purification and molecular cloning of the APO-1 cell surface antigen, a member of the tumor necrosis factor/nerve growth factor receptor superfamily. Sequence identity with the Fas antigen," J. Biol. Chem. 267 (15):10709-10715, Inazawa, J. et al., 1992, "Assignment of the human Fas antigen gene (Fas) to 10q24.1," Genomics 14 (3):821-822, Cheng, J. et al., 1994, "Protection from Fas-mediated apoptosis by a soluble form of the Fas molecule," Science 263 (5154):1759-1762, and the amino acid sequence of TNFRSF6 (identified by accession no. NP_000034) is disclosed in, e.g., Oehm, A. et al., 1992, "Purification and molecular cloning of the APO-1 cell surface antigen, a member of the tumor necrosis factor/nerve growth factor receptor superfamily. Sequence identity with the Fas antigen," J. Biol. Chem. 267 (15):10709-10715, Inazawa, J. et al., 1992, "Assignment of the human Fas antigen gene (Fas) to 10q24.1," Genomics 14 (3):821-822, Cheng, J. et al., 1994, "Protection from Fas-mediated apoptosis by a soluble form of the Fas molecule," Science 263 (5154):1759-1762, each of which is incorporated by reference herein in its entirety.

The nucleotide sequence of TNFSF10 (identified by accession no. NM_003810) is disclosed in, e.g., Wiley, S. R. et al., 1995, "Identification and characterization of a new member of the TNF family that induces apoptosis," Immunity 3 (6):673-682, Pitti, R. M. et al., 1996, "Induction of apoptosis by Apo-2 ligand, a new member of the tumor necrosis factor cytokine family," J. Biol. Chem. 271 (22): 12687-12690, Pan, G. et al., 1997, "The receptor for the cytotoxic ligand TRAIL," Science 276 (5309):111-113, and the amino acid sequence of TNFSF10 (identified by accession no. NP_003801) is disclosed in, e.g., Wiley, S. R. et al., 1995, "Identification and characterization of a new member of the TNF family that induces apoptosis," Immunity 3 (6):673-682, Pitti, R. M. et al., 1996, "Induction of apoptosis by Apo-2 ligand, a new member of the tumor necrosis factor cytokine family," J. Biol. Chem. 271 (22):12687-12690, Pan, G. et al., 1997, "The receptor for the cytotoxic ligand TRAIL," Science 276 (5309):111-113, each of which is incorporated by reference herein in its entirety.

The nucleotide sequence of TNFSF13B (identified by accession no. NM_006573) is disclosed in, e.g., Shu, H. B. et al., 1999, "TALL-1 is a novel member of the TNF family that is down-regulated by mitogens," J. Leukoc. Biol. 65 (5): 680-683, Mukhopadhyay, A. et al., 1999, "Identification and characterization of a novel cytokine, THANK, a TNF homologue that activates apoptosis, nuclear factor-kappaB, and c-Jun NH2-terminal kinase," J. Biol. Chem. 274 (23):15978-15981, Schneider, P. et al., 1999, "BAFF, a novel ligand of the tumor necrosis factor family, stimulates B cell growth," J. Exp. Med. 189 (11):1747-1756, and the amino acid sequence of TNFSF13B (identified by accession no. NP_006564) is disclosed in, e.g., Shu, H. B. et al., 1999, "TALL-1 is a novel member of the TNF family that is down-regulated by mitogens," J. Leukoc. Biol. 65 (5): 680-683, Mukhopadhyay, A. et al., 1999, "Identification and characterization of a novel cytokine, THANK, a TNF homologue that activates apoptosis, nuclear factor-kappaB, and c-Jun NH2-terminal kinase," J. Biol. Chem. 274 (23):15978-15981, Schneider, P. et al., 1999, "BAFF, a novel ligand of the tumor necrosis factor family, stimulates B cell growth," J. Exp. Med. 189 (11):1747-1756, each of which is incorporated by reference herein in its entirety.

The nucleotide sequence of VNN1 (identified by accession no. NM_004666) is disclosed in, e.g., Aurrand-Lions, M. et al., 1996, "Vanin-1, a novel GPI-linked perivascular molecule involved in thymus homing," Immunity 5 (5):391-405, Galland, F. et al., 1998, "Two human genes related to murine vanin-1 are located on the long arm of human chromosome 6," Genomics 53 (2):203-213, Maras, B. et al., 1999, "Is pantetheinase the actual identity of mouse and human vanin-1 proteins?," FEBS Lett. 461 (3):149-152, and the amino acid sequence of VNN1 (identified by accession no. NP_004657) is disclosed in, e.g., Aurrand-Lions, M. et al., 1996, "Vanin-1, a novel GPI-linked perivascular molecule involved in thymus homing," Immunity 5 (5):391-405, Galland, F. et al., 1998, "Two human genes related to murine vanin-1 are located on the long arm of human chromosome 6," Genomics 53 (2):203-213, Maras, B. et al., 1999, "Is pantetheinase the actual identity of mouse and human vanin-1 proteins?," FEBS Lett. 461 (3):149-152, each of which is incorporated by reference herein in its entirety.

5.11.2 Exemplary Combinations of Biomarkers in Accordance with Embodiments of the Invention In some embodiments, the methods or kits respectively described or referenced in Section 5.2 and Section 5.3 use at least 2, 3, 4, 5, 6, 7, 8, 9, 10, 11, 12, 13, 14, 15, 16, 17, 18, 19, 20, 21, 22, 23, 24, 25, 30, 35, 40, 45, 50, or more biomarkers selected from Table I regardless of whether each such biomarker has an "N" designation or a "P" designation in Table I. In some nonlimiting exemplary embodiments, between 2 and 53, between 3 and 40, between 4 and 30, or between 5 and 20 such biomarkers are used.

Nucleic Acid Based Kits and Methods.

In some embodiments, the methods or kits respectively described or referenced in Section 5.2 and Section 5.3 use at least 2, 3, 4, 5, 6, 7, 8, 9, 10, 11, 12, 13, 14, 15, 16, 17, 18, 19, 20, 21, 22, 23, 24, 25, 30, 35, 40, or more biomarkers selected from Table J. Typically, in these embodiments, each biomarker is a nucleic acid (e.g., DNA, such as cDNA or amplified DNA, or RNA, such as mRNA), or a discriminating molecule or discriminating fragment of a nucleic acid. In some nonlimiting exemplary embodiments, between 2 and 44, between 3 and 35, between 4 and 25, or between 5 and 20 such biomarkers are used.

Protein or Peptide Based Kits and Methods.

In some embodiments, the methods or kits respectively described or referenced in Section 5.2 and Section 5.3 use at least 2, 3, 4, 5, 6, 7, 8, 9, or 10 of the biomarkers selected from Table K. Typically, such biomarkers are peptide-based (e.g., a peptide, a full length protein, etc.), or a discriminating molecule or discriminating fragment of the foregoing. In some embodiments, the biomarkers in the kit are specific antibodies to two or more of the biomarkers listed in Table K. In some non-limiting exemplary embodiments, between 2 and 10, between 3 and 10, between 4 and 10, or between 5 and 10 such biomarkers are used.

Homogenous Kits and Methods.

In some embodiments, each of the biomarkers in the methods or kits respectively described or referenced in Section 5.2 and Section 5.3 use at least two or more biomarkers selected from Table I where each biomarker used in such methods or kits is in the same physical form. In one example in accordance with such embodiments, each biomarker in a method or kit in accordance Section 5.2 and Section 5.3, respectively, is a biomarker selected from Table I and is a nucleic acid or a discriminating molecule of a nucleic acid in the method or kit. In another example in accordance with such embodiments, each biomarker in a method or kit in accordance Section 5.2 and Section 5.3, respectively, is a biomarker selected from Table I and is peptide-based (e.g., a peptide, a full length protein, etc.) or a discriminating molecule of the forgoing. In these embodiments, biomarkers are selected without regard as to whether they are designated "P" or "N" in Table I. Thus, a kit in accordance with these embodiments can include a biomarker in nucleic acid form, even when the biomarker is designated "P" on Table I. Correspondingly, a kit in accordance with this embodiment can include a biomarker in peptidic form, even when the biomarker is designated "N" on Table I.

Heterogeneous Kits and Methods.

In some embodiments, each of the biomarkers in the methods and kits respectively described or referenced in Section 5.2 and Section 5.3 use at least two or more biomarkers selected from Table I where each such biomarker is in the same physical form that the biomarker was in when identified in Sections 6.11 through 6.13 below. In other words, if the biomarker has an "N" designation in Table I, a nucleic acid form of the biomarker is used in the methods and kits respectively described or referenced in Section 5.2 and 5.3 in accordance with this embodiment of the invention. If the biomarker has a "P" designation in Table I, a peptidic form of the biomarker is used in the methods and kits respectively described or referenced in Section 5.2 and 5.3 in accordance with this embodiment of the invention. Further, there is at least one biomarker used in such methods or kits that has an "N" designation in Table I and at least one biomarker that has a "P" designation. In such embodiments, biomarkers having an N designation in Table I are nucleic acids and biomarkers having a P designation in Table I are peptide-based or protein-based.

A non-limiting exemplary kit in accordance with such mixed embodiments use two biomarkers from among the biomarkers listed in Table J, in nucleic acid form, and three biomarkers from among the biomarkers listed in Table K, in peptidic-based form. In some embodiments, the non-limiting methods and kits respectively described or referenced in Sections 5.2 and 5.3 use at least 2, 3, 4, 5, 6, 7, 8, 9, 10, 11, 12, 13, 14, 15, 16, 17, 18, 19, 20, 21, 22, 23, 24, 25, 30, 35, 40, or more biomarkers from Table J, in nucleic acid form, and 1, 2, 3, 4, 5, 6, 7, 8, 9, or 10 biomarkers from Table K in peptide-based or protein-based form.

Additional Kits and Methods.

In some embodiments, each of the biomarkers in the methods and kits respectively described or referenced in Section 5.2 and Section 5.3 use at least one biomarkers selected from Table I and at least one different biomarker from Table 31. In some embodiments, each of the biomarkers in the methods and kits respectively described or referenced in Section 5.2 and Section 5.3 use at least 2, 3, 4, 5, 6, 7, 8, 9, or 10 biomarkers selected from Table I and at least 2, 3, 4, 5, 6, 7, 8, 9, or 10 different biomarkers from Table 31.

In some embodiments, each of the biomarkers in the methods and kits respectively described or referenced in Section 5.2 and Section 5.3 use at least one biomarker in, nucleic acid form, selected from Table J and at least one different biomarker from Table 31. In some embodiments, each of the biomarkers in the methods and kits respectively described or referenced in Section 5.2 and Section 5.3 use at least 2, 3, 4, 5, 6, 7, 8, 9, or 10 biomarkers selected from Table I, each in nucleic acid form, and at least 2, 3, 4, 5, 6, 7, 8, 9, or 10 different biomarkers from Table 31.

In some embodiments, each of the biomarkers in the methods and kits respectively described or referenced in Section 5.2 and Section 5.3 use at least one biomarker in, protein form, selected from Table K and at least one different biomarker from Table 31. In some embodiments, each of the biomarkers in the methods and kits respectively described or referenced in Section 5.2 and Section 5.3 use at least 2, 3, 4, 5, 6, 7, 8, 9, or 10 biomarkers selected from Table I, each in protein form, and at least 2, 3, 4, 5, 6, 7, 8, 9, or 10 different biomarkers from Table 31.

In some embodiments, each of the biomarkers in the methods and kits respectively described or referenced in Section 5.2 and Section 5.3 use at least one biomarker from among the biomarkers listed in Table J, in nucleic acid form, and at least one biomarkers from among the biomarkers listed in Table K, in protein form. In some embodiments, the non-limiting methods and kits respectively described or referenced in Sections 5.2 and 5.3 use at least 2, 3, 4, 5, 6, 7, 8, 9, 10, 11, 12, 13, 14, 15, 16, 17, 18, 19, 20, 21, 22, 23, 24, 25, 30, 35, 40, or more biomarkers from Table J, in nucleic acid form, and 1, 2, 3, 4, 5, 6, 7, 8, 9, or 10 biomarkers from Table K in protein form.

In some embodiments, any of the above-described combinations of biomarkers are used in methods or kits in accordance Section 5.2 and Section 5.3 with the exception that the IL-6, IL-8, MMP9, B2M, HLA-DRA, and MCP1 biomarkers are not used in such methods or kits. For example, in embodiments where certain monocytes are isolated from whole blood and tested, such biomarkers are not utilized, especially when such biomarkers are nucleic acids. In some embodiments, any of the above-described combinations of biomarkers are used in methods or kits in accordance Section 5.2 and Section 5.3 with the exception that the IL-6, IL-8, IL-10, and CRP protein biomarkers are not used in such methods or kits. In some embodiments, any of the above-described combinations of biomarkers are used in methods or kits in accordance Section 5.2 and Section 5.3 with the exception that the IL-6, IL-8, IL-10, and CRP nucleic acid biomarkers are not used in such methods or kits. In some embodiments, any of the above-described combinations of biomarkers are used in methods or kits in accordance Section 5.2 and Section 5.3 with the exception that the IL-6 and MAPK biomarkers are not used in such methods or kits. In some embodiments, any of the above-described combinations of biomarkers are used in methods or kits in accordance Section 5.2 and Section 5.3 with the exception that the IL-6, IL-8, and IL-10 biomarkers are not used in such methods or kits. In some embodiments, any of the above-described combinations of biomarkers are used in methods or kits in accordance Section 5.2 and Section 5.3 with the exception that the CD86, IL-6, IL-8, IL-10, and CRP biomarkers are not used in such methods or kits. In some embodiments, any of the above-described combinations of biomarkers are used in methods or kits in accordance Section 5.2 and Section 5.3 with the exception that the IL-6 and IL-10 biomarkers are not used in such methods or kits. In some embodiments, any of the above-described combinations of biomarkers are used in methods or kits in accordance Section 5.2 and Section 5.3 with the exception that the IL-6 and CRP biomarkers are not used in such methods or kits. In some embodiments, any of the above-described combinations of biomarkers are used in methods or kits in accordance Section 5.2 and Section 5.3 with the exception that the CRP biomarker is not used in such methods or kits. In some embodiments, any of the above-described combinations of biomarkers are used in methods or kits in accordance Section 5.2 and Section 5.3 with the exception that the IL-8 biomarker is not used in such methods or kits. In some embodiments, any of the above-described combinations of biomarkers are used in methods or kits in accordance Section 5.2 and Section 5.3 with the exception that the B2M biomarker is not used in such methods or kits.

5.11.3 Exemplary Subcombinations of Biomarkers in Accordance with Embodiments of the Invention In some embodiments, the methods or kits respectively described or referenced in Section 5.2 and Section 5.3 use any one biomarker set listed in Table L. The biomarker sets listed in Table L were identified in the computational experiments described in Section 6.14.1, below, in which 4600 random subcombinations of the biomarkers listed in Table J were tested. Table L, below, lists some of the biomarker sets that provided high accuracy scores against the validation population described in Section 6.14.1. Each row of Table L lists a single biomarker set that can be used in the methods and kits respectively referenced in Sections 5.2 and 5.3. In other words, each row of Table L describes a biomarker set that can be used to discriminate between sepsis and SIRS subjects (e.g., to determine whether a subject is likely to acquire sepsis). In some embodiments, nucleic acid forms of the biomarkers listed in a biomarker set in Table L are used in the methods and kits respectively referenced in Sections 5.2 and 5.3. In some embodiments, protein forms of the biomarkers listed in a biomarker set in Table L are used in the methods and kits respectively referenced in Sections 5.2 and 5.3. In some hybrid embodiments, some of the biomarkers in a biomarker set listed in Table L are in protein form and some of the biomarkers in the same biomarker set from Table L are in nucleic acid form in the methods and kits respectively referenced in Sections 5.2 and 5.3.

In some embodiments, a given biomarker set listed in Table L is used with the addition of one, two, three, four, five, six, seven, eight, or nine or more additional biomarkers listed in Table I that are not within the given set of biomarkers from Table L. In some embodiments, a given biomarker set listed in Table L is used with the addition of one, two, three, four, five, six, seven, eight, or nine or more additional biomarkers from any one of Tables I, 30, 31, 32, 33, 34, or 36 that are not within the given biomarker set from Table L. In Table L, accuracy, specificity, and sensitivity are described with reference to $T_{-12}$ time point data described in Section 6.14.1, below.

TABLE L

Exemplary sets of biomarkers used in the methods or kits referenced in Sections 5.2 and 5.3

| BIOMARKER SET | ACCURACY | SPECIFICITY | SENSITIVITY |
| --- | --- | --- | --- |
| INSL3, BCL2A1, CD86 | 0.82 | 0.82 | 0.83 |
| MAP2K6, INSL3, CD86 | 0.82 | 0.75 | 0.87 |
| ARG2, MAP2K6, SOCS3 | 0.82 | 0.75 | 0.87 |
| NCR1, GADD45A, OSM | 0.81 | 0.77 | 0.85 |
| GADD45B, TNFSF13B, PFKFB3 | 0.80 | 0.74 | 0.87 |
| TLR4, FCGR1A, CSF1R | 0.80 | 0.82 | 0.78 |
| SOCS3, FCGR1A, PSTPIP2 | 0.80 | 0.79 | 0.81 |
| TGFBI, MAP2K6, PSTPIP2 | 0.80 | 0.76 | 0.83 |
| IFNGR1, JAK2, TNFRSF6, OSM | 0.83 | 0.80 | 0.87 |
| IRAK2, GADD45A, CD86, JAK2 | 0.83 | 0.86 | 0.81 |
| GADD45A, PRV1, OSM, FCGR1A | 0.83 | 0.80 | 0.86 |
| IRAK4, CCL5, INSL3, CD86 | 0.83 | 0.76 | 0.90 |
| VNN1, BCL2A1, GADD45B, FAD104 | 0.82 | 0.83 | 0.81 |
| OSM, CD86, PRV1, BCL2A1 | 0.82 | 0.78 | 0.85 |
| VNN1, SOCS3, CSF1R, FCGR1A | 0.82 | 0.78 | 0.85 |
| VNN1, CCL5, ANKRD22, OSM | 0.82 | 0.77 | 0.86 |
| LDLR, SOCS3, CD86, IL10alpha | 0.81 | 0.78 | 0.85 |
| TLR4, SOCS3, IRAK2, CSF1R | 0.81 | 0.76 | 0.85 |
| IL1RN, SOCS3, ARG2, LDLR | 0.81 | 0.76 | 0.84 |
| IL18R1, MAP2K6, TGFBI, OSM | 0.80 | 0.86 | 0.75 |
| FCGR1A, HLA-DRA, IL18R1, PSTPIP2 | 0.80 | 0.79 | 0.82 |
| OSM, IL1RN, SOD2, SOCS3 | 0.80 | 0.78 | 0.82 |
| NCR1, JAK2, TNFSF13B, FCGR1A | 0.80 | 0.76 | 0.86 |
| TIFA, VNN1, ANXA3, ITGAM | 0.80 | 0.73 | 0.88 |

TABLE L-continued

Exemplary sets of biomarkers used in the methods or kits referenced in Sections 5.2 and 5.3

| BIOMARKER SET | ACCURACY | SPECIFICITY | SENSITIVITY |
|---|---|---|---|
| PFKFB3, IRAK2, CSF1R, CD86, PSTPIP2 | 0.88 | 0.83 | 0.91 |
| PSTPIP2, FAD104, TIFA, CD86, LY96 | 0.84 | 0.85 | 0.84 |
| IL1RN, IL10alpha, IFNGR1, OSM, MKNK1 | 0.83 | 0.78 | 0.89 |
| IL18R1, CCL5, JAK2, SOCS3, SOD2 | 0.83 | 0.81 | 0.84 |
| JAK2, MKNK1, TNFSF13B, PRV1, TNFSF10 | 0.83 | 0.81 | 0.84 |
| MAP2K6, ARG2, OSM, ANKRD22, Gene_MMP9 | 0.83 | 0.8 | 0.85 |
| SOCS3, IL1RN, ARG2, FCGR1A, CCL5 | 0.83 | 0.78 | 0.87 |
| CCL5, INSL3, SOD2, TLR4, ARG2 | 0.83 | 0.78 | 0.87 |
| FCGR1A, ARG2, CD86, MAPK14, TNFRSF6 | 0.82 | 0.83 | 0.82 |
| INSL3, TLR4, SOCS3, CSF1R, FCGR1A | 0.82 | 0.79 | 0.85 |
| CEACAM1, TNFRSF6, MAPK14, IL10alpha, CSF1R | 0.82 | 0.79 | 0.84 |
| ANKRD22, CD86, CRTAP, OSM, PFKFB3 | 0.82 | 0.79 | 0.84 |
| OSM, IL18R1, LDLR, GADD45B, MKNK1 | 0.82 | 0.76 | 0.86 |
| CRTAP, SOCS3, PSTPIP2, TIFA, FAD104 | 0.81 | 0.82 | 0.81 |
| PSTPIP2, ARG2, IL10alpha, TLR4, CSF1R | 0.81 | 0.81 | 0.82 |
| TIFA, PFKFB3, CSF1R, LDLR, Gene_MMP9 | 0.81 | 0.79 | 0.83 |
| NCR1, PSTPIP2, GADD45A, LY96, MAPK14 | 0.81 | 0.77 | 0.86 |
| ARG2, BCL2A1, NCR1, PSTPIP2, IL10alpha | 0.81 | 0.82 | 0.8 |
| PFKFB3, OSM, CSF1R, CD86, TIFA | 0.81 | 0.81 | 0.81 |
| IL10alpha, CD86, SOCS3, GADD45A, TGFBI | 0.81 | 0.78 | 0.84 |
| PSTPIP2, PFKFB3, INSL3, PRV1, IL1RN | 0.81 | 0.78 | 0.85 |
| ITGAM, PRV1, IL18R1, INSL3, JAK2 | 0.81 | 0.77 | 0.85 |
| PSTPIP2, OSM, IL18R1, TNFSF13B, ITGAM | 0.81 | 0.72 | 0.9 |
| CD86, TIFA, CSF1R, FCGR1A, CRTAP | 0.81 | 0.84 | 0.78 |
| LY96, TGFBI, SOCS3, ANKRD22, MAPK14 | 0.81 | 0.83 | 0.79 |
| IL1RN, SOD2, VNN1, OSM, TNFSF10 | 0.81 | 0.79 | 0.82 |
| CRTAP, NCR1, OSM, PRV1, ANXA3 | 0.81 | 0.76 | 0.85 |
| TDRD9, LY96, CEACAM1, OSM, NCR1 | 0.81 | 0.72 | 0.88 |
| TGFBI, INSL3, GADD45A, LDLR, PSTPIP2 | 0.8 | 0.75 | 0.85 |
| PFKFB3, IRAK2, CSF1R, CD86, PSTPIP2 | 0.88 | 0.83 | 0.91 |
| MAP2K6, ARG2, CD86, PRV1, FAD104, MAPK14 | 0.85 | 0.86 | 0.84 |
| ARG2, LY96, INSL3, MAP2K6, TNFSF10, NCR1 | 0.85 | 0.86 | 0.84 |
| SOCS3, GADD45B, CSF1R, ARG2, PSTPIP2, OSM | 0.85 | 0.83 | 0.86 |
| GADD45B, PFKFB3, PSTPIP2, FCGR1A, HLA-DRA, ARG2 | 0.85 | 0.81 | 0.88 |
| TIFA, IL18R1, MAPK14, CD86, ARG2, TNFSF13B | 0.84 | 0.8 | 0.88 |
| FCGR1A, ARG2, GADD45B, IL10alpha, NCR1, LDLR | 0.84 | 0.81 | 0.86 |
| TGFBI, INSL3, IRAK4, GADD45B, SOCS3, CSF1R | 0.84 | 0.8 | 0.87 |
| SOCS3, CSF1R, CEACAM1, ARG2, IL10alpha, IFNGR1 | 0.83 | 0.82 | 0.85 |
| TLR4, PFKFB3, ARG2, PRV1, LDLR, TNFSF13B | 0.83 | 0.81 | 0.85 |
| PSTPIP2, OSM, TLR4, INSL3, IRAK4, IL18R1 | 0.83 | 0.8 | 0.85 |
| GADD45A, CCL5, FCGR1A, PSTPIP2, MAP2K6, IL1RN | 0.82 | 0.83 | 0.82 |
| OSM, FAD104, JAK2, CRTAP, TDRD9, TNFSF13B | 0.82 | 0.79 | 0.85 |
| FAD104, SOCS3, TNFSF13B, GADD45B, CRTAP, TGFBI | 0.82 | 0.84 | 0.81 |
| IL18R1, TNFRSF6, INSL3, CD86, ANXA3, PSTPIP2 | 0.82 | 0.79 | 0.84 |
| HLA-DRA, INSL3, ARG2, CD86, CCL5, SOCS3 | 0.82 | 0.79 | 0.84 |
| TNFRSF6, IL18R1, CD86, PFKFB3, IL10alpha, FAD104 | 0.81 | 0.82 | 0.81 |
| FAD104, TGFBI, TDRD9, CD86, SOD2, ARG2 | 0.81 | 0.79 | 0.83 |
| CD86, ARG2, GADD45A, TLR4, BCL2A1, GADD45B | 0.81 | 0.79 | 0.83 |
| SOD2, CEACAM1, OSM, GADD45A, PSTPIP2, IL10alpha | 0.81 | 0.74 | 0.88 |
| FCGR1A, CSF1R, NCR1, ANXA3, SOCS3, Gene_MMP9 | 0.81 | 0.81 | 0.8 |
| TNFSF10, IL1RN, OSM, CSF1R, PSTPIP2, JAK2 | 0.81 | 0.78 | 0.83 |
| CD86, VNN1, LDLR, IL1RN, MAP2K6, TDRD9 | 0.81 | 0.76 | 0.84 |

TABLE L-continued

Exemplary sets of biomarkers used in the methods or kits referenced in Sections 5.2 and 5.3

| BIOMARKER SET | ACCURACY | SPECIFICITY | SENSITIVITY |
|---|---|---|---|
| ARG2, OSM, CSF1R, ITGAM, CRTAP, SOCS3 | 0.81 | 0.76 | 0.85 |
| ANXA3, CSF1R, CEACAM1, Gene_MMP9, CD86, OSM | 0.8 | 0.8 | 0.81 |
| LY96, VNN1, SOD2, TGFBI, ARG2, CSF1R | 0.8 | 0.78 | 0.83 |
| GADD45A, PSTPIP2, BCL2A1, ANKRD22, HLA-DRA, ANXA3 | 0.8 | 0.77 | 0.83 |
| TGFBI, FCGR1A, ARG2, CD86, PFKFB3, BCL2A1, TNFRSF6 | 0.86 | 0.86 | 0.85 |
| SOCS3, ITGAM, TDRD9, INSL3, PRV1, TGFBI, ARG2 | 0.84 | 0.81 | 0.87 |
| MKNK1, GADD45B, IRAK2, TIFA, OSM, VNN1, PSTPIP2 | 0.83 | 0.81 | 0.85 |
| SOCS3, PSTPIP2, TDRD9, IL10alpha, ARG2, CD86, CCL5 | 0.83 | 0.82 | 0.84 |
| CSF1R, PSTPIP2, MAPK14, INSL3, IL18R1, JAK2, OSM | 0.83 | 0.78 | 0.87 |
| MKNK1, PSTPIP2, ARG2, LY96, ANKRD22, SOCS3, IRAK4 | 0.82 | 0.85 | 0.8 |
| PSTPIP2, FAD104, TNFSF13B, ITGAM, BCL2A1, FCGR1A, ANXA3 | 0.82 | 0.83 | 0.82 |
| SOCS3, IRAK2, IFNGR1, CD86, OSM, PSTPIP2, GADD45A | 0.82 | 0.81 | 0.83 |
| INSL3, NCR1, PSTPIP2, PFKFB3, ANKRD22, HLA-DRA, MKNK1 | 0.82 | 0.8 | 0.84 |
| FCGR1A, HLA-DRA, CSF1R, SOCS3, IRAK4, TIFA, ARG2 | 0.82 | 0.76 | 0.88 |
| FAD104, TGFBI, MAP2K6, IRAK4, LY96, CD86, ANKRD22 | 0.82 | 0.81 | 0.83 |
| LDLR, INSL3, GADD45B, ARG2, PFKFB3, HLA-DRA, ITGAM | 0.82 | 0.78 | 0.86 |
| FCGR1A, TIFA, CD86, PFKFB3, TDRD9, GADD45A, LDLR | 0.82 | 0.79 | 0.85 |
| SOCS3, CSF1R, SOD2, CD86, MAP2K6, GADD45B, PSTPIP2 | 0.82 | 0.76 | 0.86 |
| MKNK1, CD86, FAD104, PRV1, SOCS3, IL10alpha, MAP2K6 | 0.82 | 0.76 | 0.87 |
| TIFA, JAK2, LDLR, IRAK2, VNN1, CD86, ARG2 | 0.81 | 0.81 | 0.81 |
| ANKRD22, MAPK14, INSL3, BCL2A1, CRTAP, IRAK2, FCGR1A | 0.81 | 0.79 | 0.83 |
| FAD104, INSL3, CD86, TNFRSF6, GADD45A, IFNGR1, JAK2 | 0.81 | 0.79 | 0.83 |
| CSF1R, INSL3, VNN1, TIFA, IFNGR1, LDLR, ARG2 | 0.81 | 0.79 | 0.83 |
| PFKFB3, BCL2A1, ANXA3, IL10alpha, FAD104, VNN1, INSL3 | 0.81 | 0.79 | 0.84 |
| CSF1R, CEACAM1, MAP2K6, GADD45B, TNFSF10, TNFSF13B, TIFA | 0.81 | 0.82 | 0.8 |
| FCGR1A, ARG2, IRAK2, GADD45A, CD86, Gene_MMP9, BCL2A1 | 0.81 | 0.82 | 0.79 |
| CRTAP, CEACAM1, FAD104, MKNK1, INSL3, ITGAM, SOD2 | 0.81 | 0.76 | 0.84 |
| OSM, TDRD9, BCL2A1, IRAK2, GADD45A, CD86, LDLR | 0.8 | 0.77 | 0.84 |
| PFKFB3, CCL5, CSF1R, LDLR, TLR4, LY96, FAD104 | 0.8 | 0.77 | 0.84 |
| IRAK4, GADD45B, CEACAM1, FAD104, CSF1R, IRAK2, MAPK14 | 0.8 | 0.75 | 0.85 |
| IFNGR1, FAD104, MAP2K6, TNFRSF6, FCGR1A, IRAK2, ARG2 | 0.8 | 0.74 | 0.86 |
| TGFBI, IRAK2, CRTAP, BCL2A1, ITGAM, ANXA3, FCGR1A | 0.8 | 0.81 | 0.79 |
| SOD2, PFKFB3, GADD45B, IRAK2, PRV1, SOCS3, FCGR1A | 0.8 | 0.77 | 0.82 |
| TNFRSF6, TLR4, IRAK2, ITGAM, JAK2, OSM, NCR1 | 0.8 | 0.77 | 0.83 |
| IL10alpha, ANKRD22, Gene_MMP9, IL1RN, LY96, FAD104, PSTPIP2 | 0.8 | 0.76 | 0.84 |
| IRAK4, INSL3, CSF1R, ITGAM, VNN1, HLA-DRA, IL18R1 | 0.8 | 0.74 | 0.86 |
| IRAK2, TGFBI, MAP2K6, IL18R1, IFNGR1, CRTAP, PSTPIP2 | 0.8 | 0.73 | 0.87 |
| TDRD9, ITGAM, OSM, NCR1, CD86, MAP2K6, CCL5 | 0.8 | 0.73 | 0.87 |

TABLE L-continued

Exemplary sets of biomarkers used in the methods or kits referenced in Sections 5.2 and 5.3

| BIOMARKER SET | ACCURACY | SPECIFICITY | SENSISTIVITY |
|---|---|---|---|
| ANXA3, FCGR1A, TNFSF10, VNN1, TNFSF13B, ARG2, 12, CD86 | 0.85 | 0.86 | 0.84 |
| INSL3, PFKFB3, MAPK14, FCGR1A, TDRD9, CSF1R, 12, IRAK4 | 0.85 | 0.84 | 0.85 |
| VNN1, CSF1R, ANKRD22, OSM, GADD45A, LY96, 12, MAP2K6 | 0.85 | 0.78 | 0.9 |
| ITGAM, OSM, LY96, TDRD9, ANKRD22, TLR4, 12, MKNK1 | 0.84 | 0.84 | 0.83 |
| ARG2, ANXA3, MAP2K6, CCL5, CD86, OSM, 12, LDLR | 0.84 | 0.84 | 0.83 |
| OSM, IL1RN, FCGR1A, GADD45A, ARG2, IL10alpha, 12, ITGAM | 0.84 | 0.82 | 0.86 |
| TIFA, ANKRD22, TNFSF13B, CRTAP, MAP2K6, IRAK4, 12, ARG2 | 0.84 | 0.81 | 0.86 |
| IRAK2, TLR4, IL10alpha, TGFBI, PRV1, FAD104, 12, MAP2K6 | 0.83 | 0.8 | 0.86 |
| IL18R1, FAD104, TNFSF13B, MAP2K6, OSM, SOD2, 12, TNFRSF6 | 0.83 | 0.81 | 0.85 |
| OSM, LDLR, VNN1, LY96, ARG2, MAPK14, 12, IRAK2 | 0.83 | 0.8 | 0.85 |
| PRV1, ITGAM, SOD2, Gene_MMP9, OSM, JAK2, 12, ARG2 | 0.83 | 0.79 | 0.86 |
| ANXA3, TNFSF10, CEACAM1, FCGR1A, HLA-DRA, IL10alpha, 12, SOCS3 | 0.83 | 0.78 | 0.86 |
| ITGAM, CD86, CEACAM1, TDRD9, GADD45A, PFKFB3, 12, SOCS3 | 0.83 | 0.77 | 0.88 |
| SOCS3, PRV1, ARG2, CEACAM1, LDLR, GADD45A, 12, IL10alpha | 0.82 | 0.83 | 0.82 |
| INSL3, CSF1R, IL1RN, PSTPIP2, MKNK1, SOCS3, 12, JAK2 | 0.82 | 0.8 | 0.84 |
| TDRD9, LY96, ITGAM, NCR1, PSTPIP2, IL10alpha, 12, OSM | 0.82 | 0.75 | 0.9 |
| PFKFB3, MAP2K6, ARG2, TGFBI, LDLR, FAD104, 12, MAPK14 | 0.82 | 0.84 | 0.8 |
| ARG2, IL18R1, NCR1, CD86, FCGR1A, TGFBI, 12, IL1RN | 0.82 | 0.79 | 0.84 |
| HLA-DRA, CEACAM1, IFNGR1, MKNK1, LDLR, GADD45B, 12, CSF1R | 0.82 | 0.76 | 0.87 |
| IL10alpha, IL1RN, OSM, PSTPIP2, INSL3, TIFA, 12, TLR4 | 0.82 | 0.81 | 0.82 |
| MKNK1, CSF1R, VNN1, OSM, ARG2, GADD45B, 12, SOCS3 | 0.81 | 0.81 | 0.82 |
| IL18R1, GADD45B, TNFRSF6, TNFSF10, TIFA, JAK2, 12, GADD45A | 0.81 | 0.79 | 0.84 |
| LDLR, IL10alpha, PRV1, LY96, ANXA3, TNFRSF6, 12, CCL5 | 0.81 | 0.76 | 0.86 |
| IL18R1, CD86, PFKFB3, ANKRD22, CSF1R, SOCS3, 12, TIFA | 0.81 | 0.8 | 0.82 |
| CCL5, TDRD9, PSTPIP2, ARG2, INSL3, OSM, 12, CSF1R | 0.81 | 0.77 | 0.85 |
| CEACAM1, IL10alpha, IL18R1, PSTPIP2, TGFBI, TIFA, 12, VNN1 | 0.81 | 0.77 | 0.85 |
| GADD45B, Gene_MMP9, TLR4, PFKFB3, VNN1, JAK2, 12, IL18R1 | 0.81 | 0.76 | 0.85 |
| FAD104, MAPK14, IFNGR1, IL18R1, TNFSF10, CD86, 12, HLA-DRA | 0.81 | 0.76 | 0.86 |
| PSTPIP2, SOCS3, OSM, CSF1R, PFKFB3, NCR1, 12, PRV1 | 0.81 | 0.75 | 0.86 |
| TGFBI, SOCS3, ITGAM, TNFSF13B, IL18R1, PSTPIP2, 12, ANKRD22 | 0.81 | 0.8 | 0.81 |
| CEACAM1, SOCS3, PFKFB3, TNFRSF6, PSTPIP2, OSM, 12, BCL2A1 | 0.81 | 0.79 | 0.82 |
| TNFRSF6, ITGAM, BCL2A1, INSL3, CD86, TIFA, 12, PFKFB3 | 0.81 | 0.77 | 0.84 |
| PFKFB3, PSTPIP2, MAP2K6, IRAK4, OSM, CCL5, 12, TNFSF10 | 0.81 | 0.76 | 0.85 |
| MKNK1, TIFA, IL1RN, ARG2, SOCS3, IL10alpha, 12, IFNGR1 | 0.81 | 0.76 | 0.85 |
| FAD104, TNFSF13B, OSM, BCL2A1, TDRD9, LY96, 12, SOD2 | 0.8 | 0.8 | 0.8 |
| CD86, SOCS3, PSTPIP2, CCL5, OSM, TLR4, 12, MAPK14 | 0.8 | 0.77 | 0.83 |
| TGFBI, LDLR, CRTAP, CSF1R, NCR1, LY96, 12, PSTPIP2 | 0.8 | 0.82 | 0.78 |
| JAK2, TIFA, TNFSF10, IL18R1, CCL5, INSL3, 12, VNN1 | 0.8 | 0.82 | 0.78 |

TABLE L-continued

Exemplary sets of biomarkers used in the methods or kits referenced in Sections 5.2 and 5.3

| BIOMARKER SET | ACCURACY | SPECIFICITY | SENSISTIVITY |
|---|---|---|---|
| TIFA, IL1RN, MAP2K6, HLA-DRA, OSM, FAD104, 12, INSL3 | 0.8 | 0.8 | 0.8 |
| JAK2, IRAK2, PRV1, TNFSF13B, OSM, HLA-DRA, 12, IFNGR1 | 0.8 | 0.8 | 0.8 |
| ANXA3, CSF1R, TLR4, SOCS3, IRAK4, PRV1, 12, INSL3 | 0.8 | 0.8 | 0.8 |
| TGFBI, IRAK4, PFKFB3, SOD2, ANXA3, ITGAM, 12, TDRD9 | 0.8 | 0.8 | 0.8 |
| TIFA, FCGR1A, TNFRSF6, LY96, IL10alpha, SOCS3, 12, OSM | 0.8 | 0.78 | 0.81 |
| PRV1, TLR4, CSF1R, IL18R1, PSTPIP2, TDRD9, 12, HLA-DRA | 0.8 | 0.78 | 0.82 |
| LY96, TNFSF13B, OSM, TGFBI, TIFA, FAD104, 12, NCR1 | 0.8 | 0.77 | 0.82 |
| ITGAM, ARG2, IL10alpha, SOD2, LY96, OSM, 12, FCGR1A | 0.8 | 0.76 | 0.83 |
| ANKRD22, HLA-DRA, PRV1, NCR1, CSF1R, PSTPIP2, 12, LY96 | 0.8 | 0.76 | 0.84 |
| Gene_MMP9, PSTPIP2, GADD45B, SOD2, ANKRD22, TNFSF13B, 12, ITGAM | 0.8 | 0.74 | 0.86 |
| ANXA3, FCGR1A, TNFSF10, VNN1, TNFSF13B, ARG2, 12, CD86 | 0.85 | 0.86 | 0.84 |
| CSF1R, PFKFB3, BCL2A1, SOCS3, NCR1, TNFSF10, FCGR1A, ARG2, CD86 | 0.86 | 0.87 | 0.85 |
| PSTPIP2, ITGAM, IRAK2, OSM, NCR1, CEACAM1, PFKFB3, TLR4, ANXA3 | 0.84 | 0.81 | 0.87 |
| INSL3, ARG2, LDLR, HLA-DRA, NCR1, TIFA, LY96, ITGAM, SOCS3 | 0.84 | 0.78 | 0.9 |
| CD86, CSF1R, SOD2, OSM, SOCS3, BCL2A1, GADD45B, ARG2, HLA-DRA | 0.83 | 0.79 | 0.87 |
| ARG2, CD86, MAP2K6, HLA-DRA, IL10alpha, IRAK2, GADD45B, MKNK1, IL18R1 | 0.83 | 0.82 | 0.84 |
| IFNGR1, BCL2A1, ARG2, TNFSF13B, GADD45A, FCGR1A, TNFRSF6, CD86, MAP2K6 | 0.83 | 0.8 | 0.86 |
| OSM, TNFSF10, CSF1R, CCL5, IRAK2, INSL3, ARG2, TNFSF13B, TNFRSF6 | 0.83 | 0.82 | 0.83 |
| LY96, TNFSF10, GADD45B, CRTAP, ARG2, ANXA3, CSF1R, CCL5, OSM | 0.82 | 0.87 | 0.77 |
| NCR1, LY96, FAD104, ANKRD22, BCL2A1, PSTPIP2, ARG2, PRV1, IL18R1 | 0.82 | 0.79 | 0.84 |
| SOD2, IRAK2, JAK2, CCL5, IL10alpha, ARG2, BCL2A1, SOCS3, CSF1R | 0.82 | 0.77 | 0.86 |
| TNFRSF6, TGFBI, FCGR1A, IRAK4, GADD45A, LDLR, IFNGR1, CSF1R, TIFA | 0.82 | 0.81 | 0.83 |
| GADD45B, ITGAM, PRV1, SOD2, TNFSF13B, HLA-DRA, FAD104, TNFRSF6, TLR4 | 0.81 | 0.79 | 0.83 |
| IRAK2, SOCS3, GADD45B, MAP2K6, PRV1, PFKFB3, CD86, IFNGR1, ANKRD22 | 0.81 | 0.83 | 0.8 |
| HLA-DRA, GADD45A, FCGR1A, ANKRD22, ARG2, NCR1, BCL2A1, IRAK2, SOCS3 | 0.81 | 0.81 | 0.81 |
| IRAK4, SOCS3, MKNK1, JAK2, OSM, ANXA3, VNN1, ITGAM, TNFRSF6 | 0.81 | 0.79 | 0.83 |
| SOD2, JAK2, FAD104, CD86, ARG2, CCL5, MAP2K6, IFNGR1, PFKFB3 | 0.81 | 0.79 | 0.83 |
| IL18R1, CSF1R, IRAK2, HLA-DRA, PFKFB3, CRTAP, CD86, TIFA, TNFSF10 | 0.81 | 0.78 | 0.83 |
| MAP2K6, FAD104, TGFBI, IRAK4, CRTAP, LDLR, IRAK2, FCGR1A, ARG2 | 0.81 | 0.77 | 0.84 |
| CEACAM1, SOD2, GADD45A, VNN1, IRAK4, OSM, TDRD9, GADD45B, PSTPIP2 | 0.81 | 0.73 | 0.88 |
| PSTPIP2, ANKRD22, TNFSF10, INSL3, HLA-DRA, NCR1, TNFSF13B, CSF1R, Gene_MMP9 | 0.81 | 0.84 | 0.78 |
| JAK2, MAP2K6, CSF1R, IRAK2, TNFSF10, LDLR, OSM, BCL2A1, ARG2 | 0.81 | 0.81 | 0.8 |
| Gene_MMP9, MAP2K6, IL18R1, VNN1, INSL3, ANKRD22, CCL5, PFKFB3, MAPK14 | 0.81 | 0.8 | 0.81 |
| IL18R1, ARG2, FCGR1A, CRTAP, GADD45B, FAD104, IRAK4, MAPK14, TDRD9 | 0.81 | 0.8 | 0.82 |

TABLE L-continued

Exemplary sets of biomarkers used in the methods or kits referenced in Sections 5.2 and 5.3

| BIOMARKER SET | ACCURACY | SPECIFICITY | SENSITIVITY |
|---|---|---|---|
| SOD2, PRV1, MKNK1, FCGR1A, CD86, GADD45A, IL18R1, TNFSF13B, HLA-DRA | 0.81 | 0.78 | 0.83 |
| ANXA3, TNFRSF6, MAP2K6, OSM, ANKRD22, IL18R1, MAPK14, GADD45A, GADD45B | 0.81 | 0.78 | 0.83 |
| OSM, IRAK2, ANXA3, TNFSF13B, IL18R1, ANKRD22, MAP2K6, IL10alpha, FAD104 | 0.81 | 0.78 | 0.83 |
| ITGAM, SOD2, CSF1R, TGFBI, IFNGR1, TDRD9, JAK2, ARG2, GADD45A | 0.81 | 0.73 | 0.87 |
| INSL3, ITGAM, OSM, TIFA, IRAK2, MKNK1, SOCS3, TNFSF10, ANKRD22 | 0.8 | 0.84 | 0.77 |
| GADD45A, PFKFB3, SOD2, IRAK2, MAPK14, INSL3, IRAK4, ITGAM, ARG2 | 0.8 | 0.79 | 0.82 |
| NCR1, INSL3, ARG2, IFNGR1, LDLR, OSM, PRV1, GADD45B, CD86 | 0.8 | 0.78 | 0.83 |
| IRAK2, FAD104, TLR4, CSF1R, PRV1, OSM, MKNK1, BCL2A1, CD86 | 0.8 | 0.77 | 0.83 |
| NCR1, SOCS3, HLA-DRA, PFKFB3, FAD104, IRAK4, VNN1, CCL5, MAP2K6 | 0.8 | 0.74 | 0.86 |
| CRTAP, TLR4, PFKFB3, CSF1R, TIFA, PSTPIP2, PRV1, IFNGR1, CCL5 | 0.8 | 0.82 | 0.78 |
| LY96, SOD2, IL18R1, TNFRSF6, TLR4, MAP2K6, FAD104, Gene_MMP9, NCR1 | 0.8 | 0.81 | 0.79 |
| ITGAM, SOD2, SOCS3, LDLR, MAP2K6, FAD104, NCR1, CSF1R, CD86 | 0.8 | 0.8 | 0.8 |
| CRTAP, ARG2, SOD2, TDRD9, TNFRSF6, TIFA, OSM, Gene_MMP9, HLA-DRA | 0.8 | 0.8 | 0.8 |
| OSM, LY96, CEACAM1, IRAK4, INSL3, PSTPIP2, PRV1, IRAK2, JAK2 | 0.8 | 0.78 | 0.82 |
| CD86, IL1RN, IFNGR1, ANXA3, CSF1R, ITGAM, NCR1, TDRD9, MAP2K6 | 0.8 | 0.78 | 0.82 |
| TNFSF13B, JAK2, IRAK4, TDRD9, HLA-DRA, SOCS3, PSTPIP2, FAD104, SOD2 | 0.8 | 0.78 | 0.82 |
| Gene_MMP9, SOD2, JAK2, CD86, HLA-DRA, IRAK2, CEACAM1, MAPK14, ANXA3 | 0.8 | 0.74 | 0.85 |
| GADD45B, ITGAM, TLR4, NCR1, CD86, TNFSF13B, HLA-DRA, FCGR1A, OSM | 0.8 | 0.71 | 0.88 |
| OSM, GADD45B, CSF1R, CCL5, ANXA3, CEACAM1, CD86, TNFSF10, ARG2, LY96, TDRD9 | 0.85 | 0.85 | 0.84 |
| NCR1, HLA-DRA, BCL2A1, ARG2, SOCS3, IL18R1, PSTPIP2, VNN1, CD86, GADD45A, CCL5 | 0.84 | 0.84 | 0.84 |
| PFKFB3, SOCS3, TNFRSF6, GADD45A, OSM, TDRD9, IL18R1, NCR1, CSF1R, ANXA3, PSTPIP2 | 0.84 | 0.8 | 0.87 |
| ARG2, IFNGR1, MAPK14, Gene_MMP9, IRAK4, CEACAM1, ITGAM, ANKRD22, GADD45B, VNN1, OSM | 0.84 | 0.8 | 0.88 |
| BCL2A1, LY96, GADD45B, IL10alpha, CRTAP, OSM, IFNGR1, IL1RN, TIFA, IRAK4, GADD45A | 0.84 | 0.82 | 0.86 |
| TGFBI, SOCS3, MAP2K6, ANXA3, TLR4, IL1RN, VNN1, HLA-DRA, TIFA, JAK2, TDRD9 | 0.83 | 0.77 | 0.89 |
| TNFSF13B, GADD45A, ANXA3, IL18R1, FCGR1A, JAK2, CD86, SOCS3, INSL3, CRTAP, NCR1 | 0.83 | 0.83 | 0.83 |
| LY96, INSL3, TNFSF10, MAP2K6, OSM, ITGAM, JAK2, CD86, FCGR1A, IL10alpha, CCL5 | 0.83 | 0.78 | 0.88 |
| ARG2, OSM, TLR4, NCR1, CCL5, BCL2A1, IL1RN, GADD45A, MAPK14, SOCS3, TDRD9 | 0.83 | 0.76 | 0.88 |
| INSL3, IL18R1, IFNGR1, ARG2, IL10alpha, LY96, CRTAP, LDLR, JAK2, CSF1R, VNN1 | 0.83 | 0.82 | 0.83 |
| ANXA3, IFNGR1, GADD45A, TNFRSF6, CCL5, JAK2, FAD104, IL1RN, ARG2, IL10alpha, INSL3 | 0.83 | 0.79 | 0.86 |
| CRTAP, TNFRSF6, LDLR, VNN1, HLA-DRA, SOCS3, TGFBI, TNFSF10, IFNGR1, ARG2, FCGR1A | 0.82 | 0.86 | 0.79 |
| GADD45A, VNN1, MKNK1, CCL5, IL10alpha, PSTPIP2, IRAK2, TNFRSF6, CEACAM1, FAD104, TGFBI | 0.82 | 0.83 | 0.82 |

TABLE L-continued

Exemplary sets of biomarkers used in the methods or kits referenced in Sections 5.2 and 5.3

| BIOMARKER SET | ACCURACY | SPECIFICITY | SENSITIVITY |
|---|---|---|---|
| HLA-DRA, BCL2A1, PSTPIP2, PFKFB3, JAK2, TNFSF10, ARG2, CEACAM1, IL18R1, MAPK14, CSF1R | 0.82 | 0.82 | 0.83 |
| GADD45B, TNFSF10, TNFSF13B, OSM, VNN1, PRV1, MKNK1, Gene_MMP9, ANXA3, TGFBI, HLA-DRA | 0.82 | 0.82 | 0.83 |
| GADD45A, IFNGR1, IRAK4, TGFBI, NCR1, FAD104, INSL3, IL10alpha, OSM, TIFA, CSF1R | 0.82 | 0.75 | 0.88 |
| Gene_MMP9, IRAK2, JAK2, TGFBI, BCL2A1, PSTPIP2, GADD45A, ARG2, OSM, CEACAM1, IFNGR1 | 0.82 | 0.83 | 0.81 |
| MAP2K6, FCGR1A, TNFSF13B, SOD2, NCR1, ANXA3, TLR4, CD86, ITGAM, IRAK2, INSL3 | 0.82 | 0.79 | 0.85 |
| FAD104, ARG2, NCR1, ANKRD22, OSM, CSF1R, BCL2A1, CRTAP, LY96, SOD2, TNFRSF6 | 0.82 | 0.78 | 0.85 |
| LY96, TDRD9, CD86, GADD45A, ARG2, VNN1, IL10alpha, SOD2, CRTAP, TIFA, FCGR1A | 0.82 | 0.82 | 0.81 |
| BCL2A1, VNN1, LDLR, TLR4, OSM, IRAK4, IRAK2, CRTAP, IFNGR1, TGFBI, CD86 | 0.82 | 0.82 | 0.81 |
| CCL5, IFNGR1, TIFA, SOCS3, INSL3, TLR4, IRAK4, ANXA3, TGFBI, TDRD9, CSF1R | 0.82 | 0.81 | 0.82 |
| VNN1, SOD2, CCL5, BCL2A1, HLA-DRA, ANKRD22, CD86, TDRD9, TLR4, FCGR1A, TNFSF10 | 0.82 | 0.79 | 0.85 |
| CEACAM1, OSM, IRAK4, MAP2K6, PSTPIP2, GADD45A, IRAK2, PRV1, IL1RN, TNFSF10, PFKFB3 | 0.82 | 0.77 | 0.85 |
| TNFSF10, IL1RN, IFNGR1, TIFA, FCGR1A, PSTPIP2, OSM, ANXA3, TGFBI, INSL3, CRTAP | 0.81 | 0.82 | 0.81 |
| LDLR, VNN1, GADD45B, IL18R1, GADD45A, Gene_MMP9, FAD104, IL1RN, IRAK4, JAK2, TGFBI | 0.81 | 0.8 | 0.83 |
| FCGR1A, OSM, GADD45A, IL18R1, GADD45B, TLR4, MAP2K6, CRTAP, TIFA, CCL5, BCL2A1 | 0.81 | 0.79 | 0.83 |
| CSF1R, ITGAM, HLA-DRA, MAP2K6, JAK2, FCGR1A, OSM, LDLR, SOCS3, TNFRSF6, IL18R1 | 0.81 | 0.78 | 0.85 |
| IL10alpha, IRAK2, OSM, TIFA, TNFSF10, FAD104, GADD45B, ITGAM, CD86, VNN1, SOD2 | 0.81 | 0.75 | 0.87 |
| ARG2, GADD45A, LDLR, TNFRSF6, CEACAM1, ANKRD22, MAPK14, IRAK4, SOD2, INSL3, PSTPIP2 | 0.81 | 0.84 | 0.78 |
| TGFBI, TNFRSF6, IRAK4, IRAK2, OSM, TNFSF13B, TIFA, FAD104, ANKRD22, MAPK14, CD86 | 0.81 | 0.82 | 0.79 |
| VNN1, INSL3, TNFSF10, TGFBI, JAK2, CRTAP, IRAK2, TNFRSF6, TNFSF13B, LY96, OSM | 0.81 | 0.82 | 0.8 |
| GADD45B, OSM, SOD2, FCGR1A, VNN1, CEACAM1, TIFA, PSTPIP2, IL1RN, TDRD9, LY96 | 0.81 | 0.77 | 0.85 |
| PFKFB3, LDLR, IL10alpha, IRAK4, ANXA3, NCR1, IL18R1, VNN1, TDRD9, TNFSF13B, CSF1R | 0.81 | 0.77 | 0.85 |
| CD86, TNFRSF6, PFKFB3, MKNK1, OSM, JAK2, FAD104, IL10alpha, BCL2A1, SOCS3, IRAK4 | 0.81 | 0.76 | 0.85 |
| OSM, GADD45A, TNFSF10, IFNGR1, CRTAP, JAK2, ANKRD22, HLA-DRA, TNFSF13B, SOCS3, FCGR1A | 0.81 | 0.75 | 0.87 |
| CCL5, CD86, HLA-DRA, SOCS3, TGFBI, PSTPIP2, ANXA3, GADD45A, CSF1R, IRAK4, FAD104, MAPK14 | 0.84 | 0.85 | 0.82 |
| IRAK2, CD86, IL1RN, TLR4, ANKRD22, ANXA3, IL10alpha, GADD45B, BCL2A1, CSF1R, INSL3, FCGR1A | 0.84 | 0.82 | 0.85 |

TABLE L-continued

Exemplary sets of biomarkers used in the methods or kits referenced in Sections 5.2 and 5.3

| BIOMARKER SET | ACCURACY | SPECIFICITY | SENSITIVITY |
|---|---|---|---|
| CD86, TNFRSF6, TIFA, GADD45B, CEACAM1, TNFSF13B, OSM, IL18R1, CCL5, ITGAM, TGFBI, FAD104 | 0.84 | 0.8 | 0.87 |
| NCR1, CCL5, BCL2A1, IL18R1, ARG2, MKNK1, FCGR1A, CD86, GADD45B, INSL3, IRAK4, ANXA3 | 0.83 | 0.82 | 0.85 |
| TNFSF13B, IFNGR1, Gene_MMP9, SOD2, LDLR, NCR1, CD86, INSL3, SOCS3, VNN1, PSTPIP2, CEACAM1 | 0.83 | 0.8 | 0.86 |
| SOD2, INSL3, TDRD9, OSM, TNFSF13B, BCL2A1, JAK2, CSF1R, ANXA3, TNFSF10, GADD45A, CRTAP | 0.83 | 0.82 | 0.84 |
| IL10alpha, MKNK1, GADD45A, TGFBI, MAPK14, IRAK4, TDRD9, IL1RN, TNFRSF6, FCGR1A, ITGAM, CD86 | 0.83 | 0.79 | 0.86 |
| TNFRSF6, IL10alpha, PSTPIP2, HLA-DRA, CRTAP, ARG2, MKNK1, NCR1, OSM, INSL3, VNN1, FAD104 | 0.83 | 0.78 | 0.87 |
| ANXA3, PRV1, LDLR, TNFSF13B, PFKFB3, TNFRSF6, VNN1, ARG2, ANKRD22, INSL3, NCR1, OSM | 0.82 | 0.8 | 0.84 |
| FCGR1A, HLA-DRA, IFNGR1, CD86, LY96, ANXA3, MAP2K6, TDRD9, IL18R1, PRV1, SOCS3, TIFA | 0.82 | 0.76 | 0.89 |
| GADD45B, OSM, ITGAM, CSF1R, CD86, CEACAM1, IFNGR1, SOCS3, MAP2K6, IL1RN, FAD104, CCL5 | 0.82 | 0.84 | 0.8 |
| TGFBI, PRV1, JAK2, FCGR1A, ANKRD22, TNFSF10, VNN1, SOCS3, PSTPIP2, IRAK2, INSL3, FAD104 | 0.82 | 0.83 | 0.81 |
| FCGR1A, GADD45A, SOD2, OSM, ARG2, PFKFB3, ANKRD22, IL10alpha, CCL5, SOCS3, CD86, ITGAM | 0.82 | 0.8 | 0.83 |
| LDLR, MAP2K6, INSL3, TDRD9, NCR1, IL1RN, HLA-DRA, ARG2, MKNK1, MAPK14, OSM, PFKFB3 | 0.82 | 0.84 | 0.79 |
| IL1RN, PFKFB3, TIFA, OSM, IRAK2, TGFBI, INSL3, TNFSF13B, TNFRSF6, MAP2K6, PSTPIP2, CEACAM1 | 0.82 | 0.83 | 0.81 |
| LY96, TNFSF13B, HLA-DRA, IRAK2, FCGR1A, ANXA3, CEACAM1, FAD104, TDRD9, IL1RN, ARG2, LDLR | 0.82 | 0.82 | 0.82 |
| IL1RN, ARG2, IRAK2, IRAK4, SOCS3, IL10alpha, CCL5, Gene_MMP9, MAPK14, FAD104, LY96, TGFBI | 0.82 | 0.81 | 0.82 |
| BCL2A1, LY96, ITGAM, OSM, TNFSF10, INSL3, CD86, IRAK2, MAP2K6, IFNGR1, PRV1, TNFRSF6 | 0.81 | 0.81 | 0.82 |
| BCL2A1, ANXA3, LY96, TNFSF10, NCR1, OSM, MAPK14, MKNK1, IFNGR1, GADD45A, INSL3, ANKRD22, TNFSF13B | 0.83 | 0.83 | 0.83 |
| LY96, GADD45B, MAPK14, OSM, MKNK1, BCL2A1, ARG2, IL1RN, INSL3, PFKFB3, LDLR, CRTAP, TIFA | 0.83 | 0.82 | 0.84 |
| OSM, CD86, GADD45B, IRAK4, MAPK14, SOCS3, VNN1, ARG2, TNFSF13B, TDRD9, PRV1, IL1RN, IL18R1 | 0.83 | 0.82 | 0.84 |
| OSM, NCR1, HLA-DRA, TNFSF10, PSTPIP2, IL1RN, SOCS3, INSL3, TNFRSF6, MAPK14, Gene_MMP9, CEACAM1, IL18R1 | 0.83 | 0.82 | 0.84 |
| CCL5, ARG2, IL10alpha, MAPK14, CSF1R, GADD45B, LDLR, SOD2, Gene_MMP9, IFNGR1, IL18R1, CEACAM1, CD86 | 0.83 | 0.8 | 0.85 |
| TDRD9, SOCS3, Gene_MMP9, IL18R1, CRTAP, ANXA3, PRV1, ARG2, CD86, ITGAM, OSM, NCR1, VNN1 | 0.83 | 0.85 | 0.81 |
| SOD2, JAK2, PSTPIP2, MAPK14, MAP2K6, FCGR1A, CCL5, ITGAM, CD86, GADD45B, IL1RN, HLA-DRA, VNN1 | 0.83 | 0.83 | 0.83 |
| IRAK4, JAK2, SOD2, Gene_MMP9, PSTPIP2, PFKFB3, HLA-DRA, TNFRSF6, FAD104, ARG2, IFNGR1, IRAK2, MAP2K6 | 0.83 | 0.81 | 0.84 |
| PSTPIP2, MAPK14, CCL5, Gene_MMP9, TNFRSF6, IL10alpha, LY96, IL1RN, ARG2, SOCS3, TLR4, OSM, HLA-DRA | 0.83 | 0.79 | 0.86 |

TABLE L-continued

Exemplary sets of biomarkers used in the methods or kits referenced in Sections 5.2 and 5.3

| BIOMARKER SET | ACCURACY | SPECIFICITY | SENSISTIVITY |
|---|---|---|---|
| CRTAP, CEACAM1, ARG2, JAK2, TNFSF10, VNN1, PSTPIP2, IRAK2, TNFRSF6, ITGAM, SOCS3, OSM, IL18R1 | 0.83 | 0.79 | 0.87 |
| VNN1, PSTPIP2, GADD45B, ITGAM, IL1RN, FAD104, NCR1, TIFA, OSM, TDRD9, SOD2, ARG2, TGFBI | 0.83 | 0.77 | 0.88 |
| TGFBI, IL1RN, INSL3, PSTPIP2, NCR1, FAD104, HLA-DRA, CD86, IRAK4, IL10alpha, ARG2, CSF1R, MAP2K6 | 0.82 | 0.84 | 0.81 |
| FAD104, IRAK2, TIFA, TGFBI, IL18R1, MAPK14, SOCS3, PSTPIP2, CD86, PRV1, NCR1, FCGR1A, ANXA3 | 0.82 | 0.82 | 0.83 |
| GADD45A, HLA-DRA, INSL3, ANKRD22, ANXA3, CD86, IRAK4, GADD45B, PFKFB3, ITGAM, VNN1, NCR1, JAK2 | 0.82 | 0.79 | 0.85 |
| MKNK1, CCL5, PSTPIP2, ANXA3, VNN1, LY96, IRAK2, IFNGR1, CRTAP, PFKFB3, IL18R1, LDLR, FAD104 | 0.82 | 0.86 | 0.78 |
| TNFSF10, OSM, FCGR1A, IRAK4, TLR4, SOCS3, IL18R1, CRTAP, GADD45B, IL1RN, IL10alpha, PRV1, JAK2 | 0.82 | 0.81 | 0.83 |
| FAD104, ITGAM, ARG2, PSTPIP2, TLR4, NCR1, IL1RN, MAP2K6, FCGR1A, PFKFB3, LDLR, IFNGR1, BCL2A1 | 0.82 | 0.79 | 0.84 |
| LDLR, ARG2, NCR1, MKNK1, GADD45B, GADD45A, CEACAM1, PSTPIP2, Gene_MMP9, CCL5, BCL2A1, TIFA, TDRD9 | 0.82 | 0.79 | 0.84 |
| IRAK2, Gene_MMP9, INSL3, ARG2, OSM, ITGAM, PSTPIP2, TNFSF13B, FCGR1A, BCL2A1, CRTAP, PRV1, MAP2K6 | 0.81 | 0.81 | 0.82 |
| CEACAM1, PSTPIP2, TLR4, IFNGR1, GADD45B, CSF1R, CD86, VNN1, IL18R1, ANKRD22, MAPK14, OSM, CCL5, IRAK4 | 0.85 | 0.89 | 0.83 |
| LY96, ANKRD22, Gene_MMP9, ARG2, GADD45A, MKNK1, CD86, PSTPIP2, OSM, FAD104, FCGR1A, IL18R1, TIFA, ITGAM | 0.85 | 0.84 | 0.86 |
| ARG2, ANKRD22, VNN1, TLR4, OSM, TIFA, TGFBI, TDRD9, ANXA3, CCL5, TNFRSF6, GADD45B, FAD104, CD86 | 0.84 | 0.82 | 0.86 |
| IFNGR1, TLR4, CRTAP, ANKRD22, Gene_MMP9, JAK2, INSL3, ITGAM, IRAK4, HLA-DRA, BCL2A1, OSM, TNFSF10, NCR1 | 0.84 | 0.79 | 0.87 |
| TNFSF10, VNN1, TDRD9, CSF1R, OSM, IFNGR1, TLR4, PSTPIP2, TIFA, ARG2, FCGR1A, CD86, MAPK14, MAP2K6 | 0.83 | 0.83 | 0.83 |
| LDLR, IL18R1, BCL2A1, IL1RN, ARG2, IRAK2, JAK2, GADD45A, ANKRD22, MAP2K6, OSM, CD86, IRAK4, SOD2 | 0.83 | 0.83 | 0.84 |
| IL1RN, IRAK4, VNN1, CRTAP, TNFSF10, IFNGR1, FAD104, ARG2, OSM, NCR1, JAK2, ANXA3, CEACAM1, TDRD9 | 0.83 | 0.8 | 0.86 |
| CD86, FCGR1A, MKNK1, TNFRSF6, GADD45B, LY96, NCR1, PSTPIP2, HLA-DRA, VNN1, ANXA3, IRAK4, ARG2, TGFBI | 0.83 | 0.78 | 0.88 |
| IRAK2, ANKRD22, JAK2, CD86, INSL3, TNFSF10, OSM, PSTPIP2, IL10alpha, CCL5, TDRD9, GADD45B, Gene_MMP9, LY96 | 0.83 | 0.77 | 0.88 |
| LY96, FCGR1A, CCL5, IL18R1, VNN1, TNFSF10, MAP2K6, PRV1, IRAK4, IL1RN, TLR4, PSTPIP2, PFKFB3, TGFBI | 0.83 | 0.83 | 0.83 |
| SOD2, IL1RN, JAK2, PRV1, IRAK2, CD86, TGFBI, CCL5, MAPK14, TLR4, INSL3, PFKFB3, GADD45B, LY96 | 0.83 | 0.83 | 0.83 |
| TDRD9, FCGR1A, NCR1, IFNGR1, ARG2, SOD2, TNFRSF6, CD86, PFKFB3, LDLR, JAK2, CCL5, ANKRD22, FAD104 | 0.83 | 0.81 | 0.85 |
| MAPK14, INSL3, MAP2K6, CCL5, CSF1R, CD86, GADD45A, SOCS3, GADD45B, ANXA3, TGFBI, TNFRSF6, IFNGR1, CRTAP | 0.83 | 0.82 | 0.83 |
| GADD45B, MAPK14, GADD45A, IL1RN, CEACAM1, CRTAP, MKNK1, IL18R1, NCR1, FCGR1A, TIFA, MAP2K6, CD86, TLR4 | 0.83 | 0.81 | 0.84 |

TABLE L-continued

Exemplary sets of biomarkers used in the methods or kits referenced in Sections 5.2 and 5.3

| BIOMARKER SET | ACCURACY | SPECIFICITY | SENSITIVITY |
|---|---|---|---|
| ARG2, ANKRD22, OSM, LDLR, CCL5, IL1RN, FCGR1A, PFKFB3, CSF1R, ANXA3, HLA-DRA, INSL3, NCR1, TIFA | 0.82 | 0.83 | 0.82 |
| TNFSF10, ANXA3, OSM, JAK2, VNN1, ANKRD22, INSL3, IFNGR1, CD86, MAPK14, GADD45B, TNFRSF6, MAP2K6, LY96 | 0.82 | 0.81 | 0.83 |
| TGFBI, IL18R1, IFNGR1, TDRD9, ANXA3, TNFSF10, ANKRD22, CD86, TNFRSF6, BCL2A1, FAD104, Gene_MMP9, TNFSF13B, CRTAP | 0.82 | 0.8 | 0.84 |
| OSM, ANXA3, SOCS3, INSL3, ITGAM, SOD2, NCR1, TNFSF10, BCL2A1, PSTPIP2, TLR4, IRAK2, Gene_MMP9, IL18R1 | 0.82 | 0.87 | 0.79 |
| SOD2, IRAK4, TNFRSF6, PRV1, FCGR1A, LDLR, MAP2K6, TIFA, CEACAM1, IL18R1, SOCS3, OSM, IL10alpha, MKNK1 | 0.82 | 0.84 | 0.8 |
| TLR4, MKNK1, SOD2, SOCS3, FAD104, HLA-DRA, PSTPIP2, ANKRD22, TIFA, TNFRSF6, JAK2, TNFSF10, ARG2, CSF1R, TLR4 | 0.85 | 0.83 | 0.86 |
| CCL5, MAP2K6, SOCS3, IFNGR1, TGFBI, ANXA3, OSM, GADD45A, TNFSF10, Gene_MMP9, TNFRSF6, TIFA, ARG2, INSL3, SOCS3 | 0.84 | 0.85 | 0.83 |
| ANXA3, IL18R1, VNN1, NCR1, TIFA, INSL3, TGFBI, MAPK14, CEACAM1, CRTAP, CSF1R, TDRD9, IL10alpha, CCL5, MAPK14 | 0.84 | 0.84 | 0.83 |
| TLR4, MKNK1, SOD2, SOCS3, FAD104, HLA-DRA, PSTPIP2, ANKRD22, TIFA, TNFRSF6, JAK2, TNFSF10, ARG2, CSF1R, IRAK4 | 0.85 | 0.83 | 0.86 |
| CCL5, MAP2K6, SOCS3, IFNGR1, TGFBI, ANXA3, OSM, GADD45A, TNFSF10, Gene_MMP9, TNFRSF6, TIFA, ARG2, INSL3, TLR4 | 0.84 | 0.85 | 0.83 |
| ANXA3, IL18R1, VNN1, NCR1, TIFA, INSL3, TGFBI, MAPK14, CEACAM1, CRTAP, CSF1R, TDRD9, IL10alpha, CCL5, SOCS3 | 0.84 | 0.84 | 0.83 |
| IL18R1, MAP2K6, INSL3, IRAK4, CCL5, PFKFB3, CSF1R, LDLR, ITGAM, GADD45A, ARG2, PSTPIP2, TLR4, CD86, MAPK14 | 0.84 | 0.79 | 0.88 |
| SOD2, IFNGR1, CEACAM1, OSM, FAD104, HLA-DRA, CRTAP, IL10alpha, TGFBI, GADD45A, ITGAM, IL18R1, CCL5, TLR4, FCGR1A | 0.83 | 0.84 | 0.83 |
| SOCS3, OSM, TIFA, TNFRSF6, INSL3, LDLR, IL18R1, PFKFB3, TGFBI, IL10alpha, GADD45B, ARG2, TNFSF10, VNN1, ANXA3 | 0.83 | 0.83 | 0.84 |
| PRV1, PFKFB3, CEACAM1, FCGR1A, TIFA, MKNK1, ARG2, GADD45B, IL18R1, CD86, ITGAM, VNN1, IFNGR1, OSM, JAK2 | 0.83 | 0.82 | 0.85 |
| NCR1, INSL3, HLA-DRA, TNFSF10, TNFRSF6, FCGR1A, OSM, GADD45B, MKNK1, TNFSF13B, CSF1R, LY96, MAPK14, PRV1, CCL5 | 0.83 | 0.82 | 0.84 |
| FCGR1A, CD86, CEACAM1, ANXA3, FAD104, CRTAP, JAK2, MKNK1, MAPK14, IFNGR1, GADD45A, PFKFB3, ANKRD22, IL18R1, LY96 | 0.83 | 0.79 | 0.87 |
| IRAK2, IL10alpha, INSL3, FAD104, TIFA, SOD2, IFNGR1, IL1RN, HLA-DRA, LY96, IL18R1, CCL5, CD86, TDRD9, TNFSF10 | 0.83 | 0.78 | 0.87 |
| LY96, BCL2A1, Gene_MMP9, OSM, ARG2, MAP2K6, INSL3, ITGAM, MAPK14, TIFA, IRAK2, PSTPIP2, FCGR1A, CEACAM1, IFNGR1 | 0.83 | 0.8 | 0.85 |
| IL18R1, BCL2A1, PFKFB3, Gene_MMP9, IL1RN, IL10alpha, SOCS3, PSTPIP2, CRTAP, OSM, CD86, FCGR1A, FAD104, JAK2, SOD2 | 0.83 | 0.76 | 0.88 |

TABLE L-continued

Exemplary sets of biomarkers used in the methods or kits referenced in Sections 5.2 and 5.3

| BIOMARKER SET | ACCURACY | SPECIFICITY | SENSITIVITY |
|---|---|---|---|
| MKNK1, CRTAP, PRV1, IL1RN, GADD45A, TNFRSF6, FAD104, HLA-DRA, CEACAM1, PSTPIP2, OSM, JAK2, IL18R1, LDLR, IRAK4 | 0.82 | 0.82 | 0.82 |
| FCGR1A, BCL2A1, IFNGR1, CRTAP, VNN1, TIFA, CCL5, NCR1, OSM, HLA-DRA, IRAK4, INSL3, MAP2K6, TNFSF13B, ARG2 | 0.82 | 0.8 | 0.84 |
| FAD104, BCL2A1, PRV1, MKNK1, CRTAP, IRAK4, PFKFB3, SOD2, CD86, ARG2, FCGR1A, ANKRD22, INSL3, IFNGR1, LDLR | 0.82 | 0.77 | 0.87 |
| SOCS3, CD86, FCGR1A, MAP2K6, TGFBI, IRAK2, PSTPIP2, CCL5, IL1RN, GADD45B, TDRD9, OSM, IL10alpha, PFKFB3, FAD104 | 0.82 | 0.84 | 0.8 |
| TIFA, SOD2, LDLR, FCGR1A, BCL2A1, TNFSF13B, ARG2, PSTPIP2, MAPK14, LY96, Gene_MMP9, IFNGR1, GADD45B, ANXA3, PRV1, CD86 | 0.86 | 0.84 | 0.87 |
| HLA-DRA, IRAK2, FCGR1A, ANXA3, ITGAM, LY96, TDRD9, SOCS3, IL1RN, PFKFB3, GADD45B, TNFSF13B, TLR4, ARG2, CSF1R, FAD104 | 0.84 | 0.83 | 0.84 |
| OSM, CRTAP, CEACAM1, NCR1, IRAK4, TLR4, FAD104, MKNK1, TDRD9, PSTPIP2, IL1RN, CSF1R, MAP2K6, ITGAM, ARG2, IFNGR1 | 0.83 | 0.81 | 0.86 |
| TIFA, IL10alpha, VNN1, OSM, MAP2K6, GADD45B, PSTPIP2, TDRD9, TNFRSF6, INSL3, IL1RN, FAD104, TNFSF10, TGFBI, IL18R1, TLR4 | 0.83 | 0.77 | 0.9 |
| GADD45A, CSF1R, INSL3, BCL2A1, TDRD9, LDLR, HLA-DRA, MAP2K6, PSTPIP2, CCL5, ANXA3, PRV1, TNFRSF6, TLR4, CD86, JAK2 | 0.83 | 0.82 | 0.84 |
| TDRD9, PFKFB3, MAPK14, IL1RN, IFNGR1, FCGR1A, MAP2K6, TNFRSF6, ARG2, VNN1, CRTAP, LDLR, CEACAM1, FAD104, NCR1, TNFSF10 | 0.83 | 0.85 | 0.8 |
| ARG2, IL10alpha, TLR4, PRV1, INSL3, OSM, CD86, TGFBI, SOCS3, GADD45B, TIFA, LDLR, IRAK2, GADD45A, SOD2, TNFSF13B | 0.83 | 0.82 | 0.83 |
| TNFSF10, PRV1, SOCS3, FAD104, TNFRSF6, ARG2, Gene_MMP9, FCGR1A, TGFBI, NCR1, CRTAP, MAP2K6, ANXA3, CSF1R, HLA-DRA, JAK2 | 0.83 | 0.8 | 0.85 |
| TNFRSF6, BCL2A1, VNN1, ANXA3, SOCS3, GADD45A, CRTAP, CCL5, FAD104, ANKRD22, MKNK1, FCGR1A, SOD2, IRAK2, MAPK14, Gene_MMP9 | 0.83 | 0.8 | 0.85 |
| FAD104, OSM, LDLR, TNFSF10, GADD45B, HLA-DRA, TNFRSF6, GADD45A, CD86, TDRD9, ITGAM, ANXA3, IFNGR1, MAPK14, CSF1R, TGFBI | 0.82 | 0.78 | 0.87 |
| CSF1R, PRV1, ANXA3, SOD2, PSTPIP2, CEACAM1, IFNGR1, IRAK4, LY96, MAPK14, IL10alpha, MKNK1, TNFRSF6, OSM, TGFBI, INSL3 | 0.82 | 0.77 | 0.87 |
| PSTPIP2, ARG2, MAP2K6, INSL3, SOCS3, JAK2, FAD104, ANKRD22, HLA-DRA, ITGAM, GADD45B, LY96, IRAK2, PFKFB3, TNFRSF6, IFNGR1 | 0.82 | 0.76 | 0.89 |
| CRTAP, MKNK1, BCL2A1, PRV1, CD86, TNFRSF6, PSTPIP2, MAPK14, TNFSF13B, ARG2, PFKFB3, CEACAM1, FAD104, Gene_MMP9, OSM, SOD2 | 0.82 | 0.88 | 0.77 |
| MKNK1, SOCS3, CRTAP, FCGR1A, CD86, IL10alpha, GADD45A, IL18R1, IRAK2, CCL5, JAK2, ANKRD22, TIFA, TGFBI, CSF1R, BCL2A1 | 0.82 | 0.82 | 0.82 |
| GADD45B, CEACAM1, ANKRD22, IRAK4, LDLR, CRTAP, MKNK1, OSM, MAPK14, MAP2K6, INSL3, GADD45A, PFKFB3, TNFSF10, CSF1R, TIFA | 0.82 | 0.81 | 0.82 |
| CSF1R, INSL3, TNFRSF6, BCL2A1, CD86, CEACAM1, IL10alpha, IL18R1, TLR4, | 0.82 | 0.79 | 0.85 |

TABLE L-continued

Exemplary sets of biomarkers used in the methods or kits referenced in Sections 5.2 and 5.3

| BIOMARKER SET | ACCURACY | SPECIFICITY | SENSISTIVITY |
|---|---|---|---|
| ITGAM, TNFSF10, OSM, ARG2, SOD2, FCGR1A, PSTPIP2 | | | |
| NCR1, LDLR, MKNK1, INSL3, BCL2A1, JAK2, FCGR1A, IL1RN, TNFRSF6, PRV1, GADD45B, ARG2, MAP2K6, OSM, VNN1, TDRD9 | 0.82 | 0.78 | 0.85 |
| TLR4, CD86, MAPK14, TNFSF13B, INSL3, CRTAP, NCR1, ARG2, GADD45A, CSF1R, TNFRSF6, MAP2K6, JAK2, MKNK1, ANKRD22, OSM | 0.82 | 0.85 | 0.79 |
| CSF1R, CCL5, ARG2, BCL2A1, FCGR1A, MKNK1, TDRD9, IFNGR1, PFKFB3, ITGAM, JAK2, OSM, GADD45B, FAD104, NCR1, HLA-DRA | 0.82 | 0.85 | 0.79 |
| IFNGR1, FCGR1A, TLR4, OSM, PSTPIP2, IL18R1, NCR1, SOCS3, PFKFB3, INSL3, LDLR, TNFRSF6, SOD2, GADD45B, IL10alpha, CCL5, IL1RN | 0.86 | 0.82 | 0.9 |
| CEACAM1, IL18R1, SOCS3, CRTAP, LDLR, HLA-DRA, LY96, IL1RN, IL10alpha, BCL2A1, GADD45A, TIFA, FAD104, ANKRD22, OSM, CCL5, IFNGR1 | 0.86 | 0.84 | 0.88 |
| FAD104, GADD45B, HLA-DRA, VNN1, IL10alpha, CD86, JAK2, INSL3, TDRD9, TLR4, IRAK4, SOD2, LDLR, CCL5, MKNK1, ARG2, IL18R1 | 0.85 | 0.79 | 0.91 |
| IL18R1, PRV1, IL1RN, TNFSF10, FAD104, ITGAM, FCGR1A, INSL3, MAP2K6, LDLR, TNFSF13B, IRAK2, OSM, PFKFB3, TGFBI, IL10alpha, LY96 | 0.85 | 0.81 | 0.89 |
| IRAK2, HLA-DRA, IFNGR1, MAP2K6, TLR4, ITGAM, SOCS3, CD86, ARG2, VNN1, IL18R1, ANXA3, FCGR1A, IL1RN, Gene_MMP9, TGFBI, IL10alpha | 0.85 | 0.81 | 0.89 |
| MAP2K6, IL18R1, IL1RN, CSF1R, TNFRSF6, FCGR1A, NCR1, TDRD9, TNFSF10, SOCS3, CCL5, IFNGR1, TIFA, CRTAP, GADD45B, IL10alpha, TGFBI | 0.84 | 0.81 | 0.87 |
| CD86, CCL5, IRAK4, GADD45A, ANXA3, OSM, JAK2, INSL3, SOCS3, BCL2A1, FAD104, MAPK14, TIFA, TLR4, NCR1, PRV1, TDRD9 | 0.84 | 0.8 | 0.88 |
| BCL2A1, IL18R1, TLR4, OSM, CD86, FAD104, PRV1, JAK2, MAPK14, TNFRSF6, CEACAM1, IL1RN, IL10alpha, SOD2, Gene_MMP9, CSF1R, PFKFB3 | 0.84 | 0.8 | 0.89 |
| LY96, TIFA, IL10alpha, ANXA3, LDLR, JAK2, IFNGR1, IRAK2, MAP2K6, TGFBI, MAPK14, TDRD9, FCGR1A, ITGAM, TNFSF10, GADD45B, SOCS3 | 0.84 | 0.81 | 0.87 |
| TNFSF13B, FAD104, SOD2, SOCS3, CEACAM1, TDRD9, ARG2, CD86, IRAK2, PFKFB3, FCGR1A, NCR1, MAPK14, CRTAP, LDLR, GADD45A, TNFRSF6 | 0.84 | 0.85 | 0.83 |
| IRAK2, MKNK1, PSTPIP2, ANXA3, HLA-DRA, TNFSF10, IFNGR1, PFKFB3, OSM, PRV1, IL1RN, IL10alpha, FAD104, CD86, TIFA, BCL2A1, TNFSF13B | 0.84 | 0.83 | 0.84 |
| VNN1, IFNGR1, LY96, SOD2, IL18R1, SOCS3, FCGR1A, ARG2, CSF1R, Gene_MMP9, IRAK4, MAP2K6, TIFA, FAD104, HLA-DRA, GADD45B, IL1RN | 0.84 | 0.82 | 0.86 |
| CD86, Gene_MMP9, IL18R1, TNFSF13B, FCGR1A, TNFRSF6, INSL3, IL1RN, PFKFB3, PSTPIP2, NCR1, GADD45B, VNN1, CRTAP, IRAK4, MAP2K6, OSM | 0.83 | 0.82 | 0.84 |
| TNFSF13B, FAD104, PRV1, TIFA, SOD2, TDRD9, TLR4, TNFRSF6, MKNK1, OSM, MAP2K6, CCL5, ARG2, LDLR, HLA-DRA, PSTPIP2, IL18R1 | 0.83 | 0.79 | 0.88 |
| IRAK4, MAP2K6, JAK2, LY96, ITGAM, CCL5, CSF1R, ARG2, FCGR1A, FAD104, CD86, TNFSF10, IL18R1, CRTAP, GADD45A, TLR4, Gene_MMP9 | 0.83 | 0.82 | 0.84 |
| IRAK2, OSM, MAP2K6, TNFSF13B, ANKRD22, HLA-DRA, SOD2, TNFSF10, | 0.83 | 0.8 | 0.86 |

TABLE L-continued

Exemplary sets of biomarkers used in the methods or kits referenced in Sections 5.2 and 5.3

| BIOMARKER SET | ACCURACY | SPECIFICITY | SENSITIVITY |
|---|---|---|---|
| VNN1, ARG2, IRAK4, LY96, IFNGR1, JAK2, BCL2A1, FCGR1A, CSF1R | | | |
| IL10alpha, FCGR1A, TGFBI, ANKRD22, IRAK4, CD86, TNFSF13B, TNFRSF6, IL18R1, JAK2, IL1RN, PSTPIP2, OSM, MAP2K6, GADD45A, Gene_MMP9, MAPK14 | 0.83 | 0.78 | 0.87 |
| PRV1, IRAK4, MKNK1, JAK2, OSM, MAP2K6, BCL2A1, GADD45B, Gene_MMP9, IL10alpha, FAD104, ARG2, PSTPIP2, SOD2, TNFRSF6, TNFSF10, IL1RN | 0.82 | 0.83 | 0.82 |
| IL1RN, OSM, FAD104, CRTAP, IRAK4, IL10alpha, LDLR, INSL3, TNFSF10, CCL5, IL18R1, ANXA3, PRV1, ARG2, Gene_MMP9, CEACAM1, SOCS3 | 0.82 | 0.82 | 0.83 |
| TNFRSF6, MAP2K6, FCGR1A, MAPK14, ARG2, INSL3, TNFSF10, NCR1, PRV1, CEACAM1, ANXA3, IL18R1, TIFA, IFNGR1, IRAK4, CCL5, VNN1 | 0.82 | 0.81 | 0.83 |
| IRAK2, ANKRD22, MAPK14, TIFA, GADD45B, OSM, IL10alpha, SOD2, CCL5, GADD45A, CD86, IRAK4, SOCS3, TDRD9, MAP2K6, FAD104, PRV1, ANXA3 | 0.85 | 0.83 | 0.87 |
| TLR4, LDLR, OSM, MAP2K6, GADD45A, TIFA, NCR1, IL18R1, IFNGR1, INSL3, ANXA3, IL10alpha, IL1RN, CSF1R, GADD45B, PFKFB3, TGFBI, CRTAP | 0.85 | 0.84 | 0.86 |
| HLA-DRA, GADD45A, ANXA3, ARG2, FAD104, PFKFB3, ITGAM, JAK2, MAPK14, OSM, CD86, LDLR, TIFA, CCL5, NCR1, IRAK2, SOD2, PRV1 | 0.84 | 0.85 | 0.83 |
| GADD45A, INSL3, IRAK2, TNFSF10, TGFBI, IRAK4, NCR1, HLA-DRA, CEACAM1, GADD45B, MAPK14, CD86, IL18R1, CRTAP, ANKRD22, PSTPIP2, LY96, PFKFB3 | 0.83 | 0.82 | 0.85 |
| MAP2K6, IL1RN, TIFA, TLR4, OSM, TGFBI, ANXA3, NCR1, IL18R1, ANKRD22, GADD45A, TNFSF10, PRV1, IRAK2, TDRD9, JAK2, Gene_MMP9, CSF1R | 0.83 | 0.85 | 0.81 |
| CD86, GADD45A, GADD45B, TNFSF13B, CRTAP, TNFRSF6, NCR1, IL10alpha, CSF1R, OSM, MKNK1, CEACAM1, TLR4, IFNGR1, IRAK2, SOCS3, TGFBI, Gene_MMP9 | 0.83 | 0.83 | 0.83 |
| BCL2A1, ANKRD22, OSM, CD86, ITGAM, ANXA3, FCGR1A, CCL5, TIFA, IRAK4, HLA-DRA, NCR1, CRTAP, TLR4, CEACAM1, FAD104, ARG2, MAP2K6 | 0.83 | 0.82 | 0.84 |
| GADD45A, IFNGR1, MAP2K6, CRTAP, MAPK14, TNFSF10, LDLR, TIFA, OSM, SOCS3, CD86, ARG2, PSTPIP2, IL1RN, LY96, GADD45B, ANKRD22, TGFBI | 0.83 | 0.82 | 0.84 |
| INSL3, TLR4, BCL2A1, ANKRD22, FAD104, MAP2K6, GADD45B, ARG2, NCR1, MKNK1, ITGAM, CSF1R, IL1RN, HLA-DRA, LDLR, CRTAP, PRV1, LY96 | 0.83 | 0.81 | 0.85 |
| CRTAP, HLA-DRA, ARG2, PSTPIP2, MKNK1, INSL3, TIFA, CEACAM1, JAK2, Gene_MMP9, TLR4, IRAK4, CD86, FAD104, CCL5, TNFSF10, LDLR, IFNGR1 | 0.83 | 0.81 | 0.86 |
| IL18R1, TNFRSF6, PFKFB3, FAD104, GADD45A, OSM, JAK2, VNN1, MKNK1, BCL2A1, SOCS3, NCR1, TLR4, FCGR1A, CSF1R, ITGAM, IRAK4, CRTAP | 0.83 | 0.8 | 0.86 |
| FAD104, TNFRSF6, OSM, TIFA, PSTPIP2, ANXA3, TLR4, CD86, IRAK4, TNFSF13B, IL1RN, IFNGR1, ITGAM, BCL2A1, CEACAM1, MKNK1, TGFBI, ARG2 | 0.83 | 0.78 | 0.87 |
| TNFSF10, BCL2A1, TGFBI, LY96, PRV1, MKNK1, SOD2, ARG2, SOCS3, CD86, IL10alpha, TNFSF13B, ITGAM, OSM, MAPK14, PSTPIP2, ANXA3, CCL5 | 0.83 | 0.85 | 0.81 |
| SOCS3, OSM, CCL5, JAK2, MAP2K6, IL18R1, NCR1, CEACAM1, IRAK2, ARG2, | 0.83 | 0.85 | 0.81 |

TABLE L-continued

Exemplary sets of biomarkers used in the methods or kits referenced in Sections 5.2 and 5.3

| BIOMARKER SET | ACCURACY | SPECIFICITY | SENSISTIVITY |
|---|---|---|---|
| LY96, PRV1, ITGAM, TNFSF13B, TNFSF10, TGFBI, IL10alpha, LDLR | | | |
| ARG2, IRAK2, Gene_MMP9, GADD45B, MKNK1, PFKFB3, MAPK14, IRAK4, CSF1R, FCGR1A, GADD45A, TDRD9, TIFA, CD86, IL18R1, BCL2A1, CRTAP, TNFRSF6 | 0.83 | 0.83 | 0.82 |
| FAD104, IL1RN, TGFBI, TLR4, BCL2A1, IFNGR1, IRAK4, PRV1, ANKRD22, CRTAP, TNFRSF6, CSF1R, ARG2, OSM, GADD45A, VNN1, INSL3, CEACAM1 | 0.83 | 0.82 | 0.83 |
| CSF1R, SOCS3, FAD104, TLR4, INSL3, ANXA3, NCR1, CRTAP, IFNGR1, TIFA, OSM, MAPK14, TDRD9, IL1RN, ANKRD22, TNFRSF6, IRAK2, BCL2A1 | 0.83 | 0.81 | 0.84 |
| MAP2K6, IFNGR1, CD86, FCGR1A, IRAK2, MKNK1, CRTAP, FAD104, IL10alpha, VNN1, ANXA3, NCR1, IL18R1, CEACAM1, CCL5, ARG2, MAPK14, SOCS3 | 0.83 | 0.81 | 0.84 |
| IL1RN, IRAK4, JAK2, CD86, BCL2A1, TGFBI, Gene_MMP9, NCR1, IFNGR1, VNN1, SOCS3, CCL5, TNFSF13B, TDRD9, MAPK14, PRV1, OSM, TLR4 | 0.83 | 0.79 | 0.86 |
| MAP2K6, CSF1R, HLA-DRA, ANKRD22, MKNK1, SOCS3, TNFSF10, LDLR, FAD104, CEACAM1, TNFSF13B, TDRD9, IRAK4, VNN1, IL18R1, OSM, PSTPIP2, Gene_MMP9 | 0.82 | 0.8 | 0.85 |
| CCL5, SOD2, JAK2, IRAK4, IRAK2, Gene_MMP9, IFNGR1, TLR4, GADD45A, TNFSF10, CSF1R, IL18R1, PRV1, TNFSF13B, HLA-DRA, LDLR, CD86, SOCS3, FAD104 | 0.84 | 0.79 | 0.89 |
| MAP2K6, TNFSF13B, SOD2, GADD45B, HLA-DRA, CSF1R, CCL5, TIFA, NCR1, IFNGR1, OSM, CD86, SOCS3, ARG2, IL10alpha, BCL2A1, TDRD9, LDLR, GADD45A | 0.84 | 0.84 | 0.84 |
| IFNGR1, OSM, MAPK14, CEACAM1, PFKFB3, TLR4, CSF1R, JAK2, IL18R1, TGFBI, CD86, IL10alpha, INSL3, BCL2A1, FCGR1A, GADD45B, LDLR, PSTPIP2, FAD104 | 0.84 | 0.83 | 0.85 |
| ARG2, PRV1, IRAK4, TNFRSF6, MAP2K6, SOCS3, IL18R1, HLA-DRA, IFNGR1, ANXA3, TNFSF10, JAK2, FCGR1A, GADD45A, INSL3, IL1RN, TNFSF13B, ITGAM, CSF1R | 0.84 | 0.8 | 0.86 |
| LDLR, INSL3, JAK2, TNFRSF6, PRV1, IFNGR1, OSM, ITGAM, FCGR1A, IL10alpha, NCR1, TDRD9, MAP2K6, TNFSF13B, TIFA, HLA-DRA, ANKRD22, GADD45B, IL1RN | 0.83 | 0.82 | 0.84 |
| MAPK14, SOD2, CSF1R, ITGAM, MAP2K6, TLR4, ANXA3, BCL2A1, CRTAP, IL10alpha, IRAK4, CCL5, SOCS3, TNFSF13B, ARG2, FCGR1A, CEACAM1, OSM, IL1RN | 0.83 | 0.82 | 0.84 |
| LY96, IL10alpha, GADD45A, GADD45B, IL1RN, IL18R1, PSTPIP2, ARG2, IRAK2, CEACAM1, MKNK1, PFKFB3, TNFSF10, ANKRD22, ANXA3, SOD2, MAP2K6, IRAK4, SOCS3 | 0.83 | 0.78 | 0.87 |
| IL18R1, MAP2K6, ARG2, CD86, TNFSF13B, MAPK14, TNFSF10, CRTAP, GADD45A, NCR1, GADD45B, JAK2, MKNK1, TNFRSF6, VNN1, FAD104, LY96, CEACAM1, PRV1 | 0.82 | 0.82 | 0.83 |
| HLA-DRA, CD86, SOCS3, TIFA, TNFSF13B, FCGR1A, JAK2, PFKFB3, MAP2K6, OSM, TGFBI, ANKRD22, CEACAM1, IRAK4, ARG2, IL18R1, SOD2, MKNK1, GADD45B | 0.82 | 0.79 | 0.85 |
| TDRD9, IRAK2, PFKFB3, CSF1R, TGFBI, SOCS3, IL10alpha, IFNGR1, TNFRSF6, VNN1, FCGR1A, PRV1, TNFSF13B, MAPK14, BCL2A1, CD86, SOD2, INSL3, ARG2 | 0.82 | 0.79 | 0.85 |

TABLE L-continued

Exemplary sets of biomarkers used in the methods or kits referenced in Sections 5.2 and 5.3

| BIOMARKER SET | ACCURACY | SPECIFICITY | SENSISTIVITY |
|---|---|---|---|
| LDLR, ITGAM, IL18R1, ANXA3, GADD45A, VNN1, TDRD9, LY96, BCL2A1, CD86, IRAK2, FAD104, Gene_MMP9, TLR4, TIFA, OSM, ARG2, CRTAP, PSTPIP2 | 0.82 | 0.79 | 0.86 |
| CCL5, TGFBI, BCL2A1, VNN1, TDRD9, SOCS3, CRTAP, CD86, TNFRSF6, LDLR, CSF1R, PRV1, IL18R1, INSL3, GADD45B, TNFSF13B, PFKFB3, JAK2, SOD2 | 0.82 | 0.8 | 0.84 |
| SOD2, ARG2, HLA-DRA, LY96, Gene_MMP9, VNN1, CD86, IL10alpha, CSF1R, PSTPIP2, JAK2, TNFSF13B, IRAK2, CCL5, ANKRD22, TLR4, IL1RN, OSM, GADD45B | 0.82 | 0.8 | 0.84 |
| SOCS3, TGFBI, FCGR1A, TDRD9, GADD45A, TIFA, IFNGR1, VNN1, ITGAM, MAPK14, OSM, ANXA3, TNFSF13B, IL1RN, HLA-DRA, ARG2, MAP2K6, TLR4, PSTPIP2 | 0.82 | 0.78 | 0.86 |
| CD86, INSL3, MAPK14, TIFA, MAP2K6, Gene_MMP9, CRTAP, CSF1R, MKNK1, IL10alpha, FAD104, PRV1, BCL2A1, NCR1, LDLR, IRAK4, HLA-DRA, IFNGR1, TDRD9 | 0.82 | 0.76 | 0.87 |
| NCR1, LDLR, IRAK2, TNFRSF6, CD86, SOD2, TNFSF13B, VNN1, GADD45A, Gene_MMP9, PFKFB3, ANKRD22, PSTPIP2, PRV1, FCGR1A, IL18R1, TIFA, INSL3, CRTAP | 0.82 | 0.74 | 0.89 |
| IL1RN, TLR4, PSTPIP2, IL18R1, GADD45A, IL10alpha, BCL2A1, MKNK1, IRAK2, HLA-DRA, ANKRD22, NCR1, CEACAM1, IRAK4, OSM, TIFA, SOD2, TGFBI, Gene_MMP9 | 0.82 | 0.82 | 0.82 |
| GADD45A, LY96, ITGAM, CCL5, TNFSF10, TNFSF13B, HLA-DRA, CSF1R, TIFA, SOCS3, MKNK1, ARG2, IFNGR1, IL1RN, BCL2A1, OSM, PFKFB3, PSTPIP2, IRAK2 | 0.82 | 0.78 | 0.85 |
| Gene_MMP9, GADD45A, PSTPIP2, INSL3, IRAK4, HLA-DRA, CCL5, TGFBI, OSM, LY96, TDRD9, NCR1, PFKFB3, IFNGR1, IRAK2, VNN1, CRTAP, TIFA, CD86 | 0.82 | 0.78 | 0.85 |
| LDLR, ARG2, MAP2K6, MAPK14, IL18R1, CCL5, PSTPIP2, ANKRD22, OSM, TDRD9, HLA-DRA, SOCS3, ANXA3, TNFRSF6, TIFA, CD86, FAD104, MKNK1, BCL2A1, IRAK2 | 0.85 | 0.81 | 0.9 |
| FCGR1A, FAD104, Gene_MMP9, LDLR, ANKRD22, VNN1, SOCS3, TNFSF13B, TLR4, TDRD9, CEACAM1, PSTPIP2, MAPK14, ARG2, IRAK4, OSM, PRV1, TNFRSF6, IL10alpha, PFKFB3 | 0.85 | 0.8 | 0.88 |
| TNFSF10, IRAK2, TDRD9, TGFBI, PFKFB3, CD86, OSM, IFNGR1, FAD104, ANXA3, CCL5, IRAK4, PSTPIP2, GADD45A, SOCS3, CSF1R, NCR1, CRTAP, IL1RN, BCL2A1 | 0.84 | 0.8 | 0.88 |
| IFNGR1, TIFA, ARG2, IRAK2, CCL5, LDLR, OSM, SOCS3, SOD2, IL1RN, PSTPIP2, BCL2A1, FAD104, IL18R1, IL10alpha, CD86, FCGR1A, ITGAM, JAK2, Gene_MMP9 | 0.84 | 0.83 | 0.85 |
| PSTPIP2, SOCS3, OSM, FCGR1A, IL1RN, IRAK4, ITGAM, ARG2, TGFBI, Gene_MMP9, CSF1R, TLR4, GADD45A, GADD45B, PRV1, IFNGR1, IL18R1, VNN1, FAD104, PFKFB3 | 0.84 | 0.82 | 0.85 |
| TNFRSF6, TIFA, PFKFB3, PRV1, OSM, JAK2, TGFBI, IL10alpha, CEACAM1, INSL3, IRAK2, LY96, ARG2, CD86, FAD104, MAP2K6, TLR4, SOCS3, IL18R1, ITGAM | 0.84 | 0.8 | 0.87 |
| FCGR1A, HLA-DRA, ARG2, CRTAP, CEACAM1, TNFSF13B, OSM, ANXA3, IL1RN, Gene_MMP9, TNFRSF6, FAD104, JAK2, IFNGR1, MKNK1, LDLR, IL10alpha, TGFBI, SOD2, CCL5 | 0.84 | 0.83 | 0.84 |
| GADD45A, MAPK14, ARG2, TDRD9, NCR1, IL18R1, SOD2, ITGAM, FCGR1A, SOCS3, HLA-DRA, IRAK4, TNFRSF6, PRV1, CD86, TGFBI, TNFSF13B, TIFA, VNN1, FAD104 | 0.84 | 0.83 | 0.85 |

TABLE L-continued

Exemplary sets of biomarkers used in the methods or kits referenced in Sections 5.2 and 5.3

| BIOMARKER SET | ACCURACY | SPECIFICITY | SENSISTIVITY |
|---|---|---|---|
| HLA-DRA, ARG2, IL1RN, SOCS3, PSTPIP2, CCL5, IFNGR1, CD86, TLR4, TGFBI, LY96, TNFRSF6, OSM, MAP2K6, VNN1, ITGAM, TNFSF10, NCR1, IRAK4, MAPK14 | 0.84 | 0.79 | 0.88 |
| BCL2A1, ITGAM, ANKRD22, ARG2, FAD104, OSM, GADD45A, CCL5, TGFBI, CD86, PSTPIP2, PFKFB3, IFNGR1, IL18R1, CEACAM1, Gene_MMP9, IRAK2, IL1RN, NCR1, LY96 | 0.84 | 0.79 | 0.87 |
| JAK2, VNN1, CSF1R, TLR4, OSM, SOCS3, ANXA3, LY96, MKNK1, TDRD9, ITGAM, Gene_MMP9, TGFBI, CEACAM1, CD86, MAP2K6, CCL5, TNFSF10, IL1RN, IL18R1 | 0.84 | 0.79 | 0.88 |
| FAD104, PSTPIP2, CEACAM1, MAP2K6, TIFA, ANKRD22, INSL3, TLR4, CRTAP, LY96, SOCS3, MAPK14, JAK2, ARG2, MKNK1, IL18R1, CSF1R, CD86, PRV1, OSM | 0.83 | 0.84 | 0.83 |
| CEACAM1, SOCS3, FCGR1A, ARG2, INSL3, FAD104, IRAK4, GADD45A, ITGAM, PRV1, TNFSF13B, NCR1, Gene_MMP9, IL18R1, SOD2, MAPK14, TIFA, IRAK2, ANKRD22, IL1RN | 0.83 | 0.8 | 0.87 |
| GADD45B, SOD2, CRTAP, OSM, TNFSF13B, CCL5, CD86, INSL3, HLA-DRA, TNFRSF6, TGFBI, GADD45A, FCGR1A, FAD104, JAK2, IL1RN, PFKFB3, MAP2K6, CEACAM1, TDRD9 | 0.83 | 0.78 | 0.88 |
| FCGR1A, GADD45A, ANKRD22, IL1RN, PFKFB3, CCL5, TIFA, IL10alpha, CRTAP, MKNK1, PSTPIP2, PRV1, CSF1R, ANXA3, NCR1, JAK2, VNN1, IRAK4, CD86, MAP2K6 | 0.83 | 0.78 | 0.88 |
| TLR4, GADD45A, JAK2, OSM, CD86, SOCS3, CEACAM1, IL18R1, MAP2K6, PRV1, FAD104, BCL2A1, VNN1, INSL3, PSTPIP2, ANKRD22, TNFSF10, IFNGR1, CRTAP, HLA-DRA | 0.83 | 0.78 | 0.88 |
| FAD104, IL18R1, TIFA, TNFRSF6, Gene_MMP9, ARG2, OSM, TNFSF13B, FCGR1A, CD86, CEACAM1, LY96, NCR1, TNFSF10, PFKFB3, PRV1, GADD45A, SOCS3, HLA-DRA, IRAK2 | 0.83 | 0.77 | 0.88 |
| TDRD9, MKNK1, PFKFB3, IRAK2, INSL3, ITGAM, MAPK14, JAK2, HLA-DRA, CSF1R, CRTAP, NCR1, SOD2, TIFA, IRAK4, CD86, OSM, BCL2A1, LY96, ANKRD22 | 0.83 | 0.82 | 0.84 |
| ANKRD22, CRTAP, NCR1, OSM, INSL3, CD86, CCL5, JAK2, CSF1R, GADD45B, ANXA3, SOCS3, PSTPIP2, FCGR1A, HLA-DRA, IRAK2, IL1RN, IL18R1, PFKFB3, Gene_MMP9 | 0.83 | 0.82 | 0.84 |
| IL1RN, LY96, ARG2, PRV1, GADD45A, TNFSF10, FCGR1A, IL10alpha, LDLR, PFKFB3, CRTAP, SOD2, CEACAM1, IL18R1, CCL5, PSTPIP2, TLR4, VNN1, HLA-DRA, JAK2, ANKRD22 | 0.85 | 0.84 | 0.85 |
| CD86, LDLR, CRTAP, OSM, TGFBI, FCGR1A, NCR1, MAPK14, GADD45A, ARG2, TLR4, GADD45B, INSL3, TNFSF10, ANXA3, MKNK1, PSTPIP2, CSF1R, SOD2, MAP2K6, BCL2A1 | 0.84 | 0.88 | 0.82 |
| IRAK4, GADD45A, MAP2K6, ANKRD22, Gene_MMP9, TDRD9, PSTPIP2, VNN1, IL18R1, ARG2, IL1RN, PFKFB3, FCGR1A, TNFRSF6, JAK2, NCR1, TLR4, FAD104, SOCS3, IFNGR1, SOD2 | 0.84 | 0.82 | 0.85 |
| SOCS3, ITGAM, Gene_MMP9, MKNK1, ARG2, CRTAP, BCL2A1, PRV1, NCR1, HLA-DRA, MAP2K6, FCGR1A, CD86, FAD104, CCL5, TGFBI, TDRD9, OSM, GADD45B, IRAK4, LY96 | 0.84 | 0.82 | 0.86 |
| INSL3, BCL2A1, PSTPIP2, OSM, MAP2K6, CCL5, MKNK1, FAD104, ITGAM, MAPK14, IL1RN, VNN1, IRAK2, FCGR1A, CD86, PFKFB3, TDRD9, HLA-DRA, ARG2, TLR4, CEACAM1 | 0.83 | 0.84 | 0.83 |

TABLE L-continued

Exemplary sets of biomarkers used in the methods or kits referenced in Sections 5.2 and 5.3

| BIOMARKER SET | ACCURACY | SPECIFICITY | SENSITIVITY |
|---|---|---|---|
| TIFA, MKNK1, TNFSF13B, CSF1R, HLA-DRA, IL18R1, MAPK14, INSL3, PFKFB3, ANKRD22, LDLR, ARG2, CCL5, LY96, PSTPIP2, GADD45A, CEACAM1, JAK2, TGFBI, VNN1, IL1RN | 0.83 | 0.82 | 0.84 |
| CRTAP, FAD104, TIFA, BCL2A1, IRAK2, PSTPIP2, PFKFB3, MKNK1, ANKRD22, IL18R1, GADD45B, TDRD9, TLR4, INSL3, CEACAM1, MAP2K6, ARG2, CD86, NCR1, TNFSF13B, PRV1 | 0.83 | 0.81 | 0.85 |
| JAK2, SOCS3, IFNGR1, IL1RN, OSM, BCL2A1, SOD2, ITGAM, FAD104, IL18R1, PSTPIP2, ARG2, PRV1, TNFSF13B, FCGR1A, IRAK2, IL10alpha, PFKFB3, MAPK14, INSL3, TGFBI | 0.83 | 0.81 | 0.85 |
| GADD45A, CCL5, LDLR, ARG2, IRAK2, SOCS3, SOD2, PRV1, MAP2K6, INSL3, TNFSF10, IL18R1, IL1RN, MAPK14, FAD104, IFNGR1, HLA-DRA, PSTPIP2, ITGAM, CSF1R, IL10alpha | 0.83 | 0.86 | 0.8 |
| CD86, TGFBI, ITGAM, IL10alpha, JAK2, TIFA, FAD104, CRTAP, IL1RN, BCL2A1, CCL5, GADD45B, HLA-DRA, SOD2, OSM, NCR1, VNN1, IL18R1, ANXA3, Gene_MMP9, PSTPIP2 | 0.83 | 0.79 | 0.86 |
| IL10alpha, TNFSF13B, GADD45B, MAP2K6, CCL5, IRAK2, MKNK1, LDLR, VNN1, GADD45A, ARG2, OSM, IFNGR1, IL18R1, ANKRD22, JAK2, TLR4, TGFBI, TNFRSF6, FAD104, PFKFB3 | 0.83 | 0.76 | 0.89 |
| MAPK14, SOD2, PRV1, GADD45B, MKNK1, IL18R1, INSL3, NCR1, LY96, IRAK2, CSF1R, TNFRSF6, HLA-DRA, VNN1, IRAK4, FAD104, CEACAM1, IFNGR1, FCGR1A, TIFA, CD86 | 0.83 | 0.83 | 0.82 |
| IL1RN, PFKFB3, IL18R1, PRV1, CRTAP, ITGAM, TNFRSF6, IL10alpha, SOCS3, VNN1, BCL2A1, MAPK14, GADD45A, IRAK2, CCL5, ARG2, TLR4, CD86, ANKRD22, TNFSF10, TGFBI | 0.83 | 0.81 | 0.84 |
| HLA-DRA, PRV1, GADD45A, IL1RN, IL18R1, TNFRSF6, LDLR, IRAK4, BCL2A1, TIFA, PSTPIP2, SOCS3, IL10alpha, FAD104, MKNK1, TNFSF13B, JAK2, TDRD9, TNFSF10, FCGR1A, CD86 | 0.83 | 0.81 | 0.84 |
| INSL3, GADD45A, TGFBI, JAK2, IRAK2, OSM, TIFA, TNFSF13B, HLA-DRA, FCGR1A, BCL2A1, PRV1, CEACAM1, SOCS3, MAPK14, IRAK4, ANXA3, TNFRSF6, FAD104, IFNGR1, Gene_MMP9 | 0.82 | 0.82 | 0.82 |
| BCL2A1, ANKRD22, IL10alpha, HLA-DRA, VNN1, GADD45B, TNFRSF6, CSF1R, IRAK4, ITGAM, IL1RN, IRAK2, LY96, MAPK14, JAK2, Gene_MMP9, TLR4, ARG2, CCL5, SOCS3, MAP2K6 | 0.82 | 0.8 | 0.84 |
| TDRD9, VNN1, GADD45A, ANKRD22, PFKFB3, TNFSF13B, SOCS3, IL18R1, IL1RN, ARG2, CSF1R, HLA-DRA, PRV1, CEACAM1, CD86, IFNGR1, CCL5, MAP2K6, TGFBI, IL10alpha, Gene_MMP9 | 0.82 | 0.79 | 0.85 |
| CRTAP, IL1RN, TIFA, IRAK4, ANXA3, SOCS3, CD86, CSF1R, FCGR1A, FAD104, ANKRD22, TNFSF13B, PSTPIP2, TDRD9, ARG2, TGFBI, Gene_MMP9, CCL5, IL10alpha, GADD45B, TNFRSF6 | 0.82 | 0.78 | 0.86 |
| ANXA3, TNFRSF6, TDRD9, IRAK2, MAP2K6, INSL3, FCGR1A, GADD45A, NCR1, ARG2, VNN1, PRV1, MAPK14, IRAK4, SOCS3, ITGAM, HLA-DRA, CD86, CEACAM1, LY96, GADD45B | 0.82 | 0.78 | 0.87 |
| VNN1, CCL5, IFNGR1, LY96, IL10alpha, ITGAM, FCGR1A, FAD104, NCR1, TNFRSF6, TNFSF13B, SOCS3, TIFA, TNFSF10, PSTPIP2, ARG2, IL18R1, CSF1R, OSM, PFKFB3, LDLR, IRAK2 | 0.87 | 0.84 | 0.89 |

TABLE L-continued

Exemplary sets of biomarkers used in the methods or kits referenced in Sections 5.2 and 5.3

| BIOMARKER SET | ACCURACY | SPECIFICITY | SENSITIVITY |
|---|---|---|---|
| IL18R1, GADD45A, BCL2A1, HLA-DRA, PSTPIP2, ANKRD22, CRTAP, FAD104, CD86, TNFRSF6, Gene_MMP9, IRAK2, SOD2, IL10alpha, IFNGR1, FCGR1A, TIFA, OSM, CCL5, GADD45B, TGFBI, TLR4 | 0.84 | 0.79 | 0.88 |
| TNFSF13B, LDLR, GADD45B, MAPK14, PFKFB3, CRTAP, MAP2K6, NCR1, CCL5, ARG2, SOD2, BCL2A1, MKNK1, TIFA, ANKRD22, Gene_MMP9, TGFBI, IL1RN, HLA-DRA, IL18R1, VNN1, CSF1R | 0.84 | 0.79 | 0.89 |
| TNFRSF6, PSTPIP2, CD86, VNN1, CCL5, MAPK14, TLR4, BCL2A1, ANKRD22, ARG2, ITGAM, IL10alpha, IRAK4, SOCS3, LY96, CRTAP, JAK2, IL1RN, FCGR1A, MAP2K6, TNFSF10, GADD45A | 0.83 | 0.85 | 0.82 |
| TDRD9, CRTAP, ANKRD22, TNFSF13B, ANXA3, CCL5, FCGR1A, TNFSF10, TNFRSF6, PRV1, IRAK2, CEACAM1, SOCS3, CSF1R, FAD104, PSTPIP2, VNN1, ARG2, IL1RN, HLA-DRA, BCL2A1, INSL3 | 0.83 | 0.82 | 0.85 |
| TNFSF10, TLR4, MAP2K6, PFKFB3, FCGR1A, INSL3, MAPK14, PSTPIP2, IFNGR1, CD86, PRV1, IL10alpha, OSM, FAD104, ITGAM, ANXA3, TIFA, CEACAM1, IL18R1, TNFRSF6, NCR1, GADD45A | 0.83 | 0.79 | 0.86 |
| GADD45B, HLA-DRA, NCR1, TGFBI, OSM, MKNK1, TLR4, ARG2, CCL5, LDLR, IFNGR1, SOCS3, INSL3, TIFA, TNFSF10, CD86, IL10alpha, GADD45A, CSF1R, TDRD9, BCL2A1, ANXA3 | 0.83 | 0.8 | 0.86 |
| TLR4, ANXA3, IL10alpha, NCR1, JAK2, TNFSF13B, GADD45A, OSM, SOCS3, CEACAM1, BCL2A1, MKNK1, ARG2, CRTAP, TNFRSF6, Gene_MMP9, PSTPIP2, SOD2, CD86, IL1RN, FCGR1A, CSF1R | 0.83 | 0.76 | 0.88 |
| LY96, TIFA, TLR4, PSTPIP2, Gene_MMP9, PRV1, HLA-DRA, CEACAM1, FCGR1A, ARG2, IRAK4, IL1RN, OSM, IFNGR1, TNFSF13B, CSF1R, TDRD9, GADD45B, ANXA3, SOCS3, GADD45A, LDLR | 0.83 | 0.82 | 0.83 |
| INSL3, PSTPIP2, MKNK1, FCGR1A, PFKFB3, OSM, TGFBI, MAPK14, IRAK2, GADD45A, ANKRD22, CCL5, HLA-DRA, IL10alpha, SOCS3, CD86, IFNGR1, ARG2, Gene_MMP9, GADD45B, VNN1, IL1RN | 0.83 | 0.82 | 0.83 |
| IL1RN, IFNGR1, CCL5, GADD45B, VNN1, CSF1R, TNFSF10, LDLR, TNFRSF6, INSL3, CD86, OSM, FCGR1A, BCL2A1, CRTAP, TLR4, NCR1, PSTPIP2, SOCS3, MAP2K6, TNFSF13B, Gene_MMP9 | 0.83 | 0.78 | 0.87 |
| ARG2, GADD45B, TNFSF10, IRAK2, MAPK14, IL1RN, MKNK1, CRTAP, TNFSF13B, PRV1, SOD2, VNN1, IL18R1, HLA-DRA, MAP2K6, INSL3, CEACAM1, IL10alpha, LY96, SOCS3, FCGR1A, ANKRD22 | 0.82 | 0.83 | 0.82 |
| IFNGR1, LDLR, ITGAM, VNN1, IL18R1, TGFBI, SOCS3, ANKRD22, HLA-DRA, TIFA, OSM, TLR4, IRAK4, INSL3, SOD2, TNFSF13B, LY96, IRAK2, BCL2A1, MAPK14, CCL5, MKNK1 | 0.82 | 0.83 | 0.82 |
| Gene_MMP9, BCL2A1, TDRD9, OSM, MAPK14, IRAK2, CRTAP, MAP2K6, TGFBI, IL18R1, TNFSF10, ANXA3, IFNGR1, GADD45A, TIFA, PSTPIP2, SOCS3, ITGAM, ARG2, HLA-DRA, FAD104, IRAK4 | 0.82 | 0.81 | 0.83 |
| IRAK2, IL1RN, ITGAM, LY96, IFNGR1, TGFBI, TIFA, PFKFB3, Gene_MMP9, FAD104, TNFSF13B, VNN1, LDLR, INSL3, HLA-DRA, NCR1, TDRD9, TNFRSF6, ANXA3, CSF1R, SOCS3, IL18R1 | 0.82 | 0.81 | 0.84 |
| TNFRSF6, INSL3, LDLR, CD86, TGFBI, NCR1, Gene_MMP9, CRTAP, HLA-DRA, | 0.82 | 0.8 | 0.84 |

TABLE L-continued

Exemplary sets of biomarkers used in the methods or kits referenced in Sections 5.2 and 5.3

| BIOMARKER SET | ACCURACY | SPECIFICITY | SENSITIVITY |
|---|---|---|---|
| BCL2A1, MKNK1, IL18R1, TLR4, CEACAM1, PRV1, CCL5, OSM, TDRD9, PFKFB3, IFNGR1, IRAK2, PSTPIP2 | | | |
| PFKFB3, ITGAM, ANKRD22, MAPK14, TGFBI, PSTPIP2, BCL2A1, IFNGR1, MKNK1, NCR1, ARG2, HLA-DRA, INSL3, CRTAP, FCGR1A, LDLR, CCL5, JAK2, IRAK4, TLR4, LY96, IL10alpha | 0.82 | 0.8 | 0.85 |
| TIFA, IFNGR1, HLA-DRA, Gene_MMP9, PRV1, FAD104, IL10alpha, GADD45B, IRAK4, IL1RN, TDRD9, IL18R1, BCL2A1, CD86, GADD45A, CCL5, ANXA3, OSM, SOCS3, PFKFB3, LDLR, CSF1R | 0.82 | 0.8 | 0.84 |
| FAD104, NCR1, BCL2A1, IRAK2, TLR4, IL18R1, SOD2, MAPK14, GADD45B, CD86, FCGR1A, CSF1R, OSM, MAP2K6, PFKFB3, LY96, TIFA, MKNK1, PSTPIP2, CRTAP, TGFBI, GADD45A | 0.82 | 0.8 | 0.84 |
| GADD45A, CSF1R, IL18R1, TGFBI, TNFSF13B, ANXA3, OSM, SOCS3, LY96, TDRD9, ITGAM, FCGR1A, IFNGR1, FAD104, HLA-DRA, PSTPIP2, MKNK1, CRTAP, GADD45B, Gene_MMP9, LDLR, TLR4, VNN1 | 0.85 | 0.81 | 0.89 |
| MAP2K6, TGFBI, HLA-DRA, IL10alpha, VNN1, GADD45B, CEACAM1, PRV1, OSM, IRAK4, IRAK2, ITGAM, CSF1R, TDRD9, NCR1, TNFSF13B, CRTAP, BCL2A1, TIFA, IFNGR1, GADD45A, IL18R1, SOD2 | 0.85 | 0.82 | 0.87 |
| GADD45B, MAPK14, TDRD9, CCL5, OSM, TNFSF13B, ANXA3, TIFA, ANKRD22, TNFRSF6, TNFSF10, PSTPIP2, TLR4, VNN1, FCGR1A, IL18R1, NCR1, GADD45A, LY96, INSL3, ITGAM, BCL2A1, IRAK2 | 0.84 | 0.83 | 0.85 |
| HLA-DRA, PFKFB3, IRAK4, MKNK1, TGFBI, CRTAP, ANXA3, CEACAM1, CCL5, JAK2, TNFSF10, IL1RN, CSF1R, IFNGR1, ARG2, LY96, Gene_MMP9, PRV1, CD86, IRAK2, ITGAM, IL10alpha, OSM | 0.84 | 0.8 | 0.88 |
| FAD104, LY96, NCR1, TLR4, TNFSF13B, MAPK14, MAP2K6, HLA-DRA, FCGR1A, CD86, ANKRD22, LDLR, IL1RN, IFNGR1, TDRD9, TGFBI, GADD45A, PRV1, PFKFB3, ITGAM, JAK2, PSTPIP2, CRTAP | 0.84 | 0.8 | 0.89 |
| BCL2A1, FCGR1A, CRTAP, Gene_MMP9, TDRD9, CEACAM1, SOCS3, SOD2, LDLR, GADD45B, LY96, CSF1R, ARG2, TNFRSF6, PSTPIP2, PFKFB3, IL1RN, IL10alpha, VNN1, GADD45A, INSL3, JAK2, IFNGR1 | 0.84 | 0.82 | 0.85 |
| Gene_MMP9, LDLR, CEACAM1, MAPK14, TLR4, ANXA3, IRAK4, FCGR1A, GADD45B, GADD45A, TGFBI, BCL2A1, CSF1R, PRV1, TNFRSF6, IFNGR1, TDRD9, LY96, MAP2K6, OSM, CRTAP, CD86, FAD104 | 0.84 | 0.82 | 0.86 |
| FCGR1A, ANXA3, MAPK14, TNFRSF6, PSTPIP2, INSL3, ANKRD22, CD86, CRTAP, FAD104, GADD45B, IL18R1, TLR4, IRAK2, ITGAM, JAK2, GADD45A, BCL2A1, IFNGR1, CSF1R, TIFA, NCR1, IRAK4 | 0.83 | 0.82 | 0.84 |
| CRTAP, OSM, TNFRSF6, IRAK2, VNN1, IRAK4, ANXA3, SOD2, ANKRD22, ITGAM, TLR4, MKNK1, IL18R1, CEACAM1, TGFBI, PRV1, Gene_MMP9, TNFSF13B, BCL2A1, HLA-DRA, INSL3, NCR1, CSF1R | 0.83 | 0.8 | 0.85 |
| FAD104, CEACAM1, CCL5, PSTPIP2, TNFSF10, VNN1, CRTAP, IRAK2, FCGR1A, TNFSF13B, CD86, IL10alpha, ARG2, BCL2A1, IFNGR1, PRV1, IL18R1, TNFRSF6, TIFA, TLR4, JAK2, MAPK14, MAP2K6 | 0.83 | 0.79 | 0.87 |
| ARG2, MAPK14, IRAK4, LDLR, IL10alpha, Gene_MMP9, NCR1, OSM, CEACAM1, SOD2, CSF1R, CCL5, GADD45A, ITGAM, BCL2A1, HLA-DRA, PFKFB3, TNFSF13B, TNFSF10, IRAK2, VNN1, JAK2, PRV1 | 0.83 | 0.84 | 0.81 |

TABLE L-continued

Exemplary sets of biomarkers used in the methods or kits referenced in Sections 5.2 and 5.3

| BIOMARKER SET | ACCURACY | SPECIFICITY | SENSITIVITY |
|---|---|---|---|
| FAD104, IFNGR1, INSL3, PFKFB3, MAP2K6, LDLR, CD86, ARG2, PRV1, IL1RN, OSM, ITGAM, VNN1, MKNK1, ANXA3, JAK2, GADD45B, CSF1R, TNFSF13B, PSTPIP2, FCGR1A, CRTAP, TGFBI | 0.83 | 0.83 | 0.83 |
| VNN1, SOCS3, ANKRD22, FAD104, IL18R1, OSM, ITGAM, CCL5, TGFBI, MAPK14, MKNK1, HLA-DRA, LDLR, PSTPIP2, ARG2, CSF1R, IL10alpha, MAP2K6, LY96, FCGR1A, TNFSF10, JAK2, TLR4 | 0.83 | 0.77 | 0.89 |
| CEACAM1, MAP2K6, IL18R1, TIFA, HLA-DRA, FAD104, TGFBI, LDLR, ANKRD22, IL1RN, SOCS3, TNFSF13B, NCR1, CD86, BCL2A1, IL10alpha, TLR4, CRTAP, MKNK1, ITGAM, JAK2, OSM, ARG2 | 0.82 | 0.82 | 0.83 |
| VNN1, FCGR1A, SOD2, CRTAP, TGFBI, LDLR, FAD104, NCR1, TNFRSF6, ARG2, GADD45A, OSM, ANXA3, ITGAM, BCL2A1, CSF1R, IFNGR1, TIFA, CEACAM1, CCL5, SOCS3, ANKRD22, Gene_MMP9 | 0.82 | 0.81 | 0.84 |
| CCL5, IL1RN, TIFA, PRV1, TNFSF13B, INSL3, IRAK2, MKNK1, MAPK14, FCGR1A, SOCS3, JAK2, FAD104, IFNGR1, CRTAP, IL18R1, GADD45B, SOD2, TNFSF10, HLA-DRA, TNFRSF6, ANKRD22, LDLR | 0.82 | 0.81 | 0.84 |
| PRV1, BCL2A1, SOD2, VNN1, FAD104, TIFA, IL10alpha, SOCS3, ITGAM, IL18R1, CEACAM1, MAP2K6, TNFSF13B, JAK2, IRAK4, TNFRSF6, OSM, CRTAP, PSTPIP2, TLR4, CSF1R, IL1RN, FCGR1A | 0.82 | 0.74 | 0.9 |
| TNFRSF6, TNFSF10, CD86, IL10alpha, ARG2, TLR4, JAK2, MAP2K6, GADD45B, LDLR, TIFA, IRAK2, BCL2A1, SOD2, LY96, PFKFB3, HLA-DRA, CSF1R, FAD104, CRTAP, FCGR1A, ANXA3, SOCS3 | 0.82 | 0.81 | 0.83 |
| TNFSF13B, IRAK4, CD86, LDLR, OSM, CCL5, ANXA3, IL1RN, GADD45B, SOCS3, TGFBI, BCL2A1, FAD104, IRAK2, IL10alpha, NCR1, MAP2K6, INSL3, TIFA, CEACAM1, MKNK1, MAPK14, JAK2 | 0.82 | 0.8 | 0.83 |
| LY96, ANXA3, TIFA, CSF1R, GADD45B, PFKFB3, IL1RN, IL18R1, LDLR, TNFRSF6, OSM, INSL3, CRTAP, MAP2K6, IRAK2, ARG2, IL10alpha, NCR1, FAD104, IRAK4, MKNK1, VNN1, IFNGR1, SOD2 | 0.85 | 0.8 | 0.89 |
| NCR1, IL1RN, PRV1, IL18R1, HLA-DRA, BCL2A1, GADD45A, FAD104, TLR4, OSM, FCGR1A, TNFSF10, CRTAP, INSL3, GADD45B, LY96, IRAK2, CD86, VNN1, CCL5, JAK2, IL10alpha, MKNK1, IRAK4 | 0.84 | 0.82 | 0.86 |
| GADD45A, MKNK1, ANXA3, TLR4, MAP2K6, TIFA, FCGR1A, IRAK2, TDRD9, VNN1, CSF1R, GADD45B, LDLR, IL1RN, ANKRD22, JAK2, HLA-DRA, IL10alpha, PSTPIP2, Gene_MMP9, CRTAP, IL18R1, MAPK14, ARG2 | 0.84 | 0.83 | 0.85 |
| FAD104, IL18R1, IRAK2, TIFA, IL10alpha, ITGAM, SOCS3, TDRD9, PSTPIP2, ARG2, INSL3, IL1RN, TLR4, IFNGR1, VNN1, MAPK14, TNFRSF6, SOD2, ANKRD22, NCR1, ANXA3, FCGR1A, CD86, OSM | 0.83 | 0.83 | 0.84 |
| TLR4, TGFBI, CEACAM1, OSM, CRTAP, IL1RN, TNFRSF6, PRV1, SOD2, MKNK1, VNN1, CSF1R, IL18R1, ANKRD22, MAPK14, ANXA3, TNFSF10, TDRD9, BCL2A1, IRAK4, FCGR1A, CCL5, TNFSF13B, GADD45B | 0.83 | 0.83 | 0.83 |
| ARG2, JAK2, CSF1R, NCR1, LY96, HLA-DRA, ANXA3, PSTPIP2, IRAK4, BCL2A1, IL1RN, IFNGR1, FCGR1A, VNN1, TNFSF10, MAPK14, TGFBI, GADD45B, INSL3, IRAK2, OSM, CD86, CRTAP, TNFSF13B | 0.83 | 0.82 | 0.84 |

TABLE L-continued

Exemplary sets of biomarkers used in the methods or kits referenced in Sections 5.2 and 5.3

| BIOMARKER SET | ACCURACY | SPECIFICITY | SENSITIVITY |
|---|---|---|---|
| HLA-DRA, INSL3, PRV1, MAP2K6, TIFA, NCR1, CSF1R, TDRD9, IL18R1, MKNK1, TNFRSF6, TNFSF10, LDLR, IRAK4, FAD104, ITGAM, PSTPIP2, MAPK14, TNFSF13B, GADD45B, CEACAM1, IL1RN, ANXA3, PFKFB3 | 0.83 | 0.81 | 0.84 |
| INSL3, TDRD9, GADD45A, BCL2A1, PFKFB3, TNFRSF6, MAP2K6, GADD45B, TGFBI, IRAK2, CEACAM1, ITGAM, IL10alpha, ANXA3, JAK2, IL1RN, CRTAP, PRV1, SOCS3, TIFA, CCL5, LY96, TNFSF10, OSM | 0.83 | 0.78 | 0.87 |
| VNN1, LDLR, FAD104, HLA-DRA, ARG2, IFNGR1, IRAK4, TNFRSF6, TIFA, MAP2K6, NCR1, OSM, PRV1, CSF1R, INSL3, TNFSF13B, JAK2, MAPK14, BCL2A1, IRAK2, TLR4, PSTPIP2, TDRD9, ANXA3 | 0.82 | 0.85 | 0.8 |
| ANXA3, TNFSF10, TGFBI, MKNK1, PSTPIP2, GADD45A, CRTAP, LDLR, INSL3, MAPK14, IFNGR1, BCL2A1, TNFSF13B, GADD45B, Gene_MMP9, IRAK2, CEACAM1, PRV1, SOD2, FAD104, JAK2, NCR1, ARG2, IL1RN | 0.82 | 0.83 | 0.82 |
| TDRD9, LY96, PFKFB3, IRAK2, FAD104, NCR1, Gene_MMP9, MAPK14, CCL5, LDLR, PSTPIP2, OSM, VNN1, IRAK4, BCL2A1, TIFA, GADD45A, TGFBI, ANKRD22, FCGR1A, IFNGR1, ARG2, CD86, IL18R1 | 0.82 | 0.8 | 0.85 |
| CD86, TNFSF13B, PSTPIP2, IL10alpha, HLA-DRA, MAP2K6, FCGR1A, Gene_MMP9, JAK2, SOCS3, CSF1R, TDRD9, ARG2, NCR1, OSM, FAD104, BCL2A1, TNFRSF6, INSL3, VNN1, ITGAM, PRV1, TLR4, CEACAM1 | 0.82 | 0.8 | 0.84 |
| IL18R1, ARG2, VNN1, TNFRSF6, TIFA, MKNK1, IL10alpha, CD86, NCR1, OSM, ANKRD22, TDRD9, PSTPIP2, ITGAM, IFNGR1, MAP2K6, BCL2A1, IRAK2, TLR4, LY96, SOCS3, GADD45B, IRAK4, PRV1 | 0.82 | 0.78 | 0.86 |
| TNFSF10, ITGAM, MAP2K6, TIFA, CSF1R, TDRD9, FAD104, TLR4, GADD45B, HLA-DRA, IRAK2, IRAK4, OSM, FCGR1A, CCL5, SOD2, VNN1, MKNK1, ARG2, Gene_MMP9, TGFBI, TNFSF13B, MAPK14, PFKFB3 | 0.82 | 0.78 | 0.86 |
| TNFSF10, CEACAM1, IFNGR1, TIFA, MKNK1, ANXA3, IL1RN, IL10alpha, IL18R1, HLA-DRA, SOCS3, Gene_MMP9, MAPK14, TGFBI, JAK2, IRAK2, TLR4, CSF1R, BCL2A1, PSTPIP2, MAP2K6, CD86, ITGAM, SOD2 | 0.82 | 0.75 | 0.88 |
| SOD2, PFKFB3, MAP2K6, HLA-DRA, ANKRD22, IL18R1, Gene_MMP9, LDLR, ARG2, GADD45A, JAK2, MKNK1, PRV1, FCGR1A, ITGAM, OSM, NCR1, VNN1, LY96, IFNGR1, TIFA, PSTPIP2, IL1RN, TLR4 | 0.82 | 0.85 | 0.79 |
| CSF1R, FCGR1A, IL18R1, ANKRD22, MKNK1, NCR1, IRAK2, TDRD9, GADD45A, CRTAP, GADD45B, JAK2, PRV1, SOCS3, CD86, MAPK14, MAP2K6, IFNGR1, LY96, FAD104, OSM, SOD2, TLR4, IL10alpha | 0.82 | 0.81 | 0.83 |
| ARG2, TGFBI, TIFA, IL18R1, TNFRSF6, CSF1R, CCL5, SOCS3, LY96, MKNK1, BCL2A1, SOD2, FCGR1A, PSTPIP2, GADD45B, IFNGR1, NCR1, TNFSF10, LDLR, PRV1, IL1RN, TDRD9, ANKRD22, TLR4 | 0.82 | 0.8 | 0.83 |
| IL1RN, IL10alpha, IFNGR1, TDRD9, PFKFB3, GADD45B, TNFSF10, PSTPIP2, SOCS3, TIFA, MAPK14, CSF1R, TNFSF13B, CRTAP, TNFRSF6, ARG2, IL18R1, LY96, TGFBI, CD86, TLR4, GADD45A, OSM, Gene_MMP9 | 0.82 | 0.8 | 0.84 |

TABLE L-continued

Exemplary sets of biomarkers used in the methods or kits referenced in Sections 5.2 and 5.3

| BIOMARKER SET | ACCURACY | SPECIFICITY | SENSITIVITY |
|---|---|---|---|
| SOD2, IRAK4, SOCS3, VNN1, IL1RN, ITGAM, TNFSF10, GADD45A, CCL5, CEACAM1, ANKRD22, NCR1, IL18R1, OSM, ARG2, INSL3, MAPK14, MAP2K6, TGFBI, TNFSF13B, PFKFB3, MKNK1, LY96, FCGR1A, CSF1R | 0.86 | 0.88 | 0.85 |
| LDLR, VNN1, GADD45A, SOCS3, TLR4, SOD2, BCL2A1, IL18R1, IRAK2, HLA-DRA, TIFA, CEACAM1, OSM, INSL3, TNFSF13B, TNFRSF6, Gene_MMP9, CRTAP, ARG2, LY96, GADD45B, CSF1R, FCGR1A, IL1RN, PFKFB3 | 0.85 | 0.85 | 0.85 |
| ARG2, PRV1, TNFSF10, FAD104, SOD2, ANXA3, IL18R1, JAK2, LDLR, OSM, IFNGR1, PSTPIP2, TNFRSF6, IRAK4, IL1RN, VNN1, FCGR1A, ITGAM, IL10alpha, IRAK2, INSL3, CD86, TDRD9, TIFA, MKNK1 | 0.85 | 0.84 | 0.86 |
| GADD45B, IRAK2, MAPK14, Gene_MMP9, CD86, CEACAM1, SOD2, SOCS3, ARG2, ANXA3, LDLR, JAK2, VNN1, IFNGR1, FAD104, NCR1, PRV1, OSM, TDRD9, MKNK1, ITGAM, INSL3, IL1RN, ANKRD22, CCL5 | 0.85 | 0.81 | 0.89 |
| IL10alpha, IRAK2, HLA-DRA, Gene_MMP9, TGFBI, LDLR, TIFA, GADD45A, ARG2, CSF1R, MAP2K6, CEACAM1, PRV1, OSM, CD86, TNFRSF6, LY96, FAD104, PSTPIP2, ANXA3, IFNGR1, NCR1, CCL5, GADD45B, PFKFB3 | 0.84 | 0.85 | 0.84 |
| GADD45A, SOCS3, SOD2, TGFBI, HLA-DRA, VNN1, CD86, CCL5, BCL2A1, CRTAP, MAP2K6, PRV1, IL18R1, CSF1R, OSM, IRAK2, PSTPIP2, TLR4, FCGR1A, ANKRD22, CEACAM1, JAK2, INSL3, TDRD9, TNFSF10 | 0.84 | 0.84 | 0.85 |
| FCGR1A, TLR4, ANKRD22, CEACAM1, IRAK4, LY96, TDRD9, ARG2, CRTAP, ANXA3, LDLR, MAPK14, CD86, Gene_MMP9, INSL3, GADD45B, TNFSF10, VNN1, IRAK2, PSTPIP2, TIFA, TNFRSF6, TGFBI, IL18R1, IL1RN | 0.84 | 0.78 | 0.9 |
| SOCS3, VNN1, FCGR1A, SOD2, OSM, TNFSF10, LY96, Gene_MMP9, GADD45B, CRTAP, PRV1, HLA-DRA, GADD45A, TLR4, ARG2, IRAK2, FAD104, INSL3, PSTPIP2, TIFA, TGFBI, IL18R1, MAP2K6, LDLR, ANXA3 | 0.84 | 0.83 | 0.84 |
| MAP2K6, LDLR, TIFA, TNFSF13B, IL18R1, ITGAM, SOCS3, OSM, ANXA3, GADD45A, Gene_MMP9, CD86, IL1RN, IFNGR1, PRV1, FCGR1A, MAPK14, CCL5, VNN1, ARG2, PSTPIP2, IRAK2, NCR1, TDRD9, TNFRSF6 | 0.84 | 0.83 | 0.84 |
| TIFA, ANKRD22, TNFSF13B, SOCS3, NCR1, IRAK4, JAK2, GADD45A, CCL5, LDLR, MAPK14, IL18R1, SOD2, TGFBI, CSF1R, IFNGR1, MAP2K6, TNFSF10, IRAK2, LY96, IL1RN, TNFRSF6, VNN1, INSL3, PFKFB3 | 0.84 | 0.82 | 0.86 |
| MAP2K6, FAD104, CCL5, IL18R1, NCR1, VNN1, IL10alpha, ANKRD22, IFNGR1, MAPK14, CD86, MKNK1, TLR4, LY96, TIFA, PSTPIP2, TNFRSF6, LDLR, CSF1R, ARG2, TGFBI, JAK2, PFKFB3, OSM, TDRD9 | 0.84 | 0.81 | 0.86 |
| JAK2, OSM, IRAK4, VNN1, SOCS3, GADD45B, IL1RN, FCGR1A, TNFRSF6, Gene_MMP9, ANKRD22, ARG2, IL10alpha, CCL5, IL18R1, ANXA3, LY96, PSTPIP2, TIFA, TNFSF10, FAD104, MAP2K6, MKNK1, PFKFB3, CRTAP | 0.83 | 0.84 | 0.83 |
| TIFA, IRAK2, ANKRD22, CCL5, IL10alpha, INSL3, CEACAM1, TLR4, FCGR1A, NCR1, CD86, BCL2A1, GADD45A, ITGAM, | 0.83 | 0.85 | 0.82 |

TABLE L-continued

Exemplary sets of biomarkers used in the methods or kits referenced in Sections 5.2 and 5.3

| BIOMARKER SET | ACCURACY | SPECIFICITY | SENSITIVITY |
|---|---|---|---|
| MAP2K6, CRTAP, VNN1, TDRD9, SOCS3, ANXA3, TNFSF10, LY96, MKNK1, JAK2, ARG2 | | | |
| PSTPIP2, CEACAM1, FAD104, TIFA, ANKRD22, OSM, TNFSF13B, IRAK4, INSL3, GADD45A, IL10alpha, CSF1R, HLA-DRA, SOCS3, GADD45B, CCL5, Gene_MMP9, LY96, TLR4, IFNGR1, TGFBI, BCL2A1, MAP2K6, CD86, PFKFB3 | 0.83 | 0.82 | 0.84 |
| IL1RN, JAK2, PFKFB3, OSM, CD86, IL18R1, SOD2, GADD45B, ITGAM, TNFRSF6, MAP2K6, LDLR, TLR4, TIFA, INSL3, SOCS3, IFNGR1, ANKRD22, GADD45A, IRAK4, CRTAP, CSF1R, TNFSF13B, PRV1, PSTPIP2 | 0.83 | 0.82 | 0.84 |
| IFNGR1, VNN1, ANKRD22, FCGR1A, JAK2, MAP2K6, SOD2, TNFSF13B, IRAK4, CEACAM1, LY96, MAPK14, INSL3, NCR1, Gene_MMP9, CCL5, HLA-DRA, LDLR, TNFRSF6, PFKFB3, ANXA3, SOCS3, ARG2, ITGAM, CSF1R | 0.83 | 0.78 | 0.87 |
| LDLR, GADD45A, IFNGR1, ARG2, MAPK14, HLA-DRA, CRTAP, OSM, TDRD9, CSF1R, FCGR1A, Gene_MMP9, NCR1, PRV1, IRAK4, TGFBI, TLR4, LY96, IL1RN, FAD104, SOD2, CCL5, TNFRSF6, MAP2K6, TNFSF13B | 0.83 | 0.83 | 0.82 |
| IL18R1, IL1RN, IRAK4, CEACAM1, ITGAM, LY96, ANKRD22, ARG2, TDRD9, LDLR, NCR1, IL10alpha, ANXA3, CD86, MAPK14, TNFRSF6, SOD2, MKNK1, GADD45B, CRTAP, PFKFB3, CSF1R, INSL3, PSTPIP2, CCL5 | 0.83 | 0.83 | 0.83 |
| PSTPIP2, NCR1, MKNK1, SOCS3, IL1RN, IFNGR1, IL18R1, CSF1R, ITGAM, LDLR, TIFA, CRTAP, OSM, TLR4, CEACAM1, Gene_MMP9, INSL3, MAP2K6, CCL5, FAD104, HLA-DRA, PRV1, VNN1, PFKFB3, JAK2 | 0.83 | 0.81 | 0.84 |

In some embodiments, the methods or kits respectively described or referenced in Section 5.2 and Section 5.3 use any one of the biomarker sets listed in Table M. The biomarker sets listed in Table M were identified in the computational experiments described in Section 6.14.2, below, in which 1600 random subcombinations of the biomarkers listed in Table K were tested. Table M lists some of the biomarker sets that provided high accuracy scores against the validation population described in Section 6.14.2. Each row of Table M lists a single biomarker set that can be used in the methods and kits respectively referenced in Sections 5.2 and 5.3. In other words, each row of Table M describes a biomarker set that can be used to discriminate between sepsis and SIRS subjects (e.g., to determine whether a subject is likely to acquire SEPSIS). In some embodiments, nucleic acid forms of the biomarkers listed in Table M are used in the methods and kits respectively referenced in Sections 5.2 and 5.3. In some embodiments, protein forms of the biomarkers listed in Table M are used. In some hybrid embodiments, some of the biomarkers in a biomarker set from Table M are in protein form and some of the biomarkers in the same biomarker set from Table M are in nucleic acid form in the methods and kits respectively referenced in Sections 5.2 and 5.3.

In some embodiments, a given biomarker set listed in Table M is used with the addition of one, two, three, four, five, six, seven, eight, or nine or more additional biomarkers from Table I that are not within the given set of biomarkers from Table M. In some embodiments, a given set of biomarkers from Table M is used with the addition of one, two, three, four, five, six, seven, eight, or nine or more additional biomarkers from any one of Table I, 30, 31, 32, 33, 34, or 36 that are not within the given biomarker set from Table M. In Table M, accuracy, specificity, and sensitivity are described with reference to $T_{-12}$ time point data described in Section 6.14.2, below.

TABLE M

Exemplary sets of biomarkers used in the methods or kits referenced in Sections 5.2 and 5.3

| BIOMARKER SET | ACCURACY | SPECIFICITY | SENSITIVITY |
|---|---|---|---|
| ALPHAFETOPROTEIN, IL6, IL8 | 0.78 | 0.76 | 0.8 |
| CREACTIVEPROTEIN, TIMP1, IL6 | 0.78 | 0.75 | 0.8 |
| PROTEIN_MMP9, IL8, IL6 | 0.77 | 0.8 | 0.74 |

TABLE M-continued

Exemplary sets of biomarkers used in the methods or kits referenced in Sections 5.2 and 5.3

| BIOMARKER SET | ACCURACY | SPECIFICITY | SENSISTIVITY |
|---|---|---|---|
| IL8, IL6, IL10 | 0.77 | 0.72 | 0.81 |
| CREACTIVEPROTEIN, IL6, PROTEIN_MMP9 | 0.77 | 0.77 | 0.76 |
| APOLIPOPROTEINCIII, IL8, IL6 | 0.76 | 0.74 | 0.78 |
| IL6, IL8, CREACTIVEPROTEIN | 0.76 | 0.74 | 0.79 |
| ALPHAFETOPROTEIN, MCP1, IL10, IL6 | 0.8 | 0.8 | 0.8 |
| ALPHAFETOPROTEIN, IL10, IL6, PROTEIN_MMP9 | 0.79 | 0.7 | 0.86 |
| ALPHAFETOPROTEIN, PROTEIN_MMP9, IL6, APOLIPOPROTEINCIII | 0.78 | 0.74 | 0.81 |
| APOLIPOPROTEINCIII, IL6, BETA2MICROGLOBULIN, TIMP1 | 0.78 | 0.73 | 0.81 |
| IL6, BETA2MICROGLOBULIN, IL10, APOLIPOPROTEINCIII | 0.77 | 0.73 | 0.81 |
| IL6, PROTEIN_MMP9, IL10, MCP1 | 0.77 | 0.81 | 0.73 |
| APOLIPOPROTEINCIII, ALPHAFETOPROTEIN, PROTEIN_MMP9, IL6 | 0.77 | 0.78 | 0.75 |
| IL10, TIMP1, IL6, ALPHAFETOPROTEIN | 0.77 | 0.71 | 0.83 |
| TIMP1, IL6, CREACTIVEPROTEIN, BETA2MICROGLOBULIN | 0.76 | 0.8 | 0.73 |
| PROTEIN_MMP9, CREACTIVEPROTEIN, MCP1, IL10, IL6 | 0.8 | 0.78 | 0.81 |
| APOLIPOPROTEINCIII, CREACTIVEPROTEIN, IL10, ALPHAFETOPROTEIN, IL6 | 0.79 | 0.81 | 0.78 |
| CREACTIVEPROTEIN, ALPHAFETOPROTEIN, IL6, PROTEIN_MMP9, IL8 | 0.79 | 0.77 | 0.81 |
| IL6, TIMP1, MCP1, APOLIPOPROTEINCIII, CREACTIVEPROTEIN | 0.78 | 0.75 | 0.82 |
| CREACTIVEPROTEIN, APOLIPOPROTEINCIII, TIMP1, IL8, PROTEIN_MMP9 | 0.78 | 0.79 | 0.76 |
| CREACTIVEPROTEIN, IL10, MCP1, IL6, TIMP1 | 0.77 | 0.78 | 0.77 |
| IL10, IL8, APOLIPOPROTEINCIII, IL6, TIMP1 | 0.77 | 0.73 | 0.8 |
| IL10, CREACTIVEPROTEIN, MCP1, IL6, APOLIPOPROTEINCIII | 0.77 | 0.72 | 0.82 |
| IL6, ALPHAFETOPROTEIN, IL8, CREACTIVEPROTEIN, TIMP1 | 0.77 | 0.75 | 0.78 |
| TIMP1, MCP1, PROTEIN_MMP9, IL6, APOLIPOPROTEINCIII, CREACTIVEPROTEIN | 0.8 | 0.81 | 0.79 |
| TIMP1, IL6, IL10, CREACTIVEPROTEIN, APOLIPOPROTEINCIII, PROTEIN_MMP9 | 0.79 | 0.77 | 0.8 |
| MCP1, PROTEIN_MMP9, APOLIPOPROTEINCIII, IL6, TIMP1, IL10 | 0.79 | 0.75 | 0.82 |
| IL10, CREACTIVEPROTEIN, IL6, ALPHAFETOPROTEIN, TIMP1, PROTEIN_MMP9 | 0.78 | 0.78 | 0.79 |
| PROTEIN_MMP9, CREACTIVEPROTEIN, ALPHAFETOPROTEIN, IL10, IL6, MCP1 | 0.78 | 0.77 | 0.79 |
| IL6, MCP1, IL10, TIMP1, APOLIPOPROTEINCIII, IL8 | 0.78 | 0.76 | 0.79 |
| TIMP1, IL6, IL10, BETA2MICROGLOBULIN, PROTEIN_MMP9, APOLIPOPROTEINCIII | 0.77 | 0.72 | 0.83 |
| IL10, MCP1, ALPHAFETOPROTEIN, APOLIPOPROTEINCIII, IL6, PROTEIN_MMP9 | 0.77 | 0.76 | 0.78 |
| BETA2MICROGLOBULIN, IL6, TIMP1, ALPHAFETOPROTEIN, CREACTIVEPROTEIN, PROTEIN_MMP9 | 0.77 | 0.74 | 0.79 |
| MCP1, IL10, IL8, IL6, TIMP1, PROTEIN_MMP9, CREACTIVEPROTEIN | 0.79 | 0.77 | 0.81 |
| PROTEIN_MMP9, BETA2MICROGLOBULIN, APOLIPOPROTEINCIII, IL8, IL6, ALPHAFETOPROTEIN, CREACTIVEPROTEIN | 0.79 | 0.77 | 0.8 |

TABLE M-continued

Exemplary sets of biomarkers used in the methods or kits referenced in Sections 5.2 and 5.3

| BIOMARKER SET | ACCURACY | SPECIFICITY | SENSISTIVITY |
|---|---|---|---|
| IL8, MCP1, CREACTIVEPROTEIN, APOLIPOPROTEINCIII, ALPHAFETOPROTEIN, PROTEIN_MMP9, IL6 | 0.79 | 0.71 | 0.85 |
| TIMP1, IL6, CREACTIVEPROTEIN, APOLIPOPROTEINCIII, PROTEIN_MMP9, IL8, ALPHAFETOPROTEIN | 0.78 | 0.76 | 0.8 |
| IL10, IL6, BETA2MICROGLOBULIN, CREACTIVEPROTEIN, APOLIPOPROTEINCIII, MCP1, IL8 | 0.78 | 0.7 | 0.85 |
| APOLIPOPROTEINCIII, PROTEIN_MMP9, MCP1, IL6, ALPHAFETOPROTEIN, IL10, TIMP1 | 0.78 | 0.8 | 0.76 |
| IL10, CREACTIVEPROTEIN, ALPHAFETOPROTEIN, BETA2MICROGLOBULIN, IL8, PROTEIN_MMP9, APOLIPOPROTEINCIII | 0.78 | 0.74 | 0.82 |
| TIMP1, IL10, CREACTIVEPROTEIN, APOLIPOPROTEINCIII, IL6, IL8, MCP1 | 0.78 | 0.81 | 0.74 |
| IL8, TIMP1, CREACTIVEPROTEIN, IL6, IL10, BETA2MICROGLOBULIN, APOLIPOPROTEINCIII | 0.78 | 0.8 | 0.76 |
| APOLIPOPROTEINCIII, CREACTIVEPROTEIN, IL8, IL10, PROTEIN_MMP9, IL6, BETA2MICROGLOBULIN | 0.78 | 0.78 | 0.77 |
| TIMP1, MCP1, IL10, BETA2MICROGLOBULIN, PROTEIN_MMP9, IL6, ALPHAFETOPROTEIN, APOLIPOPROTEINCIII | 0.8 | 0.74 | 0.86 |
| TIMP1, PROTEIN_MMP9, IL6, ALPHAFETOPROTEIN, IL10, APOLIPOPROTEINCIII, MCP1, IL8 | 0.79 | 0.77 | 0.82 |
| IL10, IL6, MCP1, CREACTIVEPROTEIN, APOLIPOPROTEINCIII, PROTEIN_MMP9, BETA2MICROGLOBULIN, ALPHAFETOPROTEIN | 0.79 | 0.79 | 0.79 |
| TIMP1, MCP1, IL10, CREACTIVEPROTEIN, ALPHAFETOPROTEIN, IL6, PROTEIN_MMP9, IL8 | 0.79 | 0.76 | 0.81 |
| APOLIPOPROTEINCIII, ALPHAFETOPROTEIN, TIMP1, BETA2MICROGLOBULIN, MCP1, IL10, IL6, IL8 | 0.79 | 0.73 | 0.83 |
| CREACTIVEPROTEIN, TIMP1, APOLIPOPROTEINCIII, MCP1, IL6, ALPHAFETOPROTEIN, BETA2MICROGLOBULIN, PROTEIN_MMP9 | 0.78 | 0.78 | 0.79 |
| BETA2MICROGLOBULIN, IL10, IL8, APOLIPOPROTEINCIII, PROTEIN_MMP9, IL6, TIMP1, CREACTIVEPROTEIN | 0.78 | 0.73 | 0.83 |
| APOLIPOPROTEINCIII, IL8, ALPHAFETOPROTEIN, IL6, PROTEIN_MMP9, IL10, TIMP1, MCP1 | 0.78 | 0.78 | 0.77 |
| APOLIPOPROTEINCIII, IL6, IL8, PROTEIN_MMP9, TIMP1, BETA2MICROGLOBULIN, IL10, CREACTIVEPROTEIN | 0.78 | 0.71 | 0.83 |
| APOLIPOPROTEINCIII, MCP1, IL10, PROTEIN_MMP9, TIMP1, ALPHAFETOPROTEIN, CREACTIVEPROTEIN, IL6 | 0.77 | 0.76 | 0.78 |
| PROTEIN_MMP9, CREACTIVEPROTEIN, IL6, TIMP1, BETA2MICROGLOBULIN, IL10, APOLIPOPROTEINCIII, MCP1, ALPHAFETOPROTEIN | 0.79 | 0.78 | 0.81 |
| APOLIPOPROTEINCIII, PROTEIN_MMP9, ALPHAFETOPROTEIN, | 0.79 | 0.77 | 0.81 |

TABLE M-continued

Exemplary sets of biomarkers used in the methods or kits referenced in Sections 5.2 and 5.3

| BIOMARKER SET | ACCURACY | SPECIFICITY | SENSISTIVITY |
|---|---|---|---|
| CREACTIVEPROTEIN, IL6, IL10, IL8, TIMP1, BETA2MICROGLOBULIN ALPHAFETOPROTEIN, TIMP1, PROTEIN_MMP9, MCP1, IL6, APOLIPOPROTEINCIII, BETA2MICROGLOBULIN, IL10, CREACTIVEPROTEIN | 0.79 | 0.79 | 0.79 |
| APOLIPOPROTEINCIII, PROTEIN_MMP9, MCP1, BETA2MICROGLOBULIN, IL8, IL6, IL10, CREACTIVEPROTEIN, TIMP1 | 0.79 | 0.78 | 0.79 |
| TIMP1, APOLIPOPROTEINCIII, IL6, CREACTIVEPROTEIN, MCP1, PROTEIN_MMP9, IL8, BETA2MICROGLOBULIN, ALPHAFETOPROTEIN | 0.79 | 0.72 | 0.84 |
| BETA2MICROGLOBULIN, IL8, CREACTIVEPROTEIN, TIMP1, IL6, ALPHAFETOPROTEIN, APOLIPOPROTEINCIII, PROTEIN_MMP9, IL10 | 0.78 | 0.77 | 0.79 |
| IL6, IL8, TIMP1, PROTEIN_MMP9, IL10, BETA2MICROGLOBULIN, APOLIPOPROTEINCIII, CREACTIVEPROTEIN, ALPHAFETOPROTEIN | 0.78 | 0.73 | 0.83 |
| PROTEIN_MMP9, IL10, MCP1, CREACTIVEPROTEIN, ALPHAFETOPROTEIN, IL6, TIMP1, APOLIPOPROTEINCIII, BETA2MICROGLOBULIN | 0.78 | 0.8 | 0.75 |
| IL10, IL8, ALPHAFETOPROTEIN, IL6, TIMP1, PROTEIN_MMP9, MCP1, BETA2MICROGLOBULIN, CREACTIVEPROTEIN | 0.78 | 0.79 | 0.76 |
| ALPHAFETOPROTEIN, MCP1, IL6, BETA2MICROGLOBULIN, PROTEIN_MMP9, CREACTIVEPROTEIN, TIMP1, APOLIPOPROTEINCIII, IL10 | 0.78 | 0.78 | 0.78 |
| TIMP1, IL6, CREACTIVEPROTEIN, ALPHAFETOPROTEIN, IL10, BETA2MICROGLOBULIN, MCP1, APOLIPOPROTEINCIII, IL8, PROTEIN_MMP9 | 0.79 | 0.78 | 0.81 |
| IL8, CREACTIVEPROTEIN, TIMP1, IL10, MCP1, IL6, ALPHAFETOPROTEIN, PROTEIN_MMP9, APOLIPOPROTEINCIII, BETA2MICROGLOBULIN | 0.79 | 0.78 | 0.8 |
| MCP1, TIMP1, APOLIPOPROTEINCIII, ALPHAFETOPROTEIN, PROTEIN_MMP9, IL10, CREACTIVEPROTEIN, BETA2MICROGLOBULIN, IL8, IL6 | 0.78 | 0.8 | 0.77 |
| BETA2MICROGLOBULIN, MCP1, IL6, CREACTIVEPROTEIN, IL10, IL8, ALPHAFETOPROTEIN, APOLIPOPROTEINCIII, TIMP1, PROTEIN_MMP9 | 0.78 | 0.78 | 0.79 |
| CREACTIVEPROTEIN, TIMP1, IL10, IL6, ALPHAFETOPROTEIN, APOLIPOPROTEINCIII, IL8, BETA2MICROGLOBULIN, MCP1, PROTEIN_MMP9 | 0.78 | 0.76 | 0.8 |
| MCP1, TIMP1, IL6, ALPHAFETOPROTEIN, PROTEIN_MMP9, BETA2MICROGLOBULIN, APOLIPOPROTEINCIII, CREACTIVEPROTEIN, IL8, IL10 | 0.78 | 0.78 | 0.78 |
| ALPHAFETOPROTEIN, APOLIPOPROTEINCIII, PROTEIN_MMP9, BETA2MICROGLOBULIN, IL10, TIMP1, MCP1, IL6, IL8, CREACTIVEPROTEIN | 0.78 | 0.8 | 0.75 |

TABLE M-continued

Exemplary sets of biomarkers used in the methods or kits referenced in Sections 5.2 and 5.3

| BIOMARKER SET | ACCURACY | SPECIFICITY | SENSITIVITY |
|---|---|---|---|
| TIMP1, IL10, BETA2MICROGLOBULIN, IL8, APOLIPOPROTEINCIII, IL6, MCP1, CREACTIVEPROTEIN, ALPHAFETOPROTEIN, PROTEIN_MMP9 | 0.78 | 0.76 | 0.8 |
| BETA2MICROGLOBULIN, ALPHAFETOPROTEIN, MCP1, IL10, APOLIPOPROTEINCIII, TIMP1, CREACTIVEPROTEIN, IL8, PROTEIN_MMP9, IL6 | 0.77 | 0.74 | 0.8 |
| IL8, MCP1, BETA2MICROGLOBULIN, PROTEIN_MMP9, IL10, TIMP1, IL6, CREACTIVEPROTEIN, ALPHAFETOPROTEIN, APOLIPOPROTEINCIII | 0.77 | 0.79 | 0.75 |

In some embodiments, the methods or kits respectively described or referenced in Section 5.2 and Section 5.3 use any one of the subsets of biomarkers listed in Table N. The subsets of biomarkers listed in Table N were identified in the computational experiments described in Section 6.14.5, below, in which 4600 random subcombinations of the biomarkers listed in Table I were tested. Table N lists some of the biomarker sets that provided high accuracy scores against the validation population described in Section 6.14.5. Each row of Table N lists a single set of biomarkers that can be used in the methods and kits respectively referenced in Sections 5.2 and 5.3. In other words, each row of Table N describes a set of biomarkers that can be used to discriminate between sepsis and SIRS subjects. In some embodiments, nucleic acid forms of the biomarkers listed in Table N are used in the methods and kits respectively referenced in Sections 5.2 and 5.3. In some embodiments, protein forms of the biomarkers listed in Table N are used. In some embodiments, some of the biomarkers in a biomarker set from Table N are in protein form and some of the biomarkers in the same biomarker set from Table N are in nucleic acid form in the methods and kits respectively referenced in Sections 5.2 and 5.3.

In some embodiments, a given set of biomarkers from Table N is used with the addition of one, two, three, four, five, six, seven, eight, or nine or more additional biomarkers from from any one of Table 30, 31, 32, 33, 34, or 36 that are not within the given set of biomarkers from Table N. In Table N, accuracy, specificity, and sensitivity are described with reference to $T_{-12}$ time point data described in Section 6.14.5, below.

TABLE N

Exemplary sets of biomarkers used in the methods or kits referenced in Sections 5.2 and 5.3

| BIOMARKER SET | ACCURACY | SPECIFICITY | SENSITIVITY |
|---|---|---|---|
| TLR4, ARG2, OSM | 0.85 | 0.83 | 0.88 |
| IRAK4, OSM, TNFSF10 | 0.83 | 0.79 | 0.87 |
| PSTPIP2, SOCS3, TIMP1 | 0.82 | 0.81 | 0.83 |
| FCGR1A, IL6, MAP2K6 | 0.81 | 0.84 | 0.79 |
| SOCS3, TNFSF10, NCR1 | 0.81 | 0.73 | 0.87 |
| IL8, IL18R1, Beta2Microglobulin | 0.81 | 0.79 | 0.82 |
| OSM, NCR1, IL8 | 0.81 | 0.77 | 0.83 |
| PFKFB3, MKNK1, FCGR1A | 0.8 | 0.79 | 0.81 |
| TIMP1, IL18R1, ARG2 | 0.8 | 0.78 | 0.83 |
| FCGR1A, MAP2K6, IRAK4 | 0.8 | 0.75 | 0.86 |
| Gene_MMP9, IL8, GADD45B | 0.8 | 0.75 | 0.84 |
| INSL3, ANKRD22, MAP2K6, LDLR | 0.87 | 0.83 | 0.9 |
| PSTPIP2, ARG2, CRTAP, GADD45A | 0.83 | 0.81 | 0.85 |
| CEACAM1, GADD45B, GADD45A, OSM | 0.83 | 0.75 | 0.91 |
| OSM, CSF1R, IL10, ANKRD22 | 0.83 | 0.88 | 0.78 |
| TIMP1, ARG2, GADD45B, VNN1 | 0.83 | 0.83 | 0.82 |
| HLA-DRA, PSTPIP2, INSL3, MKNK1 | 0.83 | 0.79 | 0.86 |
| CD86, TGFBI, ANKRD22, SOCS3 | 0.82 | 0.82 | 0.83 |
| GADD45A, PSTPIP2, GADD45B, IL18R1 | 0.82 | 0.76 | 0.86 |
| ANKRD22, MAP2K6, Protein_MMP9, FAD104 | 0.81 | 0.8 | 0.82 |
| IFNGR1, FAD104, CSF1R, IL8 | 0.81 | 0.78 | 0.84 |
| OSM, TDRD9, ARG2, HLA-DRA | 0.81 | 0.77 | 0.85 |
| ANKRD22, CReactiveProtein, OSM, IL10 | 0.81 | 0.76 | 0.85 |
| TDRD9, TNFSF13B, CReactiveProtein, MAP2K6 | 0.81 | 0.76 | 0.85 |
| TNFSF10, Gene_MMP9, IL8, FCGR1A | 0.8 | 0.79 | 0.81 |
| IL10, NCR1, IL6, INSL3 | 0.8 | 0.79 | 0.81 |
| CD86, FCGR1A, BCL2A1, LY96 | 0.8 | 0.79 | 0.81 |
| IL8, VNN1, IL6, GADD45B | 0.8 | 0.79 | 0.82 |

TABLE N-continued

Exemplary sets of biomarkers used in the methods or kits referenced in Sections 5.2 and 5.3

| BIOMARKER SET | ACCURACY | SPECIFICITY | SENSISTIVITY |
|---|---|---|---|
| HLA-DRA, TNFSF10, OSM, MKNK1 | 0.8 | 0.76 | 0.84 |
| PFKFB3, INSL3, IL10alpha, FCGR1A | 0.8 | 0.76 | 0.84 |
| TNFSF10, IRAK4, OSM, ARG2, MAPK14 | 0.85 | 0.84 | 0.86 |
| CD86, CEACAM1, IL18R1, GADD45B, CCL5 | 0.83 | 0.85 | 0.81 |
| MCP1, CSF1R, GADD45B, Protein_MMP9, Beta2Microglobulin | 0.83 | 0.83 | 0.82 |
| IL8, CD86, IRAK2, IL1RN, TIFA | 0.82 | 0.84 | 0.81 |
| IRAK4, OSM, INSL3, CEACAM1, TNFSF13B | 0.82 | 0.82 | 0.82 |
| CReactiveProtein, SOCS3, HLA-DRA, GADD45B, OSM | 0.82 | 0.76 | 0.88 |
| CD86, NCR1, PRV1, IL1RN, GADD45B | 0.82 | 0.77 | 0.86 |
| TNFRSF6, ITGAM, PSTPIP2, ARG2, BCL2A1 | 0.82 | 0.77 | 0.87 |
| IRAK4, LDLR, OSM, PSTPIP2, GADD45A | 0.81 | 0.81 | 0.82 |
| Gene_MMP9, SOD2, PFKFB3, ARG2, CD86 | 0.81 | 0.78 | 0.84 |
| CReactiveProtein, IL18R1, NCR1, CD86, GADD45A | 0.81 | 0.78 | 0.84 |
| IL8, IL18R1, LDLR, SOD2, PSTPIP2 | 0.81 | 0.77 | 0.84 |
| Gene_MMP9, CSF1R, TGFBI, MAP2K6, ANKRD22 | 0.81 | 0.8 | 0.81 |
| CReactiveProtein, LDLR, IRAK2, OSM, PSTPIP2 | 0.81 | 0.8 | 0.82 |
| ITGAM, SOCS3, IL8, ARG2, JAK2 | 0.81 | 0.79 | 0.83 |
| TNFSF10, LY96, IL10alpha, IL10, OSM | 0.8 | 0.83 | 0.78 |
| GADD45B, IL6, INSL3, ANKRD22, IL8 | 0.8 | 0.81 | 0.8 |
| CSF1R, IL6, IL1RN, TLR4, JAK2 | 0.8 | 0.79 | 0.81 |
| TDRD9, OSM, ITGAM, ANKRD22, Gene_MMP9 | 0.8 | 0.73 | 0.87 |
| IL8, TNFRSF6, CReactiveProtein, IRAK4, PRV1 | 0.8 | 0.79 | 0.81 |
| OSM, IL1RN, JAK2, GADD45B, CSF1R | 0.8 | 0.78 | 0.82 |
| CD86, Beta2Microglobulin, PFKFB3, TNFSF13B, TNFRSF6 | 0.8 | 0.78 | 0.82 |
| MAPK14, TGFBI, GADD45A, ANKRD22, CReactiveProtein | 0.8 | 0.75 | 0.85 |
| MKNK1, CD86, OSM, TIFA, HLA-DRA, SOCS3 | 0.85 | 0.79 | 0.89 |
| CD86, CEACAM1, LDLR, NCR1, AlphaFetoprotein, IRAK2 | 0.83 | 0.81 | 0.84 |
| INSL3, PRV1, LY96, Protein_MMP9, IL8, OSM | 0.82 | 0.82 | 0.82 |
| FAD104, ARG2, FCGR1A, SOCS3, HLA-DRA, ANXA3 | 0.82 | 0.8 | 0.84 |
| CCL5, TIMP1, ARG2, IL6, IFNGR1, SOD2 | 0.82 | 0.77 | 0.87 |
| CRTAP, OSM, GADD45B, TNFSF10, MKNK1, TGFBI | 0.82 | 0.75 | 0.88 |
| LDLR, OSM, IL6, JAK2, INSL3, FCGR1A | 0.82 | 0.82 | 0.81 |
| Beta2Microglobulin, FAD104, TGFBI, NCR1, ARG2, GADD45B | 0.82 | 0.82 | 0.82 |
| CSF1R, VNN1, MAP2K6, LY96, OSM, Beta2Microglobulin | 0.82 | 0.81 | 0.82 |
| ApolipoproteinCIII, HLA-DRA, GADD45A, ITGAM, TNFRSF6, MAP2K6 | 0.82 | 0.8 | 0.83 |
| PRV1, TGFBI, VNN1, GADD45B, IL1RN, CSF1R | 0.81 | 0.8 | 0.82 |
| IRAK4, TIMP1, ANKRD22, GADD45B, OSM, TLR4 | 0.81 | 0.78 | 0.83 |
| SOD2, MKNK1, MCP1, OSM, TIFA, SOCS3 | 0.81 | 0.77 | 0.84 |
| FAD104, TGFBI, ANXA3, IL18R1, PRV1, IL10alpha | 0.81 | 0.77 | 0.85 |
| FCGR1A, IL8, Beta2Microglobulin, GADD45B, ANKRD22, TNFSF10 | 0.81 | 0.83 | 0.79 |
| TIFA, Beta2Microglobulin, IL18R1, CRTAP, IL6, TGFBI | 0.81 | 0.8 | 0.81 |
| CD86, IL10, MCP1, TIMP1, OSM, ANXA3 | 0.81 | 0.79 | 0.82 |
| INSL3, FAD104, TGFBI, CEACAM1, CSF1R, PFKFB3 | 0.81 | 0.77 | 0.85 |
| PRV1, IL8, TNFSF10, FCGR1A, IFNGR1, CReactiveProtein | 0.81 | 0.77 | 0.84 |
| ANKRD22, BCL2A1, CRTAP, NCR1, SOCS3, IL18R1 | 0.81 | 0.72 | 0.88 |

TABLE N-continued

Exemplary sets of biomarkers used in the methods or kits referenced in Sections 5.2 and 5.3

| BIOMARKER SET | ACCURACY | SPECIFICITY | SENSISTIVITY |
|---|---|---|---|
| INSL3, IRAK2, CD86, JAK2, IL10, FAD104 | 0.8 | 0.84 | 0.77 |
| MCP1, PSTPIP2, AlphaFetoprotein, CReactiveProtein, IL6, ApolipoproteinCIII | 0.8 | 0.81 | 0.8 |
| CSF1R, OSM, IFNGR1, TDRD9, Gene_MMP9, FCGR1A | 0.8 | 0.8 | 0.8 |
| TIMP1, IFNGR1, TNFSF10, GADD45A, BCL2A1, SOD2 | 0.8 | 0.8 | 0.81 |
| FCGR1A, MKNK1, CRTAP, LDLR, Gene_MMP9, Beta2Microglobulin | 0.8 | 0.79 | 0.81 |
| ITGAM, AlphaFetoprotein, FCGR1A, MCP1, MKNK1, GADD45A | 0.8 | 0.78 | 0.82 |
| MCP1, FCGR1A, OSM, PFKFB3, FAD104, TDRD9 | 0.8 | 0.77 | 0.82 |
| TNFSF10, Gene_MMP9, FCGR1A, AlphaFetoprotein, INSL3, CSF1R, IL8 | 0.86 | 0.85 | 0.86 |
| OSM, Beta2Microglobulin, ANKRD22, CSF1R, GADD45B, TNFRSF6, ApolipoproteinCIII | 0.84 | 0.85 | 0.83 |
| BCL2A1, TDRD9, OSM, PRV1, IRAK2, TLR4, MAPK14 | 0.84 | 0.83 | 0.85 |
| LDLR, OSM, ApolipoproteinCIII, IL6, TIMP1, ARG2, TNFRSF6 | 0.83 | 0.83 | 0.83 |
| IL1RN, TNFSF13B, AlphaFetoprotein, MCP1, ANKRD22, ARG2, OSM | 0.83 | 0.8 | 0.85 |
| NCR1, ARG2, PSTPIP2, GADD45A, LY96, OSM, BCL2A1 | 0.83 | 0.81 | 0.84 |
| FCGR1A, TNFSF13B, INSL3, TIFA, ApolipoproteinCIII, ITGAM, CD86 | 0.83 | 0.79 | 0.87 |
| LY96, CReactiveProtein, FCGR1A, Beta2Microglobulin, IL8, OSM, VNN1 | 0.82 | 0.85 | 0.8 |
| PSTPIP2, ARG2, IRAK2, TNFSF13B, GADD45A, IL8, CRTAP | 0.82 | 0.85 | 0.8 |
| MCP1, SOCS3, HLA-DRA, ApolipoproteinCIII, IL10alpha, GADD45A, MAP2K6 | 0.82 | 0.84 | 0.81 |
| IL18R1, MAPK14, Gene_MMP9, TIFA, FCGR1A, SOCS3, MKNK1 | 0.82 | 0.75 | 0.89 |
| Beta2Microglobulin, CRTAP, ARG2, ANKRD22, TNFRSF6, IRAK4, OSM | 0.82 | 0.82 | 0.82 |
| PFKFB3, IRAK2, IRAK4, OSM, JAK2, Beta2Microglobulin, CEACAM1 | 0.82 | 0.82 | 0.82 |
| TIFA, CRTAP, PFKFB3, JAK2, IL6, TGFBI, CD86 | 0.82 | 0.82 | 0.82 |
| GADD45B, Gene_MMP9, TNFSF13B, IRAK2, VNN1, TIFA, SOCS3 | 0.82 | 0.76 | 0.88 |
| INSL3, IL6, CD86, IL10alpha, CReactiveProtein, TGFBI, ITGAM | 0.82 | 0.86 | 0.78 |
| GADD45B, MCP1, INSL3, CReactiveProtein, ARG2, CCL5, SOCS3 | 0.82 | 0.81 | 0.82 |
| TNFSF10, IL8, ApolipoproteinCIII, TGFBI, CSF1R, OSM, SOD2 | 0.82 | 0.8 | 0.83 |
| PRV1, PSTPIP2, ARG2, TIMP1, Protein_MMP9, IL6, SOD2 | 0.82 | 0.79 | 0.84 |
| CD86, LY96, MAP2K6, IL6, IL10, IRAK2, TNFSF10 | 0.81 | 0.78 | 0.84 |
| BCL2A1, MCP1, ARG2, SOCS3, NCR1, IL10, LY96 | 0.81 | 0.8 | 0.81 |
| SOCS3, ApolipoproteinCIII, NCR1, CEACAM1, ANKRD22, FCGR1A, IL6 | 0.81 | 0.8 | 0.82 |
| INSL3, TNFSF10, SOD2, FCGR1A, PSTPIP2, IL10, IL8 | 0.81 | 0.77 | 0.85 |
| FCGR1A, OSM, Protein_MMP9, GADD45A, PSTPIP2, ARG2, Gene_MMP9 | 0.81 | 0.76 | 0.84 |
| TIMP1, SOCS3, LY96, CSF1R, CReactiveProtein, CCL5, TNFSF13B | 0.81 | 0.84 | 0.77 |
| ANKRD22, CEACAM1, TLR4, ApolipoproteinCIII, SOCS3, ITGAM, IL10 | 0.81 | 0.82 | 0.8 |
| INSL3, IRAK2, FCGR1A, MAP2K6, CRTAP, ITGAM, CSF1R | 0.81 | 0.81 | 0.8 |
| VNN1, SOCS3, Beta2Microglobulin, MAP2K6, IL6, ANKRD22, IL10 | 0.81 | 0.81 | 0.81 |
| TNFSF10, TGFBI, CReactiveProtein, Beta2Microglobulin, TNFRSF6, ARG2, PRV1 | 0.81 | 0.8 | 0.82 |

TABLE N-continued

Exemplary sets of biomarkers used in the methods or kits referenced in Sections 5.2 and 5.3

| BIOMARKER SET | ACCURACY | SPECIFICITY | SENSISTIVITY |
|---|---|---|---|
| IL18R1, IL6, CRTAP, IRAK4, GADD45A, Protein_MMP9, TNFSF13B | 0.8 | 0.81 | 0.79 |
| AlphaFetoprotein, ARG2, NCR1, PSTPIP2, ApolipoproteinCIII, CD86, GADD45B | 0.8 | 0.8 | 0.81 |
| ANKRD22, TIFA, JAK2, IL10, IL6, CCL5, CSF1R | 0.8 | 0.79 | 0.82 |
| PRV1, TNFSF13B, TLR4, OSM, ARG2, AlphaFetoprotein, HLA-DRA | 0.8 | 0.78 | 0.82 |
| CSF1R, TLR4, SOD2, FCGR1A, CRTAP, TNFSF13B, GADD45A | 0.8 | 0.78 | 0.83 |
| JAK2, IRAK2, ITGAM, IL6, MKNK1, Gene_MMP9, FCGR1A | 0.8 | 0.77 | 0.83 |
| GADD45B, PRV1, CSF1R, NCR1, CD86, MKNK1, JAK2 | 0.8 | 0.76 | 0.83 |
| Beta2Microglobulin, TNFSF10, IL18R1, GADD45B, Protein_MMP9, FAD104, PSTPIP2 | 0.8 | 0.75 | 0.85 |
| MAPK14, TIFA, ITGAM, MKNK1, CSF1R, IRAK4, Protein_MMP9 | 0.8 | 0.73 | 0.86 |
| TIFA, TNFSF13B, LY96, GADD45B, IL6, INSL3, OSM | 0.8 | 0.8 | 0.8 |
| IL6, GADD45B, CEACAM1, IRAK4, TGFBI, INSL3, TNFSF13B | 0.8 | 0.8 | 0.8 |
| GADD45B, ARG2, IL18R1, ANKRD22, AlphaFetoprotein, IL10, PSTPIP2 | 0.8 | 0.8 | 0.8 |
| TNFSF13B, IFNGR1, OSM, FAD104, CSF1R, PSTPIP2, TIFA | 0.8 | 0.8 | 0.8 |
| TDRD9, ITGAM, TNFSF10, ANXA3, ApolipoproteinCIII, MCP1, INSL3 | 0.8 | 0.8 | 0.8 |
| SOCS3, Protein_MMP9, SOD2, LY96, ARG2, IRAK2, OSM | 0.8 | 0.78 | 0.82 |
| CEACAM1, IL10, TNFRSF6, IL18R1, ARG2, FCGR1A, CReactiveProtein | 0.8 | 0.78 | 0.82 |
| CCL5, FCGR1A, CReactiveProtein, ApolipoproteinCIII, IL18R1, Protein_MMP9, ITGAM | 0.8 | 0.74 | 0.86 |
| NCR1, SOD2, IRAK2, IL8, OSM, HLA-DRA, ARG2, GADD45A | 0.86 | 0.89 | 0.84 |
| PFKFB3, PSTPIP2, GADD45B, INSL3, FAD104, TNFRSF6, ARG2, IL10alpha | 0.85 | 0.86 | 0.84 |
| CSF1R, CEACAM1, GADD45B, OSM, LDLR, MCP1, ARG2, AlphaFetoprotein | 0.84 | 0.86 | 0.82 |
| TIFA, NCR1, BCL2A1, OSM, CCL5, TLR4, CD86, CEACAM1 | 0.82 | 0.82 | 0.82 |
| FAD104, LDLR, INSL3, IRAK4, LY96, TLR4, GADD45B, TIMP1 | 0.82 | 0.81 | 0.83 |
| FAD104, JAK2, TNFSF13B, ARG2, CReactiveProtein, IL10alpha, TLR4, PRV1 | 0.82 | 0.79 | 0.85 |
| CRTAP, LY96, TDRD9, Gene_MMP9, HLA-DRA, SOCS3, IL8, Protein_MMP9 | 0.82 | 0.79 | 0.85 |
| CRTAP, GADD45B, TIFA, ApolipoproteinCIII, LY96, IL8, GADD45A, MKNK1 | 0.81 | 0.83 | 0.8 |
| IL8, CSF1R, ARG2, TGFBI, PRV1, TNFRSF6, CEACAM1, JAK2 | 0.81 | 0.82 | 0.81 |
| ARG2, Beta2Microglobulin, GADD45A, IL6, INSL3, IL8, JAK2, TIMP1 | 0.81 | 0.79 | 0.83 |
| SOD2, IL10, IL8, ARG2, PSTPIP2, INSL3, CSF1R, ANXA3 | 0.81 | 0.77 | 0.86 |
| CD86, IL6, BCL2A1, CCL5, GADD45B, IRAK4, LDLR, ARG2 | 0.81 | 0.86 | 0.76 |
| ANXA3, MAP2K6, VNN1, GADD45A, CSF1R, FAD104, IL6, IRAK2 | 0.81 | 0.81 | 0.81 |
| IL8, GADD45A, TDRD9, Beta2Microglobulin, ANKRD22, GADD45B, PRV1, CSF1R | 0.81 | 0.8 | 0.82 |
| IRAK4, PRV1, GADD45A, IL8, TNFSF13B, CD86, FCGR1A, TIMP1 | 0.81 | 0.79 | 0.82 |
| IRAK4, MAPK14, GADD45B, HLA-DRA, JAK2, PRV1, SOD2, IL6 | 0.81 | 0.77 | 0.84 |
| IL18R1, IL6, GADD45B, MAPK14, IL10, JAK2, IL8, ANKRD22 | 0.81 | 0.76 | 0.86 |
| TLR4, IRAK2, TNFRSF6, TGFBI, IL8, ARG2, GADD45B, GADD45A | 0.81 | 0.88 | 0.74 |

TABLE N-continued

Exemplary sets of biomarkers used in the methods or kits referenced in Sections 5.2 and 5.3

| BIOMARKER SET | ACCURACY | SPECIFICITY | SENSISTIVITY |
|---|---|---|---|
| ANXA3, IFNGR1, SOCS3, VNN1, TIFA, CReactiveProtein, IRAK4, AlphaFetoprotein | 0.81 | 0.8 | 0.81 |
| ANKRD22, CCL5, TGFBI, CEACAM1, CD86, Gene_MMP9, IFNGR1, GADD45B | 0.81 | 0.8 | 0.82 |
| NCR1, ARG2, TIMP1, Beta2Microglobulin, ANXA3, TIFA, BCL2A1, MAP2K6 | 0.81 | 0.77 | 0.84 |
| OSM, TIMP1, IL1RN, IL8, BCL2A1, IFNGR1, CSF1R, CD86 | 0.81 | 0.76 | 0.84 |
| IL10, NCR1, IRAK2, IL18R1, ARG2, PSTPIP2, Gene_MMP9, LY96 | 0.81 | 0.76 | 0.84 |
| IL18R1, TNFSF10, SOCS3, ApolipoproteinCIII, HLA-DRA, GADD45A, Beta2Microglobulin, ARG2 | 0.81 | 0.74 | 0.88 |
| IL10alpha, IL10, MKNK1, LY96, OSM, JAK2, IFNGR1, CEACAM1 | 0.8 | 0.8 | 0.81 |
| HLA-DRA, TIMP1, OSM, CD86, NCR1, IL1RN, TNFSF10, FAD104 | 0.8 | 0.78 | 0.82 |
| CSF1R, TNFSF13B, ANKRD22, IFNGR1, Protein_MMP9, PFKFB3, NCR1, TGFBI | 0.8 | 0.77 | 0.82 |
| ANXA3, IL10alpha, PSTPIP2, CSF1R, IL1RN, FAD104, CD86, CReactiveProtein | 0.8 | 0.77 | 0.83 |
| CSF1R, ANKRD22, TGFBI, IRAK4, Protein_MMP9, TIMP1, HLA-DRA, PFKFB3 | 0.8 | 0.77 | 0.83 |
| TNFSF13B, JAK2, ARG2, CCL5, IL18R1, GADD45B, CD86, GADD45A | 0.8 | 0.76 | 0.85 |
| GADD45B, BCL2A1, IL1RN, FCGR1A, MAPK14, SOCS3, ITGAM, PRV1 | 0.8 | 0.76 | 0.84 |
| IL6, JAK2, CReactiveProtein, MCP1, TIMP1, BCL2A1, GADD45B, LY96 | 0.8 | 0.85 | 0.76 |
| AlphaFetoprotein, ApolipoproteinCIII, CEACAM1, CRTAP, IL18R1, NCR1, TIMP1, TGFBI | 0.8 | 0.84 | 0.77 |
| ANXA3, FAD104, MKNK1, CReactiveProtein, AlphaFetoprotein, CSF1R, IRAK4, IL6 | 0.8 | 0.82 | 0.78 |
| TIMP1, VNN1, TIFA, CCL5, TDRD9, FCGR1A, ApolipoproteinCIII, IL1RN | 0.8 | 0.82 | 0.78 |
| TNFSF10, TLR4, JAK2, OSM, Beta2Microglobulin, ITGAM, IL1RN, HLA-DRA | 0.8 | 0.8 | 0.81 |
| ApolipoproteinCIII, MAPK14, IRAK2, TNFSF13B, GADD45B, SOCS3, CEACAM1, TNFSF10 | 0.8 | 0.79 | 0.81 |
| IL1RN, ANKRD22, FCGR1A, GADD45A, TGFBI, CSF1R, MCP1, MAPK14 | 0.8 | 0.79 | 0.81 |
| SOCS3, HLA-DRA, IRAK2, Protein_MMP9, MAP2K6, INSL3, CReactiveProtein, Gene_MMP9 | 0.8 | 0.79 | 0.81 |
| INSL3, BCL2A1, ARG2, GADD45B, MAPK14, ITGAM, IRAK2, LDLR | 0.8 | 0.78 | 0.82 |
| GADD45B, Beta2Microglobulin, Protein_MMP9, IFNGR1, IRAK2, PSTPIP2, IL8, FCGR1A | 0.8 | 0.77 | 0.82 |
| CSF1R, HLA-DRA, IRAK4, FAD104, CRTAP, MCP1, GADD45B, CCL5, IL6 | 0.84 | 0.88 | 0.82 |
| HLA-DRA, Gene_MMP9, FAD104, IRAK2, TNFRSF6, LY96, CReactiveProtein, FCGR1A, CD86 | 0.84 | 0.85 | 0.83 |
| GADD45A, GADD45B, OSM, ARG2, FAD104, MAPK14, IRAK2, ITGAM, MKNK1 | 0.84 | 0.81 | 0.86 |
| IL6, IL18R1, IL1RN, HLA-DRA, CD86, IRAK2, NCR1, TNFSF10, CCL5 | 0.83 | 0.88 | 0.8 |
| CD86, IRAK2, ARG2, PFKFB3, MAPK14, PRV1, VNN1, HLA-DRA, FAD104 | 0.83 | 0.85 | 0.82 |
| TDRD9, FCGR1A, ARG2, AlphaFetoprotein, JAK2, ApolipoproteinCIII, TIMP1, MAP2K6, CCL5 | 0.83 | 0.8 | 0.86 |
| PFKFB3, CReactiveProtein, TDRD9, OSM, IFNGR1, CCL5, TIMP1, ARG2, ITGAM | 0.83 | 0.85 | 0.81 |
| NCR1, CSF1R, MAP2K6, INSL3, IFNGR1, FAD104, IL6, ARG2, IL18R1 | 0.83 | 0.85 | 0.81 |

TABLE N-continued

Exemplary sets of biomarkers used in the methods or kits referenced in Sections 5.2 and 5.3

| BIOMARKER SET | ACCURACY | SPECIFICITY | SENSISTIVITY |
|---|---|---|---|
| PSTPIP2, OSM, LDLR, Protein_MMP9, LY96, TNFSF13B, ANXA3, IL1RN, Beta2Microglobulin | 0.83 | 0.82 | 0.84 |
| FAD104, NCR1, VNN1, IRAK2, ApolipoproteinCIII, IL10alpha, LDLR, FCGR1A, IRAK4 | 0.83 | 0.81 | 0.84 |
| IL10alpha, HLA-DRA, TGFBI, FCGR1A, CSF1R, IRAK2, GADD45A, PFKFB3, SOCS3 | 0.82 | 0.84 | 0.81 |
| IL8, IRAK4, CSF1R, IL18R1, AlphaFetoprotein, IL1RN, BCL2A1, TNFSF13B, INSL3 | 0.82 | 0.83 | 0.81 |
| SOCS3, MAP2K6, PSTPIP2, OSM, MAPK14, MKNK1, ApolipoproteinCIII, IL18R1, TLR4 | 0.82 | 0.82 | 0.82 |
| TIMP1, IL8, PFKFB3, CD86, SOCS3, JAK2, IRAK2, IL10alpha, Protein_MMP9 | 0.82 | 0.81 | 0.83 |
| TIMP1, INSL3, TNFRSF6, PFKFB3, CD86, JAK2, IL8, CRTAP, Protein_MMP9 | 0.82 | 0.8 | 0.85 |
| IRAK4, MAPK14, ApolipoproteinCIII, IL6, MAP2K6, MCP1, TIFA, ARG2, CD86 | 0.82 | 0.88 | 0.76 |
| TLR4, IL10alpha, IL8, GADD45A, IRAK2, MAP2K6, MCP1, HLA-DRA, MAPK14 | 0.82 | 0.82 | 0.81 |
| LY96, MCP1, CD86, VNN1, OSM, ARG2, TDRD9, CCL5, INSL3 | 0.81 | 0.83 | 0.8 |
| CCL5, CRTAP, ApolipoproteinCIII, Gene_MMP9, IFNGR1, TNFSF13B, ANKRD22, GADD45A, OSM | 0.81 | 0.81 | 0.81 |
| MCP1, IL6, FCGR1A, PSTPIP2, VNN1, TNFSF10, TIMP1, Protein_MMP9, CReactiveProtein | 0.81 | 0.79 | 0.83 |
| PFKFB3, IL6, NCR1, MAP2K6, FAD104, CD86, TLR4, TDRD9, OSM | 0.81 | 0.79 | 0.84 |
| ApolipoproteinCIII, CReactiveProtein, TGFBI, MKNK1, PRV1, FAD104, HLA-DRA, ARG2, TIMP1 | 0.81 | 0.77 | 0.86 |
| IL10alpha, IL10, ANXA3, IL6, CSF1R, TGFBI, PSTPIP2, IL8, INSL3 | 0.81 | 0.82 | 0.8 |
| IL6, IRAK2, CReactiveProtein, CCL5, ANKRD22, MCP1, GADD45A, PFKFB3, IL10alpha | 0.81 | 0.8 | 0.82 |
| TIFA, IL1RN, IL6, ITGAM, CReactiveProtein, CCL5, TGFBI, IL10, NCR1 | 0.81 | 0.79 | 0.82 |
| CEACAM1, IFNGR1, TNFSF10, INSL3, BCL2A1, Beta2Microglobulin, IL10, ARG2, SOCS3 | 0.81 | 0.78 | 0.84 |
| SOCS3, LDLR, SOD2, FAD104, MAP2K6, PSTPIP2, GADD45B, IRAK4, GADD45A | 0.81 | 0.75 | 0.86 |
| MKNK1, IL8, TNFSF13B, FAD104, ITGAM, GADD45B, NCR1, IL18R1, ApolipoproteinCIII | 0.81 | 0.83 | 0.78 |
| IL8, Gene_MMP9, TNFSF10, MKNK1, MCP1, IL6, CCL5, ApolipoproteinCIII, SOD2 | 0.81 | 0.82 | 0.79 |
| NCR1, PFKFB3, ApolipoproteinCIII, INSL3, OSM, VNN1, AlphaFetoprotein, TNFSF10, CRTAP | 0.81 | 0.78 | 0.83 |
| FCGR1A, CReactiveProtein, PRV1, NCR1, ARG2, INSL3, IL10, TGFBI, MAPK14 | 0.81 | 0.75 | 0.86 |
| IL8, IRAK2, PFKFB3, CEACAM1, TIFA, Protein_MMP9, IRAK4, CRTAP, TDRD9 | 0.8 | 0.8 | 0.81 |
| ARG2, INSL3, CSF1R, TNFSF13B, Beta2Microglobulin, PRV1, FCGR1A, GADD45B, CRTAP | 0.8 | 0.79 | 0.82 |
| GADD45A, IL8, TIMP1, CReactiveProtein, MAP2K6, TGFBI, CRTAP, TNFRSF6, BCL2A1 | 0.8 | 0.77 | 0.84 |
| HLA-DRA, ApolipoproteinCIII, INSL3, FAD104, TIMP1, IRAK4, FCGR1A, IL6, GADD45A | 0.8 | 0.77 | 0.84 |
| ARG2, JAK2, IL1RN, VNN1, IRAK4, CSF1R, ANKRD22, BCL2A1, TDRD9 | 0.8 | 0.84 | 0.77 |

TABLE N-continued

Exemplary sets of biomarkers used in the methods or kits referenced in Sections 5.2 and 5.3

| BIOMARKER SET | ACCURACY | SPECIFICITY | SENSISTIVITY |
|---|---|---|---|
| CReactiveProtein, PFKFB3, CD86, IL1RN, TLR4, Beta2Microglobulin, IRAK2, TNFSF10, TNFRSF6 | 0.8 | 0.8 | 0.8 |
| GADD45B, MAP2K6, JAK2, MAPK14, TIMP1, IRAK4, CReactiveProtein, TLR4, TGFBI | 0.8 | 0.79 | 0.81 |
| JAK2, TLR4, CCL5, IL6, CReactiveProtein, IFNGR1, ApolipoproteinCIII, GADD45B, NCR1 | 0.8 | 0.73 | 0.87 |
| CSF1R, TNFRSF6, INSL3, MKNK1, IL8, MAP2K6, FAD104, NCR1, IL1RN, MCP1 | 0.86 | 0.85 | 0.86 |
| IL8, PRV1, SOCS3, IRAK2, ARG2, IL10alpha, NCR1, CCL5, CReactiveProtein, MKNK1 | 0.85 | 0.86 | 0.83 |
| TNFSF13B, TLR4, ARG2, IL6, SOCS3, Beta2Microglobulin, FAD104, MCP1, HLA-DRA, PSTPIP2 | 0.84 | 0.8 | 0.88 |
| IL6, MCP1, Beta2Microglobulin, IL1RN, TDRD9, IFNGR1, ApolipoproteinCIII, FCGR1A, OSM, IL8 | 0.84 | 0.82 | 0.86 |
| FCGR1A, IL6, LY96, LDLR, IL18R1, CSF1R, CCL5, NCR1, TNFRSF6, IRAK4 | 0.84 | 0.81 | 0.87 |
| IL6, TGFBI, IL18R1, ANXA3, IL1RN, GADD45B, ANKRD22, LDLR, TLR4, CEACAM1 | 0.83 | 0.84 | 0.82 |
| MAPK14, IL6, CSF1R, IL1RN, ITGAM, Beta2Microglobulin, MAP2K6, IL10, PSTPIP2, FAD104 | 0.83 | 0.86 | 0.79 |
| CReactiveProtein, FCGR1A, CCL5, ApolipoproteinCIII, OSM, IRAK2, GADD45A, CRTAP, PFKFB3, ITGAM | 0.83 | 0.86 | 0.8 |
| TNFSF10, AlphaFetoprotein, CCL5, IL8, IRAK4, OSM, IL10alpha, ARG2, CReactiveProtein, TIFA | 0.82 | 0.79 | 0.85 |
| TDRD9, TNFSF10, GADD45B, CReactiveProtein, IL8, ARG2, ANXA3, TGFBI, IL1RN, CCL5 | 0.82 | 0.85 | 0.78 |
| IL10alpha, ANXA3, TNFSF10, IL1RN, TGFBI, FAD104, INSL3, MAP2K6, MAPK14, ApolipoproteinCIII | 0.82 | 0.85 | 0.78 |
| TIMP1, Beta2Microglobulin, ITGAM, LDLR, MCP1, IL8, FCGR1A, TIFA, IL10alpha, MAP2K6 | 0.82 | 0.82 | 0.81 |
| TNFRSF6, TGFBI, JAK2, SOD2, ANXA3, VNN1, CCL5, INSL3, CSF1R, IL10 | 0.82 | 0.82 | 0.81 |
| TDRD9, IL10alpha, MAPK14, NCR1, LY96, GADD45B, IRAK2, CReactiveProtein, INSL3, ITGAM | 0.82 | 0.8 | 0.83 |
| LDLR, JAK2, IFNGR1, IRAK2, SOCS3, ITGAM, Protein_MMP9, INSL3, ApolipoproteinCIII, CEACAM1 | 0.82 | 0.79 | 0.84 |
| CSF1R, Beta2Microglobulin, IRAK4, MKNK1, PRV1, TNFRSF6, PSTPIP2, IL18R1, HLA-DRA, CCL5 | 0.82 | 0.78 | 0.85 |
| BCL2A1, TLR4, IL8, TIMP1, SOD2, CReactiveProtein, CRTAP, ApolipoproteinCIII, GADD45B, FAD104 | 0.82 | 0.77 | 0.86 |
| ARG2, OSM, TNFSF13B, CReactiveProtein, AlphaFetoprotein, IL6, CRTAP, Beta2Microglobulin, MCP1, TDRD9 | 0.81 | 0.86 | 0.77 |
| FAD104, TNFSF13B, IL1RN, GADD45B, IFNGR1, IL18R1, TNFRSF6, MCP1, PRV1, IL8 | 0.81 | 0.82 | 0.8 |
| IL8, ITGAM, CSF1R, TNFRSF6, INSL3, IL10alpha, IFNGR1, IL10, IL1RN, SOD2 | 0.81 | 0.82 | 0.81 |
| MCP1, IFNGR1, TNFRSF6, MAPK14, FAD104, IL18R1, IRAK4, INSL3, IL10alpha, Beta2Microglobulin | 0.81 | 0.78 | 0.84 |
| NCR1, PRV1, Protein_MMP9, TIMP1, ANKRD22, INSL3, CD86, CCL5, MKNK1, Gene_MMP9 | 0.81 | 0.74 | 0.88 |
| NCR1, INSL3, CEACAM1, FAD104, IL10alpha, TIFA, TNFSF13B, IL6, CCL5, CReactiveProtein | 0.81 | 0.86 | 0.76 |

TABLE N-continued

Exemplary sets of biomarkers used in the methods or kits referenced in Sections 5.2 and 5.3

| BIOMARKER SET | ACCURACY | SPECIFICITY | SENSISTIVITY |
|---|---|---|---|
| CRTAP, IL1RN, IL18R1, FAD104, NCR1, HLA-DRA, TGFBI, LY96, IL6, IRAK4 | 0.81 | 0.8 | 0.82 |
| OSM, NCR1, IL8, GADD45B, Protein_MMP9, TNFRSF6, TNFSF13B, Beta2Microglobulin, IL1RN, IRAK2 | 0.81 | 0.8 | 0.82 |
| CD86, IL10alpha, CSF1R, IRAK2, ANKRD22, OSM, AlphaFetoprotein, Gene_MMP9, IL10, IRAK4 | 0.81 | 0.79 | 0.83 |
| ARG2, IRAK4, GADD45A, VNN1, IL18R1, JAK2, ANXA3, CSF1R, HLA-DRA, PFKFB3 | 0.81 | 0.79 | 0.83 |
| LY96, TDRD9, NCR1, TNFRSF6, CSF1R, PRV1, IL18R1, ARG2, Beta2Microglobulin, IL10alpha | 0.81 | 0.76 | 0.86 |
| INSL3, TDRD9, CRTAP, TNFRSF6, IRAK4, SOD2, LDLR, ANKRD22, OSM, CSF1R | 0.81 | 0.75 | 0.88 |
| FAD104, PFKFB3, IL18R1, IL10, MAPK14, ARG2, CD86, IL1RN, CCL5, GADD45A | 0.81 | 0.83 | 0.79 |
| TNFSF10, CSF1R, TNFSF13B, MKNK1, ITGAM, PFKFB3, AlphaFetoprotein, SOCS3, TNFRSF6, FAD104 | 0.81 | 0.81 | 0.8 |
| CSF1R, PFKFB3, ApolipoproteinCIII, TLR4, ARG2, PRV1, ANKRD22, ITGAM, TIFA, TNFRSF6 | 0.81 | 0.81 | 0.81 |
| TGFBI, IL10, TDRD9, PFKFB3, INSL3, CSF1R, PSTPIP2, MKNK1, NCR1, HLA-DRA | 0.81 | 0.8 | 0.81 |
| ANKRD22, TIMP1, CRTAP, HLA-DRA, ApolipoproteinCIII, CD86, TNFRSF6, Gene_MMP9, VNN1, IL10 | 0.81 | 0.78 | 0.83 |
| ARG2, NCR1, IRAK4, FCGR1A, FAD104, TNFRSF6, PFKFB3, MAP2K6, TGFBI, MKNK1 | 0.81 | 0.77 | 0.84 |
| TLR4, ANKRD22, IL10alpha, VNN1, Protein_MMP9, TNFRSF6, ARG2, TNFSF10, OSM, FCGR1A | 0.81 | 0.76 | 0.84 |
| FAD104, PRV1, Protein_MMP9, IL10alpha, ARG2, TNFSF13B, FCGR1A, CEACAM1, CCL5, IL1RN | 0.81 | 0.75 | 0.86 |
| TNFRSF6, IL6, TGFBI, PSTPIP2, ANXA3, ANKRD22, ApolipoproteinCIII, OSM, SOCS3, MAPK14 | 0.8 | 0.83 | 0.78 |
| IL8, OSM, IRAK4, TDRD9, LDLR, TNFSF13B, IL10, IFNGR1, ARG2, SOD2 | 0.8 | 0.81 | 0.8 |
| PSTPIP2, BCL2A1, CD86, ANXA3, IL10alpha, SOD2, OSM, INSL3, TNFSF13B, GADD45B | 0.8 | 0.84 | 0.77 |
| IL6, ANXA3, SOCS3, MAP2K6, TGFBI, ANKRD22, CRTAP, BCL2A1, CCL5, TLR4 | 0.8 | 0.83 | 0.77 |
| HLA-DRA, CSF1R, TGFBI, MAP2K6, BCL2A1, CD86, TLR4, IL1RN, IL6, ApolipoproteinCIII | 0.8 | 0.82 | 0.78 |
| ApolipoproteinCIII, CCL5, SOCS3, TIMP1, Gene_MMP9, AlphaFetoprotein, ITGAM, INSL3, CEACAM1, LDLR | 0.8 | 0.81 | 0.79 |
| IL8, TNFRSF6, IL6, IL1RN, PSTPIP2, ApolipoproteinCIII, CD86, JAK2, TLR4, Protein_MMP9 | 0.8 | 0.79 | 0.81 |
| IL10alpha, JAK2, MCP1, CEACAM1, ApolipoproteinCIII, BCL2A1, PRV1, Protein_MMP9, MAP2K6, IFNGR1 | 0.8 | 0.78 | 0.82 |
| FCGR1A, LY96, JAK2, GADD45B, LDLR, IL6, VNN1, MCP1, Gene_MMP9, SOD2 | 0.8 | 0.77 | 0.82 |
| CSF1R, TNFRSF6, INSL3, MKNK1, IL8, MAP2K6, FAD104, NCR1, IL1RN, MCP1 | 0.86 | 0.85 | 0.86 |
| IL8, PRV1, SOCS3, IRAK2, ARG2, IL10alpha, NCR1, CCL5, CReactiveProtein, MKNK1 | 0.85 | 0.86 | 0.83 |
| LDLR, CD86, NCR1, IRAK4, IL18R1, Protein_MMP9, PRV1, GADD45B, ARG2, LY96, AlphaFetoprotein | 0.85 | 0.84 | 0.87 |
| MAP2K6, CD86, INSL3, ApolipoproteinCIII, IL8, OSM, TNFSF13B, IL1RN, BCL2A1, FAD104, GADD45A | 0.85 | 0.81 | 0.88 |

TABLE N-continued

Exemplary sets of biomarkers used in the methods or kits referenced in Sections 5.2 and 5.3

| BIOMARKER SET | ACCURACY | SPECIFICITY | SENSISTIVITY |
|---|---|---|---|
| NCR1, GADD45B, TNFSF10, IL10alpha, FAD104, LY96, IL6, IL10, ARG2, CReactiveProtein, TGFBI | 0.84 | 0.87 | 0.82 |
| CD86, CEACAM1, INSL3, PFKFB3, IL10alpha, FAD104, SOD2, Gene_MMP9, SOCS3, ApolipoproteinCIII, FCGR1A | 0.83 | 0.86 | 0.81 |
| SOCS3, ARG2, ApolipoproteinCIII, IRAK4, PFKFB3, IFNGR1, NCR1, IL8, CReactiveProtein, VNN1, TDRD9 | 0.83 | 0.84 | 0.82 |
| ARG2, OSM, CReactiveProtein, SOD2, CEACAM1, FCGR1A, TIMP1, IL10, IL18R1, ANKRD22, IRAK2 | 0.83 | 0.85 | 0.81 |
| TGFBI, SOD2, IL10, CD86, CEACAM1, TDRD9, IRAK4, ANXA3, LDLR, OSM, ARG2 | 0.83 | 0.83 | 0.83 |
| CReactiveProtein, IL10alpha, TIMP1, LY96, IL8, SOD2, MAP2K6, MAPK14, TLR4, PSTPIP2, INSL3 | 0.83 | 0.83 | 0.83 |
| ARG2, PSTPIP2, SOD2, INSL3, FAD104, JAK2, TIFA, PFKFB3, IRAK2, IL6, ANXA3 | 0.83 | 0.8 | 0.86 |
| PSTPIP2, CEACAM1, GADD45A, ApolipoproteinCIII, ITGAM, PRV1, TLR4, IL10alpha, ARG2, SOCS3, NCR1 | 0.83 | 0.84 | 0.82 |
| OSM, SOCS3, CSF1R, IRAK2, VNN1, IL6, SOD2, LDLR, BCL2A1, ANKRD22, CD86 | 0.83 | 0.82 | 0.83 |
| CRTAP, LDLR, TGFBI, INSL3, TIFA, FAD104, AlphaFetoprotein, IL8, JAK2, IRAK4, BCL2A1 | 0.83 | 0.82 | 0.83 |
| CD86, ITGAM, PSTPIP2, IL18R1, IL6, IFNGR1, GADD45B, IL10, Beta2Microglobulin, FCGR1A, FAD104 | 0.83 | 0.77 | 0.87 |
| PRV1, Beta2Microglobulin, IL1RN, NCR1, CSF1R, IFNGR1, TIMP1, SOCS3, LDLR, TIFA, ARG2 | 0.82 | 0.84 | 0.81 |
| IL10alpha, GADD45A, LDLR, SOCS3, MAP2K6, LY96, CSF1R, Protein_MMP9, MCP1, TDRD9, IL8 | 0.82 | 0.83 | 0.81 |
| CSF1R, TDRD9, TIMP1, SOD2, FCGR1A, IFNGR1, INSL3, CD86, TNFRSF6, HLA-DRA, MAP2K6 | 0.82 | 0.83 | 0.82 |
| IL8, IL18R1, BCL2A1, MKNK1, CReactiveProtein, CCL5, IL6, SOCS3, FCGR1A, PSTPIP2, ApolipoproteinCIII | 0.82 | 0.82 | 0.83 |
| ANXA3, IL6, CD86, SOD2, CEACAM1, FCGR1A, ANKRD22, NCR1, PSTPIP2, IL8, MAPK14 | 0.82 | 0.8 | 0.85 |
| Protein_MMP9, TNFRSF6, ITGAM, CSF1R, INSL3, TIFA, BCL2A1, IL1RN, TGFBI, FCGR1A, ApolipoproteinCIII | 0.82 | 0.79 | 0.85 |
| ANKRD22, IL10alpha, SOCS3, IRAK4, OSM, INSL3, TGFBI, MCP1, IL8, TNFSF13B, PRV1 | 0.82 | 0.76 | 0.88 |
| ANKRD22, LDLR, VNN1, TIMP1, IRAK2, IL10alpha, GADD45B, ARG2, MAPK14, CSF1R, TNFRSF6 | 0.82 | 0.85 | 0.8 |
| TIFA, ARG2, TNFSF10, INSL3, CD86, IL8, IRAK2, OSM, CSF1R, HLA-DRA, ITGAM | 0.82 | 0.82 | 0.82 |
| ANKRD22, TIFA, PSTPIP2, CCL5, Gene_MMP9, Beta2Microglobulin, NCR1, FCGR1A, INSL3, SOCS3, IL10alpha | 0.82 | 0.79 | 0.84 |
| ApolipoproteinCIII, AlphaFetoprotein, NCR1, CCL5, GADD45A, IL18R1, JAK2, TDRD9, OSM, TLR4, Gene_MMP9 | 0.82 | 0.82 | 0.81 |
| CReactiveProtein, IL18R1, TGFBI, TNFSF10, MAP2K6, LDLR, FAD104, ARG2, HLA-DRA, GADD45B, ANXA3 | 0.82 | 0.8 | 0.83 |
| IL18R1, IRAK4, LY96, INSL3, TNFRSF6, CReactiveProtein, CD86, GADD45B, CRTAP, IL8, MAPK14 | 0.82 | 0.8 | 0.83 |
| IL8, FCGR1A, CSF1R, VNN1, IL10alpha, PSTPIP2, IL6, IL1RN, TLR4, GADD45B, LY96 | 0.81 | 0.85 | 0.78 |

TABLE N-continued

Exemplary sets of biomarkers used in the methods or kits referenced in Sections 5.2 and 5.3

| BIOMARKER SET | ACCURACY | SPECIFICITY | SENSISTIVITY |
|---|---|---|---|
| HLA-DRA, IL6, FAD104, GADD45A, INSL3, ITGAM, CSF1R, IFNGR1, Protein_MMP9, SOCS3, NCR1 | 0.81 | 0.79 | 0.84 |
| IL10, LDLR, AlphaFetoprotein, IL1RN, INSL3, ApolipoproteinCIII, PSTPIP2, CCL5, SOD2, TGFBI, VNN1 | 0.81 | 0.79 | 0.84 |
| Protein_MMP9, IL10, TGFBI, INSL3, IRAK2, TNFRSF6, IL8, PSTPIP2, OSM, AlphaFetoprotein, NCR1 | 0.81 | 0.84 | 0.78 |
| IL8, TLR4, MCP1, ApolipoproteinCIII, Beta2Microglobulin, IL6, IL10, VNN1, CD86, PSTPIP2, ITGAM | 0.81 | 0.83 | 0.79 |
| FAD104, GADD45A, SOCS3, PSTPIP2, IL6, TGFBI, TIMP1, HLA-DRA, TNFSF10, IL10alpha, MKNK1 | 0.81 | 0.81 | 0.81 |
| PRV1, IL8, FCGR1A, GADD45A, IRAK2, VNN1, CD86, IL18R1, Protein_MMP9, MAP2K6, ITGAM | 0.81 | 0.81 | 0.81 |
| CRTAP, JAK2, IRAK2, CEACAM1, PRV1, CCL5, SOD2, BCL2A1, SOCS3, IL1RN, ApolipoproteinCIII | 0.81 | 0.79 | 0.82 |
| MCP1, CCL5, HLA-DRA, IRAK4, OSM, LDLR, PFKFB3, CReactiveProtein, MKNK1, GADD45A, LY96 | 0.81 | 0.76 | 0.85 |
| ARG2, INSL3, IL6, ITGAM, TGFBI, LDLR, IL10, CD86, IL8, TNFSF13B, IL10alpha | 0.81 | 0.82 | 0.79 |
| Protein_MMP9, CD86, GADD45B, LY96, SOD2, FCGR1A, IL8, AlphaFetoprotein, CSF1R, FAD104, CRTAP | 0.81 | 0.82 | 0.8 |
| TNFSF13B, ApolipoproteinCIII, LDLR, TDRD9, CEACAM1, AlphaFetoprotein, IRAK4, INSL3, GADD45A, CRTAP, IFNGR1 | 0.81 | 0.77 | 0.84 |
| MKNK1, PSTPIP2, Beta2Microglobulin, ANKRD22, TIFA, IL10alpha, TGFBI, AlphaFetoprotein, NCR1, PRV1, SOCS3 | 0.8 | 0.82 | 0.79 |
| TIFA, MKNK1, IL6, ANXA3, FAD104, PSTPIP2, TNFSF13B, LDLR, INSL3, SOD2, JAK2 | 0.8 | 0.82 | 0.79 |
| TNFSF13B, IFNGR1, IL18R1, CD86, Beta2Microglobulin, TGFBI, CSF1R, CReactiveProtein, CRTAP, MCP1, JAK2 | 0.8 | 0.81 | 0.8 |
| TNFSF13B, Beta2Microglobulin, CSF1R, JAK2, CRTAP, IL1RN, IL10, SOCS3, ANKRD22, PFKFB3, LDLR | 0.8 | 0.79 | 0.82 |
| TNFRSF6, OSM, PRV1, INSL3, TLR4, MKNK1, IRAK4, HLA-DRA, VNN1, IL10alpha, FCGR1A | 0.8 | 0.77 | 0.83 |
| IL8, ApolipoproteinCIII, GADD45B, SOCS3, ARG2, TNFSF13B, IL1RN, CCL5, ANXA3, CReactiveProtein, TIFA | 0.8 | 0.77 | 0.83 |
| TNFSF13B, SOCS3, Protein_MMP9, SOD2, TNFRSF6, NCR1, FAD104, IL6, OSM, CCL5, TDRD9 | 0.8 | 0.76 | 0.86 |
| CD86, INSL3, ANXA3, GADD45B, VNN1, IFNGR1, IL6, PFKFB3, PSTPIP2, Beta2Microglobulin, IRAK2 | 0.8 | 0.84 | 0.77 |
| IL6, Gene_MMP9, FAD104, TIFA, TGFBI, Beta2Microglobulin, IL10alpha, ANXA3, IL18R1, NCR1, INSL3 | 0.8 | 0.82 | 0.78 |
| CEACAM1, JAK2, MCP1, OSM, IL18R1, MKNK1, ANKRD22, TLR4, CSF1R, PSTPIP2, IL1RN | 0.8 | 0.82 | 0.78 |
| CSF1R, AlphaFetoprotein, HLA-DRA, TDRD9, ITGAM, SOCS3, FCGR1A, IRAK2, TIFA, TNFSF10, Protein_MMP9 | 0.8 | 0.8 | 0.8 |
| CSF1R, IL10alpha, TNFRSF6, TNFSF13B, LDLR, INSL3, AlphaFetoprotein, IL10, TIFA, VNN1, HLA-DRA | 0.8 | 0.79 | 0.81 |
| IL18R1, MCP1, ANKRD22, TGFBI, ARG2, ANXA3, GADD45A, IL1RN, TNFRSF6, PSTPIP2, IRAK2 | 0.8 | 0.77 | 0.83 |
| IL10alpha, IFNGR1, MAPK14, FCGR1A, Gene_MMP9, GADD45A, VNN1, ANKRD22, TNFSF13B, CCL5, IRAK2 | 0.8 | 0.76 | 0.83 |

TABLE N-continued

Exemplary sets of biomarkers used in the methods or kits referenced in Sections 5.2 and 5.3

| BIOMARKER SET | ACCURACY | SPECIFICITY | SENSISTIVITY |
|---|---|---|---|
| IL8, CReactiveProtein, CSF1R, TLR4, TNFRSF6, Gene_MMP9, TDRD9, OSM, PFKFB3, IFNGR1, ApolipoproteinCIII, PSTPIP2 | 0.85 | 0.85 | 0.85 |
| JAK2, OSM, GADD45B, MCP1, IL1RN, ANKRD22, IL18R1, Gene_MMP9, ITGAM, NCR1, ApolipoproteinCIII, PFKFB3 | 0.85 | 0.81 | 0.88 |
| TNFSF10, MKNK1, PFKFB3, ANXA3, CRTAP, CD86, MAPK14, IL8, OSM, GADD45B, HLA-DRA, INSL3 | 0.84 | 0.84 | 0.84 |
| IL1RN, AlphaFetoprotein, ARG2, MAP2K6, CEACAM1, GADD45B, CRTAP, ANXA3, INSL3, ApolipoproteinCIII, NCR1, FAD104 | 0.83 | 0.86 | 0.82 |
| IL6, LDLR, TDRD9, TNFRSF6, NCR1, ITGAM, AlphaFetoprotein, FCGR1A, ARG2, TNFSF10, OSM, BCL2A1 | 0.83 | 0.84 | 0.83 |
| IL10, SOD2, GADD45A, TNFSF13B, IRAK4, LY96, HLA-DRA, PSTPIP2, IL6, IFNGR1, ARG2, LDLR | 0.83 | 0.86 | 0.81 |
| CCL5, CSF1R, LDLR, GADD45A, INSL3, JAK2, AlphaFetoprotein, OSM, Beta2Microglobulin, PRV1, HLA-DRA, MKNK1 | 0.83 | 0.8 | 0.86 |
| ANKRD22, TNFSF13B, TIMP1, VNN1, IRAK4, FCGR1A, CEACAM1, IRAK2, ARG2, ANXA3, CD86, IL1RN | 0.83 | 0.83 | 0.83 |
| JAK2, AlphaFetoprotein, IL1RN, SOCS3, ANKRD22, IL10alpha, IL8, TGFBI, CD86, IL10, CSF1R, CReactiveProtein | 0.82 | 0.83 | 0.82 |
| VNN1, GADD45B, MAP2K6, TNFSF13B, IRAK2, TLR4, CReactiveProtein, PSTPIP2, MCP1, CSF1R, IL8, TDRD9 | 0.82 | 0.79 | 0.85 |
| SOD2, IL10, CReactiveProtein, ApolipoproteinCIII, Beta2Microglobulin, IFNGR1, OSM, TNFSF13B, VNN1, GADD45B, CD86, PFKFB3 | 0.82 | 0.77 | 0.86 |
| LDLR, CRTAP, PSTPIP2, GADD45B, IL8, TNFRSF6, MAP2K6, IL10, ARG2, LY96, MAPK14, IL18R1 | 0.82 | 0.82 | 0.82 |
| IFNGR1, NCR1, ApolipoproteinCIII, ANXA3, CSF1R, CCL5, FCGR1A, TIFA, TLR4, INSL3, IL8, ARG2 | 0.82 | 0.82 | 0.82 |
| LY96, Beta2Microglobulin, CCL5, LDLR, IRAK4, TIMP1, MKNK1, ApolipoproteinCIII, IL8, SOCS3, ANKRD22, PRV1 | 0.82 | 0.78 | 0.86 |
| Protein_MMP9, MAPK14, IL1RN, SOCS3, MKNK1, ApolipoproteinCIII, IL10, OSM, MAP2K6, TNFSF13B, NCR1, IL18R1 | 0.82 | 0.77 | 0.87 |
| TNFSF13B, FAD104, OSM, TNFRSF6, TDRD9, TIFA, IL10alpha, INSL3, Protein_MMP9, HLA-DRA, Beta2Microglobulin, ApolipoproteinCIII | 0.82 | 0.81 | 0.83 |
| TLR4, Protein_MMP9, VNN1, IFNGR1, ITGAM, MCP1, LY96, IRAK2, OSM, TDRD9, IL8, ApolipoproteinCIII | 0.82 | 0.78 | 0.85 |
| MAP2K6, OSM, GADD45B, IL1RN, MAPK14, ARG2, LY96, VNN1, TNFRSF6, TGFBI, CD86, Beta2Microglobulin | 0.81 | 0.81 | 0.81 |
| MKNK1, ARG2, CEACAM1, GADD45A, AlphaFetoprotein, GADD45B, HLA-DRA, CReactiveProtein, SOD2, TLR4, LDLR, TNFRSF6 | 0.81 | 0.81 | 0.81 |
| Protein_MMP9, TGFBI, PRV1, Beta2Microglobulin, TNFSF13B, TLR4, INSL3, Gene_MMP9, ARG2, ApolipoproteinCIII, MKNK1, IL10alpha | 0.81 | 0.81 | 0.82 |
| TLR4, TGFBI, FCGR1A, NCR1, LY96, IL10, CCL5, IRAK2, INSL3, TDRD9, OSM, BCL2A1 | 0.81 | 0.81 | 0.82 |
| Gene_MMP9, FCGR1A, PSTPIP2, TIFA, CSF1R, SOD2, ITGAM, PFKFB3, JAK2, IL8, LY96, OSM | 0.81 | 0.81 | 0.82 |
| CRTAP, MKNK1, TDRD9, LY96, TLR4, TNFSF10, SOD2, JAK2, | 0.81 | 0.8 | 0.83 |

TABLE N-continued

Exemplary sets of biomarkers used in the methods or kits referenced in Sections 5.2 and 5.3

| BIOMARKER SET | ACCURACY | SPECIFICITY | SENSISTIVITY |
|---|---|---|---|
| Beta2Microglobulin, CD86, PSTPIP2, MAP2K6 | | | |
| TGFBI, TDRD9, ARG2, OSM, TNFSF13B, CEACAM1, CCL5, CReactiveProtein, TLR4, IL10alpha, LY96, SOCS3 | 0.81 | 0.78 | 0.85 |
| IRAK2, LDLR, ARG2, SOD2, IL10alpha, ANKRD22, FCGR1A, Beta2Microglobulin, FAD104, ITGAM, PRV1, OSM | 0.81 | 0.78 | 0.84 |
| FAD104, IL10alpha, INSL3, IL18R1, IL1RN, MKNK1, MAP2K6, Gene_MMP9, IRAK2, PSTPIP2, CEACAM1, IL6 | 0.81 | 0.83 | 0.79 |
| VNN1, ApolipoproteinCIII, IL10, JAK2, Protein_MMP9, INSL3, Beta2Microglobulin, OSM, IRAK4, MAP2K6, IL1RN, AlphaFetoprotein | 0.81 | 0.82 | 0.8 |
| BCL2A1, GADD45A, JAK2, FCGR1A, FAD104, Gene_MMP9, CRTAP, TDRD9, MAP2K6, CSF1R, PRV1, Protein_MMP9 | 0.81 | 0.81 | 0.81 |
| INSL3, TIFA, LY96, FAD104, PSTPIP2, PFKFB3, Beta2Microglobulin, TIMP1, IL18R1, GADD45A, IL6, AlphaFetoprotein | 0.81 | 0.8 | 0.82 |
| TDRD9, PFKFB3, CSF1R, ITGAM, MCP1, ARG2, TNFSF13B, PSTPIP2, MAP2K6, ANXA3, OSM, TGFBI | 0.81 | 0.79 | 0.83 |
| TNFSF10, TNFRSF6, Beta2Microglobulin, PRV1, SOCS3, IL8, VNN1, TDRD9, CReactiveProtein, GADD45B, TNFSF13B, CD86 | 0.81 | 0.77 | 0.84 |
| MAP2K6, IFNGR1, LY96, Beta2Microglobulin, GADD45B, ANKRD22, SOCS3, ANXA3, INSL3, Protein_MMP9, CD86, HLA-DRA | 0.81 | 0.76 | 0.85 |
| SOD2, TIMP1, ApolipoproteinCIII, Protein_MMP9, FAD104, ANXA3, TLR4, CCL5, ITGAM, IRAK4, SOCS3, HLA-DRA | 0.81 | 0.76 | 0.85 |
| ITGAM, INSL3, FCGR1A, ARG2, IRAK2, FAD104, IRAK4, MAPK14, LY96, TIMP1, PRV1, TLR4, CD86 | 0.85 | 0.82 | 0.88 |
| PRV1, MKNK1, IL8, FAD104, VNN1, SOCS3, ARG2, MAP2K6, IL1RN, SOD2, IL18R1, NCR1, BCL2A1 | 0.85 | 0.84 | 0.86 |
| NCR1, CEACAM1, IRAK4, ARG2, TNFSF13B, PFKFB3, OSM, TNFRSF6, SOCS3, HLA-DRA, TNFSF10, JAK2, SOD2 | 0.85 | 0.79 | 0.89 |
| MCP1, Protein_MMP9, IL10alpha, FAD104, FCGR1A, ITGAM, TGFBI, ApolipoproteinCIII, ARG2, PRV1, CRTAP, TIFA, LDLR | 0.84 | 0.81 | 0.87 |
| ARG2, ANKRD22, GADD45B, IRAK2, OSM, MKNK1, ANXA3, IL18R1, TNFRSF6, MAP2K6, AlphaFetoprotein, MCP1, ApolipoproteinCIII | 0.84 | 0.83 | 0.85 |
| HLA-DRA, NCR1, CEACAM1, Beta2Microglobulin, VNN1, AlphaFetoprotein, MCP1, IL6, FCGR1A, OSM, CSF1R, IRAK2, CRTAP | 0.83 | 0.82 | 0.85 |
| CReactiveProtein, SOD2, GADD45A, ARG2, IRAK4, FCGR1A, IL18R1, TLR4, JAK2, BCL2A1, IL10alpha, TGFBI, AlphaFetoprotein | 0.83 | 0.86 | 0.81 |
| ApolipoproteinCIII, HLA-DRA, TNFSF10, TLR4, IL10, GADD45B, BCL2A1, IL6, CCL5, INSL3, MAP2K6, LDLR, IFNGR1 | 0.83 | 0.83 | 0.83 |
| TIFA, JAK2, HLA-DRA, SOCS3, ARG2, OSM, AlphaFetoprotein, MAPK14, IRAK2, IFNGR1, FCGR1A, MAP2K6, PRV1 | 0.83 | 0.79 | 0.87 |
| Beta2Microglobulin, IRAK2, MKNK1, ANKRD22, CD86, OSM, CSF1R, TNFSF10, IFNGR1, TLR4, MCP1, FAD104, TGFBI | 0.83 | 0.83 | 0.83 |
| VNN1, FCGR1A, ANKRD22, CRTAP, ANXA3, IL8, PFKFB3, NCR1, TLR4, AlphaFetoprotein, TIFA, IRAK4, CD86 | 0.83 | 0.82 | 0.84 |

TABLE N-continued

Exemplary sets of biomarkers used in the methods or kits referenced in Sections 5.2 and 5.3

| BIOMARKER SET | ACCURACY | SPECIFICITY | SENSISTIVITY |
|---|---|---|---|
| Gene_MMP9, INSL3, FCGR1A, LDLR, OSM, PFKFB3, ANKRD22, IL1RN, IL8, IFNGR1, TDRD9, BCL2A1, TNFSF13B | 0.83 | 0.81 | 0.84 |
| PFKFB3, AlphaFetoprotein, IRAK4, NCR1, TNFSF10, TDRD9, JAK2, FAD104, IL10alpha, PRV1, CReactiveProtein, TGFBI, Protein_MMP9 | 0.82 | 0.81 | 0.84 |
| Gene_MMP9, MAP2K6, MAPK14, CReactiveProtein, PFKFB3, CCL5, CSF1R, INSL3, MKNK1, ARG2, FAD104, SOD2, Protein_MMP9 | 0.82 | 0.76 | 0.88 |
| IL8, TNFSF13B, ARG2, TIFA, CRTAP, OSM, IL18R1, MCP1, IRAK4, LY96, AlphaFetoprotein, TDRD9, CReactiveProtein | 0.82 | 0.85 | 0.79 |
| PSTPIP2, CEACAM1, GADD45B, MAPK14, ARG2, FCGR1A, ITGAM, TGFBI, IL10alpha, OSM, PRV1, IL8, TLR4 | 0.82 | 0.83 | 0.81 |
| OSM, CReactiveProtein, CD86, LY96, IL10alpha, FAD104, TDRD9, IL6, ApolipoproteinCIII, LDLR, CSF1R, IL18R1, MCP1 | 0.82 | 0.82 | 0.82 |
| JAK2, IL8, ARG2, OSM, BCL2A1, TIFA, IL6, Gene_MMP9, PRV1, TLR4, IL1RN, LY96, IRAK2 | 0.82 | 0.83 | 0.8 |
| IL6, INSL3, BCL2A1, TLR4, HLA-DRA, IL10alpha, MKNK1, TDRD9, GADD45A, OSM, SOCS3, CCL5, MAPK14 | 0.82 | 0.81 | 0.82 |
| LDLR, FCGR1A, SOD2, LY96, MKNK1, PRV1, MAP2K6, NCR1, Protein_MMP9, SOCS3, AlphaFetoprotein, IFNGR1, INSL3 | 0.82 | 0.77 | 0.86 |
| TNFRSF6, ARG2, INSL3, ANXA3, IL10, TIFA, ITGAM, VNN1, SOD2, TIMP1, CSF1R, Protein_MMP9, SOCS3 | 0.82 | 0.77 | 0.87 |
| IL10alpha, TNFRSF6, ARG2, TIMP1, IL8, CSF1R, MAP2K6, IRAK4, PFKFB3, FCGR1A, AlphaFetoprotein, OSM, HLA-DRA | 0.81 | 0.85 | 0.78 |
| Protein_MMP9, CD86, IFNGR1, TIMP1, IL1RN, FCGR1A, ARG2, TIFA, IL8, CRTAP, CSF1R, IL6, ITGAM | 0.81 | 0.81 | 0.81 |
| CEACAM1, ANKRD22, CCL5, TLR4, IRAK4, Beta2Microglobulin, MAP2K6, PRV1, TGFBI, FAD104, SOD2, JAK2, MCP1 | 0.81 | 0.81 | 0.82 |
| CD86, VNN1, PSTPIP2, PFKFB3, CReactiveProtein, IL6, TLR4, CCL5, FCGR1A, TDRD9, TNFRSF6, CSF1R, CRTAP | 0.81 | 0.86 | 0.77 |
| LDLR, OSM, MCP1, CD86, IL1RN, Protein_MMP9, MAP2K6, FCGR1A, IL8, CEACAM1, PFKFB3, IRAK4, LY96 | 0.81 | 0.83 | 0.78 |
| CReactiveProtein, TNFSF13B, ApolipoproteinCIII, IRAK2, VNN1, FCGR1A, PFKFB3, HLA-DRA, ANKRD22, SOD2, CD86, TGFBI, Beta2Microglobulin | 0.81 | 0.79 | 0.82 |
| LY96, TNFSF10, PRV1, PSTPIP2, SOCS3, TIMP1, IFNGR1, ARG2, CEACAM1, CCL5, TNFSF13B, LDLR, ApolipoproteinCIII | 0.81 | 0.79 | 0.83 |
| PRV1, JAK2, FCGR1A, VNN1, SOCS3, TIFA, CRTAP, INSL3, IFNGR1, TDRD9, CEACAM1, Protein_MMP9, IL8 | 0.81 | 0.79 | 0.83 |
| GADD45A, SOCS3, OSM, CD86, ITGAM, ApolipoproteinCIII, FAD104, INSL3, PSTPIP2, IL18R1, AlphaFetoprotein, TDRD9, MAP2K6 | 0.81 | 0.77 | 0.84 |
| PSTPIP2, VNN1, IL1RN, CSF1R, CD86, TLR4, IRAK4, IFNGR1, CRTAP, TNFSF10, SOD2, TIFA, TDRD9 | 0.81 | 0.77 | 0.85 |
| TNFRSF6, IFNGR1, TNFSF13B, MAP2K6, MKNK1, ANXA3, TGFBI, OSM, ARG2, Beta2Microglobulin, CReactiveProtein, LY96, ApolipoproteinCIII, TIFA | 0.85 | 0.88 | 0.83 |

TABLE N-continued

Exemplary sets of biomarkers used in the methods or kits referenced in Sections 5.2 and 5.3

| BIOMARKER SET | ACCURACY | SPECIFICITY | SENSISTIVITY |
|---|---|---|---|
| CSF1R, TLR4, IL6, TNFSF13B, Beta2Microglobulin, IRAK4, FCGR1A, CCL5, ITGAM, VNN1, TIFA, CRTAP, PFKFB3, TDRD9 | 0.84 | 0.85 | 0.83 |
| CReactiveProtein, IL6, MAP2K6, OSM, ARG2, ANKRD22, JAK2, HLA-DRA, ApolipoproteinCIII, MAPK14, TLR4, TNFSF13B, IFNGR1, IL10alpha | 0.84 | 0.82 | 0.85 |
| VNN1, GADD45B, IRAK2, TGFBI, NCR1, IL6, CEACAM1, CRTAP, Gene_MMP9, TNFRSF6, CD86, TDRD9, CReactiveProtein, IL10 | 0.84 | 0.77 | 0.89 |
| CRTAP, IL18R1, Beta2Microglobulin, ANXA3, TDRD9, MKNK1, Protein_MMP9, IL6, TNFSF10, OSM, MCP1, PFKFB3, ApolipoproteinCIII, VNN1 | 0.83 | 0.81 | 0.85 |
| PSTPIP2, IL8, IL18R1, CEACAM1, HLA-DRA, OSM, NCR1, MCP1, FCGR1A, TNFRSF6, TLR4, IRAK2, Protein_MMP9, CReactiveProtein | 0.83 | 0.79 | 0.86 |
| PRV1, IRAK4, FAD104, TGFBI, Protein_MMP9, INSL3, AlphaFetoprotein, CD86, VNN1, CSF1R, Beta2Microglobulin, GADD45B, BCL2A1, IL10 | 0.83 | 0.83 | 0.82 |
| CD86, MAP2K6, PSTPIP2, TNFSF10, OSM, GADD45B, TLR4, HLA-DRA, LY96, TNFSF13B, ARG2, SOD2, PRV1, Beta2Microglobulin | 0.83 | 0.81 | 0.84 |
| TIFA, CSF1R, IL10alpha, IFNGR1, CEACAM1, CRTAP, ANKRD22, FCGR1A, MAP2K6, FAD104, PSTPIP2, MAPK14, ARG2, IRAK2 | 0.83 | 0.77 | 0.87 |
| CReactiveProtein, TDRD9, IL8, ITGAM, IL10alpha, TNFRSF6, SOD2, MCP1, SOCS3, MKNK1, FAD104, MAP2K6, IFNGR1, AlphaFetoprotein | 0.82 | 0.86 | 0.78 |
| TLR4, ANKRD22, IL10alpha, CReactiveProtein, ApolipoproteinCIII, BCL2A1, FCGR1A, SOD2, OSM, IFNGR1, TGFBI, TIFA, VNN1, CEACAM1 | 0.82 | 0.86 | 0.78 |
| FCGR1A, IRAK4, MAP2K6, ANXA3, MAPK14, INSL3, AlphaFetoprotein, IL8, MKNK1, ARG2, VNN1, TIMP1, CSF1R, GADD45A | 0.82 | 0.86 | 0.79 |
| ANKRD22, HLA-DRA, IFNGR1, GADD45A, TNFSF13B, FAD104, LDLR, IL10alpha, IL6, MAPK14, ApolipoproteinCIII, PRV1, CReactiveProtein, TIMP1 | 0.82 | 0.81 | 0.84 |
| IL10, PSTPIP2, INSL3, LY96, NCR1, MAPK14, VNN1, MCP1, PRV1, ApolipoproteinCIII, TIMP1, Protein_MMP9, TDRD9, PFKFB3 | 0.82 | 0.76 | 0.87 |
| TNFRSF6, TGFBI, LY96, TDRD9, CRTAP, AlphaFetoprotein, TNFSF10, CCL5, JAK2, IL6, IRAK2, HLA-DRA, OSM, ApolipoproteinCIII | 0.82 | 0.85 | 0.79 |
| TIFA, Gene_MMP9, IL18R1, TDRD9, SOCS3, TIMP1, IL6, CCL5, ARG2, CSF1R, OSM, IL10alpha, IL8, TNFSF13B | 0.82 | 0.84 | 0.8 |
| PSTPIP2, PRV1, MAPK14, OSM, CRTAP, IFNGR1, IL6, FAD104, IL18R1, JAK2, GADD45B, LY96, BCL2A1, TLR4 | 0.82 | 0.82 | 0.82 |
| GADD45A, IL6, TGFBI, BCL2A1, CRTAP, CCL5, TIFA, TLR4, CD86, PRV1, FAD104, TDRD9, TNFSF10, SOCS3 | 0.82 | 0.8 | 0.84 |
| Beta2Microglobulin, JAK2, TDRD9, PSTPIP2, HLA-DRA, IL1RN, TGFBI, INSL3, ARG2, LDLR, AlphaFetoprotein, IRAK2, SOD2, MAPK14 | 0.82 | 0.79 | 0.85 |
| CD86, FAD104, AlphaFetoprotein, Gene_MMP9, MCP1, HLA-DRA, INSL3, PSTPIP2, IL1RN, ITGAM, TIMP1, Protein_MMP9, IL6, IRAK4 | 0.82 | 0.77 | 0.86 |

TABLE N-continued

Exemplary sets of biomarkers used in the methods or kits referenced in Sections 5.2 and 5.3

| BIOMARKER SET | ACCURACY | SPECIFICITY | SENSISTIVITY |
|---|---|---|---|
| ANKRD22, MAPK14, GADD45A, TDRD9, IL10alpha, Protein_MMP9, ARG2, CD86, TIMP1, IRAK2, TIFA, VNN1, OSM, ITGAM | 0.82 | 0.88 | 0.75 |
| SOCS3, IL1RN, CEACAM1, FCGR1A, LDLR, CCL5, CReactiveProtein, AlphaFetoprotein, ARG2, IL6, CD86, MCP1, INSL3, IL18R1 | 0.82 | 0.85 | 0.79 |
| ANKRD22, FAD104, ApolipoproteinCIII, IRAK2, TNFSF13B, TGFBI, TLR4, CRTAP, MCP1, LDLR, JAK2, SOD2, PSTPIP2, Protein_MMP9 | 0.82 | 0.84 | 0.79 |
| BCL2A1, IL1RN, FCGR1A, GADD45A, JAK2, NCR1, TDRD9, TIFA, TNFSF10, Protein_MMP9, CRTAP, CSF1R, IL6, INSL3 | 0.82 | 0.84 | 0.79 |
| SOD2, ITGAM, ApolipoproteinCIII, ANXA3, FAD104, IL6, ARG2, CD86, TGFBI, SOCS3, OSM, TDRD9, IL18R1, LY96 | 0.82 | 0.8 | 0.83 |
| VNN1, IRAK2, ApolipoproteinCIII, IL10, TDRD9, FCGR1A, IL8, TIMP1, MCP1, JAK2, TIFA, TGFBI, OSM, MAPK14 | 0.82 | 0.79 | 0.84 |
| ApolipoproteinCIII, IL10, TDRD9, ARG2, IRAK4, ANXA3, TNFRSF6, CReactiveProtein, INSL3, JAK2, IL1RN, IL6, NCR1, Gene_MMP9 | 0.82 | 0.78 | 0.85 |
| CD86, CSF1R, TNFSF13B, FCGR1A, MCP1, GADD45A, LDLR, IRAK2, CCL5, Beta2Microglobulin, SOCS3, MAP2K6, LY96, INSL3 | 0.81 | 0.83 | 0.79 |
| MCP1, NCR1, TGFBI, TDRD9, MAP2K6, ApolipoproteinCIII, INSL3, LY96, IFNGR1, JAK2, Protein_MMP9, GADD45B, IRAK4, CCL5 | 0.81 | 0.83 | 0.8 |
| Beta2Microglobulin, FCGR1A, TNFSF13B, OSM, IRAK4, IRAK2, IL8, MAPK14, PSTPIP2, TIFA, TIMP1, ApolipoproteinCIII, MAP2K6, TLR4 | 0.81 | 0.82 | 0.8 |
| TNFSF13B, LY96, OSM, MAP2K6, IRAK2, CRTAP, JAK2, PFKFB3, BCL2A1, CReactiveProtein, INSL3, GADD45A, TIFA, IL10alpha | 0.81 | 0.82 | 0.81 |
| OSM, JAK2, GADD45A, CEACAM1, ARG2, NCR1, TLR4, PRV1, PFKFB3, IL8, Beta2Microglobulin, GADD45B, HLA-DRA, INSL3 | 0.81 | 0.82 | 0.81 |
| LY96, TIFA, CSF1R, IL10, SOCS3, ARG2, IRAK4, CD86, IL10alpha, Protein_MMP9, TNFSF10, ITGAM, Gene_MMP9, LDLR | 0.81 | 0.79 | 0.83 |
| AlphaFetoprotein, ApolipoproteinCIII, SOD2, PSTPIP2, CSF1R, Beta2Microglobulin, NCR1, GADD45B, FCGR1A, CReactiveProtein, CEACAM1, CD86, Protein_MMP9, HLA-DRA | 0.81 | 0.78 | 0.84 |
| MAPK14, ARG2, TNFSF10, TNFSF13B, FAD104, ANKRD22, GADD45A, ANXA3, CReactiveProtein, NCR1, IFNGR1, OSM, Protein_MMP9, IL18R1 | 0.81 | 0.74 | 0.88 |
| VNN1, NCR1, IL10alpha, ARG2, IL6, LY96, CReactiveProtein, JAK2, TGFBI, SOCS3, CRTAP, ITGAM, IRAK4, PRV1 | 0.81 | 0.84 | 0.79 |
| TNFSF13B, CReactiveProtein, INSL3, CEACAM1, Beta2Microglobulin, CD86, IL6, JAK2, ApolipoproteinCIII, IL18R1, ANXA3, PSTPIP2, SOD2, IL1RN | 0.81 | 0.78 | 0.84 |
| IRAK2, FCGR1A, Gene_MMP9, BCL2A1, TGFBI, PSTPIP2, CEACAM1, GADD45A, CCL5, TNFSF13B, ARG2, IL8, TIFA, IL18R1 | 0.81 | 0.78 | 0.84 |

In some embodiments, the methods or kits respectively described or referenced in Section 5.2 and Section 5.3 use any one of the subsets of biomarkers listed in Table O. The subsets of biomarkers listed in Table O were identified in the computational experiments described in Section 6.14.5, below, in which 4600 random subcombinations of the biomarkers listed in Table I were tested. Table O lists some of the biomarker sets that provided high accuracy scores against the validation population described in Section 6.14.5. Each row of Table O lists a single set of biomarkers that can be used in the methods and kits respectively referenced in Sections 5.2 and 5.3. In other words, each row of Table O describes a set of biomarkers that can be used to discriminate between sepsis and SIRS subjects. In some embodiments, nucleic acid forms of the biomarkers listed in Table O are used in the methods and kits respectively referenced in Sections 5.2 and 5.3. In some embodiments, protein forms of the biomarkers listed in Table O are used. In some embodiments, some of the biomarkers in a biomarker set from Table O are in protein form and some of the biomarkers in the same biomarker set from Table O are in nucleic acid form in the methods and kits respectively referenced in Sections 5.2 and 5.3.

In some embodiments, a given set of biomarkers from Table O is used with the addition of one, two, three, four, five, six, seven, eight, or nine or more additional biomarkers from from any one of Table 30, 31, 32, 33, 34, or 36 that are not within the given set of biomarkers from Table O. In Table O, accuracy, specificity, and sensitivity are described with reference to $T_{-36}$ time point data described in Section 6.14.6, below.

TABLE O

Exemplary sets of biomarkers used in the methods or kits referenced in Sections 5.2 and 5.3

| BIOMARKER SET | ACCURACY | SPECIFICITY | SENSITIVITY |
|---|---|---|---|
| SOCS3, ApolipoproteinCIII, NCR1 | 0.81 | 0.75 | 0.85 |
| IL8, PRV1, CEACAM1 | 0.8 | 0.79 | 0.8 |
| PSTPIP2, TLR4, GADD45B | 0.8 | 0.72 | 0.87 |
| ARG2, PRV1, MKNK1 | 0.79 | 0.71 | 0.85 |
| CD86, SOCS3, TLR4 | 0.79 | 0.74 | 0.82 |
| PRV1, GADD45B, TNFSF13B, ITGAM | 0.83 | 0.73 | 0.91 |
| PRV1, ApolipoproteinCIII, FCGR1A, LDLR | 0.81 | 0.78 | 0.84 |
| TNFRSF6, MAP2K6, PRV1, ANKRD22 | 0.81 | 0.77 | 0.85 |
| PRV1, ARG2, CD86, CEACAM1 | 0.81 | 0.8 | 0.82 |
| GADD45B, CReactiveProtein, PRV1, CD86 | 0.81 | 0.73 | 0.88 |
| GADD45B, TNFSF13B, FAD104, PFKFB3 | 0.81 | 0.73 | 0.86 |
| PRV1, FAD104, IL18R1, MCP1 | 0.8 | 0.69 | 0.88 |
| PRV1, IRAK2, PSTPIP2, ANXA3 | 0.8 | 0.68 | 0.87 |
| FCGR1A, JAK2, MKNK1, PRV1 | 0.8 | 0.65 | 0.91 |
| IL10, TNFSF13B, GADD45B, CEACAM1 | 0.79 | 0.73 | 0.85 |
| Beta2Microglobulin, GADD45B, ARG2, TNFSF13B, OSM | 0.81 | 0.73 | 0.88 |
| CD86, BCL2A1, PSTPIP2, PRV1, JAK2 | 0.8 | 0.71 | 0.89 |
| GADD45A, GADD45B, CSF1R, MAP2K6, PSTPIP2 | 0.8 | 0.69 | 0.88 |
| AlphaFetoprotein, CReactiveProtein, GADD45B, MAPK14, ANXA3 | 0.8 | 0.76 | 0.82 |
| PRV1, FCGR1A, NCR1, CReactiveProtein, TNFRSF6 | 0.8 | 0.74 | 0.84 |
| MAPK14, CSF1R, OSM, IL1RN, TLR4 | 0.8 | 0.74 | 0.84 |
| IRAK4, MAPK14, GADD45B, TNFSF13B, CSF1R | 0.8 | 0.71 | 0.86 |
| ITGAM, ANXA3, Beta2Microglobulin, PRV1, IRAK2 | 0.79 | 0.76 | 0.82 |
| NCR1, MCP1, PRV1, CD86, FCGR1A | 0.79 | 0.72 | 0.86 |
| CRTAP, Beta2Microglobulin, TDRD9, GADD45A, PRV1 | 0.79 | 0.65 | 0.91 |
| PRV1, PFKFB3, FCGR1A, TIFA, ANKRD22 | 0.79 | 0.73 | 0.84 |
| PRV1, ApolipoproteinCIII, FCGR1A, Protein_MMP9, TIMP1 | 0.79 | 0.72 | 0.85 |
| FCGR1A, IRAK2, TNFSF13B, OSM, CRTAP, PFKFB3 | 0.84 | 0.79 | 0.89 |
| ANXA3, CEACAM1, PRV1, OSM, MCP1, CCL5 | 0.81 | 0.77 | 0.84 |
| IRAK4, TNFSF10, MCP1, PRV1, MKNK1, SOCS3 | 0.81 | 0.75 | 0.84 |
| TGFBI, CEACAM1, CD86, MAPK14, LDLR, PRV1 | 0.8 | 0.76 | 0.83 |
| MCP1, GADD45B, CEACAM1, TIMP1, MAP2K6, IFNGR1 | 0.8 | 0.76 | 0.83 |
| LY96, PRV1, MCP1, IRAK2, CD86, TNFSF10 | 0.8 | 0.76 | 0.83 |
| BCL2A1, PRV1, LDLR, TNFSF10, IL18R1, SOCS3 | 0.8 | 0.73 | 0.85 |
| SOCS3, ApolipoproteinCIII, FCGR1A, TNFSF13B, IFNGR1, Beta2Microglobulin | 0.79 | 0.7 | 0.87 |

TABLE O-continued

Exemplary sets of biomarkers used in the methods or kits referenced in Sections 5.2 and 5.3

| BIOMARKER SET | ACCURACY | SPECIFICITY | SENSITIVITY |
|---|---|---|---|
| ARG2, PSTPIP2, TNFRSF6, GADD45B, MAPK14, TIMP1 | 0.79 | 0.82 | 0.77 |
| NCR1, IL8, FCGR1A, IL1RN, ApolipoproteinCIII, IFNGR1 | 0.79 | 0.73 | 0.84 |
| LDLR, MAP2K6, PRV1, TIMP1, HLA-DRA, CCL5 | 0.79 | 0.72 | 0.85 |
| TIFA, GADD45B, HLA-DRA, CEACAM1, OSM, ARG2 | 0.79 | 0.74 | 0.83 |
| TIMP1, GADD45A, MKNK1, SOCS3, LDLR, TNFSF10 | 0.79 | 0.73 | 0.83 |
| SOD2, LY96, PRV1, FAD104, BCL2A1, GADD45A | 0.79 | 0.72 | 0.83 |
| CEACAM1, BCL2A1, IRAK4, LDLR, TIFA, IL10alpha | 0.79 | 0.69 | 0.85 |
| TNFSF10, TIFA, GADD45B, ANXA3, BCL2A1, TNFRSF6 | 0.78 | 0.65 | 0.88 |
| Beta2Microglobulin, TIMP1, GADD45A, CRTAP, FAD104, GADD45B | 0.78 | 0.79 | 0.77 |
| ApolipoproteinCIII, IL18R1, CSF1R, LDLR, FCGR1A, MCP1 | 0.78 | 0.72 | 0.83 |
| MKNK1, GADD45B, IL1RN, NCR1, IL10, LDLR | 0.78 | 0.71 | 0.83 |
| CD86, IL10, IFNGR1, SOCS3, TDRD9, MCP1 | 0.78 | 0.7 | 0.85 |
| PRV1, SOD2, INSL3, TIFA, IRAK2, MCP1 | 0.78 | 0.7 | 0.84 |
| AlphaFetoprotein, Protein_MMP9, ANKRD22, HLA-DRA, MAP2K6, GADD45B, CEACAM1 | 0.83 | 0.79 | 0.87 |
| TNFSF13B, OSM, PRV1, CSF1R, IFNGR1, TNFRSF6, FCGR1A | 0.83 | 0.79 | 0.85 |
| FCGR1A, CCL5, TNFSF13B, Gene_MMP9, IL6, MAP2K6, OSM | 0.81 | 0.83 | 0.8 |
| GADD45B, IL1RN, Beta2Microglobulin, VNN1, PRV1, CD86, IL10 | 0.81 | 0.68 | 0.91 |
| IL8, TIFA, IL18R1, SOD2, CSF1R, FAD104, PRV1 | 0.8 | 0.81 | 0.8 |
| MAP2K6, SOD2, IL18R1, LDLR, ANXA3, CD86, GADD45B | 0.8 | 0.78 | 0.82 |
| ANKRD22, PRV1, TIMP1, NCR1, GADD45A, FCGR1A, TNFSF13B | 0.8 | 0.75 | 0.84 |
| IL10alpha, CRTAP, IL10, TIMP1, TIFA, PRV1, ARG2 | 0.8 | 0.73 | 0.87 |
| TNFRSF6, TLR4, LY96, CSF1R, GADD45B, CCL5, INSL3 | 0.8 | 0.7 | 0.88 |
| TDRD9, ANXA3, TNFSF10, TNFRSF6, PRV1, CCL5, IFNGR1 | 0.8 | 0.68 | 0.9 |
| CD86, GADD45B, CReactiveProtein, LDLR, CCL5, FAD104, IL8 | 0.8 | 0.82 | 0.78 |
| IRAK4, TGFBI, PRV1, CEACAM1, IFNGR1, PSTPIP2, TLR4 | 0.8 | 0.75 | 0.83 |
| OSM, Gene_MMP9, TLR4, TDRD9, CCL5, CRTAP, HLA-DRA | 0.8 | 0.72 | 0.84 |
| CRTAP, CEACAM1, FAD104, GADD45A, PRV1, MAP2K6, TNFSF10 | 0.79 | 0.72 | 0.84 |
| TNFRSF6, MKNK1, SOD2, TGFBI, MCP1, GADD45B, ANKRD22 | 0.79 | 0.72 | 0.86 |
| TIMP1, BCL2A1, TNFSF10, PRV1, HLA-DRA, CRTAP, PFKFB3 | 0.79 | 0.7 | 0.86 |
| INSL3, ANXA3, Beta2Microglobulin, GADD45B, TNFRSF6, ANKRD22, LDLR | 0.79 | 0.7 | 0.86 |
| TIFA, GADD45B, HLA-DRA, CD86, IL10, IL10alpha, MCP1 | 0.79 | 0.72 | 0.83 |
| FCGR1A, CReactiveProtein, BCL2A1, GADD45B, PRV1, PFKFB3, MAP2K6 | 0.79 | 0.71 | 0.83 |
| IL8, INSL3, ANKRD22, TNFSF10, HLA-DRA, PFKFB3, CSF1R | 0.79 | 0.7 | 0.85 |
| IL10alpha, MCP1, SOD2, TNFSF13B, CRTAP, MAP2K6, PRV1 | 0.78 | 0.75 | 0.81 |
| FAD104, SOD2, LY96, IL8, IRAK4, PRV1, Protein_MMP9 | 0.78 | 0.73 | 0.83 |
| MAPK14, OSM, PRV1, CRTAP, IL10alpha, MKNK1, IFNGR1 | 0.78 | 0.7 | 0.85 |
| OSM, AlphaFetoprotein, IFNGR1, SOD2, GADD45A, CEACAM1, MKNK1 | 0.78 | 0.73 | 0.82 |

TABLE O-continued

Exemplary sets of biomarkers used in the methods or kits referenced in Sections 5.2 and 5.3

| BIOMARKER SET | ACCURACY | SPECIFICITY | SENSITIVITY |
|---|---|---|---|
| IL18R1, TDRD9, INSL3, JAK2, Protein_MMP9, TNFRSF6, NCR1 | 0.78 | 0.7 | 0.85 |
| IFNGR1, CEACAM1, JAK2, SOD2, HLA-DRA, MAPK14, PRV1, VNN1 | 0.83 | 0.82 | 0.84 |
| NCR1, IRAK2, MAP2K6, CReactiveProtein, FCGR1A, ARG2, CD86, SOCS3 | 0.83 | 0.83 | 0.82 |
| GADD45B, ARG2, GADD45A, IL10alpha, TDRD9, PFKFB3, CReactiveProtein, OSM | 0.81 | 0.75 | 0.84 |
| PRV1, ITGAM, IL1RN, MAPK14, TNFSF10, SOD2, ARG2, PFKFB3 | 0.81 | 0.74 | 0.85 |
| TNFRSF6, Beta2Microglobulin, PSTPIP2, IL8, SOCS3, GADD45B, CRTAP, IFNGR1 | 0.81 | 0.73 | 0.87 |
| CReactiveProtein, LY96, MAP2K6, IL18R1, INSL3, OSM, CSF1R, IL6 | 0.8 | 0.78 | 0.82 |
| ITGAM, PRV1, MAP2K6, IL8, OSM, SOD2, IRAK4, CCL5 | 0.8 | 0.74 | 0.86 |
| CReactiveProtein, OSM, PSTPIP2, TNFSF10, ANKRD22, TDRD9, INSL3, CD86 | 0.8 | 0.73 | 0.85 |
| ANKRD22, CD86, PRV1, ANXA3, IL10, TNFSF13B, TIFA, AlphaFetoprotein | 0.79 | 0.81 | 0.78 |
| ApolipoproteinCIII, MKNK1, FCGR1A, PSTPIP2, VNN1, TNFRSF6, AlphaFetoprotein, OSM | 0.79 | 0.75 | 0.82 |
| PRV1, CCL5, PFKFB3, TNFSF13B, TIMP1, LDLR, ANKRD22, MAP2K6 | 0.79 | 0.74 | 0.83 |
| ARG2, VNN1, ANKRD22, IFNGR1, IL1RN, CD86, FAD104, GADD45B | 0.79 | 0.74 | 0.85 |
| IL10, PFKFB3, NCR1, TNFSF13B, MCP1, MAPK14, PRV1, TIMP1 | 0.79 | 0.7 | 0.86 |
| ApolipoproteinCIII, INSL3, IL10alpha, FCGR1A, IL1RN, IL6, TNFRSF6, IL8 | 0.79 | 0.74 | 0.83 |
| IL10, FAD104, CCL5, SOCS3, CD86, HLA-DRA, LDLR, GADD45A | 0.79 | 0.79 | 0.78 |
| PFKFB3, CReactiveProtein, MAPK14, TNFSF10, BCL2A1, ITGAM, IL10alpha, TDRD9 | 0.79 | 0.74 | 0.81 |
| Beta2Microglobulin, TNFSF13B, ANKRD22, MCP1, TDRD9, IRAK4, TIMP1, OSM | 0.78 | 0.73 | 0.82 |
| PSTPIP2, MAP2K6, AlphaFetoprotein, TDRD9, PFKFB3, IL8, ANXA3, PRV1 | 0.78 | 0.69 | 0.84 |
| TIFA, AlphaFetoprotein, PRV1, IL18R1, Gene_MMP9, VNN1, TDRD9, TNFRSF6 | 0.78 | 0.68 | 0.87 |
| IRAK2, FAD104, PRV1, GADD45A, TIFA, MCP1, TIMP1, SOD2 | 0.78 | 0.72 | 0.83 |
| IL6, CSF1R, MAP2K6, ANXA3, MCP1, PRV1, ITGAM, AlphaFetoprotein | 0.78 | 0.72 | 0.82 |
| CCL5, IL10alpha, GADD45B, LDLR, PSTPIP2, CD86, HLA-DRA, TLR4 | 0.78 | 0.69 | 0.84 |
| LDLR, CRTAP, NCR1, TNFRSF6, ApolipoproteinCIII, MAPK14, FCGR1A, IRAK2 | 0.78 | 0.69 | 0.84 |
| TGFBI, ANXA3, IL18R1, MAP2K6, FCGR1A, IL10, OSM, PRV1 | 0.78 | 0.67 | 0.87 |
| NCR1, JAK2, ANKRD22, IL1RN, ANXA3, LDLR, CD86, IFNGR1, OSM | 0.82 | 0.78 | 0.86 |
| CSF1R, TDRD9, FAD104, TNFSF10, OSM, LDLR, MAPK14, TIFA, BCL2A1 | 0.82 | 0.79 | 0.84 |
| TNFSF10, IFNGR1, TNFRSF6, GADD45B, CCL5, TNFSF13B, ANXA3, JAK2, PRV1 | 0.82 | 0.75 | 0.87 |
| TNFSF13B, CD86, TIFA, SOCS3, GADD45B, ARG2, TNFSF10, IRAK4, IL10 | 0.81 | 0.68 | 0.91 |
| FCGR1A, PSTPIP2, CEACAM1, IL1RN, FAD104, IL6, INSL3, CSF1R, PRV1 | 0.81 | 0.79 | 0.83 |
| IL1RN, SOD2, TGFBI, ApolipoproteinCIII, JAK2, CEACAM1, IRAK2, IFNGR1, OSM | 0.8 | 0.83 | 0.78 |
| TDRD9, CD86, Protein_MMP9, TNFRSF6, SOCS3, MCP1, AlphaFetoprotein, TIFA, INSL3 | 0.8 | 0.78 | 0.82 |
| BCL2A1, TGFBI, TLR4, IL8, LDLR, ANKRD22, TNFSF13B, IL10, GADD45B | 0.8 | 0.77 | 0.83 |

TABLE O-continued

Exemplary sets of biomarkers used in the methods or kits referenced in Sections 5.2 and 5.3

| BIOMARKER SET | ACCURACY | SPECIFICITY | SENSITIVITY |
|---|---|---|---|
| TNFSF13B, AlphaFetoprotein, TDRD9, MAPK14, SOCS3, ANXA3, IL1RN, CRTAP, TNFRSF6 | 0.8 | 0.73 | 0.86 |
| IL6, TNFRSF6, MCP1, JAK2, GADD45A, TIFA, ARG2, FCGR1A, ANKRD22 | 0.8 | 0.75 | 0.84 |
| PSTPIP2, ANXA3, MCP1, FAD104, PRV1, ANKRD22, NCR1, HLA-DRA, FCGR1A | 0.8 | 0.73 | 0.86 |
| IL8, PRV1, TDRD9, Beta2Microglobulin, IL10alpha, VNN1, INSL3, TIFA, CSF1R | 0.8 | 0.73 | 0.86 |
| GADD45B, TNFRSF6, OSM, IRAK4, AlphaFetoprotein, IL1RN, TNFSF13B, MCP1, FAD104 | 0.8 | 0.71 | 0.88 |
| ANKRD22, OSM, INSL3, IFNGR1, MKNK1, GADD45B, TDRD9, MAP2K6, IRAK4 | 0.8 | 0.69 | 0.89 |
| NCR1, JAK2, ANKRD22, IL1RN, ANXA3, LDLR, CD86, IFNGR1, OSM | 0.82 | 0.78 | 0.86 |
| ApolipoproteinCIII, ANXA3, IL18R1, PRV1, CD86, LDLR, TDRD9, CReactiveProtein, MAP2K6, CSF1R, CRTAP | 0.84 | 0.73 | 0.93 |
| CCL5, Protein_MMP9, NCR1, PRV1, TNFRSF6, TGFBI, HLA-DRA, FCGR1A, IFNGR1, CSF1R, MCP1 | 0.82 | 0.74 | 0.88 |
| GADD45B, CSF1R, IL1RN, PSTPIP2, PRV1, ApolipoproteinCIII, ARG2, SOCS3, FAD104, ITGAM, TIMP1 | 0.81 | 0.81 | 0.81 |
| JAK2, MKNK1, CRTAP, GADD45B, OSM, INSL3, TIMP1, TIFA, TNFRSF6, AlphaFetoprotein, CD86 | 0.81 | 0.79 | 0.83 |
| ApolipoproteinCIII, CD86, FCGR1A, ARG2, GADD45B, IL8, CRTAP, IFNGR1, TIMP1, ANXA3, HLA-DRA | 0.81 | 0.73 | 0.88 |
| MCP1, IL8, TNFSF13B, AlphaFetoprotein, LDLR, Protein_MMP9, JAK2, FAD104, IRAK2, TNFRSF6, GADD45B | 0.81 | 0.78 | 0.83 |
| TLR4, NCR1, CCL5, IL6, CReactiveProtein, IRAK4, AlphaFetoprotein, FCGR1A, ApolipoproteinCIII, GADD45B, PRV1 | 0.81 | 0.76 | 0.85 |
| ANKRD22, OSM, VNN1, LDLR, ApolipoproteinCIII, IL1RN, SOCS3, MAPK14, GADD45B, JAK2, ITGAM | 0.8 | 0.81 | 0.8 |
| NCR1, ARG2, GADD45B, GADD45A, CD86, TNFSF10, CCL5, PSTPIP2, Beta2Microglobulin, CRTAP, LDLR | 0.8 | 0.76 | 0.84 |
| SOCS3, JAK2, IL1RN, IFNGR1, CRTAP, TIMP1, Protein_MMP9, VNN1, TNFRSF6, CD86, ANKRD22 | 0.8 | 0.76 | 0.84 |
| OSM, PSTPIP2, IL1RN, AlphaFetoprotein, PRV1, IL6, LY96, IL18R1, CSF1R, TNFSF13B, LDLR | 0.8 | 0.86 | 0.75 |
| IL10alpha, CReactiveProtein, TIFA, NCR1, CRTAP, TGFBI, PFKFB3, LDLR, IRAK4, GADD45B, TDRD9 | 0.8 | 0.75 | 0.84 |
| ApolipoproteinCIII, ANXA3, IL18R1, PRV1, CD86, LDLR, TDRD9, CReactiveProtein, MAP2K6, CSF1R, CRTAP | 0.84 | 0.73 | 0.93 |

In some embodiments, the methods or kits respectively described or referenced in Section 5.2 and Section 5.3 use at least two different biomarkers that each contain a probeset listed in any one of FIG. 6, 14, 17, or 26. In a particular embodiment, a biomarker profile comprises at least two different biomarkers that each contain one of the probesets listed in any one of FIG. 6, 14, 17, or 26, biomarkers that each contain the complement of one of the probesets of any one of FIG. 6, 14, 17, or 26, or biomarkers that each contain an amino acid sequence encoded by a gene that either contains one of the probesets of any one of FIG. 6, 14, 17, or 26, or the complement of one of the probesets of any one of FIG. 6, 14, 17, or 26. Such biomarkers can be, for example, mRNA transcripts, cDNA or some other nucleic acid, for example, amplified nucleic acid, or proteins. The biomarker profile further comprises a respective corresponding feature for the at least two biomarkers. Generally, the at least two biomarkers are derived from at least two different genes. In the case where a biomarker is based upon a gene that includes the sequence of a probeset listed in any one of FIG. 6, 14, 17, or 26, the biomarker can be, for example, a transcript made by the gene, a complement thereof, or a discriminating fragment or complement thereof, or a cDNA thereof, or a discriminating fragment of the cDNA, or a discriminating amplified nucleic acid molecule corresponding to all or a portion of the transcript or its complement, or a protein encoded by the gene, or a discriminating fragment of the protein, or an indication of any of the above. Further still, the biomarker can be, for example, a protein encoded by a gene that includes a probeset sequence described in any one of FIG. 6, 14, 17, or 26, or a discriminating fragment of the protein, or an indication of any of the above. Here, a discriminating molecule or fragment is a molecule or fragment that, when detected, indicates presence or abundance of the above-identified transcript, cDNA, amplified nucleic acid, or protein. In some embodiments, the biomarker profile comprises at least 2, 3, 4, 5, 6, 7, 8, 9, or 10 different biomarkers that each contains a probeset listed in any one of FIG. 6, 14, 17, or 26.

In some embodiments, the methods or kits respectively described or referenced in Section 5.2 and Section 5.3 use at least two different biomarkers listed in any one of FIG. 39, 43, 52, 53, or 56. In a particular embodiment, the biomarker profile comprises at least two different biomarkers listed in any one of FIG. 39, 43, 52, 53, or 56. The biomarker profile further comprises a respective corresponding feature for the at least two biomarkers. Generally, the at least two biomarkers are derived from at least two different genes. In the case where a biomarker in the at least two different biomarkers is listed in any one of FIG. 39, 43, 52, 53, or 56, the biomarker can be, for example, a transcript made by the listed gene, a complement thereof, or a discriminating fragment or complement thereof, or a cDNA thereof, or a discriminating fragment of the cDNA, or a discriminating amplified nucleic acid molecule corresponding to all or a portion of the transcript or its complement, or a protein encoded by the gene, or a discriminating fragment of the protein, or an indication of any of the above. Further still, the biomarker can be, for example, a protein encoded by a gene listed in any one of FIG. 39, 43, 52, 53, or 56, or a discriminating fragment of the protein, or an indication of any of the above. Here, a discriminating molecule or fragment is a molecule or fragment that, when detected, indicates presence or abundance of the above-identified transcript, cDNA, amplified nucleic acid, or protein. In accordance with this embodiment, the biomarker profiles of the present invention can be obtained using any standard assay known to those skilled in the art, or in an assay described herein, to detect a biomarker. Such assays are capable, for example, of detecting the products of expression (e.g., nucleic acids and/or proteins) of a particular gene or allele of a gene of interest (e.g., a gene disclosed in Table 30). In one embodiment, such an assay utilizes a nucleic acid microarray. In some embodiments, the biomarker profile comprises at least two different biomarkers from any one of FIG. 39, 43, 52, 53, or 56. In some embodiments, the biomarker profile comprises at least 2, 3, 4, 5, 6, 7, 8, 9, 10, 11, 12, 13, 14, 15, 16, 17, 18, 19, or 20 different biomarkers from any one of FIG. 39, 43, 52, 53, or 56.

In some embodiments, the methods or kits respectively described or referenced in Section 5.2 and Section 5.3 use specific biomarkers containing probes from any one of the probeset collections listed in Table P. In a particular embodiment, a biomarker profile comprises at least two different biomarkers that each contain one of the probesets listed in any one of the probeset collections of Table P, biomarkers that each contain the complement of one of the probesets from any one of the probeset collections of Table P, or biomarkers that each contain an amino acid sequence encoded by a gene that either contains one of the probesets from any one of the probeset collections of Table P, or the complement of one of the probesets of any one of the probeset collections of Table P. Such biomarkers can be, for example, mRNA transcripts, cDNA or some other nucleic acid, for example, amplified nucleic acid, or proteins. The biomarker profile further comprises a respective corresponding feature for the at least two biomarkers. Generally, the at least two biomarkers are derived from at least two different genes. In the case where a biomarker is based upon a gene that includes the sequence of a probeset listed in any one of the probeset collections of Table P, the biomarker can be, for example, a transcript made by the gene, a complement thereof, or a discriminating fragment or complement thereof, or a cDNA thereof, or a discriminating fragment of the cDNA, or a discriminating amplified nucleic acid molecule corresponding to all or a portion of the transcript or its complement, or a protein encoded by the gene, or a discriminating fragment of the protein, or an indication of any of the above. Further still, the biomarker can be, for example, a protein encoded by a gene that includes a probeset sequence from any one of the probeset collections listed in Table P, or a discriminating fragment of the protein, or an indication of any of the above. Here, a discriminating molecule or fragment is a molecule or fragment that, when detected, indicates presence or abundance of the above-identified transcript, cDNA, amplified nucleic acid, or protein. In some embodiments, the biomarker profile comprises at least 2, 3, 4, 5, 6, 7, 8, 9, or 10 different biomarkers that each contains a probeset from any one of probeset collections listed in Table P.

TABLE P

Exemplary probesets

| PROBESET COLLECTION | IDENTITY OF PROBE IN PROBESET COLLECTION |
|---|---|
| 1 | X206513_at, X214681_at, X235359_at, X221850_x_at, X213524_s_at, X225656_a, X200881_s_at, X229743_at, X215178_x_at, X215178_x_at, X216841_s_at, X216841_at, X244158_at, X238858_at, X205287_s_at, X233651_s_at, X229572_at, X214765_s_at. |
| 2 | X206513_at, X213524_s_at, X200881_s_at, X218992_at, X238858_at, X221123_x_at, X228402_at, X230585_at, X209304_x_at, X214681_at. |
| 3 | X204102_s_at, X236013_at, X213668_s_at, X1556639_at, X218220_at, X207860_at, X232422_at, X218578_at, X205875_s_at, X226043_at, X225879_at, X224618_at, X216316_x_at, X243159_x_at, X202200_s_at, X201936_s_at, X242492_at, X216609_at, X214328_s_at, X228648_at, X223797_at, X225622_at, X205988_s_at, X201978_s_at, X200874_s_at, X210105_s_at, X203913_s_at, X204225_at, X227587_at, X220865_s_at, X206682_at, X222664_at, X212264_s_at, X219669_at, |

TABLE P-continued

Exemplary probesets

| PROBESET COLLECTION | IDENTITY OF PROBE IN PROBESET COLLECTION |
|---|---|
| | X221971_x_at, X1554464_a_at, X242590_at, X227925_at, X221926_s_at, X202101_s_at, X211078_s_at, X44563_at, X206513_at, X215178_x_at, X235359_at, X225656_at, X244158_at, X214765_s_at, X229743_at, X214681. |

In some embodiments, the methods or kits respectively described or referenced in Section 5.2 and Section 5.3 use at least two different biomarkers listed in any one of the biomarker sets in Table Q. In a particular embodiment, the biomarker profile comprises at least two different biomarkers listed in any one of the biomarker sets in Table Q. The biomarker profile further comprises a respective corresponding feature for the at least two biomarkers listed in any of the biomarker sets in Table Q. Generally, the at least two biomarkers are derived from at least two different genes. In the case where a biomarker in the at least two different biomarkers is listed in any one of biomarker sets of Table Q, the biomarker can be, for example, a transcript made by the listed gene, a complement thereof, or a discriminating fragment or complement thereof, or a cDNA thereof, or a discriminating fragment of the cDNA, or a discriminating amplified nucleic acid molecule corresponding to all or a portion of the transcript or its complement, or a protein encoded by the gene, or a discriminating fragment of the protein, or an indication of any of the above. Further still, the biomarker can be, for example, a protein encoded by a gene listed in any one of the biomarker sets in Table Q, or a discriminating fragment of the protein, or an indication of any of the above. Here, a discriminating molecule or fragment is a molecule or fragment that, when detected, indicates presence or abundance of the above-identified transcript, cDNA, amplified nucleic acid, or protein. In accordance with this embodiment, the biomarker profiles of the present invention can be obtained using any standard assay known to those skilled in the art, or in an assay described herein, to detect a biomarker. Such assays are capable, for example, of detecting the products of expression (e.g., nucleic acids and/or proteins) of a particular gene or allele of a gene of interest (e.g., a gene disclosed in any on of the biomarker sets of Table Q). In one embodiment, such an assay utilizes a nucleic acid microarray. In some embodiments, a biomarker profile comprising at least 2 or 3 different biomarkers from any one of the biomarker sets of Table Q is used.

TABLE Q

Exemplary biomarker sets

| BIOMARKER SET NUMBER | IDENTITY OF BIOMARKERS |
|---|---|
| 1 | IL18R1, ARG2, FCGR1A |
| 2 | ITGAM, TGFB1, TLR4, TNFSF, FCGR1A, IL18R1, ARG2 |
| 3 | ARG2, TGFB1, MMP9, TLR4, ITGAM, IL18R1, TNFSF, IL1RN, FCGR1A |
| 4 | OSM, GADD45B, ARG2, IL18R1, TDRD9, PFKFB3, MAPK14, PRV1, MAP2K6, TNFRSF6, FCGR1A, INSL3, LY96, PSTPIP2, ANKRD22, TNFSF10, HLA-DRA, FNDC3B, TIFA, GADD45A, VNN1, ITGAM, BCL2A1, TLR4, TNFSF13B, SOCS3, IL1RN, CEACAM1, SOD2 |

TABLE Q-continued

Exemplary biomarker sets

| BIOMARKER SET NUMBER | IDENTITY OF BIOMARKERS |
|---|---|
| 5 | ARG2, GADD45B, OSM, LY96, INSL3, ANKRD22, MAP2K6, PSTPIP2, TGFB1, GADD45B, TDRD9, MAP2K6, OSM, TNFSF10, ANKRD22 |

6. EXAMPLES

The following examples are representative of the embodiments encompassed by the present invention and in no way limit the subject embraced by the present invention. In the following examples, data was collected at twenty-four hour time intervals from each subject in a population of subjects. The population included two subject types. The first subject type was those that initially had SIRS and developed sepsis at a terminal time point in the analysis. The second subject type was those that initially had SIRS and did not develop sepsis at the terminal time point in the analysis. For subjects that initially had SIRS and developed sepsis, a $T_{-12}$ time point was defined as the time frame immediate prior to the onset of clinically-diagnosed sepsis. In practice, the $T_{-12}$ time point for each respective sepsis subject was the day the last blood sample was collected from the respective subject prior to being diagnosed with sepsis.

For each time point, two types of analyses were performed, a static and a baseline analysis. In the static analysis, only data from a single time point was considered. In particular, univariate and/or multivariate techniques were used to identify biomarkers whose abundance on corresponding microarray probesets on the U133 plus 2.0 (Affymetrix, Santa Clara, Calif.) discriminate between those subjects that develop sepsis from those subjects that do not develop sepsis during the study. To illustrate, consider the case in which there are two subjects in the population, subject A, who develops sepsis shortly after time period $T_{-12}$, and subject B, who does not develop sepsis in any of the observed time points. In the static analysis, microarray biomarker abundance data from the two subjects that was collected at a particular single time point is evaluated in order to identify those biomarkers that have different abundance levels in the two subjects, as determined by a U133 plus 2.0 microarray experiment. In fact, in the present examples, a whole population of subjects of type A and type B are evaluated and parametric and/or nonparametric statistical techniques are used to identify those biomarkers whose abundance levels discriminate between subjects that develop sepsis at some point during the observation period and subjects that do not develop sepsis during the observation period. Here, an observation period refers to a time period that was a matter of hours, days, or weeks.

In addition to static analyses, baseline analyses were performed in the examples below. In a baseline analysis, rather than identifying biomarkers whose corresponding features (e.g. abundance value) at a single time point discriminate between sepsis subjects (subjects that develop sepsis at some point during the observation time period) and subjects that do not develop sepsis during the observed time frame, biomarkers whose change in abundance value across two or more time points discriminates between the two populations types were identified. For example, again consider subject A, who develops sepsis shortly after time period $T_{-12}$, and subject B, who does not develop sepsis in any of the observed time points. In the baseline analysis, what were needed are biomarker abundance values for each subject from two different time points (e.g., time point 1 and time point 2). For each respective biomarker considered, the difference in the abundance of the biomarker at the two different time points was computed. These differential abundances from each of the subjects is then used to determine which corresponding biomarkers, expressed as a differential between two different time points, discriminate between subjects that develop sepsis during the observation period and subjects that do not develop sepsis during the observation time period.

6.1 Data Collection

SIRS positive subjects admitted to an ICU were recruited for the study. Subjects were eighteen years of age or older and gave informed consent to comply with the study protocol. Subjects were excluded from the study if they were (i) pregnant, (ii) taking antibiotics to treat a suspected infection, (iii) were taking systemic corticosteroids (total dosage greater than 100 mg hydrocortisone or equivalent in the past 48 hours prior to study entry), (iv) had a spinal cord injury or other illness requiring high-dose corticosteroid therapy, (v) pharmacologically immunosuppressed (e.g., azathioprine, methotrexate, cyclosporin, tacrolimus, cyclophosphamide, etanercept, anakinra, infliximab, leuflonamide, mycophenolic acid, OKT3, pentoxyphylin, etc.), (vi) were an organ transplant recipient, (vii) had active or metastatic cancer, (viii) had received chemotherapy or radiation therapy within 8 weeks prior to enrollment, and/or (ix) had taken investigational use drugs within thirty days prior to enrollment.

In the study SIRS criteria were evaluated daily. APACHE II and SOFA scoring was performed following ICU admission. APACHE II is a system for rating the severity of medical illness. APACHE stands for "Acute Physiology And Chronic Health Evaluation," and is most frequently used to predict in-hospital death for patients in an intensive care unit. See, for example, Gupta et al., 2004, Indian Journal of Medical Research 119, 273-282, which is hereby incorporated herein by reference in its entirety. SOFA is a test to measure the severity of sepsis. See, for example, Vincent et al., 1996, Intensive Care Med. 22, 707-710, which is hereby incorporated herein by reference in its entirety. Patients were monitored daily for up to two weeks for clinical suspicion of sepsis including, but not limited to, any of the following signs and symptoms:

- pneumonia: temperature >38.3° C. or <36° C.+white blood cell count (WBC) >12,000/mm³ or <4,000/mm³+ new-onset of purulent sputum+new or progressive infiltrate on chest radiograph (3 out of 4 findings);
- wound infection: temperature >38.3° C. or <36° C.+pain+ erythema+purulent discharge (3 out of 4 findings);
- urinary tract infection: temperature >38.3° C. or WBC >12,000/mm³ or <4,000/mm³+bacteruria and pyuria (>10 WBC/hpf or positive leukocyte esterase) (all findings);
- line sepsis: temperature >38.3° C. or <36° C.+erythema/ pain/purulence at catheter exit site (3 out of 4 findings, including fever);
- intra-abdominal abscess: temperature >38.3° C. or <36° C.+WBC >12,000/mm³ or <4,000/mm³+radiographic evidence of fluid collection (2 out of 3 criteria);
- CNS Infection: temperature >38.3° C. or <36° C.+ WBC >12,000/mm³ or <4,000/mm³+CSF pleocytosis via LP or Ventricular drainage.

Blood was drawn daily for a minimum of four consecutive days beginning within 24 hours following study entry. Patients were followed and blood samples were drawn daily for a maximum of fourteen consecutive days unless clinical suspicion of infection occurred. The maximum volume of blood drawn from any one subject did not exceed 210 mL over the course of a 14 day study maximum. Blood draws for the study were discontinued if the loss of blood posed risk to the patient as defined by physician's judgment. Each patient had two Paxgene (RNA) tubes drawn on each day. One tube was used for the microarray analysis described in Section 6.2. The other tube was used for the RT-PCR analysis described in Section 6.10.

6.2 Microarray Analysis

RNA was extracted from each blood sample described in Section 6.1, labeled, reversed transcribed to generate cDNA which was labeled, and the labeled cDNA was hybridized to Affymetrix (Santa Clara, Calif.) U133 plus 2.0 human genome chips containing 54,675 probesets. To enhance detection sensitivity of the microarray, globin mRNA molecules were removed from the total RNA extracted from the blood samples using the methods described in, for example, U.S. Patent Publication 20050221310, filed Aug. 9, 2004, and Ser. No. 10/948,635, filed Sep. 24, 2004, both entitled "Methods of Enhancing Gene Expression Analysis," each of which is incorporated by reference herein in its entirety. The U133 plus 2.0 has 62 probesets designed for special functions, such as measuring supplementally added transcripts. This leaves 54,613 probesets designed specifically for the detection of human genes. The Affymetrix human genome U133 (HG-U133) set, consisting of two microarrays, contains almost 45,000 probesets representing more than 39,000 transcripts derived from approximately 33,000 human genes. This set design uses sequences selected from GenBank, dbEST, and RefSeq. As used herein, the abundance value measured for each of the biomarkers that bind to these probesets is referred to as a feature. The examples below discuss abundance values of biomarkers that bind to particular probesets in the U133 plus 2.0 human genome chip.

6.3 Static $T_{-36}$ Data Analysis

In one experiment, a $T_{-36}$ static analysis was performed. In the $T_{-36}$ static analysis, biomarkers features are determined using a specific blood sample, designated the $T_{-36}$ blood sample, from each subject in a training population. The identity of this specific blood sample from each respective subject in the training population is dependent upon whether the subject was a SIRS subject (did not develop sepsis during the observation period) or was a sepsis subject (did develop sepsis during the observation period). In the case of a sepsis subject, the $T_{-36}$ sample is defined as the second to last blood sample taken from the subject before the subject acquired sepsis. Identification of $T_{-36}$ samples in the SIRS subjects in the training population was more discretionary than for the sepsis counterpart subjects because there was no significant event in which the SIRS subjects became septic. Because of this, the identity of the $T_{-36}$ samples for the sepsis subjects in the training population was used to identify the $T_{-36}$ samples in the SIRS subjects in the training population. Specifically, $T_{-36}$ time points (blood samples) for SIRS subjects in the training population were identified by "time-matching" a septic subject and a SIRS subject. For example, consider the case in which a subject that entered the study became clinically-defined as septic on their sixth day of enrollment. For this subject, $T_{-36}$ is day four of the study, and the $T_{-36}$ blood sample is the blood sample that was obtained on day four of the study. Likewise, $T_{-36}$ for the SIRS subject that was matched to this sepsis subject is deemed to be day four of the study on this paired SIRS subject.

Although SIRS subjects did not progress on to develop sepsis, they did have changes in their expressed genes (and proteins, etc.) over time. Thus, a one-to-one time matching of sepsis subjects to SIRS subjects for the purpose of obtaining a relevant set of $T_{-36}$ blood samples from the SIRS subjects was sought in the manner described above. Just as subjects who progressed to become septic did so at varying rates, this time matching was done to mimic feature variability in SIRS subjects. While time matching between arbitrary pairs of SIRS and sepsis subjects was done to identify $T_{-36}$ blood samples for as many of the SIRS subjects in the training population as possible, in some instances, $T_{-36}$ samples from SIRS subjects had to be selected from time points based on sample availability.

For the $T_{-36}$ static analysis there were 54,613 biomarkers measured on 84 samples for a total of 84 corresponding microarray experiments from 84 different subjects. Each sample was collected from a different subject in the population of 84 subject. Of the 54,613 probesets measured in each microarray experiment, 30,464 were transformed by log transformations. The log transformation is described in Draghici, 2003, *Data Analysis Tools for DNA Microarrays*, Chapman & Hall/CRC, Boca Raton, pp. 309-311, which is hereby incorporated by reference in its entirety. Further, of the 54,613 probesets in each microarray experiment, 2317 were transformed by a square root transformation. The square root transformation is described in Ramdas, 2001, Genome Biology 2, 47.1-47.7, which is hereby incorporated by reference in its entirety. The remaining 21,832 probesets in each microarray experiment were not transformed.

The 84 member population was initially split into a training set (n=64) and a validation set (n=20). The training set was used to estimate the appropriate classification algorithm parameters while the trained algorithm was applied to the validation set to independently assess performance. Of the 64 training samples, 35 were Sepsis, meaning that the subjects developed sepsis at some point during the observation time period, and 29 were SIRS, meaning that they did not develop sepsis during the observation time period. Table 1 provides distributions of the race, gender and age for these samples.

TABLE 1

Distributions of the race, gender, and age for the training data

| Group | Gender | Black | Caucasian | Other |
|---|---|---|---|---|
| Sepsis | Male | 10 | 13 | 1 |
|  | Female | 0 | 10 | 1 |
| SIRS | Male | 5 | 17 | 0 |
|  | Female | 0 | 7 | 0 |

| Group | Minimum | Mean | Median | Maximum |
|---|---|---|---|---|
| Sepsis | 18 | 42 | 41 | 80 |
| SIRS | 18 | 43 | 40 | 90 |

For the 20 validation samples, 9 were Sepsis and 11 were SIRS. Table 2 provides distributions of the race, gender and age for these samples.

TABLE 2

Distributions of the race, gender, and age for the validation data

| Group | Gender | Black | Caucasian | Other |
|---|---|---|---|---|
| Sepsis | Male | 1 | 7 | 0 |
|  | Female | 0 | 3 | 0 |
| SIRS | Male | 0 | 6 | 0 |
|  | Female | 0 | 3 | 0 |

| Group | Minimum | Mean | Median | Maximum |
|---|---|---|---|---|
| Sepsis | 18 | 41.8 | 43 | 81 |
| SIRS | 19 | 47.7 | 51 | 77 |

Each sample in the training data was randomly assigned to one of ten groups used for cross-validation. The number of training samples in these groups ranged from 6 to 7. The samples were assigned in way that attempted to balance the number of sepsis and SIRS samples across folds. As described in more detail below, several different methods were used to judge whether select biomarkers, which bind to particular probesets in the microarray, discriminate between the Sepsis and SIRS groups.

Wilcoxon and Q-Value Tests.

The first method used to identify discriminating biomarkers was a Wilcoxon test (unadjusted). The Wilcoxon test is a distribution-free test is resistant to extreme values. The Wilcoxon test is described in Agresti, 1996, *An Introduction to Categorical Data Analysis*, John Wiley & Sons, Inc, New York, Chapter 2, which is hereby incorporated by reference in its entirety. The Wilcoxon test produces a p value. The abundance value for a given biomarker from all samples in the training data is subjected to the Wilcoxon test. The Wilcoxon test considers both group classification (sepsis versus SIRS) and abundance value in order to compute a p value for the given biomarker. The p value provides an indication of how well the abundance value for the given biomarker across the samples collected in the training set discriminates between the sepsis and SIRS state. When the p value is less than a specific confidence level, such as 0.05, an inference is made that the biomarker discriminates between Sepsis and SIRS. There were 9520 significant biomarkers using this method (see Table 3).

The second method used to identify discriminating biomarkers was the Wilcoxon Test (adjusted). Due to the large number of biomarkers, 54613, and the relatively small number of samples, 84, there was a high risk of finding falsely significant biomarkers. An adjusted p-value was used to counter this risk. In particular, the method of Benjamini and Hochberg, 1995, J. R. Statist. Soc. B 57, pp 289-300, which is hereby incorporated by reference in its entirety, was used to control the false discovery rate. Here, the false discovery rate is defined as the number of biomarkers truly significant divided by the number of biomarkers declared significant. For example, if the adjusted p-value is less than 0.05, there is a 5% chance that the biomarker is a false discovery. Results using this test are reported in Table 3. There were 1618 significant biomarkers using this method (see Table 3). As used, herein, a biomarker is considered significant if the feature values corresponding to the biomarker have a p-value of less than 0.05 as determined by the Wilcoxon test (adjusted).

The third method used to identify discriminating biomarkers was the use of Q values. Q-values are described in Storey, 2002, J. R. Statist. Soc. B 64, Part 3, pp. 479-498, which is hereby incorporated by reference in its entirety. The biomarkers are ordered by their q-values and if a biomarker has a q-value of X, then this biomarker and all others more significant have a combined false discovery rate of X. However, the false discovery rate for any one biomarker may be much larger. There were 2431 significant markers using this method (see Table 3).

TABLE 3

Cumulative number of significant calls for the three methods.
Note that all 84 samples (training and validation)
were used to compare converters and nonconverters.
Missing biomarker values were not included in the analyses.

| | ≤1e−04 | ≤0.001 | ≤0.01 | ≤0.025 | ≤0.05 | ≤0.1 | ≤1 |
|---|---|---|---|---|---|---|---|
| p-value (unadjusted) | 0 | 1362 | 4210 | 6637 | 9520 | 13945 | 54613 |
| p-value (adjusted) | 0 | 0 | 0 | 584 | 1618 | 3315 | 54613 |
| q-value | 0 | 0 | 0 | 1055 | 2431 | 4785 | 54613 |

CART.

In addition to analyzing the microarray data using Wilcoxon test and Q-value tests in order to identify biomarkers that discriminate between the sepsis and SIRS subpopulations in the training set, classification and regression tree (CART) analysis was used. CART is described in Section 5.5.1, above. Specifically, the data summarized above was used to predict the disease state by iteratively partitioning the data based on the best single-variable (feature of biomarker across training set) split of the data. In other words, at each stage of the tree building process, the biomarker whose abundance value across the training population best discriminates between the sepsis and SIRS population was invoked as a decision branch. Cross-validation was carried out, with the optimal number of splits estimated independently in each of the 10 iterations. The final tree is depicted in FIG. 1. In FIG. 1, decision 102 makes a decision based on the abundance of the biomarker that binds to X204319_s_at. If the biomarker that binds to X204319_s_at has an abundance that is greater than 2.331 units in a biological sample from a subject to be diagnosed (test biological sample), then control passes to decision 104. If, on the other hand, the biomarker that binds to probeset X204319_s_at has abundance that is less than 2.331 units in the test biological sample, decision control passes to decision 106. Decisions are made in this manner until a terminal leaf of the decision tree is reached, at which point diagnoses of sepsis or SIRS is made. The decision tree in FIG. 1 makes use of the biomarkers that bind to the following five probesets: X204319_s_at, X1562290_at, X1552501_a_at, X1552283_s_at, and X117_at.

Figure 2:
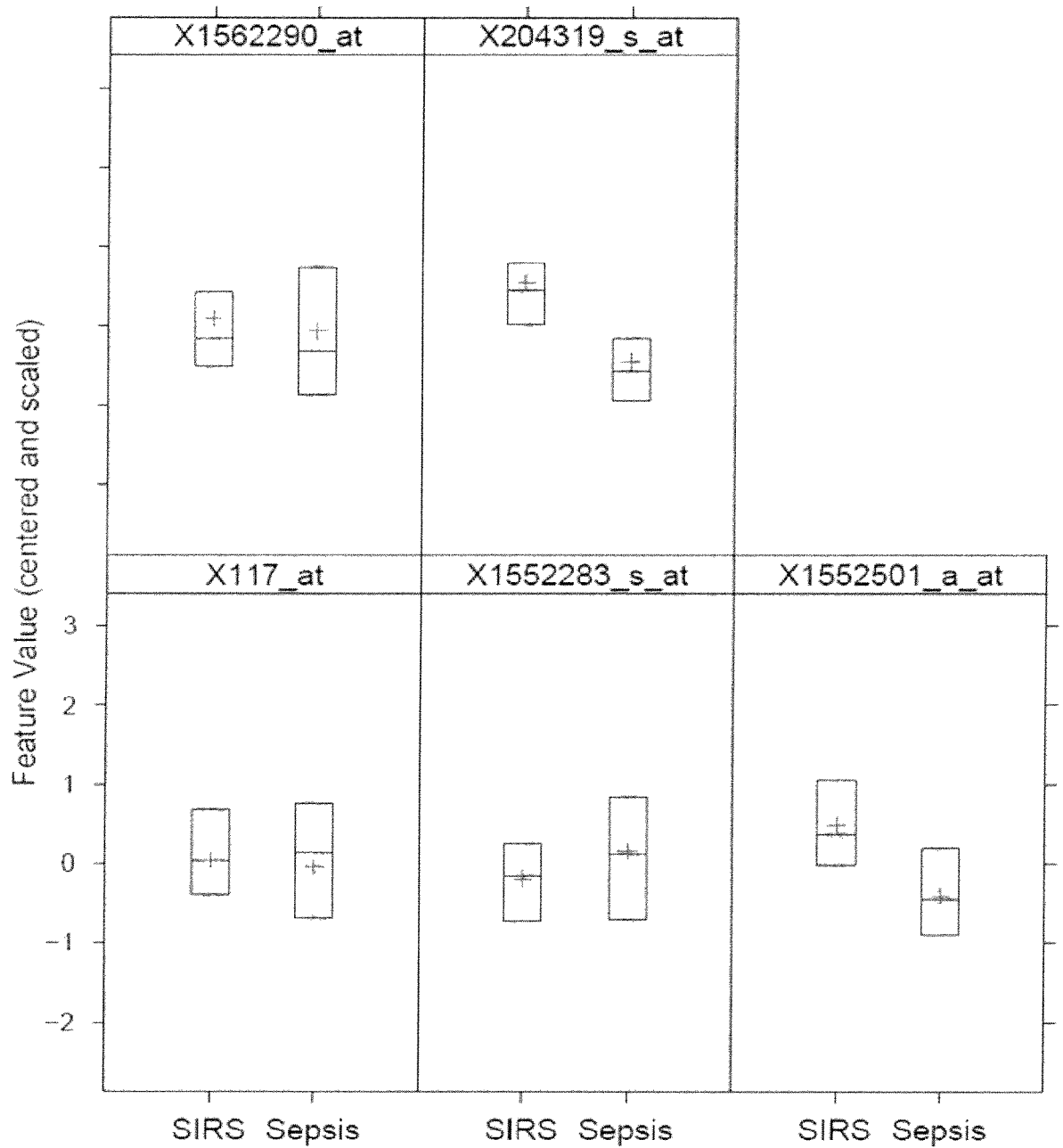
FIG. 2 shows the distribution of feature values for five biomarkers used in the decision tree of FIG. 1 across $T_{-36}$ static data obtained from a training population in accordance with an embodiment of the present invention. The biomarkers are referenced by their corresponding Affymetrix U133 plus 2.0 probeset names given in Table 30.

FIG. 2 shows the distribution of the biomarkers that bind to the five probesets used in the decision tree between the sepsis and SIRS groups in the training data set. In FIG. 2, the top of each box denotes the 75$^{th}$ percentile of the data across the training set and the bottom of each box denotes the 25$^{th}$ percentile, and the median value for each biomarker across the training set is drawn as a line within each box. The confusion matrix for the training data where the predicted classifications were made from the cross-validated model is given in Table 4. From this confusion matrix, the overall accuracy was estimated to be 70.3% with a 95% confidence interval of 57.6% to 81.1%. The estimated sensitivity was 60% and the estimated specificity was 82.8%.

TABLE 4

Confusion matrix for training samples using
the cross-validated CART algorithm of FIG. 1.

| | True Diagnosis | |
|---|---|---|
| Predicted | Sepsis | SIRS |
| Sepsis | 21 | 5 |
| SIRS | 14 | 24 |

For the 20 validation samples held back from training data set, the overall accuracy was estimated to be 70% with a 95% confidence interval of 45.7% to 88.1%, sensitivity 88.9% and specificity 54.5%. Table 5 shows the confusion matrix for the validation samples.

TABLE 5

Confusion matrix for validation samples using
the cross-validated CART algorithm of FIG. 1.

| | True Diagnosis | |
|---|---|---|
| Predicted | Sepsis | SIRS |
| Sepsis | 8 | 5 |
| SIRS | 1 | 6 |

Random Forests.

Figure 3:
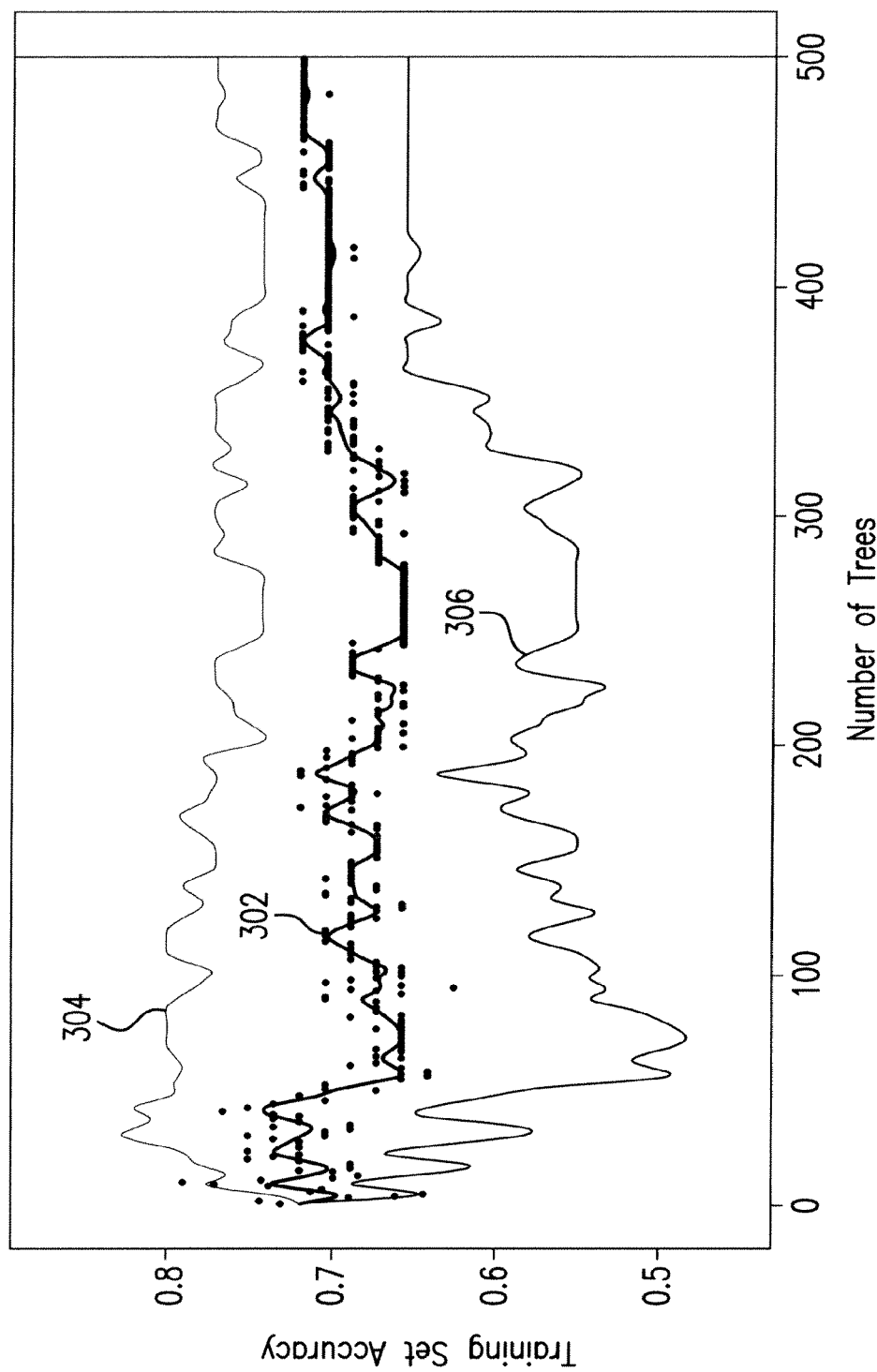
FIG. 3 illustrates the overall accuracy, sensitivity, and specificity of 500 trees used to train a decision tree using the Random Forests method based upon $T_{-36}$ static data obtained from a training population in accordance with an embodiment of the present invention.
Figure 4:
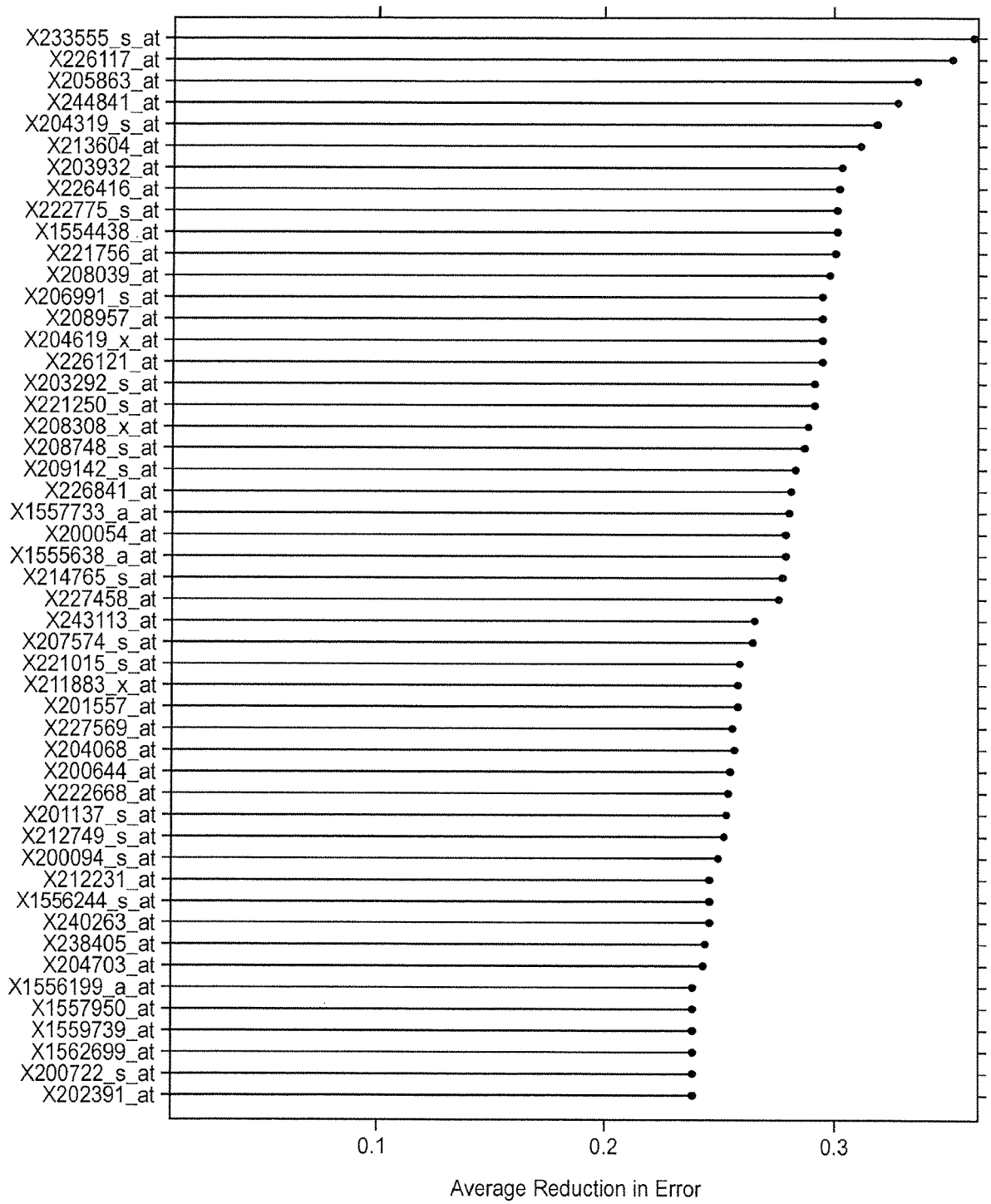
FIG. 4 illustrates the biomarker importance in the decision rule trained using the trees of FIG. 3.

Another decision rule that can be developed using biomarkers of the present invention is a Random Forests decision tree. Random Forests is a tree based method that uses bootstrapping instead of cross-validation. For each iteration, a random sample (with replacement) is drawn and the largest tree possible is grown. Each tree receives a vote in the final class prediction. To fit a random forest, the number of trees (e.g. bootstrap iterations) is specified. No more than 500 were used in this example, but at least 50 are needed for a burn-in period. The number of trees was chosen based on the accuracy of the training data. For this data, 500 trees were used to train the algorithm (see FIG. 3). In FIG. 3, curve 302 is a smoothed estimate of overall accuracy as a function of tree number. Curve 304 is a smoothed curve of tree sensitivity as a function of tree number. Curve 306 is a smoothed curve of tree specificity as a function of tree number. Using this algorithm, 901 biomarkers had non-zero importance and were used in the model. The random forest algorithm gauges biomarker importance by the average reduction in the training accuracy. The biomarkers were ranked by this method and are shown in FIG. 4. In FIG. 4, the biomarkers are labeled by the name of the U133 plus 2.0 probeset to which they bind. The figure only reflects the 50 most important biomarkers found by using Random Forest analysis. However, 901 biomarkers were actually found to have discriminating significance. The random forest method uses a number of different decision trees. A biomarker is considered to have discriminating significance if it served as a decision branch of a decision tree from a significant random forest analysis. As used herein, a significant random forest analysis is one where the lower 95% confidence interval on accuracy by cross validation on a training data set is greater than 50% and the point estimate for accuracy on a validation set is greater than 65%.

The predicted confusion matrix for the training dataset using the decision tree developed using the Random Forest method is given in Table 6. From this confusion matrix, the overall accuracy was estimated to be 68.8% (confidence intervals cannot be computed when using the bootstrap accuracy estimate). The estimated sensitivity was 74.3% and the estimated specificity was 62.1%.

TABLE 6

Confusion matrix for training samples against the decision tree developed using the Random Forest method.

| Predicted | True Diagnosis | |
|---|---|---|
| | Sepsis | SIRS |
| Sepsis | 18 | 9 |
| SIRS | 11 | 26 |

For the 20 validation samples held back from training, the overall accuracy was estimated to be 65% with a 95% confidence interval of 40.8% to 84.6%, sensitivity 66.7% and specificity 63.6%. Table 7 shows the confusion matrix for the validation samples.

TABLE 7

Confusion matrix for the 20 validation samples against the decision tree developed using the Random Forest method.

| Predicted | True Diagnosis | |
|---|---|---|
| | Sepsis | SIRS |
| Sepsis | 6 | 4 |
| SIRS | 3 | 7 |

PAM.

Figure 5:
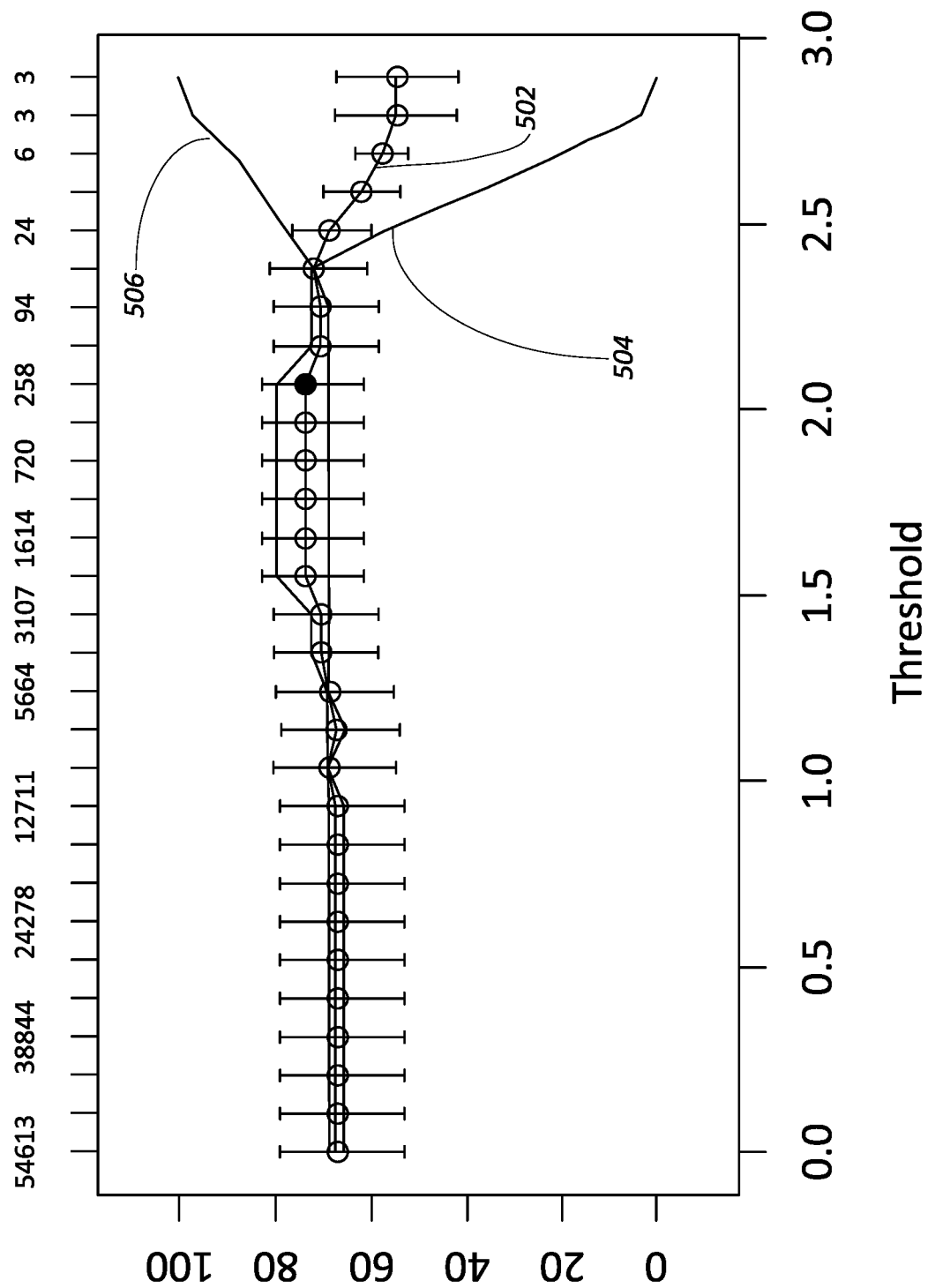
FIG. 5 illustrates the overall accuracy, with 95% confidence interval bars, specificity, and sensitivity of a decision rule developed with predictive analysis of microarrays (PAM) using the biomarkers of the present invention across $T_{-36}$ static data obtained from a training population.

Yet another decision rule developed using the biomarkers of the present invention is predictive analysis of microarrays (PAM), which is described in Section 5.5.2, above. In this method, a shrinkage parameter that determines the number of biomarkers used to classify samples is specified. This parameter was chosen via cross-validation. There were no biomarkers with missing values. Based on cross-validation, the optimal threshold value was 2.07, corresponding to 258 biomarkers. FIG. 5 shows the accuracy across different thresholds. In FIG. 5, curve 502 is the overall accuracy (with 95% confidence interval bars). Curve 504 shows decision rule sensitivity as a function of threshold value. Curve 506 shows decision rule specificity as a function of threshold value. Using the threshold of 2.07, the overall accuracy for the training samples was estimated to be 73.4% with 95% a confidence interval of 61.4% to 82.8%. The estimated sensitivity was 79.3% and the estimated specificity was 68.6%.

TABLE 8

Confusion matrix for training samples using cross-validated PAM algorithm

| Predicted | True Diagnosis | |
|---|---|---|
| | Sepsis | SIRS |
| Sepsis | 23 | 11 |
| SIRS | 6 | 24 |

For the twenty validation samples held back from training, the overall accuracy was estimated to be 70% with a 95% confidence interval of 45.7% to 88.1%, sensitivity 66.7% and specificity 72.7%. Table 9 shows the confusion matrix for the validation samples.

TABLE 9

Confusion matrix for training samples using cross-validated PAM algorithm

| Predicted | True Diagnosis | |
|---|---|---|
| | Sepsis | SIRS |
| Sepsis | 6 | 3 |
| SIRS | 3 | 8 |

Figure 6:
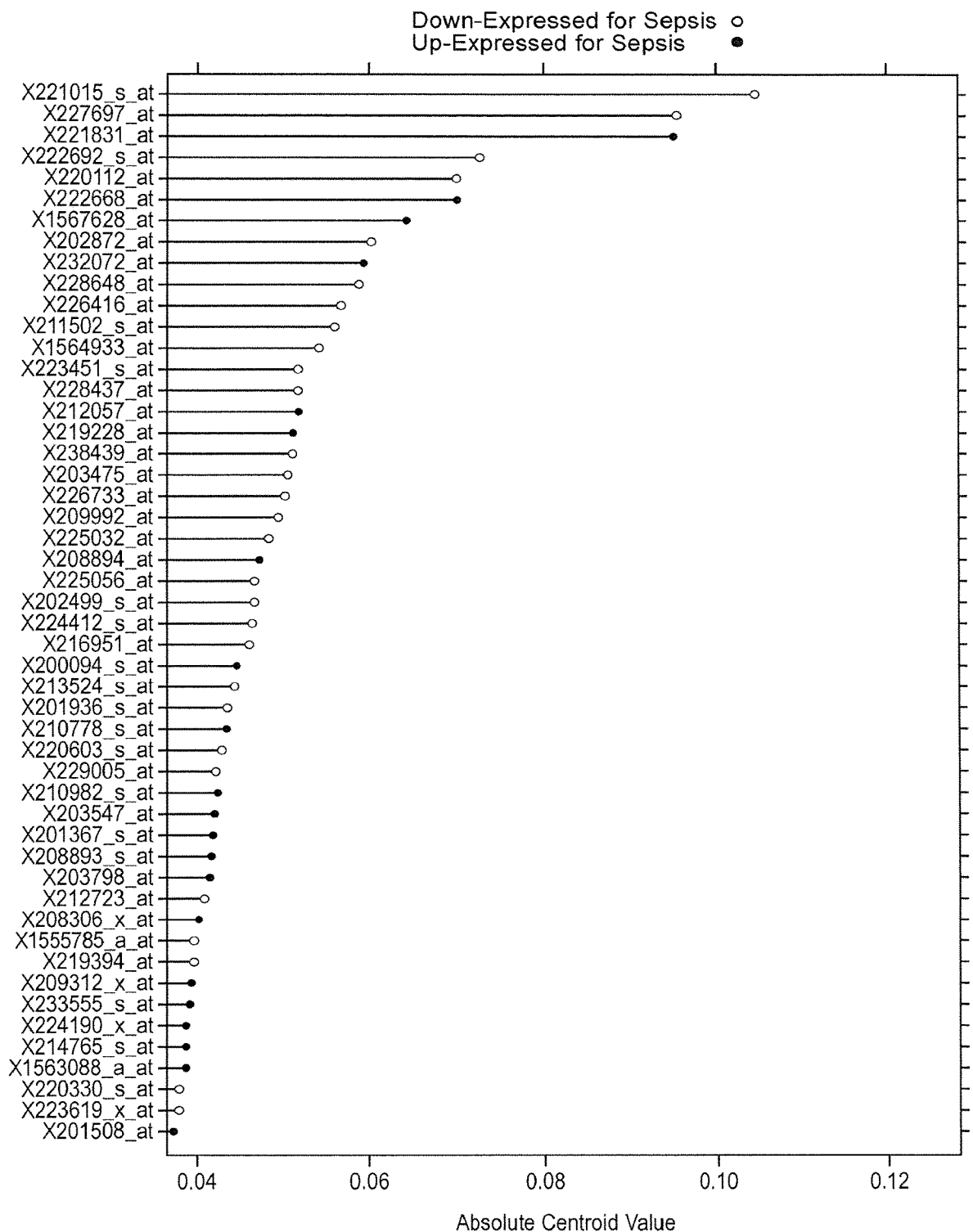
FIG. 6 is a list of biomarkers, rank-ordered by their respective degrees of discriminatory power, identified by PAM using $T_{-36}$ static data obtained from a training population. The biomarkers are referenced by their corresponding Affymetrix U133 plus 2.0 probeset names given in Table 30.

FIG. 6 shows the selected biomarkers, ranked by their relative discriminatory power, and their relative importance in the model. FIG. 6 only shows the fifty most important biomarkers found using the PAM analysis. However, 258 important biomarkers were found. The biomarkers in FIG. 6 are labeled based upon the U133 plus 2.0 probeset to which they bind.

Figure 7:
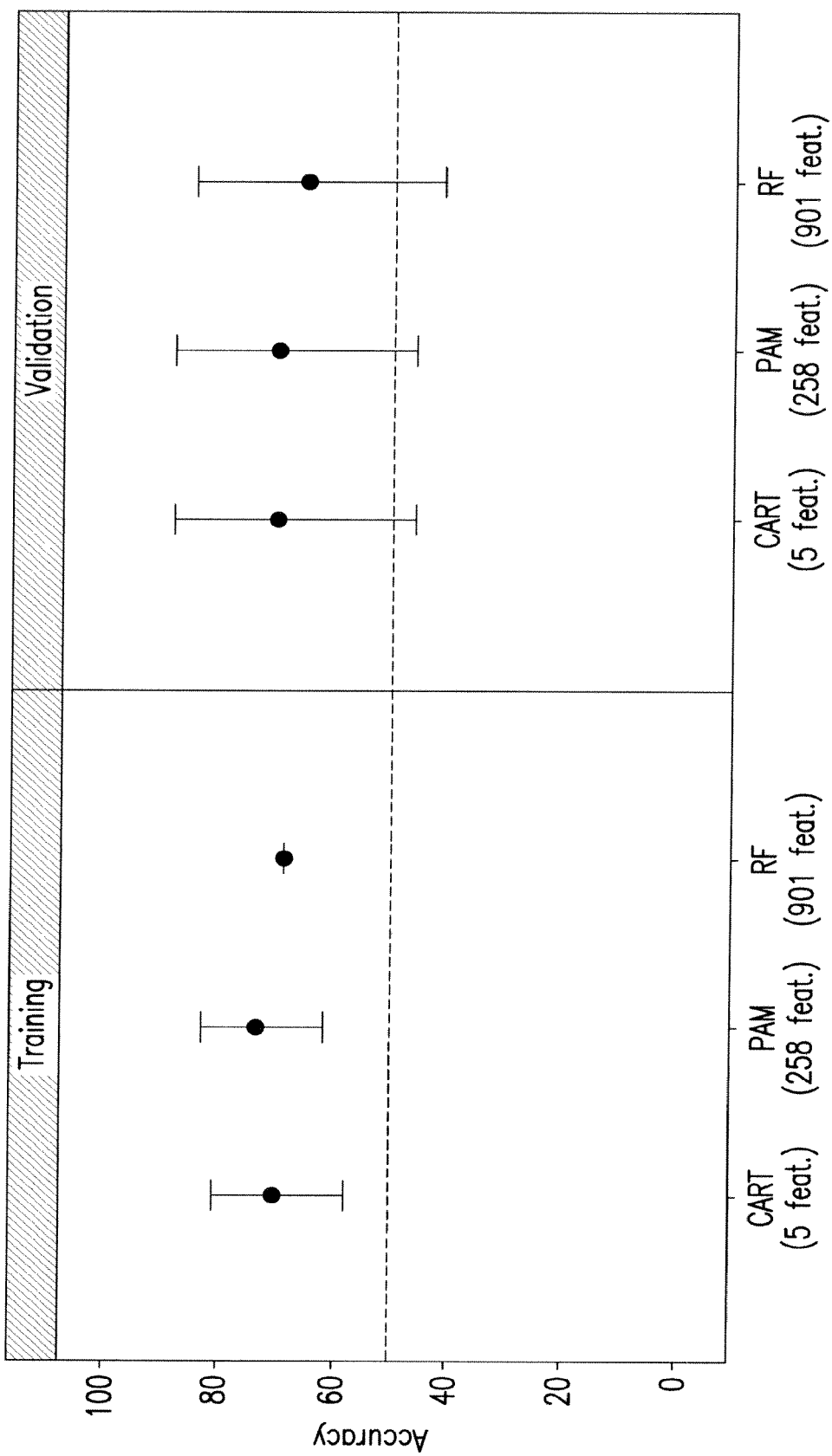
FIG. 7 illustrates CART, PAM, and random forests classification algorithm performance data, and associated 95% confidence intervals, for $T_{-36}$ static data obtained from a training population.
Figure 8:
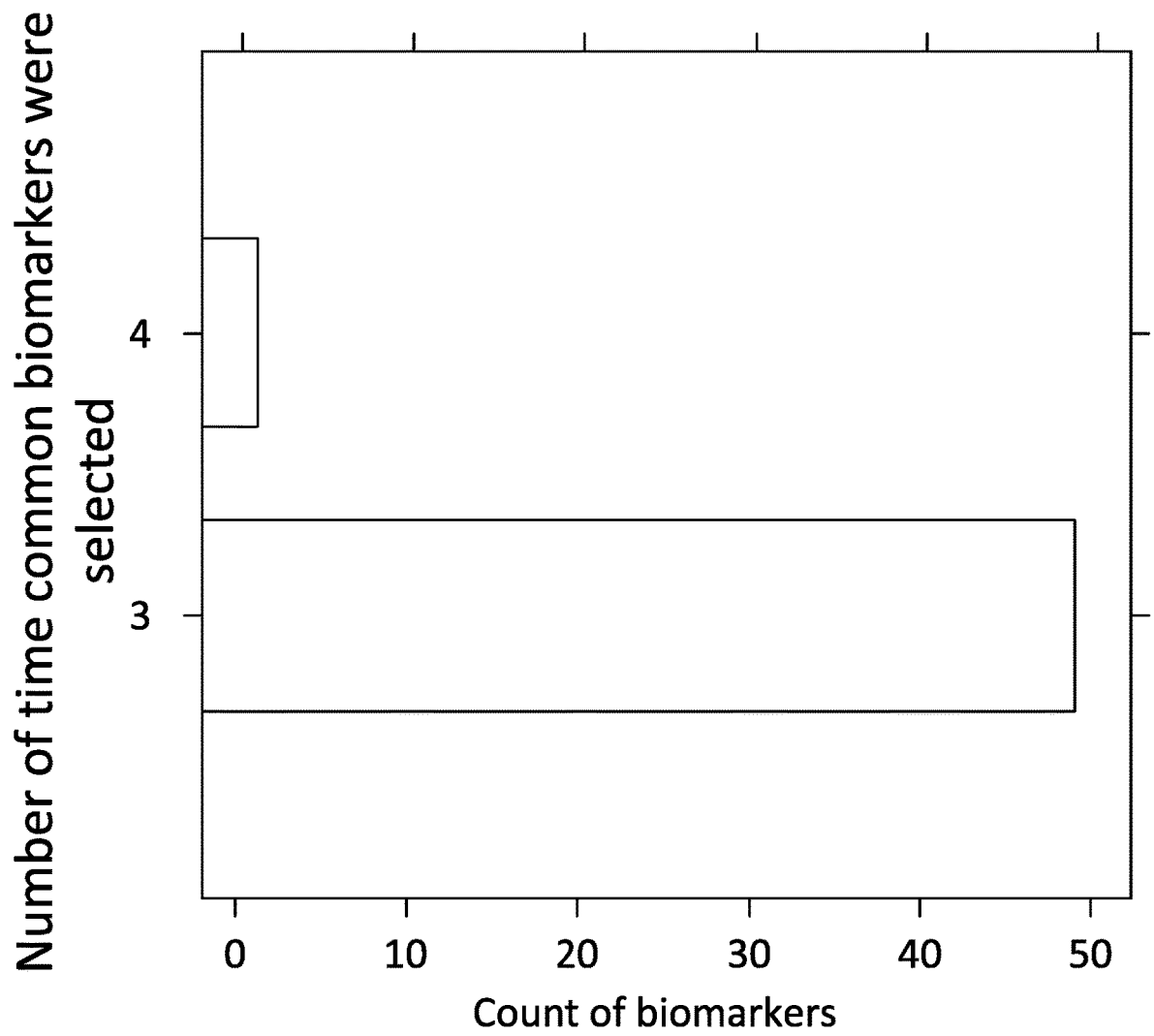
FIG. 8 illustrates the number of times that common biomarkers were found to be important across the decision rules developed using (i) CART, (ii) PAM, (iii) random forests, and (iv) the Wilcoxon (adjusted) test, for $T_{-36}$ static data obtained from a training population.
Figure 9:
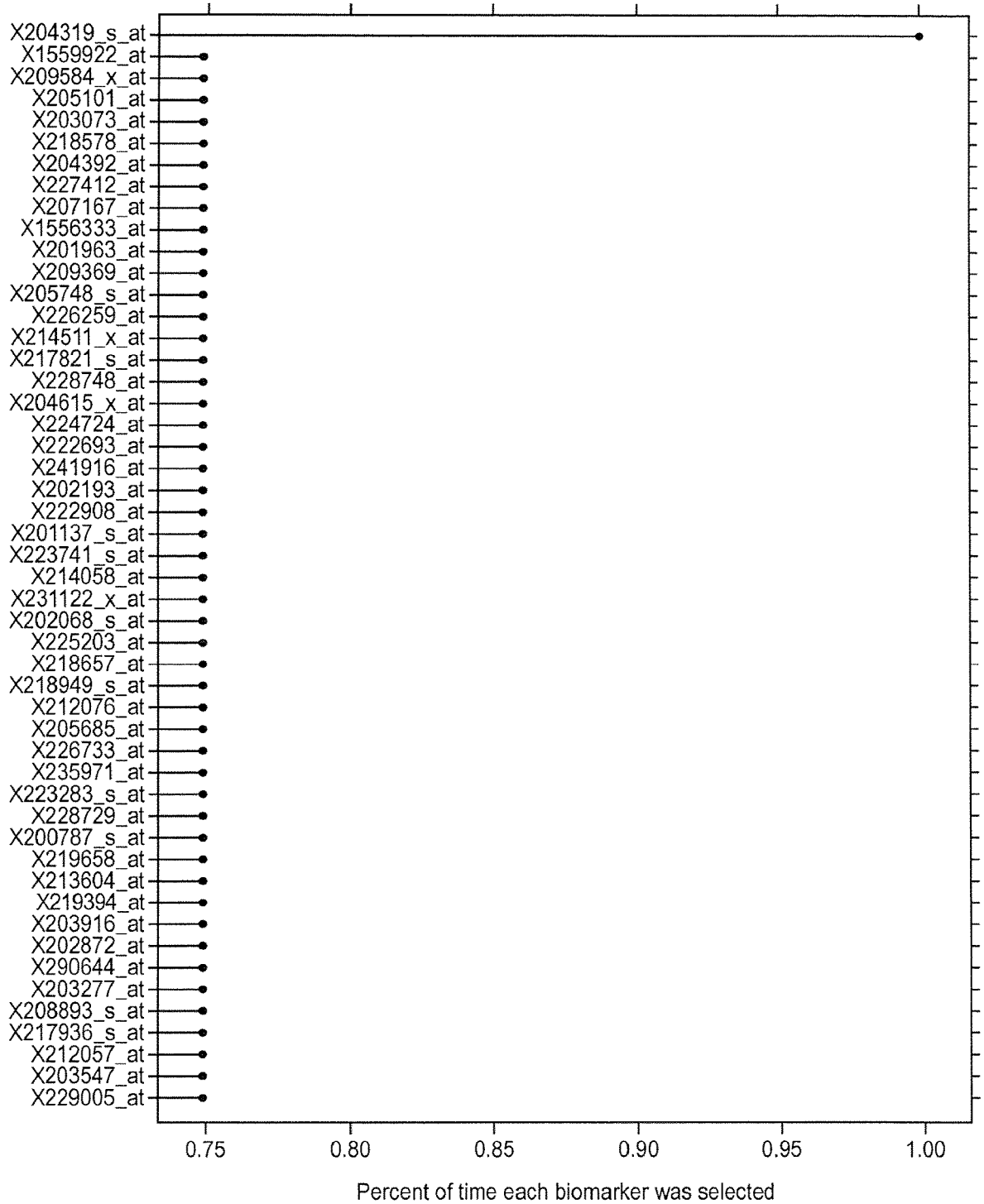
FIG. 9 illustrates an overall ranking of biomarkers for $T_{-36}$ static data obtained from a training population. The biomarkers are referenced by their corresponding Affymetrix U133 plus 2.0 probeset names given in Table 30.

FIG. 7 provides a summary of the CART, PAM, and random forests classification algorithm (decision rule) performance and associated 95% confidence intervals. Fifty distinct biomarkers were selected from across all the algorithms illustrated in FIG. 7. FIG. 8 illustrates the number of times that common biomarkers were selected across the techniques of Wilcoxon (adjusted), CART, PAM, and RF. FIG. 9 illustrates an overall ranking of biomarkers for the $T_{-36}$ data set. For the selected biomarkers, the x-axis depicts the percentage of times that it was selected. Within the percentage of times that biomarkers were selected, the biomarkers are ranked. The biomarkers in FIG. 7 are labeled based upon the probeset (oligonucleotide identity) to which they bind.

6.4 Static $T_{-12}$ Data Analysis

In another experiment, a $T_{-12}$ static analysis was performed. In the $T_{-12}$ static analysis, biomarkers features were measured using a specific blood sample, designated the $T_{-12}$ blood sample, obtained from each subject in the training population. The identity of this specific blood sample from a given subject in the training population was dependent upon whether the subject was a SIRS subject (did not develop sepsis during the observation period) or a sepsis subject (did develop sepsis during the observation period). In the case of a sepsis subject, the $T_{-12}$ sample was defined as the last blood sample taken from the subject before the subject acquired sepsis. Identification of $T_{-12}$ samples in the SIRS subjects in the training population was more discretionary than for the sepsis counterpart subjects because there was no significant event in which the SIRS subjects became septic. Because of this, the identity of the $T_{-12}$ samples for the sepsis subjects in the training population was used to identify the $T_{-12}$ samples in the SIRS subjects in the training population. Specifically, $T_{-12}$ time points (blood samples) for SIRS subjects in the training population were identified by "time-matching" a septic subject and a SIRS subject. For example, consider the case in which a subject that entered the study became clinically-defined as septic on their sixth day of enrollment. For this subject, $T_{-12}$ was day five of the study (1-24 hours prior to sepsis), and the $T_{-12}$ blood sample was the blood sample that was obtained on day five of the study. Likewise, $T_{-12}$ for the SIRS subject that was matched to this sepsis subject was deemed to be day five of study on this paired SIRS subject. While time matching between arbitrary pairs of SIRS and sepsis subjects was done to identify $T_{-12}$ blood samples for as many of the SIRS subjects in the training population as possible, in some instances, $T_{-12}$ samples from SIRS subjects had to be selected from the time points based on sample availability.

For the $T_{-12}$ static analysis, there were 54,613 biomarkers measured on 90 samples for a total of 90 corresponding microarray experiments from 90 different subjects. Each sample was collected from a different member the population. Of the 54,613 probesets in each microarray experiment, 31,047 were transformed by log transformations. Further, of the 54,613 probesets in each microarray experiment, 2518 were transformed by a square root transformation. The remaining 21,048 probesets in each microarray experiment were not transformed.

The 90 member population was initially split into a training set (n=69) and a validation set (n=21). The training set was used to estimate the appropriate classification algorithm parameters while the trained algorithm was applied to the validation set to independently assess performance. Of the 69 training samples, 34 were labeled Sepsis, meaning that the subjects developed sepsis at some point during the observation time period, and 35 were SIRS, meaning that they did not develop sepsis during the observation time period. Table 10 provides distributions of the race, gender and age for these samples.

TABLE 10

Distributions of the race, gender, and age for the training data

| Group | Gender | Black | Caucasian | Other |
|---|---|---|---|---|
| Sepsis | Male | 9 | 13 | 1 |
| | Female | 0 | 10 | 1 |
| SIRS | Male | 5 | 20 | 0 |
| | Female | 0 | 10 | 0 |

| Group | Minimum | Mean | Median | Maximum |
|---|---|---|---|---|
| Sepsis | 18 | 42.1 | 39 | 80 |
| SIRS | 18 | 44.1 | 40 | 90 |

For the 21 validation samples, 11 were labeled Sepsis and 10 were labeled SIRS. Table 11 provides distributions of the race, gender and age for these samples.

TABLE 11

Distributions of the race, gender, and age for the validation data

| Group | Gender | Black | Caucasian | Other |
|---|---|---|---|---|
| Sepsis | Male | 0 | 7 | 0 |
| | Female | 0 | 3 | 0 |
| SIRS | Male | 2 | 6 | 0 |
| | Female | 0 | 3 | 0 |

| Group | Minimum | Mean | Median | Maximum |
|---|---|---|---|---|
| Sepsis | 18 | 43.3 | 40 | 81 |
| SIRS | 19 | 53 | 52 | 85 |

Each sample in the training data was randomly assigned to one of ten groups used for cross-validation. The number of training samples in these groups ranged from 6 to 8. The samples were assigned in way that attempted to balance the number of sepsis and SIRS samples across folds. As described in more detail below, several different methods were used to judge whether select biomarkers discriminate between the Sepsis and SIRS groups.

Wilcoxon and Q-Value Tests.

The first method used to identify discriminating biomarkers was a Wilcoxon test (unadjusted). The abundance value for a given biomarker across the samples in the training data was subjected to the Wilcoxon test. The Wilcoxon test considers both group classification (sepsis versus SIRS) and abundance value in order to compute a p value for the given biomarker. The p value provides an indication of how well the abundance value for the given biomarker across the samples collected in the training set discriminates between the sepsis and SIRS state. The lower the p value, the better the discrimination. When the p value is less than a specific confidence level, such as 0.05, an inference is made that the biomarker discriminates between the sepsis and SIRS phenotype. There were 19,791 significant biomarkers using this method (see Table 12).

The second method used to identify discriminating biomarkers was the Wilcoxon Test (adjusted). Due to the large number of biomarkers, 54613, and the relatively small number of samples, 90, there was a high risk of finding falsely significant biomarkers. An adjusted p-value was used to counter this risk. In particular, the method of Benjamini and Hochberg, 1995, J. R. Statist. Soc. B 57, pp 289-300, which is hereby incorporated by reference in its entirety, was used to control the false discovery rate. Here, the false discovery rate is defined as the number of biomarkers truly significant divided by the number of biomarkers declared significant. For example, if the adjusted p-value is less than 0.05, there is a 5% chance that the biomarker is a false discovery. Results using this test are reported in Table 12. There were 11851 significant biomarkers using this method (see Table 12). As used, herein, a biomarker is considered significant if it has a p-value of less than 0.05 as determined by the Wilcoxon test (adjusted).

The third method used to identify discriminating biomarkers was the use of Q values. In such an approach, the biomarkers are ordered by their q-values and if a respective biomarker has a q-value of X, then respective biomarker and all others more significant have a combined false discovery rate of X. However, the false discovery rate for any one biomarker may be much larger. There were 11851 significant biomarkers using this method (see Table 12).

TABLE 12

Cumulative number of significant calls for the three methods. Note that all 90 samples (training and validation) were used to compare Sepsis and SIRS groups. Missing biomarker feature values were not included in the analyses.

|  | ≤1e−04 | ≤0.001 | ≤0.01 | ≤0.025 | ≤0.05 | ≤0.1 | ≤1 |
|---|---|---|---|---|---|---|---|
| p-value (unadjusted) | 0 | 5417 | 11537 | 15769 | 19791 | 24809 | 54613 |
| p-value (adjusted) | 0 | 0 | 5043 | 8374 | 11851 | 16973 | 54613 |
| q-value | 0 | 0 | 7734 | 12478 | 17820 | 24890 | 54613 |

CART.

Figure 10:
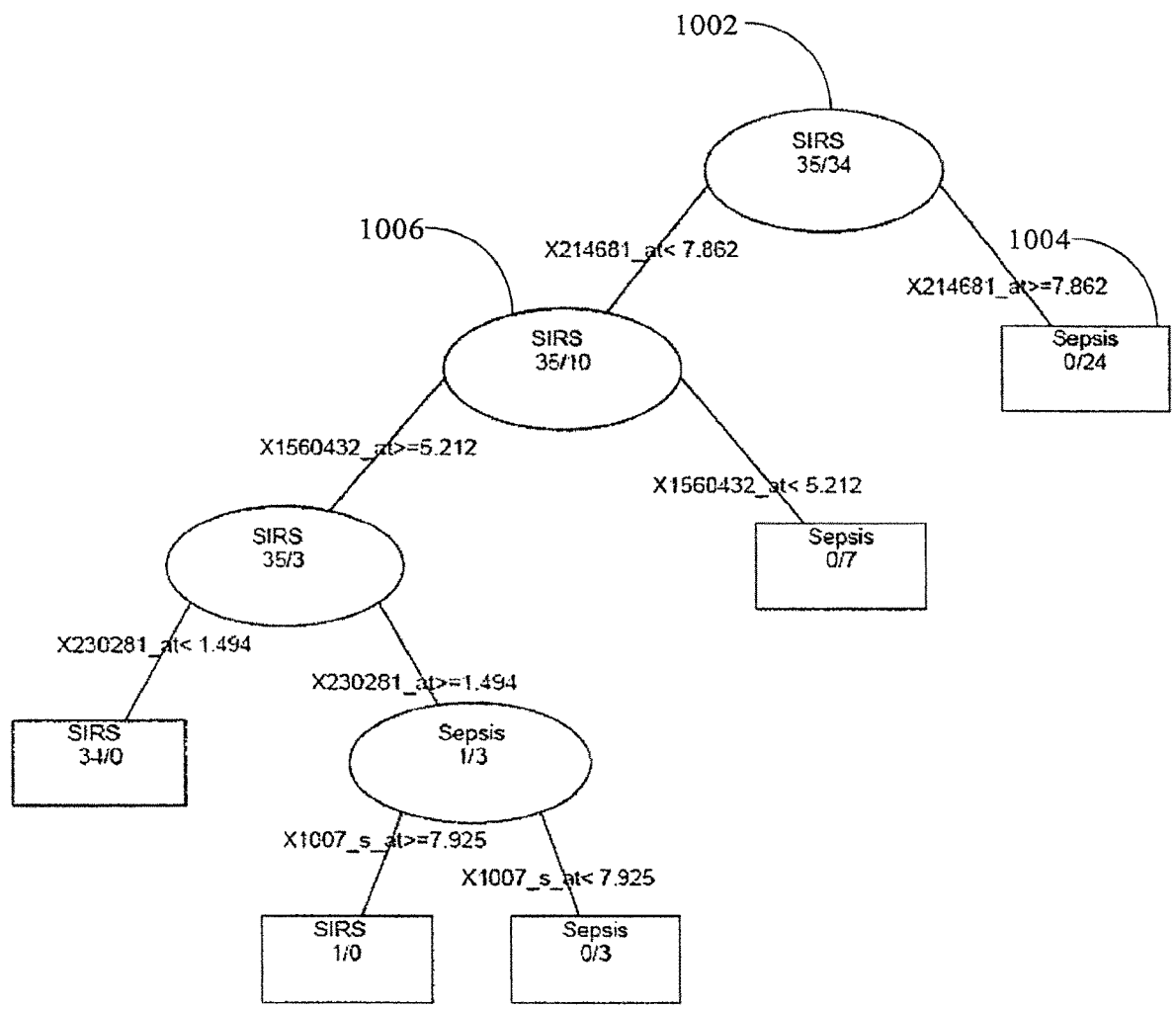
FIG. 10 illustrates a classification and regression tree for discriminating between a SIRS phenotypic state characterized by the onset of sepsis and a SIRS phenotypic state characterized by the absence of sepsis using data using $T_{-12}$ static data obtained from a training population in accordance with an embodiment of the present invention.

In addition to analyzing the microarray data using Wilcoxon test and Q-value tests in order to identify biomarkers that discriminate between the sepsis and SIRS subpopulations in the training set, classification and regression tree (CART) analysis was used. CART is described in Section 5.5.1, above. Specifically, the data summarized above was used to predict the disease state by iteratively partitioning the data based on the best single-variable split of the data. In other words, at each stage of the tree building process, the biomarker whose expression values across the training population best discriminate between the sepsis and SIRS population was invoked as a decision branch. Cross-validation was carried out, with the optimal number of splits estimated independently in each of the 10 iterations. The final tree is depicted in FIG. 10. In FIG. 10, decision 1002 makes a decision based on the abundance of the biomarker that binds to probeset X214681_at. If biomarker X214681_at has an abundance that is greater than 7.862 units in a biological sample from a subject to be diagnosed (test biological sample), than control passes to decision 1004. If, on the other hand, if the biomarker that binds to probeset (U133 plus 2.0 oligonucleotide) X214681_at has an abundance that is less than 7.862 units in the test biological sample, decision control passes to decision 1006. Decisions are made in this manner until a terminal leaf of the decision tree is reached, at which point diagnoses of sepsis or SIRS is made. The decision tree in FIG. 10 makes use of the biomarkers that bind to the following four probesets: X214681_at, X1560432_at, X230281_at, and X1007_s_at.

Figure 11:
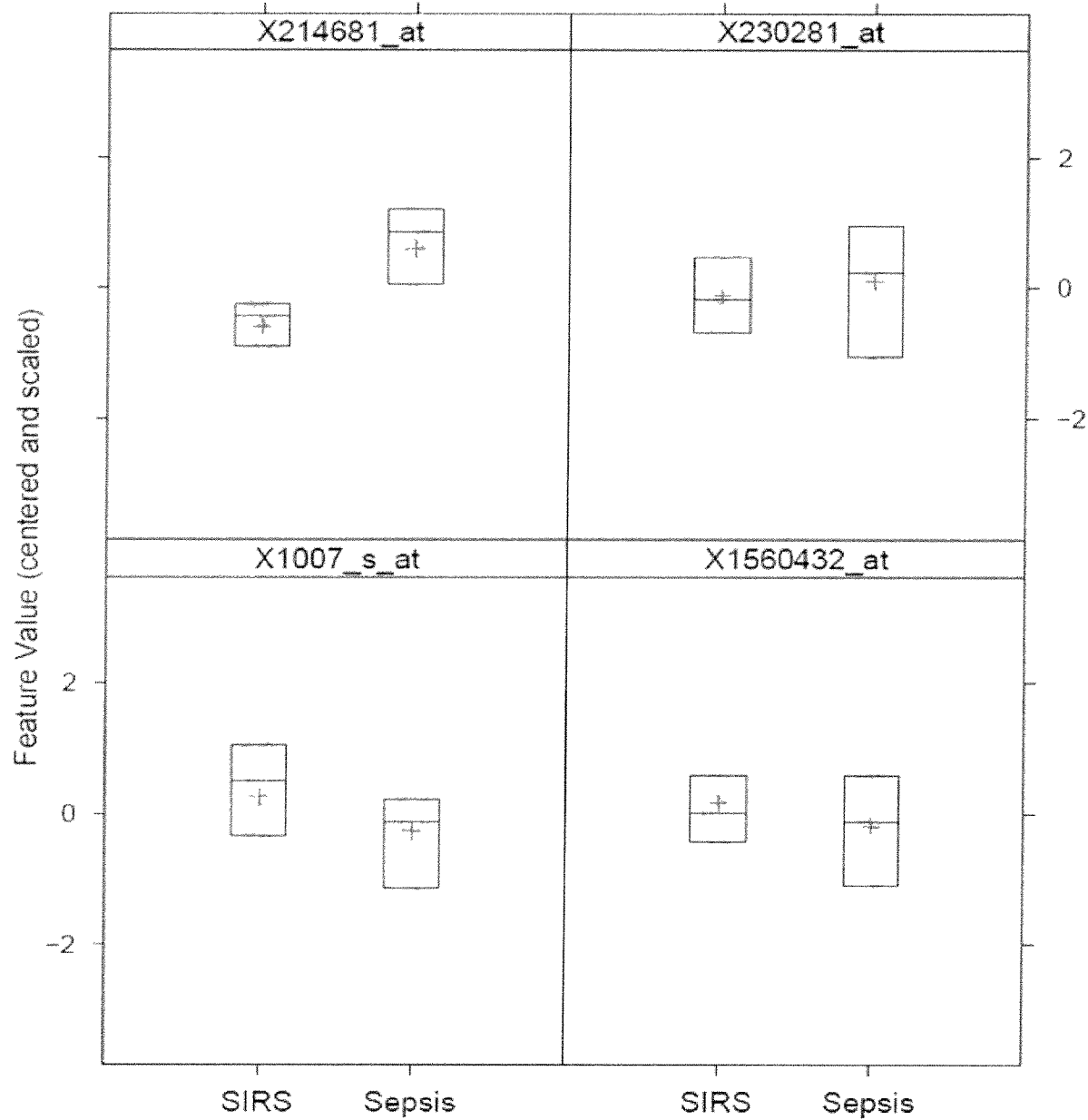
FIG. 11 shows the distribution of feature values for four biomarkers used in the decision tree of FIG. 10 using $T_{-12}$ static data obtained from a training population in accordance with an embodiment of the present invention. The biomarkers are referenced by their corresponding Affymetrix U133 plus 2.0 probeset names given in Table 30.

FIG. 11 shows the distribution of the four biomarkers used in the decision tree between the sepsis and SIRS groups in the training data set. In FIG. 11, the top of each box denotes the $75^{th}$ percentile of the data across the training set and the bottom of each box denotes the $25^{th}$ percentile, and the median value for each biomarker across the training set is drawn as a line within each box. The biomarkers are labeled in FIG. 11 based on the identity of the U133 plus 2.0 probes to which they bind). The confusion matrix for the training data where the predicted classifications were made from the cross-validated model is given in Table 13. From this confusion matrix, the overall accuracy was estimated to be 65.2% with a 95% confidence interval of 52.8% to 76.3%. The estimated sensitivity was 61.8% and the estimated specificity was 68.6%.

TABLE 13

Confusion matrix for training samples using the cross-validated CART algorithm of FIG. 10

|  | True Diagnosis | |
|---|---|---|
| Predicted | Sepsis | SIRS |
| Sepsis | 21 | 11 |
| SIRS | 13 | 24 |

For the 21 validation samples held back from training data set, the overall accuracy was estimated to be 71.4% with a 95% confidence interval of 47.8% to 88.7%, sensitivity 90.9% and specificity 50%. Table 14 shows the confusion matrix for the validation samples.

TABLE 14

Confusion matrix for validation samples using the cross-validated CART algorithm of FIG. 10

|  | True Diagnosis | |
|---|---|---|
| Predicted | Sepsis | SIRS |
| Sepsis | 10 | 5 |
| SIRS | 1 | 5 |

Random Forests.

Figure 12:
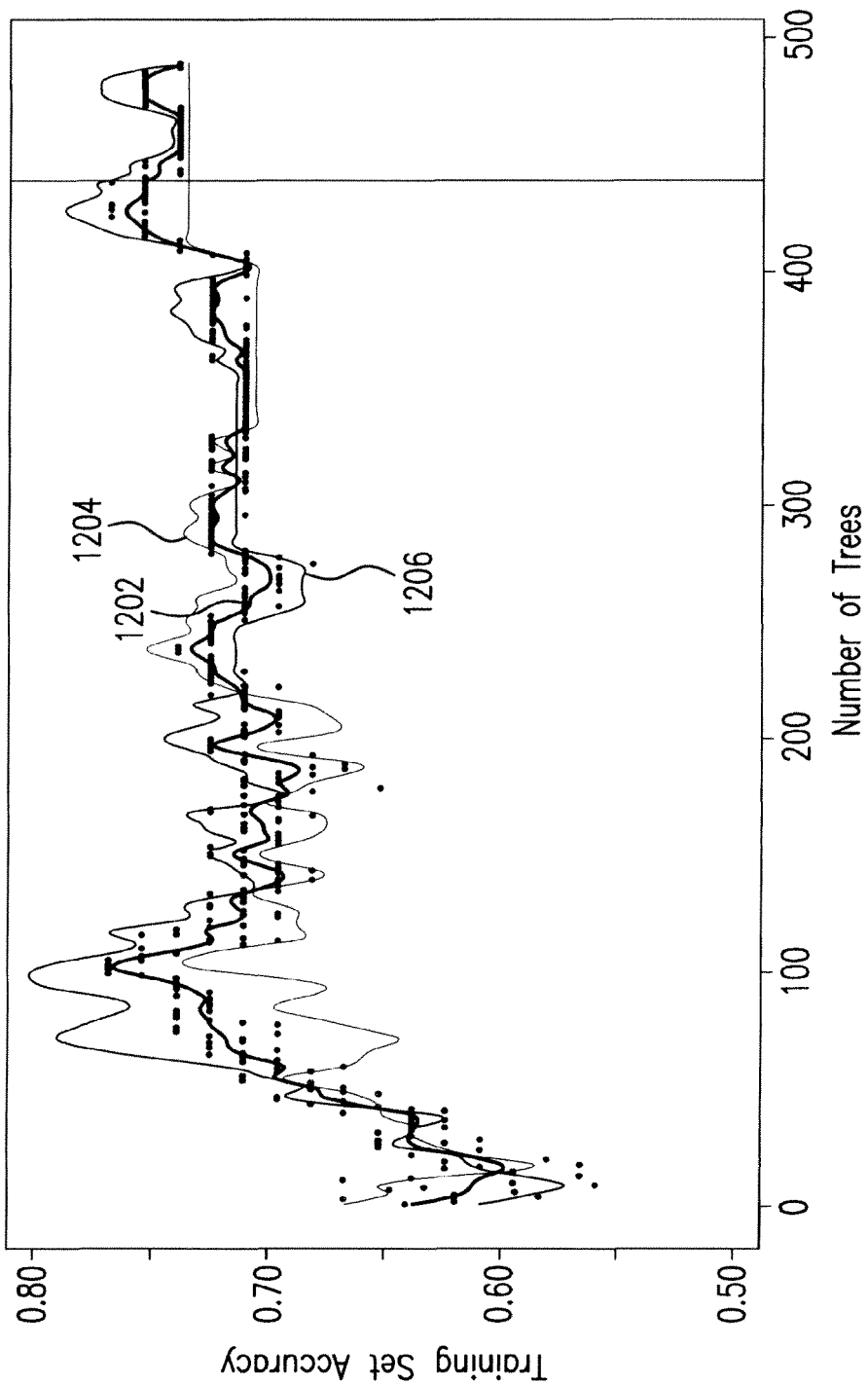
FIG. 12 illustrates the overall accuracy, sensitivity, and specificity of 500 trees used to train a decision tree using the Random Forests method based upon $T_{-12}$ static data obtained from a training population in accordance with an embodiment of the present invention.
Figure 13:
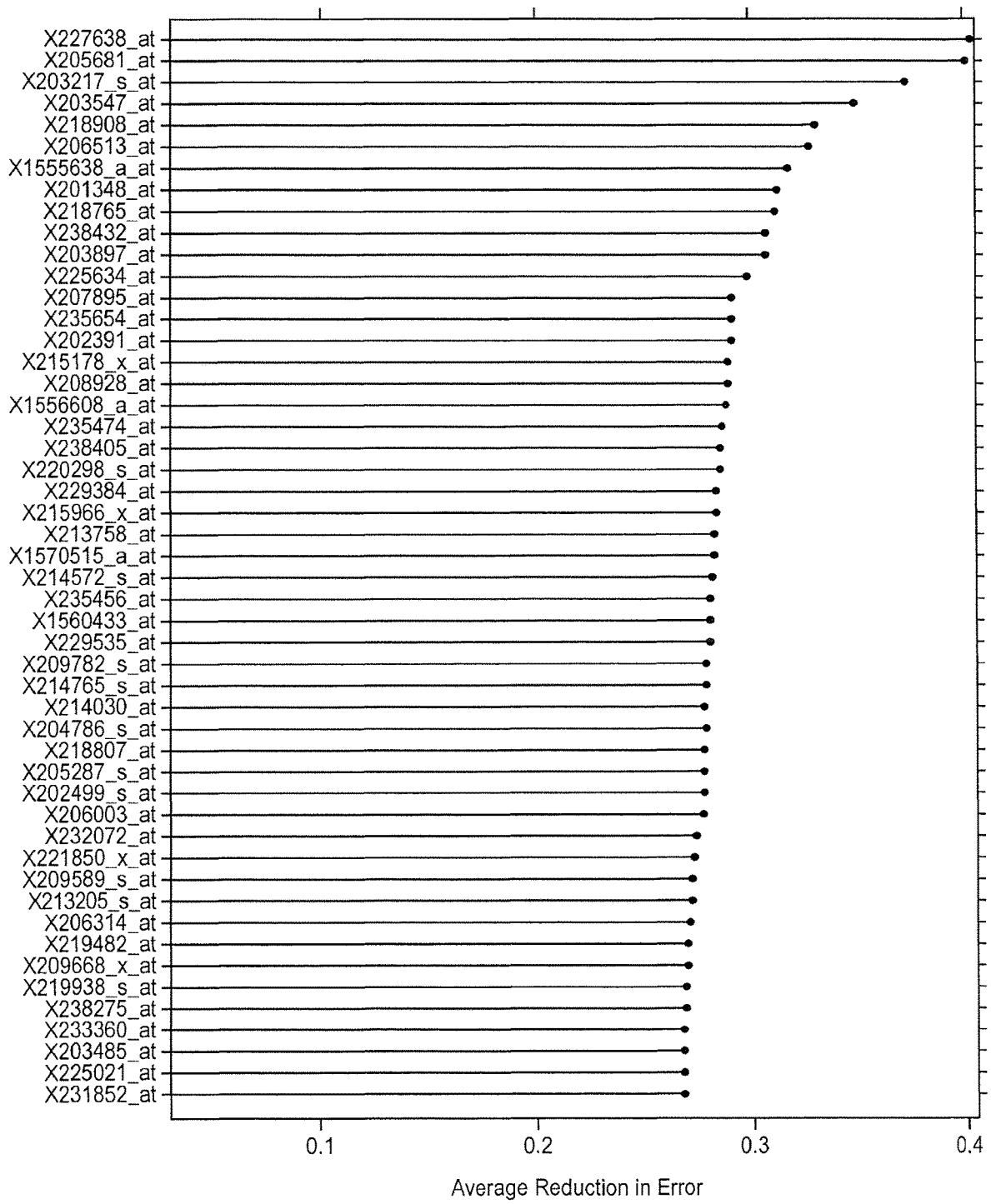
FIG. 13 illustrates the biomarker importance in the decision rule trained using the trees of FIG. 12. The biomarkers are referenced by their corresponding Affymetrix U133 plus 2.0 probeset names given in Table 30.

Another decision rule that can be developed using biomarkers of the present invention is a Random Forests decision tree. Random Forests is a tree based method that uses bootstrapping instead of cross-validation. For each iteration, a random sample (with replacement) is drawn and the largest tree possible is grown. Each tree receives a vote in the final class prediction. To fit a random forest, the number of trees (e.g. bootstrap iterations) is specified. No more than 500 were used in this example, but at least 50 are needed for a burn-in period. The number of trees was chosen based on the accuracy of the training data. For this data, 439 trees were used to train the algorithm (see FIG. 12). In FIG. 12, curve 1202 is a smoothed estimate of overall accuracy as a function of tree number. Curve 1204 is a smoothed curve of tree sensitivity as a function of tree number. Curve 1206 is a smoothed curve of tree specificity as a function of tree number. Using this algorithm, 845 biomarkers had non-zero importance and were used in the model. The random forest algorithm gauges biomarker importance by the average reduction in the training accuracy. The biomarkers were ranked by this method and are shown in FIG. 13. The figure only reflects the 50 most important biomarkers found by using Random Forest analysis. However, 845 biomarkers were actually found to have discriminating significance. The random forest method uses a number of different decision trees. A biomarker is considered to have discriminating significance if it served as a decision branch of a decision tree from a significant random forest analysis. As used herein, a significant random forest analysis is one where the lower 95% confidence interval on accuracy by cross validation on a training data set is greater than 50% and the point estimate for accuracy on a validation set is greater than 65%.

The predicted confusion matrix for the training dataset using the decision tree developed using the Random Forest method is given in Table 15. From this confusion matrix, the overall accuracy was estimated to be 75.4% (confidence intervals cannot be computed when using the bootstrap accuracy estimate). The estimated sensitivity was 73.5% and the estimated specificity was 77.1%.

TABLE 15

Confusion matrix for training samples against the decision
tree developed using the Random Forest method.

|           | True Diagnosis | |
|-----------|--------|------|
| Predicted | Sepsis | SIRS |
| Sepsis    | 27     | 9    |
| SIRS      | 8      | 25   |

For the 21 validation samples held back from training, the overall accuracy was estimated to be 95.2% with a 95% confidence interval of 76.2% to 99.9%, sensitivity 100% and specificity 90%. Table 16 shows the confusion matrix for the validation samples.

TABLE 16

Confusion matrix for the 20 validation samples against the
decision tree developed using the Random Forest method.

|           | True Diagnosis | |
|-----------|--------|------|
| Predicted | Sepsis | SIRS |
| Sepsis    | 11     | 1    |
| SIRS      | 0      | 9    |

MART.

Multiple Additive Regression Trees (MART), also known as "gradient boosting machines," was used to simultaneously assess the importance of biomarkers and classify the subject samples. Several fitting parameters are specified in this approach including (i) number of trees, (ii) step size (commonly referred to as "shrinkage"), and (iii) degree of interaction (related to the number of splits for each tree). More information on MART is described in Section 5.5.4 above. The degree of interaction was set to 1 to enforce an additive model (e.g. each tree has one split and only uses one biomarker).

Estimating interactions may require more data to function well. The step size was set to 0.05 so that the model complexity was dictated by the number of trees. The optimal number of trees was estimated by leaving out a random subset of cases at each fitting iteration, then assessing quality of prediction on that subset. After fitting more trees than were warranted, the point at which prediction performance stopped improving was estimated as the optimal point.

Figure 14:
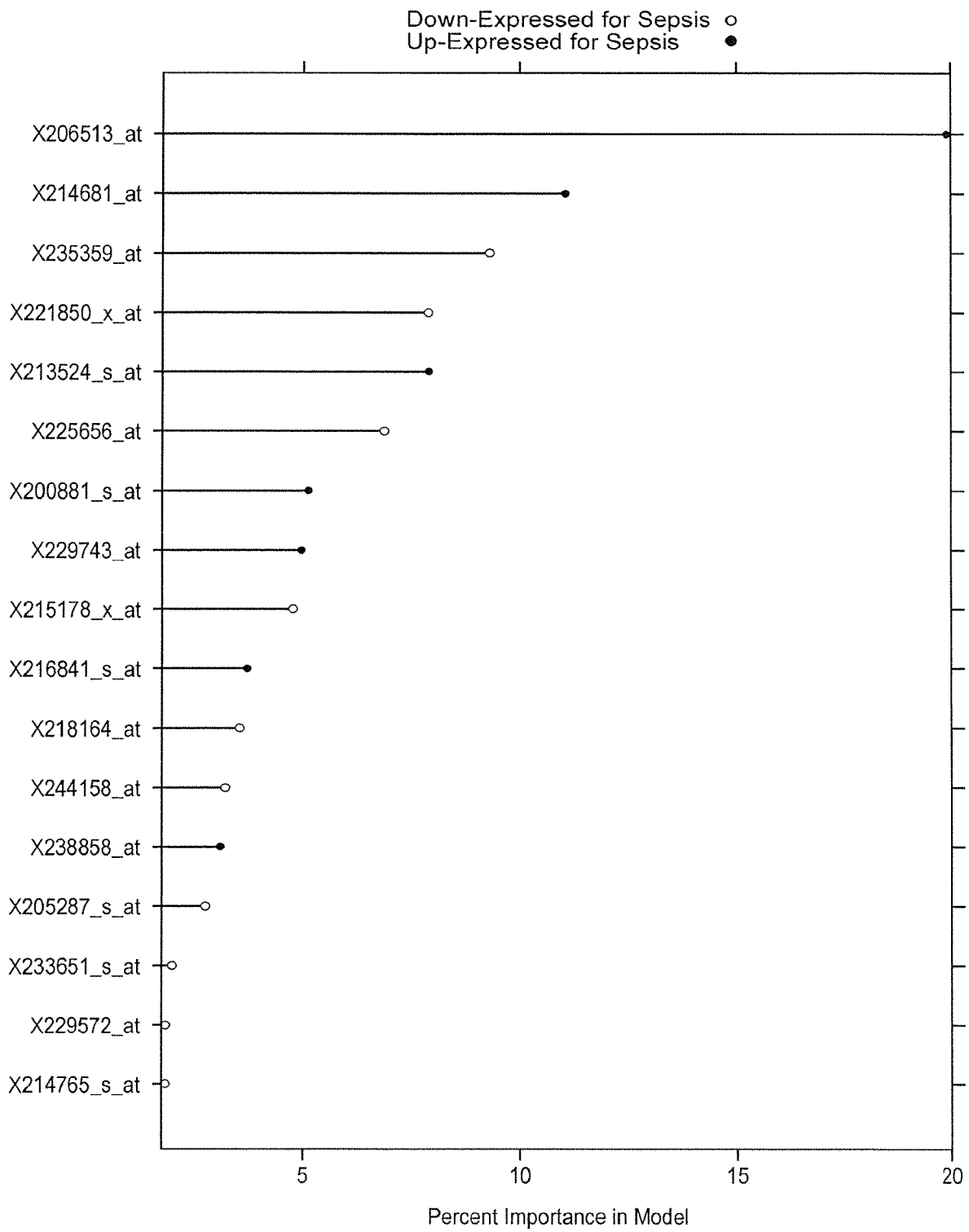
FIG. 14 illustrates a calculation of biomarker importance, summing to 100%, determined by a multiple additive regression tree (MART) approach using $T_{-12}$ static data obtained from a training population. The biomarkers are referenced by their corresponding Affymetrix U133 plus 2.0 probeset names given in Table 30.
Figure 15:
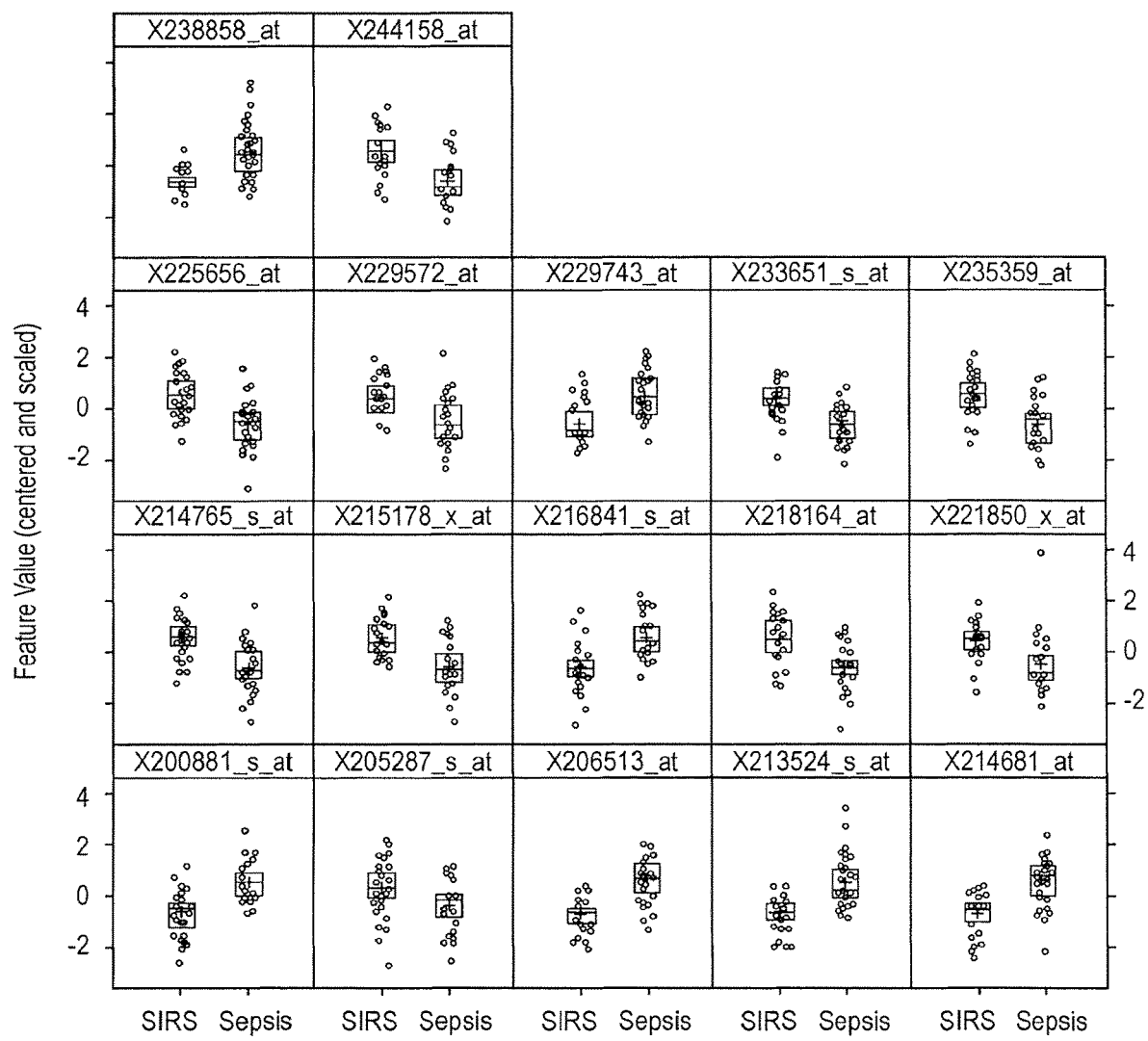
FIG. 15 illustrates the distribution of feature values of the biomarkers selected by the MART approach illustrated in FIG. 14 between the Sepsis and SIRS groups using $T_{-12}$ static data obtained from a training population. The biomarkers are referenced by their corresponding Affymetrix U133 plus 2.0 probeset names given in Table 30.

The estimated model used 28 trees and 17 biomarkers across all trees. The MART algorithm also provides a calculation of biomarker importance (summing to 100%), which are given in FIG. 14. Biomarkers with zero importance were excluded. In FIG. 14, biomarkers are labeled by the U133 plus 2.0 oligonucleotide to which they bind. FIG. 15 shows the distribution of the selected biomarkers between the Sepsis and SIRS groups. In FIG. 15, biomarkers are labeled by the U133 plus 2.0 oligonucleotide to which they bind.

Cross-validation was carried out, with the optimal number of trees estimated independently in each of the 10 iterations. The confusion matrix for the training data where the predicted classifications were made from the cross-validated model is given in Table 17. From this confusion matrix, the overall accuracy was estimated to be 76.8% with a 95% confidence interval of 65.1% to 86.1%. The estimated sensitivity was 76.5% and the estimated specificity was 77.1%.

TABLE 17

Confusion matrix for the training samples using the
cross-validated MART algorithm.

|           | True Diagnosis | |
|-----------|--------|------|
| Predicted | Sepsis | SIRS |
| Sepsis    | 26     | 8    |
| SIRS      | 8      | 27   |

For the 21 validation samples held back from training, the overall accuracy was estimated to be 85.7% with a 95% confidence interval of 63.7% to 97%, sensitivity 80% and specificity 90.9%. Table 18 shows the confusion matrix for the validation samples.

TABLE 18

Confusion matrix for the validation samples
using the MART algorithm.

|           | True Diagnosis | |
|-----------|--------|------|
| Predicted | Sepsis | SIRS |
| Sepsis    | 8      | 1    |
| SIRS      | 2      | 10   |

PAM.

Figure 16:
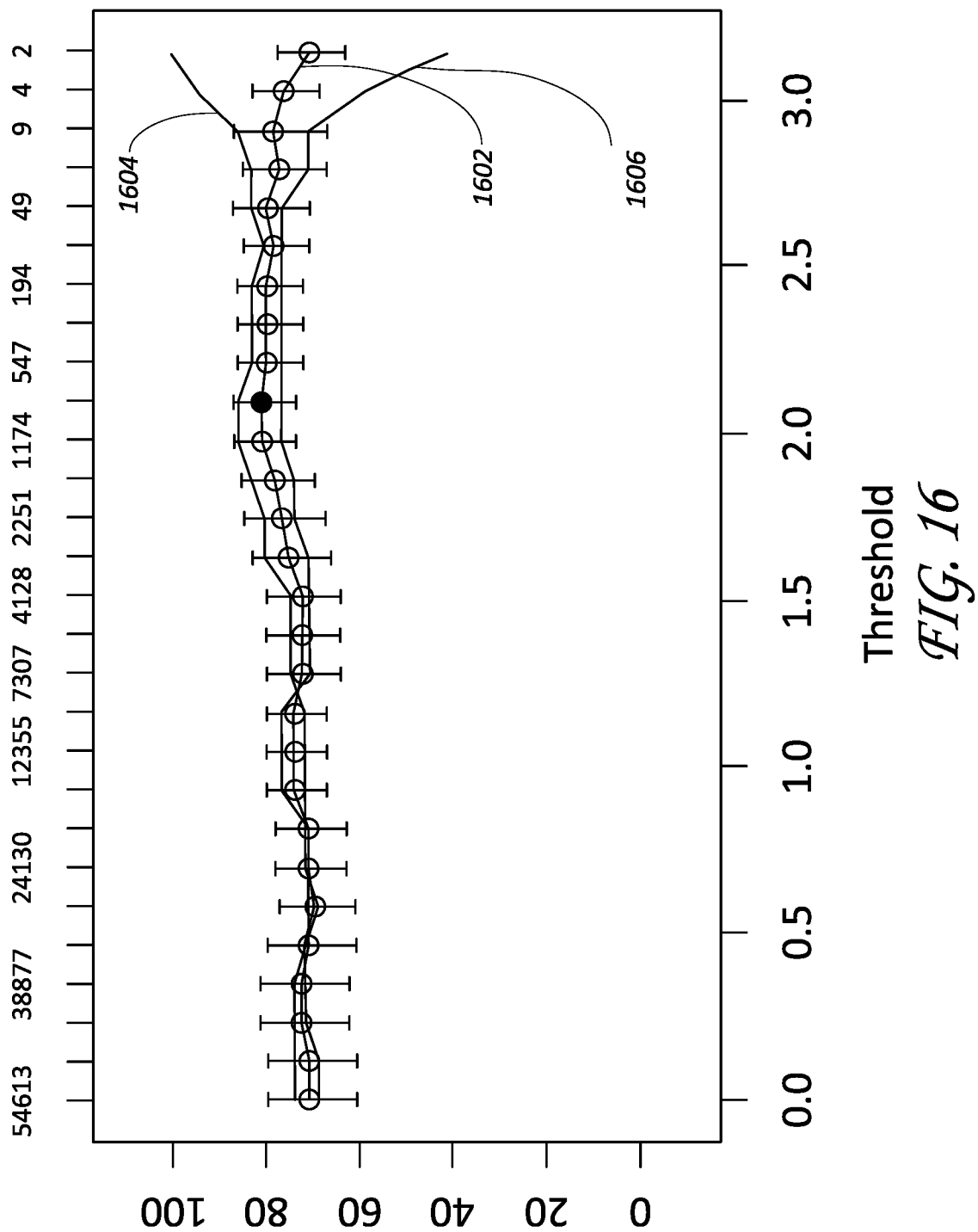
FIG. 16 illustrates the overall accuracy, with 95% confidence interval bars, specificity, and sensitivity of a decision rule developed with predictive analysis of microarrays (PAM) using the biomarkers of the present invention using $T_{-12}$ static data obtained from a training population.

Yet another decision rule developed using biomarkers of the present invention is predictive analysis of microarrays (PAM), which is described in Section 5.5.2, above. In this method, a shrinkage parameter that determines the number of biomarkers used to classify samples is specified. This parameter was chosen via cross-validation. There were no biomarkers with missing values. Based on cross-validation, the optimal threshold value was 2.1, corresponding to 820 biomarkers. FIG. 16 shows the accuracy across different thresholds. In FIG. 16, curve 1602 is the overall accuracy (with 95% confidence interval bars). Curve 1604 shows decision rule sensitivity as a function of threshold value. Curve 1606 shows decision rule specificity as a function of threshold value. Using the threshold of 2.1, the overall accuracy for the training samples was estimated to be 80.9% with a 95% confidence interval of 73.4% to 86.7%. The estimated sensitivity was 85.7% and the estimated specificity was 76.5%. Table 19 shows the confusion matrix for the training data where the predicted classifications were made from the cross-validated models.

TABLE 19

Confusion matrix for training samples using cross-validated
PAM algorithm

|           | True Diagnosis | |
|-----------|--------|------|
| Predicted | Sepsis | SIRS |
| Sepsis    | 30     | 8    |
| SIRS      | 5      | 26   |

For the 21 validation samples held back from training, the overall accuracy was estimated to be 95.2% with a 95% confidence interval of 76.2% to 99.9%, sensitivity 100% and specificity 90%. Table 20 shows the confusion matrix for the validation samples.

TABLE 20

Confusion matrix for validation samples using cross-validated PAM algorithm

| | True Diagnosis | |
|---|---|---|
| Predicted | Sepsis | SIRS |
| Sepsis | 11 | 1 |
| SIRS | 0 | 9 |

Figure 17:
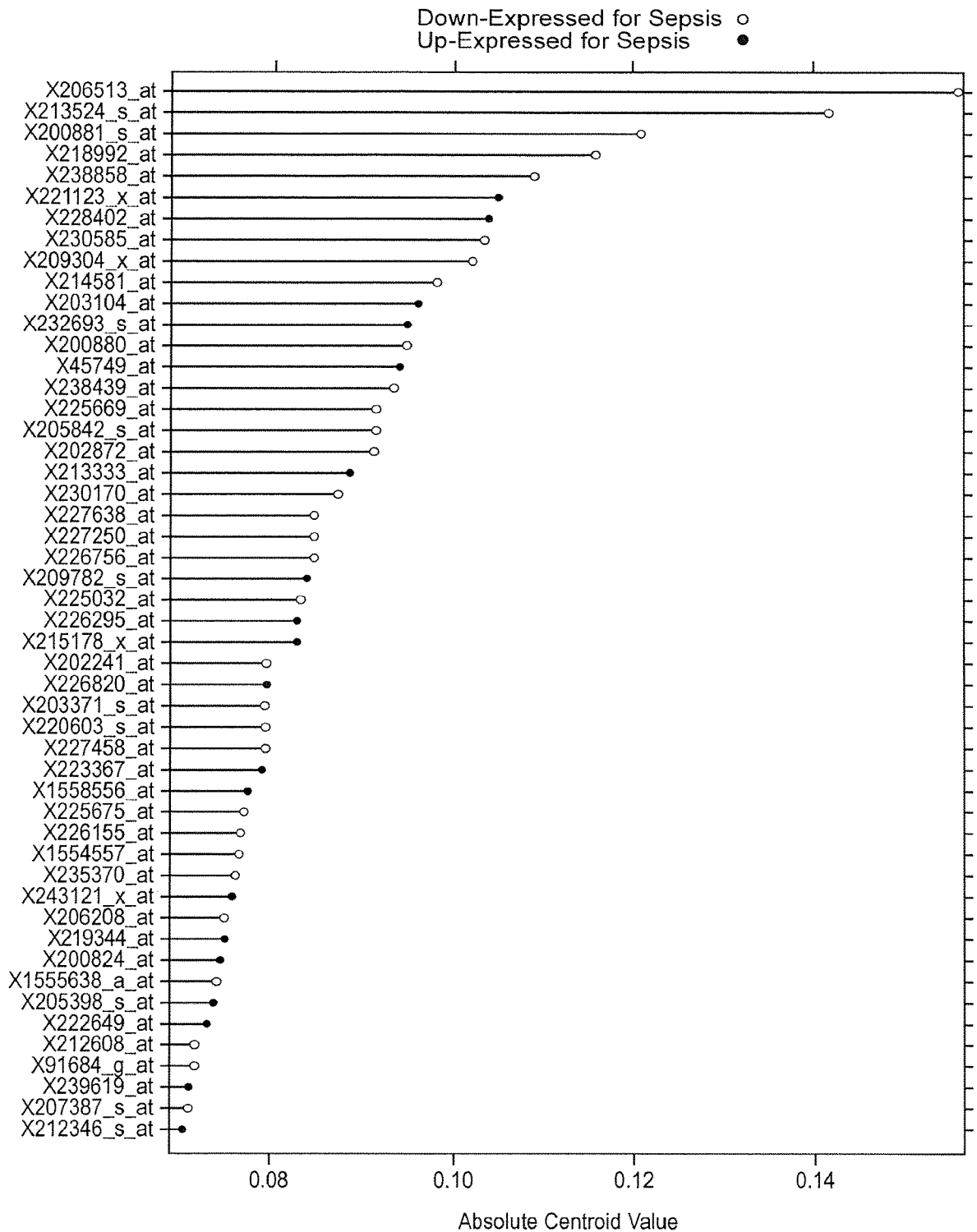
FIG. 17 is a list of biomarkers, rank-ordered by their respective degrees of discriminatory power, identified by PAM using $T_{-12}$ static data obtained from a training population. The biomarkers are referenced by their corresponding Affymetrix U133 plus 2.0 probeset names given in Table 30.

FIG. 17 shows the selected biomarkers, ranked by their relative discriminatory power, and their relative importance in the model. FIG. 17 only shows the fifty most important biomarkers found using the PAM analysis. However, 820 important biomarkers were found. In FIG. 17, biomarkers are labeled by the U133 plus 2.0 oligonucleotide to which they bind.

FIG. 18 provides a summary of the CART, MART, PAM, and random forests (RF) classification algorithm (decision rule) performance and associated 95% confidence intervals. Fifty distinct biomarkers were selected from across all the algorithms illustrated in FIG. 18. The identity of these fifty selected features is shown in FIG. 20. FIG. 19 illustrates the number of times that common biomarkers were selected across the techniques of CART, MART, PAM, RF, and Wilcoxon (adjusted). FIG. 20 illustrates an overall ranking of biomarkers for the $T_{-12}$ data set. For the selected biomarkers, the x-axis depicts the percentage of times that it was selected. Within the percentage of times that biomarkers were selected, the biomarkers are ranked. In FIG. 20, biomarkers are labeled by the U133 plus 2.0 oligonucleotide to which they bind.

6.5 Baseline $T_{-12}$ Data Analysis

In another example, a baseline $T_{-12}$ analysis was performed. Feature values for biomarkers in this example were computed as the differential between two time points. The two time points for each respective subject in a training population were (i) the $T_{-12}$ time point and (ii) the first measurement, $T_{first}$, taken of the respective subject. It will be appreciated that $T_{first}$ could differ across the training population. For example, in some subjects, $T_{first}$ was two days before $T_{-12}$, in some subjects $T_{first}$ was three days before $T_{-12}$, and so forth. To illustrate the computation of a feature value in accordance with the $T_{-12}$ baseline analysis, consider the case in which biomarker A was evaluated. To compute a feature value for biomarker A for the purposes of the baseline $T_{-12}$ analysis, the abundance of biomarker A in the $T_{-12}$ blood sample for a respective subject in the training population $[A]_{T-12}$, was obtained. Further, the abundance of biomarker A from the first blood sample taken for the respective subject, $[A]_{first}$, was obtained. The feature value for A for this respective subject was then computed as $\Delta A = [A]_{T-12} - [A]_{first}$. This calculation was repeated for each subject in the training population and for each biomarker under consideration.

For the baseline $T_{-12}$ analysis, there were 54,613 probesets measured on 89 samples for a total of 89 corresponding microarray experiments from 89 different subjects. Each sample was collected from a different member of the population. Of the 54,613 probesets in each microarray experiment, 31,047 were transformed by log transformations. Further, of the 54,613 probesets in each microarray experiment, 2518 were transformed by a square root transformation. The remaining 21,048 probesets in each microarray experiment were not transformed.

The 89 member population was initially split into a training set (n=68) and a validation set (n=21). The training set was used to estimate the appropriate classification algorithm parameters while the trained algorithm was applied to the validation set to independently assess performance. Of the 68 training samples, 33 were Sepsis, meaning that the subjects developed sepsis at some point during the observation time period, and 35 were SIRS, meaning that they did not develop sepsis during the observation time period. Table 21 provides distributions of the race, gender and age for these samples.

TABLE 21

Distributions of the race, gender, and age for the training data

| Group | Gender | Black | Caucasian | Other |
|---|---|---|---|---|
| Sepsis | Male | 9 | 12 | 1 |
| | Female | 0 | 10 | 1 |
| SIRS | Male | 5 | 20 | 0 |
| | Female | 0 | 10 | 0 |

| Group | Minimum | Mean | Median | Maximum |
|---|---|---|---|---|
| Sepsis | 18 | 42.7 | 39 | 80 |
| SIRS | 18 | 44.1 | 40 | 90 |

For the 21 validation samples, 11 were Sepsis and 10 were SIRS. Table 22 provides distributions of the race, gender and age for these samples.

TABLE 22

Distributions of the race, gender, and age for the validation data

| Group | Gender | Black | Caucasian | Other |
|---|---|---|---|---|
| Sepsis | Male | 0 | 7 | 0 |
| | Female | 0 | 3 | 0 |
| SIRS | Male | 2 | 6 | 0 |
| | Female | 0 | 3 | 0 |

| Group | Minimum | Mean | Median | Maximum |
|---|---|---|---|---|
| Sepsis | 18 | 43.3 | 40 | 81 |
| SIRS | 19 | 53 | 52 | 85 |

Each sample in the training data was randomly assigned to one of ten groups used for cross-validation. The number of training samples in these groups ranged from 6 to 8. The samples were assigned in way that attempted to balance the number of sepsis and SIRS samples across folds. As described in more detail below, several different methods were used to judge whether select biomarkers discriminate between the Sepsis and SIRS groups.

Wilcoxon and Q-Value Tests.

The first method used to identify discriminating biomarkers was a Wilcoxon test (unadjusted). The abundance value for a given biomarker from all samples in the training data was subjected to the Wilcoxon test. The Wilcoxon test considers both group classification (sepsis versus SIRS) and abundance value in order to compute a p value for the given biomarker. The p value provides an indication of how well the abundance value for the given biomarker across the samples collected in the training set discriminates between the sepsis and SIRS state. The lower the p value, the better the discrimination. When the p value is less than a specific confidence level, such as 0.05, an inference is made that the biomarker discriminates between the sepsis and SIRS phenotype. There were 6427 significant biomarkers using this method (see Table 23).

The second method used to identify discriminating biomarkers was the Wilcoxon Test (adjusted). Due to the large number of biomarkers, 54613, and the relatively small number of samples, 89, there was a high risk of finding falsely significant biomarkers. An adjusted p-value was used to counter this risk. In particular, the method of Benjamini and Hochberg, 1995, J. R. Statist. Soc. B 57, pp 289-300, which is hereby incorporated by reference in its entirety, was used to control the false discovery rate. Here, the false discovery rate is defined as the number of biomarkers truly significant divided by the number of biomarkers declared significant. For example, if the adjusted p-value is less than 0.05, there is a 5% chance that the biomarker is a false discovery. Results using this test are reported in Table 12. There were 482 significant biomarkers using this method (see Table 23). As used, herein, a biomarker is considered significant if it has a p-value of less than 0.05 as determined by the Wilcoxon test (adjusted).

The third method used to identify discriminating biomarkers was the use of Q values. The biomarkers are ordered by their q-values and if a biomarker has a q-value of X, then this biomarker and all others more biomarkers have a combined false discovery rate of X. However, the false discovery rate for any one biomarker may be much larger. There were 482 significant biomarkers using this method (see Table 23).

TABLE 23

Cumulative number of significant calls for the three methods.
Note that all 89 samples (training and validation)
were used to compare Sepsis and SIRS groups. Missing
biomarker values were not included in the analyses.

| | ≤1e−04 | ≤0.001 | ≤0.01 | ≤0.025 | ≤0.05 | ≤0.1 | ≤1 |
|---|---|---|---|---|---|---|---|
| p-value (un-adjusted) | 0 | 808 | 2486 | 4230 | 6427 | 10051 | 54613 |
| p-value (adjusted) | 0 | 0 | 0 | 0 | 482 | 1035 | 54613 |
| q-value | 0 | 0 | 0 | 0 | 606 | 1283 | 54613 |

CART.

In addition to analyzing the microarray data using Wilcoxon test and Q-value tests in order to identify biomarkers that discriminate between the sepsis and SIRS subpopulations in the training set, classification and regression tree (CART) analysis was used. CART is described in Section 5.5.1, above. Specifically, the data summarized above was used to predict the disease state by iteratively partitioning the data based on the best single-variable (biomarker) split of the data. In other words, at each stage of the tree building process, the biomarker whose abundance value across the training population best discriminates between the sepsis and SIRS population was invoked as a decision branch. Cross-validation was carried out, with the optimal number of splits estimated independently in each of the 10 iterations. The final tree is depicted in FIG. 21. In FIG. 21, decision 2102 makes a decision based on the abundance of the biomarker that bind to U133 plus 2.0 probe X210119_at. If this biomarker that binds to X210119_at has an abundance that is less than −0.03669 units in a biological sample from a subject to be diagnosed (test biological sample), then control passes to decision 2104. If, on the other hand, the biomarker that binds to probeset X210119_at has an abundance that is greater than −0.03669 units in the test biological sample, decision control passes to decision 2106. Decisions are made in this manner until a terminal leaf of the decision tree is reached, at which point diagnoses of sepsis or SIRS is made. The decision tree in FIG. 21 makes use of the biomarkers that bind to the following five U133 plus 2.0 oligonucleotides: X210119_at, X1552554_a_at, X1554390_s_at, X1552301_a_at, and X1555868_at.

FIG. 22 shows the distribution of the five biomarkers used in the decision tree between the sepsis and SIRS groups in the training data set. In FIG. 22, the top of each box denotes the $75^{th}$ percentile of the data across the training set and the bottom of each box denotes the $25^{th}$ percentile, and the median value for each biomarker across the training set is drawn as a line within each box. In FIG. 22, biomarkers are labeled by the U133 plus 2.0 oligonucleotides to which they bind. The confusion matrix for the training data where the predicted classifications were made from the cross-validated model is given in Table 24. From this confusion matrix, the overall accuracy was estimated to be 80.9% with a 95% confidence interval of 69.5% to 89.4%. The estimated sensitivity was 93.9% and the estimated specificity was 68.6%.

TABLE 24

Confusion matrix for training samples using the cross-validated
CART algorithm of FIG. 21.

| | True Diagnosis | |
|---|---|---|
| Predicted | Sepsis | SIRS |
| Sepsis | 31 | 11 |
| SIRS | 2 | 24 |

For the 21 validation samples held back from training data set, the overall accuracy was estimated to be 71.4% with a 95% confidence interval of 47.8% to 88.7%, sensitivity 72.7% and specificity 70%. Table 25 shows the confusion matrix for the validation samples.

TABLE 25

Confusion matrix for validation samples using the
cross-validated CART algorithm of FIG. 21.

| | True Diagnosis | |
|---|---|---|
| Predicted | Sepsis | SIRS |
| Sepsis | 10 | 5 |
| SIRS | 1 | 5 |

Random Forests.

Another decision rule that can be developed using biomarkers is a Random Forests decision tree. To fit a random forest, the number of trees (e.g. bootstrap iterations) is specified. No more than 500 were used in this example, but at least 50 are needed for a burn-in period. The number of trees was chosen based on the accuracy of the training data. For this data, 482 trees were used to train the algorithm (see FIG. 23). In FIG. 23, curve 2302 is a smoothed estimate of overall accuracy as a function of tree number. Curve 2304 is a smoothed curve of tree sensitivity as a function of tree number. Curve 2306 is a smoothed curve of tree specificity as a function of tree number. Using this algorithm, 482 biomarkers had non-zero importance and were used in the model. The random forest algorithm gauges biomarker importance by the average reduction in the training accuracy. The biomarkers were ranked by this method and are shown in FIG. 24. The figure only reflects the 50 most important biomarkers found by using Random Forest analysis. However, 893 biomarkers were actually found to have discriminating significance. The random forest method uses a number of different decision trees. A biomarker is considered to have discriminating significance if it served as a decision branch of a decision tree from a significant random forest analysis. As used herein, a significant random forest analysis is one where the lower 95% confidence interval on accuracy by cross validation on a training data set is greater than 50% and the point estimate for accuracy on a validation set is greater than 65%.

The predicted confusion matrix for the training dataset using the decision tree developed using the Random Forest method is given in Table 26. From this confusion matrix, the overall accuracy was estimated to be 61.8% (confidence intervals cannot be computed when using the bootstrap accuracy estimate). The estimated sensitivity was 57.6% and the estimated specificity was 65.7%.

TABLE 26

Confusion matrix for training samples against the decision tree developed using the Random Forest method.

|  | True Diagnosis | |
| --- | --- | --- |
| Predicted | Sepsis | SIRS |
| Sepsis | 23 | 14 |
| SIRS | 12 | 19 |

For the 21 validation samples held back from training, the overall accuracy was estimated to be 72.6% with a 95% confidence interval of 52.8% to 91.8%, sensitivity 63.9% and specificity 90%. Table 27 shows the confusion matrix for the validation samples.

TABLE 27

Confusion matrix for the 20 validation samples against the decision tree developed using the Random Forest method.

|  | True Diagnosis | |
| --- | --- | --- |
| Predicted | Sepsis | SIRS |
| Sepsis | 7 | 1 |
| SIRS | 4 | 9 |

PAM.

Yet another decision rule developed using biomarkers is predictive analysis of microarrays (PAM), which is described in Section 5.5.2, above. In this method, a shrinkage parameter that determines the number of biomarkers used to classify samples is specified. This parameter was chosen via cross-validation. There were no biomarkers with missing values. Based on cross-validation, the optimal threshold value was 1.62, corresponding to 269 biomarkers. FIG. 25 shows the accuracy across different thresholds. In FIG. 25, curve 2502 is the overall accuracy (with 95% confidence interval bars). Curve 2504 shows decision rule sensitivity as a function of threshold value. Curve 2506 shows decision rule specificity as a function of threshold value. Using the threshold of 1.62, the overall accuracy for the training samples was estimated to be 67.7% with a 95% confidence interval of 55.9% to 77.6%. The estimated sensitivity was 68.6% and the estimated specificity was 66.7%. Table 28 shows the confusion matrix for the training data where the predicted classifications were made from the cross-validated models.

TABLE 28

Confusion matrix for training samples using cross-validated PAM algorithm

|  | True Diagnosis | |
| --- | --- | --- |
| Predicted | Sepsis | SIRS |
| Sepsis | 24 | 11 |
| SIRS | 11 | 22 |

For the 21 validation samples held back from training, the overall accuracy was estimated to be 81% with a 95% confidence interval of 58.1% to 94.6%, sensitivity 72.7% and specificity 100%. Table 26 shows the confusion matrix for the validation samples.

TABLE 29

Confusion matrix for validation samples using cross-validated PAM algorithm

|  | True Diagnosis | |
| --- | --- | --- |
| Predicted | Sepsis | SIRS |
| Sepsis | 8 | 1 |
| SIRS | 3 | 9 |

FIG. 26 shows the selected biomarkers, ranked by their relative discriminatory power, and their relative importance in the model. FIG. 26 only shows the fifty most important biomarkers found using the PAM analysis. However, 269 biomarker were found. In FIG. 26, biomarkers are labeled by the U133 plus 2.0 oligonucleotides to which they bind.

FIG. 27 provides a summary of the CART, PAM and random forests classification algorithm (decision rule) performance and associated 95% confidence intervals. Fifty distinct biomarkers were selected from across all the algorithms illustrated in FIG. 27. FIG. 28 illustrates the number of times that common biomarkers were selected across the techniques of CART, PAM, RF, and Wilcoxon (adjusted). In FIG. 28, biomarkers are labeled by the U133 plus 2.0 oligonucleotide to which they bind. FIG. 29 illustrates an overall ranking of biomarkers for the $T_0$ base data set. In FIG. 29, biomarkers are labeled by the U133 plus 2.0 oligonucleotide to which they bind. For the selected biomarkers, the x-axis depicts the percentage of times that it was selected. Within the percentage of times that biomarkers were selected, the biomarkers are ranked.

6.6 Select Biomarkers

Sections 6.3 through 6.5 describe experiments in which blood samples from SIRS positive subjects have been tested using Affymetrix U133 plus 2.0 human genome chips containing 54,613 probesets. This section describes the criteria applied to the data described in Sections 6.3 through 6.5 in order to identify a list of biomarkers that discriminate between subjects likely to develop sepsis in a defined time period (sepsis subjects) and subjects not likely to develop sepsis in a defined time period (SIRS subjects). FIG. 30 illustrates the filters applied to identify this list of biomarkers.

A first criterion that was imposed was a requirement that a biomarker discriminate between SIRS and sepsis with a p value of 0.05 or less, as determined by the Wilcoxon test after correction for multiple comparisons, at any time point measured or the biomarker was used in a multivariate analysis with significant classification performance where significant classification performance is defined by having a lower $95^{th}$ percentile for accuracy on a training data set that is greater than 50% and a point estimate for accuracy on the validation set greater than 65% at any time point measured. At $T_{-36}$ (Section 6.3), 1,618 biomarkers met this criterion. At $T_{-12}$ (Section 6.4), 12,728 biomarkers met this criterion. Some biomarkers met this criterion at both $T_{-12}$ and $T_{-36}$ time points. In total, there were 14,346 biomarkers (including duplicates from $T_{-12}$ and $T_{-36}$ time points) that discriminated between the sepsis and SIRS states. Thus, the first filter criterion reduced the number of eligible biomarkers from 54,613 to 14,346.

The second criterion that was imposed was a requirement that each respective biomarker under consideration exhibit at least a 1.2× fold change between the median value for the respective biomarker among the subjects that acquired sepsis during a defined time period (sepsis subjects) and the median value for the respective biomarker among subjects that do not acquire sepsis during the defined time period (SIRS subjects) at the $T_{-36}$ time or the $T_{-12}$ time point period. Furthermore, to satisfy the second criterion, the biomarker must have been used in at least one multivariate analysis with significant classification performance where significant classification performance is defined by having a lower $95^{th}$ percentile for accuracy on a training data set that is greater than 50% and a point estimate for accuracy on the validation set that is greater then 65% at any time point measured. As noted in FIG. 30, application of the third filter criterion reduced the number of eligible biomarkers from 14,346 to 626.

In column one of Table 30, each biomarker is listed by a gene name, such as, for example, a Human Gene Nomenclature Database (HUGO) symbol set forth by the Gene Nomenclature Committee, Department of Biology, University College London. As is known in the art, some human genome genes are represented by more than one probeset in the U133 plus 2.0 array. Furthermore, some of the oligonucleotides in the U133 plus 2.0 array represent expressed sequence tags (ESTs) that do not correspond to a known gene (see column two of Table 30). Where known, the names of the different human genes are listed in column three of Table 30.

In the case where a biomarker is based upon a gene that includes the sequence of a probeset listed in Table 30 or a complement thereof, the biomarker can be, for example, a transcript made by the gene, a complement thereof, or a discriminating fragment or complement thereof, or a cDNA thereof, or a discriminating fragment of the cDNA, or a discriminating amplified nucleic acid molecule corresponding to all or a portion of the transcript or its complement, or a protein encoded by the gene, or a discriminating fragment of the protein, or an indication of any of the above. Further still, the biomarker can be, for example, a protein encoded by a gene that includes a probeset sequence described in Table 30 or a discriminating fragment of the protein, or an indication of the above. Here, a discriminating molecule or fragment is a molecule or fragment that, when detected, indicates presence or abundance of the above-identified transcript, cDNA, amplified nucleic acid, or protein. In one embodiment, a biomarker profile of the present invention comprises a plurality of biomarkers that contain at least five, at least ten at least fifteen, at least twenty, at least thirty, between 2 and 5, between 3 and 7, or less than 15 of the sequences of the probesets of Table 30, or complements thereof, or genes including one of at least five of the sequences or complements thereof, or a discriminating fragment thereof, or an amino acid sequence encoded by any of the foregoing nucleic acid sequences, or any discriminating fragment of such an amino acid sequence. Such biomarkers can be mRNA transcripts, cDNA or some other form of amplified nucleic acid or proteins. In some embodiments a biomarker is any gene that includes the sequence in an Affymetrix probeset given in Table 30, or any gene that includes a complement of the sequence in an Affymetrix probeset given in Table 30, or any mRNA, cDNA or other form of amplified nucleic acid of the foregoing, for any discriminating fragment of the foregoing, or any amino acid sequence coded by the foregoing, or any discriminating fragment of such a protein.

TABLE 30

Exemplary biomarkers that discriminate between responders and nonresponders

| Gene Symbol Column 1 | Affymetrix Probeset name Column 2 | Gene Name Column 3 | Gene Accession Number Column 4 | Protein Accession Number Column 5 |
|---|---|---|---|---|
| FLJ20445 | 218582_at | HYPOTHETICAL PROTEIN FLJ20445 | NM_017824 | |
| 3'HEXO | 231852_at | HISTONE MRNA 3' END EXORIBONUCLEASE | NM_153332 | NP_699163 |
| 3'HEXO | 226416_at | HISTONE MRNA 3' END EXORIBONUCLEASE | NM_153332 | NP_699163 |
| ABCA2 | 212772_s_at | ATP-BINDING CASSETTE, SUB-FAMILY A (ABC1), MEMBER 2 | NM_001606 NM_212533 | NP_001597 NP_997698 |
| ABHD2 | 228490_at | ABHYDROLASE DOMAIN CONTAINING 2 | NM_007011 NM_152924 | NP_008942 NP_690888 |
| ACN9 | 218981_at | ACN9 HOMOLOG (S. CEREVISIAE) | NM_020186 | NP_064571 |
| ACSL1 | 201963_at | ACYL-COA SYNTHETASE LONG-CHAIN FAMILY MEMBER 1 | NM_001995 | NP_001986 |
| ACSL3 | 201660_at | ACYL-COA SYNTHETASE LONG-CHAIN FAMILY MEMBER 3 | NM_004457 NM_203372 | NP_004448 NP_976251 |

TABLE 30-continued

Exemplary biomarkers that discriminate between responders and nonresponders

| Gene Symbol Column 1 | Affymetrix Probeset name Column 2 | Gene Name Column 3 | Gene Accession Number Column 4 | Protein Accession Number Column 5 |
|---|---|---|---|---|
| ACSL4 | 202422_s_at | ACYL-COA SYNTHETASE LONG-CHAIN FAMILY MEMBER 4 | NM_004458 NM_022977 | NP_004449 NP_075266 |
| ACTR3 | 213101_s_at | ARP3 ACTIN-RELATED PROTEIN 3 HOMOLOG (YEAST) | NM_005721 | NP_005712 |
| ADM | 202912_at | ADRENOMEDULLIN | NM_001124 | NP_001115 |
| ADORA2A | 205013_s_at | ADENOSINE A2 RECEPTOR | NM_000675 | NP_000666 |
| AIM2 | 206513_at | ABSENT IN MELANOMA 2 | NM_004833 | NP_004824 |
| ALOX5AP | 204174_at | ARACHIDONATE 5-LIPOXYGENASE-ACTIVATING PROTEIN | NM_001629 | NP_001620 |
| AMPD2 | 212360_at | ADENOSINE MONOPHOSPHATE DEAMINASE 2 (ISOFORM L) | NM_004037 NM_139156 NM_203404 | NP_004028 NP_631895 NP_981949 |
| ANKRD22 | 238439_at | ANKYRIN REPEAT DOMAIN 22 | NM_144590 | NP_653191 |
| ANKRD22 | 239196_at | ANKYRIN REPEAT DOMAIN 22 | NM_144590 | NP_653191 |
| ANXA3 | 209369_at | ANNEXIN A3 | NM_005139 | NP_005130 |
| APG3L | 220237_at | APG3 AUTOPHAGY 3-LIKE (S. CEREVISIAE) | NM_022488 | NP_071933 |
| ARHGAP8 | 47069_at | RHO GTPASE ACTIVATING PROTEIN 8 | NM_015366 NM_017701 NM_181333 NM_181334 NM_181335 | NP_056181 NP_060171 NP_851850 NP_851851 NP_851852 |
| ARID5B | 212614_at | AT RICH INTERACTIVE DOMAIN 5B (MRF1-LIKE) | XM_084482 | XP_084482 |
| ASAHL | 214765_s_at | N-ACYLSPHINGOSINE AMIDOHYDROLASE-LIKE PROTEIN | NM_014435 | NP_055250 |
| ASAHL | 232072_at | N-ACYLSPHINGOSINE AMIDOHYDROLASE-LIKE PROTEIN | NM_014435 | NP_055250 |
| ASAHL | 227135_at | N-ACYLSPHINGOSINE AMIDOHYDROLASE-LIKE PROTEIN | NM_014435 | NP_055250 |
| ASPH | 242037_at | ASPARTATE BETA-HYDROXYLASE | NM_004318 NM_020164 NM_032466 NM_032467 NM_032468 | NP_004309 NP_064549 NP_115855 NP_115856 NP_115857 |
| ATP11B | 1554557_at | ATPASE, CLASS VI, TYPE 11B | XM_087254 | XP_087254 |
| ATP11B | 1564064_a_at | ATPASE, CLASS VI, TYPE 11B | XM_087254 | XP_087254 |
| ATP11B | 1554556_a_at | ATPASE, CLASS VI, TYPE 11B | XM_087254 | XP_087254 |
| ATP11B | 212536_at | ATPASE, CLASS VI, TYPE 11B | XM_087254 | XP_087254 |
| ATP11B | 1564063_a_at | ATPASE, CLASS VI, TYPE 11B | XM_087254 | XP_087254 |
| ATP6V1C1 | 202872_at | ATPASE, H+ TRANSPORTING, LYSOSOMAL, 42-KD, V1 SUBUNIT C, ISOFORM 1 | NM_001007254 NM_001695 | NP_001007255 NP_001686 |
| ATP6V1C1 | 202874_s_at | ATPASE, H+ TRANSPORTING, LYSOSOMAL, 42-KD, V1 SUBUNIT C, ISOFORM 1 | NM_001007254 NM_001695 | NP_001007255 NP_001686 |
| ATP6V1C1 | 226463_at | ATPASE, H+ TRANSPORTING, LYSOSOMAL, 42-KD, V1 SUBUNIT C, ISOFORM 1 | NM_001007254 NM_001695 | NP_001007255 NP_001686 |
| ATP9A | 212062_at | ATPASE, CLASS II, TYPE 9A | XM_030577 | XP_030577 |
| B4GALT5 | 221485_at | BETA-1,4-GALACTOSYLTRANSFERASE | NM_004776 | NP_004767 |
| BASP1 | 202391_at | BRAIN-ABUNDANT SIGNAL PROTEIN | NM_006317 | NP_006308 |

TABLE 30-continued

Exemplary biomarkers that discriminate between responders and nonresponders

| Gene Symbol Column 1 | Affymetrix Probeset name Column 2 | Gene Name Column 3 | Gene Accession Number Column 4 | Protein Accession Number Column 5 |
|---|---|---|---|---|
| BAT5 | 224756_s_at | HLA-B ASSOCIATED TRANSCRIPT 5 | NM_021160 | NP_066983 |
| BATF | 205965_at | BASIC LEUCINE ZIPPER TRANSCRIPTION FACTOR, ATF-LIKE | NM_006399 | NP_006390 |
| BAZ1A | 217986_s_at | BROMODOMAIN ADJACENT TO ZINC FINGER DOMAIN, 1A | NM_013448 NM_182648 | NP_038476 NP_872589 |
| BAZ1A | 217985_s_at | BROMODOMAIN ADJACENT TO ZINC FINGER DOMAIN, 1A | NM_013448 NM_182648 | NP_038476 NP_872589 |
| BCL2A1 | 205681_at | BCL2-RELATED PROTEIN A1 | NM_004049 | NP_004040 |
| BCL3 | 204908_s_at | B-CELL CLL/LYMPHOMA 3 | NM_005178 | NP_005169 |
| BCL3 | 204907_s_at | B-CELL CLL/LYMPHOMA 3 | NM_005178 | NP_005169 |
| BCL6 | 203140_at | B-CELL LYMPHOMA 6 | NM_001706 NM_138931 | NP_001697 NP_620309 |
| BCL6 | 215990_s_at | B-CELL LYMPHOMA 6 | NM_001706 NM_138931 | NP_001697 NP_620309 |
| BIK | 205780_at | BCL2-INTERACTING KILLER (APOPTOSIS-INDUCING) | NM_001197 | NP_001188 |
| BMX | 206464_at | BONE MARROW KINASE, X-LINKED | NM_001721 NM_203281 | NP_001712 NP_975010 |
| C13orf12 | 217769_s_at | CHROMOSOME 13 OPEN READING FRAME 12 | NM_015932 | NP_057016 |
| C14orf101 | 225675_at | CHROMOSOME 14 OPEN READING FRAME 101 | NM_017799 | NP_060269 |
| C14orf101 | 219757_s_at | CHROMOSOME 14 OPEN READING FRAME 101 | NM_017799 | NP_060269 |
| C14orf147 | 213508_at | CHROMOSOME 14 OPEN READING FRAME 147 | NM_138288 | NP_612145 |
| C16orf30 | 219315_s_at | CHROMOSOME 16 OPEN READING FRAME 30 | NM_024600 | NP_078876 |
| C16orf7 | 205781_at | CHROMOSOME 16 OPEN-READING FRAME 7 | NM_004913 | NP_004904 |
| C1GALT1 | 219439_at | CORE 1 SYNTHASE, GLYCOPROTEIN-N-ACETYLGALACTOSAMINE 3-BETA-GALACTOSYLTRANSFERASE | NM_020156 | NP_064541 |
| C1GALT1C1 | 219283_at | C1GALT1-SPECIFIC CHAPERONE 1 | NM_001011551 NM_152692 | NP_001011551 NP_689905 |
| C1GALT1C1 | 238989_at | C1GALT1-SPECIFIC CHAPERONE 1 | NM_001011551 NM_152692 | NP_001011551 NP_689905 |
| C1orf8 | 200620_at | CHROMOSOME 1 OPEN READING FRAME 8 | NM_004872 | NP_004863 |
| C1RL | 218983_at | COMPLEMENT COMPONENT 1, R SUBCOMPONENT-LIKE | NM_016546 | NP_057630 |
| C20orf24 | 217835_x_at | CHROMOSOME 20 OPEN READING FRAME 24 | NM_018840 NM_199483 NM_199484 NM_199485 | NP_061328 NP_955777 NP_955778 NP_955779 |
| C20orf24 | 223880_x_at | CHROMOSOME 20 OPEN READING FRAME 24 | NM_018840 NM_199483 NM_199484 NM_199485 | NP_061328 NP_955777 NP_955778 NP_955779 |
| C20orf32 | 1554786_at | CHROMOSOME 20 OPEN-READING FRAME 32 | NM_020356 | NP_065089 |
| C21orf91 | 220941_s_at | CHROMOSOME 21 OPEN READING FRAME 91 | NM_017447 | NP_059143 |
| C2orf25 | 217883_at | CHROMOSOME 2 OPEN READING FRAME 25 | NM_015702 | NP_056517 |
| C2orf33 | 223354_x_at | CHROMOSOME 2 OPEN READING FRAME 33 | NM_020194 | NP_064579 |
| C6orf83 | 225850_at | CHROMOSOME 6 OPEN READING FRAME 83 | NM_145169 | NP_660152 |
| C9orf19 | 225604_s_at | CHROMOSOME 9 OPEN READING FRAME 19 | NM_022343 | NP_071738 |
| C9orf46 | 218992_at | CHROMOSOME 9 OPEN READING FRAME 46 | NM_018465 | NP_060935 |

TABLE 30-continued

Exemplary biomarkers that discriminate between responders and nonresponders

| Gene Symbol Column 1 | Affymetrix Probeset name Column 2 | Gene Name Column 3 | Gene Accession Number Column 4 | Protein Accession Number Column 5 |
|---|---|---|---|---|
| C9orf84 | 1553920_at | CHROMOSOME 9 OPEN READING FRAME 84 | NM_173521 | NP_775792 |
| CA4 | 206208_at | CARBONIC ANHYDRASE IV | NM_000717 | NP_000708 |
| CA4 | 206209_s_at | CARBONIC ANHYDRASE IV | NM_000717 | NP_000708 |
| CAB39 | 217873_at | CALCIUM BINDING PROTEIN 39 | NM_016289 | NP_057373 |
| CACNA1E | 236013_at | CALCIUM CHANNEL, VOLTAGE-DEPENDENT, ALPHA 1E SUBUNIT | NM_000721 | NP_000712 |
| CACNA2D3 | 219714_s_at | CALCIUM CHANNEL, VOLTAGE-DEPENDENT, ALPHA 2/DELTA 3 SUBUNIT | NM_018398 | NP_060868 |
| CAPZA2 | 1569450_at | CAPPING PROTEIN (ACTIN FILAMENT) MUSCLE Z-LINE, ALPHA 2 | NM_006136 | NP_006127 |
| CARD12 | 1552553_a_at | CASPASE RECRUITMENT DOMAIN FAMILY, MEMBER 12 | NM_021209 | NP_067032 |
| CASP4 | 209310_s_at | CASPASE 4, APOPTOSIS-RELATED CYSTEINE PROTEASE | NM_001225 NM_033306 NM_033307 | NP_001216 NP_150649 NP_150650 |
| CCL5 | 1555759_a_at | CHEMOKINE (C-C MOTIF) LIGAND 5 | NM_002985 | NP_002976 |
| CCPG1 | 221511_x_at | CELL CYCLE PROGRESSION 1 | NM_004748 NM_020739 | NP_004739 NP_065790 |
| CD4 | 203547_at | CD4 ANTIGEN (P55) | NM_000616 | NP_000607 |
| CD48 | 237759_at | CD48 ANTIGEN (B-CELL MEMBRANE PROTEIN) | NM_001778 | NP_001769 |
| CD58 | 211744_s_at | CD58 ANTIGEN, (LYMPHOCYTE FUNCTION-ASSOCIATED ANTIGEN 3) | NM_001779 | NP_001770 |
| CD58 | 205173_x_at | CD58 ANTIGEN, (LYMPHOCYTE FUNCTION-ASSOCIATED ANTIGEN 3) | NM_001779 | NP_001770 |
| CD58 | 216942_s_at | CD58 ANTIGEN, (LYMPHOCYTE FUNCTION-ASSOCIATED ANTIGEN 3) | NM_001779 | NP_001770 |
| CD59 | 228748_at | CD59 ANTIGEN P18-20 (ANTIGEN IDENTIFIED BY MONOCLONAL ANTIBODIES 16.3A5, EJ16, EJ30, EL32 AND G344) | NM_000611 NM_203329 NM_203330 NM_203331 | NP_000602 NP_976074 NP_976075 NP_976076 |
| CD59 | 200985_s_at | CD59 ANTIGEN P18-20 (ANTIGEN IDENTIFIED BY MONOCLONAL ANTIBODIES 16.3A5, EJ16, EJ30, EL32 AND G344) | NM_000611 NM_203329 NM_203330 NM_203331 | NP_000602 NP_976074 NP_976075 NP_976076 |
| CD59 | 200984_s_at | CD59 ANTIGEN P18-20 (ANTIGEN IDENTIFIED BY MONOCLONAL ANTIBODIES 16.3A5, EJ16, EJ30, EL32 AND G344) | NM_000611 NM_203329 NM_203330 NM_203331 | NP_000602 NP_976074 NP_976075 NP_976076 |
| CD59 | 212463_at | CD59 ANTIGEN P18-20 (ANTIGEN IDENTIFIED BY MONOCLONAL ANTIBODIES 16.3A5, EJ16, EJ30, EL32 AND G344) | NM_000611 NM_203329 NM_203330 NM_203331 | NP_000602 NP_976074 NP_976075 NP_976076 |
| CD74 | 209619_at | CD74 ANTIGEN (INVARIANT POLYPEPTIDE OF MAJOR HISTOCOMPATIBILITY COMPLEX, CLASS II ANTIGEN-ASSOCIATED) | NM_004355 | NP_004346 |
| CD74 | 1567628_at | CD74 ANTIGEN (INVARIANT POLYPEPTIDE OF MAJOR HISTOCOMPATIBILITY | NM_004355 | NP_004346 |

TABLE 30-continued

Exemplary biomarkers that discriminate between responders and nonresponders

| Gene Symbol Column 1 | Affymetrix Probeset name Column 2 | Gene Name Column 3 | Gene Accession Number Column 4 | Protein Accession Number Column 5 |
|---|---|---|---|---|
| | | COMPLEX, CLASS II ANTIGEN-ASSOCIATED) | | |
| CD86 | 210895_s_at | CD86 ANTIGEN (CD28 ANTIGEN LIGAND 2, B7-2 ANTIGEN) | NM_006889 NM_175862 | NP_008820 NP_787058 |
| CDKN3 | 209714_s_at | CYCLIN-DEPENDENT KINASE INHIBITOR 3 (CDK2-ASSOCIATED DUAL SPECIFICITY PHOSPHATASE) | NM_005192 | NP_005183 |
| CEACAM1 | 209498_at | CARCINOEMBRYONIC ANTIGEN-RELATED CELL ADHESION MOLECULE 1 | NM_001712 | NP_001703 |
| CEACAM1 | 206576_s_at | CARCINOEMBRYONIC ANTIGEN-RELATED CELL ADHESION MOLECULE 1 | NM_001712 | NP_001703 |
| CEACAM1 | 211889_x_at | CARCINOEMBRYONIC ANTIGEN-RELATED CELL ADHESION MOLECULE 1 | NM_001712 | NP_001703 |
| CEACAM1 | 211883_x_at | CARCINOEMBRYONIC ANTIGEN-RELATED CELL ADHESION MOLECULE 1 | NM_001712 | NP_001703 |
| CEACAM3 | 208052_x_at | CARCINOEMBRYONIC ANTIGEN-RELATED CELL ADHESION MOLECULE 3 | NM_001815 | NP_001806 |
| CECR1 | 219505_at | CAT EYE SYNDROME CHROMOSOME REGION, CANDIDATE 1 | NM_017424 NM_177405 | NP_059120 NP_803124 |
| CHCHD7 | 222701_s_at | COILED-COIL-HELIX DOMAIN-CONTAINING PROTEIN 7 | NM_001011667 NM_001011668 NM_001011669 NM_001011670 NM_001011671 NM_024300 | NP_001011667 NP_001011668 NP_001011669 NP_001011670 NP_001011671 NP_077276 |
| CHSY1 | 203044_at | CARBOHYDRATE SYNTHASE 1 | NM_014918 | NP_055733 |
| CIR | 209571_at | CBF1 INTERACTING COREPRESSOR | NM_004882 NM_199075 | NP_004873 NP_951057 |
| CKLF | 223451_s_at | CHEMOKINE-LIKE FACTOR | NM_016326 NM_016951 NM_181640 NM_181641 | NP_057410 NP_058647 NP_857591 NP_857592 |
| CKLF | 219161_s_at | CHEMOKINE-LIKE FACTOR | NM_016326 NM_016951 NM_181640 NM_181641 | NP_057410 NP_058647 NP_857591 NP_857592 |
| CKLF | 221058_s_at | CHEMOKINE-LIKE FACTOR | NM_016326 NM_016951 NM_181640 NM_181641 | NP_057410 NP_058647 NP_857591 NP_857592 |
| CKLFSF1 | 235286_at | CHEMOKINE-LIKE FACTOR SUPER FAMILY 1 | NM_052999 NM_181268 NM_181269 NM_181270 NM_181271 NM_181272 NM_181283 NM_181285 NM_181286 NM_181287 NM_181288 NM_181289 NM_181290 NM_181292 NM_181293 NM_181294 NM_181295 NM_181296 NM_181297 NM_181298 NM_181299 | NP_443725 NP_851785 NP_851786 NP_851787 NP_851788 NP_851789 NP_851800 NP_851802 NP_851803 NP_851804 NP_851805 NP_851806 NP_851807 NP_851809 NP_851810 NP_851811 NP_851812 NP_851813 NP_851814 NP_851815 NP_851816 |

TABLE 30-continued

Exemplary biomarkers that discriminate between responders and nonresponders

| Gene Symbol Column 1 | Affymetrix Probeset name Column 2 | Gene Name Column 3 | Gene Accession Number Column 4 | Protein Accession Number Column 5 |
|---|---|---|---|---|
| | | | NM_181300 | NP_851817 |
| | | | NM_181301 | NP_851818 |
| CLEC10A | 206682_at | C-TYPE LECTIN DOMAIN FAMILY 10, MEMBER A | NM_006344 NM_182906 | NP_006335 NP_878910 |
| CLEC4D | 1552772_at | C-TYPE LECTIN DOMAIN FAMILY 4, MEMBER D | NM_080387 | NP_525126 |
| CLEC4E | 219859_at | C-TYPE LECTIN DOMAIN FAMILY 4, MEMBER E | NM_014358 | NP_055173 |
| CLEC5A | 219890_at | C-TYPE LECTIN DOMAIN FAMILY 5, MEMBER A | NM_013252 | NP_037384 |
| COL4A3BP | 223465_at | COLLAGEN, TYPE IV, ALPHA 3 (GOODPASTURE ANTIGEN) BINDING PROTEIN | NM_005713 NM_031361 | NP_005704 NP_112729 |
| COP1 | 1552701_a_at | CARD ONLY PROTEIN | NM_052889 | NP_443121 |
| COX15 | 235204_at | COX15 HOMOLOG, CYTOCHROME C OXIDASE ASSEMBLY PROTEIN (YEAST) | NM_004376 NM_078470 | NP_004367 NP_510870 |
| CPD | 201941_at | CARBOXYPEPTIDASE D | NM_001304 | NP_001295 |
| CPD | 201940_at | CARBOXYPEPTIDASE D | NM_001304 | NP_001295 |
| CPEB4 | 242384_at | CYTOPLASMIC POLYADENYLATION ELEMENT BINDING PROTEIN 4 | NM_030627 | NP_085130 |
| CPEB4 | 224829_at | CYTOPLASMIC POLYADENYLATION ELEMENT BINDING PROTEIN 4 | NM_030627 | NP_085130 |
| CPVL | 208146_s_at | CARBOXYPEPTIDASE, VITELLOGENIC-LIKE | NM_019029 NM_031311 | NP_061902 NP_112601 |
| CR1 | 206244_at | COMPLEMENT COMPONENT (3B/4B) RECEPTOR 1, INCLUDING KNOPS BLOOD GROUP SYSTEM | NM_000573 NM_000651 | NP_000564 NP_000642 |
| CRTAP | 1554464_a_at | CARTILAGE-ASSOCIATED PROTEIN | NM_006371 | NP_006362 |
| CRTAP | 1555889_a_at | CARTILAGE-ASSOCIATED PROTEIN | NM_006371 | NP_006362 |
| CSF1R | 203104_at | COLONY STIMULATING FACTOR 1 RECEPTOR, FORMERLY MCDONOUGH FELINE SARCOMA VIRAL (V-FMS) ONCOGENE HOMOLOG | NM_005211 | NP_005202 |
| CTGLF1 | 221850_x_at | CENTAURIN, GAMMA-LIKE FAMILY, MEMBER 1 | NM_133446 | NP_597703 |
| CYP4F2 | 210452_x_at | CYTOCHROME P450, FAMILY 4, SUBFAMILY F, POLYPEPTIDE 2 | NM_001082 | NP_001073 |
| DCP2 | 235258_at | DCP2 DECAPPING ENZYME HOMOLOG (S. CEREVISIAE) | NM_152624 | NP_689837 |
| DDAH2 | 202262_x_at | DIMETHYLARGININE DIMETHYLAMINOHYDROLASE 2 | NM_013974 | NP_039268 |
| DDAH2 | 215537_x_at | DIMETHYLARGININE DIMETHYLAMINOHYDROLASE 2 | NM_013974 | NP_039268 |
| DDAH2 | 214909_s_at | DIMETHYLARGININE DIMETHYLAMINOHYDROLASE 2 | NM_013974 | NP_039268 |
| DDX26 | 222239_s_at | DEAD/H (Asp-Glu-Ala-Asp/His) BOX POLYPEPTIDE 26 | NM_012141 | NP_036273 |
| DHRS9 | 223952_x_at | MEMBRANE PROTEIN, PALMITOYLATED 3; MPP3 | NM_005771 NM_199204 | NP_005762 NP_954674 |
| DHRS9 | 224009_x_at | MEMBRANE PROTEIN, PALMITOYLATED 3; MPP3 | NM_005771 NM_199204 | NP_005762 NP_954674 |
| DHRS9 | 219799_s_at | MEMBRANE PROTEIN, PALMITOYLATED 3; MPP3 | NM_005771 NM_199204 | NP_005762 NP_954674 |
| DKFZP564B1023 | 228385_at | KINESIN FAMILY MEMBER 14 (KIF14) | XM_375825 | XP_375825 |
| DKFZP566M1046 | 223637_s_at | HYPOTHETICAL PROTEIN DKFZP566M1046 | NM_032127 | NP_115503 |

TABLE 30-continued

Exemplary biomarkers that discriminate between responders and nonresponders

| Gene Symbol Column 1 | Affymetrix Probeset name Column 2 | Gene Name Column 3 | Gene Accession Number Column 4 | Protein Accession Number Column 5 |
|---|---|---|---|---|
| DKFZp667F0711 | 1559756_at | HYPOTHETICAL PROTEIN DKFZp667F0711 | XM_374767 | XP_374767 |
| DLGAP1 | 239421_at | DISCS, LARGE (DROSOPHILA) HOMOLOG-ASSOCIATED PROTEIN 1 | NM_001003809 NM_004746 | NP_001003809 NP_004737 |
| DNAJA1 | 200881_s_at | DNAJ (HSP40) HOMOLOG, SUBFAMILY A, MEMBER 1 | NM_001539 | NP_001530 |
| DR1 | 216652_s_at | DOWN-REGULATOR OF TRANSCRIPTION 1, TBP-BINDING (NEGATIVE COFACTOR 2) | NM_001938 | NP_001929 |
| E2F3 | 203693_s_at | E2F TRANSCRIPTION FACTOR 3 | NM_001949 | NP_001940 |
| EFHC1 | 225656_at | EF-HAND DOMAIN (C-TERMINAL) CONTAINING 1 | NM_018100 | NP_060570 |
| EGFL5 | 212831_at | EGF-LIKE-DOMAIN, MULTIPLE 5 | XM_376905 | XP_376905 |
| EIF4E | 201435_s_at | EUKARYOTIC TRANSLATION INITIATION FACTOR 4E | NM_001968 | NP_001959 |
| EIF4E3 | 225941_at | EUKARYOTIC TRANSLATION INITIATION FACTOR 4E MEMBER 3 | NM_173359 | NP_775495 |
| EIF4E3 | 225940_at | EUKARYOTIC TRANSLATION INITIATION FACTOR 4E MEMBER 3 | NM_173359 | NP_775495 |
| EIF4E3 | 238461_at | EUKARYOTIC TRANSLATION INITIATION FACTOR 4E MEMBER 3 | NM_173359 | NP_775495 |
| EIF4G3 | 201935_s_at | EUKARYOTIC TRANSLATION INITIATION FACTOR 4-GAMMA, 3 | NM_003760 | NP_003751 |
| EIF4G3 | 201936_s_at | EUKARYOTIC TRANSLATION INITIATION FACTOR 4-GAMMA, 3 | NM_003760 | NP_003751 |
| EIF4G3 | 243149_at | EUKARYOTIC TRANSLATION INITIATION FACTOR 4-GAMMA, 3 | NM_003760 | NP_003751 |
| EMILIN2 | 242288_s_at | ELASTIN MICROFIBRIL INTERFACER 2 | NM_032048 | NP_114437 |
| ETS2 | 201328_at | V-ETS ERYTHROBLASTOSIS VIRUS E26 ONCOGENE HOMOLOG 2 (AVIAN) | NM_005239 | NP_005230 |
| EXOSC4 | 91684_g_at | EXOSOME COMPONENT 4 | NM_019037 | NP_061910 |
| EXOSC4 | 218695_at | EXOSOME COMPONENT 4 | NM_019037 | NP_061910 |
| EXOSC4 | 58696_at | EXOSOME COMPONENT 4 | NM_019037 | NP_061910 |
| FAD104 | 244022_at | FIBRONECTIN TYPE III DOMAIN CONTAINING 3B (FNDC3B) | NM_022763 | NP_073600 |
| FAM53C | 218023_s_at | FAMILY WITH SEQUENCE SIMILARITY 53, MEMBER C | NM_016605 | NP_057689 |
| FAS | 204781_s_at | FAS (TNF RECEPTOR SUPERFAMILY, MEMBER 6) | NM_000043 NM_152871 NM_152872 NM_152873 NM_152874 NM_152875 NM_152876 NM_152877 | NP_000034 NP_690610 NP_690611 NP_690612 NP_690613 NP_690614 NP_690615 NP_690616 |
| FAS | 204780_s_at | FAS (TNF RECEPTOR SUPERFAMILY, MEMBER 6) | NM_000043 NM_152871 NM_152872 NM_152873 | NP_000034 NP_690610 NP_690611 NP_690612 |

TABLE 30-continued

Exemplary biomarkers that discriminate between responders and nonresponders

| Gene Symbol Column 1 | Affymetrix Probeset name Column 2 | Gene Name Column 3 | Gene Accession Number Column 4 | Protein Accession Number Column 5 |
|---|---|---|---|---|
| | | | NM_152874 | NP_690613 |
| | | | NM_152875 | NP_690614 |
| | | | NM_152876 | NP_690615 |
| | | | NM_152877 | NP_690616 |
| FBXL13 | 1553798_a_at | F-BOX AND LEUCINE-RICH REPEAT PROTEIN 13 | NM_145032 | NP_659469 |
| FBXO9 | 1559094_at | F-BOX PROTEIN 9 | NM_012347 | NP_036479 |
| | | | NM_033480 | NP_258441 |
| | | | NM_033481 | NP_258442 |
| FBXO9 | 1559096_x_at | F-BOX PROTEIN 9 | NM_012347 | NP_036479 |
| | | | NM_033480 | NP_258441 |
| | | | NM_033481 | NP_258442 |
| FCAR | 211307_s_at | FC FRAGMENT OF IGA, RECEPTOR FOR | NM_002000 | NP_001991 |
| | | | NM_133269 | NP_579803 |
| | | | NM_133271 | NP_579805 |
| | | | NM_133272 | NP_579806 |
| | | | NM_133273 | NP_579807 |
| | | | NM_133274 | NP_579808 |
| | | | NM_133277 | NP_579811 |
| | | | NM_133278 | NP_579812 |
| | | | NM_133279 | NP_579813 |
| | | | NM_133280 | NP_579814 |
| FCAR | 211306_s_at | FC FRAGMENT OF IGA, RECEPTOR FOR | NM_002000 | NP_001991 |
| | | | NM_133269 | NP_579803 |
| | | | NM_133271 | NP_579805 |
| | | | NM_133272 | NP_579806 |
| | | | NM_133273 | NP_579807 |
| | | | NM_133274 | NP_579808 |
| | | | NM_133277 | NP_579811 |
| | | | NM_133278 | NP_579812 |
| | | | NM_133279 | NP_579813 |
| | | | NM_133280 | NP_579814 |
| FCAR | 207674_at | FC FRAGMENT OF IGA, RECEPTOR FOR | NM_002000 | NP_001991 |
| | | | NM_133269 | NP_579803 |
| | | | NM_133271 | NP_579805 |
| | | | NM_133272 | NP_579806 |
| | | | NM_133273 | NP_579807 |
| | | | NM_133274 | NP_579808 |
| | | | NM_133277 | NP_579811 |
| | | | NM_133278 | NP_579812 |
| | | | NM_133279 | NP_579813 |
| | | | NM_133280 | NP_579814 |
| FCAR | 211305_x_at | FC FRAGMENT OF IGA, RECEPTOR FOR | NM_002000 | NP_001991 |
| | | | NM_133269 | NP_579803 |
| | | | NM_133271 | NP_579805 |
| | | | NM_133272 | NP_579806 |
| | | | NM_133273 | NP_579807 |
| | | | NM_133274 | NP_579808 |
| | | | NM_133277 | NP_579811 |
| | | | NM_133278 | NP_579812 |
| | | | NM_133279 | NP_579813 |
| | | | NM_133280 | NP_579814 |
| FCGR1A | 216950_s_at | FC FRAGMENT OF IGG, HIGH AFFINITY IA | NM_000566 | NP_000557 |
| FCGR1A | 216951_at | FC FRAGMENT OF IGG, HIGH AFFINITY IA | NM_000566 | NP_000557 |
| FCGR1A LOC440607 | 214511_x_at | | | |
| FEM1C | 213341_at | FEM-1 HOMOLOG C (C. ELEGANS) | NM_020177 | NP_064562 |
| FLJ10213 | 219906_at | HYPOTHETICAL PROTEIN FLJ10213 | NM_018029 | NP_060499 |
| FLJ10521 | 1570511_at | HYPOTHETICAL PROTEIN FLJ10521 | NM_001011722 | NP_001011722 |
| | | | NM_018125 | NP_060595 |
| FLJ11011 | 222657_s_at | HYPOTHETICAL PROTEIN FLJ11011 | NM_001001481 | NP_001001481 |
| | | | NM_001001482 | NP_001001482 |
| | | | NM_018299 | NP_060769 |
| FLJ11259 | 218627_at | HYPOTHETICAL PROTEIN FLJ11259 | NM_018370 | NP_060840 |
| FLJ11795 | 220112_at | HYPOTHETICAL PROTEIN FLJ11795 | NM_024669 | NP_078945 |

TABLE 30-continued

Exemplary biomarkers that discriminate between responders and nonresponders

| Gene Symbol Column 1 | Affymetrix Probeset name Column 2 | Gene Name Column 3 | Gene Accession Number Column 4 | Protein Accession Number Column 5 |
|---|---|---|---|---|
| FLJ12770 | 226059_at | HYPOTHETICAL PROTEIN FLJ12770 | NM_032174 | NP_115550 |
| FLJ13154 | 218060_s_at | HYPOTHETICAL PROTEIN FLJ13154 | NM_024598 | NP_078874 |
| FLJ13448 | 219397_at | HYPOTHETICAL PROTEIN FLJ13448 | NM_025147 | NP_079423 |
| FLJ14001 | 238983_at | HYPOTHETICAL PROTEIN FLJ14001 | NM_024677 | NP_078953 |
| FLJ20273 | 218035_s_at | RNA-BINDING PROTEIN | NM_019027 | NP_061900 |
| FLJ20273 | 222496_s_at | RNA-BINDING PROTEIN | NM_019027 | NP_061900 |
| FLJ20481 | 227889_at | HYPOTHETICAL PROTEIN FLJ20481 | NM_017839 | NP_060309 |
| FLJ20481 | 222833_at | HYPOTHETICAL PROTEIN FLJ20481 | NM_017839 | NP_060309 |
| FLJ20701 | 219093_at | HYPOTHETICAL PROTEIN FLJ20701 | NM_017933 | NP_060403 |
| FLJ22833 | 219334_s_at | HYPOTHETICAL PROTEIN FLJ22833 | NM_022837 | NP_073748 |
| FLJ22833 | 233085_s_at | HYPOTHETICAL PROTEIN FLJ22833 | NM_022837 | NP_073748 |
| FLJ22833 | 222872_x_at | HYPOTHETICAL PROTEIN FLJ22833 | NM_022837 | NP_073748 |
| FLJ23231 | 218810_at | MCP-1 TREATMENT-INDUCED PROTEIN (MCPIP) | NM_025079 | NP_079355 |
| FLJ25416 | 228281_at | HYPOTHETICAL PROTEIN FLJ25416 | NM_145018 | NP_659455 |
| FLJ31033 | 228152_s_at | HYPOTHETICAL PROTEIN FLJ31033 | XM_037817 XM_376353 | XP_037817 XP_376353 |
| FLJ36031 | 226756_at | HYPOTHETICAL PROTEIN FLJ36031 | NM_175884 | NP_787080 |
| FLJ37858 | 227354_at | FLJ37858 PROTEIN | NM_001007549 | NP_001007550 |
| FLOT1 | 210142_x_at | FLOTILLIN 1 | NM_005803 | NP_005794 |
| FNDC3B | 225032_at | FIBRONECTIN TYPE III DOMAIN CONTAINING 3B | NM_022763 | NP_073600 |
| FNDC3B | 222692_s_at | FIBRONECTIN TYPE III DOMAIN CONTAINING 3B | NM_022763 | NP_073600 |
| FNDC3B | 222693_at | FIBRONECTIN TYPE III DOMAIN CONTAINING 3B | NM_022763 | NP_073600 |
| FNDC3B | 229865_at | FIBRONECTIN TYPE III DOMAIN CONTAINING 3B | NM_022763 | NP_073600 |
| FNDC3B | 218618_s_at | FIBRONECTIN TYPE III DOMAIN CONTAINING 3B | NM_022763 | NP_073600 |
| FTS | 218373_at | FUSED TOES HOMOLOG (MOUSE) | NM_001012398 NM_022476 | NP_001012398 NP_071921 |
| FYB | 227266_s_at | FYN BINDING PROTEIN (FYB-120/130) | NM_001465 NM_199335 | NP_001456 NP_955367 |
| FYB | 211795_s_at | FYN BINDING PROTEIN (FYB-120/130) | NM_001465 NM_199335 | NP_001456 NP_955367 |
| G0S2 | 213524_s_at | PUTATIVE LYMPHOCYTE G0/G1 SWITCH GENE | NM_015714 | NP_056529 |
| GAB2 | 238405_at | GRB2-ASSOCIATED BINDING PROTEIN 2 | NM_012296 NM_080491 | NP_036428 NP_536739 |
| GADD45A | 203725_at | GROWTH ARREST AND DNA-DAMAGE-INDUCIBLE, ALPHA | NM_001924 | NP_001915 |
| GADD45B | 209304_x_at | GROWTH ARREST- AND DNA DAMAGE-INDUCIBLE GENE GADD45 | NM_015675 | NP_056490 |
| GADD45B | 207574_s_at | GROWTH ARREST- AND DNA DAMAGE-INDUCIBLE GENE GADD45 | NM_015675 | NP_056490 |
| GALNT3 | 203397_s_at | UDP-N-ACETYL-ALPHA-D-GALACTOSAMINE:POLYPEPTIDE N-ACETYLGALACTOSAMINYL TRANSFERASE 3 (GALNAC-T3) | NM_004482 | NP_004473 |

TABLE 30-continued

Exemplary biomarkers that discriminate between responders and nonresponders

| Gene Symbol Column 1 | Affymetrix Probeset name Column 2 | Gene Name Column 3 | Gene Accession Number Column 4 | Protein Accession Number Column 5 |
|---|---|---|---|---|
| GBA | 210589_s_at | GLUCOSIDASE, BETA; ACID (INCLUDES GLUCOSYLCERAMIDASE) | NM_000157 NM_001005741 NM_001005742 NM_001005749 NM_001005750 | NP_000148 NP_001005741 NP_001005742 NP_001005749 NP_001005750 |
| GBA | 209093_s_at | GLUCOSIDASE, BETA; ACID (INCLUDES GLUCOSYLCERAMIDASE) | NM_000157 NM_001005741 NM_001005742 NM_001005749 NM_001005750 | NP_000148 NP_001005741 NP_001005742 NP_001005749 NP_001005750 |
| GBP2 | 242907_at | GUANYLATE BINDING PROTEIN 2, INTERFERON-INDUCIBLE | NM_004120 | NP_004111 |
| GCA | 203765_at | GRANCALCIN, EF-HAND CALCIUM BINDING PROTEIN | NM_012198 | NP_036330 |
| GCLM | 203925_at | GLUTAMATE-CYSTEINE LIGASE, MODIFIER SUBUNIT | NM_002061 | NP_002052 |
| GK | 214681_at | GLYCEROL KINASE | NM_000167 NM_203391 | NP_000158 NP_976325 |
| GK | 207387_s_at | GLYCEROL KINASE | NM_000167 NM_203391 | NP_000158 NP_976325 |
| GK | 217167_x_at | GLYCEROL KINASE | NM_000167 NM_203391 | NP_000158 NP_976325 |
| GK | 216316_x_at | GLYCEROL KINASE | NM_000167 NM_203391 | NP_000158 NP_976325 |
| GK | 215977_x_at | GLYCEROL KINASE | NM_000167 NM_203391 | NP_000158 NP_976325 |
| GNAI3 | 201180_s_at | GUANINE NUCLEOTIDE BINDING PROTEIN (G PROTEIN), ALPHA INHIBITING ACTIVITY POLYPEPTIDE 3 | NM_006496 | NP_006487 |
| GNG5 | 207157_s_at | GUANINE NUCLEOTIDE BINDING PROTEIN (G PROTEIN), GAMMA 5 | NM_005274 | NP_005265 |
| GNS | 212335_at | GLUCOSAMINE (N-ACETYL)-6-SULFATASE (SANFILIPPO DISEASE IIID) | NM_002076 | NP_002067 |
| GPR160 | 223423_at | G PROTEIN-COUPLED RECEPTOR 160 | NM_014373 | NP_055188 |
| GPR43 | 221345_at | G PROTEIN-COUPLED RECEPTOR 43 | NM_005306 | NP_005297 |
| GPR84 | 223767_at | G PROTEIN-COUPLED RECEPTOR 84 | NM_020370 | NP_065103 |
| GPR97 | 220404_at | G PROTEIN-COUPLED RECEPTOR 97 | NM_170776 | NP_740746 |
| GTDC1 | 219770_at | GLYCOSYLTRANSFERASE-LIKE DOMAIN CONTAINING 1 | NM_001006636 NM_024659 | NP_001006637 NP_078935 |
| GTF2B | 208066_s_at | GENERAL TRANSCRIPTION FACTOR IIB | NM_001514 | NP_001505 |
| GYG | 201554_x_at | GLYCOGENIN | NM_004130 | NP_004121 |
| GYG | 211275_s_at | GLYCOGENIN | NM_004130 | NP_004121 |
| HAGH | 205012_s_at | HYDROXYACYLGLUTATHIONE HYDROLASE | NM_005326 | NP_005317 |
| HDAC4 | 204225_at | HISTONE DEACETYLASE 4 | NM_006037 | NP_006028 |
| HGF | 209960_at | HEPATOCYTE GROWTH FACTOR (HEPAPOIETIN A; SCATTER FACTOR) | NM_000601 NM_001010931 NM_001010932 NM_001010933 NM_001010934 | NP_000592 NP_001010931 NP_001010932 NP_001010933 NP_001010934 |
| HIP1 | 226364_at | HUNTINGTIN INTERACTING PROTEIN 1 | NM_005338 | NP_005329 |
| HIP1 | 205425_at | HUNTINGTIN INTERACTING PROTEIN 1 | NM_005338 | NP_005329 |
| HIP1 | 205426_s_at | HUNTINGTIN INTERACTING PROTEIN 1 | NM_005338 | NP_005329 |

TABLE 30-continued

Exemplary biomarkers that discriminate between responders and nonresponders

| Gene Symbol Column 1 | Affymetrix Probeset name Column 2 | Gene Name Column 3 | Gene Accession Number Column 4 | Protein Accession Number Column 5 |
|---|---|---|---|---|
| HIST1H2BD | 209911_x_at | HISTONE 1, H2BD | NM_021063 NM_138720 | NP_066407 NP_619790 |
| HIST2H2AA | 214290_s_at | HISTONE 2, H2AA | NM_003516 | NP_003507 |
| HLA-DMA | 217478_s_at | HLA-D HISTOCOMPATIBILITY TYPE | NM_006120 | NP_006111 |
| HLA-DMB | 203932_at | MAJOR HISTOCOMPATIBILITY COMPLEX, CLASS II, DM BETA | NM_002118 | NP_002109 |
| HLA-DPA1 | 211990_at | MAJOR HISTOCOMPATIBILITY COMPLEX, CLASS II, DP ALPHA 1 | NM_033554 | NP_291032 |
| HLA-DPA1 | 211991_s_at | MAJOR HISTOCOMPATIBILITY COMPLEX, CLASS II, DP ALPHA 1 | NM_033554 | NP_291032 |
| HLA-DPB1 | 201137_s_at | MAJOR HISTOCOMPATIBILITY COMPLEX, CLASS II, DP BETA 1 | NM_002121 | NP_002112 |
| HLA-DQB1 | 209823_x_at | MAJOR HISTOCOMPATIBILITY COMPLEX, CLASS II, DQ BETA 1 | NM_002123 | NP_002114 |
| HLA-DQB1 | 211656_x_at | MAJOR HISTOCOMPATIBILITY COMPLEX, CLASS II, DQ BETA 1 | NM_002123 | NP_002114 |
| HLA-DRA | 208894_at | MAJOR HISTOCOMPATIBILITY COMPLEX, CLASS II, DR ALPHA | NM_002123 | NP_002114 |
| HLA-DRA | 210982_s_at | MAJOR HISTOCOMPATIBILITY COMPLEX, CLASS II, DR ALPHA | NM_002123 | NP_002114 |
| HLA-DRB1 | 208306_x_at | MAJOR HISTOCOMPATIBILITY COMPLEX, CLASS II, DR BETA 1 | NM_002124 | NP_002115 |
| HLA-DRB1 | 204670_x_at | MAJOR HISTOCOMPATIBILITY COMPLEX, CLASS II, DR BETA 1 | NM_002124 | NP_002115 |
| HLA-DRB1 | 209312_x_at | MAJOR HISTOCOMPATIBILITY COMPLEX, CLASS II, DR BETA 1 | NM_002124 | NP_002115 |
| HLA-DRB1 | 215193_x_at | MAJOR HISTOCOMPATIBILITY COMPLEX, CLASS II, DR BETA 1 | NM_002124 | NP_002115 |
| HNRPLL | 241692_at | HETEROGENEOUS NUCLEAR RIBONUCLEOPROTEIN L-LIKE | NM_138394 | NP_612403 |
| HPGD | 203913_s_at | HYDROXYPROSTAGLANDIN DEHYDROGENASE 15-(NAD) | NM_000860 | NP_000851 |
| HRPT2 | 218578_at | HYPERPARATHYROIDISM 2 (WITH JAW TUMOR) | NM_024529 | NP_078805 |
| HSPC163 | 228306_at | HSPC163 PROTEIN | NM_014184 | NP_054903 |
| HSPC163 | 218728_s_at | HSPC163 PROTEIN | NM_014184 | NP_054903 |
| HSPC163 | 228437_at | HSPC163 PROTEIN | NM_014184 | NP_054903 |
| HSPC163 | 223993_s_at | HSPC163 PROTEIN | NM_014184 | NP_054903 |
| HSPC163 | 243051_at | HSPC163 PROTEIN | NM_014184 | NP_054903 |
| HSPCA | 214328_s_at | HEAT SHOCK 90 KDA PROTEIN 1, ALPHA | NM_005348 | NP_005339 |

TABLE 30-continued

Exemplary biomarkers that discriminate between responders and nonresponders

| Gene Symbol Column 1 | Affymetrix Probeset name Column 2 | Gene Name Column 3 | Gene Accession Number Column 4 | Protein Accession Number Column 5 |
|---|---|---|---|---|
| HTATIP2 | 209448_at | HIV-1 TAT INTERACTIVE PROTEIN 2, 30 KDA | NM_006410 | NP_006401 |
| HTATIP2 | 210253_at | HIV-1 TAT INTERACTIVE PROTEIN 2, 30 KDA | NM_006410 | NP_006401 |
| IDI1 | 204615_x_at | ISOPENTENYL-DIPHOSPHATE DELTA ISOMERASE | NM_004508 | NP_004499 |
| IDI1 | 208881_x_at | ISOPENTENYL-DIPHOSPHATE DELTA ISOMERASE | NM_004508 | NP_004499 |
| IFNAR1 | 225669_at | INTERFERON (ALPHA, BETA AND OMEGA) RECEPTOR 1 | NM_000629 | NP_000620 |
| IFNAR1 | 225661_at | INTERFERON (ALPHA, BETA AND OMEGA) RECEPTOR 1 | NM_000629 | NP_000620 |
| IFNAR2 | 204786_s_at | INTERFERON (ALPHA, BETA AND OMEGA) RECEPTOR 2 | NM_000874 NM_207584 NM_207585 | NP_000865 NP_997467 NP_997468 |
| IFNGR1 | 202727_s_at | INTERFERON GAMMA RECEPTOR 1 | NM_000416 | NP_000407 |
| IGSF2 | 207167_at | IMMUNOGLOBULIN SUPERFAMILY, MEMBER 2 | NM_004258 | NP_004249 |
| IL10RA | 204912_at | INTERLEUKIN 10 RECEPTOR, ALPHA | NM_001558 | NP_001549 |
| IL18R1 | 206618_at | INTERLEUKIN 18 RECEPTOR 1 | NM_003855 | NP_003846 |
| IL1R1 | 202948_at | INTERLEUKIN 1 RECEPTOR, TYPE I | NM_000877 | NP_000868 |
| IL1R2 | 211372_s_at | INTERLEUKIN 1 RECEPTOR, TYPE II | NM_004633 NM_173343 | NP_004624 NP_775465 |
| IL1R2 | 205403_at | INTERLEUKIN 1 RECEPTOR, TYPE II | NM_004633 NM_173343 | NP_004624 NP_775465 |
| IL1RAP | 205227_at | INTERLEUKIN 1 RECEPTOR ACCESSORY PROTEIN | NM_002182 NM_134470 | NP_002173 NP_608273 |
| INSL3 | 214572_s_at | INSULIN-LIKE 3 (LEYDIG CELL) | NM_005543 | NP_005534 |
| IRAK2 | 231779_at | INTERLEUKIN-1 RECEPTOR-ASSOCIATED KINASE 2 | NM_001570 | NP_001561 |
| IRAK3 | 220034_at | INTERLEUKIN-1 RECEPTOR-ASSOCIATED KINASE 3 | NM_007199 | NP_009130 |
| IRAK4 | 219618_at | INTERLEUKIN-1 RECEPTOR-ASSOCIATED KINASE 4 | NM_016123 | NP_057207 |
| ITGAM | 205786_s_at | INTEGRIN, ALPHA M (COMPLEMENT COMPONENT RECEPTOR 3, ALPHA; ALSO KNOWN AS CD11B (P170), MACROPHAGE ANTIGEN ALPHA POLYPEPTIDE) | NM_000632 | NP_000623 |
| ITGB3 | 216261_at | INTEGRIN, BETA 3 (PLATELET GLYCOPROTEIN IIIA, ANTIGEN CD61) | NM_000212 | NP_000203 |
| IVNS1ABP | 201362_at | INFLUENZA VIRUS NS1A BINDING PROTEIN | NM_006469 NM_016389 | NP_006460 NP_057473 |
| JAK2 | 205842_s_at | JANUS KINASE 2 (A PROTEIN TYROSINE KINASE) | NM_004972 | NP_004963 |
| JAK2 | 205841_at | JANUS KINASE 2 (A PROTEIN TYROSINE KINASE) | NM_004972 | NP_004963 |
| JAK3 | 211108_s_at | JANUS KINASE 3 (A PROTEIN TYROSINE KINASE, LEUKOCYTE) | NM_000215 | NP_000206 |

TABLE 30-continued

Exemplary biomarkers that discriminate between responders and nonresponders

| Gene Symbol Column 1 | Affymetrix Probeset name Column 2 | Gene Name Column 3 | Gene Accession Number Column 4 | Protein Accession Number Column 5 |
|---|---|---|---|---|
| JAK3 | 227677_at | JANUS KINASE 3 (A PROTEIN TYROSINE KINASE, LEUKOCYTE) | NM_000215 | NP_000206 |
| JUNB | 201473_at | JUN B PROTO-ONCOGENE | NM_002229 | NP_002220 |
| KCNE1 | 236407_at | POTASSIUM VOLTAGE-GATED CHANNEL, ISK-RELATED FAMILY, MEMBER 1 | NM_000219 | NP_000210 |
| KCNJ15 | 238428_at | POTASSIUM INWARDLY-RECTIFYING CHANNEL, SUBFAMILY J, MEMBER 15 | NM_002243 NM_170736 NM_170737 | NP_002234 NP_733932 NP_733933 |
| KCNJ15 | 210119_at | POTASSIUM INWARDLY-RECTIFYING CHANNEL, SUBFAMILY J, MEMBER 15 | NM_002243 NM_170736 NM_170737 | NP_002234 NP_733932 NP_733933 |
| KIAA0040 | 203144_s_at | KIAA0040 | NM_014656 | NP_055471 |
| KIAA0103 | 203584_at | KIAA0103 | NM_014673 | NP_055488 |
| KIAA0182 | 212057_at | KIAA0182 PROTEIN | NM_014615 | NP_055430 |
| KIAA0261 | 212264_s_at | KIAA0261 | NM_015045 | NP_055860 |
| KIAA0635 | 206003_at | CENTROSOMAL PROTEIN 4 | NM_025009 | NP_079285 |
| KIAA0746 | 212314_at | KIAA0746 PROTEIN | NM_015187 | NP_056002 |
| KIAA1160 | 223831_x_at | KIAA1160 PROTEIN | NM_020701 | NP_065752 |
| KIAA1533 | 244808_at | KIAA1533 | NM_020895 | NP_065946 |
| KIAA1533 | 224807_at | KIAA1533 | NM_020895 | NP_065946 |
| KIAA1600 | 226155_at | KIAA1600 | NM_020940 | NP_065991 |
| KIAA1632 | 227638_at | KIAA1632 | NM_020964 | NP_066015 |
| KIAA1991 | 242808_at | HYPOTHETICAL PROTEIN KIAA1991 | XM_495886 | XP_495886 |
| KIF1B | 225878_at | KINESIN FAMILY MEMBER 1B | NM_015074 NM_183416 | NP_055889 NP_904325 |
| KIF1B | 209234_at | KINESIN FAMILY MEMBER 1B | NM_015074 NM_183416 | NP_055889 NP_904325 |
| KIF1B | 241216_at | KINESIN FAMILY MEMBER 1B | NM_015074 NM_183416 | NP_055889 NP_904325 |
| KLF11 | 218486_at | KRUPPEL-LIKE FACTOR 11 | NM_003597 | NP_003588 |
| KLF7 | 204334_at | KRUPPEL-LIKE FACTOR 7 (UBIQUITOUS) | NM_003709 | NP_003700 |
| KLHL2 | 219157_at | KELCH-LIKE 2, MAYVEN (DROSOPHILA) | NM_007246 | NP_009177 |
| KLHL6 | 1560396_at | KELCH-LIKE 6 (DROSOPHILA) | NM_130446 | NP_569713 |
| KPNA4 | 225267_at | KARYOPHERIN ALPHA 4 (IMPORTIN ALPHA 3) | NM_002268 | NP_002259 |
| KPNA4 | 209653_at | KARYOPHERIN ALPHA 4 (IMPORTIN ALPHA 3) | NM_002268 | NP_002259 |
| KREMEN1 | 227250_at | KRINGLE CONTAINING TRANSMEMBRANE PROTEIN 1 | NM_032045 NM_153379 | NP_114434 NP_700358 |
| KREMEN1 | 235370_at | KRINGLE CONTAINING TRANSMEMBRANE PROTEIN 1 | NM_032045 NM_153379 | NP_114434 NP_700358 |
| KREMEN1 | 224534_at | KRINGLE CONTAINING TRANSMEMBRANE PROTEIN 1 | NM_032045 NM_153379 | NP_114434 NP_700358 |
| LDLR | 202068_s_at | LOW DENSITY LIPOPROTEIN RECEPTOR | NM_000527 | NP_000518 |
| LFNG | 228762_at | LUNATIC FRINGE HOMOLOG (DROSOPHILA) | NM_002304 | NP_002295 |
| LGALS8 | 208934_s_at | LECTIN, GALACTOSIDE-BINDING, SOLUBLE, 8 (GALECTIN 8) | NM_006499 NM_201543 NM_201544 NM_201545 | NP_006490 NP_963837 NP_963838 NP_963839 |
| LIMK2 | 1561654_at | LIM DOMAIN KINASE 2 | NM_005569 NM_016733 | NP_005560 NP_057952 |
| LIMK2 | 202193_at | LIM DOMAIN KINASE 2 | NM_005569 NM_016733 | NP_005560 NP_057952 |
| LIMK2 | 210582_s_at | LIM DOMAIN KINASE 2 | NM_005569 NM_016733 | NP_005560 NP_057952 |
| LIMK2 | 217475_s_at | LIM DOMAIN KINASE 2 | NM_005569 NM_016733 | NP_005560 NP_057952 |
| LIN7A | 240027_at | LIN-7 HOMOLOG A (C. ELEGANS) | NM_004664 | NP_004655 |

TABLE 30-continued

Exemplary biomarkers that discriminate between responders and nonresponders

| Gene Symbol Column 1 | Affymetrix Probeset name Column 2 | Gene Name Column 3 | Gene Accession Number Column 4 | Protein Accession Number Column 5 |
|---|---|---|---|---|
| LIN7A | 206440_at | LIN-7 HOMOLOG A (C. ELEGANS) | NM_004664 | NP_004655 |
| LIR9 | 1555634_a_at | LEUKOCYTE IMMUNOGLOBULIN-LIKE RECEPTOR, SUBFAMILY B (WITH TM AND ITIM DOMAINS), MEMBER 7 (LILRB7) | NM_021250 NM_181879 NM_181985 NM_181986 | NP_067073 NP_870994 NP_871714 NP_871715 |
| LMNB1 | 203276_at | LAMIN B1 | NM_005573 | NP_005564 |
| LMTK2 | 226375_at | LEMUR TYROSINE KINASE 2 | NM_014916 | NP_055731 |
| LOC145758 | 226513_at | HYPOTHETICAL PROTEIN LOC145758 | | |
| LOC153561 | 232889_at | HYPOTHETICAL PROTEIN LOC153561 | NM_207331 | NP_997214 |
| LOC199675 | 235568_at | HYPOTHETICAL PROTEIN LOC199675 | NM_174918 | NP_777578 |
| LOC220929 | 229743_at | HYPOTHETICAL PROTEIN LOC220929 | NM_182755 | NP_877432 |
| LOC285771 | 237870_at | HYPOTHETICAL PROTEIN LOC285771 | | |
| LOC286044 | 222662_at | HYPOTHETICAL PROTEIN LOC286044 | | |
| LOC338758 | 238893_at | HYPOTHETICAL PROTEIN LOC338758 | | |
| LOC401152 | 224602_at | HCV F-TRANSACTIVATED PROTEIN 1 | NM_001001701 | NP_001001701 |
| LOC440731 | 237563_s_at | LOC440731 | XM_498838 | XP_498838 |
| LOC440823 | 227168_at | | | |
| LOC57149 | 203897_at | HYPOTHETICAL PROTEIN A-211C6.1 | NM_020424 | NP_065157 |
| LOC88523 | 214748_at | CG016 | NM_033111 | NP_149102 |
| LRG1 | 228648_at | LEUCINE-RICH ALPHA-2-GLYCOPROTEIN 1 | NM_052972 | NP_443204 |
| LRPAP1 | 201186_at | LOW DENSITY LIPOPROTEIN RECEPTOR-RELATED PROTEIN ASSOCIATED PROTEIN 1 | NM_002337 | NP_002328 |
| LRRC17 | 1560527_at | LEUCINE RICH REPEAT CONTAINING 17 | NM_005824 | NP_005815 |
| LTB4R | 236172_at | LEUKOTRIENE B4 RECEPTOR | NM_181657 | NP_858043 |
| LTBP2 | 204682_at | LATENT TRANSFORMING GROWTH FACTOR BETA BINDING PROTEIN 2 | NM_000428 | NP_000419 |
| LY86 | 205859_at | LYMPHOCYTE ANTIGEN 86 | NM_004271 | NP_004262 |
| LY96 | 206584_at | LYMPHOCYTE ANTIGEN 96 | NM_015364 | NP_056179 |
| MAP2K1IP1 | 217971_at | MITOGEN-ACTIVATED PROTEIN KINASE KINASE 1 INTERACTING PROTEIN 1 | NM_021970 | NP_068805 |
| MAP2K6 | 205698_s_at | MITOGEN-ACTIVATED PROTEIN KINASE KINASE 6 | NM_002758 NM_031988 | NP_002749 NP_114365 |
| MAPK14 | 210449_x_at | MAPK14 MITOGEN-ACTIVATED PROTEIN KINASE 14 | NM_001315 NM_139012 NM_139013 NM_139014 | NP_001306 NP_620581 NP_620582 NP_620583 |
| MAPK14 | 211561_x_at | MAPK14 MITOGEN-ACTIVATED PROTEIN KINASE 14 | NM_001315 NM_139012 NM_139013 NM_139014 | NP_001306 NP_620581 NP_620582 NP_620583 |
| MAPK14 | 211087_x_at | MAPK14 MITOGEN-ACTIVATED PROTEIN KINASE 14 | NM_001315 NM_139012 NM_139013 NM_139014 | NP_001306 NP_620581 NP_620582 NP_620583 |
| MAPK14 | 202530_at | MAPK14 MITOGEN-ACTIVATED PROTEIN KINASE 14 | NM_001315 NM_139012 NM_139013 NM_139014 | NP_001306 NP_620581 NP_620582 NP_620583 |
| MARCKSL1 | 200644_at | MARCKS-LIKE 1 | NM_023009 | NP_075385 |
| MCTP2 | 220603_s_at | MULTIPLE C2-DOMAINS WITH TWO | NM_018349 | NP_060819 |

TABLE 30-continued

Exemplary biomarkers that discriminate between responders and nonresponders

| Gene Symbol Column 1 | Affymetrix Probeset name Column 2 | Gene Name Column 3 | Gene Accession Number Column 4 | Protein Accession Number Column 5 |
|---|---|---|---|---|
| MCTP2 | 229005_at | MULTIPLE C2-DOMAINS WITH TWO TRANSMEMBRANE REGIONS 2 | NM_018349 | NP_060819 |
| MCTP2 | 239893_at | MULTIPLE C2-DOMAINS WITH TWO TRANSMEMBRANE REGIONS 2 | NM_018349 | NP_060819 |
| MEF2A | 214684_at | MADS BOX TRANSCRIPTION ENHANCER FACTOR 2, POLYPEPTIDE A (MYOCYTE ENHANCER FACTOR 2A) | NM_005587 | NP_005578 |
| MEF2C | 236395_at | MADS BOX TRANSCRIPTION ENHANCER FACTOR 2, POLYPEPTIDE C (MYOCYTE ENHANCER FACTOR 2C) | NM_002397 | NP_002388 |
| MGC11324 | 224480_s_at | HYPOTHETICAL PROTEIN MGC11324 | NM_032717 | NP_116106 |
| MGC15619 | 226879_at | HYPOTHETICAL PROTEIN MGC15619 | NM_032369 | NP_115745 |
| MGC15887 | 226448_at | HYPOTHETICAL GENE SUPPORTED BY BC009447 | NM_198552 | NP_940954 |
| MGC17301 | 227055_at | HYPOTHETICAL PROTEIN MGC17301 | NM_152637 | NP_689850 |
| MGC23280 | 226121_at | HYPOTHETICAL PROTEIN MGC23280 | NM_144683 | NP_653284 |
| MKNK1 | 209467_s_at | MAP KINASE INTERACTING SERINE/THREONINE KINASE 1 | NM_003684 NM_198973 | NP_003675 NP_945324 |
| MLKL | 238025_at | MIXED LINEAGE KINASE DOMAIN-LIKE | NM_152649 | NP_689862 |
| MLLT2 | 201924_at | MYELOID/LYMPHOID OR MIXED-LINEAGE LEUKEMIA (TRITHORAX HOMOLOG, *DROSOPHILA*); TRANSLOCATED TO, 2 | NM_005935 | NP_005926 |
| MMP9 | 203936_s_at | MATRIX METALLOPROTEINASE 9 (GELATINASE B, 92 KDA GELATINASE, 92 KDA TYPE IV COLLAGENASE) | NM_004994 | NP_004985 |
| MOBK1B | 201298_s_at | MOB1, MPS ONE BINDER KINASE ACTIVATOR-LIKE 1B (YEAST) | NM_018221 | NP_060691 |
| MOBKL2C | 227066_at | MOB1, MPS ONE BINDER KINASE ACTIVATOR-LIKE 2C (YEAST) | NM_145279 NM_201403 | NP_660322 NP_958805 |
| MPEG1 | 226818_at | MACROPHAGE EXPRESSED GENE 1 | XM_166227 | XP_166227 |
| MPEG1 | 226841_at | MACROPHAGE EXPRESSED GENE 1 | XM_166227 | XP_166227 |
| MSL3L1 | 207551_s_at | MALE-SPECIFIC LETHAL 3-LIKE 1 (*DROSOPHILA*) | NM_006800 NM_078628 NM_078629 NM_078630 | NP_006791 NP_523352 NP_523353 NP_523354 |
| MSL3L1 | 214009_at | MALE-SPECIFIC LETHAL 3-LIKE 1 (*DROSOPHILA*) | NM_006800 NM_078628 NM_078629 NM_078630 | NP_006791 NP_523352 NP_523353 NP_523354 |
| MSRB2 | 218773_s_at | METHIONINE SULFOXIDE REDUCTASE B2 | NM_012228 | NP_036360 |
| MTF1 | 227150_at | METAL-REGULATORY TRANSCRIPTION FACTOR 1 | NM_005955 | NP_005946 |

TABLE 30-continued

Exemplary biomarkers that discriminate between responders and nonresponders

| Gene Symbol Column 1 | Affymetrix Probeset name Column 2 | Gene Name Column 3 | Gene Accession Number Column 4 | Protein Accession Number Column 5 |
|---|---|---|---|---|
| MTMR6 | 214429_at | MYOTUBULARIN RELATED PROTEIN 6 | NM_004685 | NP_004676 |
| MYO10 | 201976_s_at | MYOSIN X | NM_012334 | NP_036466 |
| NALP1 | 210113_s_at | NACHT, LEUCINE RICH REPEAT AND PYD (PYRIN DOMAIN) CONTAINING 1 | NM_014922 NM_033004 NM_033006 NM_033007 | NP_055737 NP_127497 NP_127499 NP_127500 |
| NALP1 | 211824_x_at | NACHT, LEUCINE RICH REPEAT AND PYD (PYRIN DOMAIN) CONTAINING 1 | NM_014922 NM_033004 NM_033006 NM_033007 | NP_055737 NP_127497 NP_127499 NP_127500 |
| NARF | 219862_s_at | NUCLEAR PRELAMIN A RECOGNITION FACTOR | NM_012336 NM_031968 | NP_036468 NP_114174 |
| NBS1 | 202906_s_at | NIJMEGEN BREAKAGE SYNDROME 1 (NIBRIN) | NM_002485 | NP_002476 |
| NBS1 | 217299_s_at | NIJMEGEN BREAKAGE SYNDROME 1 (NIBRIN) | NM_002485 | NP_002476 |
| NCR1 | 207860_at | NATURAL CYTOTOXICITY TRIGGERING RECEPTOR 1 | NM_004829 | NP_004820 |
| NDST2 | 203916_at | N-DEACETYLASE/N-SULFOTRANSFERASE (HEPARAN GLUCOSAMINYL) 2 | NM_003635 | NP_003626 |
| NDUFA1 | 202298_at | NADH DEHYDROGENASE (UBIQUINONE) 1 ALPHA SUBCOMPLEX, 1, 7.5 KDA | NM_004541 | NP_004532 |
| NDUFB3 | 203371_s_at | NADH DEHYDROGENASE (UBIQUINONE) 1 BETA SUBCOMPLEX, 3, 12 KDA | NM_002491 | NP_002482 |
| NFKBIZ | 223218_s_at | NUCLEAR FACTOR OF KAPPA LIGHT POLYPEPTIDE GENE ENHANCER IN B-CELLS INHIBITOR, ZETA | NM_001005474 NM_031419 | NP_001005474 NP_113607 |
| NMI | 203964_at | N-MYC (AND STAT) INTERACTOR | NM_004688 | NP_004679 |
| NT5C2 | 209155_s_at | 5'-NUCLEOTIDASE, CYTOSOLIC II | NM_012229 | NP_036361 |
| NTNG2 | 233072_at | NETRIN G2 | NM_032536 | NP_115925 |
| NUPL1 | 204435_at | NUCLEOPORIN LIKE 1 | NM_001008564 NM_001008565 NM_014089 | NP_001008564 NP_001008565 NP_054808 |
| OACT2 | 226726_at | O-ACYLTRANSFERASE (MEMBRANE BOUND) DOMAIN CONTAINING 2 | NM_138799 | NP_620154 |
| OAT | 201599_at | ORNITHINE AMINOTRANSFERASE (GYRATE ATROPHY) | NM_000274 | NP_000265 |
| OMG | 207093_s_at | OLIGODENDROCYTE MYELIN GLYCOPROTEIN | NM_002544 | NP_002535 |
| OPLAH | 222025_s_at | 5-OXOPROLINASE (ATP-HYDROLYSING) | NM_017570 | NP_060040 |
| ORF1-FL49 | 224707_at | PUTATIVE NUCLEAR PROTEIN ORF1-FL49 | NM_032412 | NP_115788 |
| OSM | 230170_at | ONCOSTATIN M | NM_020530 | NP_065391 |
| OSTalpha | 229230_at | ORGANIC SOLUTE TRANSPORTER ALPHA | NM_152672 | NP_689885 |
| OTUD1 | 226140_s_at | OTU DOMAIN CONTAINING 1 | XM_166659 | XP_166659 |
| P2RX1 | 210401_at | PURINERGIC RECEPTOR P2X, LIGAND-GATED ION CHANNEL, 1 | NM_002558 | NP_002549 |
| PAG | 225622_at | PHOSPHOPROTEIN ASSOCIATED WITH GLYCOSPHINGOLIPID-ENRICHED MICRODOMAINS | NM_018440 | NP_060910 |

TABLE 30-continued

Exemplary biomarkers that discriminate between responders and nonresponders

| Gene Symbol Column 1 | Affymetrix Probeset name Column 2 | Gene Name Column 3 | Gene Accession Number Column 4 | Protein Accession Number Column 5 |
|---|---|---|---|---|
| PAM | 202336_s_at | PEPTIDYLGLYCINE ALPHA-AMIDATING MONOOXYGENASE | NM_000919 NM_138766 NM_138821 NM_138822 | NP_000910 NP_620121 NP_620176 NP_620177 |
| PAPSS1 | 209043_at | 3'-PHOSPHOADENOSINE 5'-PHOSPHOSULFATE SYNTHASE 1 | NM_005443 | NP_005434 |
| PBEF1 | 217738_at | PRE-B-CELL COLONY ENHANCING FACTOR 1 | NM_005746 NM_182790 | NP_005737 NP_877591 |
| PBEF1 | 217739_s_at | PRE-B-CELL COLONY ENHANCING FACTOR 1 | NM_005746 NM_182790 | NP_005737 NP_877591 |
| PBEF1 | 1555167_s_at | PRE-B-CELL COLONY ENHANCING FACTOR 1 | NM_005746 NM_182790 | NP_005737 NP_877591 |
| PBEF1 | 243296_at | PRE-B-CELL COLONY ENHANCING FACTOR 1 | NM_005746 NM_182790 | NP_005737 NP_877591 |
| PCGF5 | 227935_s_at | POLYCOMB GROUP RING FINGER 5 | NM_032373 | NP_115749 |
| PCMT1 | 208857_s_at | PROTEIN-L-ISOASPARTATE (D-ASPARTATE) O-METHYLTRANSFERASE | NM_005389 | NP_005380 |
| PCMT1 | 210156_s_at | PROTEIN-L-ISOASPARTATE (D-ASPARTATE) O-METHYLTRANSFERASE | NM_005389 | NP_005380 |
| PCMT1 | 205202_at | PROTEIN-L-ISOASPARTATE (D-ASPARTATE) O-METHYLTRANSFERASE | NM_005389 | NP_005380 |
| PDCD1LG1 | 227458_at | CD274 ANTIGEN (CD274) | NM_014143 | NP_054862 |
| PDCD1LG1 | 223834_at | CD274 ANTIGEN (CD274) | NM_014143 | NP_054862 |
| PDE5A | 239556_at | PHOSPHODIESTERASE 5A, CGMP-SPECIFIC | NM_001083 NM_033430 NM_033437 NM_033431 | NP_001074 NP_236914 NP_246273 NP_237223 |
| PDK1 | 226452_at | PYRUVATE DEHYDROGENASE KINASE, ISOENZYME 1 | NM_002610 | NP_002601 |
| PEA15 | 200788_s_at | PHOSPHOPROTEIN ENRICHED IN ASTROCYTES 15 | NM_003768 | NP_003759 |
| PFKFB2 | 209992_at | 6-PHOSPHOFRUCTO-2-KINASE/FRUCTOSE-2,6-BIPHOSPHATASE 2 | NM_006212 | NP_006203 |
| PFKFB2 | 226733_at | 6-PHOSPHOFRUCTO-2-KINASE/FRUCTOSE-2,6-BIPHOSPHATASE 2 | NM_006212 | NP_006203 |
| PFKFB3 | 202464_s_at | 6-PHOSPHOFRUCTO-2-KINASE/FRUCTOSE-2,6-BISPHOSPHATASE 3 | NM_004566 | NP_004557 |
| PFTK1 | 204604_at | PFTAIRE PROTEIN KINASE 1 | NM_012395 | NP_036527 |
| PGLYRP1 | 207384_at | PEPTIDOGLYCAN RECOGNITION PROTEIN 1 | NM_005091 | NP_005082 |
| PGM2 | 225366_at | PHOSPHOGLUCOMUTASE 2 | NM_018290 | NP_060760 |
| PGS1 | 219394_at | PHOSPHATIDYLGLYCERO-PHOSPHATE SYNTHASE | NM_024419 | NP_077733 |
| PHTF1 | 210191_s_at | PUTATIVE HOMEODOMAIN TRANSCRIPTION FACTOR 1 | NM_006608 | NP_006599 |
| PHTF1 | 215285_s_at | PUTATIVE HOMEODOMAIN TRANSCRIPTION FACTOR 1 | NM_006608 | NP_006599 |
| PHTF1 | 205702_at | PUTATIVE HOMEODOMAIN TRANSCRIPTION FACTOR 1 | NM_006608 | NP_006599 |
| PIK3AP1 | 226459_at | PHOSPHOINOSITIDE-3-KINASE ADAPTOR PROTEIN 1 | NM_152309 | NP_689522 |

TABLE 30-continued

Exemplary biomarkers that discriminate between responders and nonresponders

| Gene Symbol Column 1 | Affymetrix Probeset name Column 2 | Gene Name Column 3 | Gene Accession Number Column 4 | Protein Accession Number Column 5 |
|---|---|---|---|---|
| PIK3CB | 212688_at | PHOSPHOINOSITIDE-3-KINASE, CATALYTIC, BETA POLYPEPTIDE | NM_006219 | NP_006210 |
| PIM3 | 224739_at | PIM-3 ONCOGENE | NM_001001852 | NP_001001852 |
| PIP5K1A | 235646_at | PHOSPHATIDYLINOSITOL-4-PHOSPHATE 5-KINASE, TYPE I, ALPHA | NM_003557 | NP_003548 |
| PLSCR1 | 244315_at | PHOSPHOLIPID SCRAMBLASE 1 | NM_021105 | NP_066928 |
| PLSCR1 | 241916_at | PHOSPHOLIPID SCRAMBLASE 1 | NM_021105 | NP_066928 |
| POR | 208928_at | P450 (CYTOCHROME) OXIDOREDUCTASE | NM_000941 | NP_000932 |
| PPP1R12A | 201602_s_at | PROTEIN PHOSPHATASE 1, REGULATORY (INHIBITOR) SUBUNIT 12A | NM_002480 | NP_002471 |
| PPP4R2 | 225519_at | PROTEIN PHOSPHATASE 4, REGULATORY SUBUNIT 2 | NM_174907 | NP_777567 |
| PPP4R2 | 226317_at | PROTEIN PHOSPHATASE 4, REGULATORY SUBUNIT 2 | NM_174907 | NP_777567 |
| PRO0149 | 225183_at | PRO0149 PROTEIN | NM_014117 | NP_054836 |
| PRV1 | 219669_at | NEUTROPHIL-SPECIFIC ANTIGEN 1 (POLYCYTHEMIA RUBRA VERA 1) | NM_020406 | NP_065139 |
| PSTPIP2 | 219938_s_at | PROLINE/SERINE/THREONINE PHOSPHATASE-INTERACTING PROTEIN 1 (PROLINE-SERINE-THREONINE PHOSPHATASE INTERACTING PROTEIN 2) | NM_024430 | NP_077748 |
| PTDSR | 212723_at | CHROMOSOME 17 GENOMIC CONTIG, ALTERNATE ASSEMBLY (PHOSPHATIDYLSERINE RECEPTOR) | NM_015167 | NP_055982 |
| PTDSR | 212722_s_at | CHROMOSOME 17 GENOMIC CONTIG, ALTERNATE ASSEMBLY (PHOSPHATIDYLSERINE RECEPTOR) | NM_015167 | NP_055982 |
| PTGFR | 207177_at | CHROMOSOME 17 GENOMIC CONTIG, ALTERNATE ASSEMBLY (PHOSPHATIDYLSERINE RECEPTOR) | NM_015167 | NP_055982 |
| PTPN1 | 202716_at | PROTEIN TYROSINE PHOSPHATASE, NON-RECEPTOR TYPE 1 | NM_002827 | NP_002818 |
| PTX1 | 226422_at | PTX1 PROTEIN | NM_016570 | NP_057654 |
| QSCN6 | 201482_at | QUIESCIN Q6 | NM_001004128 NM_002826 | NP_001004128 NP_002817 |
| RAB10 | 222981_s_at | RAB10, MEMBER RAS ONCOGENE FAMILY | NM_016131 | NP_057215 |
| RAB20 | 219622_at | RAB20, MEMBER RAS ONCOGENE FAMILY | NM_017817 | NP_060287 |
| RAB24 | 225251_at | RAB24, MEMBER RAS ONCOGENE FAMILY | NM_130781 | NP_570137 |
| RAB27A | 209514_s_at | RAB27A, MEMBER RAS ONCOGENE FAMILY | NM_004580 NM_183234 NM_183235 NM_183236 | NP_004571 NP_899057 NP_899058 NP_899059 |
| RAB27A | 210951_x_at | RAB27A, MEMBER RAS ONCOGENE FAMILY | NM_004580 NM_183234 NM_183235 NM_183236 | NP_004571 NP_899057 NP_899058 NP_899059 |
| RAB43 | 225632_s_at | RAB43, MEMBER RAS ONCOGENE FAMILY | NM_198490 | NP_940892 |
| RAB8B | 219210_s_at | RAB8B, MEMBER RAS ONCOGENE FAMILY | NM_016530 | NP_057614 |

TABLE 30-continued

Exemplary biomarkers that discriminate between responders and nonresponders

| Gene Symbol Column 1 | Affymetrix Probeset name Column 2 | Gene Name Column 3 | Gene Accession Number Column 4 | Protein Accession Number Column 5 |
|---|---|---|---|---|
| RABGEF1 | 218310_at | RAB GUANINE NUCLEOTIDE EXCHANGE FACTOR (RAB GUANINE NUCLEOTIDE EXCHANGE FACTOR (GEF) 1) | NM_014504 | NP_055319 |
| RAD23B | 201222_s_at | RAD23 HOMOLOG B (S. CEREVISIAE) | NM_002874 | NP_002865 |
| RALB | 202101_s_at | V-RAL SIMIAN LEUKEMIA VIRAL ONCOGENE HOMOLOG B (RAS RELATED; GTP BINDING PROTEIN) | NM_002881 | NP_002872 |
| RAPGEFL1 | 218657_at | RAP GUANINE NUCLEOTIDE EXCHANGE FACTOR (GEF)-LIKE 1 | NM_014504 | NP_055319 |
| RARA | 228037_at | RETINOIC ACID RECEPTOR, ALPHA | NM_000964 | NP_000955 |
| RASSF4 | 226436_at | RAS ASSOCIATION (RALGDS/AF-6) DOMAIN FAMILY 4 | NM_032023 NM_178145 | NP_114412 NP_835281 |
| RB1CC1 | 202033_s_at | RB1-INDUCIBLE COILED-COIL 1 | NM_014781 | NP_055596 |
| RBMS1 | 225265_at | RNA BINDING MOTIF, SINGLE STRANDED INTERACTING PROTEIN 1 | NM_002897 NM_016836 NM_016839 | NP_002888 NP_058520 NP_058523 |
| RBMS1 | 238317_x_at | RNA BINDING MOTIF, SINGLE STRANDED INTERACTING PROTEIN 1 | NM_002897 NM_016836 NM_016839 | NP_002888 NP_058520 NP_058523 |
| RFWD2 | 234950_s_at | RING FINGER AND WD REPEAT DOMAIN 2 | NM_001001740 NM_022457 | NP_001001740 NP_071902 |
| Rgr | 235816_s_at | RAL-GDS RELATED PROTEIN RGR | NM_153615 | NP_705843 |
| RGS10 | 204319_s_at | REGULATOR OF G-PROTEIN SIGNALLING 10 | NM_001005339 NM_002925 | NP_001005339 NP_002916 |
| RHOT1 | 222148_s_at | RAS HOMOLOG GENE FAMILY, MEMBER T1 | NM_018307 | NP_060777 |
| RIT1 | 209882_at | RAS-LIKE WITHOUT CAAX 1 | NM_006912 | NP_008843 |
| RNASE6 | 213566_at | RIBONUCLEASE, RNASE A FAMILY, K6 | NM_005615 | NP_005606 |
| RNASEL | 229285_at | RIBONUCLEASE L (2',5'-OLIGOISOADENYLATE SYNTHETASE-DEPENDENT) | NM_021133 | NP_066956 |
| RNF13 | 201779_s_at | RING FINGER PROTEIN 13 | NM_007282 NM_183381 NM_183382 NM_183383 NM_183384 | NP_009213 NP_899237 NP_899238 NP_899239 NP_899240 |
| RNF13 | 201780_s_at | RING FINGER PROTEIN 13 | NM_007282 NM_183381 NM_183382 NM_183383 NM_183384 | NP_009213 NP_899237 NP_899238 NP_899239 NP_899240 |
| ROD1 | 224618_at | ROD1 REGULATOR OF DIFFERENTIATION 1 (S. POMBE) | NM_005156 | NP_005147 |
| ROD1 | 214697_s_at | ROD1 REGULATOR OF DIFFERENTIATION 1 (S. POMBE) | NM_005156 | NP_005147 |
| RRM2 | 209773_s_at | RIBONUCLEOTIDE REDUCTASE M2 POLYPEPTIDE | NM_001034 | NP_001025 |
| RSBN1 | 213694_at | ROUND SPERMATID BASIC PROTEIN 1 | NM_018364 | NP_060834 |
| RTN1 | 203485_at | RETICULON 1 | NM_021136 NM_206852 NM_206857 | NP_066959 NP_996734 NP_996739 |

TABLE 30-continued

Exemplary biomarkers that discriminate between responders and nonresponders

| Gene Symbol Column 1 | Affymetrix Probeset name Column 2 | Gene Name Column 3 | Gene Accession Number Column 4 | Protein Accession Number Column 5 |
|---|---|---|---|---|
| RTN4 | 214629_x_at | RETICULON 4 | NM_007008 | NP_008939 |
| | | | NM_020532 | NP_065393 |
| | | | NM_153828 | NP_722550 |
| | | | NM_207520 | NP_997403 |
| | | | NM_207521 | NP_997404 |
| RY1 | 212438_at | PUTATIVE NUCLEIC ACID BINDING PROTEIN RY-1 | NM_006857 | NP_006848 |
| S100A12 | 205863_at | S100 CALCIUM BINDING PROTEIN A12 (CALGRANULIN C) | NM_005621 | NP_005612 |
| SAMSN1 | 1555638_a_at | SAM DOMAIN, SH3 DOMAIN, AND NUCLEAR LOCALIZATION SIGNALS, 1 | NM_022136 | NP_071419 |
| SAMSN1 | 220330_s_at | SAM DOMAIN, SH3 DOMAIN, AND NUCLEAR LOCALIZATION SIGNALS, 1 | NM_022136 | NP_071419 |
| SAP30L | 219129_s_at | SIN3A ASSOCIATED PROTEIN P30-LIKE | NM_024632 | NP_078908 |
| SART2 | 218854_at | SQUAMOUS CELL CARCINOMA ANTIGEN RECOGNIZED BY T CELLS 2 | NM_013352 | NP_037484 |
| SBNO1 | 218737_at | SNO, STRAWBERRY NOTCH HOMOLOG 1 (*DROSOPHILA*) | NM_018183 | NP_060653 |
| SDF2 | 203090_at | STROMAL CELL-DERIVED FACTOR 2 | NM_006923 | NP_008854 |
| SDHC | 238056_at | SUCCINATE DEHYDROGENASE COMPLEX, SUBUNIT C, INTEGRAL MEMBRANE PROTEIN, 15 KDA | NM_003001 | NP_002992 |
| SEC15L1 | 226259_at | SEC15-LIKE 1 (*S. CEREVISIAE*) | NM_019053 | NP_061926 |
| | | | NM_001013848 | NP_001013870 |
| SEC15L1 | 233924_s_at | SEC15-LIKE 1 (*S. CEREVISIAE*) | NM_019053 | NP_061926 |
| | | | NM_001013848 | NP_001013870 |
| SEC24A | 212902_at | SEC24 RELATED GENE FAMILY, MEMBER A (*S. CEREVISIAE*) | XM_094581 | XP_094581 |
| SEL1L | 202064_s_at | SEL-1 SUPPRESSOR OF LIN-12-LIKE (*C. ELEGANS*) | NM_005065 | NP_005056 |
| SERPINB1 | 228726_at | SERINE (OR CYSTEINE) PROTEINASE INHIBITOR, CLADE B (OVALBUMIN), MEMBER 1 | NM_030666 | NP_109591 |
| SERPINB1 | 212268_at | SERINE (OR CYSTEINE) PROTEINASE INHIBITOR, CLADE B (OVALBUMIN), MEMBER 1 | NM_030666 | NP_109591 |
| SF3B14 | 223416_at | SPLICING FACTOR 3B, 14 KDA SUBUNIT | NM_016047 | NP_057131 |
| SH3GLB1 | 209091_s_at | SH3-DOMAIN GRB2-LIKE ENDOPHILIN B1 | NM_016009 | NP_057093 |
| SH3GLB1 | 210101_x_at | SH3-DOMAIN GRB2-LIKE ENDOPHILIN B1 | NM_016009 | NP_057093 |
| SIPA1L2 | 225056_at | SIGNAL-INDUCED PROLIFERATION-ASSOCIATED GENE 1 (SIGNAL-INDUCED PROLIFERATION-ASSOCIATED 1 LIKE 2) | NM_020808 | NP_065859 |
| SLA | 203761_at | SRC-LIKE-ADAPTOR | NM_006748 | NP_006739 |
| SLA | 244492_at | SRC-LIKE-ADAPTOR | NM_006748 | NP_006739 |
| SLC22A4 | 205896_at | SOLUTE CARRIER FAMILY 22 (ORGANIC CATION TRANSPORTER), MEMBER 4 | NM_003059 | NP_003050 |
| SLC25A28 | 221432_s_at | SOLUTE CARRIER FAMILY 25, MEMBER 28 | NM_031212 | NP_112489 |
| SLC26A8 | 237340_at | SOLUTE CARRIER FAMILY 26, MEMBER 8 | NM_052961 | NP_443193 |
| | | | NM_138718 | NP_619732 |

TABLE 30-continued

Exemplary biomarkers that discriminate between responders and nonresponders

| Gene Symbol Column 1 | Affymetrix Probeset name Column 2 | Gene Name Column 3 | Gene Accession Number Column 4 | Protein Accession Number Column 5 |
|---|---|---|---|---|
| SLC2A3 | 202497_x_at | SOLUTE CARRIER FAMILY 2 (FACILITATED GLUCOSE TRANSPORTER), MEMBER 3 | NM_006931 | NP_008862 |
| SLC2A3 | 202498_s_at | SOLUTE CARRIER FAMILY 2 (FACILITATED GLUCOSE TRANSPORTER), MEMBER 3 | NM_006931 | NP_008862 |
| SLC2A3 | 216236_s_at | SOLUTE CARRIER FAMILY 2 (FACILITATED GLUCOSE TRANSPORTER), MEMBER 3 | NM_006931 | NP_008862 |
| SLC2A3 | 202499_s_at | SOLUTE CARRIER FAMILY 2 (FACILITATED GLUCOSE TRANSPORTER), MEMBER 3 | NM_006931 | NP_008862 |
| SLC2A3 | 222088_s_at | SOLUTE CARRIER FAMILY 2 (FACILITATED GLUCOSE TRANSPORTER), MEMBER 3 | NM_006931 | NP_008862 |
| SLC2A3 | 236571_at | SOLUTE CARRIER FAMILY 2 (FACILITATED GLUCOSE TRANSPORTER), MEMBER 3 | NM_006931 | NP_008862 |
| SLC37A3 | 223304_at | SOLUTE CARRIER FAMILY 37 (GLYCEROL-3-PHOSPHATE TRANSPORTER), MEMBER 3 | NM_032295 NM_207113 | NP_115671 NP_996996 |
| SLC38A2 | 220924_s_at | SOLUTE CARRIER FAMILY 38, MEMBER 2 | NM_018976 | NP_061849 |
| SMPDL3A | 213624_at | SPHINGOMYELIN PHOSPHODIESTERASE, ACID-LIKE 3A | NM_006714 | NP_006705 |
| SOCS3 | 227697_at | SUPPRESSOR OF CYTOKINE SIGNALING 3 | NM_003955 | NP_003946 |
| SOCS3 | 206359_at | SUPPRESSOR OF CYTOKINE SIGNALING 3 | NM_003955 | NP_003946 |
| SOD2 | 216841_s_at | SUPEROXIDE DISMUTASE 2, MITOCHONDRIAL | NM_000636 | NP_000627 |
| SP100 | 202863_at | NUCLEAR ANTIGEN SP100 | NM_003113 | NP_003104 |
| SPPL2A | 226353_at | SIGNAL PEPTIDE PEPTIDASE-LIKE 2A | NM_032802 | NP_116191 |
| SQRDL | 217995_at | SULFIDE QUINONE REDUCTASE-LIKE (YEAST) | NM_021199 | NP_067022 |
| SRPK1 | 202200_s_at | PROTEIN KINASE, SERINE/ARGININE-SPECIFIC, 1 (SFRS PROTEIN KINASE 1) | NM_003137 | NP_003128 |
| ST3GAL4 | 203759_at | ST3 BETA-GALACTOSIDE ALPHA-2,3-SIALYLTRANSFERASE 4 | NM_006278 | NP_006269 |
| ST6GALNAC4 | 223285_s_at | ST6 (ALPHA-N-ACETYL-NEURAMINYL-2,3-BETA-GALACTOSYL-1,3)-N-ACETYLGALACTOSAMINIDE ALPHA-2,6-SIALYLTRANSFERASE 4 | NM_014403 NM_175039 NM_175040 | NP_055218 NP_778204 NP_778205 |
| STAT5B | 1555086_at | SIGNAL TRANSDUCER AND ACTIVATOR OF TRANSCRIPTION 5B | NM_012448 | NP_036580 |
| STK17B | 205214_at | SERINE/THREONINE KINASE 17B (APOPTOSIS-INDUCING) | NM_004226 | NP_004217 |
| STK3 | 204068_at | SERINE/THREONINE PROTEIN KINASE 3 (SERINE/THREONINE KINASE 3 (STE20 HOMOLOG, YEAST)) | NM_006281 | NP_006272 |
| STOM | 201060_x_at | STOMATIN | NM_004099 NM_198194 | NP_004090 NP_937837 |

TABLE 30-continued

Exemplary biomarkers that discriminate between responders and nonresponders

| Gene Symbol Column 1 | Affymetrix Probeset name Column 2 | Gene Name Column 3 | Gene Accession Number Column 4 | Protein Accession Number Column 5 |
|---|---|---|---|---|
| STX3A | 209238_at | SYNTAXIN 3A | NM_004177 | NP_004168 |
| SULF2 | 233555_s_at | SULFATASE 2 | NM_018837 | NP_061325 |
|  |  |  | NM_198596 | NP_940998 |
| SULF2 | 224724_at | SULFATASE 2 | NM_018837 | NP_061325 |
|  |  |  | NM_198596 | NP_940998 |
| SULT1A1 | 203615_x_at | SULFOTRANSFERASE FAMILY, CYTOSOLIC, 1A, PHENOL-PREFERRING, MEMBER 1 | NM_001055 | NP_001046 |
|  |  |  | NM_177529 | NP_803565 |
|  |  |  | NM_177530 | NP_803566 |
|  |  |  | NM_177534 | NP_803878 |
|  |  |  | NM_177536 | NP_803880 |
| SULT1B1 | 207601_at | SULFOTRANSFERASE FAMILY, CYTOSOLIC, 1B, MEMBER 1 | NM_014465 | NP_055280 |
| TBC1D15 | 218268_at | TBC1 DOMAIN FAMILY, MEMBER 15 | NM_022771 | NP_073608 |
| TBC1D8 | 204526_s_at | TBC1 DOMAIN FAMILY, MEMBER 8 (WITH GRAM DOMAIN) | NM_007063 | NP_008994 |
| TCTEL1 | 201999_s_at | T-COMPLEX-ASSOCIATED-TESTIS-EXPRESSED 1 (T-COMPLEX-ASSOCIATED-TESTIS-EXPRESSED 1-LIKE 1 | NM_006519 | NP_006510 |
| TCTEL1 | 242109_at | T-COMPLEX-ASSOCIATED-TESTIS-EXPRESSED 1 (T-COMPLEX-ASSOCIATED-TESTIS-EXPRESSED 1-LIKE 1 | NM_006519 | NP_006510 |
| TDRD9 | 228285_at | TUDOR DOMAIN CONTAINING 9 | NM_153046 | NP_694591 |
| TGFBI | 201506_at | TRANSFORMING GROWTH FACTOR, BETA-1 (TRANSFORMING GROWTH FACTOR, BETA-INDUCED, 68 KDA) | NM_000358 | NP_000349 |
| TIAM2 | 222942_s_at | T-CELL LYMPHOMA INVASION AND METASTASIS 2 | NM_001010927 | NP_001010927 |
|  |  |  | NM_012454 | NP_036586 |
| TIFA | 238858_at | TRAF-INTERACTING PROTEIN WITH A FORKHEAD-ASSOCIATED DOMAIN | NM_052864 | NP_443096 |
| TIFA | 226117_at | TRAF-INTERACTING PROTEIN WITH A FORKHEAD-ASSOCIATED DOMAIN | NM_052864 | NP_443096 |
| TIFA | 235971_at | TRAF-INTERACTING PROTEIN WITH A FORKHEAD-ASSOCIATED DOMAIN | NM_052864 | NP_443096 |
| TLR5 | 210166_at | TOLL-LIKE RECEPTOR 5 | NM_003268 | NP_003259 |
| TMEM2 | 218113_at | TRANSMEMBRANE PROTEIN 2 | NM_013390 | NP_037522 |
| TMEM33 | 235907_at | TRANSMEMBRANE PROTEIN 33 | NM_018126 | NP_060596 |
| TMOD3 | 223078_s_at | TROPOMODULIN 3 (UBIQUITOUS) | NM_014547 | NP_055362 |
| TncRNA | 214657_s_at | TROPHOBLAST-DERIVED NONCODING RNA |  |  |
| TNFAIP6 | 206026_s_at | TUMOR NECROSIS FACTOR, ALPHA-INDUCED PROTEIN 6 | NM_007115 | NP_009046 |
| TNFAIP6 | 206025_s_at | TUMOR NECROSIS FACTOR, ALPHA-INDUCED PROTEIN 6 | NM_007115 | NP_009046 |
| TNFAIP9 | 225987_at | TUMOR NECROSIS FACTOR, ALPHA-INDUCED PROTEIN 9 | NM_024636 | NP_078912 |
| TNFSF10 | 202687_s_at | TUMOR NECROSIS FACTOR (LIGAND) SUPERFAMILY, MEMBER 10 | NM_003810 | NP_003801 |

TABLE 30-continued

Exemplary biomarkers that discriminate between responders and nonresponders

| Gene Symbol Column 1 | Affymetrix Probeset name Column 2 | Gene Name Column 3 | Gene Accession Number Column 4 | Protein Accession Number Column 5 |
|---|---|---|---|---|
| TNFSF13B | 223501_at | TUMOR NECROSIS FACTOR (LIGAND) SUPERFAMILY, MEMBER 13B | NM_006573 | NP_006564 |
| TOP1 | 208901_s_at | TOPOISOMERASE (DNA) I | NM_003286 | NP_003277 |
| TOSO | 221602_s_at | FAS APOPTOTIC INHIBITORY MOLECULE (FAIM3) | NM_005449 | NP_005440 |
| TPARL | 218095_s_at | TPA REGULATED LOCUS | NM_018475 | NP_060945 |
| TPCN1 | 242108_at | TWO PORE SEGMENT CHANNEL 1 | NM_017901 | NP_060371 |
| TPRT | 220865_s_at | TRANS-PRENYLTRANSFERASE | NM_014317 | NP_055132 |
| TRA@ | 234013_at | T CELL RECEPTOR ALPHA LOCUS | | |
| TRA@ | 211902_x_at | T CELL RECEPTOR ALPHA LOCUS | | |
| TRBC1 | 211796_s_at | T CELL RECEPTOR BETA CONSTANT 1 | | |
| TRIB1 | 202241_at | TRIBBLES HOMOLOG 1 (*DROSOPHILA*) | NM_025195 | NP_079471 |
| TRPM6 | 224412_s_at | TRANSIENT RECEPTOR POTENTIAL CATION CHANNEL, SUBFAMILY M, MEMBER 6 | NM_017662 | NP_060132 |
| TTN | 240793_at | TITIN | NM_003319 NM_133378 NM_133379 NM_133432 NM_133437 | NP_003310 NP_596869 NP_596870 NP_597676 NP_597681 |
| TTYH2 | 223741_s_at | TWEETY, *DROSOPHILA*, HOMOLOG OF, 2 | NM_032646 NM_052869 | NP_116035 NP_443101 |
| TXN | 208864_s_at | THIOREDOXIN | NM_003329 | NP_003320 |
| UBE2H | 222421_at | UBIQUITIN-CONJUGATING ENZYME E2H (UBC8 HOMOLOG, YEAST) | NM_003344 NM_182697 | NP_003335 NP_874356 |
| UBE2J1 | 217826_s_at | UBIQUITIN-CONJUGATING ENZYME E2, J1 (UBC6 HOMOLOG, YEAST) | NM_016021 | NP_057105 |
| UBQLN2 | 215884_s_at | UBIQUILIN 2 | NM_013444 | NP_038472 |
| UNC84B | 229548_at | UNC-84 HOMOLOG B (*C. ELEGANS*) | NM_015374 | NP_056189 |
| USP38 | 223289_s_at | UBIQUITIN SPECIFIC PROTEASE 38 | NM_032557 | NP_115946 |
| USP9X | 201099_at | UBIQUITIN SPECIFIC PROTEASE 9, X-LINKED (FAT FACETS-LIKE, *DROSOPHILA*) | NM_004652 NM_021906 | NP_004643 NP_068706 |
| VAV3 | 218807_at | VAV 3 ONCOGENE | NM_006113 | NP_006104 |
| WBP4 | 203598_s_at | WW DOMAIN BINDING PROTEIN 4 (FORMIN BINDING PROTEIN 21) | NM_007187 | NP_009118 |
| WDFY3 | 212606_at | WD REPEAT AND FYVE DOMAIN CONTAINING 3 | NM_014991 NM_178583 NM_178585 | NP_055806 NP_848698 NP_848700 |
| WDFY3 | 212602_at | WD REPEAT AND FYVE DOMAIN CONTAINING 3 | NM_014991 NM_178583 NM_178585 | NP_055806 NP_848698 NP_848700 |
| WDFY3 | 212598_at | WD REPEAT AND FYVE DOMAIN CONTAINING 3 | NM_014991 NM_178583 NM_178585 | NP_055806 NP_848698 NP_848700 |
| WSB1 | 227501_at | WD REPEAT AND SOCS BOX-CONTAINING 1 | NM_015626 NM_134264 NM_134265 | NP_056441 NP_599026 NP_599027 |
| WSB1 | 210561_s_at | WD REPEAT AND SOCS BOX-CONTAINING 1 | NM_015626 NM_134264 NM_134265 | NP_056441 NP_599026 NP_599027 |
| WSB1 | 201296_s_at | WD REPEAT AND SOCS BOX-CONTAINING 1 | NM_015626 NM_134264 NM_134265 | NP_056441 NP_599026 NP_599027 |

TABLE 30-continued

Exemplary biomarkers that discriminate between responders and nonresponders

| Gene Symbol Column 1 | Affymetrix Probeset name Column 2 | Gene Name Column 3 | Gene Accession Number Column 4 | Protein Accession Number Column 5 |
|---|---|---|---|---|
| XRN1 | 1555785_a_at | 5'-3' EXORIBONUCLEASE 1 | NM_019001 | NP_061874 |
| XRN1 | 233632_s_at | 5'-3' EXORIBONUCLEASE 1 | NM_019001 | NP_061874 |
| ZC3HAV1 | 225634_at | ZINC FINGER CCCH TYPE, ANTIVIRAL 1 | NM_020119 NM_024625 | NP_064504 NP_078901 |
| ZCSL2 | 225195_at | ZINC FINGER, CSL DOMAIN CONTAINING 2 | NM_206831 | NP_996662 |
| ZDHHC19 | 231122_x_at | ZINC FINGER, DHHC DOMAIN CONTAINING 19 | NM_144637 | NP_653238 |
| ZDHHC19 | 1553952_at | ZINC FINGER, DHHC DOMAIN CONTAINING 19 | NM_144637 | NP_653238 |
| ZFP276 | 213778_x_at | ZINC FINGER PROTEIN 276 HOMOLOG (MOUSE) | NM_152287 | NP_689500 |
| ZFP36L2 | 201367_s_at | ZINC FINGER PROTEIN 36, C3H TYPE-LIKE 2; ZFP36L2 | NM_006887 | NP_008818 |
| ZFP36L2 | 201369_s_at | ZINC FINGER PROTEIN 36, C3H TYPE-LIKE 2; ZFP36L2 | NM_006887 | NP_008818 |
| ZNF167 | 206314_at | ZINC FINGER PROTEIN 167 | NM_018651 NM_025169 | NP_061121 NP_079445 |
| | 230585_at | EST | | |
| | 200880_at | EST | | |
| | 230267_at | EST | | |
| | 215966_x_at | EST | | |
| | 237071_at | EST | | |
| | 230683_at | EST | | |
| | 241388_at | EST | | |
| | 204166_at | EST | | |
| | 241652_x_at | EST | | |
| | 229968_at | EST | | |
| | 223596_at | EST | | |
| | 240310_at | EST | | |
| | 216609_at | EST | | |
| | 224604_at | EST | | |
| | 223797_at | EST | | |
| | 238973_s_at | EST | | |
| | 230632_at | EST | | |
| | 230575_at | EST | | |
| | 1559777_at | EST | | |
| | 244313_at | EST | | |
| | 242582_at | EST | | |
| | 233264_at | EST | | |
| | 219253_at | EST | | |
| | 235427_at | EST | | |
| | 1555311_at | EST | | |
| | 229934_at | EST | | |
| | 231035_s_at | EST | | |
| | 230999_at | EST | | |
| | 224261_at | EST | | |
| | 239780_at | EST | | |
| | 239669_at | EST | | |
| | 213002_at | EST | | |
| | 227925_at | EST | | |
| | 235456_at | EST | | |
| | 233312_at | EST | | |
| | 239167_at | EST | | |
| | 1569263_at | EST | | |
| | 216198_at | EST | | |
| | 232876_at | EST | | |
| | 237387_at | EST | | |
| | 216621_at | EST | | |
| | 235352_at | EST | | |
| | 1564933_at | EST | | |
| | 222376_at | EST | | |
| | 205922_at | EST | | |
| | 1557626_at | EST | | |
| | 228758_at | EST | | |
| | 1557733_a_at | EST | | |
| | 236898_at | EST | | |

Each of the sequences, genes, proteins, and probesets identified in Table 30 is hereby incorporated by reference.

6.7 Exemplary Biomarker Combinations

In one embodiment of the present invention, an additional criterion was applied to the set of biomarkers identified in Section 6.6. Specifically, the additional criterion that was imposed was a requirement that each respective biomarker under consideration exhibit at least a 1.2× fold change between the median value for the respective biomarker among the subjects that acquired sepsis during a defined time period (sepsis subjects) and the median value for the respective biomarker among subjects that do not acquire sepsis during the defined time period (SIRS subjects) at the $T_{-12}$ static time and at the $T_{-36}$ static time periods. Furthermore, to satisfy the third criterion, the biomarker must have been used in at least one multivariate analysis with significant classification performance where significant classification performance is defined by having a lower $95^{th}$ percentile for accuracy on a training data set that is grater than 50% and a point estimate for accuracy on the validation set that is greater than 65% at any time point measured. As noted in FIG. 30, application of this third filter criterion reduced the number of eligible biomarkers from 626 to 130. These biomarkers are listed column two of Table 31. In column two of Table 31, the biomarkers are indicated by the U133 plus 2.0 probeset to which they bind. However, in some embodiments, each such biomarker is, in fact, an mRNA, cDNA, or other such nucleic acid molecule corresponding to the identified U133 plus 2.0 oligonucleotide probe listed in column two of Table 31.

In column one of Table 31, each biomarker is listed by a gene name, such as, for example, a Human Gene Nomenclature Database (HUGO) symbol set forth by the Gene Nomenclature Committee, Department of Biology, University College London. As is known in the art, some human genome genes are represented by more than one probeset in the U133 plus 2.0 array. Furthermore, some of the oligonucleotides in the U133 plus 2.0 array represent expression sequence tags (ESTs) that do not correspond to a known gene. As a result, the 130 biomarkers listed in Table 31, in fact, represent 95 different known genes (see FIG. 30). Where known, the names of the 95 different human genes are listed in column three of Table 31.

In column four of Table 31, the median fold change between the mean value of the biomarker measured from $T_{-12}$ samples of those subjects in the training population that develop sepsis (sepsis subjects) versus the mean value of the biomarker measured from $T_{-12}$ samples of those subjects in the training population that do not develop sepsis (SIRS subjects) is given. In column five of Table 31, the direction of the fold change, where "+" indicates that the mean value in the sepsis subjects is greater than in the SIRS subjects, is given.

In column six of Table 31, the median fold change between the mean value of the biomarker measured from $T_{-36}$ samples of those subjects in the training population that develop sepsis (sepsis subjects) versus the mean value of the biomarker measured from $T_{-36}$ samples of those subjects in the training population that do not develop sepsis (SIRS subjects) is given. In column seven of Table 31, the direction of the fold change, where "+" indicates that the mean value in the sepsis subjects is greater than in the SIRS subjects, is given.

In a particular embodiment, the biomarker profile comprises at least two different biomarkers that each contain one of the probesets of Table 32, biomarkers that contain the complement of one of the probesets of Table 32, or biomarkers that contain an amino acid sequence encoded by a gene that contains one of the probesets of Table 32. Such biomarkers can be, for example, mRNA transcripts, cDNA or some other nucleic acid, for example amplified nucleic acid, or proteins. The biomarker profile further comprises a respective corresponding feature for the at least two biomarkers. Generally, the at least two biomarkers are derived from at least two different genes. In the case where a biomarker is based upon a gene that includes the sequence of a probeset listed in Table 32 or a complement thereof, the biomarker can be, for example, a transcript made by the gene, a complement thereof, or a discriminating fragment or complement thereof, or a cDNA thereof, or a discriminating fragment of the cDNA, or a discriminating amplified nucleic acid molecule corresponding to all or a portion of the transcript or its complement, or a protein encoded by the gene, or a discriminating fragment of the protein, or an indication of any of the above. Further still, the biomarker can be, for example, a protein encoded by a gene that includes a probeset sequence described in Table 32 or a discriminating fragment of the protein, or an indication of the above. Here, a discriminating molecule or fragment is a molecule or fragment that, when detected, indicates presence or abundance of the above-identified transcript, cDNA, amplified nucleic acid, or protein. In one embodiment, a biomarker profile of the present invention comprises a plurality of biomarkers that contain at least five, at least ten at least fifteen, at least twenty, at least thirty, between 2 and 5, between 3 and 7, or less than 15 of the sequences of the probesets of Table 32, or complements thereof, or genes including one of at least five of the sequences or complements thereof, or a discriminating fragment thereof, or an amino acid sequence encoded by any of the foregoing nucleic acid sequences, or any discriminating fragment of such an amino acid sequence. Such biomarkers can be, for example, mRNA transcripts, cDNA or some other nucleic acid, for example amplified nucleic acid, or proteins. In some embodiments a biomarker is any gene that includes the sequence in an Affymetrix probeset given in Table 31, or any gene that includes a complement of the sequence in an Affymetrix probeset given in Table 32, or any mRNA, cDNA or other form of amplified nucleic acid of the foregoing, for any discriminating fragment of the foregoing, or any amino acid sequence coded by the foregoing, or any discriminating fragment of such a protein.

TABLE 31

Exemplary biomarkers that discriminate between converters and non-converters

| | | | $T_{-12}$ Values | | $T_{-36}$ Values | |
|---|---|---|---|---|---|---|
| Gene Symbol Column 1 | Affymetrix Probeset name Column 2 | Gene Name Column 3 | Median FC Column 3 | Direction Column 4 | Median FC Column 5 | Direction Column 6 |
| | 1555785_a_at | EST | 1.34 | Up | 1.31 | up |
| | 227150_at | EST | 1.45 | Up | 1.34 | up |
| | 238973_s_at | EST | 1.33 | Up | 1.25 | up |
| | 239893_at | EST | 1.89 | Up | 1.46 | up |
| | 237563_s_at | EST | 1.84 | Up | 1.60 | up |
| | 244313_at | EST | 1.87 | Up | 1.80 | up |
| | 237071_at | EST | 1.73 | up | 1.37 | up |
| | 229934_at | EST | 1.67 | up | 1.41 | up |
| | 1555311_at | EST | 1.31 | up | 1.21 | up |
| | 233264_at | EST | 1.52 | up | 1.36 | up |
| | 239780_at | EST | 1.93 | up | 1.42 | up |
| | 238405_at | EST | 3.02 | up | 2.23 | up |
| 3'HEXO | 226416_at | HISTONE MRNA 3' END EXORIBO-NUCLEASE | 1.70 | up | 1.41 | up |
| 3'HEXO | 231852_at | | 1.45 | up | 1.22 | up |
| ADORA2A | 205013_s_at | ADENOSINE A2 RECEPTOR | 1.32 | up | 1.33 | up |
| ANXA3 | 209369_at | ANNEXIN A3 | 2.82 | up | 2.23 | up |
| ASAHL | 214765_s_at | N-ACYLSPHINGOSINE AMIDO-HYDROLASE-LIKE PROTEIN | 1.28 | down | 1.29 | down |
| ASAHL | 232072_at | | 1.23 | down | 1.31 | down |
| ASAHL | 227135_at | | 1.24 | down | 1.26 | down |
| ATP11B | 1554557_at | ATPASE, CLASS VI, TYPE 11B | 1.70 | up | 1.49 | up |
| ATP6V1C1 | 202872_at | ATPASE, H+ TRANSPORTING, LYSOSOMAL, 42-KD, V1 SUBUNIT C, ISOFORM 1 | 1.85 | up | 1.49 | up |
| B4GALT5 | 221485_at | BETA-1,4-GALACTOSYL-TRANSFERASE | 1.67 | up | 1.43 | up |
| BASP1 | 202391_at | BRAIN-ABUNDANT SIGNAL PROTEIN | 1.42 | up | 1.23 | up |
| BAZ1A | 217986_s_at | BROMODOMA IN ADJACENT TO ZINC FINGER DOMAIN, 1A | 1.89 | up | 1.57 | up |
| BCL6 | 203140_at | B-CELL LYMPHOMA 6 | 1.46 | up | 1.33 | up |
| BMX | 206464_at | BONE MARROW KINASE, X-LINKED | 1.87 | up | 1.52 | up |
| C16orf7 | 205781_at | CHROMOSOME 16 OPEN-READING FRAME 7 | 1.96 | up | 1.49 | up |
| C20orf32 | 1554786_at | CHROMOSOME 20 OPEN-READING FRAME 32 | 1.27 | down | 1.24 | down |
| C3F | 203547_at | COMPLEMENT COMPONENT 3 | 1.28 | down | 1.26 | down |
| C8FW | 202241_at | C8FW GENE; PHOSPHO-PROTEIN. | 1.57 | up | 1.34 | up |
| CEACAM1 | 209498_at | CARCINO-EMBRYONIC | 2.78 | up | 2.20 | up |

TABLE 31-continued

Exemplary biomarkers that discriminate between converters and non-converters

| | | | $T_{-12}$ Values | | $T_{-36}$ Values | |
|---|---|---|---|---|---|---|
| Gene Symbol Column 1 | Affymetrix Probeset name Column 2 | Gene Name Column 3 | Median FC Column 3 | Direction Column 4 | Median FC Column 5 | Direction Column 6 |
| CEACAM1 | 211883_x_at | ANTIGEN-RELATED CELL ADHESION MOLECULE 1 | 1.87 | up | 1.61 | up |
| CECR1 | 219505_at | CAT EYE SYNDROME CHROMOSOME REGION, CANDIDATE 1 | 1.25 | down | 1.26 | down |
| CHCHD7 | 222701_s_at | COILED-COIL-HELIX DOMAIN-CONTAINING PROTEIN 7 | 1.58 | up | 1.26 | up |
| CHSY1 | 203044_at | CARBO-HYDRATE SYNTHASE 1 | 1.78 | up | 1.24 | up |
| CKLF | 223451_s_at | CHEMOKINE-LIKE FACTOR | 1.59 | up | 1.40 | up |
| CKLF | 219161_s_at | | 1.38 | up | 1.31 | up |
| CL25022 | 217883_at | | 1.36 | up | 1.31 | up |
| CPD | 201940_at | CARBOXY-PEPTIDASE D | 1.61 | up | 1.38 | up |
| CPD | 201941_at | | 1.61 | up | 1.35 | up |
| CRTAP | 1554464_a_at | CARTILAGE-ASSOCIATED PROTEIN | 1.23 | down | 1.21 | down |
| DHRS9 | 219799_s_at | MEMBRANE PROTEIN, PALM-ITOYLATED 3; MPP3 | 1.94 | up | 1.52 | up |
| EIF4G3 | 201936_s_at | EUKARYOTIC TRANSLATION INITIATION FACTOR 4-GAMMA, 3 | 1.58 | up | 1.28 | up |
| FAD104 | 218618_s_at | FIBRONECTIN TYPE III DOMAIN CONTAINING 3B (FNDC3B | 1.61 | up | 1.38 | up |
| FAD104 | 225032_at | | 1.63 | up | 1.41 | up |
| FAD104 | 222692_s_at | | 1.74 | up | 1.59 | up |
| FAD104 | 222693_at | | 1.88 | up | 1.92 | up |
| FCGR1A | 214511_x_at | FC FRAGMENT OF IGG, HIGH AFFINITY IA | 2.37 | up | 1.71 | up |
| FCGR1A | 216950_s_at | | 2.56 | up | 1.60 | up |
| FLJ11175 | 229005_at | | 1.77 | up | 1.50 | up |
| FLJ11175 | 220603_s_at | | 2.12 | up | 1.77 | up |
| FLJ11259 | 218627_at | | 1.54 | up | 1.25 | up |
| FLJ11795 | 220112_at | | 1.80 | up | 1.62 | up |
| FLJ22833 | 219334_s_at | | 1.49 | up | 1.28 | up |
| G0S2 | 213524_s_at | | 1.69 | up | 1.30 | up |
| GADD45B | 207574_s_at | GROWTH ARREST-AND DNA DAMAGE-INDUCIBLE GENE GADD45 | 1.55 | up | 1.37 | up |
| GADD45B | 209304_x_at | | 1.42 | up | 1.25 | up |
| GK | 214681_at | GLYCEROL KINASE | 1.76 | up | 1.39 | up |
| GPR160 | 223423_at | G PROTEIN-COUPLED RECEPTOR 160 | 1.83 | up | 1.54 | up |

TABLE 31-continued

Exemplary biomarkers that discriminate between converters and non-converters

| Gene Symbol Column 1 | Affymetrix Probeset name Column 2 | Gene Name Column 3 | $T_{-12}$ Values | | $T_{-36}$ Values | |
|---|---|---|---|---|---|---|
| | | | Median FC Column 3 | Direction Column 4 | Median FC Column 5 | Direction Column 6 |
| HLA-DMA | 217478_s_at | HLA-D HISTOCOMPAT-IBILITY TYPE | 1.32 | down | 1.27 | down |
| HLA-DMB | 203932_at | | 1.29 | down | 1.27 | down |
| HLA-DPA1 | 211991_s_at | | 1.34 | down | 1.27 | down |
| HLA-DQB1 | 209823_x_at | | 1.31 | down | 1.20 | down |
| HLA-DRA | 210982_s_at | | 1.25 | down | 1.24 | down |
| HLA-DRA | 208894_at | | 1.29 | down | 1.23 | down |
| HLA-DRB1 | 215193_x_at | | 1.30 | down | 1.30 | down |
| HLA-DRB1 | 209312_x_at | | 1.27 | down | 1.30 | down |
| HLA-DRB4 | 204670_x_at | | 1.25 | down | 1.27 | down |
| HLA-DRB4 | 208306_x_at | | 1.27 | down | 1.27 | down |
| HPGD | 203913_s_at | 15-HYDROXY-PROSTA-GLANDIN DEHYDRO-GENASE | 2.01 | up | 1.57 | up |
| HRPT2 | 218578_at | HYPERPARA-THYROIDISM 2 | 1.43 | up | 1.27 | up |
| HSPC163 | 228437_at | HSPC163 PROTEIN | 1.64 | up | 1.46 | up |
| HSPC163 | 218728_s_at | | 2.00 | up | 1.52 | up |
| IDI1 | 204615_x_at | ISOPENTENYL-DIPHOSPHATE DELTA-ISOMERASE | 1.51 | up | 1.31 | up |
| IL18R1 | 206618_at | INTERLEUKIN 18 RECEPTOR 1 | 3.18 | up | 2.37 | up |
| KCNE1 | 236407_at | POTASSIUM CHANNEL, VOLTAGE-GATED, ISK-RELATED SUBFAMILY | 1.68 | up | 1.45 | up |
| KIF1B | 225878_at | KINESIN FAMILY MEMBER 1B; | 2.04 | up | 1.62 | up |
| KREMEN1 | 227250_at | KRINGLE CONTAINING TRANS-MEMBRANE PROTEIN 1 | 2.11 | up | 1.32 | up |
| LDLR | 202068_s_at | LOW DENSITY LIPOPROTEIN RECEPTOR | 1.55 | up | 1.52 | up |
| LIMK2 | 202193_at | LIM DOMAIN KINASE 2 | 2.05 | up | 1.51 | up |
| LOC199675 | 235568_at | | 2.91 | up | 2.03 | up |
| LOC284829 | 225669_at | | 1.48 | up | 1.30 | up |
| LOC285771 | 237870_at | | 1.40 | up | 1.34 | up |
| LRG1 | 228648_at | LEUCINE-RICH ALPHA-2-GLYCO-PROTEIN 1 | 2.08 | up | 1.62 | up |
| MGC22805 | 239196_at | NOVEL GENE (MGC22805), | 2.30 | up | 1.86 | up |
| MGC22805 | 238439_at | | 3.38 | up | 2.24 | up |
| MPEG1 | 226841_at | MACROPHAGE EXPRESSED GENE 1 | 1.23 | down | 1.21 | down |
| OAT | 201599_at | ORNITHINE AMINOTRANS- | 1.53 | up | 1.44 | up |

TABLE 31-continued

Exemplary biomarkers that discriminate between converters and non-converters

| Gene Symbol Column 1 | Affymetrix Probeset name Column 2 | Gene Name Column 3 | $T_{-12}$ Values | | $T_{-36}$ Values | |
|---|---|---|---|---|---|---|
| | | | Median FC Column 3 | Direction Column 4 | Median FC Column 5 | Direction Column 6 |
| | | FERASE DEFICIENCY | | | | |
| ORF1-FL49 | 224707_at | | 1.75 | up | 1.65 | up |
| PDCD1LG1 | 227458_at | PROGRAMMED CELL DEATH 1 LIGAND 1 | 2.22 | up | 1.86 | up |
| PFKFB2 | 226733_at | 6-PHOSPHO-FRUCTO-2-KINASE | 1.70 | up | 1.28 | up |
| PFKFB2 | 209992_at | | 1.65 | up | 1.43 | up |
| PFKFB3 | 202464_s_at | 6-PHOSPHO-FRUCTO-2-KINASE/ FRUCTOSE-2,6-BISPHOSPHA-TASE 3 | 3.02 | up | 1.95 | up |
| PGS1 | 219394_at | PHOSPHA-TIDYLGLYCERO-PHOSPHATE SYNTHASE | 2.32 | up | 1.70 | up |
| PHTF1 | 205702_at | PUTATIVE HOMEODOMAIN TRANSCRIPTION FACTOR 1 | 1.37 | up | 1.20 | up |
| PIK3AP1 | 226459_at | PHOSPHO-INOSITIDE 3-KINASE ADAPTOR PROTEIN 1 | 1.64 | up | 1.39 | up |
| PLSCR1 | 241916_at | PHOSPHOLIPID SCRAMBLASE 1 | 2.01 | up | 1.57 | up |
| PRO2852 | 223797_at | | 1.62 | up | 1.42 | up |
| PRV1 | 219669_at | NEUTROPHIL-SPECIFIC ANTIGEN 1 | 7.08 | up | 4.72 | up |
| PSTPIP2 | 219938_s_at | PROLINE/ SERINE/ THREONINE PHOSPHATASE-INTERACTING PROTEIN 1 | 2.54 | up | 1.82 | up |
| PTDSR | 212723_at | CHROMOSOME 17 GENOMIC CONTIG, ALTERNATE ASSEMBLY | 1.45 | up | 1.34 | up |
| RABGEF1 | 218310_at | RAB GUANINE NUCLEOTIDE EXCHANGE FACTOR | 2.03 | up | 1.59 | up |
| RARA | 228037_at | RETINOIC ACID RECEPTOR, ALPHA | 1.54 | up | 1.20 | up |
| RNASEL | 229285_at | RIBONUCLEASE L | 1.68 | up | 1.36 | up |
| SAMSN1 | 1555638_a_at | SAM DOMAIN, SH3 DOMAIN, AND NUCLEAR LOCALIZATION SIGNALS 1 | 2.22 | up | 1.42 | up |
| SAMSN1 | 220330_s_at | | 2.29 | up | 2.10 | up |
| SEC15L1 | 226259_at | SEC15-LIKE 1 (S. CEREVISIAE) (SEC15L1), MRNA | 1.64 | up | 1.43 | up |

TABLE 31-continued

Exemplary biomarkers that discriminate between converters and non-converters

| Gene Symbol Column 1 | Affymetrix Probeset name Column 2 | Gene Name Column 3 | $T_{-12}$ Values | | $T_{-36}$ Values | |
|---|---|---|---|---|---|---|
| | | | Median FC Column 3 | Direction Column 4 | Median FC Column 5 | Direction Column 6 |
| SIPA1L2 | 225056_at | SIGNAL-INDUCED PROLIFERATION-ASSOCIATED GENE 1 | 2.02 | up | 1.52 | up |
| SLC26A8 | 237340_at | | 2.01 | up | 1.48 | up |
| SLC2A3 | 202499_s_at | SOLUTE CARRIER FAMILY 2 (FACILITATED GLUCOSE TRANSPORTER), MEMBER 3 | 1.87 | up | 1.71 | up |
| SOCS3 | 227697_at | SUPPRESSOR OF CYTOKINE SIGNALING 3 | 2.84 | up | 2.15 | up |
| SOD2 | 216841_s_at | SUPEROXIDE DISMUTASE 2 | 1.56 | up | 1.55 | up |
| SPPL2A | 226353_at | SIGNAL PEPTIDE PEPTIDASE-LIKE 2A | 1.48 | up | 1.51 | up |
| SRPK1 | 202200_s_at | PROTEIN KINASE, SERINE/ARGININE-SPECIFIC, 1 | 1.80 | up | 1.46 | up |
| STK3 | 204068_at | SERINE/THREONINE PROTEIN KINASE 3 | 1.74 | up | 1.33 | up |
| SULF2 | 224724_at | SULFATASE 2 (SULF2), TRANSCRIPT VARIANT 2 | 1.36 | down | 1.35 | down |
| SULF2 | 233555_s_at | | 1.37 | down | 1.30 | down |
| T2BP | 226117_at | TRAF-2 BINDING PROTEIN | 2.90 | up | 1.90 | up |
| T2BP | 235971_at | | 1.47 | up | 1.27 | up |
| T2BP | 238858_at | | 1.32 | up | 1.21 | up |
| TBC1D8 | 204526_s_at | TBC1 DOMAIN FAMILY, MEMBER 8 | 1.55 | up | 1.40 | up |
| TCTEL1 | 201999_s_at | T-COMPLEX-ASSOCIATED-TESTIS-EXPRESSED 1 | 1.46 | up | 1.22 | up |
| TGFBI | 201506_at | TRANSFORMING GROWTH FACTOR, BETA-1 | 1.38 | down | 1.41 | down |
| TTYH2 | 223741_s_at | TWEETY, *DROSOPHILA*, HOMOLOG OF, 2 | 1.28 | down | 1.24 | down |
| WDFY3 | 212598_at | WD REPEAT AND FYVE DOMAIN CONTAINING 3 | 1.77 | up | 1.35 | up |
| WDFY3 | 212606_at | | 1.56 | up | 1.35 | up |
| WSB1 | 201296_s_at | WD REPEAT AND SOCS BOX-CONTAINING 1 | 1.74 | up | 1.52 | up |
| ZDHHC19 | 231122_x_at | ZINC FINGER, DHHC DOMAIN CONTAINING 19 (ZDHHC19 | 2.08 | up | 2.13 | up |

TABLE 31-continued

Exemplary biomarkers that discriminate between converters and non-converters

| | | | $T_{-12}$ Values | | $T_{-36}$ Values | |
|---|---|---|---|---|---|---|
| Gene Symbol Column 1 | Affymetrix Probeset name Column 2 | Gene Name Column 3 | Median FC Column 3 | Direction Column 4 | Median FC Column 5 | Direction Column 6 |
| ZDHHC19 | 1553952_at | | 1.37 | up | 1.38 | up |
| ZFP36L2 | 201367_s_at | ZINC FINGER PROTEIN 36, C3H TYPE-LIKE 2; ZFP36L2 | 1.23 | down | 1.28 | down |

Each of the sequences, genes, proteins, and probesets identified in Table 31 is hereby incorporated by reference herein in its entirety.

Table 31, above, provides a list of select biomarkers of the present invention. Where known, gene names are provided. Column two of Table 32, below, provides the GenBank® database accession numbers for the human nucleotide sequences of the biomarkers listed in Table 31, where known. Column three of Table 32 further provides the GenBank® database accession numbers for the corresponding amino acid sequences of the biomarkers of Table 31, where known. The biomarkers of the present invention include, but are not limited to, the genes and proteins identified by the accession numbers of Table 32, splicing variants thereof, discriminating fragments of mRNA, cDNA or other nucleic acids and/or peptides corresponding to all or a discriminating portion of such genes and proteins, etc.

These gene and protein accession numbers are provided in order to identify some of the biomarkers of the present invention. GenBank® is the publicly available genetic sequence database of the National Institutes of Health (NIH), and is an annotated collection of all publicly available DNA sequences (see, e.g., Nucleic Acids Research 2004 Jan. 1; 32(1):23-26, which is incorporated by reference herein in its entirety). GenBank® is part of the International Nucleotide Sequence Database Collaboration, which comprises the DNA DataBank of Japan (DDBJ), the European Molecular Biology Laboratory (EMBL), and GenBank at the National Center for Biotechnology Information (NCBI).

TABLE 32

Gene and protein accession numbers for exemplary biomarkers that discriminate between converters and non-converters

| Gene Symbol Column 1 | Affymetrix Probeset name Column 2 | Gene Name Column 3 | Gene Accession Number Column 4 | Protein Accession Number Column 5 |
|---|---|---|---|---|
| | 1555785_a_at | EST | | |
| <NA> | 227150_at | EST | | |
| <NA> | 238973_s_at | EST | | |
| <NA> | 239893_at | EST | | |
| <NA> | 237563_s_at | EST | | |
| <NA> | 244313_at | EST | | |
| <NA> | 237071_at | EST | | |
| <NA> | 229934_at | EST | | |
| <NA> | 1555311_at | EST | | |
| <NA> | 233264_at | EST | | |
| <NA> | 239780_at | EST | | |
| <NA> | 238405_at | EST | | |
| 3'HEXO | 226416_at | HISTONE MRNA 3' END EXORIBONUCLEASE | NM_153332 | NP_699163 |
| 3'HEXO | 231852_at | | | |
| ADORA2A | 205013_s_at | ADENOSINE A2 RECEPTOR | NM_000675 | NP_000666 |
| ANXA3 | 209369_at | ANNEXIN A3 | NM_005139 | NP_005130 |
| ASAHL | 214765_s_at | N-ACYLSPHINGOSINE AMIDOHYDROLASE-LIKE PROTEIN | NM_014435 | NP_055250 |
| ASAHL | 232072_at | | | |
| ASAHL | 227135_at | | | |
| ATP11B | 1554557_at | ATPASE, CLASS VI, TYPE 11B | XM_087254 | XP_087254 |
| ATP6V1C1 | 202872_at | ATPASE, H+ TRANSPORTING, LYSOSOMAL, 42-KD, V1 SUBUNIT C, ISOFORM 1 | NM_001695 NM_001007254 | NP_001686 NP_001007255 |
| B4GALT5 | 221485_at | BETA-1,4-GALACTOSYLTRANSFERASE | NM_004776 | NP_004767 |
| BASP1 | 202391_at | BRAIN-ABUNDANT SIGNAL PROTEIN | NM_006317 | NP_006308 |
| BAZ1A | 217986_s_at | BROMODOMAIN ADJACENT TO ZINC FINGER DOMAIN, 1A | NM_013448 NM_182648 | NP_038476 NP_872589 |

TABLE 32-continued

Gene and protein accession numbers for exemplary biomarkers that discriminate between converters and non-converters

| Gene Symbol Column 1 | Affymetrix Probeset name Column 2 | Gene Name Column 3 | Gene Accession Number Column 4 | Protein Accession Number Column 5 |
|---|---|---|---|---|
| BCL6 | 203140_at | B-CELL LYMPHOMA 6 | NM_001706 | NP_001697 |
| | | | NM_138931 | NP_620309 |
| BMX | 206464_at | BONE MARROW KINASE, X-LINKED | NM_001721 | NP_001712 |
| | | | NM_203281 | NP_975010 |
| C16orf7 | 205781_at | CHROMOSOME 16 OPEN-READING FRAME 7 | NM_004913 | NP_004904 |
| C20orf32 | 1554786_at | CHROMOSOME 20 OPEN-READING FRAME 32 | NM_020356 | NP_065089 |
| C3F | 203547_at | COMPLEMENT COMPONENT 3 | NM_005768 | NP_005759 |
| C8FW | 202241_at | C8FW GENE; PHOSPHOPROTEIN. | NM_025195 | NP_079471 |
| CEACAM1 | 209498_at | CARCINOEMBRYONIC ANTIGEN-RELATED CELL ADHESION MOLECULE 1 | NM_001712 | NP_001703 |
| CEACAM1 | 211883_x_at | | | |
| CECR1 | 219505_at | CAT EYE SYNDROME CHROMOSOME REGION, CANDIDATE 1 | NM_017424 | NP_059120 |
| | | | NM_177405 | NP_803124 |
| CHCHD7 | 222701_s_at | COILED-COIL-HELIX DOMAIN-CONTAINING PROTEIN 7 | NM_001011667 | NP_001011667 |
| | | | NM_001011668 | NP_001011668 |
| | | | NM_001011669 | NP_001011669 |
| | | | NM_001011670 | NP_001011670 |
| | | | NM_001011671 | NP_001011671 |
| | | | NM_024300 | NP_077276 |
| CHSY1 | 203044_at | CARBOHYDRATE SYNTHASE 1 | NM_014918 | NP_055733 |
| CKLF | 223451_s_at | CHEMOKINE-LIKE FACTOR | NM_016326 | NP_057410 |
| | | | NM_016951 | NP_058647 |
| | | | NM_181640 | NP_857591 |
| | | | NM_181641 | NP_857592 |
| CKLF | 219161_s_at | | | |
| CL25022 | 217883_at | C2ORF25 | NM_015702 | NP_056517 |
| CPD | 201940_at | CARBOXYPEPTIDASE D | NM_001304 | NP_001295 |
| CPD | 201941_at | | | |
| CRTAP | 1554464_a_at | CARTILAGE-ASSOCIATED PROTEIN | NM_006371 | NP_006362 |
| DHRS9 | 219799_s_at | MEMBRANE PROTEIN, PALMITOYLATED 3; MPP3 | NM_005771 | NP_005762 |
| | | | NM_199204 | NP_954674 |
| EIF4G3 | 201936_s_at | EUKARYOTIC TRANSLATION INITIATION FACTOR 4-GAMMA, 3 | NM_003760 | NP_003751 |
| FAD104 | 218618_s_at | FIBRONECTIN TYPE III DOMAIN CONTAINING 3B (FNDC3B) | NM_022763 | NP_073600 |
| FAD104 | 225032_at | | | |
| FAD104 | 222692_s_at | | | |
| FAD104 | 222693_at | | | |
| FCGR1A | 214511_x_at | FC FRAGMENT OF IGG, HIGH AFFINITY IA | NM_000566 | NP_000557 |
| FCGR1A | 216950_s_at | | | |
| FLJ11175 | 229005_at | | NM_018349 | NP_060819 |
| FLJ11175 | 220603_s_at | | | |
| FLJ11259 | 218627_at | | NM_018370 | NP_060840 |
| FLJ11795 | 220112_at | | NM_024669 | NP_078945 |
| FLJ22833 | 219334_s_at | HYPOTHETICAL PROTEIN FLJ22833 | NM_022837 | |
| G0S2 | 213524_s_at | | NM_015714 | NP_056529 |
| GADD45B | 207574_s_at | GROWTH ARREST- AND DNA DAMAGE-INDUCIBLE GENE GADD45 | NM_015675 | NP_056490 |
| GADD45B | 209304_x_at | | | |
| GK | 214681_at | GLYCEROL KINASE | NM_000167 | NP_000158 |
| | | | NM_203391 | NP_976325 |
| GPR160 | 223423_at | G PROTEIN-COUPLED RECEPTOR 160 | NM_014373 | NP_055188 |
| HLA-DMA | 217478_s_at | HLA-D HISTOCOMPATIBILITY TYPE | NM_006120 | NP_006111 |
| HLA-DMB | 203932_at | | NM_002118 | NP_002109 |
| HLA-DPA1 | 211991_s_at | | NM_033554 | NP_291032 |
| HLA-DQB1 | 209823_x_at | | NM_002123 | NP_002114 |
| HLA-DRA | 210982_s_at | | NM_002123 | NP_002114 |
| HLA-DRA | 208894_at | | | |

TABLE 32-continued

Gene and protein accession numbers for exemplary biomarkers that discriminate between converters and non-converters

| Gene Symbol Column 1 | Affymetrix Probeset name Column 2 | Gene Name Column 3 | Gene Accession Number Column 4 | Protein Accession Number Column 5 |
|---|---|---|---|---|
| HLA-DRB1 | 215193_x_at | | NM_002124 | NP_002115 |
| HLA-DRB1 | 209312_x_at | | | |
| HLA-DRB4 | 204670_x_at | | NM_021983 | NP_068818 |
| HLA-DRB4 | 208306_x_at | | | |
| HPGD | 203913_s_at | 15-HYDROXYPROSTAGLANDIN DEHYDROGENASE HYDROXYPROSTAGLANDIN DEHYDROGENASE 15-(NAD) | NM_000860 | NP_000851 |
| HRPT2 | 218578_at | HYPERPARATHYROIDISM 2 | NM_024529 | NP_078805 |
| HSPC163 | 228437_at | HSPC163 PROTEIN | NM_014184 | NP_054903 |
| HSPC163 | 218728_s_at | | | |
| IDI1 | 204615_x_at | ISOPENTENYL-DIPHOSPHATE DELTA-ISOMERASE | NM_004508 | NP_004499 |
| IL18R1 | 206618_at | INTERLEUKIN 18 RECEPTOR 1 | NM_003855 | NP_003846 |
| KCNE1 | 236407_at | POTASSIUM CHANNEL, VOLTAGE-GATED, ISK-RELATED SUBFAMILY | NM_000219 | NP_000210 |
| KIF1B | 225878_at | KINESIN FAMILY MEMBER 1B | NM_015074 NM_183416 | NP_055889 NP_904325 |
| KREMEN1 | 227250_at | KRINGLE CONTAINING TRANSMEMBRANE PROTEIN 1 | NM_032045 NM_153379 | NP_114434 NP_700358 |
| LDLR | 202068_s_at | LOW DENSITY LIPOPROTEIN RECEPTOR | NM_000527 | NP_000518 |
| LIMK2 | 202193_at | LIM DOMAIN KINASE 2 | NM_005569 NM_016733 | NP_005560 NP_057952 |
| LOC199675 | 235568_at | HYPOTHETICAL PROTEIN LOC199675 | NM_174918 | NP_777578 |
| LOC284829 | 225669_at | | | |
| LOC285771 | 237870_at | HYPOTHETICAL PROTEIN LOC285771) | | |
| LRG1 | 228648_at | LEUCINE-RICH ALPHA-2-GLYCOPROTEIN 1 | NM_052972 | NP_443204 |
| MGC22805 | 239196_at | NOVEL GENE (MGC22805), | | |
| MGC22805 | 238439_at | | | |
| MPEG1 | 226841_at | MACROPHAGE EXPRESSED GENE 1 | XM_166227 | XP_166227 |
| OAT | 201599_at | ORNITHINE AMINOTRANSFERASE DEFICIENCY | NM_000274 | NP_000265 |
| ORF1-FL49 | 224707_at | PUTATIVE NUCLEAR PROTEIN ORF1-FL49 | NM_032412 | NP_115788 |
| PDCD1LG1 | 227458_at | PROGRAMMED CELL DEATH 1 LIGAND 1 | NM_014143 | NP_054862 |
| PFKFB2 | 226733_at | 6-PHOSPHOFRUCTO-2-KINASE | NM_006212 | NP_006203 |
| PFKFB2 | 209992_at | | | |
| PFKFB3 | 202464_s_at | 6-PHOSPHOFRUCTO-2-KINASE/FRUCTOSE-2,6-BISPHOSPHATASE 3 | NM_004566 | NP_004557 |
| PGS1 | 219394_at | PHOSPHATIDYLGLYCERO-PHOSPHATE SYNTHASE | NM_024419 | NP_077733 |
| PHTF1 | 205702_at | PUTATIVE HOMEODOMAIN TRANSCRIPTION FACTOR 1 | NM_006608 | NP_006599 |
| PIK3AP1 | 226459_at | PHOSPHOINOSITIDE 3-KINASE ADAPTOR PROTEIN 1 | NM_152309 | NP_689522 |
| PLSCR1 | 241916_at | PHOSPHOLIPID SCRAMBLASE 1 | NM_021105 | NP_066928 |
| PRO2852 | 223797_at | HYPOTHETICAL PROTEIN PRO2852 | | |
| PRV1 | 219669_at | NEUTROPHIL-SPECIFIC ANTIGEN 1 (POLYCYTHEMIA RUBRA VERA 1) | NM_020406 | NP_065139 |

TABLE 32-continued

Gene and protein accession numbers for exemplary biomarkers that discriminate between converters and non-converters

| Gene Symbol Column 1 | Affymetrix Probeset name Column 2 | Gene Name Column 3 | Gene Accession Number Column 4 | Protein Accession Number Column 5 |
|---|---|---|---|---|
| PSTPIP2 | 219938_s_at | PROLINE/SERINE/THREONINE PHOSPHATASE-INTERACTING PROTEIN 1 (PROLINE-SERINE-THREONINE PHOSPHATASE INTERACTING PROTEIN 2) | NM_024430 | NP_077748 |
| PTDSR | 212723_at | CHROMOSOME 17 GENOMIC CONTIG, ALTERNATE ASSEMBLY (PHOSPHATIDYLSERINE RECEPTOR) | NM_015167 | NP_055982 |
| RABGEF1 | 218310_at | RAB GUANINE NUCLEOTIDE EXCHANGE FACTOR (RAB GUANINE NUCLEOTIDE EXCHANGE FACTOR (GEF) 1) | NM_014504 | NP_055319 |
| RARA | 228037_at | RETINOIC ACID RECEPTOR, ALPHA | NM_000964 | NP_000955 |
| RNASEL | 229285_at | RIBONUCLEASE L | NM_021133 | NP_066956 |
| SAMSN1 | 1555638_a_at | SAM DOMAIN, SH3 DOMAIN, AND NUCLEAR LOCALIZATION SIGNALS 1 | NM_022136 | NP_071419 |
| SAMSN1 | 220330_s_at | | | |
| SEC15L1 | 226259_at | SEC15-LIKE 1 (*S. CEREVISIAE*) (SEC15L1), MRNA | NM_019053 | NP_061926 |
| SIPA1L2 | 225056_at | SIGNAL-INDUCED PROLIFERATION-ASSOCIATED GENE 1 (SIGNAL-INDUCED PROLIFERATION-ASSOCIATED 1 LIKE 2) | NM_020808 | NP_065859 |
| SLC26A8 | 237340_at | SOLUTE CARRIER FAMILY 26, MEMBER 8 | NM_052961 NM_138718 | NP_443193 NP_619732 |
| SLC2A3 | 202499_s_at | SOLUTE CARRIER FAMILY 2 (FACILITATED GLUCOSE TRANSPORTER), MEMBER 3 | NM_006931 | NP_008862 |
| SOCS3 | 227697_at | SUPPRESSOR OF CYTOKINE SIGNALING 3 | NM_003955 | NP_003946 |
| SOD2 | 216841_s_at | SUPEROXIDE DISMUTASE 2 | NM_000636 | NP_000627 |
| SPPL2A | 226353_at | SIGNAL PEPTIDE PEPTIDASE-LIKE 2A | NM_032802 | NP_116191 |
| SRPK1 | 202200_s_at | PROTEIN KINASE, SERINE/ARGININE-SPECIFIC, 1 (SFRS PROTEIN KINASE 1) | NM_003137 | NP_003128 |
| STK3 | 204068_at | SERINE/THREONINE PROTEIN KINASE 3 | NM_006281 | NP_006272 |
| SULF2 | 224724_at | SULFATASE 2 (SULF2), TRANSCRIPT VARIANT 2 | NM_198596 | NP_940998 |
| SULF2 | 233555_s_at | | | |
| T2BP | 226117_at | TRAF-2 BINDING PROTEIN (TRAF-INTERACTING PROTEIN WITH A FORKHEAD-ASSOCIATED DOMAIN) | NM_052864 | NP_443096 |
| T2BP | 235971_at | | | |
| T2BP | 238858_at | | | |
| TBC1D8 | 204526_s_at | TBC1 DOMAIN FAMILY, MEMBER 8 | NM_007063 | NP_008994 |
| TCTEL1 | 201999_s_at | T-COMPLEX-ASSOCIATED-TESTIS-EXPRESSED 1 | NM_006519 | NP_006510 |
| TGFBI | 201506_at | TRANSFORMING GROWTH FACTOR, BETA-1 | NM_000358 | NP_000349 |
| TTYH2 | 223741_s_at | TWEETY, *DROSOPHILA*, HOMOLOG OF, 2 | NM_032646 NM_052869 | NP_116035 NP_443101 |
| WDFY3 | 212598_at | WD REPEAT AND FYVE DOMAIN CONTAINING 3 | NM_014991 NM_178583 NM_178585 | NP_055806 NP_848698 NP_848700 |
| WDFY3 | 212606_at | | | |
| WSB1 | 201296_s_at | WD REPEAT AND SOCS BOX-CONTAINING 1 | NM_015626 NM_134264 NM_134265 | NP_056441 NP_599026 NP_599027 |

TABLE 32-continued

Gene and protein accession numbers for exemplary biomarkers that discriminate between converters and non-converters

| Gene Symbol Column 1 | Affymetrix Probeset name Column 2 | Gene Name Column 3 | Gene Accession Number Column 4 | Protein Accession Number Column 5 |
|---|---|---|---|---|
| ZDHHC19 | 231122_x_at | ZINC FINGER, DHHC DOMAIN CONTAINING 19 (ZDHHC19) | NM_144637 | NP_653238 |
| ZDHHC19 | 1553952_at | | | |
| ZFP36L2 | 201367_s_at | ZINC FINGER PROTEIN 36, C3H TYPE-LIKE 2; ZFP36L2 | NM_006887 | NP_008818 |

Each of the sequences, genes, proteins, and probesets identified in Table 32 is hereby incorporated by reference herein in its entirety.

6.8 Biomarker Combinations Based on Additional Filtering Criteria

Section 6.6 describes exemplary biomarkers that discriminate between converters and nonconverters. Section 6.7 describes one exemplary combination of the biomarkers of Section 6.6. The biomarkers of Section 6.7 were identified by the application of an additional filtering criterion to the biomarkers of Section 6.6. This section describes additional combinations of the biomarkers identified in Section 6.7. The subsections identified in this section discriminate between converters and nonconverters.

Table 33 lists biomarkers in one exemplary combination. The combination detailed in Table 33 was identified by taking the list of biomarkers in Table 31 and imposing additional filtering criteria. These additional criteria include a requirement that each respective biomarker under consideration exhibit at least a 1.2× fold change between the median feature value for the respective biomarker among the subjects that acquired sepsis during a defined time period (sepsis subjects) and the median value for the respective biomarker among subjects that do not acquire sepsis during the defined time period (SIRS subjects) in the $T_{-12}$ baseline data described in Section 6.5. Furthermore, the summation of the PAM score, CART score, and RF score for the biomarker in the $T_{-12}$ baseline data time period had to exceed unity. Application of these additional filtering criteria reduced the biomarkers from the 130 found in Table 31, to ten biomarkers.

TABLE 33

Exemplary combination of biomarkers that discriminate between converters and non-converters

| | Affymetrix | | $T_{-12}$ Values | | $T_{-36}$ Values | |
|---|---|---|---|---|---|---|
| Gene Symbol Column 1 | Probeset name Column 2 | Gene Name Column 3 | Median FC Column 4 | Direction Column 5 | Median FC Column 6 | Direction Column 7 |
| | 1555785_a_at | EST | 1.34 | up | 1.31 | up |
| CL25022 | 217883_at | | 1.36 | up | 1.31 | up |
| IDI1 | 204615_x_at | ISOPENTENYL-DIPHOSPHATE DELTA-ISOMERASE | 1.51 | up | 1.31 | up |
| MGC22805 | 239196_at | NOVEL GENE (MGC22805) | 2.30 | up | 1.86 | up |
| ORF1-FL49 | 224707_at | | 1.75 | up | 1.65 | up |
| ZDHHC19 | 1553952_at | | 1.37 | up | 1.38 | up |
| CHSY1 | 203044_at | CARBOHYDRATE SYNTHASE 1 | 1.78 | up | 1.24 | up |
| SLC2A3 | 202499_s_at | SOLUTE CARRIER FAMILY 2 (FACILITATED GLUCOSE TRANSPORTER), MEMBER 3 | 1.87 | up | 1.71 | up |
| FAD104 | 225032_at | | 1.63 | up | 1.41 | up |
| T2BP | 235971_at | | 1.47 | up | 1.27 | up |

Each of the sequences, genes, proteins, and probesets identified in Table 33 is hereby incorporated by reference.

Table 34 lists biomarkers in yet another exemplary combination of biomarkers. The combination detailed in Table 34 was identified by taking the list of biomarkers in Table 31 and imposing the additional requirement that each biomarker is annotated with a corresponding known gene and that such a gene has a known biological function. Methods, tables, software and other resources for addressing this latter question are available from the Gene Ontology Consortium, (www.geneontology.org), which is hereby incorporated by reference in its entirety. Application of these additional filtering criteria reduced the biomarkers from the 130 found in the set of Table 31, to 52 biomarkers, representing 42 unique gene sequences (see FIG. 30).

TABLE 34

Exemplary combination of biomarkers that discriminate between converters and non-converters

| Gene Symbol | Corresponding Gene Name |
| --- | --- |
| (BCL6 na) | (B-cell CLL/lymphoma 6 (zinc finger protein 51) LOC389185) |
| (HLA-DRB1,3,4,5) | (major histocompatibility complex class II DR beta 1 3,4,5) |
| (RABGEF1 na) | (LOC401368 LOC402538 RAB guanine nucleotide exchange factor (GEF) 1) |
| 3HEXO | 3 exoribonuclease |
| ADORA2A | adenosine A2a receptor |
| ANKRD22 | ankyrin repeat domain 22 |
| ANXA3 | annexin A3 |
| ATP11B | ATPase Class VI type 11B |
| ATP6V1C1 | ATPase H+ transporting lysosomal 42 kDa V1 subunit C isoform 1 |
| BASP1 | brain abundant membrane attached signal protein 1 |
| BAZ1A | bromodomain adjacent to zinc finger domain 1A |
| C16orf7 | chromosome 16 open reading frame 7 |
| CD4 | CD4 antigen (p55) |
| CEACAM1 | carcinoembryonic antigen-related cell adhesion molecule 1 (biliary glycoprotein) |
| CECR1 | cat eye syndrome chromosome region candidate 1 |
| CKLF | chemokine-like factor |
| CPD | carboxypeptidase D |
| EIF4G3 | eukaryotic translation initiation factor 4 gamma 3 |
| FCGR1A | Fc fragment of IgG high affinity Ia receptor for (CD64) |
| G0S2 | putative lymphocyte G0/G1 switch gene |
| GADD45B | growth arrest and DNA-damage-inducible beta |
| HLA-DMB | major histocompatibility complex class II DM beta |
| HLA-DPA1 | major histocompatibility complex class II DP alpha 1 |
| HLA-DQB1 | major histocompatibility complex class II DQ beta 1 |
| HLA-DRA | major histocompatibility complex class II DR alpha |
| HPGD | hydroxyprostaglandin dehydrogenase 15-(NAD) |
| IL18R1 | interleukin 18 receptor 1 |
| KCNE1 | potassium voltage-gated channel Isk-related family member 1 |
| LDLR | low density lipoprotein receptor (familial hypercholesterolemia) |
| PDCD1LG1 | programmed cell death 1 ligand 1 |
| PHTF1 | putative homeodomain transcription factor 1 |
| PRV1 | polycythemia rubra vera 1 |
| PTDSR | phosphatidylserine receptor |
| RARA | retinoic acid receptor alpha |
| RNASEL | ribonuclease L (25-oligoisoadenylate synthetase-dependent) |
| SEC15L1 | SEC 15-like 1 (*S. cerevisiae*) |
| SLC26A8 | solute carrier family 26 member 8 |
| SLC2A3 | solute carrier family 2 (facilitated glucose transporter) member 3 |
| STK3 | serine/threonine kinase 3 (STE20 homolog yeast) |
| TGFBI | transforming growth factor beta-induced 68 kDa |
| XRN1 | 5-3 exoribonuclease 1 |
| ZFP36L2 | zinc finger protein 36 C3H type-like 2 |

Each of the sequences, genes, proteins, and probesets identified in Table 34 is hereby incorporated by reference.

In one embodiment, the biomarker profile comprises a plurality of biomarkers that collectively contain at least five, at least ten at least fifteen, at least twenty, at least thirty, between 2 and 5, between 3 and 7, or less than 15 of the sequences of the probesets of Table 32, or complements thereof, or genes including one of at least five of the sequences or complements thereof, or a discriminating fragment thereof, or an amino acid sequence encoded by any of the foregoing nucleic acid sequences, or any discriminating fragment of such an amino acid sequence. Such biomarkers can be mRNA transcripts, cDNA or some other form of amplified nucleic acid or proteins.

In one embodiment, the biomarker profile comprises a plurality of biomarkers that collectively contain at least five, at least ten at least fifteen, at least twenty, at least thirty, between 2 and 5, between 3 and 7, or less than 15 of the sequences of the probesets of Table 33, or complements thereof, or genes including one of at least five of the sequences or complements thereof, or a discriminating fragment thereof, or an amino acid sequence encoded by any of the foregoing nucleic acid sequences, or any discriminating fragment of such an amino acid sequence. Such biomarkers can be, for example, mRNA transcripts, cDNA or some other nucleic acid, for example amplified nucleic acid, or proteins.

In one embodiment, the biomarker profile comprises a plurality of biomarkers that collectively contain at least five, at least ten at least fifteen, at least twenty, at least thirty, between 2 and 5, between 3 and 7, or less than 15 of the sequences of the probesets of Table 34, or complements thereof, or genes including one of at least five of the sequences or complements thereof, or a discriminating fragment thereof, or an amino acid sequence encoded by any of the foregoing nucleic acid sequences, or any discriminating fragment of such an amino acid sequence. Such biomarkers can be, for example, mRNA transcripts, cDNA or some other nucleic acid, for example amplified nucleic acid, or proteins.

In one embodiment, the biomarker profile comprises a plurality of biomarkers that collectively contain at least five, at least ten at least fifteen, at least twenty, at least thirty, between 2 and 5, between 3 and 7, or less than 15 of the sequences of the probesets of Table 33 or Table 34, or complements thereof, or genes including one of at least five of the sequences or complements thereof, or a discriminating fragment thereof, or an amino acid sequence encoded by any of the foregoing nucleic acid sequences, or any discriminating fragment of such an amino acid sequence. Such biomarkers can be, for example, mRNA transcripts, cDNA or some other nucleic acid, for example amplified nucleic acid, or proteins.

In one embodiment, the biomarker profile comprises a biomarker that has the sequence of U133 plus 2.0 probeset SLC2A3 or a complement thereof, or a gene including the sequence of the probeset SLC2A3 or a complement thereof, or a discriminating fragment thereof, or an amino acid sequence encoded by any of the foregoing nucleic acid sequences, or any discriminating fragment of such an amino acid sequence. Such biomarkers can be, for example, mRNA transcripts, cDNA or some other nucleic acid, for example amplified nucleic acid, or proteins.

In the case where a biomarker is based upon a gene that includes the sequence of a probeset listed in Table 30, 31, 32, 33, or 34 or a complement thereof, the biomarker can be, for example, a transcript made by the gene, a complement thereof, or a discriminating fragment or complement thereof, or a cDNA thereof, or a discriminating fragment of the cDNA, or a discriminating amplified nucleic acid molecule corresponding to all or a portion of the transcript or its complement, or a protein encoded by the gene, or a discriminating fragment of the protein, or an indication of any of the above. Further still, the biomarker can be, for example, a protein encoded by a gene that includes a probeset sequence described in Table 30, 31, 32, 33 or 34, or a discriminating fragment of the protein, or an indication of the above. Here, a discriminating molecule or fragment is a molecule or fragment that, when detected, indicates presence or abundance of the above-identified transcript, cDNA, amplified nucleic acid, or protein.

6.9 Differential Gene Expression in the Th1/Th2 Pathway in SIRS and Sepsis Patients This section describes methods used to identify a set of biomarkers that discriminate between converters and nonconverters, using the methods described, e.g., in Section 5.10, supra. Briefly, 97 SIRS subject were admitted to critical care units of a major university trauma center were evaluated using the methods described in Section 6.1. Comparisons were made using $T_{-36}$ and $T_{-12}$ static data described in Sections 6.3 and 6.4, respectively. The subjects were divided into two classes: converters (47) and nonconverters (50). Blood samples drawn from converters were time matched to samples from nonconverters in order to perform comparisons, as described in Sections 6.3 and 6.4, respectively. The blood samples were collected and analyzed as described in Section 6.2.

Biomarkers that discriminated between converters and nonconverters with (i) a Wilcoxon (adjusted) p value of 0.05 or less and (ii) an exhibited a mean fold differential expression value between converters and nonconverters of 1.2 or greater in either the $T_{-36}$ or the $T_{-12}$ static test were selected as the set of discriminating biomarkers. This set of discriminating biomarkers was then filtered using an annotation data based filtering rule imposed by DAVID 2.0, which is available from the National Institutes of Health (see, http://apps1.niaid.nih.gov/david/, the contents of which are incorporated by reference herein in their entirety). Specifically, that annotation data based filtering rule imposed by David 2.0 had the form of annotation rule 4 in Section 5.10, reproduce below Annotation Rule 4.

Select all biomarkers that are in biological pathway X.

The specific form of this annotation data based filtering rule in this example was Select all biomarkers that are in the Th1/Th2 biological pathway (cell differentiation pathway).

Table 35 below lists the Affymetrix U133 plus 2.0 probesets that are in genes known to be involved in this Th1/Th2 cell differentiation pathway.

TABLE 35

U133 plus 2.0 Probesets in genes involved in the Th1/Th2 cell differentiation pathway.

| Symbol | U133 + 2.0 probeset | P value (adjusted) |
|---|---|---|
| CD28 | 211856_x_at | 0.018 |
| CD28 | 211861_x_at | |
| CD28 | 206545_at | |
| CD86 | 205685_at | 0.0034 |
| CD86 | 205685_at | 0.0187 |
| CD86 | 210895_s_at | 0.0034 |
| CD86 | 210895_s_at | 0.0187 |
| CD86 | 205686_s_at | 0.0114 |
| HLA-DRA | 210982_s_at | 0.0034 |
| HLA-DRA | 210982_s_at | 0.0187 |
| HLA-DRA | 208894_at | 0.0034 |
| HLA-DRA | 208894_at | 0.0187 |
| HLA-DRB1 | 221491_x_at | |
| HLA-DRB1 | 217323_at | |
| HLA-DRB1 | 217362_x_at | 0.0034 |
| HLA-DRB1 | 217362_x_at | 0.0472 |
| HLA-DRB1 | 215193_x_at | 0.0034 |
| HLA-DRB1 | 215193_x_at | 0.0187 |
| HLA-DRB1 | 209728_at | |
| HLA-DRB1 | 204670_x_at | 0.0034 |
| HLA-DRB1 | 204670_x_at | 0.0187 |
| HLA-DRB1 | 208306_x_at | 0.0034 |
| HLA-DRB1 | 208306_x_at | 0.0187 |
| HLA-DRB1 | 209312_x_at | 0.0034 |
| HLA-DRB1 | 209312_x_at | 0.0187 |
| HLA-DRB1 | 215666_at | |
| HLA-DRB1 | 215669_at | |
| HLA-DRB3 | 221491_x_at | |
| HLA-DRB3 | 217323_at | |
| HLA-DRB3 | 217362_x_at | 0.0034 |
| HLA-DRB3 | 217362_x_at | 0.0472 |
| HLA-DRB3 | 215193_x_at | 0.0034 |
| HLA-DRB3 | 215193_x_at | 0.0187 |
| HLA-DRB3 | 209728_at | |
| HLA-DRB3 | 204670_x_at | 0.0034 |
| HLA-DRB3 | 204670_x_at | 0.0187 |
| HLA-DRB3 | 208306_x_at | 0.0034 |
| HLA-DRB3 | 208306_x_at | 0.0187 |
| HLA-DRB3 | 209312_x_at | 0.0034 |
| HLA-DRB3 | 209312_x_at | 0.0187 |
| HLA-DRB3 | 215666_at | |
| HLA-DRB3 | 215669_at | |
| HLA-DRB4 | 221491_x_at | |
| HLA-DRB4 | 217323_at | |
| HLA-DRB4 | 217362_x_at | 0.0034 |
| HLA-DRB4 | 217362_x_at | 0.0472 |
| HLA-DRB4 | 215193_x_at | 0.0034 |
| HLA-DRB4 | 215193_x_at | 0.0187 |
| HLA-DRB4 | 209728_at | |
| HLA-DRB4 | 204670_x_at | 0.0034 |
| HLA-DRB4 | 204670_x_at | 0.0187 |
| HLA-DRB4 | 208306_x_at | 0.0034 |
| HLA-DRB4 | 208306_x_at | 0.0187 |
| HLA-DRB4 | 209312_x_at | 0.0034 |
| HLA-DRB4 | 209312_x_at | 0.0187 |
| HLA-DRB4 | 215666_at | |

TABLE 35-continued

U133 plus 2.0 Probesets in genes involved in the Th1/Th2 cell differentiation pathway.

| Symbol | U133 + 2.0 probeset | P value (adjusted) |
|---|---|---|
| HLA-DRB4 | 215669_at | |
| HLA-DRB5 | 221491_x_at | |
| HLA-DRB5 | 217323_at | |
| HLA-DRB5 | 217362_x_at | 0.0034 |
| HLA-DRB5 | 217362_x_at | 0.0472 |
| HLA-DRB5 | 215193_x_at | 0.0034 |
| HLA-DRB5 | 215193_x_at | 0.0187 |
| HLA-DRB5 | 209728_at | |
| HLA-DRB5 | 204670_x_at | 0.0034 |
| HLA-DRB5 | 204670_x_at | 0.0187 |
| HLA-DRB5 | 208306_x_at | 0.0034 |
| HLA-DRB5 | 208306_x_at | 0.0187 |
| HLA-DRB5 | 209312_x_at | 0.0034 |
| HLA-DRB5 | 209312_x_at | 0.0187 |
| HLA-DRB5 | 215666_at | |
| HLA-DRB5 | 215669_at | |
| IFNG | 210354_at | |
| IFNGR1 | 211676_s_at | 0.00342 |
| IFNGR1 | 242903_at | 0.0034 |
| IFNGR1 | 202727_s_at | 0.0054 |
| IFNGR2 | 231696_x_at | |
| IFNGR2 | 201642_at | 0.0034 |
| IL12A | 207160_at | |
| IL12B | 207901_at | |
| IL12RB1 | 239522_at | |
| IL12RB1 | 206890_at | |
| IL12RB2 | 206999_at | |
| IL18 | 206295_at | |
| IL18R1 | 206618_at | 0.0034 |
| IL18R1 | 206618_at | 0.0187 |
| IL2 | 207849_at | |
| IL2RA | 211269_s_at | |
| IL2RA | 206341_at | 0.0247 |
| IL4 | 207538_at | |
| IL4 | 207539_s_at | |
| IL4R | 203233_at | 0.0034 |
| IL4R | 203233_at | 0.0187 |
| TNFRSF5 | 222292_at | 0.0126 |
| TNFRSF5 | 215346_at | |
| TNFRSF5 | 205153_s_at | |
| TNFRSF5 | 35150_at | 0.0086 |
| TNFSF5 | 207892_at | 0.0034 |

Table 36 below identifies the genes that contain the probesets that remained in the set of discriminating biomarkers upon application of the annotation data based filtering rule.

TABLE 36

Identified genes.

| Gene name | Data source (static) | Adjusted p value | Fold-change (Median sepsis vs. Median SIRS) | Relative regulation |
|---|---|---|---|---|
| CD86 | $T_{-12}$ | 0.003 | 1.56 | Down |
| | $T_{-36}$ | 0.019 | 1.23 | Down |
| HLA-DRA | $T_{-12}$ | 0.003 | 1.29 | Down |
| | $T_{-36}$ | 0.019 | 1.23 | Down |
| HLA-DRB1,3,4,5 | $T_{-12}$ | 0.003 | 1.25 | Down |
| | $T_{-36}$ | 0.019 | 1.27 | Down |
| IFNGR1 | $T_{-12}$ | 0.003 | 1.39 | Up |
| IFNGR2 | $T_{-12}$ | 0.003 | 1.25 | Up |
| IL18R1 | $T_{-12}$ | 0.003 | 3.17 | Up |
| | $T_{-36}$ | 0.019 | 2.37 | Up |
| IL4R | $T_{-12}$ | 0.003 | 1.61 | Up |
| | $T_{-36}$ | 0.019 | 1.39 | Up |

The genes in Table 36 represent biomarkers that discriminate between converters and converters. Further, these genes are in the Th1/Th2 cell differentiation pathway. The results in the table show that, although clinically similar, SIRS patients who subsequently developed sepsis expressed genes related to Th1/Th2 Cells differently than SIRS patients who remained uninfected. These differences occurred prior to the onset of clinical sepsis. For a discussion of Th1/Th2 cell differentiation pathway genes and related genes, see, e.g., Abbas et al., 1996, Functional diversity of helper T lymphocytes, Nature 383:787-793; Fearon and Locksley, 1996, Science 272:50-53; and Mossman and Sad, 1996, Immunol. Today 17:138-146; each of which is hereby incorporated by reference in its entirety.

6.10 RT-PCR

In Section 6.1, it was noted that two Paxgene (RNA) tubes were drawn from each subject in the study on each day of the study. One tube was used for microarray analysis as described in Section 6.2. The other tube was used for RT-PCR analysis. In this section, the correlation between the gene expression values obtained by RT-PCR and the gene expression values obtained by microarray is presented for three of the genes listed in Table 30, IL18R1, FCGR1A, and MMP9. In this comparison, static expression data from both assays (RT-PCR and microarray) for all time points measured in the subject were correlated to obtain a correlation coefficient. The correlations were computed within 'R', a public domain statistical computing language (http://www.r-project.org/, which is hereby incorporated by reference), using the following code:

```
corCalc <- function(x,y){
    n <- length(x)
    ## if there are any missing values in the data
    if(any(is.na(x)) || any(is.na(y))){
        ## index where missing values occur
        rm.idx <- which(is.na(x))
        rm.idx <- c(rm.idx, which(is.na(y)))
        ## remove missing values
        x <- x[-rm.idx]
        y <- y[-rm.idx]
        ## update length
        n <- length(x)
    }
    R <- (n*sum(x*y)-sum(x)*sum(y))/(sqrt((n*sum(x^2)-
    (sum(x))^2)*(n*sum(y^2) - (sum(y))^2)))
    return(R)
}
```

FIG. 31 shows the correlation between IL18R1 expression, as determined by RT-PCR, and the intensity of the X206618_at probeset, as determined using the techniques described in Section 6.2, using all available time points across the training population. Each point in FIG. 31 is the gene expression value for a given subject in the training population from the RT-PCR data and the microarray data. Substantial correlation between the RT-PCR and the microarray data was found. In particular, the overall correlation between expression of IL18R1 as determined by RT-PCR and microarray data for X206618_at was 0.85.

FIG. 32 shows the correlation between FCGR1A expression, as determined by RT-PCR, and the intensity of the X214511_x_at, X216950_s_at and X216951_at probesets, as determined using the techniques described in Section 6.2, using all available time points in the training population. Each point in FIG. 32 is the gene expression value for a given subject in the training population from the RT-PCR data and the microarray data. As is evident in FIG. 32, the overall correlation between expression of FCGR1A and each of the two FCGR1A probesets that are found in Table 30, X214511_x_at and X216950_s_at, was significant. In particular the correlation coefficient between FCGR1A and X214511_x_at was 0.88. Likewise, the correlation coefficient between and FCGR1A and X216950_s_at was 0.88. The overall correlation between expression of FCGR1A and the FCGR1A probeset not found in Table 30, X216951_at, was 0.53, which was not as significant as the other two probesets.

FIG. 33 shows the correlation between MMP9 expression, as determined by RT-PCR, and the intensity of the X203936_s_at probeset, as determined using the techniques described in Section 6.2, using all available time points in the training population. Each point in FIG. 32 is the gene expression value for a given subject in the study from the RT-PCR data and the microarray data. Substantial correlation between the RT-PCR and the microarray data was found. In particular, the overall correlation between expression of MMP9 as determined by RT-PCR and microarray data for X203936_s_at was 0.87.

FIG. 34 shows the correlation between CD86 expression, as determined by RT-PCR, and the intensity of the X205685_at, X205686_s_at, and X210895_s_at probesets, as determined using the techniques described in Section 6.2, using all available time points. Each point in FIG. 34 is the gene expression value for a given subject in the study from the RT-PCR data and the microarray data. As is evident in FIG. 34, the overall correlation between expression of CD86 and CD86 probeset that is found in Table 30, 210895_s_at, was significant (correlation coefficient of 0.71). The overall correlation between expression of CD86 and the probesets not found in Table 30, X205685_at, X205686_s_at, was not as significant (correlation coefficient of 0.66 and 0.56, respectively).

In one embodiment, a biomarker profile of the present invention comprises a plurality of biomarkers selected from Table 30, including at least one sequence of a probeset in the set of:
{X206618_at, X214511_x_at, X216950_s_at, X203936_s_at, and 210895_s_at}
or complements thereof, or genes including the sequence or a complement of the sequence thereof, or a discriminating fragment thereof, or an amino acid sequence encoded by any of the foregoing nucleic acid sequences, or any discriminating fragment of such an amino acid sequence. Such biomarkers can be, for example, mRNA transcripts, cDNA or some other nucleic acid, for example, amplified nucleic acid or proteins. In one embodiment, a biomarker profile the of the present invention comprises a nucleic acid that codes for TGFB1, IL18R1, or FCGR1A, a discriminating portion of TGFB1, IL18R1, or FCGR1A, complements of such nucleic acids, proteins encoded by such nucleic acids, or antibodies that selectively bind to any of the foregoing.

6.11 Discovery of Select Nucleic Acid Biomarkers

The experiments described above identified a number of biomarkers that discriminate between sepsis and SIRS. In this example, a discovery process was performed in order to confirm which biomarkers differentiate between patients who subsequently develop sepsis ("sepsis patients") and patients who do not ("SIRS patients"). In the discovery process, samples from SIRS patients and sepsis patients taken at: (i) date of entry, (ii) $T_{-60}$, (iii) $T_{-36}$, and (iv) $T_{-12}$ data points were studied by RT-PCR, as described in Section 6.11.1 and by Affymetrix gene chip analysis, as described in Section 6.11.2.

6.11.1 RT-PCR Analysis

Biomarkers in multiple samples were measured by RT-PCR at multiple time points and analyzed in several different ways: static time of entry, static $T_{-60}$, static $T_{-36}$, baseline $T_{-60}$, baseline $T_{-36}$, and baseline $T_{-12}$ data points. RT-PCR is described in Section 5.4.1.2, and 6.10, above. Representative of these analyses is the static $T_{-12}$ data analysis which is described in detail below. In the $T_{-12}$ static analysis, biomarkers features were measured using a specific blood sample, designated the $T_{-12}$ blood sample, as defined in Section 6.4, above.

For the $T_{-12}$ static analysis, there were 72 biomarkers measured on 96 samples. Each sample was collected from a different member the population. Of these features, 15 were transformed by log transformations, 5 by square root transformations and the remaining 52 were not transformed.

The 96 member population was initially split into a training set (n=73) and a validation set (n=23). The training set was used to estimate the appropriate classification algorithm parameters while the trained algorithm was applied to the validation set to independently assess performance. Of the 73 training samples, 36 were labeled Sepsis, meaning that the subjects developed sepsis at some point during the observation time period, and 37 were SIRS, meaning that they did not develop sepsis during the observation time period. Table 37 provides distributions of the race, gender and age for these samples.

TABLE 37

Distributions of the race, gender, and age for the training data

| Group | Gender | Black | Caucasian | Other |
|---|---|---|---|---|
| Sepsis | Male | 10 | 14 | 1 |
|  | Female | 0 | 10 | 1 |
| SIRS | Male | 5 | 22 | 0 |
|  | Female | 0 | 10 | 0 |

| Group | Minimum | Mean | Median | Maximum |
|---|---|---|---|---|
| Sepsis | 18 | 43.2 | 40 | 80 |
| SIRS | 18 | 44.6 | 40 | 90 |

For the 23 validation samples, 12 were labeled Sepsis and 11 were labeled SIRS. Table 38 provides distributions of the race, gender and age for these samples.

TABLE 38

Distributions of the race, gender, and age for the validation data

| Group | Gender | Black | Caucasian | Other |
|---|---|---|---|---|
| Sepsis | Male | 0 | 7 | 0 |
|  | Female | 0 | 4 | 0 |
| SIRS | Male | 2 | 6 | 0 |
|  | Female | 0 | 4 | 0 |

| Group | Minimum | Mean | Median | Maximum |
|---|---|---|---|---|
| Sepsis | 18 | 43.4 | 43 | 81 |
| SIRS | 19 | 51.9 | 51.5 | 85 |

Each sample in the training data was randomly assigned to one of ten groups used for cross-validation. The number of training samples in these groups ranged from 6 to 8. The samples were assigned in way that attempted to balance the number of sepsis and SIRS samples across folds. As described in more detail below, several different methods were used to judge whether select biomarkers discriminate between the Sepsis and SIRS groups.

Wilcoxon and Q-Value Tests.

The first method used to identify discriminating biomarkers was a Wilcoxon test (unadjusted). The abundance value for a given biomarker across the samples in the training data was subjected to the Wilcoxon test. The Wilcoxon test considers both group classification (sepsis versus SIRS) and abundance value in order to compute a p value for the given biomarker. The p value provides an indication of how well the abundance value for the given biomarker across the samples collected in the training set discriminates between the sepsis and SIRS state. The lower the p value, the better the discrimination. When the p value is less than a specific confidence level, such as 0.05, an inference is made that the biomarker discriminates between the sepsis and SIRS phenotype. There were 33 significant biomarkers using this method (see Table 39).

The second method used to identify discriminating biomarkers was the Wilcoxon Test (adjusted). Due to the large number of biomarkers, 72, and the relatively small number of samples, 96, there was a high risk of finding falsely significant biomarkers. An adjusted p-value was used to counter this risk. In particular, the method of Benjamini and Hochberg, 1995, J. R. Statist. Soc. B 57, pp 289-300, which is hereby incorporated herein by reference in its entirety, was used to control the false discovery rate. Here, the false discovery rate is defined as the number of biomarkers truly significant divided by the number of biomarkers declared significant. For example, if the adjusted p-value is less than 0.05, there is a 5% chance that the biomarker is a false discovery. Results using this test are reported in Table 39. There were 11851 significant biomarkers using this method (see Table 39). As used, herein, a biomarker is considered significant if it has a p-value of less than 0.05 as determined by the Wilcoxon test (adjusted).

The third method used to identify discriminating biomarkers was the use of Q values. In such an approach, the biomarkers are ordered by their q-values and if a respective biomarker has a Q value of X, then respective biomarker and all others more significant have a combined false discovery rate of X. However, the false discovery rate for any one biomarker may be much larger. There were 27 significant biomarkers using this method (see Table 39).

TABLE 39

Cumulative number of significant calls for the three methods.
Note that all samples (training and validation)
were used to compare Sepsis and SIRS groups. Missing
biomarker feature values were not included in the analyses.

|  | ≤1e−04 | ≤0.001 | ≤0.01 | ≤0.025 | ≤0.05 | ≤0.1 | ≤1 |
|---|---|---|---|---|---|---|---|
| p-value (unadjusted) | 0 | 22 | 25 | 29 | 33 | 38 | 72 |
| p-value (adjusted) | 0 | 16 | 25 | 25 | 27 | 33 | 72 |
| q-value | 0 | 0 | 28 | 38 | 47 | 59 | 72 |

CART.

In addition to analyzing the microarray data using Wilcoxon and Q-value tests in order to identify biomarkers that discriminate between the sepsis and SIRS subpopulations in the training set, classification and regression tree (CART) analysis was used. CART is described in Section 5.5.1, above. Specifically, the data summarized above was used to predict the disease state by iteratively partitioning the data based on the best single-variable split of the data. In other words, at each stage of the tree building process, the biomarker whose expression values across the training population best discriminate between the sepsis and SIRS population was invoked as a decision branch. Cross-validation was carried out, with the optimal number of splits estimated independently in each of the 10 iterations. The final tree is depicted in FIG. 36, and uses seven biomarkers: TNFSF13B, FCGR1A, HMOX1, MMP9, APAF1, APAF1.1, and CCL3.

FIG. 37 shows the distribution of the seven biomarkers used in the decision tree between the sepsis and SIRS groups in the training data set. In FIG. 37, the top of each box denotes the $75^{th}$ percentile of the data across the training set and the bottom of each box denotes the $25^{th}$ percentile, and the median value for each biomarker across the training set is drawn as a line within each box. The confusion matrix for the training data where the predicted classifications were made from the cross-validated model is given in Table 40. From this confusion matrix, the overall accuracy was estimated to be 68.5% with a 95% confidence interval of 56.6% to 78.9%. The estimated sensitivity was 72.2% and the estimated specificity was 64.9%.

TABLE 40

Confusion matrix for training samples using the cross-validated CART algorithm of FIG. 36

|  | True Diagnosis | |
|---|---|---|
| Predicted | Sepsis | SIRS |
| Sepsis | 26 | 13 |
| SIRS | 10 | 24 |

For the 23 validation samples held back from training data set, the overall accuracy was estimated to be 78.3% with a 95% confidence interval of 56.3% to 92.5%, sensitivity 66.7% and specificity 90.9%. Table 41 shows the confusion matrix for the validation samples.

TABLE 41

Confusion matrix for validation samples using the cross-validated CART algorithm

|  | True Diagnosis | |
|---|---|---|
| Predicted | Sepsis | SIRS |
| Sepsis | 8 | 1 |
| SIRS | 4 | 10 |

Random Forests.

Another decision rule that can be developed using biomarkers of the present invention is a Random Forests decision tree. Random Forests is a tree based method that uses bootstrapping instead of cross-validation. For each iteration, a random sample (with replacement) is drawn and the largest tree possible is grown. Each tree receives a vote in the final class prediction. To fit a random forest, the number of trees (e.g. bootstrap iterations) is specified. No more than 500 were used in this example, but at least 50 are needed for a burn-in period. The number of trees was chosen based on the accuracy of the training data. For this data, 462 trees were used to train the algorithm (see FIG. 38). In FIG. 38, curve 3202 is a smoothed estimate of overall accuracy as a function of tree number. Curve 3804 is a smoothed curve of tree sensitivity as a function of tree number. Curve 3806 is a smoothed curve of tree specificity as a function of tree number. Using this algorithm, 49 biomarkers had non-zero importance and were used in the model. The random forest algorithm gauges biomarker importance by the average reduction in the training accuracy. The biomarkers were ranked by this method and are shown in FIG. 39. The random forest method uses a number of different decision trees. A biomarker is considered to have discriminating significance if it served as a decision branch of a decision tree from a significant random forest analysis. As used herein, a significant random forest analysis is one where the lower 95% confidence interval on accuracy by cross validation on a training data set is greater than 50% and the point estimate for accuracy on a validation set is greater than 65%.

The predicted confusion matrix for the training dataset using the decision tree developed using the Random Forest method is given in Table 42. From this confusion matrix, the overall accuracy was estimated to be 76.7% (confidence intervals cannot be computed when using the bootstrap accuracy estimate). The estimated sensitivity was 77.8% and the estimated specificity was 75.7%.

TABLE 42

Confusion matrix for training samples against the decision tree developed using the Random Forest method.

|  | True Diagnosis | |
|---|---|---|
| Predicted | Sepsis | SIRS |
| Sepsis | 28 | 8 |
| SIRS | 9 | 28 |

For the 23 validation samples held back from training, the overall accuracy was estimated to be 78.3% with a 95% confidence interval of 56.3% to 92.5%, sensitivity 75% and specificity 81.8%. Table 43 shows the confusion matrix for the validation samples.

TABLE 43

Confusion matrix for the validation samples against the decision tree developed using the Random Forest method.

|  | True Diagnosis | |
|---|---|---|
| Predicted | Sepsis | SIRS |
| Sepsis | 9 | 2 |
| SIRS | 3 | 9 |

MART.

Multiple Additive Regression Trees (MART), also known as "gradient boosting machines," was used to simultaneously assess the importance of biomarkers and classify the subject samples. Several fitting parameters are specified in this approach including (i) number of trees, (ii) step size (commonly referred to as "shrinkage"), and (iii) degree of interaction (related to the number of splits for each tree). More information on MART is described in Section 5.5.4 above. The degree of interaction was set to 1 to enforce an additive model (e.g. each tree has one split and only uses one biomarker).

Estimating interactions may require more data to function well. The step size was set to 0.05 so that the model complexity was dictated by the number of trees. The optimal number of trees was estimated by leaving out a random subset of cases at each fitting iteration, then assessing quality of prediction on that subset. After fitting more trees than were warranted, the point at which prediction performance stopped improving was estimated as the optimal point.

The estimated model used 15 trees and 6 biomarkers across all trees. The MART algorithm also provides a calculation of biomarker importance (summing to 100%), which are given in FIG. 40. Biomarkers with zero importance were excluded. FIG. 41 shows the distribution of the selected biomarkers between the Sepsis and SIRS groups.

Cross-validation was carried out, with the optimal number of trees estimated independently in each of the 10 iterations. The confusion matrix for the training data where the predicted classifications were made from the cross-validated model is given in Table 44. From this confusion matrix, the overall accuracy was estimated to be 75.3% with a 95% confidence interval of 63.9% to 84.7%. The estimated sensitivity was 72.2% and the estimated specificity was 78.4%.

TABLE 44

Confusion matrix for the training samples using the cross-validated MART algorithm.

|  | True Diagnosis | |
|---|---|---|
| Predicted | Sepsis | SIRS |
| Sepsis | 26 | 8 |
| SIRS | 10 | 29 |

For the 23 validation samples held back from training, the overall accuracy was estimated to be 78.3% with a 95% confidence interval of 56.3% to 92.5%, sensitivity 81.8% and specificity 75%. Table 45 shows the confusion matrix for the validation samples.

TABLE 45

Confusion matrix for the validation samples using the MART algorithm.

|  | True Diagnosis | |
|---|---|---|
| Predicted | Sepsis | SIRS |
| Sepsis | 9 | 3 |
| SIRS | 2 | 9 |

PAM.

Yet another decision rule developed using biomarkers of the present invention is predictive analysis of microarrays (PAM), which is described in Section 5.5.2, above. In this method, a shrinkage parameter that determines the number of biomarkers used to classify samples is specified. This parameter was chosen via cross-validation. There were no biomarkers with missing values. Based on cross-validation, the optimal threshold value was 2.12, corresponding to 5 biomarkers. FIG. 42 shows the accuracy across different thresholds. In FIG. 42, curve 4202 is the overall accuracy (with 95% confidence interval bars). Curve 4204 shows decision rule sensitivity as a function of threshold value. Curve 4206 shows decision rule specificity as a function of threshold value. Using the threshold of 2.12, the overall accuracy for the training samples was estimated to be 80.8% with a 95% confidence interval of 70.9% to 87.9%. The estimated sensitivity was 89.2% and the estimated specificity was 72.2%. Table 46 shows the confusion matrix for the training data where the predicted classifications were made from the cross-validated models.

TABLE 46

Confusion matrix for training samples using cross-validated PAM algorithm

| Predicted | True Diagnosis | |
|---|---|---|
| | Sepsis | SIRS |
| Sepsis | 33 | 10 |
| SIRS | 4 | 26 |

For the 23 validation samples held back from training, the overall accuracy was estimated to be 82.6% with a 95% confidence interval of 61.2% to 95%, sensitivity 91.7% and specificity 72.7%. Table 47 shows the confusion matrix for the validation samples.

TABLE 47

Confusion matrix for validation samples using cross-validated PAM algorithm

| Predicted | True Diagnosis | |
|---|---|---|
| | Sepsis | SIRS |
| Sepsis | 11 | 3 |
| SIRS | 1 | 8 |

FIG. 43 shows the selected biomarkers, ranked by their relative discriminatory power, and their relative importance in the model.

FIG. 44 provides a summary of the CART, MART, PAM, and random forests (RF) classification algorithm (decision rule) performance and associated 95% confidence intervals. Fifty distinct biomarkers were selected from across all the algorithms illustrated in FIG. 44. The identity of these fifty selected features is found in FIG. 45, which further illustrates an overall ranking of these biomarkers for the $T_{-12}$ data set. For the selected biomarkers, the x-axis depicts the percentage of times that it was selected. Within the percentage of times that biomarkers were selected, the biomarkers are ranked.

From the analysis of the $T_{-12}$ data set and the other data sets, biomarkers were ranked according to how often they were included in the CART, MART, PAM, random forests. The results of this ranking is summarized in Table 48 below:

TABLE 48

Top ranked biomarkers as determined by RT-PCR

| Gene symbol | Gene Name | Gene Accession Number | Protein Accession Number | $T_{-12}$ Hours | $T_{-36}$ Hours |
|---|---|---|---|---|---|
| FCGR1A | FC FRAGMENT OF IGG, HIGH AFFINITY IA | NM_000566 | NP_000557 | 1 | 1 |
| MMP9 | MATRIX METALLOPROTEINASE 9 (GELATINASE B, 92 KDA GELATINASE, 92 KDA TYPE IV COLLAGENASE) | NM_004994 | NP_004985 | 2 | 5 |
| IL18R1 | INTERLEUKIN 18 RECEPTOR 1 | NM_003855 | NP_003846 | 3 | 2 |
| ARG2 | ARGINASE TYPE II | NM_001172 | CAG38787 | 4 | 3 |
| IL1RN | INTERLEUKIN-1 RECEPTOR ANTAGONIST GENE | NM_000577, NM_173841, NM_173842, NM_173843 | AAN87150 | 4 | 4 |
| TNFSF13B | TUMOR NECROSIS FACTOR (LIGAND) SUPERFAMILY, MEMBER 13B | NM_006573 | NP_006564 | 4 | 5 |
| ITGAM | INTEGRIN, ALPHA M (COMPLEMENT COMPONENT RECEPTOR 3, ALPHA; ALSO KNOWN AS CD11B (P170), MACROPHAGE ANTIGEN ALPHA POLYPEPTIDE) | NM_000632 | NP_000623 | 5 | 7 |
| CD4 | CD4 ANTIGEN (P55) | NM_000616 | NP_000607 | 6 | 7 |
| TGFBI | TRANSFORMING GROWTH FACTOR, BETA-1 (TRANSFORMING GROWTH FACTOR, BETA-INDUCED, 68 KDA) | NM_000358 | NP_000349 | 6 | 9 |
| CD86 | CD86 ANTIGEN (CD28 ANTIGEN LIGAND 2, B7-2 ANTIGEN) | NM_006889, NM_175862 | NP_008820, NP_787058 | 6 | 6 |
| TLR4 | TOLL-LIKE RECEPTOR 4 | AH009665 | AAF05316 | 6 | 6 |
| IFI16 | INTERFRON, GAMMA-INDUCIBLE PROTEIN 16 | NM_005531 | AAH17059 | 6 | 9 |
| ICAM1 | INTERCELLULAR ADHESION MOLECULE 1 | NM_010493 | NP_000192, AAQ14902, AAQ14901 | 6 | 10 |

TABLE 48-continued

Top ranked biomarkers as determined by RT-PCR

| Gene symbol | Gene Name | Gene Accession Number | Protein Accession Number | $T_{-12}$ Hours | $T_{-36}$ Hours |
|---|---|---|---|---|---|
| TGFBR2 | TRANSFORMING GROWTH FACTOR, BETA RECEPTOR II | NM_003242 | AAF27281 | 6 | 8 |
| PLA2G7 | PLATELET-ACTIVATING FACTOR ACETYLHYDROLASE | NM_005084 | CAH73907 | 7 | 6 |
| IL-10 | INTERLEUKIN 10 | NM_000572 | CAH73907 | 8 | 7 |

As Table 48 indicates, in general, important biomarkers at $T_{-12}$ were also important biomarkers at earlier time points. The ten biomarkers that are italicized in Table 48 were carried forward to confirmation as described in Section 6.12.1, below. CD4 was excluded in this embodiment because it was found to be different on day of entry.

6.11.2 Discovery Affymetrix Gene Chip Analysis

The patients were also analyzed using Affymetrix gene chip analysis. Such an analysis is described in Section 6.2 Biomarkers in multiple samples were measured by Affymetrix gene chip analysis at multiple time points and analyzed in several different ways: static time of entry, static $T_{-60}$, static $T_{-36}$, baseline $T_{-60}$, baseline $T_{-36}$, and baseline $T_{-12}$ data points. The Affymetrix gene chip assay is described in Section 6.2, above. Representative of these analyses is the static $T_{-12}$ data analysis described in detail below. In the $T_{-12}$ static analysis, biomarkers features were measured using a specific blood sample, designated the $T_{-12}$ blood sample, as defined in Section 6.4, above.

For the $T_{-12}$ static analysis, there were 54,613 biomarkers measured on 90 samples. Each sample was collected from a different member the population. Of these features, 31,047 were transformed by log transformations, 2518 by square root transformations and the remaining 21,048 were not transformed.

The 90 member population was initially split into a training set (n=69) and a validation set (n=21). The training set was used to estimate the appropriate classification algorithm parameters while the trained algorithm was applied to the validation set to independently assess performance. Of the 69 training samples, 34 were labeled Sepsis, meaning that the subjects developed sepsis at some point during the observation time period, and 35 were SIRS, meaning that they did not develop sepsis during the observation time period. Table 49 provides distributions of the race, gender and age for these samples.

TABLE 49

Distributions of the race, gender, and age for the training data

| Group | Gender | Black | Caucasian | Other |
|---|---|---|---|---|
| Sepsis | Male | 9 | 13 | 1 |
| | Female | 0 | 10 | 1 |
| SIRS | Male | 5 | 20 | 0 |
| | Female | 0 | 10 | 0 |

| Group | Minimum | Mean | Median | Maximum |
|---|---|---|---|---|
| Sepsis | 18 | 44.1 | 39 | 80 |
| SIRS | 18 | 44.1 | 40 | 90 |

For the 21 validation samples, 11 were labeled Sepsis and 10 were labeled SIRS. Table 50 provides distributions of the race, gender and age for these samples.

TABLE 50

Distributions of the race, gender, and age for the validation data

| Group | Gender | Black | Caucasian | Other |
|---|---|---|---|---|
| Sepsis | Male | 0 | 7 | 0 |
| | Female | 0 | 3 | 0 |
| SIRS | Male | 2 | 6 | 0 |
| | Female | 0 | 3 | 0 |

| Group | Minimum | Mean | Median | Maximum |
|---|---|---|---|---|
| Sepsis | 18 | 43.4 | 40 | 81 |
| SIRS | 19 | 53 | 52 | 85 |

Each sample in the training data was randomly assigned to one of ten groups used for cross-validation. The number of training samples in these groups ranged from 6 to 8. The samples were assigned in way that attempted to balance the number of sepsis and SIRS samples across folds. As described in more detail below, several different methods were used to judge whether select biomarkers discriminate between the Sepsis and SIRS groups.

Wilcoxon and Q-Value Tests.

The first method used to identify discriminating biomarkers was a Wilcoxon test (unadjusted). The abundance value for a given biomarker across the samples in the training data was subjected to the Wilcoxon test. The Wilcoxon test considers both group classification (sepsis versus SIRS) and abundance value in order to compute a p value for the given biomarker. The p value provides an indication of how well the abundance value for the given biomarker across the samples collected in the training set discriminates between the sepsis and SIRS state. The lower the p value, the better the discrimination. When the p value is less than a specific confidence level, such as 0.05, an inference is made that the biomarker discriminates between the sepsis and SIRS phenotype. There were 19791 significant biomarkers using this method (see Table 51).

The second method used to identify discriminating biomarkers was the Wilcoxon Test (adjusted). Due to the large number of biomarkers, 54613, and the relatively small number of samples, 90, there was a high risk of finding falsely significant biomarkers. An adjusted p-value was used to counter this risk. In particular, the method of Benjamini and Hochberg, 1995, J. R. Statist. Soc. B 57, pp 289-300, which is hereby incorporated herein by reference in its entirety, was used to control the false discovery rate. Here, the false discovery rate is defined as the number of biomarkers truly significant divided by the number of biomarkers declared significant. For example, if the adjusted p value is less than 0.05, there is a 5% chance that the biomarker is a false discovery. Results using this test are reported in Table 51. There were 11851 significant biomarkers using this method (see Table 51). As used, herein, a biomarker is considered significant if it has a p-value of less than 0.05 as determined by the Wilcoxon test (adjusted).

The third method used to identify discriminating biomarkers was the use of Q values. In such an approach, the biomarkers are ordered by their q-values and if a respective biomarker has a Q value of X, then respective biomarker and all others more significant have a combined false discovery rate of X. However, the false discovery rate for any one biomarker may be much larger. There were 11581 significant biomarkers using this method (see Table 51).

TABLE 51

Cumulative number of significant calls for the three methods.
Note that all 96 samples (training and validation)
were used to compare Sepsis and SIRS groups. Missing
biomarker feature values were not included in the analyses.

|  | ≤1e−04 | ≤0.001 | ≤0.01 | ≤0.025 | ≤0.05 | ≤0.1 | ≤1 |
|---|---|---|---|---|---|---|---|
| p-value (unadjusted) | 0 | 5417 | 11537 | 15769 | 19791 | 24809 | 54613 |
| p-value (adjusted) | 0 | 0 | 5043 | 8374 | 11851 | 16973 | 54613 |
| q-value | 0 | 0 | 7734 | 12478 | 17820 | 24890 | 54613 |

CART.

In addition to analyzing the microarray data using Wilcoxon and Q-value tests in order to identify biomarkers that discriminate between the sepsis and SIRS subpopulations in the training set, classification and regression tree (CART) analysis was used. CART is described in Section 5.5.1, above. Specifically, the data summarized above was used to predict the disease state by iteratively partitioning the data based on the best single-variable split of the data. In other words, at each stage of the tree building process, the biomarker whose expression values across the training population best discriminate between the sepsis and SIRS population was invoked as a decision branch. Cross-validation was carried out, with the optimal number of splits estimated independently in each of the 10 iterations. The final tree uses four probesets: X214681_at, X230281_at, X1007_s_at, and X1560432_at, where each given probeset is the U133 plus 2.0 Affymetrix probe set name. The confusion matrix for the training data, based on the final tree from the cross-validated CART algorithm is given in Table 52. From this confusion matrix, the overall accuracy was estimated to be 65.2% with a 95% confidence interval of 52.8% to 76.3%. The estimated sensitivity was 61.8% and the estimated specificity was 68.6%.

TABLE 52

Confusion matrix for training samples using the cross-validated
CART algorithm

|  | True Diagnosis | |
|---|---|---|
| Predicted | Sepsis | SIRS |
| Sepsis | 21 | 11 |
| SIRS | 13 | 24 |

For the 21 validation samples held back from training data set, the overall accuracy was estimated to be 71.4% with a 95% confidence interval of 47.8% to 88.7%, sensitivity 90.9% and specificity 50%. The confusion matrix for the validation samples was predicted Sepsis/true Sepsis 10, predicted SIRS/true Sepis 1, predicted Sepsis/true SIRS 5, predicted SIRS/true SIRS 5.

Random Forests.

Another decision rule that can be developed using biomarkers of the present invention is a Random Forests decision tree. Random Forests is a tree based method that uses bootstrapping instead of cross-validation. For each iteration, a random sample (with replacement) is drawn and the largest tree possible is grown. Each tree receives a vote in the final class prediction. To fit a random forest, the number of trees (e.g. bootstrap iterations) is specified. No more than 500 were used in this example, but at least 50 are needed for a burn-in period. The number of trees was chosen based on the accuracy of the training data. For this data, 439 trees were used to train the algorithm. Using this algorithm, 845 biomarkers had non-zero importance and were used in the model. The random forest algorithm gauges biomarker importance by the average reduction in the training accuracy.

The random forest method uses a number of different decision trees. A biomarker is considered to have discriminating significance if it served as a decision branch of a decision tree from a significant random forest analysis. As used herein, a significant random forest analysis is one where the lower 95% confidence interval on accuracy by cross validation on a training data set is greater than 50% and the point estimate for accuracy on a validation set is greater than 65%.

The predicted confusion matrix for the training dataset using the decision tree developed using the Random Forest method is given in Table 53. From this confusion matrix, the overall accuracy was estimated to be 75.4% (confidence intervals cannot be computed when using the bootstrap accuracy estimate). The estimated sensitivity was 73.5% and the estimated specificity was 77.1%.

TABLE 53

Confusion matrix for training samples against the decision tree
developed using the Random Forest method.

|  | True Diagnosis | |
|---|---|---|
| Predicted | Sepsis | SIRS |
| Sepsis | 27 | 9 |
| SIRS | 8 | 25 |

For the 21 validation samples held back from training, the overall accuracy was estimated to be 76.2% with a 95% confidence interval of 76.2% to 99.9%, sensitivity 100% and specificity 90%. Table 54 shows the confusion matrix for the validation samples.

TABLE 54

Confusion matrix for the validation samples against the decision
tree developed using the Random Forest method.

|  | True Diagnosis | |
|---|---|---|
| Predicted | Sepsis | SIRS |
| Sepsis | 11 | 1 |
| SIRS | 0 | 9 |

MART.

Multiple Additive Regression Trees (MART), also known as "gradient boosting machines," was used to simultaneously assess the importance of biomarkers and classify the subject samples. Several fitting parameters are specified in this approach including (i) number of trees, (ii) step size (commonly referred to as "shrinkage"), and (iii) degree of interaction (related to the number of splits for each tree). More information on MART is described in Section 5.5.4 above. The degree of interaction was set to 1 to enforce an additive model (e.g. each tree has one split and only uses one biomarker).

Estimating interactions may require more data to function well. The step size was set to 0.05 so that the model complexity was dictated by the number of trees. The optimal number of trees was estimated by leaving out a random subset of cases at each fitting iteration, then assessing quality of prediction on that subset. After fitting more trees than were warranted, the point at which prediction performance stopped improving was estimated as the optimal point.

The estimated model used 28 trees and 17 biomarkers across all trees. The MART algorithm also provides a calculation of biomarker importance (summing to 100%). Biomarkers ranked in decreasing order of importance to the model, with the most important biomarker first were: X206513_at, X214681_at, X235359_at, X221850_x_at, X213524_s_at, X225656_a, X200881_s_at, X229743_at, X215178_x_at, X215178_x_at, X216841_s_at, X216841_at, X244158_at, X238858_at, X205287_s_at, X233651_s_at, X229572_at, X214765_s_at.

Cross-validation was carried out, with the optimal number of trees estimated independently in each of the 10 iterations. The confusion matrix for the training data where the predicted classifications were made from the cross-validated model is given in Table 55. From this confusion matrix, the overall accuracy was estimated to be 76.8% with a 95% confidence interval of 65.1% to 86.1%. The estimated sensitivity was 76.5% and the estimated specificity was 77.1%.

TABLE 55

Confusion matrix for the training samples using the cross-validated MART algorithm.

| Predicted | True Diagnosis | |
| --- | --- | --- |
| | Sepsis | SIRS |
| Sepsis | 26 | 8 |
| SIRS | 8 | 27 |

For the 21 validation samples held back from training, the overall accuracy was estimated to be 85.7% with a 95% confidence interval of 63.7% to 97%, sensitivity 80% and specificity 90.9%. Table 56 shows the confusion matrix for the validation samples.

TABLE 56

Confusion matrix for the validation samples using the MART algorithm.

| Predicted | True Diagnosis | |
| --- | --- | --- |
| | Sepsis | SIRS |
| Sepsis | 8 | 1 |
| SIRS | 2 | 10 |

PAM.

Yet another decision rule developed using biomarkers of the present invention is predictive analysis of microarrays (PAM), which is described in Section 5.5.2, above. In this method, a shrinkage parameter that determines the number of biomarkers used to classify samples is specified. This parameter was chosen via cross-validation. There were no biomarkers with missing values. Based on cross-validation, the optimal threshold value was 2.1, corresponding to 820 biomarkers.

Using the threshold of 2.1, the overall accuracy for the training samples was estimated to be 80.9% with a 95% confidence interval of 73.4% to 86.7%. The estimated sensitivity was 85.7% and the estimated specificity was 76.5%. Table 57 shows the confusion matrix for the training data where the predicted classifications were made from the cross-validated models.

TABLE 57

Confusion matrix for training samples using cross-validated PAM algorithm

| Predicted | True Diagnosis | |
| --- | --- | --- |
| | Sepsis | SIRS |
| Sepsis | 11 | 1 |
| SIRS | 0 | 9 |

For the 21 validation samples held back from training, the overall accuracy was estimated to be 95.2% with a 95% confidence interval of 76.2% to 99.9%, sensitivity 100% and specificity 90%. Table 58 shows the confusion matrix for the validation samples.

TABLE 58

Confusion matrix for validation samples using cross-validated PAM algorithm

| Predicted | True Diagnosis | |
| --- | --- | --- |
| | Sepsis | SIRS |
| Sepsis | 11 | 1 |
| SIRS | 0 | 9 |

The top ten biomarkers identified by PAM, ranked from most important to least important were: X206513_at, X213524_s_at, X200881_s_at, X218992_at, X238858_at, X221123_x_at, X228402_at, X230585_at, X209304_x_at, X214681_at.

FIG. 46 provides a summary of the CART, MART, PAM, and random forests (RF) classification algorithm (decision rule) performance and associated 95% confidence intervals using $T_{-12}$ static data obtained from an Affymetrix gene chip discovery training population. Fifty distinct biomarkers were selected from across all the algorithms illustrated in FIG. 46. The identity of the top 50 biomarkers, ranked from most to least significant is: X204102_s_at, X236013_at, X213668_s_at, X1556639_at, X218220_at, X207860_at, X232422_at, X218578_at, X205875_s_at, X226043_at, X225879_at, X224618_at, X216316_x_at, X243159_x_at, X202200_s_at, X201936_s_at, X242492_at, X216609_at, X214328_s_at, X228648_at, X223797_at, X225622_at, X205988_at, X201978_s_at, X200874_s_at, X210105_s_at, X203913_s_at, X204225_at, X227587_at, X220865_s_at, X206682_at, X222664_at, X212264_s_at, X219669_at, X221971_x_at, X1554464_a_at, X242590_at, X227925_at, X221926_s_at, X202101_s_at, X211078_s_at, X44563_at, X206513_at, X215178_x_at, X235359_at, X225656_at, X244158_at, X214765_s_at, X229743_at, X214681.

From the analysis of the $T_{-12}$ data set and the other data sets, the 34 biomarkers indicated in Table 59 below were selected for confirmation. As indicated in Table 59, biomarkers were selected based on the Affymetrix gene chip analysis for one of three criteria, biological relevance (BR), high fold change (HF), or statistical importance (SI) in the Affymetrix gene chip analysis.

TABLE 59

Nucleic acid based biomarkers selected for confirmation from Affymetrix Assay

| Gene Symbol | Gene Name | Gene Accession Number | Protein Accession Number | Selection Criterion |
|---|---|---|---|---|
| BCL2A1 | BCL2-RELATED PROTEIN A1 | NM_004049 | NP_004040 | BR |
| CCL5 | CHEMOKINE (C-C MOTIF) LIGAND 5 | NM_002985 | NP_002976 | BR |
| CSF1R | COLONY STIMULATING FACTOR 1 RECEPTOR, FORMERLY MCDONOUGH FELINE SARCOMA VIRAL (V-FMS) ONCOGENE HOMOLOG | NM_005211 | NP_005202 | BR |
| GADD45A | GROWTH ARREST AND DNA-DAMAGE-INDUCIBLE, ALPHA | NM_001924 | NP_001915 | BR |
| GADD45B | GROWTH ARREST- AND DNA DAMAGE-INDUCIBLE GENE GADD45 | NM_015675 | NP_056490 | BR |
| IFNGR1 | INTERFERON GAMMA RECEPTOR 1 | NM_000416 | NP_000407 | BR |
| IL10RA | INTERLEUKIN 10 RECEPTOR, ALPHA | NM_001558 | NP_001549 | BR |
| IRAK2 | INTERLEUKIN-1 RECEPTOR-ASSOCIATED KINASE 2 | NM_001570 | NP_001561 | BR |
| IRAK4 | INTERLEUKIN-1 RECEPTOR-ASSOCIATED KINASE 4 | NM_016123 | NP_057207 | BR |
| JAK2 | JANUS KINASE 2 (A PROTEIN TYROSINE KINASE) | NM_004972 | NP_004963 | BR |
| LY96 | LYMPHOCYTE ANTIGEN 96 | NM_015364 | NP_056179 | BR |
| MAP2K6 | MITOGEN-ACTIVATED PROTEIN KINASE KINASE 6 | NM_002758 NM_031988 | NP_002749 NP_114365 | BR |
| MAPK14 | MAPK14 MITOGEN-ACTIVATED PROTEIN KINASE 14 | NM_001315 NM_139012 NM_139013 NM_139014 | NP_001306 NP_620581 NP_620582 NP_620583 | BR |
| MKNK1 | MAP KINASE INTERACTING SERINE/THREONINE KINASE 1 | NM_003684 NM_198973 | NP_003675 NP_945324 | BR |
| OSM | ONCOSTATIN M | NM_020530 | NP_065391 | BR |
| SOCS3 | SUPPRESSOR OF CYTOKINE SIGNALING 3 | NM_003955 | NP_003946 | BR |
| TDRD9 | TUDOR DOMAIN CONTAINING 9 | NM_153046 | NP_694591 | BR |
| TNFRSF6 | TUMOR NECROSIS FACTOR RECEPTOR SUPERFAMILY, MEMBER 6 | NM_152877 | NP_000034 | BR |
| TNFSF10 | TUMOR NECROSIS FACTOR (LIGAND) SUPERFAMILY, MEMBER 10 | NM_003810 | NP_003801 | BR |
| ANKRD22 | ANKYRIN REPEAT DOMAIN 22 | NM_144590 | NP_653191 | HF |
| ANXA3 | ANNEXIN A3 | NM_005139 | NP_005130 | HF |
| CEACAM1 | CARCINOEMBRYONIC ANTIGEN-RELATED CELL ADHESION MOLECULE 1 | NM_001712 | NP_001703 | HF |
| LDLR | LOW DENSITY LIPOPROTEIN RECEPTOR | NM_000527 | NP_000518 | HF |
| PFKFB3 | 6-PHOSPHOFRUCTO-2-KINASE/FRUCTOSE-2,6-BISPHOSPHATASE 3 | NM_004566 | NP_004557 | HF |

TABLE 59-continued

Nucleic acid based biomarkers selected for confirmation from Affymetrix Assay

| Gene Symbol | Gene Name | Gene Accession Number | Protein Accession Number | Selection Criterion |
|---|---|---|---|---|
| PRV1 | NEUTROPHIL-SPECIFIC ANTIGEN 1 (POLYCYTHEMIA RUBRA VERA 1) | NM_020406 | NP_065139 | HF |
| PSTPIP2 | PROLINE/SERINE/THREONINE PHOSPHATASE-INTERACTING PROTEIN 1 (PROLINE-SERINE-THREONINE PHOSPHATASE INTERACTING PROTEIN 2) | NM_024430 | NP_077748 | HF |
| TIFA | TRAF-INTERACTING PROTEIN WITH A FORKHEAD-ASSOCIATED DOMAIN | NM_052864 | NP_443096 | HF |
| VNN1 | VANIN 1 | NM_004666 | NP004657 | HF |
| NCR1 | NATURAL CYTOTOXICITY TRIGGERING RECEPTOR 1 | NM_004829 | NP_004820 | SI |
| FAD104 | FIBRONECTIN TYPE III DOMAIN CONTAINING 3B (FNDC3B) | NM_022763 | NP_073600 | SI |
| INSL3 | INSULIN-LIKE 3 (LEYDIG CELL) | NM_005543 | NP_005534 | SI |
| CRTAP | CARTILAGE-ASSOCIATED PROTEIN | NM_006371 | NP_006362 | SI |
| HLA-DRA | MAJOR HISTOCOMPATIBILITY COMPLEX, CLASS II, DR ALPHA | NM_002123 | NP_002114 | SI |
| SOD2 | SUPEROXIDE DISMUTASE 2, MITOCHONDRIAL | NM_000636 | NP_000627 | SI |

6.12 Confirmation of Select Nucleic Acid Biomarkers

In this example, a confirmatory process was performed in order to confirm which biomarkers differentiate between patients who subsequently develop sepsis ("sepsis patients") and patients who do not ("SIRS patients").

6.12.1 Confirmatory Analysis of Biomarkers Identified by RT-PCR

The biomarkers identified by italicizes in Table 48 of Section 6.11.1, namely FCGR1A, MMP9, IL18R1, ARG2, IL1RN, TNFSF13B, ITGAM, TGFBI, CD86, and TLR4, were analyzed using RT-PCR at multiple time points and analyzed in several different ways: static time of entry, static $T_{-60}$, static $T_{-36}$, baseline $T_{-60}$, baseline $T_{-36}$, and baseline $T_{-12}$ data points. RT-PCR is described in Section 5.4.1.2, above. Representative of these analyses is the static $T_{-12}$ data analysis described in detail below. In the $T_{-12}$ static analysis, biomarkers features were measured using a specific blood sample, designated the $T_{-12}$ blood sample, as defined in Section 6.4, above.

For the $T_{-12}$ static analysis, the biomarkers FCGR1A, MMP9, IL18R1, ARG2, IL1RN, TNFSF13B, ITGAM, TGFBI, CD86, and TLR4, were measured from 50 samples. Each sample was collected from a different member of the population. Of these biomarkers, seven were transformed by log transformations, and three by square root transformations.

The 50 member population was initially split into a training set (n=39) and a validation set (n=11). The training set was used to estimate the appropriate classification algorithm parameters while the trained algorithm was applied to the validation set to independently assess performance. Of the 50 training samples, 23 were labeled Sepsis, meaning that the subjects developed sepsis at some point during the observation time period, and 16 were SIRS, meaning that they did not develop sepsis during the observation time period. Table 60 provides distributions of the race, gender and age for these samples.

TABLE 60

Distributions of the race, gender, and age for the training data

| Group | Gender | Black | Caucasian | Other |
|---|---|---|---|---|
| Sepsis | Male | 3 | 13 | 0 |
|  | Female | 0 | 7 | 0 |
| SIRS | Male | 5 | 7 | 1 |
|  | Female | 0 | 2 | 0 |

| Group | Minimum | Mean | Median | Maximum |
|---|---|---|---|---|
| Sepsis | 20 | 52.3 | 56 | 80 |
| SIRS | 20 | 39.9 | 32.5 | 79 |

For the 11 validation samples, five were labeled Sepsis and six were labeled SIRS. Table 61 provides distributions of the race, gender and age for these samples.

TABLE 61

Distributions of the race, gender, and age for the validation data

| Group | Gender | Black | Caucasian | Other |
|---|---|---|---|---|
| Sepsis | Male | 2 | 1 | 0 |
| | Female | 0 | 3 | 0 |
| SIRS | Male | 0 | 3 | 0 |
| | Female | 0 | 2 | 0 |

| Group | Minimum | Mean | Median | Maximum |
|---|---|---|---|---|
| Sepsis | 18 | 51.7 | 59.5 | 76 |
| SIRS | 24 | 47.2 | 43 | 76 |

Each sample in the training data was randomly assigned to one of ten groups used for cross-validation. The number of training samples in these groups ranged from three to five. The samples were assigned in way that attempted to balance the number of sepsis and SIRS samples across folds. As described in more detail below, several different methods were used to judge whether select biomarkers discriminate between the Sepsis and SIRS groups.

Wilcoxon and Q-Value Tests.

The first method used to identify discriminating biomarkers was a Wilcoxon test (unadjusted). The abundance value for a given biomarker across the samples in the training data was subjected to the Wilcoxon test. The Wilcoxon test considers both group classification (sepsis versus SIRS) and abundance value in order to compute a p value for the given biomarker. The p value provides an indication of how well the abundance value for the given biomarker across the samples collected in the training set discriminates between the sepsis and SIRS state. The lower the p value, the better the discrimination. When the p value is less than a specific confidence level, such as 0.05, an inference is made that the biomarker discriminates between the sepsis and SIRS phenotype. There were nine significant biomarkers using this method (see Table 62).

The second method used to identify discriminating biomarkers was the Wilcoxon Test (adjusted). Due to the large number of biomarkers, 10, and the relatively small number of samples, 50, there was a high risk of finding falsely significant biomarkers. An adjusted p value was used to counter this risk. In particular, the method of Benjamini and Hochberg, 1995, J. R. Statist. Soc. B 57, pp 289-300, which is hereby incorporated herein by reference in its entirety, was used to control the false discovery rate. Here, the false discovery rate is defined as the number of biomarkers truly significant divided by the number of biomarkers declared significant. For example, if the adjusted p value is less than 0.05, there is a 5% chance that the biomarker is a false discovery. Results using this test are reported in Table 62. There were nine significant biomarkers using this method (see Table 62). As used, herein, a biomarker is considered significant if it has a p value of less than 0.05 as determined by the Wilcoxon test (adjusted).

The third method used to identify discriminating biomarkers was the use of Q values. In such an approach, the biomarkers are ordered by their Q values and if a respective biomarker has a Q value of X, then respective biomarker and all others more significant have a combined false discovery rate of X. However, the false discovery rate for any one biomarker may be much larger. There were nine significant biomarkers using this method (see Table 62).

TABLE 62

Cumulative number of significant calls for the three methods. Note that all samples (training and validation) were used to compare Sepsis and SIRS groups. Missing biomarker feature values were not included in the analyses.

| | ≤1e−04 | ≤0.001 | ≤0.01 | ≤0.025 | ≤0.05 | ≤0.1 | ≤1 |
|---|---|---|---|---|---|---|---|
| p-value (unadjusted) | 0 | 7 | 9 | 9 | 9 | 9 | 10 |
| p-value (adjusted) | 0 | 7 | 9 | 9 | 9 | 9 | 10 |
| q-value | 0 | 0 | 0 | 0 | 0 | 0 | 10 |

CART.

In addition to analyzing the microarray data using Wilcoxon and Q-value tests in order to identify biomarkers that discriminate between the sepsis and SIRS subpopulations in the training set, classification and regression tree (CART) analysis was used. CART is described in Section 5.5.1, above. Specifically, the data summarized above was used to predict the disease state by iteratively partitioning the data based on the best single-variable split of the data. In other words, at each stage of the tree building process, the biomarker whose expression values across the training population best discriminate between the sepsis and SIRS population was invoked as a decision branch. Cross-validation was carried out, with the optimal number of splits estimated independently in each of the 10 iterations. The final tree uses three biomarkers which are listed in order of importance IL18R1, ARG2, and FCGR1A, where IL18R1 was the most important. The confusion matrix for the training data, based on the final tree from the cross-validated CART algorithm is given in Table 63. From this confusion matrix, the overall accuracy was estimated to be 82.1% with a 95% confidence interval of 66.5% to 92.5%. The estimated sensitivity was 82.6% and the estimated specificity was 81.2%.

TABLE 63

Confusion matrix for training samples using the cross-validated CART algorithm

| | True Diagnosis | |
|---|---|---|
| Predicted | Sepsis | SIRS |
| Sepsis | 19 | 3 |
| SIRS | 4 | 13 |

For the 11 validation samples held back from training data set, the overall accuracy was estimated to be 100% with a 95% confidence interval of 71.5% to 100%, sensitivity 100% and specificity 100%. Table 64 shows the confusion matrix for the validation samples.

TABLE 64

Confusion matrix for validation samples using the cross-validated CART algorithm

| | True Diagnosis | |
|---|---|---|
| Predicted | Sepsis | SIRS |
| Sepsis | 5 | 0 |
| SIRS | 0 | 6 |

Random Forests.

Another decision rule that can be developed using biomarkers of the present invention is a Random Forests decision tree. Random Forests is a tree based method that uses bootstrapping instead of cross-validation. For each iteration, a random sample (with replacement) is drawn and the largest tree possible is grown. Each tree receives a vote in the final class prediction. To fit a random forest, the number of trees (e.g. bootstrap iterations) is specified. For this data, 1000 trees were used to train the algorithm. Using this algorithm, 9 of the 10 biomarkers had non-zero importance and were used in the model. Biomarker importance, from greatest to smallest, was: TGFB1, MMP9, TLR4, IL1RN, TNFSF, ARG2, FCGR1A, and IL18R1.

The random forest method uses a number of different decision trees. A biomarker is considered to have discriminating significance if it served as a decision branch of a decision tree from a significant random forest analysis. As used herein, a significant random forest analysis is one where the lower 95% confidence interval on accuracy by cross validation on a training data set is greater than 50% and the point estimate for accuracy on a validation set is greater than 65%.

The predicted confusion matrix for the training dataset using the decision tree developed using the Random Forest method is given in Table 65. From this confusion matrix, the overall accuracy was estimated to be 79.5% with a 95% confidence interval between 63.5% and 90.7%. The estimated sensitivity was 87% and the estimated specificity was 68.8%.

TABLE 65

Confusion matrix for training samples against the decision tree developed using the Random Forest method.

| | True Diagnosis | |
|---|---|---|
| Predicted | Sepsis | SIRS |
| Sepsis | 20 | 5 |
| SIRS | 3 | 11 |

For the 11 validation samples held back from training, the overall accuracy was estimated to be 81.8% with a 95% confidence interval of 48.2% to 97.7%, sensitivity 60% and specificity 100%. Table 66 shows the confusion matrix for the validation samples.

TABLE 66

Confusion matrix for the 11 validation samples against the decision tree developed using the Random Forest method.

| | True Diagnosis | |
|---|---|---|
| Predicted | Sepsis | SIRS |
| Sepsis | 6 | 0 |
| SIRS | 2 | 3 |

MART.

Multiple Additive Regression Trees (MART), also known as "gradient boosting machines," was used to simultaneously assess the importance of biomarkers and classify the subject samples. Several fitting parameters are specified in this approach including (i) number of trees, (ii) step size (commonly referred to as "shrinkage"), and (iii) degree of interaction (related to the number of splits for each tree). More information on MART is described in Section 5.5.4 above. The degree of interaction was set to 1 to enforce an additive model (e.g. each tree has one split and only uses one biomarker).

Estimating interactions may require more data to function well. The step size was set to 0.05 so that the model complexity was dictated by the number of trees. The optimal number of trees was estimated by leaving out a random subset of cases at each fitting iteration, then assessing quality of prediction on that subset. After fitting more trees than were warranted, the point at which prediction performance stopped improving was estimated as the optimal point.

The estimated model used 30 trees and 7 biomarkers across all trees. The MART algorithm also provides a calculation of biomarker importance (summing to 100%). Biomarkers ranked in decreasing order of importance to the model, with the most important biomarker first were: ITGAM, TGFB1, TLR4, TNFSF, FCGR1A, IL18R1, and ARG2.

Cross-validation was carried out, with the optimal number of trees estimated independently in each of the 10 iterations. The confusion matrix for the training data where the predicted classifications were made from the cross-validated model is given in Table 67. From this confusion matrix, the overall accuracy was estimated to be 74.4% with a 95% confidence interval of 57.9% to 87%. The estimated sensitivity was 73.8% and the estimated specificity was 68.8%.

TABLE 67

Confusion matrix for the training samples using the cross-validated MART algorithm.

| | True Diagnosis | |
|---|---|---|
| Predicted | Sepsis | SIRS |
| Sepsis | 18 | 5 |
| SIRS | 5 | 11 |

For the 11 validation samples held back from training, the overall accuracy was estimated to be 74.4% with a 95% confidence interval of 57.9% to 87%, sensitivity 78.3% and specificity 68.8%. Table 68 shows the confusion matrix for the validation samples.

TABLE 68

Confusion matrix for the validation samples using the MART algorithm.

| | True Diagnosis | |
|---|---|---|
| Predicted | Sepsis | SIRS |
| Sepsis | 6 | 2 |
| SIRS | 0 | 3 |

PAM.

Yet another decision rule developed using biomarkers of the present invention is predictive analysis of microarrays (PAM), which is described in Section 5.5.2, above. In this method, a shrinkage parameter that determines the number of biomarkers used to classify samples is specified. This parameter was chosen via cross-validation. There were no biomarkers with missing values. Based on cross-validation, the optimal threshold value was 0.55, corresponding to 9 biomarkers.

Using the threshold of 0.55, the overall accuracy for the training samples was estimated to be 82.3% with a 95% confidence interval of 68.8% to 90.7%. The estimated sensitivity was 68.8% and the estimated specificity was 91.3%.

Table 69 shows the confusion matrix for the training data where the predicted classifications were made from the cross-validated models.

TABLE 69

Confusion matrix for training samples using cross-validated PAM algorithm

| Predicted | True Diagnosis | |
|---|---|---|
| | Sepsis | SIRS |
| Sepsis | 11 | 2 |
| SIRS | 5 | 21 |

For the 11 validation samples held back from training, the overall accuracy was estimated to be 72.67% with a 95% confidence interval of 39% to 94%, sensitivity 40% and specificity 100%. Table 70 shows the confusion matrix for the validation samples.

TABLE 70

Confusion matrix for validation samples using cross-validated PAM algorithm

| Predicted | True Diagnosis | |
|---|---|---|
| | Sepsis | SIRS |
| Sepsis | 2 | 0 |
| SIRS | 3 | 6 |

The top nine biomarkers identified by PAM, ranked from most important to least important were: ARG2, TGFB1, MMP9, TLR4, ITGAM, IL18R1, TNFSF, IL1RN, and FCGR1A. FIG. 47 provides a summary of the CART, MART, PAM, and random forests (RF) classification algorithm (decision rule) performance and associated 95% confidence intervals using $T_{-12}$ static data obtained from an Affymetrix gene chip confirmatory training population. Based on the results of the RT-PCR analysis summarized in FIG. 47 and at other time points, all ten biomarkers under study in this confirmation process were significant. Some of the biomarkers discriminated as early as $T_{-60}$.

6.12.2 Confirmatory Analysis of Biomarkers Identified by Affymetrix Gene Chip Analysis The biomarkers identified in Table 59 of Section 6.11.2 and the ten biomarkers identified in Table 48 of Section 6.11.1 (FCGR1A, MMP9, IL18R1, ARG2, IL1RN, TNFSF13B, ITGAM, TGFBI, CD86, and TLR4), a total of 44 biomarkers, were analyzed using RT-PCR at multiple time points and analyzed in several different ways: static time of entry, static $T_{-60}$, static $T_{-36}$, baseline $T_{-60}$, baseline $T_{-36}$, and baseline $T_{-12}$ data points. RT-PCR is described in Section 5.4.1.2, above. Representative of these analyses is the static $T_{-12}$ data analysis described in detail below. In the $T_{-12}$ static analysis, biomarkers features were measured using a specific blood sample, designated the $T_{-12}$ blood sample, as defined in Section 6.4, above.

For the $T_{-12}$ static analysis, the 44 biomarkers were measured from 37 samples. Each sample was collected from a different member of the population. Of these biomarkers, 23 were transformed by log transformations, and 21 by square root transformations.

The 37 member population was initially split into a training set (n=28) and a validation set (n=9). The training set was used to estimate the appropriate classification algorithm parameters while the trained algorithm was applied to the validation set to independently assess performance. Of the 28 training samples, 14 were labeled Sepsis, meaning that the subjects developed sepsis at some point during the observation time period, and 14 were SIRS, meaning that they did not develop sepsis during the observation time period. Table 71 provides distributions of the race, gender and age for these samples.

TABLE 71

Distributions of the race, gender, and age for the training data

| Group | Gender | Black | Caucasian | Other |
|---|---|---|---|---|
| Sepsis | Male | 1 | 7 | 0 |
| | Female | 0 | 6 | 0 |
| SIRS | Male | 4 | 6 | 1 |
| | Female | 0 | 2 | 0 |

| Group | Minimum | Mean | Median | Maximum |
|---|---|---|---|---|
| Sepsis | 28 | 58 | 56 | 76 |
| SIRS | 20 | 42.5 | 39.5 | 79 |

For the 9 validation samples, five were labeled Sepsis and four were labeled SIRS. Table 72 provides distributions of the race, gender and age for these samples.

TABLE 72

Distributions of the race, gender, and age for the validation data

| Group | Gender | Black | Caucasian | Other |
|---|---|---|---|---|
| Sepsis | Male | 2 | 0 | 0 |
| | Female | 0 | 3 | 0 |
| SIRS | Male | 0 | 2 | 0 |
| | Female | 0 | 2 | 0 |

| Group | Minimum | Mean | Median | Maximum |
|---|---|---|---|---|
| Sepsis | 18 | 49.8 | 58 | 76 |
| SIRS | 24 | 45.8 | 41.5 | 76 |

Each sample in the training data was randomly assigned to one of ten groups used for cross-validation. The number of training samples in these groups ranged from two to four. The samples were assigned in way that attempted to balance the number of sepsis and SIRS samples across folds. As described in more detail below, several different methods were used to judge whether select biomarkers discriminate between the Sepsis and SIRS groups.

Wilcoxon and Q-Value Tests.

The first method used to identify discriminating biomarkers was a Wilcoxon test (unadjusted). The abundance value for a given biomarker across the samples in the training data was subjected to the Wilcoxon test. The Wilcoxon test considers both group classification (sepsis versus SIRS) and abundance value in order to compute a p value for the given biomarker. The p value provides an indication of how well the abundance value for the given biomarker across the samples collected in the training set discriminates between the sepsis and SIRS state. The lower the p value, the better the discrimination. When the p value is less than a specific confidence level, such as 0.05, an inference is made that the biomarker discriminates between the sepsis and SIRS phenotype. There were 38 significant biomarkers using this method (see Table 73).

The second method used to identify discriminating biomarkers was the Wilcoxon Test (adjusted). Due to the large number of biomarkers, 44, and the relatively small number of samples, 37, there was a high risk of finding falsely significant biomarkers. An adjusted p value was used to counter this risk. In particular, the method of Benjamini and Hochberg, 1995, J. R. Statist. Soc. B 57, pp 289-300, which is hereby incorporated herein by reference in its entirety, was used to control the false discovery rate. Here, the false discovery rate is defined as the number of biomarkers truly significant divided by the number of biomarkers declared significant. For example, if the adjusted p value is less than 0.05, there is a five percent chance that the biomarker is a false discovery. Results using this test are reported in Table 73. There were 38 significant biomarkers using this method (see Table 73). As used, herein, a biomarker is considered significant if it has a p value of less than 0.05 as determined by the Wilcoxon test (adjusted).

The third method used to identify discriminating biomarkers was Q values. In this third approach, the biomarkers were ordered by their Q values and if a respective biomarker has a Q value of X, then respective biomarker and all others more significant have a combined false discovery rate of X. However, the false discovery rate for any one biomarker may be much larger. There were 38 significant biomarkers using this method (see Table 73).

TABLE 73

Cumulative number of significant calls for the three methods. Note that all samples (training and validation) were used to compare sepsis and SIRS groups. Missing biomarker feature values were not included in the analyses.

|  | ≤1e-04 | ≤0.001 | ≤0.01 | ≤0.025 | ≤0.05 | ≤0.1 | ≤1 |
|---|---|---|---|---|---|---|---|
| p-value (unadjusted) | 0 | 27 | 38 | 38 | 38 | 38 | 44 |
| p-value (adjusted) | 0 | 23 | 38 | 38 | 38 | 38 | 44 |
| q-value | 0 | 36 | 38 | 39 | 39 | 39 | 44 |

CART.

In addition to analyzing the microarray data using Wilcoxon and Q-value tests in order to identify biomarkers that discriminate between the sepsis and SIRS subpopulations in the training set, classification and regression tree (CART) analysis was used. CART is described in Section 5.5.1, above. Specifically, the data summarized above was used to predict the disease state by iteratively partitioning the data based on the best single-variable split of the data. In other words, at each stage of the tree building process, the biomarker whose expression values across the training population best discriminate between the sepsis and SIRS population was invoked as a decision branch. Cross-validation was carried out with the optimal number of splits estimated independently in each of the 10 iterations. The final tree uses three biomarkers which are listed in order of importance OSM, HLA-DRA, and IL-18, where OSM was the most important. The confusion matrix for the training data, based on the final tree from the cross-validated CART algorithm is given in Table 74. From this confusion matrix, the overall accuracy was estimated to be 67.9% with a 95% confidence interval of 47.6% to 84.1%. The estimated sensitivity was 64.3% and the estimated specificity was 71.4%.

TABLE 74

Confusion matrix for training samples using the cross-validated CART algorithm

|  | True Diagnosis | |
|---|---|---|
| Predicted | Sepsis | SIRS |
| Sepsis | 9 | 4 |
| SIRS | 5 | 10 |

For the 9 validation samples held back from training data set, the overall accuracy was estimated to be 88.9% with a 95% confidence interval of 51.8% to 99.7%, sensitivity 75% and specificity 100%. Table 75 shows the confusion matrix for the validation samples.

TABLE 75

Confusion matrix for validation samples using the cross-validated CART algorithm

|  | True Diagnosis | |
|---|---|---|
| Predicted | Sepsis | SIRS |
| Sepsis | 3 | 0 |
| SIRS | 1 | 5 |

Random Forests.

Another decision rule that can be developed using biomarkers of the present invention is a Random Forests decision tree. Random Forests is a tree based method that uses bootstrapping instead of cross-validation. For each iteration, a random sample (with replacement) is drawn and the largest tree possible is grown. Each tree receives a vote in the final class prediction. To fit a random forest, the number of trees (e.g. bootstrap iterations) is specified. For this data, 1000 trees were used to train the algorithm. Using this algorithm, 35 of the 44 biomarkers had non-zero importance and were used in the model. Biomarker importance, from greatest to smallest, was: OSM, GADD45B, ARG2, IL18R1, TDRD9, PFKFB3, MAPK14, PRV1, MAP2K6, TNFRSF6, FCGR1A, INSL3, LY96, PSTPIP2, ANKRD22, TNFSF10, HLA-DRA, FNDC3B, TIFA, GADD45A, VNN1, ITGAM, BCL2A1, TLR4, TNFSF13B, SOCS3, IL1RN, CEACAM1, and SOD2.

The random forest method uses a number of different decision trees. A biomarker is considered to have discriminating significance if it served as a decision branch of a decision tree from a significant random forest analysis. As used herein, a significant random forest analysis is one where the lower 95% confidence interval on accuracy by cross validation on a training data set is greater than 50% and the point estimate for accuracy on a validation set is greater than 65%.

The predicted confusion matrix for the training dataset using the decision tree developed using the Random Forest method is given in Table 76. From this confusion matrix, the overall accuracy was estimated to be 78.6%. The estimated sensitivity was 78.6% and the estimated specificity was also 78.6%.

TABLE 76

Confusion matrix for training samples against the decision tree developed using the Random Forest method.

| Predicted | True Diagnosis | |
|---|---|---|
|  | Sepsis | SIRS |
| Sepsis | 11 | 3 |
| SIRS | 3 | 11 |

For the 9 validation samples held back from training, the overall accuracy was estimated to be 77.8% with a 95% confidence interval of 40.0% to 97.2%, sensitivity 50% and specificity 100%. Table 77 shows the confusion matrix for the validation samples.

TABLE 77

Confusion matrix for validation samples against the decision tree developed using the Random Forest method.

| Predicted | True Diagnosis | |
|---|---|---|
|  | Sepsis | SIRS |
| Sepsis | 5 | 0 |
| SIRS | 2 | 2 |

MART.

Multiple Additive Regression Trees (MART), also known as "gradient boosting machines," was used to simultaneously assess the importance of biomarkers and classify the subject samples. Several fitting parameters are specified in this approach including (i) number of trees, (ii) step size (commonly referred to as "shrinkage"), and (iii) degree of interaction (related to the number of splits for each tree). More information on MART is described in Section 5.5.4 above. The degree of interaction was set to 1 to enforce an additive model (e.g. each tree has one split and only uses one biomarker).

Estimating interactions may require more data to function well. The step size was set to 0.05 so that the model complexity was dictated by the number of trees. The optimal number of trees was estimated by leaving out a random subset of cases at each fitting iteration, then assessing quality of prediction on that subset. After fitting more trees than were warranted, the point at which prediction performance stopped improving was estimated as the optimal point.

The estimated model used 21 trees and 9 biomarkers across all trees. The MART algorithm also provides a calculation of biomarker importance (summing to 100%). Biomarkers ranked in decreasing order of importance to the model, with the most important biomarker first were: ARG2, GADD45B, OSM, LY96, INSL3, ANKRD22, MAP2K6, PSTPIP2, and TGFB1.

Cross-validation was carried out, with the optimal number of trees estimated independently in each of the 10 iterations. The confusion matrix for the training data where the predicted classifications were made from the cross-validated model is given in Table 78. From this confusion matrix, the overall accuracy was estimated to be 75% with a 95% confidence interval of 55.1 to 89.3%. The estimated sensitivity was 71.4% and the estimated specificity was 78.6%.

TABLE 78

Confusion matrix for the training samples using the cross-validated MART algorithm.

| Predicted | True Diagnosis | |
|---|---|---|
|  | Sepsis | SIRS |
| Sepsis | 10 | 3 |
| SIRS | 4 | 11 |

For the 9 validation samples held back from training, the overall accuracy was estimated to be 88.9% with a 95% confidence interval of 51.8% to 99.7%, sensitivity 100% and specificity 75%. Table 79 shows the confusion matrix for the validation samples.

TABLE 79

Confusion matrix for the validation samples using the MART algorithm.

| Predicted | True Diagnosis | |
|---|---|---|
|  | Sepsis | SIRS |
| Sepsis | 5 | 1 |
| SIRS | 0 | 3 |

PAM.

Yet another decision rule developed using biomarkers of the present invention is predictive analysis of microarrays (PAM), which is described in Section 5.5.2, above. In this method, a shrinkage parameter that determines the number of biomarkers used to classify samples is specified. This parameter was chosen via cross-validation. There were no biomarkers with missing values. Based on cross-validation, the optimal threshold value was 2.05, corresponding to 6 biomarkers.

Using the threshold of 2.05, the overall accuracy for the training samples was estimated to be 82.5% with a 95% confidence interval of 68.7% to 91%. The estimated sensitivity was 78.6% and the estimated specificity was 85.7%. Table 80 shows the confusion matrix for the training data where the predicted classifications were made from the cross-validated models.

TABLE 80

Confusion matrix for training samples using cross-validated PAM algorithm

| Predicted | True Diagnosis | |
|---|---|---|
|  | Sepsis | SIRS |
| Sepsis | 11 | 2 |
| SIRS | 3 | 12 |

For the 9 validation samples held back from training, the overall accuracy was estimated to be 77.8% with a 95% confidence interval of 40% to 97.2%, sensitivity 50% and specificity 100%. Table 81 shows the confusion matrix for the validation samples.

TABLE 81

Confusion matrix for validation samples using cross-validated PAM algorithm

| Predicted | True Diagnosis | |
| --- | --- | --- |
| | Sepsis | SIRS |
| Sepsis | 2 | 0 |
| SIRS | 2 | 5 |

The top six biomarkers identified by PAM, ranked from most important to least important were: GADD45B, TDRD9, MAP2K6, OSM, TNFSF10, and ANKRD22. FIG. 48 provides a summary of the CART, MART, PAM, and random forests (RF) classification algorithm (decision rule) performance and associated 95% confidence intervals using $T_{-12}$ static data for the 44 biomarkers analyzed in this Section. Based on the results of the RT-PCR analysis summarized in FIG. 48 and at other time points, all forty-four biomarkers under study in this confirmation process were significant. Some of the biomarkers discriminated as early as $T_{-60}$.

6.13 Select Protein Biomarkers

In this example, experiments were performed in order to confirm which protein based biomarkers differentiate between patients who subsequently develop sepsis ("sepsis patients) and patients who do not ("SIRS patients). In the discovery process, samples were analyzed by a bead based protein immunoassay, as described in Section 6.13.1.

6.13.1 Discovery of Protein Biomarkers Using a Bead Based Protein Immunoassay Multiplex Analysis.

A set of biomarkers was analyzed simultaneously in real time, using a multiplex analysis method described in U.S. Pat. No. 5,981,180 ("the '180 patent"), herein incorporated by reference in its entirety, and in particular for its teachings of the general methodology, bead technology, system hardware and antibody detection. For this analysis, a matrix of microparticles was synthesized, where the matrix consisted of different sets of microparticles. Each set of microparticles had thousands of molecules of a distinct antibody capture reagent immobilized on the micro particle surface and was color-coded by incorporation of varying amounts of two fluorescent dyes. The ratio of the two fluorescent dyes provided a distinct emission spectrum for each set of microparticles, allowing the identification of a microparticle within a set following the pooling of the various sets of microparticles. U.S. Pat. Nos. 6,268,222 and 6,599,331 also are incorporated herein by reference in their entirety, and in particular for their teachings of various methods of labeling microparticles for multiplex analysis.

The sets of labeled beads were pooled and combined with a plasma sample from individuals. The labeled beads were identified by passing them single file through a flow device that interrogated each microparticle with a laser beam that excited the fluorophore labels. An optical detector then measured the emission spectrum of each bead to classify the beads into the appropriate set. Because the identity of each antibody capture reagent was known for each set of microparticles, each antibody specificity was matched with an individual microparticle that passes through the flow device. U.S. Pat. No. 6,592,822 is also incorporated herein by reference in its entirety, and in particular for its teachings of multi-analyte diagnostic system that can be used in this type of multiplex analysis.

To determine the amount of analyte that bound a given set of microparticles, a reporter molecule was added such that it formed a complex with the antibodies bound to their respective analyte. In the present example, the reporter molecule was a fluorophore-labeled secondary antibody. The fluorophore on the reporter was excited by a second laser having a different excitation wavelength, allowing the fluorophore label on the secondary antibody to be distinguished from the fluorophores used to label the microparticles. A second optical detector measured the emission from the fluorophore label on the secondary antibody to determine the amount of secondary antibody complexed with the analyte bound by the capture antibody. In this manner, the amount of multiple analytes captured to beads could be measured in a single reaction.

Data Analysis and Results.

For each sample, the concentrations of analytes that bound several different antibodies were measured. Each analyte is a biomarker, and the concentration of each analyte in the sample can be a feature of that biomarker. The biomarkers were analyzed with select antibody reagents listed in Table 14 of United States Patent Publication Number U.S. 2004/0096917 A1, which is hereby incorporated herein by reference in its entirety. These antibody reagents are commercially available from Rules Based Medicine (Austin, Tex.). The antibody reagents are categorized as specifically binding either (1) circulating protein biomarker components of blood, (2) circulating antibodies that normally bind molecules associated with various pathogens (identified by the pathogen that each biomarker is associated with, where indicated), or (3) autoantibody biomarkers that are associated with various disease states. Various approaches may be used to identify features that can inform a decision rule to classify individuals into the SIRS or sepsis groups. The methods chosen were CART, MART, PAM and random forests.

Biomarkers in multiple samples were measured using the above described assay at multiple time points and analyzed in several different ways: static time of entry, static $T_{-60}$, static $T_{-36}$, baseline $T_{-60}$, baseline $T_{-36}$, and baseline $T_{-12}$ data points. Representative of these analyses is the static $T_{-12}$ data analysis which is described in detail below. In the $T_{-12}$ static analysis, biomarkers features were measured using a specific blood sample, designated the $T_{-12}$ blood sample, as defined in Section 6.4, above.

For the $T_{-12}$ static analysis, there were 60 biomarkers measured on 97 samples. Each sample was collected from a different member the population. Of these features, 53 were transformed by log transformations, 11 by square root transformations and the remaining 2 were not transformed.

The 97 member population was initially split into a training set (n=74) and a validation set (n=23). The training set was used to estimate the appropriate classification algorithm parameters while the trained algorithm was applied to the validation set to independently assess performance. Of the 74 training samples, 36 were labeled Sepsis, meaning that the subjects developed sepsis at some point during the observation time period, and 38 were labeled SIRS, meaning that they did not develop sepsis during the observation time period. Table 82 provides distributions of the race, gender and age for these samples.

TABLE 82

Distributions of the race, gender, and age for the training data

| Group | Gender | Black | Caucasian | Other |
|---|---|---|---|---|
| Sepsis | Male | 10 | 14 | 1 |
| | Female | 0 | 10 | 1 |
| SIRS | Male | 5 | 24 | 0 |
| | Female | 0 | 9 | 0 |

| Group | Minimum | Mean | Median | Maximum |
|---|---|---|---|---|
| Sepsis | 18 | 43.2 | 40 | 80 |
| SIRS | 18 | 44.9 | 40 | 90 |

For the 23 validation samples, 12 were labeled Sepsis and 11 were labeled SIRS. Table 83 provides distributions of the race, gender and age for these samples.

TABLE 83

Distributions of the race, gender, and age for the validation data

| Group | Gender | Black | Caucasian | Other |
|---|---|---|---|---|
| Sepsis | Male | 0 | 7 | 0 |
| | Female | 0 | 4 | 0 |
| SIRS | Male | 2 | 6 | 0 |
| | Female | 0 | 4 | 0 |

| Group | Minimum | Mean | Median | Maximum |
|---|---|---|---|---|
| Sepsis | 18 | 43.4 | 43 | 81 |
| SIRS | 19 | 51.9 | 51.5 | 85 |

Each sample in the training data was randomly assigned to one of ten groups used for cross-validation. The number of training samples in these groups ranged from 6 to 8. The samples were assigned in way that attempted to balance the number of sepsis and SIRS samples across folds. As described in more detail below, several different methods were used to judge whether select biomarkers discriminate between the Sepsis and SIRS groups.

Wilcoxon and Q-Value Tests.

The first method used to identify discriminating biomarkers was a Wilcoxon test (unadjusted). The abundance value for a given biomarker across the samples in the training data was subjected to the Wilcoxon test. The Wilcoxon test considers both group classification (sepsis versus SIRS) and abundance value in order to compute a p value for the given biomarker. The p value provides an indication of how well the abundance value for the given biomarker across the samples collected in the training set discriminates between the sepsis and SIRS state. The lower the p value, the better the discrimination. When the p value is less than a specific confidence level, such as 0.05, an inference is made that the biomarker discriminates between the sepsis and SIRS phenotype. There were 24 significant biomarkers using this method (see Table 84).

The second method used to identify discriminating biomarkers was the Wilcoxon Test (adjusted). Due to the large number of biomarkers, 60, in combination with the relatively small number of samples, 97, there was a high risk of finding falsely significant biomarkers. An adjusted p-value was used to counter this risk. In particular, the method of Benjamini and Hochberg, 1995, J. R. Statist. Soc. B 57, pp 289-300, which is hereby incorporated herein by reference in its entirety, was used to control the false discovery rate. Here, the false discovery rate is defined as the number of biomarkers truly significant divided by the number of biomarkers declared significant. For example, if the adjusted p-value is less than 0.05, there is a 5% chance that the biomarker is a false discovery. Results using this test are reported in Table 84. There were 16 significant biomarkers using this method (see Table 84). As used, herein, a biomarker is considered significant if it has a p-value of less than 0.05 as determined by the Wilcoxon test (adjusted).

The third method used to identify discriminating biomarkers was the use of Q values. In such an approach, the biomarkers are ordered by their q-values and if a respective biomarker has a q-value of X, then respective biomarker and all others more significant have a combined false discovery rate of X. However, the false discovery rate for any one biomarker may be much larger. There were 16 significant biomarkers using this method (see Table 84).

TABLE 84

Cumulative number of significant calls for the three methods. Note that all samples (training and validation) were used to compare Sepsis and SIRS groups. Missing biomarker feature values were not included in the analyses.

| | ≤1e−04 | ≤0.001 | ≤0.01 | ≤0.025 | ≤0.05 | ≤0.1 | ≤1 |
|---|---|---|---|---|---|---|---|
| p-value (unadjusted) | 0 | 6 | 14 | 20 | 24 | 25 | 60 |
| p-value (adjusted) | 0 | 0 | 6 | 13 | 16 | 24 | 60 |
| q-value | 0 | 0 | 13 | 20 | 25 | 31 | 60 |

CART.

In addition to analyzing the microarray data using Wilcoxon and Q-value tests in order to identify biomarkers that discriminate between the sepsis and SIRS subpopulations in the training set, classification and regression tree (CART) analysis was used. CART is described in Section 5.5.1, above. Specifically, the data summarized above was used to predict the disease state by iteratively partitioning the data based on the best single-variable split of the data. In other words, at each stage of the tree building process, the biomarker whose expression values across the training population best discriminate between the sepsis and SIRS population was invoked as a decision branch. Cross-validation was carried out, with the optimal number of splits estimated independently in each of the 10 iterations. The final tree is depicted in FIG. 49, and uses ten biomarkers: MIP1beta, thrombopoietin, C reactive protein, IL-10, IL-16, beta-2 microglobulin, alpha fetoprotein, IL-6, adiponectin, and ICAM1.

FIG. 50 shows the distribution of the ten biomarkers used in the decision tree between the sepsis and SIRS groups in the training data set. In FIG. 50, the top of each box denotes the $75^{th}$ percentile of the data across the training set and the bottom of each box denotes the $25^{th}$ percentile, and the median value for each biomarker across the training set is drawn as a line within each box. The confusion matrix for the training data where the predicted classifications were made from the cross-validated model is given in Table 85. From this confusion matrix, the overall accuracy was estimated to be 63.5% with a 95% confidence interval of 51.5% to 74.4%. The estimated sensitivity was 66.7% and the estimated specificity was 60.5%.

TABLE 85

Confusion matrix for training samples using cross-validated CART

| Predicted | True Diagnosis | |
| --- | --- | --- |
| | Sepsis | SIRS |
| Sepsis | 24 | 15 |
| SIRS | 12 | 23 |

For the 23 validation samples held back from training data set, the overall accuracy was estimated to be 65.2% with a 95% confidence interval of 42.7% to 83.6%, sensitivity 66.7% and specificity 63.6%. Table 86 shows the confusion matrix for the validation samples.

TABLE 86

Confusion matrix for validation samples using cross-validated CART

| Predicted | True Diagnosis | |
| --- | --- | --- |
| | Sepsis | SIRS |
| Sepsis | 8 | 1 |
| SIRS | 4 | 10 |

Random Forests.

Another decision rule that can be developed using biomarkers of the present invention is a Random Forests decision tree. Random Forests is a tree based method that uses bootstrapping instead of cross-validation. For each iteration, a random sample (with replacement) is drawn and the largest tree possible is grown. Each tree receives a vote in the final class prediction. To fit a random forest, the number of trees (e.g. bootstrap iterations) is specified. No more than 500 were used in this example, but at least 50 are needed for a burn-in period. The number of trees was chosen based on the accuracy of the training data. For this data, 64 trees were used to train the algorithm (see FIG. 51). In FIG. 51, curve 4802 is a smoothed estimate of overall accuracy as a function of tree number. Curve 4804 is a smoothed curve of tree sensitivity as a function of tree number. Curve 4806 is a smoothed curve of tree specificity as a function of tree number. Using this algorithm, 34 biomarkers had non-zero importance and were used in the model. The random forest algorithm gauges biomarker importance by the average reduction in the training accuracy. The biomarkers were ranked by this method and are shown in FIG. 52. The random forest method uses a number of different decision trees. A biomarker is considered to have discriminating significance if it served as a decision branch of a decision tree from a significant random forest analysis. As used herein, a significant random forest analysis is one where the lower 95% confidence interval on accuracy by cross validation on a training data set is greater than 50% and the point estimate for accuracy on a validation set is greater than 65%.

The predicted confusion matrix for the training dataset using the decision tree developed using the Random Forest method is given in Table 87. From this confusion matrix, the overall accuracy was estimated to be 70.3% (confidence intervals cannot be computed when using the bootstrap accuracy estimate). The estimated sensitivity was 69.4% and the estimated specificity was 71.1%.

TABLE 87

Confusion matrix for training samples against the decision tree developed using the Random Forest method.

| Predicted | True Diagnosis | |
| --- | --- | --- |
| | Sepsis | SIRS |
| Sepsis | 27 | 11 |
| SIRS | 11 | 25 |

For the 23 validation samples held back from training, the overall accuracy was estimated to be 60.9% with a 95% confidence interval of 38.5% to 80.3%, sensitivity 83.3% and specificity 36.4%. Table 88 shows the confusion matrix for the validation samples.

TABLE 88

Confusion matrix for the 23 validation samples against the decision tree developed using the Random Forest method.

| Predicted | True Diagnosis | |
| --- | --- | --- |
| | Sepsis | SIRS |
| Sepsis | 10 | 7 |
| SIRS | 2 | 4 |

MART.

MART was used to simultaneously assess the importance of biomarkers and classify the subject samples. Several fitting parameters are specified in this approach including (i) number of trees, (ii) step size (commonly referred to as "shrinkage"), and (iii) degree of interaction (related to the number of splits for each tree). More information on MART is described in Section 5.5.4 above. The degree of interaction was set to 1 to enforce an additive model (e.g. each tree has one split and only uses one biomarker).

The degree of interaction was set to 1 to enforce an additive model (e.g. each tree has one split and only uses one feature), because this often works well even when a weak interaction is present. Moreover, estimating interactions may require more data to function well. The step size was set to 0.05 so that the model complexity was dictated by the number of trees. The optimal number of trees was estimated by leaving out a random subset of cases at each fitting iteration, then assessing quality of prediction on that subset. After fitting more trees than were warranted, the point at which prediction performance stopped improving was estimated as the optimal point.

The estimated model used 11 trees and 4 biomarkers across all trees. The MART algorithm also provides a calculation of biomarker importance (summing to 100%), which are given in FIG. 53. Biomarkers with zero importance were excluded. FIG. 54 shows the distribution of the selected biomarkers between the Sepsis and SIRS groups.

Cross-validation was carried out, with the optimal number of trees estimated independently in each of the 10 iterations. The confusion matrix for the training data where the predicted classifications were made from the cross-validated model is given in Table 89. From this confusion matrix, the overall accuracy was estimated to be 70.3% with a 95% confidence interval of 58.5% to 80.3%. The estimated sensitivity was 63.9% and the estimated specificity was 76.3%.

TABLE 89

Confusion matrix for the training samples
using the cross-validated MART algorithm.

| | True Diagnosis | |
|---|---|---|
| Predicted | Sepsis | SIRS |
| Sepsis | 23 | 9 |
| SIRS | 13 | 29 |

For the 23 validation samples held back from training, the overall accuracy was estimated to be 73.9% with a 95% confidence interval of 51.6% to 89.8%, sensitivity 63.6% and specificity 83.3%. Table 90 shows the confusion matrix for the validation samples.

TABLE 90

Confusion matrix for the validation
samples using the MART algorithm.

| | True Diagnosis | |
|---|---|---|
| Predicted | Sepsis | SIRS |
| Sepsis | 7 | 2 |
| SIRS | 4 | 10 |

PAM.

Yet another decision rule developed using biomarkers of the present invention is predictive analysis of microarrays (PAM), which is described in Section 5.5.2, above. In this method, a shrinkage parameter that determines the number of biomarkers used to classify samples is specified. This parameter was chosen via cross-validation. There were no biomarkers with missing values. Based on cross-validation, the optimal threshold value was 0.08, corresponding to 59 biomarkers. FIG. 55 shows the accuracy across different thresholds. In FIG. 55, curve 5202 is the overall accuracy (with 95% confidence interval bars). Curve 5204 shows decision rule sensitivity as a function of threshold value. Curve 5206 shows decision rule specificity as a function of threshold value. Using the threshold of 0.08, the overall accuracy for the training samples was estimated to be 74.9 with a 95% confidence interval of 65.3% to 82.5%. The estimated sensitivity was 78.9% and the estimated specificity was 69.4%. Table 91 shows the confusion matrix for the training data where the predicted classifications were made from the cross-validated models.

TABLE 91

Confusion matrix for training samples
using cross-validated PAM algorithm

| | True Diagnosis | |
|---|---|---|
| Predicted | Sepsis | SIRS |
| Sepsis | 30 | 11 |
| SIRS | 8 | 25 |

For the 23 validation samples held back from training, the overall accuracy was estimated to be 65.2% with a 95% confidence interval of 42.7% to 83.6%, sensitivity 91.7% and specificity 36.4%. Table 92 shows the confusion matrix for the validation samples.

TABLE 92

Confusion matrix for validation samples
using cross-validated PAM algorithm

| | True Diagnosis | |
|---|---|---|
| Predicted | Sepsis | SIRS |
| Sepsis | 11 | 7 |
| SIRS | 1 | 4 |

FIG. 56 shows the selected biomarkers, ranked by their relative discriminatory power, and their relative importance in the model.

FIG. 57 provides a summary of the CART, MART, PAM, and random forests (RF) classification algorithm (decision rule) performance and associated 95% confidence intervals. Fifty distinct biomarkers were selected from across all the algorithms illustrated in FIG. 58. The identity of these fifty selected features is found in FIG. 58. FIG. 58 illustrates an overall ranking of biomarkers for the $T_{-12}$ data set. For the selected biomarkers, the x-axis depicts the percentage of times that it was selected. Within the percentage of times that biomarkers were selected, the biomarkers are ranked.

From the analysis of the $T_{-12}$ data set and the other data sets, ten protein based biomarkers were selected for confirmation using the methodology described in Section 16.3.2. These biomarkers are listed in Table 93, below.

TABLE 93

Protein based biomarkers selected
for confirmation from immunoassay

| Gene Symbol | Gene Name | Gene Accession Number | Protein Accession Number |
|---|---|---|---|
| IL-6 | INTERLEUKIN 6 | NM_000600 | NP_000591 |
| IL-8 | INTERLEUKIN 8 | M28130 | AAA59158 |
| CRP | C Reactive protein | CAA39671 | NM_000567 |
| IL-10 | INTERLEUKIN 10 | NM_000572 | CAH73907 |
| APOC3 | APOLIPOPROTEIN CIII | NM_000040 | CAA25648 |
| MMP9 | MATRIX METALLOPROTEINASE 9 (GELATINASE B, 92 KDA GELATINASE, 92 KDA TYPE IV COLLAGENASE) | NM_004994 | NP_004985 |
| TIMP1 | TISSUE INHIBITOR OF METALLOPROTEINASE 1 | NM_003254 | AAA75558 |
| MCP1 | MONOCYTE CHEMOATTRACTANT PROTEIN 1 | AF493698, AF493697 | AAQ75526 |
| AFP | ALPHA-FETOPROTEIN | NM_001134 | CAA79592 |
| B2M | BETA-2 MICROGLOBULIN | NM_004048 | AAA51811 |

Each of the sequences, genes, proteins, and probesets identified in Table 93 is hereby incorporated by reference.

6.13.2 Confirmation of Protein Biomarkers Using a Bead Based Protein Immunoassay Confirmation of the biomarkers identified in Table 93 was performed using the same assay described in Section 6.13.1 at multiple time points and analyzed in several different ways: static time of entry, static $T_{-60}$, static $T_{-36}$, baseline $T_{-60}$, baseline $T_{-36}$, and baseline $T_{-12}$ data points. Representative of these analyses is the static $T_{-12}$ data analysis which is described in detail below. In the $T_{-12}$ static analysis, biomarkers features were measured using a specific blood sample, designated the $T_{-12}$ blood sample, as defined in Section 6.4, above. FIG. 59 illustrates the results of the analysis of static $T_{-12}$ bead based protein assay, using CART, MART, PAM and random forests, where the static $T_{-12}$ time point is as described in Section 6.4. The best decision tree in both the training and validation datasets for CART used six biomarkers. For both the training data and the validation data, the estimated model for MART used 4 biomarkers across all trees. A total of 7 biomarkers were of significance in both the training and the validation sets using PAM. Using random forest, 4 biomarkers under study were actually found to have discriminating significance in both the training and validation data sets. Based on the results of the analysis of the bead based protein immunoassay summarized in FIG. 59, each of the ten protein based biomarkers identified in Section 6.13.1 were confirmed by this experiment.

6.13.3 Confirmation of Protein Biomarkers Using BD Cytometric Bead Array Assay IL-6, IL-8, and IL-10 proteins were confirmed using the BD™ Cytometric Bead Array (CBA) assay as embodied in the BD™ CBA Human Inflammation Kit. Flow cytometry is an analysis tool that allows for the discrimination of different particles on the basis of size and color. Multiplexing is the simultaneous assay of many analytes in a single sample. CBA employs a series of particles with discrete fluorescence intensities to simultaneously detect multiple soluble analytes. CBA is combined with flow cytometry to create a multiplexed assay. The BD CBA system uses the sensitivity of amplified fluorescence detection by flow cytometry to measure soluble analytes in a particle-based immunoassay. Each bead in a CBA provides a capture surface for a specific protein and is analogous to an individually coated well in an ELISA plate. The BD CBA capture bead mixture is in suspension to allow for the detection of multiple analytes in a small volume sample.

The combined advantages of the broad dynamic range of fluorescent detection via flow cytometry and the efficient capturing of analytes via suspended particles enable CBA to use fewer sample dilutions and to obtain the value of an unknown in substantially less time (compared to conventional ELISA). The BD™ CBA Human Inflammation Kit can be used to quantitatively measure Interleukin-8 (IL-8), Interleukin-1β (IL-1β), Interleukin-6 (IL-6), Interleukin-10 (IL-10), Tumor Necrosis Factor (TNF), and Interleukin-12p70 (IL-12p70) protein levels in a single sample. The kit performance has been optimized for analysis of specific proteins in tissue culture supernatants, EDTA plasma, and serum samples.

Six bead populations with distinct fluorescence intensities have been coated with capture antibodies specific for IL-8, IL-1β, IL-6, IL-10, TNF, and IL-12p70 proteins. The six bead populations are mixed together to form the BD™ CBA which is resolved in the FL3 channel of a flow cytometer such as the BD FACScan™ or BD FACSCalibur™ flow cytometer. The capture beads, PE-conjugated detection antibodies, and recombinant standards or test samples are incubated together to form sandwich complexes. Following acquisition of sample data using the flow cytometer, the sample results are generated in graphical and tabular format using the BD™ CBA Analysis Software. More details about the BD™ CBA Human Inflammation Kit are described in the BD™ CBA Human Inflammation Kit Instruction Manual, catalog number 551811, available from BD biosciences, which is hereby incorporated by reference herein in its entirety. Using the BD™ CBA Human Inflammation Kit, the biomarkers IL-6, IL-8, and IL-10 were confirmed as discriminating between sepsis and SIRS.

6.14 Assessing Subcombinations of the Biomarkers Identified in Table I

One embodiment of the present invention encompasses any 2 or more of the 53 biomarkers listed in Table I as predictors for classifying a subject as sepsis or SIRS. One embodiment of the present invention encompasses any 3 or more of the 53 biomarkers listed in Table I as predictors for classifying a subject as sepsis or SIRS. As such, the present invention further encompasses any subcombination of the 53 biomarkers listed in Table I as predictors for classifying a subject as sepsis or SIRS provided that there are at least 2 or 3 biomarkers in the subcombination. This section discloses experiments that demonstrate the predictive power of exemplary subcombinations of the 53 biomarkers listed in Table I. Several thousand subcombinations were tested and the vast majority of those subcombinations had an accuracy of at least seventy percent. This indicates that the vast majority of the possible subcombinations of the 53 biomarkers listed in Table I will discriminate between sepsis and SIRS subjects.

6.14.1 Subcombinations of Nucleic Acid Biomarkers at $T_{-12}$

There are a total of 44 biomarkers for which RT-PCR nucleic acid data is available as reported in Table J. A total of 4800 different subcombinations of this set of biomarkers were constructed using the $T_{-12}$ time point data described in Section 6.12. Each different subcombination was then tested for its ability to discriminate between sepsis subjects and SIRS subjects. The 4800 subcombinations represent a random sampling of the total number of possible subcombinations possible for the 44 biomarkers of the present invention reported in Table J. Randomness of the 4800 subcombinations was ensured using the following algorithm:

```
CONSIDER 2 to 25 biomarkers from Table J
{
  LET the current number be k;
  DO the following 200 times
  {
    SELECT k biomarkers at random from Table J;
    LET the current set of biomarkers be S;
  }
  DO the following 10 times
  {
    FOR biomarker set S, randomly set aside 10% of patients as a
    validation population and 90% as a training population;
    FIT a model to the training population using Random Forest with
    T_-12 time point data;
    PREDICT results for the validation population;
    CALCULATE agreement with the known status of the validation
    population;
  }
  AVERAGE the ten agreement rates and report;
  SET k = k+1;
  IF k > 10 then END; ELSE return to top;
}
END
```

There were a total of 152 patients for which $T_{-12}$ data was available from a combination of discovery and confirmatory data described above. Of these 152 patients, 80 were sepsis and 72 were SIRs. The calculations described above test 200 subcombinations at each interval 2 through 25. In other words, 200 subcombinations each consisting of two biomarkers randomly selected from Table J were tested, 200 subcombinations each consisting of three biomarkers randomly selected from Table J were tested, and so forth, through 200 subcombinations each consisting of twenty-five biomarkers randomly selected from Table J for a total of 24 families of subcombinations, where each family of subcombinations consists of 200 subcombinations of biomarkers each having k biomarkers, where k is a number in the set 2 through 25.

The data set with assay results for all biomarkers under consideration was maintained in memory, as were a list of unique biomarker names. To evaluate subsets of a specific size (say, k=three), then that many (three) biomarker names were selected randomly from the set of unique biomarker names, using a pseudorandom number generators provided in the R software package. See Venables and Smith, *An Introduction to R*, ISBN 0-9541617-4-2, which is hereby incorporated by reference in its entirety. A matrix of assay results for the selected biomarker names was constructed. This matrix could have more columns than the number of selected biomarker names, since some biomarkers have more than one assay result. An estimate of true predictive accuracy, when using the modeling technique "Random Forest," was then constructed for this matrix. The Random Forest algorithm was implemented as described in Breiman, 2001, "Random Forests," Machine Learning 45(1), pp. 5-32, which is hereby incorporated by reference in its entirety.

For a given data matrix, the prediction of true predictive accuracy was calculated as follows: 10% of patients were randomly selected in a balanced manner, i.e., 10% of septic patients and 10% of SIRS patients were selected. Selected patients were set aside for the validation population, and a random forest model was fitted to the remaining data (the training population). If there were any missing values in the training data or the set-aside data, a recursive partitioning model was fitted to other assay results as well as the Sepsis/SIRS information in order to predict assay values. The recursive partitioning model is described in Breiman et al., 1984, *Classification and Regression Trees*, Wadsworth, which is hereby incorporated by reference in its entirety. Missing values were then replaced with their predicted values. Missing values in the set-aside data were replaced with predictions from the recursive-partition model fitted to the training data, so that knowledge of the SIRS/Sepsis status for the validation population was not used in any way to classify validation patients.

By comparing the true status of the 10% set aside (the validation population) with the predicted status according to the random forest model fitted to the other 90% (the training population), sensitivity, specificity, and agreement were calculated. This process was repeated 10 times, and the final sensitivity, specificity, and agreement estimates (also termed accuracy, also termed performance) for the given marker subset were those values averaged across the 10 iterations. This process was applied to every subset. For each size considered (k value, i.e., number of biomarkers), 200 random subsets were selected and evaluated. These 200 performance (accuracy) estimates form an estimate of the distribution of performances of all subsets of biomarkers of a given size (k value).

FIG. 60 plots the accuracy of each of these 24 families of subcombinations as bar graphs. FIG. 61 plots the accuracy (performance) of each individual subcombination in each of the 24 families of subcombinations. Thus, FIG. 61 plots the accuracy (performance) of a total of 4800 subcombinations of the set of biomarkers listed in Table J.

FIGS. 60 and 61 indicate that for k>5, the distributions are Gaussian, (bell-shaped), indicating that each respective family (k=5, . . . , 24) is an accurate depiction of the subcombination space represented by the family. For k<=5, a handful of subsets give lower accuracy (performance) estimates. However, the results available for k<=5 indicate that this class of biomarker subcombinations discriminate between sepsis and SIRS as well. The results reported in FIGS. 60 and 61 show that, with as few as two biomarkers randomly selected from Table J, an accuracy (performance) estimate above 50% was virtually always obtained. Table 94 contains the number of subcombinations in each family (k=2, 4, . . . , 25) that performed with a threshold accuracy of greater than 60% (column 2), greater than 70% (column 3), greater than 80% (column 4), greater than 90% (column 5), or an accuracy of less than 60% (column 6). The data summarized in FIGS. 60 and 61, as well as Table 94, demonstrates that, for time $T_{-12}$ data, almost all subcombinations of biomarkers comprising between 2 and 25 biomarkers from Table J will discriminate between sepsis and SIRs subjects.

TABLE 94

Number of subcombinations from Table J that performed with a given threshold accuracy using $T_{-12}$ nucleic acid data

| Column 1 Number of Biomarkers | Column 2 Greater than 60% | Column 3 Greater than 70% | Column 4 Greater than 80% | Column 5 Greater than 90% | Column 6 Less than 60% |
|---|---|---|---|---|---|
| 2 | 197 | 145 | 17 | 0 | 3 |
| 3 | 199 | 160 | 25 | 0 | 1 |
| 4 | 199 | 174 | 38 | 0 | 1 |
| 5 | 200 | 186 | 51 | 0 | 0 |
| 6 | 200 | 194 | 50 | 0 | 0 |
| 7 | 200 | 195 | 48 | 0 | 0 |
| 8 | 200 | 194 | 64 | 0 | 0 |
| 9 | 200 | 200 | 61 | 1 | 0 |
| 10 | 200 | 196 | 64 | 0 | 0 |
| 11 | 200 | 196 | 70 | 0 | 0 |
| 12 | 200 | 199 | 70 | 0 | 0 |
| 13 | 200 | 199 | 73 | 0 | 0 |
| 14 | 200 | 198 | 67 | 0 | 0 |
| 15 | 200 | 198 | 79 | 0 | 0 |
| 16 | 200 | 198 | 70 | 0 | 0 |
| 17 | 200 | 198 | 64 | 0 | 0 |
| 18 | 200 | 199 | 84 | 0 | 0 |
| 19 | 200 | 197 | 83 | 0 | 0 |
| 20 | 200 | 199 | 82 | 0 | 0 |
| 21 | 200 | 199 | 85 | 0 | 0 |
| 22 | 200 | 198 | 80 | 0 | 0 |
| 23 | 200 | 200 | 83 | 0 | 0 |
| 24 | 200 | 198 | 83 | 0 | 0 |
| 25 | 200 | 198 | 81 | 0 | 0 |

6.14.2 Subcombinations of Protein Biomarkers at $T_{-12}$

There are a total of 10 biomarkers for which protein abundance data is available as reported in Table K. A total of 1600 different subcombinations of this set of biomarkers were constructed using the $T_{-12}$ time point data described in Section 6.13. Each different subcombination was then tested for its ability to discriminate between sepsis and SIRS subjects. The 1600 subcombinations represent a random sampling of the total number of possible subcombinations possible for the 10 biomarkers of the present invention reported in Table K. Randomness of the 1600 subcombinations was ensured using the following algorithm:

```
CONSIDER 3 to 10 biomarkers from Table K
{
  LET the current number be k;
  DO the following 200 times
  {
    SELECT k biomarkers at random from Table K;
    LET the current set of biomarkers be S;
  }
  DO the following 10 times
  {
    FOR biomarker set S, randomly set aside 10% of patients as a
    validation population and 90% as a training population;
    FIT a model to the training population using Random Forest with
    $T_{-12}$ time point data;
    PREDICT results for the validation population;
    CALCULATE agreement with the known status of the validation
    population;
  }
  AVERAGE the ten agreement rates and report;
  SET k = k+1;
  IF k > 10 then END; ELSE return to top;
}
END
```

Computations were performed as described in further detail in Section 6.14.1. There were a total of 152 patients for which $T_{-12}$ data was available from a combination of discovery and confirmatory data described above. Of these 152 patients, 80 were sepsis and 72 were SIRs. For some biomarkers in Table K, there were multiple data sources. For instance, there is IL-6, IL-8, and IL-10 protein data from three different labs. Thus, there is a complex pattern of incidence among patients. Some patients may be tested by one lab, others by two, etc. This was determined by how the project evolved and what samples were available (some patient samples were exhausted before they could be tested with assays developed later). To handle this complex incidence, the following strategy was used. In any given iteration, if a protein that was tested in multiple labs was selected, all assay results for the protein were selected. A missing-value imputation scheme was then used to fill out missing values, making it look like all patients were tested with all assays. This data was then fed into the Random Forest model as correlated inputs that measure the same underlying compound. Thus, consider the case where k is equal to 3 and one of the randomly chosen proteins from Table K is IL-8, from 3 different laboratories, and the other 2 proteins are unique meaning that they are each from only one laboratory. The data from all three IL-8 sources are selected, plus the other two unique assays for the other two proteins, for a total of five assays. The missing-value imputation scheme is then used to fill out missing values, making it look like all patients had results from three different sources for a total of nine assays.

The calculations described above test 200 subcombinations at each interval 3 through 10. In other words, 200 subcombinations each consisting of three randomly selected biomarkers from Table K were tested, 200 subcombinations each consisting of four biomarkers randomly selected from Table K were tested, and so forth, through 200 subcombinations each consisting of ten biomarkers randomly selected from Table K for a total of 8 families of subcombinations, where each family of subcombinations consists of 200 subcombinations of biomarkers all having k biomarkers, where k is a number in the set 3 through 10. FIG. 62 plots the accuracy of each of these eight families of subcombinations as bar graphs. FIG. 63 plots the accuracy (performance) of each individual subcombination in each of the eight families of subcombinations. Thus, FIG. 63 plots the accuracy (performance) of a total of 1600 subcombinations of the set of biomarkers listed in Table K.

FIGS. 62 and 63 show that the distribution for each family of subcombinations is Gaussian (bell-shaped), indicating that each respective family (k=3, 4, . . . , 10) is an accurate depiction of the subcombination space represented by the family. The results reported in FIGS. 62 and 63 show that, with as few as three biomarkers randomly selected from Table K, an accuracy (performance) estimate above 50% was virtually always obtained. Table 95 contains the number of subcombinations in each family (k=3, 4, . . . , 10) that performed with a threshold accuracy of greater than 60% (column 2), greater than 70% (column 3), greater than 80% (column 4), greater than 90% (column 5), or an accuracy of less than 60% (column 6). The data summarized in FIGS. 62 and 63, as well as Table 95, demonstrates that, for time $T_{-12}$ data, almost all subcombinations of biomarkers comprising between 3 and 10 biomarkers from Table K will discriminate between sepsis and SIRs subjects.

TABLE 95

Number of subcombinations from Table K that performed
with a given threshold accuracy using $T_{-12}$ protein data

| Column 1 Number of Biomarkers | Column 2 Greater than 60% | Column 3 Greater than 70% | Column 4 Greater than 80% | Column 5 Greater than 90% | Column 6 Less than 60% |
|---|---|---|---|---|---|
| 3 | 192 | 58 | 0 | 0 | 8 |
| 4 | 196 | 106 | 1 | 0 | 4 |
| 5 | 200 | 117 | 1 | 0 | 0 |
| 6 | 200 | 136 | 0 | 0 | 0 |
| 7 | 200 | 151 | 1 | 0 | 0 |
| 8 | 200 | 172 | 1 | 0 | 0 |
| 9 | 200 | 188 | 1 | 0 | 0 |
| 10 | 200 | 187 | 0 | 0 | 0 |

6.14.3 Subcombinations of Protein Biomarkers at $T_{-36}$

A total of 1600 different subcombinations of the set of biomarkers of Table K were constructed for the $T_{-36}$ time point using the protein based data described in Section 6.13. Each different subcombination was then tested for its ability to discriminate between sepsis and SIRS subjects. There were a total of 142 patients for which $T_{-36}$ data was available from a combination of discovery and confirmatory data described above. Of these 142 patients, 79 were sepsis and 63 were SIRs. The 1600 subcombinations represent a random sampling of the total number of possible subcombinations possible for the 10 biomarkers of the present invention reported in Table K. Randomness of the 1600 subcombinations was ensured using the algorithm identified in Section 6.14.2, the only difference being that $T_{-36}$ data rather than $T_{-12}$ data was used. Computations were performed as described in further detail in Section 6.14.1. FIG. 64 plots the accuracy of each of these eight families of subcombinations as bar graphs. FIG. 65 plots the accuracy (performance) of each individual subcombination in each of the eight families of subcombinations. Thus, FIG. 65 plots the accuracy (performance) of a total of 1600 subcombinations of the set of biomarkers listed in Table K.

The results reported in FIGS. 64 and 65 show that, with as few as three biomarkers randomly selected from Table K, an accuracy (performance) estimate above 60% was typically obtained. Table 95 contains the number of subcombinations in each family (k=3, 4, . . . , 10) that performed with a threshold accuracy of greater than 60% (column 2), greater than 70% (column 3), greater than 80% (column 4), greater than 90% (column 5), or an accuracy of less than 60% (column 6). The data summarized in FIGS. 64 and 65, as well as Table 95, demonstrates that, for time $T_{-36}$ data, most subcombinations of biomarkers comprising between 3 and 10 biomarkers from Table K will discriminate between sepsis and SIRs subjects.

TABLE 96

Number of subcombinations from Table K that performed with a given threshold accuracy using $T_{-36}$ protein data

| Column 1 Number of Biomarkers | Column 2 Greater than 60% | Column 3 Greater than 70% | Column 4 Greater than 80% | Column 5 Greater than 90% | Column 6 Less than 60% |
|---|---|---|---|---|---|
| 3 | 138 | 23 | 0 | 0 | 62 |
| 4 | 152 | 25 | 0 | 0 | 48 |
| 5 | 171 | 32 | 0 | 0 | 29 |
| 6 | 180 | 30 | 0 | 0 | 20 |
| 7 | 188 | 37 | 0 | 0 | 12 |
| 8 | 194 | 40 | 0 | 0 | 6 |
| 9 | 194 | 27 | 0 | 0 | 6 |
| 10 | 199 | 20 | 0 | 0 | 1 |

6.14.4 Subcombinations of Nucleic Acid Biomarkers at $T_{-36}$

A total of 4600 different subcombinations of the set of biomarkers of Table J were constructed for the $T_{-36}$ time point using the nucleic acid based data described in Section 6.13. Each different subcombination was then tested for its ability to discriminate between sepsis and SIRS subjects. There were a total of 142 patients for which $T_{-36}$ data was available from a combination of discovery and confirmatory data described above. Of these 142 patients, 79 were sepsis and 63 were SIRs. The 4600 subcombinations represent a random sampling of the total number of possible subcombinations possible for the 44 biomarkers of the present invention reported in Table J at the $T_{-36}$ time point. Randomness of the 4600 subcombinations was ensured using the algorithm identified in Section 6.14.1, the only difference being that $T_{-36}$ data rather than $T_{-12}$ data was used and that the minimum k value was 3. Computations were performed as described in further detail in Section 6.14.1. FIG. 66 plots the accuracy of each of these 23 families of subcombinations as bar graphs. FIG. 67 plots the accuracy (performance) of each individual subcombination in each of the 23 families of subcombinations. Thus, FIG. 67 plots the accuracy (performance) of a total of 4600 subcombinations of the set of biomarkers listed in Table J.

The results reported in FIGS. 66 and 67 show that, with as few as three biomarkers randomly selected from Table J, an accuracy (performance) estimate above 60% was typically obtained. Table 97 contains the number of subcombinations in each family (k=3, 4, . . . , 25) that performed with a threshold accuracy of greater than 60% (column 2), greater than 70% (column 3), greater than 80% (column 4), greater than 90% (column 5), or an accuracy of less than 60% (column 6). The data summarized in FIGS. 66 and 67, as well as Table 97, demonstrate that, for time $T_{-36}$ data, most subcombinations of biomarkers comprising between 3 and 25 biomarkers from Table J will discriminate between sepsis and SIRs subjects.

TABLE 97

Number of subcombinations from Table J that performed with a given threshold accuracy using $T_{-36}$ nucleic acid data

| Column 1 Number of Biomarkers | Column 2 Greater than 60% | Column 3 Greater than 70% | Column 4 Greater than 80% | Column 5 Greater than 90% | Column 6 Less than 60% |
|---|---|---|---|---|---|
| 3 | 194 | 115 | 4 | 0 | 6 |
| 4 | 196 | 128 | 8 | 0 | 4 |
| 5 | 200 | 159 | 6 | 0 | 0 |
| 6 | 200 | 161 | 6 | 0 | 0 |
| 7 | 200 | 173 | 10 | 0 | 0 |
| 8 | 200 | 182 | 10 | 0 | 0 |
| 9 | 200 | 189 | 8 | 0 | 0 |
| 10 | 200 | 188 | 10 | 0 | 0 |
| 11 | 200 | 194 | 10 | 0 | 0 |
| 12 | 200 | 193 | 13 | 0 | 0 |
| 13 | 200 | 190 | 19 | 0 | 0 |
| 14 | 200 | 192 | 24 | 0 | 0 |
| 15 | 200 | 196 | 20 | 0 | 0 |
| 16 | 200 | 195 | 16 | 0 | 0 |
| 17 | 200 | 196 | 22 | 0 | 0 |
| 18 | 200 | 195 | 18 | 0 | 0 |
| 19 | 200 | 196 | 14 | 0 | 0 |
| 20 | 200 | 194 | 14 | 0 | 0 |
| 21 | 200 | 197 | 14 | 0 | 0 |
| 22 | 200 | 197 | 11 | 0 | 0 |
| 23 | 200 | 200 | 15 | 0 | 0 |
| 24 | 200 | 199 | 20 | 0 | 0 |
| 25 | 200 | 199 | 19 | 0 | 0 |

6.14.5 Subcombinations of Combined Nucleic Acid and Protein Biomarker Data at $T_{-12}$ There are a total of 53 biomarkers listed Table I. A total of 4600 different subcombinations of this set of biomarkers were constructed using all available $T_{-12}$ time point data. For the subset of biomarkers in Table I that are listed in Table J, the $T_{-12}$ time point data consisted of RT-PCR data described above. For the subset of biomarkers that are listed in Table K, the $T_{-12}$ time point data consisted of bead based data described above. The one exception to this was "MMP9" for which both protein and gene-expression data was available. Therefore, MMP9 gene and protein abundance data was treated as separate biomarkers. To accomplish this, MMP9 nucleic data was termed "MMP9.GE" and MMP9 protein abundance data from the bead based assays was termed MMP9.Protein.

Each different subcombination was tested for its ability to discriminate between sepsis subjects and SIRS subjects. The 4600 subcombinations represent a random sampling of the total number of possible subcombinations possible for the 53 biomarkers of the present invention reported in Table I. Randomness of the 4600 subcombinations was ensured using the following algorithm:

```
CONSIDER 3 to 25 biomarkers from Table I
{
  LET the current number be k;
  DO the following 200 times
  {
    SELECT k biomarkers at random from Table I;
    LET the current set of biomarkers be S;
  }
  DO the following 10 times
  {
    FOR biomarker set S, randomly set aside 10% of patients as a
    validation population and 90% as a training population;
    FIT a model to the training population using Random Forest with
    T_-12 time point data;
```

```
    PREDICT results for the validation population;
    CALCULATE agreement with the known status of the validation
    population;
  }
  AVERAGE the ten agreement rates and report;
  SET k = k+1;
  IF k > 10 then END; ELSE return to top;
}
END
```

There were a total of 152 patients for which $T_{-12}$ data was available from a combination of discovery and confirmatory data described above. Of these 152 patients, 80 were sepsis and 72 were SIRs. Computations were performed as described in further detail in Section 6.14.1. The calculations described above test 200 subcombinations at each interval 2 through 25. In other words, 200 subcombinations each consisting of three biomarkers randomly selected from Table I were tested, 200 subcombinations each consisting of four biomarkers randomly selected from Table I were tested, and so forth, through 200 subcombinations each consisting of twenty-five biomarkers randomly selected from Table I for a total of 23 families of subcombinations, where each family of subcombinations consists of 200 subcombinations of biomarkers each having k biomarkers, where k is a number in the set 3 through 25. FIG. 68 plots the accuracy of each of these 23 families of subcombinations as bar graphs. FIG. 69 plots the accuracy (performance) of each individual subcombination in each of the 23 families of subcombinations. Thus, FIG. 69 plots the accuracy (performance) of a total of 4600 subcombinations of the set of biomarkers listed in Table I.

FIGS. 68 and 69 indicate that for k>5, the distributions are Gaussian, (bell-shaped), indicating that each respective family (k=5, . . . , 25) is an accurate depiction of the subcombination space represented by the family. For k<=5, a handful of subsets give lower accuracy (performance) estimates. The results reported in FIGS. 68 and 69 show that, with as few as three biomarkers randomly selected from Table I, an accuracy (performance) estimate above 50% was virtually always obtained. Table 98 contains the number of subcombinations in each family (k=3, 4, . . . , 25) that performed with a threshold accuracy of greater than 60% (column 2), greater than 70% (column 3), greater than 80% (column 4), greater than 90% (column 5), or an accuracy of less than 60% (column 6). The data summarized in FIGS. 68 and 69, as well as Table 98, demonstrate that, for time $T_{-12}$ data, almost all subcombinations of biomarkers comprising between 3 and 25 biomarkers from Table I will discriminate between sepsis and SIRs subjects.

TABLE 98

Number of subcombinations from Table I that performed with a given threshold accuracy using $T_{-12}$ combined nucleic acid and protein data

| Column 1 Number of Biomarkers | Column 2 Greater than 60% | Column 3 Greater than 70% | Column 4 Greater than 80% | Column 5 Greater than 90% | Column 6 Less than 60% |
|---|---|---|---|---|---|
| 3 | 200 | 157 | 11 | 0 | 0 |
| 4 | 200 | 166 | 12 | 0 | 0 |
| 5 | 200 | 191 | 25 | 0 | 0 |
| 6 | 200 | 191 | 30 | 0 | 0 |
| 7 | 200 | 195 | 33 | 0 | 0 |
| 8 | 200 | 198 | 44 | 0 | 0 |
| 9 | 200 | 200 | 49 | 0 | 0 |
| 10 | 200 | 198 | 63 | 0 | 0 |
| 11 | 200 | 199 | 65 | 0 | 0 |
| 12 | 200 | 200 | 71 | 0 | 0 |
| 13 | 200 | 200 | 64 | 0 | 0 |
| 14 | 200 | 200 | 66 | 0 | 0 |
| 15 | 200 | 200 | 74 | 0 | 0 |
| 16 | 200 | 199 | 74 | 0 | 0 |
| 17 | 200 | 200 | 73 | 0 | 0 |
| 18 | 200 | 200 | 76 | 0 | 0 |
| 19 | 200 | 200 | 87 | 0 | 0 |
| 20 | 200 | 199 | 94 | 0 | 0 |
| 21 | 200 | 200 | 77 | 0 | 0 |
| 22 | 200 | 200 | 84 | 0 | 0 |
| 23 | 200 | 200 | 81 | 0 | 0 |
| 24 | 200 | 200 | 93 | 0 | 0 |
| 25 | 200 | 200 | 85 | 0 | 0 |

6.14.6 Subcombinations of Combined Nucleic Acid and Protein Biomarker Data at $T_{-36}$ Subcombinations of biomarkers were selected as described in Section 6.14.5, the only difference being that $T_{-36}$ data rather than $T_{-12}$ data was used. A total of 4600 different subcombinations of Table I were constructed using all available $T_{-36}$ time point data. There were a total of 142 patients for which $T_{-36}$ data was available from a combination of discovery and confirmatory data described above. Of these 142 patients, 79 were sepsis and 63 were SIRs. Computations were performed as described in further detail in Section 6.14.1. The calculations described above test 200 subcombinations at each interval 3 through 25. In other words, 200 subcombinations each consisting of three biomarkers randomly selected from Table I were tested, 200 subcombinations each consisting of four biomarkers randomly selected from Table I were tested, and so forth, through 200 subcombinations each consisting of twenty-five biomarkers randomly selected from Table I for a total of 23 families of subcombinations, where each family of subcombinations consists of 200 subcombinations of biomarkers each having k biomarkers, where k is a number in the set 3 through 25. FIG. 70 plots the accuracy of each of these 23 families of subcombinations as bar graphs. FIG. 71 plots the accuracy (performance) of each individual subcombination in each of the 23 families of subcombinations. Thus, FIG. 71 plots the accuracy (performance) of a total of 4600 subcombinations of the set of biomarkers listed in Table I.

FIGS. 70 and 71 indicate that for k>5, the distributions are Gaussian, (bell-shaped), indicating that each respective family (k=5, . . . , 25) is an accurate depiction of the subcombination space represented by the family. For k<=5, a handful of subsets give lower accuracy (performance) estimates. The results reported in FIGS. 70 and 71 show that, with as few as three biomarkers randomly selected from Table I, an accuracy (performance) estimate above 50% was virtually always obtained. Table 99 contains the number of subcombinations in each family (k=3, 4, . . . , 25) that performed with a threshold accuracy of greater than 60% (column 2), greater than 70% (column 3), greater than 80% (column 4), greater than 90% (column 5), or an accuracy of less than 60% (column 6). The data summarized in FIGS. 70 and 71, as well as Table 99, demonstrate that, for time $T_{-36}$ data, almost all subcombinations of biomarkers comprising between 3 and 25 biomarkers from Table I will discriminate between sepsis and SIRs subjects.

TABLE 99

Number of subcombinations from Table I that performed with a given threshold accuracy using $T_{-36}$ combined nucleic acid and protein data

| Column 1 Number of Biomarkers | Column 2 Greater than 60% | Column 3 Greater than 70% | Column 4 Greater than 80% | Column 5 Greater than 90% | Column 6 Less than 60% |
|---|---|---|---|---|---|
| 3 | 187 | 96 | 4 | 0 | 13 |
| 4 | 199 | 127 | 5 | 0 | 1 |
| 5 | 200 | 145 | 7 | 0 | 0 |
| 6 | 200 | 149 | 9 | 0 | 0 |
| 7 | 200 | 148 | 9 | 0 | 0 |
| 8 | 200 | 157 | 8 | 0 | 0 |
| 9 | 200 | 175 | 13 | 0 | 0 |
| 10 | 199 | 179 | 7 | 0 | 1 |
| 11 | 200 | 180 | 11 | 0 | 0 |
| 12 | 200 | 175 | 11 | 0 | 0 |
| 13 | 200 | 184 | 15 | 0 | 0 |
| 14 | 200 | 184 | 10 | 0 | 0 |
| 15 | 200 | 180 | 5 | 0 | 0 |
| 16 | 200 | 190 | 17 | 0 | 0 |
| 17 | 200 | 191 | 16 | 0 | 0 |
| 18 | 200 | 190 | 15 | 0 | 0 |
| 19 | 200 | 191 | 8 | 0 | 0 |
| 20 | 200 | 196 | 13 | 0 | 0 |
| 21 | 200 | 198 | 15 | 0 | 0 |
| 22 | 200 | 195 | 9 | 0 | 0 |
| 23 | 200 | 195 | 14 | 0 | 0 |
| 24 | 200 | 195 | 10 | 0 | 0 |
| 25 | 200 | 196 | 18 | 0 | 0 |

6.15 Mean Expression Value of Biomarkers in Sepsis and SIRS Patients Identified in Table I The mean expression values of the biomarkers of Table I were determined for subjects that acquired sepsis (Sepsis subjects) and subjects that did not acquire sepsis (SIRS subjects) in the populations described in Sections 6.11.2, 6.12.2 (Affymetrix data), 611.1, 6.12.1 (RT-PCR data), 6.13.3 (bead data), and 6.13.1 and 6.13.2 (bead data) at the $T_{-12}$, $T_{-36}$, and $T_{-60}$ time points. This data is set forth in Table 100 below. In Table 100, a biomarker with the _Affy extension represents the combined data of Sections 6.11.2 and 6.11.2 (Affymetrix data), a biomarker with the 0.18S extension represents the combined data of Sections 6.11.1 and 6.12.1 (RT-PCR data), a biomarker with the BDB extension represents the data of Section 6.13.3, and a biomarker with the RBM extension represents the data of Sections 6.13.1 and 6.13.2.

For nucleic acid biomarkers in Table 100 that were identified by gene arrays (.Affy), the values in Table 100 represent mean relative fluorescence intensity units obtained for the specific probe sequences examined. As such, they are not actual units of measure, just relative quantity of one group to another. Additionally, as part of the data analysis, some of these values may have undergone a log transformation or other adjustment, prior to being reported. The expression values for the nucleic acid biomarkers (0.18S) found in Table 100 are defined by the relative "cycle-time to threshold." As such, they do not cite actual units of measure, just relative quantity of one group to another. A sample with a higher amount of nucleic acid will become positive sooner (fewer cycles) than one with less nucleic acid, which will require more cycles before the resultant signal crosses a positivity threshold. For the protein biomarkers in Table 101, the units were as follows alphafetoprotein (AFP) µg/mL (micrograms per milliliter of plasma), Beta-2-Microglobulin B2M) µg/mL, Interleukin-6 (IL-6) pg/mL (picograms/milliliter), Interleukin-8 (IL-8) pg/mL, Interleukin-10 (IL-10) pg/mL, Monocyte Chemoatractant Protein 1 (MCP) pg/mL, Matrix Metalloproteinase 9 (MMP9) ng/mL (nanogram/milliliter), Tissue Inhibitor of Metalloproteinase 1 (TIMP1) ng/mL (nanogram/mL), C Reactive protein (CRP) µg/mL, and Apolipoprotein CIII µg/mL.

TABLE 100

Mean expression values for the biomarkers of Table I as measured in the experimental Affymetrix, RT-PCR, and bead data of Section 6.

| Marker | SIRS $T_{-12}$ | Sepsis $T_{-12}$ | SIRS $T_{-36}$ | Sepsis $T_{-36}$ | SIRS $T_{-60}$ | Sepsis $T_{-60}$ |
|---|---|---|---|---|---|---|
| ANKRD22_Affy | 8.33 | 9.72 | 8.28 | 9.27 | 8.51 | 9.17 |
| ANXA3_Affy | 10.06 | 11.28 | 10.19 | 11.197 | 10.49 | 11.14 |
| BCL2A1_Affy | 8.55 | 9.87 | 8.73 | 9.48 | 9.01 | 9.60 |
| CCL5_Affy | 11.69 | 11.30 | 11.73 | 11.22 | 11.49 | 11.29 |
| CD86_Affy | 8.59 | 8.10 | 8.68 | 8.13 | 8.57 | 8.20 |
| CEACAM1_Affy | 7.81 | 8.74 | 7.83 | 8.43 | 7.91 | 8.43 |
| CRTAP_Affy | 9.30 | 8.81 | 9.31 | 8.87 | 9.31 | 8.96 |
| CSF1R_Affy | 9.36 | 8.79 | 9.34 | 8.93 | 9.40 | 8.89 |
| FAD104_Affy | 7.89 | 8.63 | 8.04 | 8.39 | 8.18 | 8.36 |
| FCGR1A_Affy | 7.38 | 8.10 | 7.34 | 7.90 | 7.53 | 7.76 |
| GADD45A_Affy | 8.26 | 9.03 | 8.36 | 8.95 | 8.53 | 9.01 |
| GADD45B_Affy | 8.81 | 9.40 | 8.80 | 9.21 | 8.91 | 9.20 |
| HLA.DRA_Affy | 11.91 | 11.22 | 11.80 | 11.13 | 11.78 | 11.28 |
| IFNGR1_Affy | 11.20 | 11.51 | 11.25 | 11.53 | 11.38 | 11.52 |
| IL18R1_Affy | 6.65 | 8.23 | 6.81 | 7.90 | 7.00 | 7.95 |
| INSL3_Affy | 6.93 | 7.37 | 7.01 | 7.31 | 7.10 | 7.23 |
| IRAK2_Affy | 7.13 | 7.66 | 7.20 | 7.52 | 7.19 | 7.50 |
| IRAK4_Affy | 7.76 | 8.052 | 7.90 | 7.90 | 7.88 | 7.96 |
| ITGAM_Affy | 11.26 | 11.80 | 11.36 | 11.78 | 11.53 | 11.78 |
| JAK2_Affy | 6.85 | 7.523 | 7.02 | 7.35 | 7.08 | 7.38 |
| LDLR_Affy | 7.05 | 7.788 | 7.09 | 7.76 | 7.12 | 7.75 |
| LY96_Affy | 9.50 | 10.26 | 9.65 | 10.03 | 9.76 | 10.02 |
| MAP2K6_Affy | 8.261 | 9.17 | 8.49 | 9.02 | 8.59 | 9.05 |
| MAPK14_Affy | 8.75 | 9.75 | 8.99 | 9.51 | 9.16 | 9.48 |
| MKNK1_Affy | 10.02 | 10.59 | 10.07 | 10.50 | 10.30 | 10.60 |

TABLE 100-continued

Mean expression values for the biomarkers of Table I as measured in the experimental Affymetrix, RT-PCR, and bead data of Section 6.

| Marker | SIRS $T_{-12}$ | Sepsis $T_{-12}$ | SIRS $T_{-36}$ | Sepsis $T_{-36}$ | SIRS $T_{-60}$ | Sepsis $T_{-60}$ |
|---|---|---|---|---|---|---|
| Gene_MMP9_Affy | 12.05 | 13.03 | 12.28 | 12.95 | 12.41 | 12.93 |
| NCR1_Affy | 5.64 | 5.94 | 5.645 | 5.90 | 5.77 | 5.91 |
| OSM_Affy | 6.70 | 7.51 | 6.79 | 7.25 | 7.00 | 7.32 |
| PFKFB3_Affy | 9.60 | 10.92 | 9.78 | 10.83 | 10.18 | 10.82 |
| PRV1_Affy | 9.79 | 11.99 | 9.89 | 11.81 | 10.58 | 11.72 |
| PSTPIP2_Affv | 8.63 | 9.64 | 8.68 | 9.45 | 8.90 | 9.44 |
| SOCS3_Affy | 7.26 | 8.43 | 7.31 | 8.10 | 7.69 | 8.12 |
| SOD2_Affy | 9.94 | 10.66 | 10.07 | 10.69 | 10.27 | 10.59 |
| TDRD9_Affy | 6.84 | 8.30 | 7.02 | 8.30 | 7.43 | 8.18 |
| TGFBI_Affy | 10.17 | 9.31 | 10.27 | 9.45 | 10.37 | 9.63 |
| TIFA_Affy | 5.99 | 6.51 | 5.94 | 6.31 | 6.01 | 6.27 |
| TNFSF10_Affy | 10.38 | 10.77 | 10.51 | 10.56 | 10.47 | 10.52 |
| TNFSF13B_Affy | 10.23 | 10.70 | 10.24 | 10.56 | 10.48 | 10.58 |
| IL10alpha_Affy | 9.91 | 9.53 | 9.87 | 9.56 | 9.91 | 9.63 |
| ANKRD22.18S | 20.35 | 18.33 | 20.31 | 18.65 | 20.01 | 18.70 |
| ANXA3.18S | 17.29 | 15.52 | 17.00 | 15.50 | 16.78 | 15.68 |
| ARG2.18S | 20.36 | 19.09 | 20.12 | 19.26 | 19.93 | 19.13 |
| BCL2A1.18S | 18.58 | 17.00 | 18.20 | 17.05 | 17.84 | 17.04 |
| CD86.18S | 19.81 | 20.19 | 19.70 | 20.15 | 19.68 | 20.10 |
| CEACAM1.18S | 19.98 | 18.34 | 19.84 | 18.39 | 19.73 | 18.36 |
| FCGR1A.18S | 16.78 | 15.03 | 16.51 | 15.32 | 16.329 | 15.59 |
| GADD45A.18S | 19.73 | 18.46 | 19.69 | 18.45 | 19.38 | 18.53 |
| GADD45B.18S | 16.72 | 15.52 | 16.61 | 15.65 | 16.50 | 15.86 |
| IFNGR1.18S | 16.00 | 15.23 | 15.77 | 15.20 | 15.68 | 15.23 |
| IL1RN.18S | 17.24 | 16.01 | 17.03 | 16.05 | 16.95 | 16.27 |
| IL18R1.18S | 20.56 | 18.71 | 20.15 | 18.72 | 20.04 | 18.72 |
| INSL3.18S | 21.41 | 20.03 | 21.22 | 20.01 | 21.00 | 20.22 |
| IRAK2.18S | 20.45 | 19.20 | 20.28 | 19.29 | 20.32 | 19.49 |
| IRAK4.18S | 18.25 | 17.74 | 18.06 | 17.65 | 17.98 | 17.71 |
| ITGAM.18S | 15.45 | 14.51 | 15.27 | 14.57 | 15.12 | 14.60 |
| JAK2.18S | 17.77 | 16.90 | 17.56 | 16.97 | 17.50 | 17.06 |
| LDLR.18S | 20.34 | 19.31 | 20.19 | 19.10 | 20.28 | 19.24 |
| LY96.18S | 19.24 | 18.20 | 18.95 | 18.27 | 18.75 | 18.35 |
| MAP2K6.18S | 18.11 | 16.78 | 17.86 | 16.62 | 17.73 | 16.74 |
| MKNK1.18S | 17.61 | 16.48 | 17.37 | 16.48 | 17.22 | 16.58 |
| Gene_MMP9.18S | 14.89 | 13.40 | 14.70 | 13.27 | 14.53 | 13.15 |
| NCR1.18S | 21.89 | 21.06 | 21.79 | 20.99 | 21.82 | 21.11 |
| OSM.18S | 19.98 | 18.41 | 19.71 | 18.51 | 19.49 | 18.57 |
| PFKFB3.18S | 17.83 | 15.86 | 17.53 | 15.85 | 17.IS | 16.00 |
| PRV1.18S | 16.87 | 13.49 | 16.28 | 13.08 | 15.42 | 13.34 |
| PSTP1P2.18S | 17.45 | 16.18 | 17.24 | 16.31 | 17.13 | 16.37 |
| SOCS3.18S | 16.83 | 15.09 | 16.57 | 15.12 | 16.20 | 15.30 |
| SOD2.18S | 13.62 | 12.83 | 13.50 | 12.87 | 13.41 | 13.12 |
| TDRD9.18S | 22.65 | 20.64 | 22.32 | 20.45 | 21.95 | 20.57 |
| TIFA.18S | 19.02 | 17.40 | 18.89 | 17.69 | 18.70 | 17.97 |
| TLR4.18S | 17.93 | 17.03 | 17.83 | 17.24 | 17.73 | 17.33 |
| TNFRSF6.18S | 17.31 | 16.51 | 17.02 | 16.74 | 17.05 | 16.88 |
| TNFSF10.18S | 16.21 | 15.32 | 15.98 | 15.49 | 16.00 | 15.68 |
| TNFSF13B.18S | 16.32 | 15.43 | 16.16 | 15.72 | 16.01 | 15.71 |
| VNN1.18S | 17.16 | 15.39 | 16.70 | 15.19 | 16.51 | 15.12 |
| AlphaFetoprotein_RBM | 3.77 | 4.22 | 3.70 | 4.34 | 3.34 | 4.01 |
| ApolipoproteinCIII_RBM | 59.72 | 38.05 | 53.84 | 38.34 | 53.38 | 40.03 |
| Beta2Microglobulin_RBM | 2.83 | 3.63 | 2.57 | 3.02 | 2.43 | 2.89 |
| CReactiveProtein_RBM | 146.95 | 261.16 | 206.21 | 258.20 | 171.76 | 245.76 |
| IL6_RBM | 82.87 | 4858.72 | 99.21 | 308.50 | 98.28 | 341.38 |
| IL8_RBM | 31.03 | 121.58 | 36.78 | 78.93 | 30.15 | 69.30 |
| IL10_RBM | 21.92 | 64.45 | 33.16 | 38.60 | 21.12 | 37.43 |
| MCP1_RBM | 237.84 | 796.87 | 259.82 | 505.33 | 229.04 | 558.73 |
| Protein_MMP9_RBM | 1143.25 | 1809.30 | 992.84 | 1390.05 | 961.12 | 1364.40 |
| TIMP1_RBM | 226.68 | 406.90 | 237.22 | 351.29 | 235.05 | 344.12 |
| ARG2_SPM | 21.34 | 20.25 | 21.30 | 20.43 | 21.32 | 20.56 |
| CD86_SPM | 17.31 | 17.95 | 17.47 | 17.90 | 17.53 | 17.87 |
| FCGR1A_SPM | 16.16 | 14.48 | 15.98 | 14.85 | 15.80 | 15.13 |
| IL1RN_SPM | 15.75 | 14.81 | 15.59 | 14.95 | 15.55 | 15.10 |
| IL6_SPM | 23.58 | 23.55 | 23.71 | 23.67 | 23.70 | 23.58 |
| IL8_SPM | 21.97 | 21.99 | 22.46 | 22.48 | 22.68 | 22.41 |
| IL10_SPM | 21.15 | 20.02 | 21.10 | 20.26 | 20.96 | 20.24 |
| IL18R1_SPM | 18.33 | 16.54 | 18.06 | 16.75 | 18.04 | 16.83 |
| ITGAM_SPM | 14.66 | 13.82 | 14.53 | 13.84 | 14.53 | 13.96 |
| Gene_MMP9_SPM | 13.14 | 11.71 | 12.90 | 11.82 | 13.01 | 11.95 |
| TIMP1_SPM | 13.57 | 13.00 | 13.38 | 12.95 | 13.47 | 13.02 |
| TLR4_SPM | 14.86 | 14.22 | 14.80 | 14.35 | 14.71 | 14.41 |
| TNFSF13B_SPM | 14.63 | 13.91 | 14.56 | 14.13 | 14.52 | 14.21 |
| CReactiveProtein_SPM | 23.19 | 23.00 | 23.26 | 23.20 | 23.27 | 23.25 |

TABLE 100-continued

Mean expression values for the biomarkers of Table I as measured in the experimental Affymetrix, RT-PCR, and bead data of Section 6.

| Marker | SIRS $T_{-12}$ | Sepsis $T_{-12}$ | SIRS $T_{-36}$ | Sepsis $T_{-36}$ | SIRS $T_{-60}$ | Sepsis $T_{-60}$ |
|---|---|---|---|---|---|---|
| IL6_BDB | −0.15 | 0.59 | −0.25 | −0.02 | −0.19 | 0.147 |
| IL8_BDB | −0.24 | 0.74 | −0.30 | 0.24 | −0.32 | 0.20 |
| IL10_BDB | −0.18 | 0.57 | −0.27 | 0.35 | −0.20 | 0.10 |
| MCP1_BDB | −0.18 | 0.58 | −0.18 | 0.01 | −0.25 | 0.20 |

The range of expression values of the biomarkers of Table I were determined for subjects that acquired sepsis (Sepis subjects) and subjects that did not acquire sepsis (SIRS subjects) in the populations described in Sections 6.11.2, 6.12.2 (Affymetrix data), 611.1, 6.12.1 (RT-PCR data), 6.13.3 (bead data), and 6.13.1 and 6.13.2 (bead data) at the $T_{-12}$, and $T_{-36}$ time points. This data is set forth in Table 101 below. In Table 101, a biomarker with the _Affy extension represents the combined data of Sections 6.11.2 and 6.11.2 (Affymetrix data), a biomarker with the 0.18S extension represents the combined data of Sections 6.11.1 and 6.12.1 (RT-PCR data), a biomarker with the BDB extension represents the data of Section 6.13.3, and a biomarker with the RBM extension represents the data of Sections 6.13.1 and 6.13.2. Time points are given in column 6, where $T_{-12}$ represents the $T_{-12}$ time point, and $T_{-36}$ represents the $T_{-36}$ time point. Units in Table 101 are as described for Table 100.

TABLE 101

Expression value ranges for the biomarkers of Table I as measured in the experimental Affymetrix, RT-PCR, and bead data of Section 6.

| Biomarker 1 | Minimum value in sepsis subjects 2 | Maximum value in sepsis subjects 3 | Minimum value in SIRS subjects 4 | Maximum value in SIRS subjects 5 | Time 6 |
|---|---|---|---|---|---|
| ANKRD22_Affy | 7.953749641 | 12.12893617 | 7.152671629 | 11.15686619 | T-12 |
| ANXA3_Affy | 8.694223626 | 12.60070358 | 7.888396707 | 11.77082747 | T-12 |
| BCL2A1_Affy | 7.44669819 | 11.98497181 | 6.831314584 | 10.15766376 | T-12 |
| CCL5_Affy | 8.898803629 | 12.84470384 | 10.18676932 | 12.76079187 | T-12 |
| CD86_Affy | 7.053070944 | 9.279967603 | 7.868508261 | 9.428684419 | T-12 |
| CEACAM1_Affy | 7.392836443 | 10.11429986 | 6.897178024 | 8.990696622 | T-12 |
| CRTAP_Affy | 7.96569575 | 10.04792044 | 8.402744052 | 10.11557268 | T-12 |
| CSF1R_Affy | 8.12973354 | 9.802040206 | 8.308888545 | 10.10429638 | T-12 |
| FAD104_Affy | 7.670795141 | 10.63246961 | 5.857923276 | 9.290926038 | T-12 |
| FCGR1A_Affy | 6.796282224 | 9.51719797 | 6.335911956 | 9.135545399 | T-12 |
| GADD45A_Affy | 7.874842459 | 10.63426409 | 6.244572007 | 9.859106279 | T-12 |
| GADD45B_Affy | 8.479965651 | 10.29001883 | 7.992247915 | 9.49903678 | T-12 |
| HLA.DRA_Affy | 9.174921757 | 12.40164437 | 10.91664573 | 12.59721891 | T-12 |
| IFNGR1_Affy | 9.881934243 | 12.20352664 | 10.20622485 | 12.04433802 | T-12 |
| IL18R1_Affy | 5.617961135 | 10.58599306 | 5.401354816 | 8.680200674 | T-12 |
| INSL3_Affy | 6.498476621 | 8.453102101 | 6.380834209 | 7.658960107 | T-12 |
| IRAK2_Affy | 6.875497116 | 9.68130844 | 6.749722992 | 8.274075293 | T-12 |
| IRAK4_Affy | 7.433778424 | 8.878566727 | 7.144224029 | 8.232236692 | T-12 |
| ITGAM_Affy | 10.49945783 | 12.40537329 | 10.40124379 | 12.02696288 | T-12 |
| JAK2_Affy | 5.855248527 | 8.799277378 | 5.832795685 | 7.719583127 | T-12 |
| LDLR_Affy | 6.257275326 | 9.674292614 | 6.131286337 | 7.912581783 | T-12 |
| LY96_Affy | 8.415332968 | 11.70570487 | 8.133946247 | 10.62910735 | T-12 |
| MAP2K6_Affy | 7.596722579 | 10.56652274 | 7.340508485 | 9.871737402 | T-12 |
| MAPK14_Affy | 8.070466208 | 10.92164826 | 7.114917424 | 10.02925699 | T-12 |
| MKNK1_Affy | 9.279266935 | 11.72051891 | 8.987912062 | 11.32996284 | T-12 |
| Gene_MMP9_Affy | 11.53180146 | 14.23119077 | 10.53501559 | 13.54148736 | T-12 |
| NCR1_Affy | 5.317900783 | 6.518234278 | 5.112152822 | 6.108537679 | T-12 |
| OSM_Affy | 6.711016689 | 8.50414686 | 5.914544406 | 7.870308905 | T-12 |
| PFKFB3_Affy | 8.872516729 | 12.35520872 | 8.119052014 | 11.65471067 | T-12 |
| PRV1_Affy | 8.247231438 | 14.06000214 | 7.787420639 | 12.82213193 | T-12 |
| PSTPIP2_Affy | 7.917121337 | 10.93727651 | 7.633999161 | 10.56933315 | T-12 |
| SOCS3_Affy | 6.800978821 | 10.18734767 | 6.095547925 | 8.999643638 | T-12 |
| SOD2_Affy | 9.638778614 | 11.7873112 | 8.477270195 | 11.33496413 | T-12 |
| TDRD9_Affy | 5.982800228 | 10.55761021 | 5.394035579 | 9.208195372 | T-12 |
| TGFBI_Affy | 7.954609344 | 11.19226116 | 8.973848308 | 11.1560402 | T-12 |
| TIFA_Affy | 5.620694754 | 8.03295421 | 5.430693745 | 7.140866404 | T-12 |
| TNFSF10_Affy | 9.847323138 | 11.63713214 | 9.035999538 | 11.33035464 | T-12 |
| TNFSF13B_Affy | 8.585414556 | 11.79818987 | 8.90534601 | 11.34212616 | T-12 |
| IL10alpha_Affy | 8.690880784 | 10.54878771 | 9.024669305 | 10.52469989 | T-12 |
| ANKRD22.18S | 14.554 | 20.607 | 18.026 | 22.621 | T-12 |
| ANXA3.18S | 12.994 | 18.89 | 14.989 | 20.069 | T-12 |
| ARG2.18S | 16.703 | 22.511 | 17.729 | 23.054 | T-12 |
| BCL2A1.18S | 14.219 | 19.664 | 15.565 | 20.206 | T-12 |
| CD86.18S | 18.391 | 22.429 | 18.245 | 21.426 | T-12 |
| CEACAM1.18S | 15.174 | 20.37 | 16.808 | 21.929 | T-12 |
| FCGR1A.18S | 12.273 | 17.502 | 14.289 | 19.097 | T-12 |

TABLE 101-continued

Expression value ranges for the biomarkers of Table I as measured
in the experimental Affymetrix, RT-PCR, and bead data of Section 6.

| Biomarker 1 | Minimum value in sepsis subjects 2 | Maximum value in sepsis subjects 3 | Minimum value in SIRS subjects 4 | Maximum value in SIRS subjects 5 | Time 6 |
|---|---|---|---|---|---|
| GADD45A.18S | 15.697 | 20.631 | 18.602 | 21.118 | T-12 |
| GADD45B.18S | 14.214 | 17.599 | 15.52 | 18.143 | T-12 |
| IFNGR1.18S | 13.746 | 17.418 | 14.233 | 17.389 | T-12 |
| IL1RN.18S | 13.7 | 18.656 | 14.995 | 19.231 | T-12 |
| IL18R1.18S | 15.6 | 21.649 | 16.63 | 23.144 | T-12 |
| INSL3.18S | 18.077 | 22.515 | 19.735 | 23.106 | T-12 |
| IRAK2.18S | 16.851 | 21.205 | 17.775 | 22.286 | T-12 |
| IRAK4.18S | 16.637 | 19.164 | 17.001 | 19.648 | T-12 |
| ITGAM.18S | 12.6 | 17.346 | 13.709 | 17.172 | T-12 |
| JAK2.18S | 15.292 | 19.228 | 16.431 | 19.001 | T-12 |
| LDLR.18S | 16.909 | 21.4 | 18.195 | 22.081 | T-12 |
| LY96.18S | 16.811 | 20.726 | 17.543 | 20.956 | T-12 |
| MAP2K6.18S | 14.062 | 18.942 | 16.2005 | 20.678 | T-12 |
| MKNK1.18S | 14.677 | 18.261 | 15.589 | 19.195 | T-12 |
| Gene_MMP9.18S | 10.128 | 16.281 | 12.644 | 17.265 | T-12 |
| NCR1.18S | 18.175 | 23.462 | 19.544 | 23.756 | T-12 |
| OSM.18S | 16.6 | 20.544 | 17.835 | 22.174 | T-12 |
| PFKFB3.18S | 12.897 | 18.994 | 14.446 | 20.982 | T-12 |
| PRV1.18S | 9.4745 | 19.6 | 11.749 | 23.823 | T-12 |
| PSTPIP2.18S | 14.243 | 18.013 | 16.098 | 18.792 | T-12 |
| SOCS3.18S | 13.312 | 18.094 | 14.603 | 18.51 | T-12 |
| SOD2.18S | 10.822 | 14.875 | 11.836 | 15.269 | T-12 |
| TDRD9.18S | 17.069 | 23.9 | 20.012 | 25.404 | T-12 |
| TIFA.18S | 14.66 | 20.607 | 16.122 | 20.522 | T-12 |
| TLR4.18S | 15.013 | 19.366 | 15.452 | 19.347 | T-12 |
| TNFRSF6.18S | 14.771 | 18.42 | 16.046 | 18.633 | T-12 |
| TNFSF10.18S | 14.175 | 16.71 | 14.913 | 18.005 | T-12 |
| TNFSF13B.18S | 13.296 | 17.2755 | 14.113 | 18.23 | T-12 |
| VNN1.18S | 12.363 | 19.695 | 14.788 | 20.209 | T-12 |
| AlphaFetoprotein_RBM | 0.465 | 28.9 | 0.862 | 15 | T-12 |
| ApolipoproteinCIII_RBM | 9.1 | 104 | 14 | 170 | T-12 |
| Beta2Microglobulin_RBM | 0.912 | 17 | 0.815 | 14.2 | T-12 |
| CReactiveProtein_RBM | 5.2 | 743 | 9.3 | 435 | T-12 |
| IL6_RBM | 11.9 | 350000 | 5.85 | 1090 | T-12 |
| IL8_RBM | 5.7 | 2430 | 4.6 | 136 | T-12 |
| IL10_RBM | 9.4 | 1080 | 6.73 | 115 | T-12 |
| MCP1_RBM | 68 | 20100 | 54 | 1860 | T-12 |
| Protein_MMP9_RBM | 82.7 | 6100 | 37 | 5500 | T-12 |
| TIMP1_RBM | 99.6 | 1670 | 91.7 | 777 | T-12 |
| ARG2_SPM | 18.19 | 22.88 | 19.11 | 23.53 | T-12 |
| CD86_SPM | 16.51 | 20.02 | 15.83 | 18.57 | T-12 |
| FCGR1A_SPM | 11.78 | 16.69 | 13.448 | 18.43 | T-12 |
| IL1RN_SPM | 12.82 | 17.055 | 12.92 | 17.13 | T-12 |
| IL6_SPM | 22.71 | 24.493 | 22.61 | 24.22 | T-12 |
| IL8_SPM | 17.728 | 23.645 | 19.218 | 24.27 | T-12 |
| IL10_SPM | 16.905 | 22.09 | 17.41 | 23.38 | T-12 |
| IL18R1_SPM | 13.69 | 19.36 | 13.628 | 20.7 | T-12 |
| ITGAM_SPM | 12.33 | 16.26 | 12.21 | 16.24 | T-12 |
| Gene_MMP9_SPM | 8.53 | 14.62 | 9.58 | 15.92 | T-12 |
| TIMP1_SPM | 11.63 | 15.048 | 11.71 | 14.93 | T-12 |
| TLR4_SPM | 12.5 | 16.64 | 13.61 | 16.06 | T-12 |
| TNFSF13B_SPM | 12.29 | 15.86 | 12.37 | 15.998 | T-12 |
| CReactiveProtein_SPM | 16.23 | 24.313 | 18.803 | 24.245 | T-12 |
| IL6_BDB | −0.158501071 | 12.45941145 | −0.166932601 | −0.076083727 | T-12 |
| IL8_BDB | −0.260734671 | 10.31273265 | −0.284430649 | −0.128681359 | T-12 |
| IL10_BDB | −0.317504403 | 4.487381808 | −0.541755786 | 0.071431589 | T-12 |
| MCP1_BDB | −0.215354271 | 11.61107183 | −0.231122309 | −0.10084064 | T-12 |
| IL6_CBA | −0.674647421 | 5.170323126 | −0.825867097 | −0.022530263 | T-12 |
| IL8_CBA | −0.620553789 | 5.923519248 | −0.821374574 | 2.902006709 | T-12 |
| IL10_CBA | −0.661588916 | 4.74196577 | −0.730146126 | 6.047793474 | T-12 |
| ANKRD22_Affy | 7.396771628 | 11.57062629 | 7.129021339 | 9.443944368 | T-36 |
| ANXA3_Affy | 8.70013622 | 12.54023119 | 8.331913923 | 12.10925762 | T-36 |
| BCL2A1_Affy | 7.183882918 | 11.76715511 | 6.405590222 | 10.37097944 | T-36 |
| CCL5_Affy | 9.328902305 | 12.61675161 | 10.40637568 | 12.86027708 | T-36 |
| CD86_Affy | 6.732706362 | 9.538835708 | 7.716006192 | 9.498278669 | T-36 |
| CEACAM1_Affy | 7.13157116 | 9.873881135 | 7.032079139 | 9.080997559 | T-36 |
| CRTAP_Affy | 7.558590076 | 9.700256103 | 8.59265066 | 10.03618173 | T-36 |
| CSF1R_Affy | 7.837660302 | 9.949036275 | 8.464494614 | 10.30550413 | T-36 |
| FAD104_Affy | 7.014972123 | 10.15391937 | 6.239710352 | 8.845757597 | T-36 |
| FCGR1A_Affy | 6.911908197 | 9.049485977 | 6.738241369 | 8.397213121 | T-36 |
| GADD45A_Affy | 7.56337487 | 10.85396197 | 6.589642416 | 9.749741171 | T-36 |
| GADD45B_Affy | 8.51689696 | 10.06660743 | 8.254872004 | 9.532337644 | T-36 |
| HLA.DRA_Affy | 9.633249373 | 12.27644605 | 10.46875169 | 12.67263889 | T-36 |

TABLE 101-continued

Expression value ranges for the biomarkers of Table I as measured
in the experimental Affymetrix, RT-PCR, and bead data of Section 6.

| Biomarker<br>1 | Minimum value<br>in sepsis subjects<br>2 | Maximum value<br>in sepsis subjects<br>3 | Minimum value<br>in SIRS subjects<br>4 | Maximum value<br>in SIRS subjects<br>5 | Time<br>6 |
| --- | --- | --- | --- | --- | --- |
| IFNGR1_Affy | 10.57959732 | 12.27228887 | 9.808984607 | 11.81736908 | T-36 |
| IL18R1_Affy | 5.49992437 | 10.36284472 | 5.348365647 | 9.056683263 | T-36 |
| INSL3_Affy | 6.751235769 | 8.470974618 | 6.354223568 | 7.671828775 | T-36 |
| IRAK2_Affy | 6.667783945 | 8.746281062 | 6.803703241 | 7.823003239 | T-36 |
| IRAK4_Affy | 7.263029682 | 8.81320843 | 7.431560803 | 8.530795242 | T-36 |
| ITGAM_Affy | 10.78220173 | 12.65177246 | 10.81608481 | 11.95316198 | T-36 |
| JAK2_Affy | 6.39933742 | 8.609398755 | 6.113876348 | 7.761009287 | T-36 |
| LDLR_Affy | 6.592115082 | 9.576882573 | 6.429539125 | 7.875471828 | T-36 |
| LY96_Affy | 8.653718448 | 11.10873698 | 7.823465941 | 10.99470657 | T-36 |
| MAP2K6_Affy | 7.76590836 | 10.96962704 | 7.656234297 | 9.824692325 | T-36 |
| MAPK14_Affy | 8.115337243 | 10.65189637 | 8.035017587 | 10.2553217 | T-36 |
| MKNK1_Affy | 9.648189763 | 11.7078247 | 9.01371136 | 10.87910413 | T-36 |
| Gene_MMP9_Affy | 11.11827617 | 14.10554558 | 11.20801397 | 13.49402871 | T-36 |
| NCR1_Affy | 5.193987983 | 6.909045684 | 5.005834897 | 6.207479976 | T-36 |
| OSM_Affy | 6.580322029 | 7.935265514 | 6.196973735 | 7.452713795 | T-36 |
| PFKFB3_Affy | 9.424977102 | 12.34048574 | 8.499191685 | 11.18985748 | T-36 |
| PRV1_Affy | 8.075175165 | 13.89885359 | 7.885024966 | 13.11270704 | T-36 |
| PSTPIP2_Affy | 8.014852906 | 10.87208092 | 7.546671853 | 9.463070109 | T-36 |
| SOCS3_Affy | 7.377913606 | 9.55384035 | 6.2535144 | 8.311473326 | T-36 |
| SOD2_Affy | 9.246088148 | 11.68031375 | 9.036280605 | 11.01924042 | T-36 |
| TDRD9_Affy | 6.248252454 | 11.18511333 | 5.639880173 | 9.344436192 | T-36 |
| TGFBI_Affy | 7.994695342 | 11.02064264 | 9.079527674 | 11.18636937 | T-36 |
| TIFA_Affy | 5.521978531 | 7.303421302 | 5.384514217 | 6.593248984 | T-36 |
| TNFSF10_Affy | 9.60197872 | 11.18227009 | 9.614398352 | 11.21902779 | T-36 |
| TNFSF13B_Affy | 9.376572388 | 11.47004606 | 8.423154647 | 11.14896209 | T-36 |
| IL10alpha_Affy | 8.838180931 | 10.20810676 | 9.056040579 | 10.61188847 | T-36 |
| ANKRD22.18S | 16.059 | 21.635 | 18.344 | 22.188 | T-36 |
| ANXA3.18S | 13.508 | 18.565 | 14.637 | 19.196 | T-36 |
| ARG2.18S | 16.7215 | 22.085 | 16.452 | 23.1025 | T-36 |
| BCL2A1.18S | 14.892 | 20.169 | 15.558 | 21.208 | T-36 |
| CD86.18S | 18.109 | 22.671 | 17.734 | 21.408 | T-36 |
| CEACAM1.18S | 15.864 | 20.381 | 17.141 | 21.711 | T-36 |
| FCGR1A.18S | 12.919 | 17.238 | 13.773 | 18.616 | T-36 |
| GADD45A.18S | 16.021 | 20.468 | 17.567 | 21.221 | T-36 |
| GADD45B.18S | 14.051 | 16.799 | 15.43 | 18.189 | T-36 |
| IFNGR1.18S | 13.89 | 16.44 | 14.532 | 17.1035 | T-36 |
| IL1RN.18S | 14.2965 | 18.584 | 14.569 | 18.818 | T-36 |
| IL18R1.18S | 15.6475 | 21.683 | 17.068 | 21.9465 | T-36 |
| INSL3.18S | 18.708 | 21.952 | 19.775 | 23.714 | T-36 |
| IRAK2.18S | 17.563 | 20.591 | 18.878 | 21.765 | T-36 |
| IRAK4.18S | 16.688 | 18.592 | 16.633 | 19.467 | T-36 |
| ITGAM.18S | 12.974 | 16.862 | 12.696 | 16.597 | T-36 |
| JAK2.18S | 15.659 | 18.42 | 16.185 | 18.67 | T-36 |
| LDLR.18S | 16.925 | 20.765 | 18.764 | 21.351 | T-36 |
| LY96.18S | 17.018 | 20.384 | 17.293 | 21.37 | T-36 |
| MAP2K6.18S | 14.375 | 19.44 | 15.5485 | 20.507 | T-36 |
| MKNK1.18S | 15.064 | 17.922 | 15.281 | 19.103 | T-36 |
| Gene_MMP9.18S | 10.4315 | 16.075 | 12.673 | 16.9025 | T-36 |
| NCR1.18S | 18.189 | 22.531 | 20.01 | 23.281 | T-36 |
| OSM.18S | 16.79 | 20.311 | 18.219 | 21.612 | T-36 |
| PFKFB3.18S | 13.095 | 18.678 | 14.042 | 19.647 | T-36 |
| PRV1.18S | 9.732 | 18.921 | 10.63 | 20.57 | T-36 |
| PSTPIP2.18S | 14.568 | 17.943 | 15.363 | 18.848 | T-36 |
| SOCS3.18S | 13.309 | 16.962 | 14.629 | 18.503 | T-36 |
| SOD2.18S | 11.004 | 15.117 | 12.246 | 14.872 | T-36 |
| TDRD9.18S | 17.108 | 22.863 | 19.203 | 24.013 | T-36 |
| TIFA.18S | 15.498 | 20.069 | 16.808 | 20.769 | T-36 |
| TLR4.18S | 15.77 | 19.352 | 15.578 | 19.604 | T-36 |
| TNFRSF6.18S | 14.782 | 17.867 | 15.952 | 18.014 | T-36 |
| TNFSF10.18S | 14.049 | 16.332 | 14.388 | 17.196 | T-36 |
| TNFSF13B.18S | 13.898 | 16.896 | 13.276 | 18.038 | T-36 |
| VNN1.18S | 12.406 | 18.076 | 13.061 | 20.4895 | T-36 |
| AlphaFetoprotein_RBM | 0.0878 | 45.2 | 0.399 | 14 | T-36 |
| ApolipoproteinCIII_RBM | 8.1 | 105 | 17 | 143 | T-36 |
| Beta2Microglobulin_RBM | 0.857 | 13.4 | 0.953 | 10.6 | T-36 |
| CReactiveProtein_RBM | 9.3 | 548 | 45 | 735 | T-36 |
| IL6_RBM | 8.93 | 6140 | 5.85 | 1480 | T-36 |
| IL8_RBM | 2.4 | 977 | 2.5 | 429 | T-36 |
| IL10_RBM | 2.68 | 397 | 4.4 | 760 | T-36 |
| MCP1_RBM | 77 | 4280 | 60 | 2170 | T-36 |
| Protein_MMP9_RBM | 59 | 9000 | 73 | 3840 | T-36 |
| TIMP1_RBM | 89.9 | 1130 | 85.2 | 1050 | T-36 |
| ARG2_SPM | 17.868 | 23.15 | 17.68 | 23.42 | T-36 |

TABLE 101-continued

Expression value ranges for the biomarkers of Table I as measured
in the experimental Affymetrix, RT-PCR, and bead data of Section 6.

| Biomarker<br>1 | Minimum value<br>in sepsis subjects<br>2 | Maximum value<br>in sepsis subjects<br>3 | Minimum value<br>in SIRS subjects<br>4 | Maximum value<br>in SIRS subjects<br>5 | Time<br>6 |
|---|---|---|---|---|---|
| CD86_SPM | 16.15 | 20.528 | 16.36 | 18.78 | T-36 |
| FCGR1A_SPM | 12.53 | 17.43 | 13.633 | 17.868 | T-36 |
| IL1RN_SPM | 13.375 | 17.043 | 13.98 | 17.695 | T-36 |
| IL6_SPM | 23.12 | 24.378 | 23.17 | 24.46 | T-36 |
| IL8_SPM | 20.33 | 23.78 | 19.38 | 24.24 | T-36 |
| IL10_SPM | 16.785 | 23.34 | 18.648 | 23.63 | T-36 |
| IL18R1_SPM | 14.16 | 19.13 | 15.98 | 19.68 | T-36 |
| ITGAM_SPM | 12.55 | 15.84 | 12.683 | 15.79 | T-36 |
| Gene_MMP9_SPM | 9.163 | 15 | 10.66 | 14.91 | T-36 |
| TIMP1_SPM | 11.53 | 14.895 | 11.77 | 15.08 | T-36 |
| TLR4_SPM | 13.2 | 15.91 | 13.52 | 16 | T-36 |
| TNFSF13B_SPM | 12.56 | 15.415 | 13.19 | 16.725 | T-36 |
| CReactiveProtein_SPM | 19.6 | 23.97 | 20.8 | 24 | T-36 |
| IL6_BDB | −0.684465464 | 2.880494108 | −0.730942369 | 1.994658691 | T-36 |
| IL8_BDB | −0.825836521 | 3.74397758 | −1.025991342 | 0.789180774 | T-36 |
| IL10_BDB | −1.371058252 | 8.324182809 | −1.079489666 | 2.72772331 | T-36 |
| MCP1_BDB | −0.80163532 | 2.625526703 | −0.828696306 | 2.820125749 | T-36 |

7. REFERENCES CITED

The present invention can be implemented as a computer program product that comprises a computer program mechanism embedded in a computer readable storage medium. For instance, the computer program product could contain the program modules shown in FIG. 35. These program modules can be stored on a CD-ROM, DVD, magnetic disk storage product, or any other computer readable data or program storage product. The program modules can also be embedded in permanent storage, such as ROM, one or more programmable chip, or one or more application specific integrated circuits (ASICs). Such permanent storage can be localized in a server, 802.11 access point, 802.11 wireless bridge/station, repeater, router, mobile phone, or other electronic devices. The software modules in the computer program product can also be distributed electronically, via the Internet or otherwise, by transmission of a computer data signal (in which the software modules are embedded) either digitally or on a carrier wave.

Having now fully described the invention with reference to certain representative embodiments and details, it will be apparent to one of ordinary skill in the art that changes and modifications can be made thereto without departing from the spirit or scope of the invention as set forth herein. The specific embodiments described herein are offered by way of example only, and the invention is to be limited only by the terms of the appended claims, along with the full scope of equivalents to which such claims are entitled.

We claim:

1. A method of treating sepsis in a subject at risk for developing sepsis, the method comprising:
obtaining from at least one blood sample taken from a SIRS-positive subject an expression level of IL-6 protein, IL-8 protein, MMP9 nucleic acid and/or protein, and OSM nucleic acid;
determining that the subject is likely to develop sepsis based on the expression level of each of IL-6 protein, IL-8 protein, MMP9 nucleic acid and/or protein and OSM nucleic acid being elevated compared to a control expression level of each, wherein said control expression level of each is from SIRS patients that did not develop sepsis; and
administering to said subject that is determined to be likely to develop sepsis a therapeutically effective sepsis treatment regimen.

2. The method of claim 1, wherein the at least one blood sample was taken from said subject at a single point in time.

3. The method of claim 1, wherein the expression level of IL-6 protein, IL-8 protein, MMP9 nucleic acid and/or protein, and OSM nucleic acid is determined from a plurality of blood samples taken from said subject at different points in time.

4. The method of claim 3, wherein a first blood sample in said plurality of blood samples is taken on a first day before the subject acquires sepsis and a second blood sample in said plurality of blood samples is taken on a second day before the subject acquires sepsis.

5. The method of claim 1, the method further comprising constructing, prior to the determining step, a biomarker profile of said subject comprising the expression level of IL-6 protein, IL-8 protein, MMP9 nucleic acid and/or protein, and OSM nucleic acid.

6. The method of claim 5, wherein the constructing step comprises applying a data analysis algorithm to the expression level of IL-6 protein, IL-8 protein, MMP9 nucleic acid and/or protein, and OSM nucleic acid of the subject, wherein the data analysis algorithm is derived from an expression level of IL-6 protein, IL-8 protein, MMP9 nucleic acid and/or protein, and OSM nucleic acid that are obtained from members of a population,
wherein said population comprises SIRS-positive subjects that develop sepsis subsequent to obtaining said expression level of IL-6 protein, IL-8 protein, MMP9 nucleic acid and/or protein, and OSM nucleic acid and SIRS-positive subjects that do not develop sepsis subsequent to obtaining said expression level of IL-6 protein, IL-8 protein, MMP9 nucleic acid and/or protein, and OSM nucleic acid.

7. The method of claim 2, wherein the expression level of IL-6 protein and IL-8 protein in said blood sample was determined using a method comprising detection via interaction with protein-specific antibodies.

8. The method of claim 7, wherein one or more of the protein-specific antibodies is selected from the group consisting of a polyclonal antibody, a monoclonal antibody, an antibody fragment, a scFv fragment, a Fab fragment, a F(ab')$_2$ fragment.

* * * * *